(12) United States Patent
Kroth et al.

(10) Patent No.: US 7,553,861 B2
(45) Date of Patent: Jun. 30, 2009

(54) DIPEPTIDYL PEPTIDASE-IV INHIBITORS

(75) Inventors: Heiko Kroth, Leimen (DE); Tim Feuerstein, Neckargemuend (DE); Arthur Taveras, Southborough, MA (US)

(73) Assignee: Alantos Pharmaceuticals Holding, Inc., Cambridge, MA (US)

(*) Notice: Subject to any disclaimer, the term of this patent is extended or adjusted under 35 U.S.C. 154(b) by 622 days.

(21) Appl. No.: 11/409,481

(22) Filed: Apr. 21, 2006

(65) Prior Publication Data

US 2006/0270701 A1 Nov. 30, 2006

Related U.S. Application Data

(60) Provisional application No. 60/674,151, filed on Apr. 22, 2005.

(51) Int. Cl.
- A61K 31/41 (2006.01)
- C07D 257/04 (2006.01)
- C07D 257/10 (2006.01)
- C07D 403/00 (2006.01)
- C07D 487/00 (2006.01)
- C07D 295/00 (2006.01)
- C07D 207/00 (2006.01)

(52) U.S. Cl. ............... 514/381; 548/250; 548/517; 548/518; 548/524; 548/528

(58) Field of Classification Search ............ 514/381; 548/250, 517, 518, 523, 524, 528
See application file for complete search history.

(56) References Cited

U.S. PATENT DOCUMENTS

| | | |
|---|---|---|
| 3,297,709 A * | 1/1967 | Davis ............... 548/254 |
| 5,064,853 A | 11/1991 | Gasc et al. |
| 5,118,811 A | 6/1992 | Uchida et al. |
| 5,254,543 A | 10/1993 | Hanko et al. |
| 5,262,386 A | 11/1993 | Lüthy et al. |
| 5,338,860 A | 8/1994 | Baasner et al. |
| 5,391,556 A | 2/1995 | Heckel et al. |
| 5,407,950 A | 4/1995 | Okubo et al. |
| 5,437,969 A | 8/1995 | Schmuck et al. |
| 5,445,928 A | 8/1995 | Schmuck et al. |
| 5,475,016 A | 12/1995 | Hanko et al. |
| 5,482,920 A | 1/1996 | Lüthy |
| 5,492,916 A | 2/1996 | Morriello et al. |
| 5,492,920 A | 2/1996 | Chen et al. |
| 5,494,919 A | 2/1996 | Morriello et al. |
| 5,514,505 A | 5/1996 | Limburg et al. |
| 5,563,014 A | 10/1996 | Malhotra et al. |
| 5,569,662 A | 10/1996 | Satake et al. |
| 5,618,808 A | 4/1997 | Nagel |
| 5,622,973 A | 4/1997 | Morriello et al. |
| 5,627,285 A | 5/1997 | Hanko et al. |
| 5,665,719 A | 9/1997 | Bock et al. |
| 5,674,905 A | 10/1997 | Kalindjian et al. |
| 5,714,471 A | 2/1998 | Rowe et al. |
| 5,767,097 A | 6/1998 | Tam |
| 5,795,894 A | 8/1998 | Shue et al. |
| 5,804,560 A | 9/1998 | McDonald et al. |
| 5,914,150 A | 6/1999 | Porter et al. |
| 5,939,560 A | 8/1999 | Jenkins et al. |
| 5,962,419 A | 10/1999 | McDonald et al. |
| 5,968,929 A | 10/1999 | Blythin et al. |
| 5,969,100 A | 10/1999 | Munoz et al. |
| 6,011,155 A | 1/2000 | Villhauer |
| 6,015,879 A | 1/2000 | McDonald et al. |
| 6,017,929 A | 1/2000 | Tanaka et al. |
| 6,051,575 A | 4/2000 | Blythin et al. |
| 6,051,684 A | 4/2000 | McDonald et al. |
| 6,057,314 A | 5/2000 | Dimaio et al. |
| 6,110,909 A | 8/2000 | Yukimasa et al. |
| 6,124,305 A | 9/2000 | Villhauer |
| 6,153,171 A | 11/2000 | Rowe et al. |
| 6,166,063 A | 12/2000 | Villhauer |
| 6,180,698 B1 | 1/2001 | Porter et al. |
| 6,191,161 B1 | 2/2001 | Kánai et al. |
| 6,201,132 B1 | 3/2001 | Jenkins et al. |
| 6,207,668 B1 | 3/2001 | Braun et al. |
| 6,228,885 B1 | 5/2001 | Palla et al. |
| 6,303,661 B1 | 10/2001 | Demuth et al. |

(Continued)

FOREIGN PATENT DOCUMENTS

| | | |
|---|---|---|
| DE | 36 07 194 A1 | 9/1987 |
| DE | 3633485 | 4/1988 |
| DE | 19826972 | 12/1999 |
| DE | 10309005 | 9/2004 |
| EP | 0 411 495 | 2/1991 |
| EP | 0 802 184 | 10/1997 |
| EP | 1 422 293 | 5/2004 |
| FR | 2711992 | 5/1995 |

(Continued)

OTHER PUBLICATIONS

Jiaang et al.; Novel Isoindoline compounds for potent and selective inhibition of prolyl dipeptidase DPP8; Bioorganic & Medicinal Chemistry Letters, GB, vol. 15, No. 3, Feb. 1, 2005; pp. 687-691.

Pettibone et al.; Heterogeneity of [3H]neurotensin bindings: studies with dynorphin, L-156,903 and levocabastine: Brain Research, Aug. 9, 1988; vol. 457, No. 2, pp. 212-218.

Asakawa Masumi et al.; Switiching "on" and "off" the expression of chirality in peptide rotaxanes; Journal of the American Chemical Society; Mar. 27, 2002; vol. 124, No. 12, pp. 2939-2950.

*Primary Examiner*—Kamal A Saeed
*Assistant Examiner*—Samantha L Shterengarts
(74) *Attorney, Agent, or Firm*—Hoffmann & Baron, LLP

(57) ABSTRACT

The present invention relates generally to pyrrolidine and thiazolidine DPP-IV inhibitor compounds. The present invention also provides synthetic methods for preparation of such compounds, methods of inhibiting DPP-IV using such compounds and pharmaceutical formulations containing them for treatment of DPP-IV mediated diseases, in particular, Type-2 diabetes.

6 Claims, No Drawings

U.S. PATENT DOCUMENTS

| | | |
|---|---|---|
| 6,316,486 B1 | 11/2001 | Lieb et al. |
| 6,319,902 B1 | 11/2001 | Sugawara et al. |
| 6,331,537 B1 | 12/2001 | Hamilton et al. |
| 6,337,340 B1 | 1/2002 | Ross et al. |
| 6,358,887 B1 | 3/2002 | Fischer et al. |
| 6,358,991 B2 | 3/2002 | Jenkins |
| 6,369,051 B1 | 4/2002 | Jenkins |
| 6,376,486 B1 | 4/2002 | Jenkins et al. |
| 6,380,246 B1 | 4/2002 | Lieb et al. |
| 6,380,398 B2 | 4/2002 | Kanstrup et al. |
| 6,387,893 B1 | 5/2002 | Evans et al. |
| 6,432,969 B1 | 8/2002 | Villhauer |
| 6,455,502 B1 | 9/2002 | Bryant et al. |
| 6,455,568 B2 | 9/2002 | Jenkins et al. |
| 6,465,454 B2 | 10/2002 | Jenkins et al. |
| 6,476,026 B1 | 11/2002 | Bryant et al. |
| 6,500,885 B1 | 12/2002 | Porter et al. |
| 6,509,332 B2 | 1/2003 | Jenkins |
| 6,518,299 B1 | 2/2003 | Chand et al. |
| 6,521,644 B1 | 2/2003 | Broqua |
| 6,537,987 B1 | 3/2003 | Hamanaka et al. |
| 6,559,163 B2 | 5/2003 | Cai et al. |
| 6,583,170 B1 | 6/2003 | Pickar et al. |
| 6,593,327 B2 | 7/2003 | Bryant et al. |
| 6,613,761 B1 | 9/2003 | Yukimasa et al. |
| 6,635,658 B2 | 10/2003 | Madera et al. |
| 6,635,660 B2 | 10/2003 | Jenkins et al. |
| 6,645,995 B2 | 11/2003 | Kanstrup et al. |
| 6,673,815 B2 | 1/2004 | Devasthale et al. |
| 6,706,742 B2 | 3/2004 | De Nanteuil et al. |
| 6,713,487 B2 | 3/2004 | Yu et al. |
| 6,716,843 B2 | 4/2004 | De Nanteuil et al. |
| 6,746,990 B2 | 6/2004 | Fischer et al. |
| 6,767,864 B2 | 7/2004 | Fischer et al. |
| 6,774,112 B2 | 8/2004 | Gougoutas |
| 6,777,414 B1 | 8/2004 | Ohkura et al. |
| 6,803,357 B1 | 10/2004 | Bachovchin et al. |
| 6,806,278 B2 | 10/2004 | Madera et al. |
| 6,861,440 B2 | 3/2005 | Boehringer et al. |
| 6,911,467 B2 | 6/2005 | Evans |
| 2001/0025023 A1 | 9/2001 | Carr |
| 2001/0031780 A1 | 10/2001 | Kanstrup et al. |
| 2002/0006899 A1 | 1/2002 | Pospisilik et al. |
| 2002/0016318 A1 | 2/2002 | Miller |
| 2002/0019373 A1 | 2/2002 | Jenkins et al. |
| 2002/0019377 A1 | 2/2002 | Jenkins et al. |
| 2002/0019391 A1 | 2/2002 | Jenkins et al. |
| 2002/0019392 A1 | 2/2002 | Jenkins |
| 2002/0019433 A1 | 2/2002 | Jenkins |
| 2002/0022617 A1 | 2/2002 | Adelman et al. |
| 2002/0022618 A1 | 2/2002 | Jenkins et al. |
| 2002/0022619 A1 | 2/2002 | Bakthavatachalam |
| 2002/0025952 A1 | 2/2002 | Jenkins et al. |
| 2002/0028792 A1 | 3/2002 | Jenkins et al. |
| 2002/0028800 A1 | 3/2002 | Jenkins et al. |
| 2002/0042432 A1 | 4/2002 | Jenkins |
| 2002/0045641 A1 | 4/2002 | Hamilton et al. |
| 2002/0052510 A1 | 5/2002 | Hamilton et al. |
| 2002/0052514 A1 | 5/2002 | Hamilton et al. |
| 2002/0086996 A1 | 7/2002 | Bryant et al. |
| 2002/0103384 A1 | 8/2002 | Kanstrup et al. |
| 2002/0128305 A1 | 9/2002 | Jenkins et al. |
| 2002/0161008 A1 | 10/2002 | Cai et al. |
| 2002/0165164 A1 | 11/2002 | Demuth et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2003/0008905 A1 | 1/2003 | Demuth et al. |
| 2003/0032625 A1 | 2/2003 | Jensen et al. |
| 2003/0045432 A1 | 3/2003 | Fischer et al. |
| 2003/0064935 A1 | 4/2003 | Gougoutas |
| 2003/0069169 A1 | 4/2003 | Macor et al. |
| 2003/0073701 A1 | 4/2003 | Thompson et al. |
| 2003/0078247 A1 | 4/2003 | De Nanteuil et al. |
| 2003/0087950 A1 | 5/2003 | DeNanteuil et al. |
| 2003/0092732 A1 | 5/2003 | Yu et al. |
| 2003/0096796 A1 | 5/2003 | Bryant et al. |
| 2003/0096827 A1 | 5/2003 | Yu et al. |
| 2003/0096857 A1 | 5/2003 | Evans |
| 2003/0114389 A1 | 6/2003 | Webb |
| 2003/0119750 A1 | 6/2003 | Demuth et al. |
| 2003/0119788 A1 | 6/2003 | Bryant et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0135023 A1 | 7/2003 | Demuth et al. |
| 2003/0139434 A1 | 7/2003 | Balkan et al. |
| 2003/0148961 A1 | 8/2003 | Heiser et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0171362 A1 | 9/2003 | Madera et al. |
| 2003/0175350 A1 | 9/2003 | Sugita et al. |
| 2003/0176357 A1 | 9/2003 | Pospisilik et al. |
| 2003/0199527 A1 | 10/2003 | Hamanaka et al. |
| 2003/0203890 A1 | 10/2003 | Steiner et al. |
| 2003/0216450 A1 | 11/2003 | Evans et al. |
| 2003/0225102 A1 | 12/2003 | Sankaranarayanan |
| 2003/0232985 A1 | 12/2003 | Thompson et al. |
| 2004/0002495 A1 | 1/2004 | Sher et al. |
| 2004/0002519 A1 | 1/2004 | Damon et al. |
| 2004/0009877 A1 | 1/2004 | Fischer et al. |
| 2004/0048867 A1 | 3/2004 | Cai et al. |
| 2004/0058876 A1 | 3/2004 | Hoffmann et al. |
| 2004/0063935 A1 | 4/2004 | Yasuda et al. |
| 2004/0072819 A1 | 4/2004 | Yukimasa et al. |
| 2004/0072892 A1 | 4/2004 | Fukushima et al. |
| 2004/0077601 A1 | 4/2004 | Adams et al. |
| 2004/0077645 A1 | 4/2004 | Himmelsbach et al. |
| 2004/0077761 A1 | 4/2004 | Pavez Aranguiz |
| 2004/0082497 A1 | 4/2004 | Evans et al. |
| 2004/0082607 A1 | 4/2004 | Oi et al. |
| 2004/0082622 A1 | 4/2004 | Hamilton et al. |
| 2004/0087587 A1 | 5/2004 | Himmelsbach et al. |
| 2004/0092604 A1 | 5/2004 | Madera et al. |
| 2004/0106655 A1 | 6/2004 | Kitajima et al. |
| 2004/0106802 A1 | 6/2004 | Sankaranarayanan |
| 2004/0121964 A1 | 6/2004 | Madar et al. |
| 2004/0121994 A1 | 6/2004 | Anderson et al. |
| 2004/0132639 A1 | 7/2004 | Ansorge et al. |
| 2004/0138214 A1 | 7/2004 | Himmelsbach et al. |
| 2004/0138215 A1 | 7/2004 | Eckhardt et al. |
| 2004/0147434 A1 | 7/2004 | Ansorge et al. |
| 2004/0147745 A1 | 7/2004 | Bryant et al. |
| 2004/0152745 A1 | 8/2004 | Jackson et al. |
| 2004/0167118 A1 | 8/2004 | Yamamoto et al. |
| 2004/0167191 A1 | 8/2004 | Demuth et al. |
| 2004/0167341 A1 | 8/2004 | Haffner et al. |
| 2004/0171848 A1 | 9/2004 | Haffner et al. |
| 2004/0176307 A1 | 9/2004 | Bachovchin et al. |
| 2004/0176428 A1 | 9/2004 | Edmondson et al. |
| 2004/0180925 A1 | 9/2004 | Matsuno et al. |
| 2004/0186098 A1 | 9/2004 | Magal |
| 2004/0192680 A1 | 9/2004 | Anderson et al. |
| 2004/0209891 A1 | 10/2004 | Broqua et al. |
| 2004/0214762 A1 | 10/2004 | Demuth et al. |
| 2004/0220243 A1 | 11/2004 | Fischer et al. |
| 2004/0224875 A1 | 11/2004 | Schilling et al. |
| 2004/0224959 A1 | 11/2004 | Ohkura et al. |
| 2004/0229882 A1 | 11/2004 | Yu et al. |
| 2004/0229926 A1 | 11/2004 | Yasuda et al. |
| 2004/0235752 A1 | 11/2004 | Pitt et al. |
| 2004/0235926 A1 | 11/2004 | Sakya |

| | | | | | | |
|---|---|---|---|---|---|---|
| 2004/0242636 A1 | 12/2004 | Haffner et al. | | WO | WO 02/101003 | 12/2002 |
| 2004/0254226 A1 | 12/2004 | Feng et al. | | WO | WO 03/004468 | 1/2003 |
| 2004/0259843 A1 | 12/2004 | Madar et al. | | WO | WO 03/035057 | 5/2003 |
| 2004/0259883 A1 | 12/2004 | Sakashita et al. | | WO | WO 03/037327 | 5/2003 |
| 2004/0259903 A1 | 12/2004 | Boehringer et al. | | WO | WO 03/038123 | 5/2003 |
| 2004/0259919 A1 | 12/2004 | Magnin et al. | | WO | WO 03/045977 | 6/2003 |
| 2004/0266758 A1 | 12/2004 | Hadida-Ruah et al. | | WO | WO 03/051848 | 6/2003 |
| 2005/0004205 A1 | 1/2005 | Evans et al. | | WO | WO 03/054228 | 6/2003 |
| 2005/0014699 A1 | 1/2005 | Ansorge et al. | | WO | WO 03/057144 | 7/2003 |
| 2005/0014703 A1 | 1/2005 | Demuth et al. | | WO | WO 03/057666 | 7/2003 |
| 2005/0014747 A1 | 1/2005 | Reinhard et al. | | WO | WO 03/062392 | 7/2003 |
| 2005/0020677 A1 | 1/2005 | Gynther et al. | | WO | WO 03/063903 | 8/2003 |
| 2005/0038020 A1 | 2/2005 | Hamann et al. | | WO | WO 03/074500 | 9/2003 |
| 2005/0042614 A1 | 2/2005 | Hughes et al. | | WO | WO 03/077935 | 9/2003 |
| 2005/0043299 A1 | 2/2005 | Evans et al. | | WO | WO 03/084940 | 10/2003 |
| 2005/0054678 A1 | 3/2005 | Yasuda et al. | | WO | WO 03/091211 | 11/2003 |
| 2005/0058635 A1 | 3/2005 | Demuth et al. | | WO | WO 03/095425 | 11/2003 |
| 2005/0070482 A1 | 3/2005 | Bachovchin | | WO | WO 03/099279 | 12/2003 |
| 2005/0070719 A1 | 3/2005 | Belyakov et al. | | WO | WO 03/101445 | 12/2003 |
| 2005/0085497 A1 | 4/2005 | Ahmad et al. | | WO | WO 03/106456 | 12/2003 |
| 2005/0096348 A1 | 5/2005 | Boehringer et al. | | WO | WO 2004/009544 | 1/2004 |
| 2005/0101638 A1 | 5/2005 | Webb | | WO | WO 2004/013125 | 2/2004 |
| 2005/0113310 A1 | 5/2005 | Striggow et al. | | WO | WO 2004/013135 | 2/2004 |
| 2005/0113344 A1 | 5/2005 | Li et al. | | WO | WO 2004/013138 | 2/2004 |
| 2005/0130981 A1 | 6/2005 | Aranyl et al. | | WO | WO 2004/016587 | 2/2004 |
| 2005/0131019 A1 | 6/2005 | Pei et al. | | WO | WO 2004/016606 | 2/2004 |
| 2005/0137142 A1 | 6/2005 | Schulz et al. | | WO | WO 2004/020407 | 3/2004 |
| 2005/0137224 A1 | 6/2005 | Shima et al. | | WO | WO 2004/031374 | 4/2004 |
| 2005/0153885 A1 | 7/2005 | Yun et al. | | WO | WO 2004/043940 | 5/2004 |
| 2005/0153962 A1 | 7/2005 | Nettekoven et al. | | WO | WO 2004/048352 | 6/2004 |
| 2005/0153973 A1 | 7/2005 | Aranyl et al. | | WO | WO 2004/050022 | 6/2004 |
| 2005/0158374 A1 | 7/2005 | Wong et al. | | WO | WO 2004/052362 | 6/2004 |
| 2005/0163841 A1 | 7/2005 | Wong et al. | | WO | WO 2004/067509 | 8/2004 |
| 2005/0163849 A1 | 7/2005 | Wong et al. | | WO | WO 2004/076433 | 9/2004 |
| 2005/0163850 A1 | 7/2005 | Wong et al. | | WO | WO 2004/076434 | 9/2004 |
| 2005/0165102 A1 | 7/2005 | Wong et al. | | WO | WO 2004/080463 | 9/2004 |
| 2005/0171112 A1 | 8/2005 | Schulz et al. | | WO | WO 2004/089362 | 10/2004 |
| 2005/0176622 A1 | 8/2005 | Kuhn-Wache et al. | | WO | WO 2004/092127 | 10/2004 |
| 2005/0176771 A1 | 8/2005 | Hayakawa et al. | | WO | WO 2004/092128 | 10/2004 |
| 2005/0176806 A1 | 8/2005 | Holmes et al. | | WO | WO 2004/099185 | 11/2004 |
| 2005/0182110 A1 | 8/2005 | Yang | | WO | WO 2004/101514 | 11/2004 |
| 2005/0192324 A1 | 9/2005 | Thomas et al. | | WO | WO 2004/110436 | 12/2004 |
| 2005/0203031 A1 | 9/2005 | Evans | | WO | WO 2004/110453 | 12/2004 |
| 2005/0215573 A1 | 9/2005 | Schilling et al. | | WO | WO 2004/111041 | 12/2004 |
| 2005/0215784 A1 | 9/2005 | Madar et al. | | WO | WO 2004/112701 | 12/2004 |
| 2005/0222140 A1 | 10/2005 | Colandrea et al. | | WO | WO 2005/004906 | 1/2005 |
| 2005/0222221 A1 | 10/2005 | Demuth et al. | | WO | WO 2005/009956 | 2/2005 |
| 2005/0222222 A1 | 10/2005 | Jiaang et al. | | WO | WO 2005/016880 | 2/2005 |
| 2005/0228021 A1 | 10/2005 | Hamann et al. | | WO | WO 2005/021536 | 3/2005 |
| | | | | WO | WO 2005/023762 | 3/2005 |
| FOREIGN PATENT DOCUMENTS | | | | WO | WO 2005/023814 | 3/2005 |
| JP | 04-134070 | 5/1992 | | WO | WO 2005/033099 | 4/2005 |
| JP | 05-155771 | 6/1993 | | WO | WO 2005/033106 | 4/2005 |
| JP | 2518965 | 5/1996 | | WO | WO 2004/042533 | 5/2005 |
| JP | 08-231512 | 9/1996 | | WO | WO 2005/042003 | 5/2005 |
| JP | 2002-265439 | 9/2002 | | WO | WO 2005/044195 | 5/2005 |
| JP | 2004 002367 | 1/2004 | | WO | WO 2005/049022 | 6/2005 |
| JP | 2004-002367 | 1/2004 | | WO | WO 2005/049027 | 6/2005 |
| JP | 2004-002368 | 1/2004 | | WO | WO 2005/049088 | 6/2005 |
| JP | 2004-026820 | 1/2004 | | WO | WO 2005/051914 | 6/2005 |
| JP | 2004-244412 | 9/2004 | | WO | WO 2005/056451 | 6/2005 |
| JP | 3599403 | 9/2004 | | WO | WO 2005/058849 | 6/2005 |
| JP | 2005-023038 | 1/2005 | | WO | WO 2005/067976 | 7/2005 |
| JP | 2005-047853 | 2/2005 | | WO | WO 2005/073186 | 8/2005 |
| JP | 2005-139107 | 6/2005 | | WO | WO 2005/073221 | 8/2005 |
| WO | WO 97/26240 | 7/1997 | | WO | WO 2005/075421 | 8/2005 |
| WO | WO 98/01133 | 1/1998 | | WO | WO 2005/077900 | 8/2005 |
| WO | WO 99/62880 | 12/1999 | | WO | WO 2005/079795 | 9/2005 |
| WO | WO 99/62881 | 12/1999 | | ZA | 9207782 | 4/1993 |
| WO | WO 01/81337 | 11/2001 | | | | |
| WO | WO 02/096420 | 12/2002 | | * cited by examiner | | | ns
DIPEPTIDYL PEPTIDASE-IV INHIBITORS

CROSS REFERENCE TO RELATED APPLICATION

This application claims the benefit of U.S. Provisional Application No. 60/674,151, filed on Apr. 22, 2005, which is incorporated herein by reference in its entirety.

FIELD OF THE INVENTION

The present invention relates to pyrrolidine and thiazolidine-based inhibitors of dipeptidyl peptidase-IV (DPP-IV) and to methods for treating diabetes, particularly Type-2 diabetes as well as impaired glucose tolerance, impaired glucose homeostasis and complications associated with diabetes by inhibiting DPP-IV with such cyclic amido and cyclic ureido pyrrolidine and thiazolidine inhibitors.

BACKGROUND OF THE INVENTION

Diabetes results from the occurrence of one or more of several causative factors, and is characterized by an abnormal elevation in levels of plasma glucose (hyperglycemia). Persistent or uncontrolled hyperglycemia results in an increased probability of premature morbidity and mortality. Abnormal glucose homeostasis is usually associated with changes in the lipid, lipoprotein and apolipoprotein metabolism, or due to other metabolic and hemodynamic diseases.

Patients afflicted with Type-2 diabetes mellitus or noninsulin dependent diabetes mellitus (NIDDM), are especially at increased risk of suffering from macrovascular and microvascular complications, including coronary heart disease, stroke, peripheral vascular disease, hypertension, nephropathy, neuropathy and retinopathy. Therapeutic control of glucose homeostasis, lipid metabolism and hypertension are critical in the clinical management and treatment of Type-2 diabetes mellitus.

The currently available therapeutics for treating available Type-2 diabetes, although effective, have recognized limitations. Compounds based on sulfonylureas (e.g. tolbutamide, glipizide, etc.), which stimulate the pancreatic beta-cells to secrete more insulin, are limited by the development of inhibitor resistant tissues, causing them to become inefficient or ineffective, even at high doses. Biguanide compounds, on the other hand, increase insulin sensitivity so as to cause correction of hyperglycemia to some extent. However, clinically used biguanides such as phenformin and metformin can induce side-effects such as lactic acidosis, nausea and diarrhea.

The more recent glitazone-type compounds (i.e. 5-benzylthiazolidine-2,4-diones) substantially increase insulin sensitivity in muscle, liver and adipose tissue resulting in either partial or complete correction of the elevated plasma levels of glucose without occurrence of hypoglycemia. Currently used glitazones are agonists of the peroxisome proliferator activated receptor (PPAR), which is attributed to be responsible for their improved insulin sensitization. However, serious side effects (e.g. liver toxicity) have been known to occur with some glitazones such as, for example, troglitazone. Compounds that are inhibitors of the dipeptidyl peptidase-IV ("DPP-IV", "DPP-4" or "DP-IV") enzyme are also under investigation as drugs that may be useful in the treatment of diabetes, and particularly Type-2 diabetes. See for example, WO 97/40832, WO 98/19998, and U.S. Pat. No. 5,939,560.

DPP-IV is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (e.g. GHRH, NPY, GLP-2, VIP) in vitro.

The usefulness of DPP-IV inhibitors in the treatment of Type-2 diabetes is based on the fact that DPP-IV in vivo readily inactivates glucagon like peptide-1 (GLP-1) and gastric inhibitory peptide (GLP). GLP-1(7-36) is a 29 aminoacid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of Type-2 diabetes, and potentially obesity. To support this claim, exogenous administration of GLP-1(7-36) (continuous infusion) in diabetic patients has demonstrated efficacy in this patient population. GLP-1(7-36) is degraded rapidly in vivo and has been shown to have a short half-life in vivo (t½ of about 1.5 min). Based on a study of genetically bred DPP-IV KO mice and on in vivo/in vitro studies with selective DPP-IV inhibitors, DPP-IV has been shown to be the primary degrading enzyme of GLP-1(7-36) in vivo. GLP-1(7-36) is degraded by DPP-IV efficiently to GLP-1(9-36), which has been speculated to act as a physiological antagonist to GLP-1(7-36). Inhibition of DPP-IV in vivo should, therefore, potentiate endogenous levels of GLP-1(7-36) and attenuate formation of its antagonist GLP-1(9-36) and serve to ameliorate the diabetic condition.

GLP-1 and GIP are incretins that are produced upon ingestion of food, and which stimulate production of insulin. Inhibition of DPP-IV causes decreased inactivation of the incretins, which in turn, results in an increase in their effectiveness in stimulating pancreatic production of insulin. DPP-IV inhibition therefore, results in an increase in the level of serum insulin. Since the incretins are produced upon consumption of food only, DPP-IV inhibition is not expected to increase insulin levels when not required, thereby precluding excessive lowering of blood sugar (hypoglycemia). Inhibition of DPP-IV, is therefore, is expected to increase insulin levels without increasing the risk of hypoglycemia, thereby lowering deleterious side effects associated with currently used insulin secretagogues. Although DPP-IV inhibitors have not been studied extensively as therapeutics for diseases other than diabetes, they are expected to have other potential therapeutic utilities.

SUMMARY OF THE INVENTION

The present invention relates to a class of pyrrolidine-based inhibitors of dipeptidyl peptidase-IV (DPP-IV). In particular, the present invention provides a new class of pyrrolidine and thiazolidine DPP-IV inhibiting compounds ("DPP-IV inhibitors").

One aspect of the present invention includes a compound of formula (I):

A-B-D     (I)

and all stereoisomers, diastereomers, racemic mixtures and pharmaceutically acceptable salts thereof and all polymorphs; wherein A is:

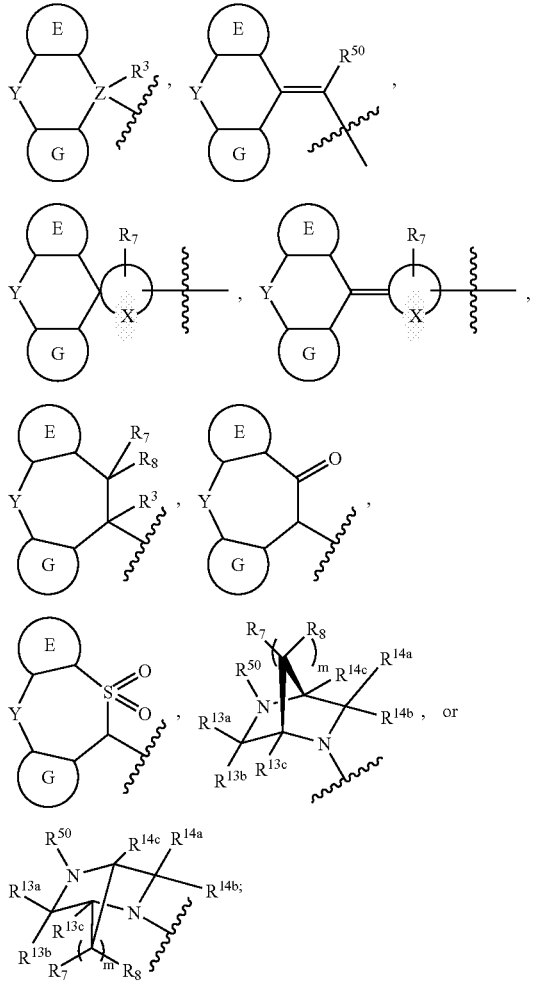

B is:

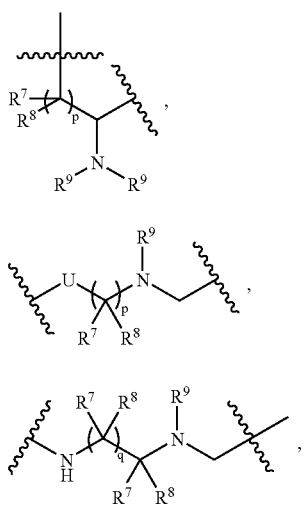

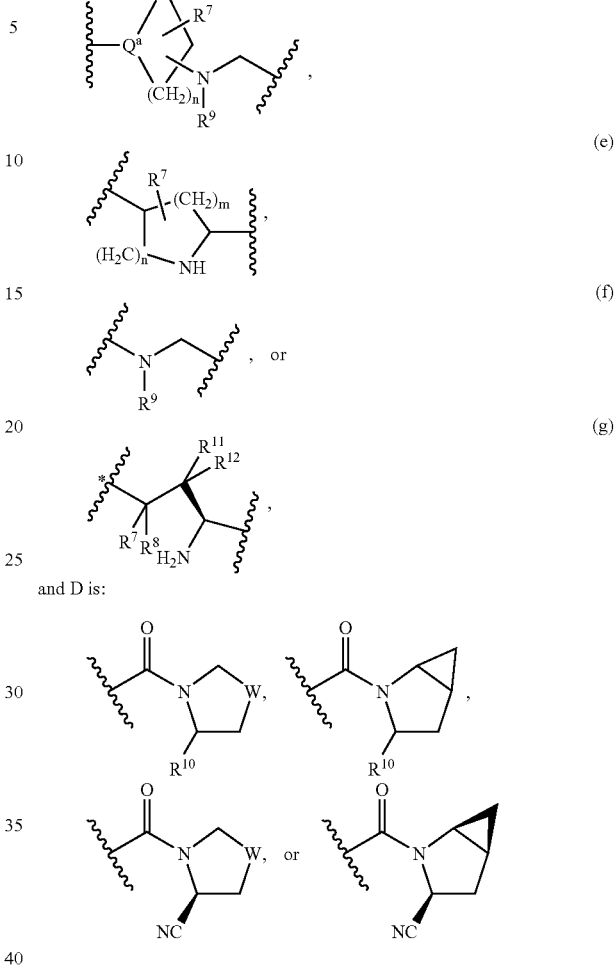

and D is:

wherein
E and G are independently 6-membered aryl, or 5-membered heteroaryl or 6-membered heteroaryl;
E may be substituted with one or more $R^1$ groups;
G may be substituted with one or more $R^2$ groups;
X and Y are divalent and are each independently: a bond, $CR^4R^5$, O, $NR^4$, S, S=O, $S(=O)_2$, C(=O), (C=O)N($R^4$), $S(=O)_2N(R^4)$, C=N—$OR^4$, —C($R^4R^5$)C($R^4R^5$)—, —C($R^4R^5$) C($R^4R^5$)C($R^4R^5$)—, —C($R^4R^5$)C($R^4R^5$)C($R^4R^5$)—, —C($R^4$)=C($R^5$)—, —C($R^4R^5$)$NR^4$—, —C($R^4R^5$)O—, —C($R^4R^5$)S(=O)$_t$—, —(C=O)O—, —(C=$NR^a$)N($R^4$)—, —(C=$NR^a$)—, N(C=O)$NR^4$ $NR^5$, N(C=O)$R^4$, N(C=O)$OR^4$, NS(=O)$_2NR^4NR^5$, NS(=O)$_2R^4$; or aryl, heteroaryl, cycloalkyl or heterocyclic ring, all of which may be optionally substituted;
$R^1$ and $R^2$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, OC(O)$NR^4R^5$, $NR^4C(O)R^5$, $NR^4CO_2R^5$, ($C_0$-$C_6$)-alkyl-C(=$NR^a$)$NHR^4$, ($C_0$-$C_6$)-alkyl-C(=$NR^4$)$NHR^a$, ($C_0$-$C_6$)-alkyl-$NR^4$C(=$NR^4$)$NR^4R^5$, ($C_0$-$C_6$)-alkyl-C(O)$OR^4$, ($C_0$-$C_6$)-alkyl-C(O)$NR^4R^5$, ($C_0$-$C_6$)-alkyl-C(O)—NH—CN, O—($C_0$-$C_6$)-alkyl-C(O)$NR^4R^5$, $S(O)_t$-($C_0$-$C_6$)-alkyl-C(O)$OR^4$, $S(O)_t$-($C_0$-$C_6$)-alkyl-C(O)$NR^4R^5$, ($C_0$-$C_6$)-alkyl-C(O)$NR^4$—($C_0$-$C_6$)-alkyl- $NR^4R^5$, $(C_0$-$C_6)$-alkyl-$NR^4R^5$, $(C_0$-$C_6)$-alkyl-$NR^4$—C(O)$R^5$, $(C_0$-$C_6)$-alkyl-$NR^4$—C(O)O$R^4$, $(C_0$-$C_6)$-alkyl-$NR^4$—C(O)—$NR^4R^5$, $(C_0$-$C_6)$-alkyl-$NR^4$—SO$_2NR^4R^5$, $(C_0$-$C_6)$-alkyl-$NR^4$—SO$_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all of which may be optionally substituted;

$R^3$ is absent or is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0$-$C_6)$-alkyl-C(=$NR^a$)$NHR^4$, $(C_0$-$C_6)$-alkyl-C(=$NR^4$)$NHR^a$, $(C_0$-$C_6)$-alkyl-$NR^4$C(=$NR^4$)$NR^4R^5$, $(C_0$-$C_6)$-alkyl-C(O)O$R^4$, $(C_0$-$C_6)$-alkyl-C(O)$NR^4R^5$, $(C_0$-$C_6)$-alkyl-C(O)—NH—CN, O—$(C_0$-$C_6)$-alkyl-C(O)$NR^4R^5$, $S(O)_t$—$(C_0$-$C_6)$-alkyl-C(O)O$R^4$, $S(O)_t$-$(C_0$-$C_6)$-alkyl-C(O)$NR^4R^5$, $(C_0$-$C_6)$-alkyl-C(O)$NR^4$—$(C_0$-$C_6)$-alkyl-$NR^4R^5$, $(C_0$-$C_6)$-alkyl-$NR^4R^5$, $(C_0$-$C_6)$-alkyl-$NR^4$—C(O)$R^5$, $(C_0$-$C_6)$-alkyl-$NR^4$—C(O)O$R^4$, $(C_0$-$C_6)$-alkyl-$NR^4$—C(O)—$NR^4R^5$, $(C_0$-$C_6)$-alkyl-$NR^4$—SO$_2NR^4R^5$, $(C_0$-$C_6)$-alkyl-$NR^4$—SO$_2R^4$, hydrogen, alkyl, cycloalkyl, cycloalkylalkyl, heterocycloalkyl, fluoroalkyl, heterocyclyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all of which may be optionally substituted;

$R^a$ is hydrogen, CN, $NO_2$, alkyl, haloalkyl, $S(O)_tNR^4R^5$, $S(O)_tR^4$, C(O)O$R^4$, C(O)$R^4$, or C(O)$NR^4R^5$; each occurrence of $R^4$, $R^5$, $R^{20}$ and $R^{21}$ are each independently: hydrogen, alkyl, cycloalkyl, cycloalkylalkyl, heterocycloalkyl, fluoroalkyl, heterocycloalkylalkyl, alkynyl, aryl, heteroaryl, arylalkyl, heteroarylalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are all optionally substituted, or $R^4$ and $R^5$ when taken together with the nitrogen to which they are attached complete a 3- to 8-membered ring containing carbon atoms and may optionally contain a heteroatom selected from O, S, or $NR^{50}$ and the 3- to 8-membered ring may be optionally substituted;

$R^{50}$ is, in each occurrence, $R^{20}$, CN, $NO_2$, $S(O)_tNR^{20}R^{21}$, $S(O)R^{20}$, C(O)O$R^{20}$, C(O)$R^{20}$C(=$NR^a$)$NR^{20}R^{21}$, C(=$NR^{20}$)$NR^{21}R^a$, C(=$NOR^{20}$)$R^{21}$ or C(O)$NR^{20}R^{21}$;

each occurrence of $R^7$ and $R^8$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0$-$C_6)$-alkyl-C(=$NR^a$)$NHR^4$, $(C_0$-$C_6)$-alkyl-C(=$NR^4$)$NHR^a$, $(C_0$-$C_6)$-alkyl-$NR^4$C(=$NR^4$)$NR^4R^5$, $(C_0$-$C_6)$-alkyl-C(O)O$R^4$, $(C_0$-$C_6)$-alkyl-C(O)$NR^4R^5$, $(C_0$-$C_6)$-alkyl-C(O)—NH—CN, O—$(C_0$-$C_6)$-alkyl-C(O)$NR^4R^5$, $S(O)_t$-$(C_0$-$C_6)$-alkyl-C(O)O$R^4$, $S(O)_t$-$(C_0$-$C_6)$-alkyl-C(O)$NR^4R^5$, $(C_0$-$C_6)$-alkyl-C(O)$NR^4$—$(C_0$-$C_6)$-alkyl-$NR^4R^5$, $(C_0$-$C_6)$-alkyl-$NR^4R^5$, $(C_0$-$C_6)$-alkyl-$NR^4$—C(O)$R^5$, $(C_0$-$C_6)$-alkyl-$NR^4$—C(O)O$R^4$, $(C_0$-$C_6)$-alkyl-$NR^4$—C(O)—$NR^4R^5$, $(C_0$-$C_6)$-alkyl-$NR^4$—SO$_2NR^4R^5$, $(C_0$-$C_6)$-alkyl-$NR^4$—SO$_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;

$R^9$ is H or $C_{1-6}$ alkyl;

$R^{10}$ is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0$-$C_6)$-alkyl-C(=$NR^a$)$NHR^4$, $(C_0$-$C_6)$-alkyl-C(=$NR^4$)$NHR^a$, $(C_0$-$C_6)$-alkyl-$NR^4$C(=$NR^4$)$NR^4R^5$, $(C_0$-$C_6)$-alkyl-C(O)O$R^4$, $(C_0$-$C_6)$-alkyl-C(O)$NR^4R^5$, $(C_0$-$C_6)$-alkyl-C(O)—NH—CN, O—$(C_0$-$C_6)$-alkyl-C(O)$NR^4R^5$, $S(O)_t$—$(C_0$-$C_6)$-alkyl-C(O)O$R^4$, $S(O)_t$—$(C_0$-$C_6)$-alkyl-C(O)$NR^4R^5$, $(C_0$-$C_6)$-alkyl-C(O)$NR^4$—$(C_0$-$C_6)$-alkyl-$NR^4R^5$, $(C_0$-$C_6)$-alkyl-$NR^4R^5$, $(C_0$-$C_6)$-alkyl-$NR^4$—C(O)$R^5$, $(C_0$-$C_6)$-alkyl-$NR^4$—C(O)O$R^4$, $(C_0$-$C_6)$-alkyl-$NR^4$—C(O)—$NR^4R^5$, $(C_0$-$C_6)$-alkyl-$NR^4$—SO$_2NR^4R^5$, $(C_0$-$C_6)$-alkyl-$NR^4$—SO$_2R^4$, hydrogen, B(OH)$_2$, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;

$R^{11}$ and $R^{12}$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0$-$C_6)$-alkyl-C(=$NR^a$)$NHR^4$, $(C_0$-$C_6)$-alkyl-C(=$NR^4$)$NHR^a$, $(C_0$-$C_6)$-alkyl-$NR^4$C(=$NR^4$)$NR^4R^5$, $(C_0$-$C_6)$-alkyl-C(O)O$R^4$, $(C_0$-$C_6)$-alkyl-C(O)$NR^4R^5$, $(C_0$-$C_6)$-alkyl-C(O)—NH—CN, O—$(C_0$-$C_6)$-alkyl-C(O)$NR^4R^5$, $S(O)_t$—$(C_0$-$C_6)$-alkyl-C(O)O$R^4$, $S(O)_t$—$(C_0$-$C_6)$-alkyl-C(O)$NR^4R^5$, $(C_0$-$C_6)$-alkyl-C(O)$NR^4$—$(C_0$-$C_6)$-alkyl-$NR^4R^5$, $(C_0$-$C_6)$-alkyl-$NR^4R^5$, $(C_0$-$C_6)$-alkyl-$NR^4$—C(O)$R^5$, $(C_0$-$C_6)$-alkyl-$NR^4$—C(O)O$R^4$, $(C_0$-$C_6)$-alkyl-$NR^4$—C(O)—$NR^4R^5$, $(C_0$-$C_6)$-alkyl-$NR^4$—SO$_2NR^4R^5$, $(C_0$-$C_6)$-alkyl-$NR^4$—SO$_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;

$R^{13a}$ and $R^{13b}$ are each independently $R^5$ or together are =O;

$R^{14a}$ and $R^{14b}$ are each independently $R^5$ or together are =O;

$R^{13c}$ and $R^{14c}$ are each independently $R^5$;

$Q^a$ is CH or N;

U is —C(O)—, —C(=$NR^4$)—, —(C$R^4R^5$—)$_p$, $NR^{50}$, S(=O)$_2$, C(=O), (C=O)N($R^4$), N($R^4$)(C=O), S(=O)$_2$N($R^4$), N($R^4$)S(=O)$_2$, C=N—O$R^4$, —C($R^4$)=C($R^5$)—, —C($R^4R^5$)$_p$$NR^{50}$—, N($R^{50}$)C($R^4R^5$)$_p$—, —O—C($R^4R^5$)—, —C($R^4R^5$)S(=O)$_t$—, —(C=O)O—, —(C=$NR^a$)N($R^4$)—, —(C=$NR^a$)—, N(C=O)$NR^4$ $NR^5$, N(C=O)$R^4$, N(C=O)O$R^4$, NS(=O)$_2NR^4$ $NR^5$, NS(=O)$_2R^4$, or an optionally substituted aryl, heteroaryl, cycloalkyl or heterocyclic ring, all of which may be optionally substituted;

W is —CH$_2$—, —S—, —CHF— or —CF$_2$—;

Z is C or N;

m is 1, or 2;

n is 0, 1, or 2;

p is 0 to 6;

q is 0 to 6; and t is 0, 1, or 2.

Another aspect of the present invention includes a method of preparing a compound of the following formula:

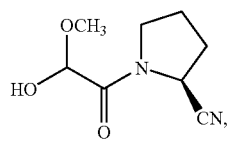

comprising (a) coupling prolinamide with fumarylchloride to provide a compound of the following formula:

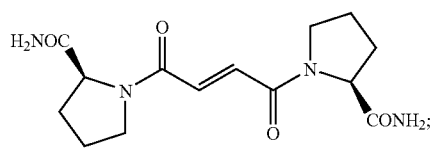

(b) dehydrating the carboxamides of the compound from step (a) to cyano to provide a compound of formula:

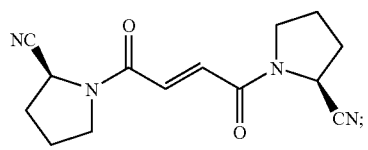

and (c) cleaving the C=C bond with an oxidizing agent either: (1) in the presence of methanol, and then adding a reducing agent to the reaction mixture, or (2) and reacting the cleavage products with a reducing agent and subsequently adding methanol to the cleavage product mixture.

A further aspect of the present invention provides a method of preparing a compound of the following formula:

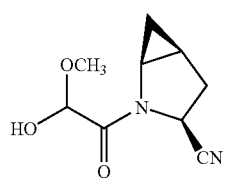

comprising: (a) coupling a compound of formula:

with fumaryl chloride to provide a compound of formula

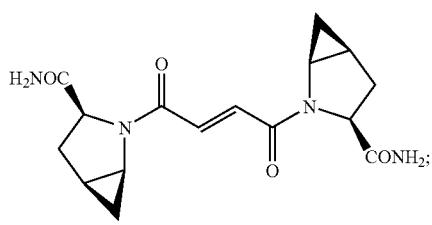

(b) dehydrating the carboxamide in the compound from step (a) to provide a compound of formula:

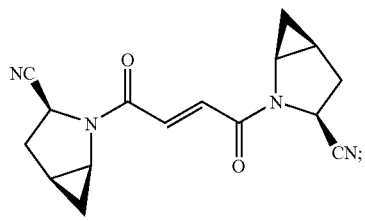

and (c) cleaving the C=C bond with an oxidizing agent either: (1) in the presence of methanol, and then adding a reducing agent to the reaction mixture, or (2) and reacting the cleavage products with a reducing agent and subsequently adding methanol to the cleavage product mixture.

Another aspect of the present invention provides a compound of formula A compound of formula (I):

A-B-D    (I)

wherein A is:

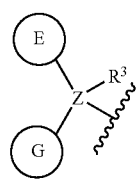

B is:

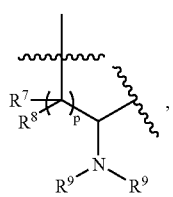

(a)

-continued

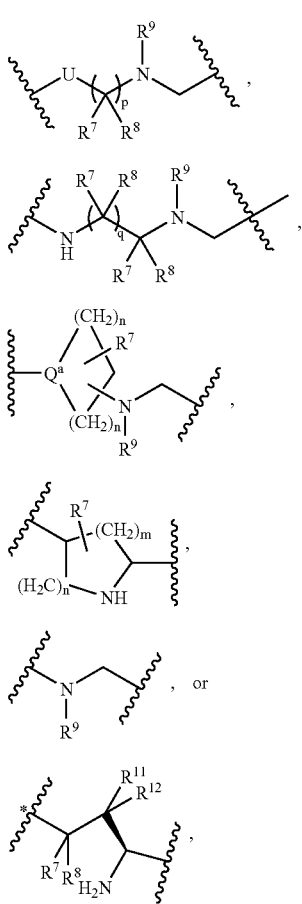

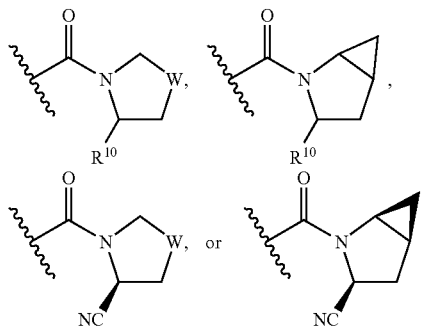

and D is:

wherein
E and G are independently selected from 6-membered aryl, 5-membered heteroaryl, 6-membered heteroaryl, and 5-6-membered saturated or partially saturated carbocyclic or heterocyclic rings;
E may be substituted with one or more $R^1$ groups;
G may be substituted with one or more $R^2$ groups;
$R^1$ and $R^2$ are independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_rR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$—$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl-$NR^4$—$SO_2NR^4R^5$, $(C_0\text{-}C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;
$R^3$ is absent or is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_rR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$—$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl-$NR^4$—$SO_2NR^4R^5$, $(C_0\text{-}C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;
$R^a$ is hydrogen, CN, $NO_2$, alkyl, haloalkyl, $S(O)_rNR^4R^5$, $S(O)_rR^4$, $C(O)OR^4$, $C(O)R^4$, or $C(O)NR^4R^5$;
each occurrence of $R^4$, $R^5$, $R^{20}$ and $R^{21}$ are each independently: hydrogen, alkyl, cycloalkyl, cycloalkylalkyl, heterocycloalkyl, fluoroalkyl, heterocycloalkylalkyl, alkynyl, aryl, heteroaryl, arylalkyl, heteroarylalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are all optionally substituted, or $R^4$ and $R^5$ when taken together with the nitrogen to which they are attached complete a 3- to 8-membered ring containing carbon atoms and may be optionally containing a heteroatom selected from O, S, or $NR^{50}$ and the 3- to 8-membered ring may be optionally substituted;
$R^{50}$ is, in each occurrence, $R^{20}$, CN, $NO_2$, $S(O)_rNR^{20}R^{21}$, $S(O)_rR^{20}$, $C(O)OR^{20}$, $C(O)R^{20}C(=NR^a)NR^{20}R^{21}$, $C(=NR^{20})NR^{21}R^a$, $C(=NOR^{20})R^{21}$ or $C(O)NR^{20}R^{21}$;
each occurrence of $R^7$ and $R^8$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_rR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$—$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl- NR$^4$—SO$_2$NR$^4$R$^5$, (C$_0$-C$_6$)-alkyl-NR$^4$—SO$_2$R$^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

R$^9$ is H or C$_{1-6}$ alkyl;

R$^{10}$ is halogen, CF$_3$, COR$^4$, OR$^4$, NR$^4$R$^5$, NO$_2$, CN, SO$_2$OR$^4$, CO$_2$R$^4$, CONR$^4$R$^5$, CO$_2$H, SO$_2$NR$^4$R$^5$, S(O)$_t$R$^4$, SO$_3$H, OC(O)R$^4$, OC(O)NR$^4$R$^5$, NR$^4$C(O)R$^5$, NR$^4$CO$_2$R$^5$, (C$_0$-C$_6$)-alkyl-C(=NR$^a$)NHR$^4$, (C$_0$-C$_6$)-alkyl-C(=NR$^4$)NHR$^a$, (C$_0$-C$_6$)-alkyl-NR$^4$C(=NR$^4$)NR$^4$R$^5$, (C$_0$-C$_6$)-alkyl-C(O)OR$^4$, (C$_0$-C$_6$)-alkyl-C(O)NR$^4$R$^5$, (C$_0$-C$_6$)-alkyl-C(O)—NH—CN, O—(C$_0$-C$_6$)-alkyl-C(O)NR$^4$R$^5$, S(O)$_t$—(C$_0$-C$_6$)-alkyl-C(O)OR$^4$, S(O)$_t$—(C$_0$-C$_6$)-alkyl-C(O)NR$^4$R$^5$, (C$_0$-C$_6$)-alkyl-C(O)NR$^4$—(C$_0$-C$_6$)-alkyl-NR$^4$R$^5$, (C$_0$-C$_6$)-alkyl-NR$^4$R$^5$, (C$_0$-C$_6$)-alkyl-NR$^4$—C(O)R$^5$, (C$_0$-C$_6$)-alkyl-NR$^4$—C(O)OR$^4$, (C$_0$-C$_6$)-alkyl-NR$^4$—C(O)—NR$^4$R$^5$, (C$_0$-C$_6$)-alkyl-NR$^4$—SO$_2$NR$^4$R$^5$, (C$_0$-C$_6$)-alkyl-NR$^4$—SO$_2$R$^4$, hydrogen, B(OH)$_2$, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

R$^{11}$ and R$^{12}$ are each independently: halogen, CF$_3$, COR$^4$, OR$^4$, NR$^4$R$^5$, NO$_2$, CN, SO$_2$OR$^4$, CO$_2$R$^4$, CONR$^4$R$^5$, CO$_2$H, SO$_2$NR$^4$R$^5$, S(O)$_t$R$^4$, SO$_3$H, OC(O)R$^4$, OC(O)NR$^4$R$^5$, NR$^4$C(O)R$^5$, NR$^4$CO$_2$R$^5$, (C$_0$-C$_6$)-alkyl-C(=NR$^a$)NHR$^4$, (C$_0$-C$_6$)-alkyl-C(=NR$^4$)NHR$^a$, (C$_0$-C$_6$)-alkyl-NR$^4$C(=NR$^4$)NR$^4$R$^5$, (C$_0$-C$_6$)-alkyl-C(O)OR$^4$, (C$_0$-C$_6$)-alkyl-C(O)NR$^4$R$^5$, (C$_0$-C$_6$)-alkyl-C(O)—NH—CN, O—(C$_0$-C$_6$)-alkyl-C(O)NR$^4$R$^5$, S(O)$_t$—(C$_0$-C$_6$)-alkyl-C(O)OR$^4$, S(O)$_t$—(C$_0$-C$_6$)-alkyl-C(O)NR$^4$R$^5$, (C$_0$-C$_6$)-alkyl-C(O)NR$^4$—(C$_0$-C$_6$)-alkyl-NR$^4$R$^5$, (C$_0$-C$_6$)-alkyl-NR$^4$R$^5$, (C$_0$-C$_6$)-alkyl-NR$^4$—C(O)R$^5$, (C$_0$-C$_6$)-alkyl-NR$^4$—C(O)OR$^4$, (C$_0$-C$_6$)-alkyl-NR$^4$—C(O)—NR$^4$R$^5$, (C$_0$-C$_6$)-alkyl-NR$^4$—SO$_2$NR$^4$R$^5$, (C$_0$-C$_6$)-alkyl-NR$^4$—SO$_2$R$^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

R$^{13a}$ and R$^{13b}$ are each independently R$^5$ or together are =O;

R$^{14a}$ and R$^{14b}$ are each independently R$^5$ or together are =O;

R$^{13c}$ and R$^{14c}$ are each independently R$^5$;

Q$^a$ is CH or N;

U is —C(O)—, —C(=NR$^4$)—, —(CR$^4$R$^5$)$_p$—, NR$^{50}$, S(=O)$_2$, C(=O), (C=O)N(R$^4$), N(R$^4$)(C=O), S(=O)$_2$N(R$^4$), N(R$^4$)S(=O)$_2$, C=N—OR$^4$, —C(R$^4$)=C(R$^5$)—, —C(R$^4$R$^5$)$_p$NR$^{50}$—, N(R$^{50}$)C(R$^4$R$^5$)$_p$—, —O—, —(C=NR$^a$)N(R$^4$)—, —(C=NR$^a$)—, N(C=O)NR$^4$ NR$^5$, N(C=O)R$^4$, N(C=O)OR$^4$, NS(=O)$_2$NR$^4$ NR$^5$, NS(=O)$_2$R$^4$, or an optionally substituted aryl, heteroaryl, cycloalkyl or heterocyclic ring, all of which may be optionally substituted;

W is —CH$_2$—, —S—, —CHF— or —CF$_2$—;

Z is C or N;

m is 1, or 2;

n is 0, 1, or 2;

p is 0 to 6;

q is 0 to 6; and t is 0, 1, or 2 wherein: when E and G are both phenyl either:

(1) at least one of R$^1$ or R$^2$ is present and is:

CF$_3$, COR$^4$, OR$^4$, NR$^4$R$^5$, NO$_2$, CN, SO$_2$OR$^4$, CO$_2$R$^4$, CONR$^4$R$^5$, CO$_2$H, SO$_2$NR$^4$R$^5$, S(O)$_t$R$^4$, SO$_3$H, OC(O)R$^4$, OC(O)NR$^4$R$^5$, NR$^4$C(O)R$^5$, NR$^4$CO$_2$R$^5$, (C$_0$-C$_6$)-alkyl-C(=NR$^a$)NHR$^4$, (C$_0$-C$_6$)-alkyl-C(=NR$^4$)NHR$^a$, (C$_0$-C$_6$)-alkyl-NR$^4$C(=NR$^4$)NR$^4$R$^5$, (C$_0$-C$_6$)-alkyl-C(O)OR$^4$, (C$_0$-C$_6$)-alkyl-C(O)NR$^4$R$^5$, (C$_0$-C$_6$)-alkyl-C(O)—NH—CN, O—(C$_0$-C$_6$)-alkyl-C(O)NR$^4$R$^5$, S(O)$_t$—(C$_0$-C$_6$)-alkyl-C(O)OR$^4$, S(O)$_t$—(C$_0$-C$_6$)-alkyl-C(O)NR$^4$R$^5$, (C$_0$-C$_6$)-alkyl-C(O)NR$^4$—(C$_0$-C$_6$)-alkyl-NR$^4$R$^5$, (C$_0$-C$_6$)-alkyl-NR$^4$R$^5$, (C$_0$-C$_6$)-alkyl-NR$^4$—C(O)R$^5$, (C$_0$-C$_6$)-alkyl-NR$^4$—C(O)OR$^4$, (C$_0$-C$_6$)-alkyl-NR$^4$—C(O)—NR$^4$R$^5$, (C$_0$-C$_6$)-alkyl-NR$^4$—SO$_2$NR$^4$R$^5$, (C$_0$-C$_6$)-alkyl-NR$^4$—SO$_2$R$^4$, hydrogen, (C$_{5-20}$)alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted; and wherein OR$^4$ is alkoxy, OR$^4$ is (C$_{5-20}$)alkoxy; or (2) and when B is (b) R$^7$ and R$^8$ are not selected from hydrogen, hydroxy, hydroxymethyl, and phenyl; or (3) and when B is (b) or (f), R9 is: C$_{1-6}$ alkyl.

Another aspect of the present invention provides a compound of formula A compound of formula (I):

A-B-D    (I)

wherein A is:

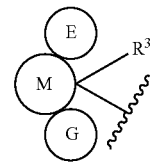

B is:

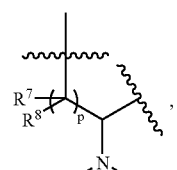

(a)

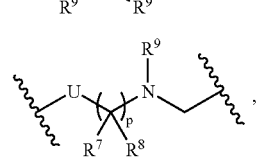

(b)

-continued

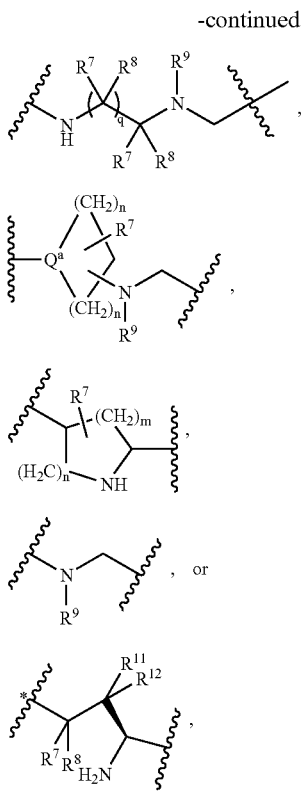

and D is:

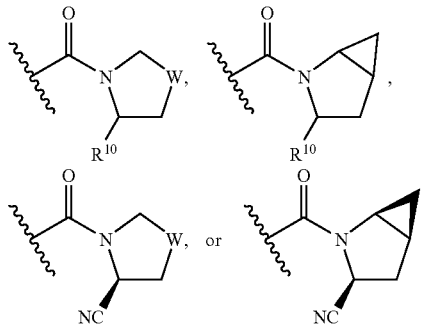

wherein
E, G, and M include a three ring system wherein M shares two carbon atoms with each of E and G;
E, G and M are each independently selected from a 5-7-membered saturated or partially saturated carbocyclic ring, a 5-7 membered saturated or partially saturated heterocyclic ring, a 5-6-membered aromatic ring, and a 5-6-membered heteroaromatic ring;
E may be substituted with one or more $R^1$ groups;
G may be substituted with one or more $R^2$ groups;
$R^1$ and $R^2$ are independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-$C(=NR^a)NHR^4$, $(C_0-C_6)$-alkyl-$C(=NR^4)NHR^a$, $(C_0-C_6)$-alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$—$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;

$R^3$ is absent or is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-$C(=NR^a)NHR^4$, $(C_0-C_6)$-alkyl-$C(=NR^4)NHR^a$, $(C_0-C_6)$-alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$—$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted;

$R^a$ is hydrogen, CN, $NO_2$, alkyl, haloalkyl, $S(O)_tNR^4R^5$, $S(O)_tR^4$, $C(O)OR^4$, $C(O)R^4$, or $C(O)NR^4R^5$;

each occurrence of $R^4$, $R^5$, $R^{20}$ and $R^{21}$ are each independently: hydrogen, alkyl, cycloalkyl, cycloalkylalkyl, heterocycloalkyl, fluoroalkyl, heterocycloalkylalkyl, alkynyl, aryl, heteroaryl, arylalkyl, heteroarylalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are all optionally substituted, or $R^4$ and $R^5$ when taken together with the nitrogen to which they are attached complete a 3- to 8-membered ring containing carbon atoms and may be optionally containing a heteroatom selected from O, S, or $NR^{50}$ and the 3- to 8-membered ring may be optionally substituted;

$R^{50}$ is, in each occurrence, $R^{20}$, CN, $NO_2$, $S(O)_tNR^{20}R^{21}$, $S(O)_tR^{20}$, $C(O)OR^{20}$, $C(O)R^{20}C(=NR^a)NR^{20}R^{21}$, $C(=NR^{20})NR^{21}R^a$, $C(=NOR^{20})R^{21}$ or $C(O)NR^{20}R^{21}$;

each occurrence of $R^7$ and $R^8$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-$C(=NR^a)NHR^4$, $(C_0-C_6)$-alkyl-$C(=NR^4)NHR^a$, $(C_0-C_6)$-alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$—$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

$R^9$ is H or $C_{1-6}$ alkyl;

$R^{10}$ is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4$—$C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$—$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl-$NR^4$—$SO_2NR^4R^5$, $(C_0\text{-}C_6)$-alkyl-$NR^4$—$SO_2R^4$, hydrogen, $B(OH)_2$, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

$R^{11}$ and $R^{12}$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$-$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl-$NR^4$—$SO_2NR^4R^5$, $(C_0\text{-}C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

$R^{13a}$ and $R^{13b}$ are each independently $R^5$ or together are =O;

$R^{14a}$ and $R^{14b}$ are each independently $R^5$ or together are =O;

$R^{13c}$ and $R^{14c}$ are each independently $R^5$;

$Q^a$ is CH or N;

U is —C(O)—, —C(=$NR^4$)—, —$(CR^4R^5)_p$—, $NR^{50}$, $S(=O)_2$, C(=O), (C=O)N($R^4$), N($R^4$)(C=O), S(=O)$_2$N($R^4$), N($R^4$)S(=O)$_2$, C=N—$OR^4$, —C($R^4$)=C($R^5$)—, —C($R^4R^5)_pNR^{50}$—, N($R^{50}$)C($R^4R^5)_p$—, —O—C($R^4R^5$)—, —C($R^4R^5$)S(=O)$_t$—, —(C=O) O—, —(C=$NR^a$)N($R^4$)—, —(C=$NR^a$)—, N(C=O) $NR^4$ $NR^5$, N(C=O)$R^4$, N(C=O)$OR^4$, NS(=O)$_2NR^4NR^5$, NS(=O)$_2R^4$, or an optionally substituted aryl, heteroaryl, cycloalkyl or heterocyclic ring, all of which may be optionally substituted;

W is —$CH_2$—, —S—, —CHF— or —$CF_2$—;

Z is C or N;

m is 1, or 2;

n is 0, 1, or 2;

p is 0 to 6;

q is 0 to 6; and t is 0, 1, or 2 wherein: when E and G are both phenyl either:
(1) at least one of $R^1$ or $R^2$ is present and is: $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0\text{-}C_6)$-alkyl-$C(=NR^a)NHR^4$, $(C_0\text{-}C_6)$-alkyl-$C(=NR^4)NHR^a$, $(C_0\text{-}C_6)$-alkyl-$NR^4C(=NR^4)NR^4R^5$, $(C_0\text{-}C_6)$-alkyl-$C(O)OR^4$, $(C_0\text{-}C_6)$-alkyl-$C(O)NR^4R^5$, $(C_0\text{-}C_6)$-alkyl-$C(O)$—NH—CN, O—$(C_0\text{-}C_6)$-alkyl-$C(O)NR^4R^5$, $S(O)_t$—$(C_0\text{-}C_6)$-alkyl-$C(O)OR^4$, $S(O)_t$—$(C_0\text{-}C_6)$-alkyl-$C(O)NR^4R^5$, $(C_0\text{-}C_6)$-alkyl-$C(O)NR^4$—$(C_0\text{-}C_6)$-alkyl-$NR^4R^5$, $(C_0\text{-}C_6)$-alkyl-$NR^4R^5$, $(C_0\text{-}C_6)$-alkyl-$NR^4$—$C(O)R^5$, $(C_0\text{-}C_6)$-alkyl-$NR^4$—$C(O)OR^4$, $(C_0\text{-}C_6)$-alkyl-$NR^4$—$C(O)$—$NR^4R^5$, $(C_0\text{-}C_6)$-alkyl-$NR^4$—$SO_2NR^4R^5$, $(C_0\text{-}C_6)$-alkyl-$NR^4$—$SO_2R^4$, hydrogen, $(C_{5-20})$alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted; and wherein $OR^4$ is alkoxy, $OR^4$ is $(C_{5-20})$alkoxy; or (2) and when B is (b) $R^7$ and $R^8$ are not selected from hydrogen, hydroxy, hydroxymethyl, and phenyl; or (3) and when B is (b) or (f), R9 is: $C_{1-6}$ alkyl.

Compounds of the present invention having one or more optically active carbons can exist as racemates and racemic mixtures, diasteromeric mixtures and individual diastereomers, enatiomeric mixtures and single enantiomers, tautomers, atropisomers, and rotamers, with all isomeric forms being included in the present invention. Compounds described in this invention containing olefinic double bonds include both E and Z geometric isomers. Also included in this invention are all salt forms, polymorphs, hydrates and solvates. All of the above mentioned compounds are included within the scope of the invention.

The present invention also provides methods of inhibiting the DPP-IV enzyme.

The present invention further provides methods of treatment or prevention of diseases in which the dipeptidyl peptidase-IV enzyme is involved, such as diabetes and particularly Type-2 diabetes.

The present invention also provides methods for obtaining the DPP-IV inhibiting compounds and pharmaceutical compositions comprising them either singly or in combination with one or more additional therapeutic agents for the prevention or treatment of DPP-IV enzyme mediacted diseases, particularly Type-2 diabetes.

DETAILED DESCRIPTION OF THE INVENTION

Definitions

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^4$)($R^5$)N—CO— wherein $R^4$ or $R^5$ are as defined below, except that at least one of $R^4$ or $R^5$ is not hydrogen), amino, heterocyclo, mono- or dialkylamino, or thiol (—SH).

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^4$)($R^5$)N—CO— wherein $R^4$ or $R^5$ are as defined below, except that at least one of $R^4$ or $R^5$ is not hydrogen), amino, heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^4$)($R^5$)N—CO— wherein $R^4$ or $R^5$ are as defined below, except that at least one of $R^4$ or $R^5$ is not hydrogen), amino, heterocyclo, mono- or dialkylamino, or thiol (—SH).

The term "cycloalkyl", as used herein alone or as part of another group, denotes optionally substituted, saturated cyclic hydrocarbon ring systems, including bridged ring systems, desirably containing 1 to 3 rings and 3 to 9 carbons per ring. Exemplary unsubstituted such groups include, but are not limited to, cyclopropyl, cyclobutyl, cyclopentyl, cyclohexyl, cycloheptyl, cyclooctyl, cyclodecyl, cyclododecyl, and adamantyl. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from the group consisting of N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, flirazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more subsituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, morpholino, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The term "amino" denotes the radical —$NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. Illustrative examples include, but are not limited to, fluorene, 10,11-dihydro-5H-dibenzo[a,d]cycloheptene and 2,2a,7,7a-tetrahydro-1H-cyclobuta[a]indene.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences,* 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present invention are defined as being unsubstituted, the moieties of the compound may be substituted. In addition to any substituents provided above, the moieties of the compounds of the present invention may be optionally substituted with one or more groups independently selected from, but not limited to:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
$COCF_3$;
OC(O)—($C_1$-$C_4$ alkyl);
OC(O)NH—($C_1$-$C_4$ alkyl);
OC(O)N($C_1$-$C_4$ alkyl)$_2$;
OC(S)NH—($C_1$-$C_4$ alkyl);
OC(S)N($C_1$-$C_4$ alkyl)$_2$;
$ONO_2$;
SH;
S—($C_1$-$C_4$ alkyl);
S(O)—($C_1$-$C_4$ alkyl);
S(O)$_2$—($C_1$-$C_4$ alkyl);
SC(O)—($C_1$-$C_4$ alkyl);
SC(O)O—($C_1$-$C_4$ alkyl);
$NH_2$;
N(H)—($C_1$-$C_4$ alkyl);
N($C_1$-$C_4$ alkyl)$_2$;
N(H)C(O)—($C_1$-$C_4$ alkyl);
N($CH_3$)C(O)—($C_1$-$C_4$ alkyl);
N(H)C(O)—$CF_3$;
N($CH_3$)C(O)—$CF_3$;
N(H)C(S)—($C_1$-$C_4$ alkyl);
N($CH_3$)C(S)—($C_1$-$C_4$ alkyl);
N(H)S(O)$_2$—($C_1$-$C_4$ alkyl);
N(H)C(O)$NH_2$;
N(H)C(O)NH—($C_1$-$C_4$ alkyl);
N($CH_3$)C(O)NH—($C_1$-$C_4$ alkyl);
N(H)C(O)N($C_1$-$C_4$ alkyl)$_2$;
N($CH_3$)C(O)N($C_1$-$C_4$ alkyl)$_2$;
N(H)S(O)$_2$$NH_2$;
N(H)S(O)$_2$NH—($C_1$-$C_4$ alkyl);
N($CH_3$)S(O)$_2$NH—($C_1$-$C_4$ alkyl);
N(H)S(O)$_2$N($C_1$-$C_4$ alkyl)$_2$;
N($CH_3$)S(O)$_2$N($C_1$-$C_4$ alkyl)$_2$;
N(H)C(O)O—($C_1$-$C_4$ alkyl);
N($CH_3$)C(O)O—($C_1$-$C_4$ alkyl);
N(H)S(O)$_2$O—($C_1$-$C_4$ alkyl);
N($CH_3$)S(O)$_2$O—($C_1$-$C_4$ alkyl);
N($CH_3$)C(S)NH—($C_1$-$C_4$ alkyl);
N($CH_3$)C(S)N($C_1$-$C_4$ alkyl)$_2$;
N($CH_3$)C(S)O—($C_1$-$C_4$ alkyl);
N(H)C(S)$NH_2$;
$NO_2$;
$CO_2H$;
$CO_2$—($C_1$-$C_4$ alkyl);
C(O)N(H)OH;
C(O)N($CH_3$)OH:
C(O)N($CH_3$)OH;
C(O)N($CH_3$)O—($C_1$-$C_4$ alkyl);
C(O)N(H)—($C_1$-$C_4$ alkyl);
C(O)N($C_1$-$C_4$ alkyl)$_2$;
C(S)N(H)—($C_1$-$C_4$ alkyl);
C(S)N($C_1$-$C_4$ alkyl)$_2$;
C(NH)N(H)—($C_1$-$C_4$ alkyl);
C(NH)N($C_1$-$C_4$ alkyl)$_2$;
C(N$CH_3$)N(H)—($C_1$-$C_4$ alkyl);
C(N$CH_3$)N($C_1$-$C_4$ alkyl)$_2$;
C(O)—($C_1$-$C_4$ alkyl);
C(NH)—($C_1$-$C_4$ alkyl);
C(N$CH_3$)—($C_1$-$C_4$ alkyl);1
C(NOH)—($C_1$-$C_4$ alkyl);
C(NO$CH_3$)—($C_1$-$C_4$ alkyl);
CN;
CHO;
$CH_2$OH;
$CH_2$O—($C_1$-$C_4$ alkyl);
$CH_2NH_2$;
$CH_2$N(H)—($C_1$-$C_4$ alkyl);
$CH_2$N($C_1$-$C_4$ alkyl)$_2$;
aryl;
heteroaryl;
cycloalkyl; and
heterocyclyl.

The term "cleave" or "cleaving" means splitting a complex molecule into at least two separate molecules. "Cleavage products" are the separate molecules which result from cleaving.

The term "metabolite" refers to a composition which results from a metabolic process. Examples of the results of metabolism on the compounds of the present invention include addition of —OH, hydrolysis, and cleavage.

The term "polymorphs" refers to the various crystalline structures of the compounds of the present invention. This may include, but is not limited to, crystal morphologies (and amorphous materials), all crystal lattice forms, and all salts. Salts of the present invention can be crystalline and may exist as more than one polymorph. Each polymorph forms another aspect of the invention. Hydrates as well as anhydrous forms of the salt are also encompassed by the invention.

"Teoc" is 2-(trimethylsilyl)ethoxycarbonyl

"Et" is ethyl (—$CH_2CH_3$) or ethylene (—$CH_2CH_2$—).

"Me" is methyl (—$CH_3$) or methylene (—$CH_2$—).

"Boc" is tert-butyloxycarbonyl.

"$PhCH_2$" is benzyl.

The term "pharmaceutically-acceptable tricyclic moiety" is meant to include, but is not limited to, benzocycloheptapyridyl, benzodiazepinyl, and benzoxazepinyl In another embodiment of the present invention, the DPP-IV inhibiting compounds are used in the manufacture of a medicament for the treatment of a disease mediated by an DPP-IV enzyme.

In another aspect, the DPP-IV inhibiting compounds of the present invention are used in combination with another disease modifying drug. Examples of other disease modifying drugs include, but are not limited to: (a) other dipeptidyl peptidase IV (DPP-IV) inhibitors such as Vildagliptin (Novartis), Sitagliptin (Merck & Co.), Saxagliptin (BMS); (b) insulin sensitizers including (i) PPARγ agonists such as the glitazones (e.g. troglitazone, pioglitazone, edaglitazone, rosiglitazone, and the like) and other PPAR/ligands, including PPARα/γ dual agonists such as muraglitazar (BMS) and tesaglitazar (AstraZeneca), and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors; (c) insulin or insulin mimetics; (d) incretin and incretin mimetics such as (i) Exenatide available from Amylin Pharmaceuticals, (i) amylin and amylin mimetics such as pramlintide acetate, available as Symlin®, (iii) GLP-1, GLP-1 mimetics, and GLP-1 receptor agonists, (iv) GIP, GIP mimetics and GIP receptor agonists; (e) sulfonylureas and other insulin secretagogues, such as tolbutamide, glyburide, glipizide, glimepiride, meglitinides, and repaglinide; (f) α-glucosidase inhibitors (such as acarbose and miglitol); (g) glucagon receptor antagonists; (h) PACAP, PACAP mimetics, and PACAP receptor agonists; (i) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants such as cholestyramine, colestipol and dialkylaminoalkyl derivatives of a cross-linked dextran, (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists such as muraglitazar (BMS) and tesaglitazar (AstraZeneca), (vi) inhibitors of cholesterol absorption, such as beta-sitosterol and ezetimibe, (vii) acyl CoA:cholesterol acyltransferase inhibitors such as avasimibe, and (viii) antioxidants such as probucol; (j) PPARδ agonists such as GW-501516 from GSK; (k) anti-obesity compounds such as fenfluramine, dexfenfluramine, phentemine, sibutramine, orlistat, neuropeptide Y1 or Y5 antagonists, MTP inhibitors, squalene synthase inhibitor, lipoxygenase inhibitor, ACAT inhibitor, Neuropeptide Cannabinoid CB-1 receptor antagonists, CB-1 receptor inverse agonists and antagonists, fatty acid oxidation inhibitors, appetite suppressants (1) adrenergic receptor agonists, melanocortin receptor agonists, in particular—melanocortin-4 receptor agonists, ghrelin antagonists, and melanin-concentrating hormone (MCH) receptor antagonists; (m) ileal bile acid transporter inhibitors; (n) agents intended for use in inflammatory conditions such as aspirin, non steroidal anti-inflammatory drugs, glucocorticoids, azalfidine, and selective cyclooxygenase-2 inhibitors; (o) antihypertensive agents such as ACE inhibitors (enalapril, lisinopril, captopril, quinapril, fosinoprol, ramipril, spirapril, tandolapril), angiotensin-II (AT-1) receptor blockers (losartan, candesartan, irbesartan, valsartan, telmisartan, eprosartan), beta blockers and calcium channel blockers; and (p) glucokinase activators (GKAs); (q) agents which can be used for the prevention, delay of progression or treatment of neurodegenerative disorders, cognitive disorders or a drug for improving memory such as anti-inflammatory drugs, antioxidants, neuroprotective agents, glutamate receptor antagonists, acetylcholine esterase inhibitors, butyrylcholinesterase inhibitors, MAO inhibitors, dopamine agonists or antagonists, inhibitors of gamma and beta secretases, inhibitors of amyloid aggregation, amyloid beta peptide, antibodies to amyloid beta peptide, inhibitors of acetylcholinesterase, glucokinase activators, agents directed at modulating GABA, NMDA, cannabinoid, AMPA, kainate, phosphodiesterase (PDE), PKA, PKC, CREB or nootropic systems; (r) leukocyte growth promotors intended for the treatment and prevention of reduced bone marrow production, infectious diseases, hormone dependent disorders, inflammatory diseases, HIV, allergies, leukocytopenia, and rheumatism; (s) SGLT2 inhibitor; (t) glycogen phosphorylase inhibitor; (u) aP2 inhibitors; (v) aminopeptidase N inhibitor (w) vasopeptidase inhibitors like neprilysin inhibitors and/or ACE inhibitors or dual NEP/ACE inhibitor; (x) growth hormone secretagogue for enhancing growth hormone levels and for treating growth retardation/dwarfism or metabolic disorders or where the disorder is an injury, or a wound in need of healing, or a mammalian patient recovering from surgery; (y) 5-HT 3 or 5-HT 4 receptor modulators (tegaserod, cisapride, nor-cisapride, renzapride, zacopride, mosapride, prucalopride, buspirone, nor-cisapride, cilansetron, ramosetron, azasetron, ondansetron, etc.); (Za) aldose reductase inhibitors; (Zb) sorbitol dehydrogenase inhibitors; (Zc) AGE inhibitors; (Zd) erythropoietin agonist such as EPO, EPO mimetics, and EPO receptor agonists.

In a further aspect, the DPP-IV inhibiting compounds of the present invention are used in the treatment diseases or symptoms mediated by an DPP-IV enzyme. Examples of diseases or symptoms mediated by a DPP-IV enzyme include, but are not limited to, Type II (Type-2) Diabetes and Related Disorders, such as hyperglycemia, low glucose tolerance, insulin resistance, obesity, lipid disorders, dyslipidemia, hyperlipidemia, hypertriglyceridemia, hypercholesterolemia, low HDL levels, high. LDL levels, atherosclerosis and its 30 sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, cataracts, glaucoma, glomerulosclerosis, foot ulcerations and unlcerative colitis, altered gastrointestinal motility, Syndrome X, ovarian hyperandrogenism, polycystic ovarian syndrome, premenstrual syndrome, other disorders where insulin resistance is a component. In Syndrome X, also known as Metabolic Syndrome, obesity is thought to promote insulin resistance, diabetes, dyslipidemia, hypertension, and increased cardiovascular risk, growth hormone deficiency, neutropenia, neuronal disorders, tumor invasion and metastasis, benign prostatic hypertrophy, gingivitis, osteoporosis, frailty of aging, intestinal injury, benign prostatic hypertrophy (BPH), and sperm motility/male contraception.

In a further aspect, the DPP-IV inhibiting compounds of the present invention are useful for the prevention, delay of progression or the treatment of an early cardiac or early cardiovascular diseases or damages, renal diseases or damages, heart Failure, or heart Failure associated diseases like (i)

cardiovascular diseases or damages e.g. cardiac hypertrophy, cardiac remodelling after myocardial infarction, pulmonary congestion and cardiac fibrosis in dilated or in hypertrophic cardiomyopathy, cardiomyopathy-such as dilated cardiomyopathy or hypertrophic cardiomyopathy, mesanglial hypertrophy, or diabetic cardiomyopathy, left or right ventricular hypertrophy, arrhythmia, cardiac dysrhythmia, syncopy, angina pectoris, cardiac bypass reocclusion, intermittent claudication, diastolic and/or systolic dysfunction, diabetic myopathy, stroke prevention in congestive heart failure, hypertrophic medial thickening in arteries and/or large vessels, mesenteric vasculature hypertrophy or artherosclerosis, preferably atherosclerosis in mammalian patients with hypertension of diabetes; (ii) renal diseases or damages like renal hyperfiltration such as after portal renal ablation, proteinuria in chronic renal disease, renal arteriopathy as a consequence of hypertension, nephrosclerosis, hypertensive nephrosclerosis or mesanglial hypertrophy; (iii) Heart Failure to be treated is secondary to idiopathic dilated cardiomyopathy and/or coronary ischemic disease;

In another aspect, the DPP-FV inhibiting compounds of the present invention are used for the prevention, the delay of the onset, the delay of progression or the treatment of neurodegenerative disorders, cognitive disorders and for improving memory (both short term and long term) and learning ability wherin the (i) neurodegenerative disorder is dementia, senile dementia, schizophrenia, mild cognitive impairment, Alzheimer related dementia, Huntington's chores, tardive dyskinesia, hyperkinesias, mania, Morbus Parkinson, Steel-Richard syndrome, Down's syndrome, myasthenia gravis, nerve and brain trauma, vascular amyloidosis, cerebral haemorrhage I with amyloidosis, brain inflammation, Friedrich ataxia, acute confusion disorders, acute confusion disorders with apoptotic necrocytosis, amyotrophic lateral sclerosis, glaucoma, and Alzheimer's disease; (ii) cognitive disorders like cognitive deficits associated with schizophrenia, age-induced memory impairment, cognitive deficits associated with psychosis, cognitive impairment associated with diabetes, cognitive deficits associated with post-stroke, memory defects associated hypoxia, cognitive and attention deficits associated with senile dementia, attention deficits disorders, memory problems associated with mild cognitive impairment, impaired cognitice function associated with vascular dementia, cognitive problems associated with brain tumors, Pick's disease, cognitive deficits due to autism, cognitive deficits post electroconvulsive therapy, cognitive deficits associated with traumatic brain injury, amnesic disorders, deliriums, vitamin deficiency, dementias, impaired cognitive function associated with Parkinson's disease, attention-deficit disorders; (iii) prevention of memory impairment as a result of Alzheimer disease, Creutzfeld-Jakob disease, Pick disease, Huntington disease, AIDS, brain injury, brain aneurysm, epilepsy, stroke, toxicant exposure, mental retardation in children, Huntington's disease; (iv) to improve learning speed and potential in educational and rehabilitation contexts.

In another aspect, the DPP-IV inhibiting compounds of the present invention are used for stimulating an immune response in a subject having or at risk of having cancer wherein the cancer is selected from the group consisting of basal cell carcinomas including cancers of the binary tract, bladder, urinary system, bone, brain, breast, cervical, endometrial, ovarian, uterine, choriocarcinoma, central nervous system, colon and rectal cancers, connective tissue cancer, cancer of the digestive system, esophageal, gastric, stomach, larynx, liver, pancreatic, colorectal, renal cancers; cancers of the urinary system; cancers of eye, head and neck, oral cavity, skin, prostate; cancers of biliary tract, testicular, thyroid; intra-epithelial neoplasm, leukemia, acute myeloid leukemia, acute lymphoid leukemia, chronic myeloid leukemia, chronic lymphoid leukemia; and other cancers of the respiratory system, lung, small cell lung, non-small cell lung; lymphoma, Hodgkin's lymphoma, Non-Hodgkin's lymphoma; melanoma, myeloma, neuroblastoma, retinoblastoma, fibrosarcoma (bone or connective tissue sarcoma), rhabdomyosarcoma; and other cancers including neoplastic conditions, adipose cell tumors, adipose cell carcinomas, such as liposarcoma;

In a further aspect, the DPP-IV inhibiting compounds of the present invention are useful for the treatment or prophylaxis of chronic inflammatory diseases such as autoimmune disorders like rheumatoid arthritis, systemic lupus erythematosus, multiple sclerosis, psoriasis, allergies or asthma.

In another aspect, the DPP-IV inhibiting compounds of the present invention may be useful in the treatment of pain, neuropathic pain, rheumatoid pain, osteoarthritis pain, anesthesia adjunct in mammalian patients undergoing surgery, chronic pain in advanced cancer, treatment of refractory diarrhea, biliary pain caused by gallstones.

In a further aspect, the DPP-IV inhibiting compounds of the present invention are useful for the treatment of mammalian patients undergoing islet/pancreas transplantation, for the prevention or the delay of transplant rejection, or allograft rejection in transplantation, for improving pancreatic function by increasing the number and size of pancreatic beta-cells in the treatment of Type 1 diabetes patients, and for improving pancreatic function by increasing the number and size of pancreatic beta-cells in general.

Furthermore, the DPP-IV inhibiting compounds of the present invention are useful for the treatment of mammalian patients with acne, skin disorders (e.g. pigmentation disorders or psoriasis), scleroderma, mycoses; anxiety, anxiety neurosis, major depression disorder, drug abuse, alcohol addiction, insomnia, chronic fatigue, sleep apnea; anorexia nervosa; epilepsy; migrane; encephalomyelitis; osteoarthritis, osteoporosis, calcitonin-induced osteoporosis; male and female sexual dysfunction, infertility; Type 1 diabetes; immunosuppression, HIV infection; hematopoiesis, anemia; and for weight reduction.

In a further aspect, the DPP-IV inhibiting compounds of the present invention are useful for the prevention, delay of progression or treatment of (i) bacterial infections from *Escherichia coli, Staphylococcus, Streptooccoccus, Pseudomonas, Clostridium difficile* infection, *Legionella, Pneumococcus, Haemophilus, Klebsiella, Enterobacter, Citrobacter, Neisseria, Shigella, Salmonella, Listeria, Pasteurella, Streptobacillus, Spirillum, Treponema, Actinomyces, Borrelia, Corynebacterium, Nocardia, Gardnerella, Campylobacter, Spirochaeta, Proteus, Bacteriodes, Helicobacter pylori,* and anthrax infection; (ii) mycobacterial infection from tuberculosis and leprosy; (iii) viral infection from HIV, Herpes simplex virus 1, Herpes simplex virus 2, Cytomegalovirus, hepatitis A virus, hepatitis B virus, hepatitis C virus, human papilloma virus, Epstein Barr virus, rotavirus, adenovirus, influenza A virus, respiratory syncytial virus, varicella-zoster virus, small pox, monkey pox and SARS; (iv) fungal infection from candidiasis, ringworm, histoplasmosis, blastomycosis, paracoccidioidomycosis, cryptococcosis, aspergillosis, chromomycosis, mycetoma infections, pseudallescheriasis, Tinea versicolor infection; (v) parasite infection from amebiasis, *Trypanosoma cruzi, Fascioliasis, Leishmaniasis, Plasmodium, Onchocerciasis, Paragonimiasis, Trypanosoma brucei, Pneumocystis, Trichomonas vaginalis, Taenia, Hymenolepsis, Echinococcus, Schistosomiasis, neurocysticerosis, Necator americanus,* and *Trichuris trichuria.*

The compounds from this invention are suitable for oral, sublingual, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. The compounds from this invention are conveniently presented in unit dosage form and prepared by any of the methods well-known in the art of pharmacy.

The DPP-IV inhibiting compounds of the present invention are synthesized by the general method shown in Schemes 1-14.

Generic Schemes

General synthetic schemes for the preparation of tricyclic building blocks of this invention:

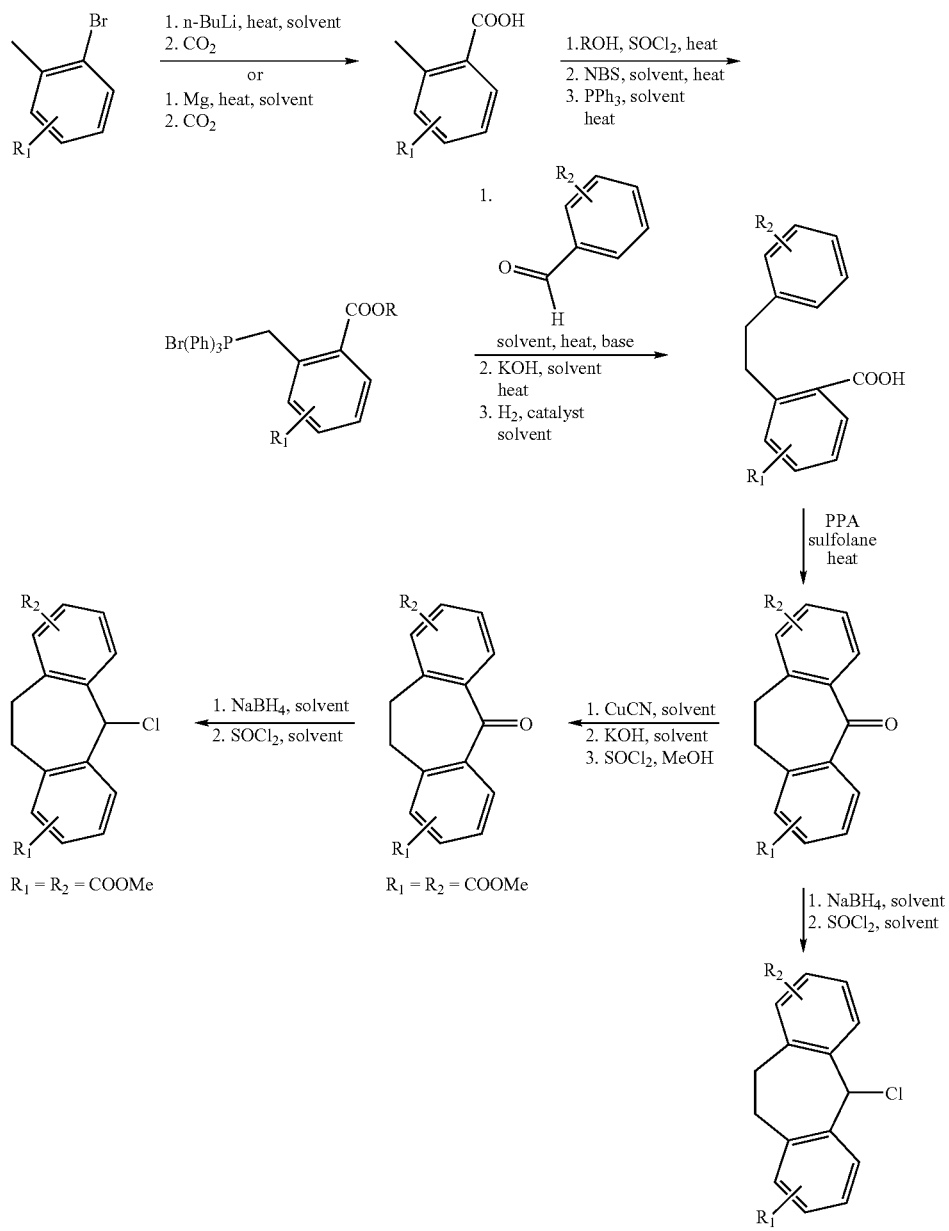

Commercially available bromotoluene derivatives were treated with n-butyllithium and heated, followed by treatment with dry-ice in an appropriate solvent to afford the desired compound. Alternatively, the acid can be prepared by Grignard reaction followed by treatment with dry-ice in an appropriate solvent. Esterification of the compound followed by NBS bromination and subsequent conversion to the phosphonium salt in a suitable solvent and heating affords the desired compound. Wittig reaction of the phosphonium salt with a suitable aldehyde in an appropriate solvent and heating, followed by saponification of the ester moiety and subsequent catalytic hydrogenation affords the desired compound. Cyclisation of the compound with polyphosphoric acid in sulfolane and heating affords the desired compound after purification. For R$_1$=COOMe the tricyclic product from the polyphosphoric acid step was treated with thionylchloride in an alcohol. Reduction of the ketone with a metal hydride in an appropriate solvent yields the compound after purification. Treatment of the alcohol with thionylchloride in a suitable solvent affords the final desired compound. In order to obtain the compounds with R$_1$=R$_2$=COOMe, the tricyclic product from the polyphosphoric acid step with R$_1$=COOH and R$_2$=Br was treated with CuCN in a suitable solvent, followed by saponification of the nitrile to the acid. Ester formation using thionylchloride in an alcohol and reduction of the ketone with a metal hydride in an appropriate solvent yields the compound after purification. Treatment of the alcohol with thionylchloride in a suitable solvent affords the final desired compound.

Alternative synthetic scheme for the preparation of tricyclic building blocks of this invention:

ment of the alcohol with thionylchloride in a suitable solvent affords the final desired compound.

General synthetic scheme for the preparation of aldehyde building blocks of this invention:

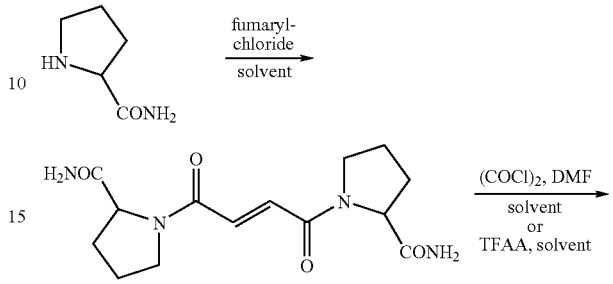

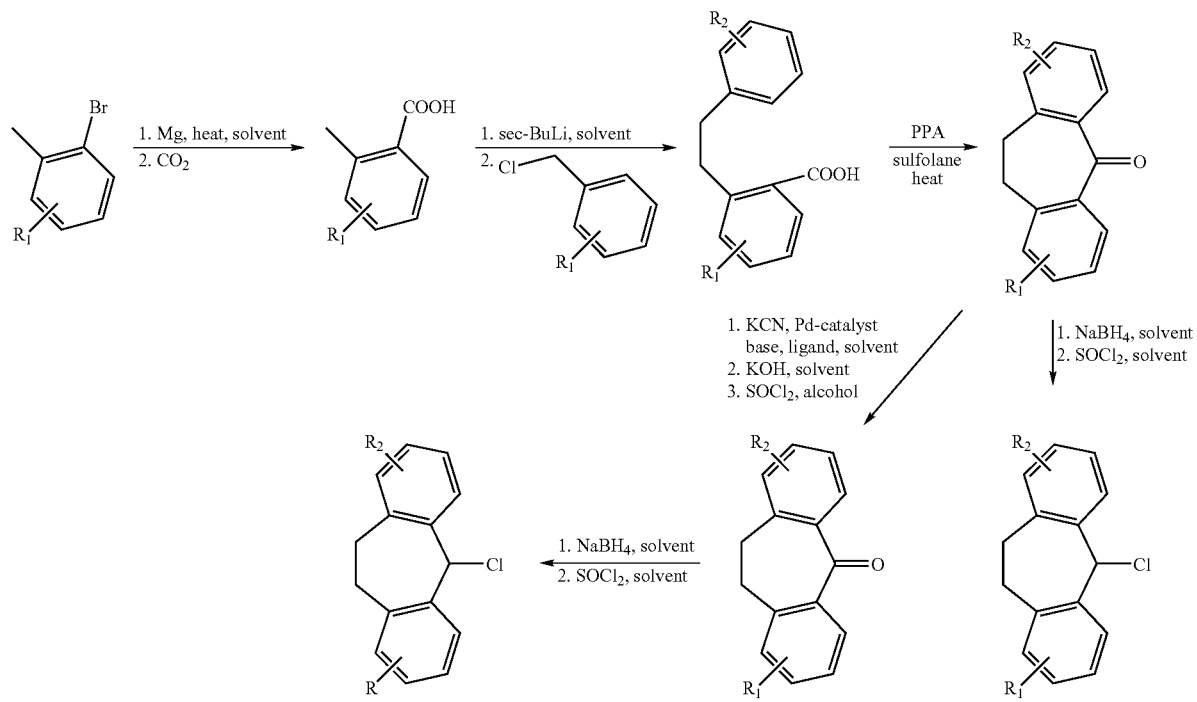

Commercially available bromotoluene derivatives are treated with Magnesium in a Grignard reaction followed by treatment with dry-ice in an appropriate solvent to yield the desired acid. This acid is then treated with sec-butyllithium in an appropriate solvent at lower temperature. The anion is added at lower temperature to a solution of a commercially available benzylchloride in an appropriate solvent to afford the desired compound. Cyclisation of the compound with polyphosphoric acid in sulfolane and heating affords the desired compound. To obtain the compounds with R$_1$=R$_2$=COOMe, the tricyclic product from the polyphosphoric acid step with R$_1$=R$_2$=Cl was treated with KCN, a Pd-catalyst, a suitable ligand and a suitable base in an appropriate solvent to afford the dicyano compound, which was converted to the diacid by treatment with base in a suitable solvent. Ester formation using thionylchloride in an alcohol and reduction of the ketone with a metal hydride in an appropriate solvent yields the compound after purification. Treat- -continued

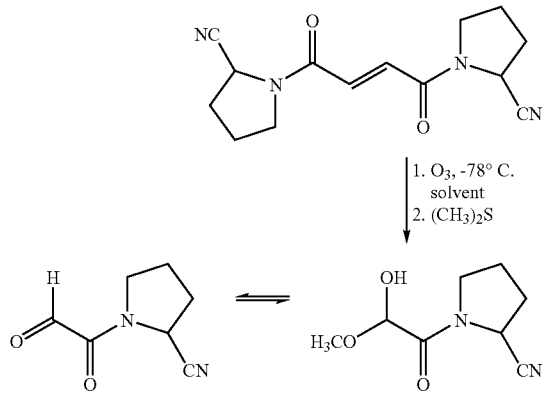

Commercially available prolinamide is treated with fumarylchloride in an appropriate solvent to afford the desired compound. This compound is then treated with oxalylchloride in dimethylformamide to afford the desired compound after purification. Alternatively, the coupling product of prolinamide with fumarylchloride can be treated with trifluoroacetic acid anhydride in a suitable solvent to afford the desired compound. Ozonolysis of this compound at −78° C. in a suitable solvent, followed by reductive workup affords the desired final compound as a mixture of the aldehyde and its methyl hemiacetal.

Treatment of 2-Aza-bicyclo[3.1.0]hexane-3-carboxylic acid amide, prepared according to WO 01/68603, in the same manner as described above yields the desired final compound containing a cyclopropyl moiety at the 4,5-position of the pyrrolidine moiety.

General synthetic scheme for the preparation of tricyclic compounds of this invention with $R^3$=H:

SCHEME 4

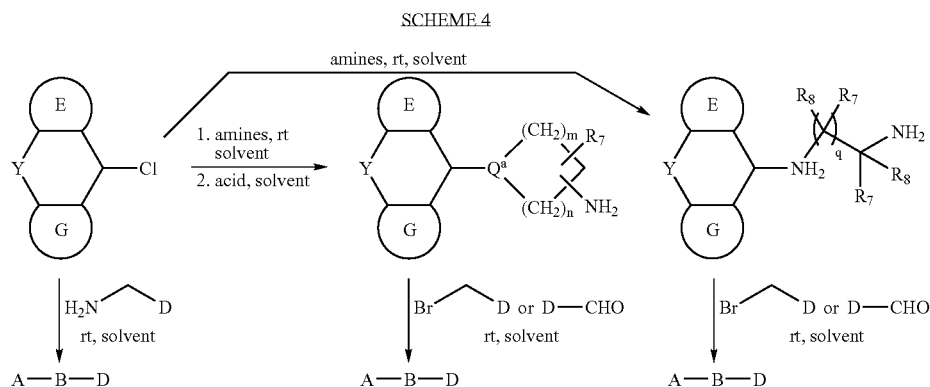

The reaction of substituted or unsubstituted tricyclic chlorides with an amino derivative in a suitable solvent as described above affords the desired final product after purification. Substituted or unsubstituted tricyclic chlorides are treated in an appropriate solvent with an excess of suitable amines to afford the desired product after purification. In case the reaction product contains additional amino protecting groups like Boc, they are cleaved by acid treatment to afford the desired compound. Using these amines for a nucleophilic displacement reaction in a suitable solvent with a suitable bromo derivative yields the final desired product after purification. Alternatively, the amines are treated with a suitable aldehyde (D-CHO) via reductive amination to afford the final compound after purification.

General synthetic scheme for the preparation of tricyclic compounds of this invention with Z=N:

SCHEME 5

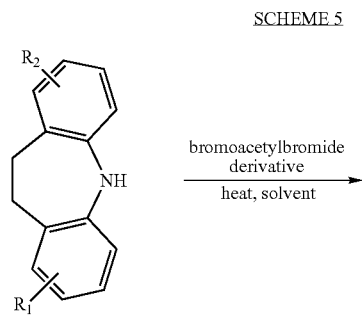

-continued

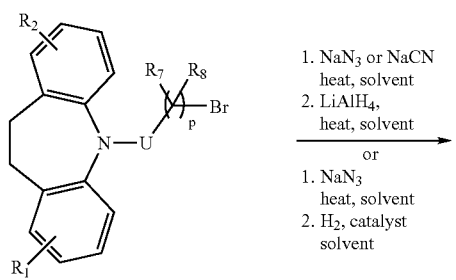

-continued

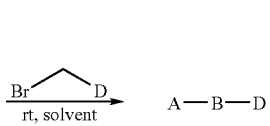

Substituted or unsubstituted tricycles containing a nitrogen at the doubly benzylic position are treated with bromoacetylbromide and heated to afford the desired compounds. Treating these compounds with sodium azide or sodium cyanide in a suitable solvent and heating affords the desired azido or cyano compounds after purification. Catalytic hydrogenation or reduction with Lithium aluminium hydride in a suitable solvent affords the desired amine compounds. Using these amines for a nucleophilic displacement reaction in a suitable solvent with a suitable bromo derivative yields the final desired product after purification.

General synthetic scheme for the preparation of tricyclic compounds of this invention having H, OH or no substituent at $R^3$

SCHEME 6

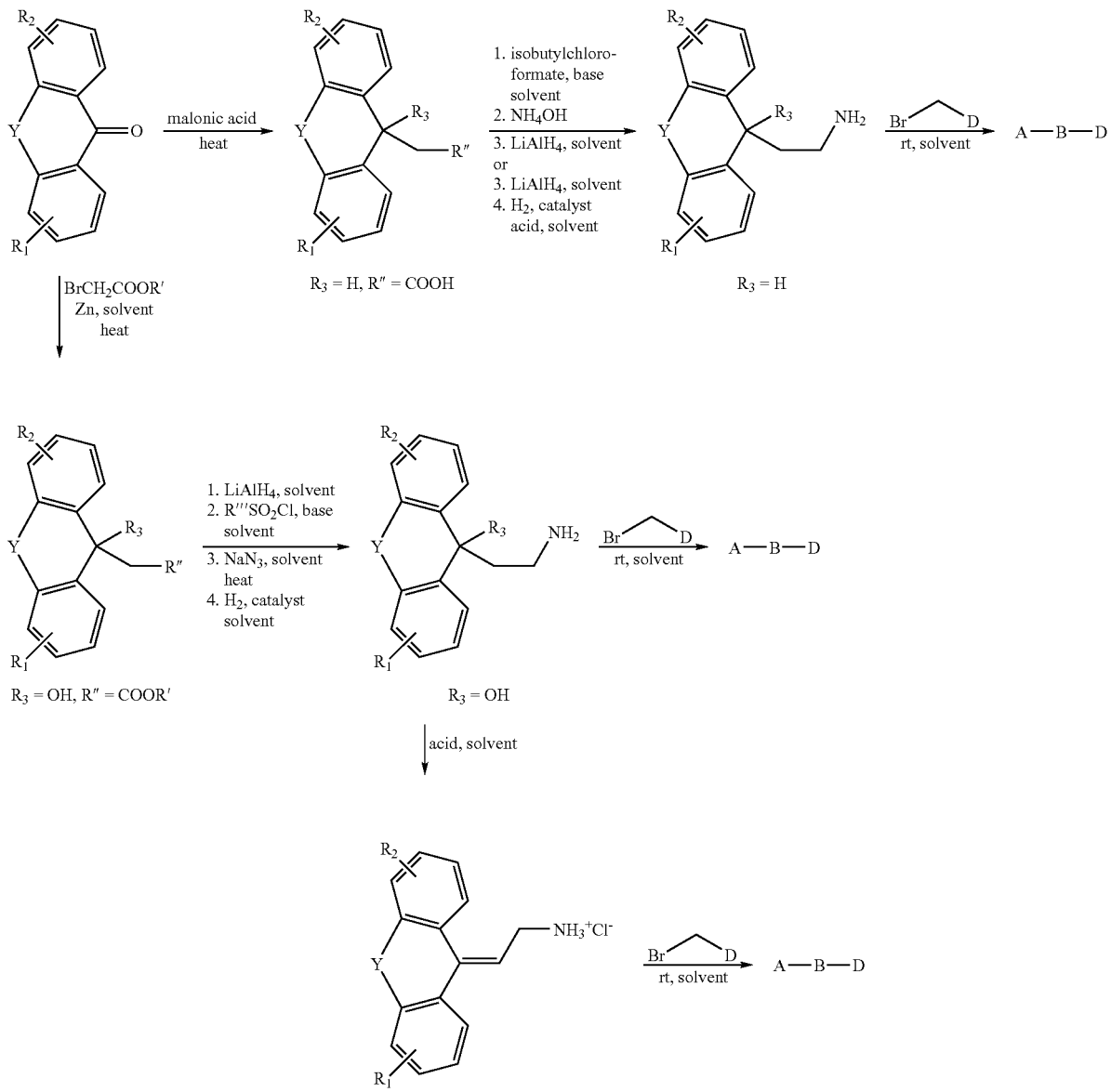

Substituted or unsubstitued tricyclic ketones with Y=C(R$_4$)=C(R$_5$) are treated with malonic acid at elevated temperatures to afford the desired product after purification. These compounds are converted to the corresponding amides by treatment with isobutylchloroformate and ammonia. The amides are then converted to the desired amine products with Y=C(R$_4$)=C(R$_5$) by reduction with lithium aluminium hydride or to the desired amine products with Y=C(R$_4$R$_5$)C(R$_4$R$_5$) by reduction with lithium aluminium hydride followed by catalytic hydrogenation with a suitable catalyst. Using these amines for a nucleophilic displacement reaction in a suitable solvent with a suitable bromo derivative described above yields the final desired product after purification.

Treating tricyclic ketones in a Reformatskij reaction affords the desired product after purification. Reduction with LiAlH$_4$ in a suitable solvent affords the alcohol products with R$_3$=OH after purification. Activation of one of the hydroxyl groups with sulfonylchlorides in a suitable solvent followed by treatment with NaN$_3$ affords the desired compounds after purification. Reduction of the azide reaction products with a catalyst in a suitable solvent affords the desired amine compounds after purification. Using these amines for a nucleophilic displacement reaction in a suitable solvent with a suitable bromo derivative described above yields the final desired products after purification.

Treating the amines with R$_3$=OH with acid in a suitable solvent yields the desired unsaturated amine products. Using these amines for a nucleophilic displacement reaction in a suitable solvent with a suitable bromo derivative described above yields the final desired products after purification.

General synthetic schemes (7-9) for the preparation of tricyclic compounds of this invention with R$^3$=nitrile, amide, tetrazolyl or N-alkyl-tetrazolyl

SCHEME 7

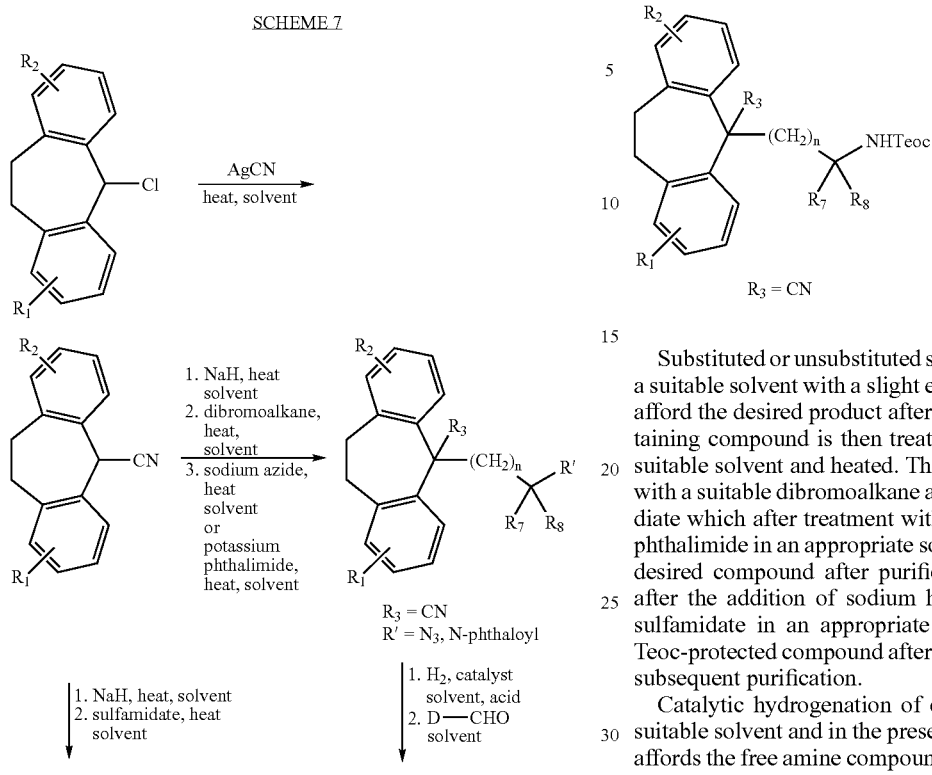

Substituted or unsubstituted suberylchlorides are treated in a suitable solvent with a slight excess of AgCN and heated to afford the desired product after purification. The nitrile containing compound is then treated with sodium hydride in a suitable solvent and heated. The mixture is then treated at rt with a suitable dibromoalkane and heated to give an intermediate which after treatment with sodium azide or potassium phthalimide in an appropriate solvent and heating affords the desired compound after purification. Treating the mixture after the addition of sodium hydride at rt with a suitable sulfamidate in an appropriate solvent affords the desired Teoc-protected compound after heating for several hours and subsequent purification.

Catalytic hydrogenation of compounds with R'=$N_3$ in a suitable solvent and in the presence of a slight excess of acid affords the free amine compounds. Coupling of these amines with a suitable aldehyde (CHO-D) via reductive amination and subsequent purification affords the final desired compounds with $R^3$=CN.

SCHEME 8

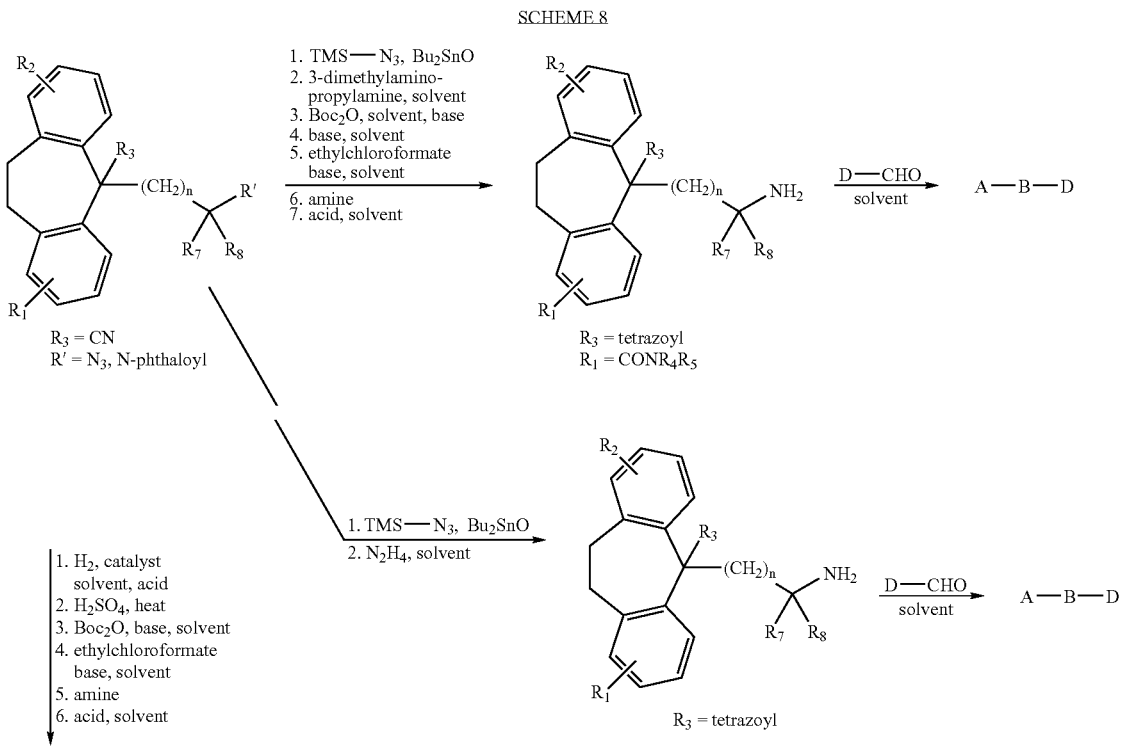

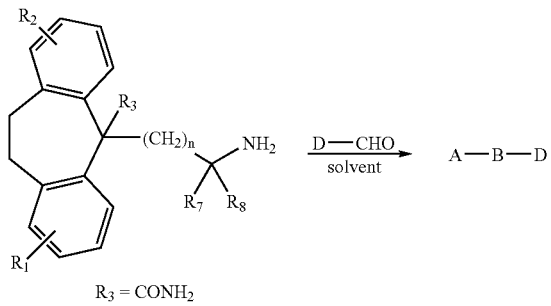

R₃ = CONH₂

Catalytic hydrogenation of compounds with $R_3$=CN and R'=$N_3$ in a suitable solvent and in the presence of a slight excess of acid affords the free amine compounds. Treatment of the hydrogenation products with sulphuric acid affords the desired compounds after purification. In case $R_1$=$R_2$≠COOH, the amines are reacted with a suitable aldehyde (D-CHO) in an appropriate solvent to yield the desired final compounds with $R_3$=CONH₂ and $R_1$=$R_2$≠COOH, CONR₄R₅, COOMe. In case $R_1$=COOH, the amines are treated with Boc₂O in a suitable solvent to afford the Boc-protected amines. These compounds are then treated with ethylchloroformate, followed by treatment with an amine to yield the desired compounds after purification. The compounds are then treated with acid, followed by reaction with a suitable aldehyde (D-CHO) in an appropriate solvent to yield the desired final compounds with $R_3$=CONH₂ and $R_1$=CONR₄R₅ after purification.

The compounds with $R_3$=CN and R'=N-phthaloyl are treated with an excess of trimethylsilyl azide and Bu₂SnO in an appropriate solvent and heating to afford the desired compounds with $R_3$=tetrazolyl and R'=N-phthaloyl. In case $R_1$=$R_2$≠COOH, the compounds are treated with hydrazine hydrate at elevated temperature in an appropriate solvent to yield the desired amines with $R_3$=tetrazoyl. The reaction of these amines with a suitable aldehyde (D-CHO) in an appropriate solvent affords the desired final compound with $R_3$=tetrazoyl and $R_1$=$R_2$≠COOH, CONR₄R₅, COOMe after purification. In case $R_1$=COOMe, the compounds are treated with an appropriate amine in a suitable solvent to afford the free amine compounds. Protection of the amines with Boc₂O affords the Boc-protected products after purification. Saponification of the ester moieties affords the desired NH-Boc-protected carboxylic acid derivatives. The acid derivates are then treated with ethylchloroformate, followed by an amine to afford the desired products after acid treatment. The reaction of these amines with a suitable aldehyde (D-CHO) in an appropriate solvent affords the desired final compound with $R_3$=tetrazoyl and $R_1$=CONR₄R₅ after purification.

SCHEME 9

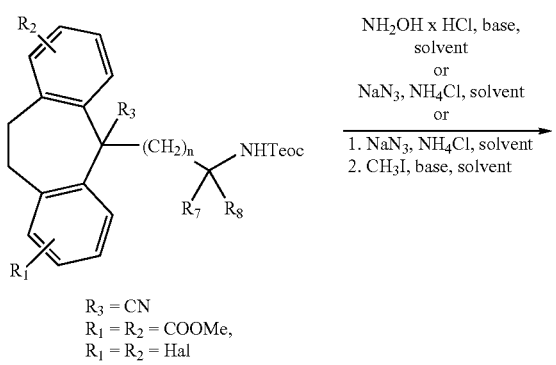

$R_3$ = CN
$R_1$ = $R_2$ = COOMe,
$R_1$ = $R_2$ = Hal

NH₂OH x HCl, base, solvent
or
NaN₃, NH₄Cl, solvent
or
1. NaN₃, NH₄Cl, solvent
2. CH₃I, base, solvent -continued

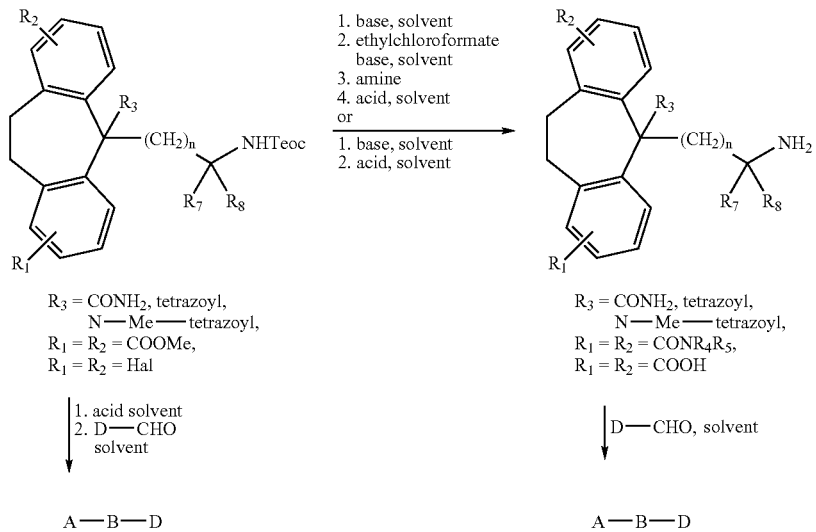

The NH Teoc-protected compounds with $R_3$=CN and $R_1$=$R_2$=COOMe or $R_1$=$R_2$=Hal were treated with hydroxylamine hydrochloride and an excess of base at elevated temperatures in an appropriate solvent to afford the desired compounds with $R_3$=CONH$_2$ after purification. The same NH Teoc protected compounds are also reacted with sodium azide and ammonium chloride in a suitable solvent to yield the desired compounds with $R_3$=tetrazoyl after purification. Further reaction of the compound with $R_3$=tetrazoyl with methyl iodide and base in a suitable solvent leads to the formation of the desired compound with $R_3$=N-Me-tetrazoyl after purification. For the compounds with $R_3$=tetrazoyl, N-Me-tetrazoyl and $R_1$=$R_2$=COOMe, Hal, the Teoc protecting group is removed by treatment with acid to afford the desired amine compounds. The reaction of these amines with a suitable aldehyde (D-CHO) in an appropriate solvent affords the desired final compound with $R_3$=tetrazoyl, N-Me-tetrazoyl and $R_1$=$R_2$=COOMe, Hal after purification. For the compounds with $R_3$=tetrazoyl, N-Me-tetrazoyl and $R_1$=$R_2$=COOMe, the ester moieties are removed by treatment with base in an appropriate solvent to afford the desired dicarboxylic acid derivatives after purification. Treatment of these compounds with ethylchloroformate, followed by an amine yields the desired amine compounds with $R_3$=tetrazoyl, N-Me-tetrazoyl and $R_1$=$R_2$=CONR$_4$R$_5$ after purification. Cleavage of the Teoc protecting group with acid affords the corresponding amine compounds. The reaction of these amines with a suitable aldehyde (D-CHO) in an appropriate solvent affords the desired final compounds with $R_3$=tetrazoyl, N-Me-tetrazoyl and $R_1$=$R_2$=CONR$_4$R$_5$ after purification. To obtain the desired final compounds with $R_3$=tetrazoyl, N-Me-tetrazoyl and $R_1$=$R_2$=COOH after purification, the amide formation steps 2 and 3 are omitted.

General synthetic scheme for the preparation of tricyclic compounds of this invention with $R^3$=heteroaryl (e.g., oxadiazolone or trifluroroxadiazole)

SCHEME 10

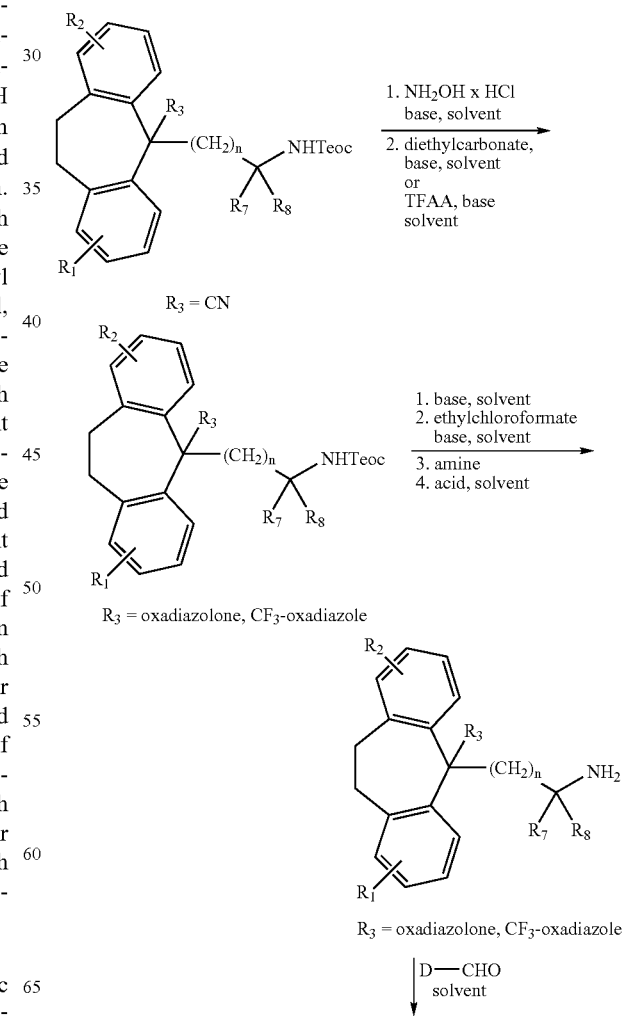

-continued

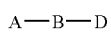

The NH Teoc-protected compounds with $R_3$=CN and $R_1$=$R_2$=COOMe were treated with hydroxylamine hydrochloride and a base at elevated temperatures, followed by diethylcarbonate in an appropriate solvent to afford the desired compounds with $R_3$=oxadiazolone after purification. In case trifluoroacetic acid anhydride and base are used in a suitable solvent for step 2 of the above scheme, the desired compounds with $R_3$=$CF_3$-oxadiazole are obtained after purification. The compounds with $R_3$=oxadiazolone and $R_3$=$CF_3$-oxadiazole are then treated with base to afford the dicarboxylic acid derivatives. These acids are treated with ethylchloroformate, followed by an amine to afford the desired NH-Teoc protected compounds with $R_3$=oxadiazolone, $CF_3$-oxadiazole and $R_1$=$R_2$=$CONR_4R_5$ after purification. Cleavage of the Teoc protecting group with acid affords the corresponding amine compounds. The reaction of these amines with a suitable aldehyde (D-CHO) in an appropriate solvent affords the desired final compounds with $R_3$=oxadiazolone, $CF_3$-oxadiazole and $R_1$=$R_2$=$CONR_4R_5$ after purification.

General synthetic scheme for the preparation of tricyclic compounds of this invention with $R^3$=tetrazole and Y=$CONR^4$

SCHEME 11

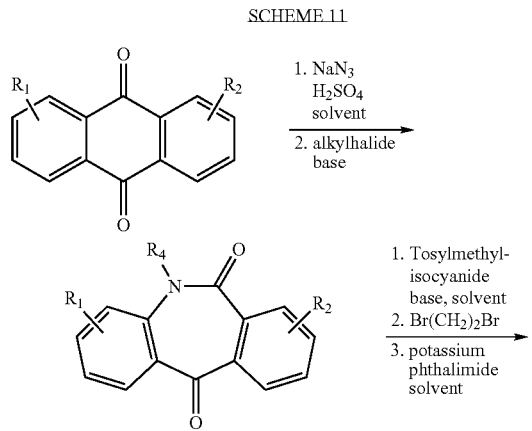

-continued

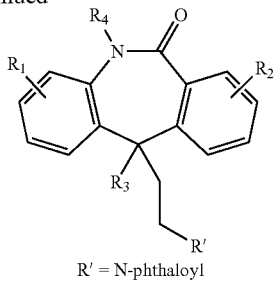

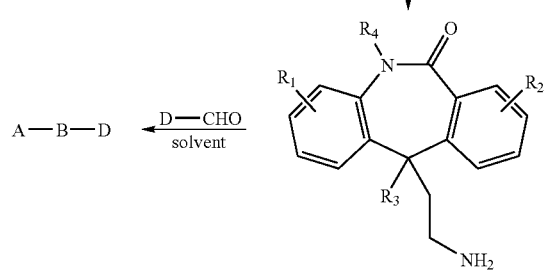

Anthraquinone derivatives are treated with sodium azide and sulphuric acid in a suitable solvent to yield the desired compounds. These compounds are then treated with alkyl halides and base in a suitable solvent to obtain the desired compounds after purification. Reaction of theses compounds with tosylmethyl isocyanide and base in a suitable solvent, follwed by treatment with dibromoethane and potassium phthalimide affords the desired compounds with R3=CN and R'=N-phthaloyl after purification. The reaction of these compounds with trimethylsilyl-azide and dibutyltin oxide in a suitable solvent affords the compounds with R3=tetrazoyl and R'=N-phthaloyl. Cleavage of the protecting group with hydrazine hydrate affords the desired amines, which are reacted with a suitable aldehyde (D-CHO) in an appropriate solvent to afford the desired final compound with R3=tetrazoyl. The desired final compound with $R_3$=tetrazoyl and $R_4$=H can be obtained by omitting the alkylation step with alkyl halides in the above scheme.

General synthetic scheme for the preparation of compounds with bridged piperazinones of this invention with $R^{14a,b}$=(=O)

SCHEME 12

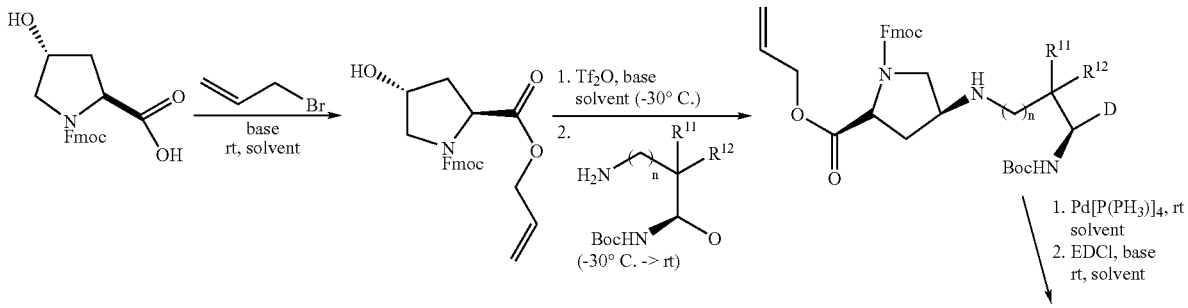

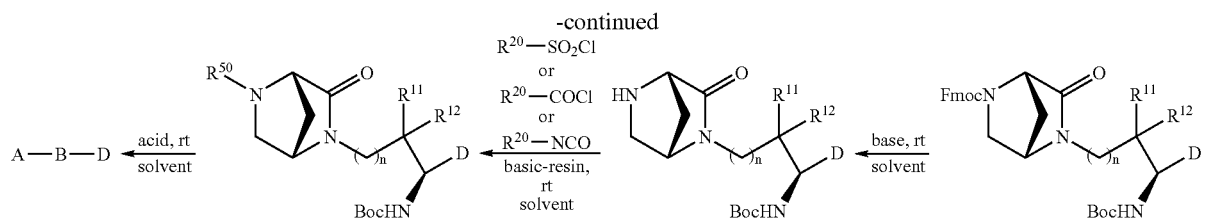

A commercially available hydroxyl-proline derivative is treated with base and alkylated with allylbromide in an appropriate solvent to afford the allyl-protected amino acid after purification. This compound is then treated at −30° C. with an appropriate base, triflic anhydride and then an appropriately protected diamino acid in an appropriate solvent to afford the desired compound after purification. After cleavage of the ester moiety with palladium(0) in an appropriate solvent, the compound is treated with EDCI and base in an appropriate solvent to afford the desired compound after purification. Cleavage of Fmoc protecting group by treatment with an suitable base affords the desired product. The free amine is then treated in the presence of an suitable polymer supported base with sulfonyl chlorides, acid chlorides or isocyanates to afford the desired compounds after purification. Removal of the Boc-protecting group with acid in a suitable solvent affords the final desired compounds after purification.

Starting with the enantiomers of the amino acid derivatives above, and proceeding through the general procedures as described above, the enantiomeric piperazinone derivatives can be made.

General synthetic scheme for the preparation of compounds with bridged piperazinones of this invention with $R^{13a,b}$=(=O)

tive amination reaction to afford the desired products. Alternatively, the commercially available N-Boc-protected hydroxy amino acid ester can be treated with trifluoroacetic acid anhydride. The nucleophilic displacement reaction of the triflate with commercially available amines affords the desired products, after saponification of the ester moiety with base and purification. These compounds are then treated with EDCl and a base in an suitable solvent to afford the cyclic amides after purification. These compounds are converted to the desired products by removing the Boc-protection group. These compounds are then reacted in a suitable solvent with a cyclic sulfamidate, derived from a serine derivative, in the presence of base. Saponification of the ester of the reaction product with a suitable base yields the desired acid compounds after purification. Further treatment of the free acids with EDCl in the presence of an appropriate base and a suitable amine derivative, followed by acidic removal of the Boc-protecting group yields the desired compounds after purification.

Starting with the enantiomers of the amino acid and amine derivatives above, and proceeding through the general procedures as described above, the enantiomeric piperazinone derivatives can be made.

SCHEME 13

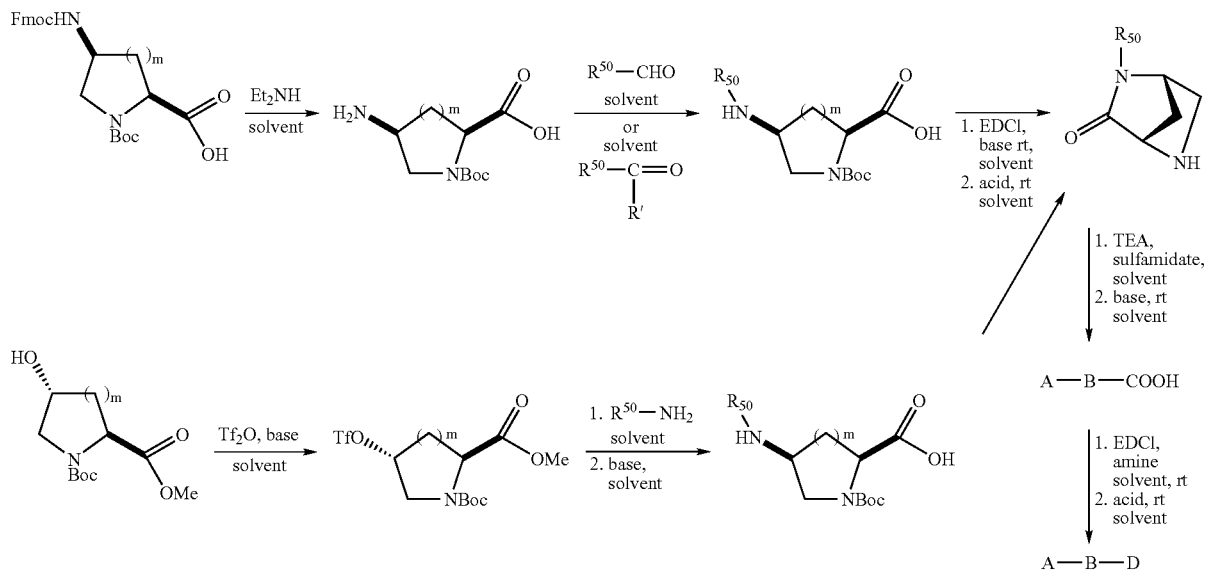

After removing the Fmoc group of the commercially available amino acid with Et$_2$NH, the primary amine is treated in an appropriate solvent with aldehydes or ketones in a reduc- General synthetic scheme for the preparation of compounds with bridged piperazines of this invention with $R^{13a,b}$ and $R^{14a,b}$=H

SCHEME 14

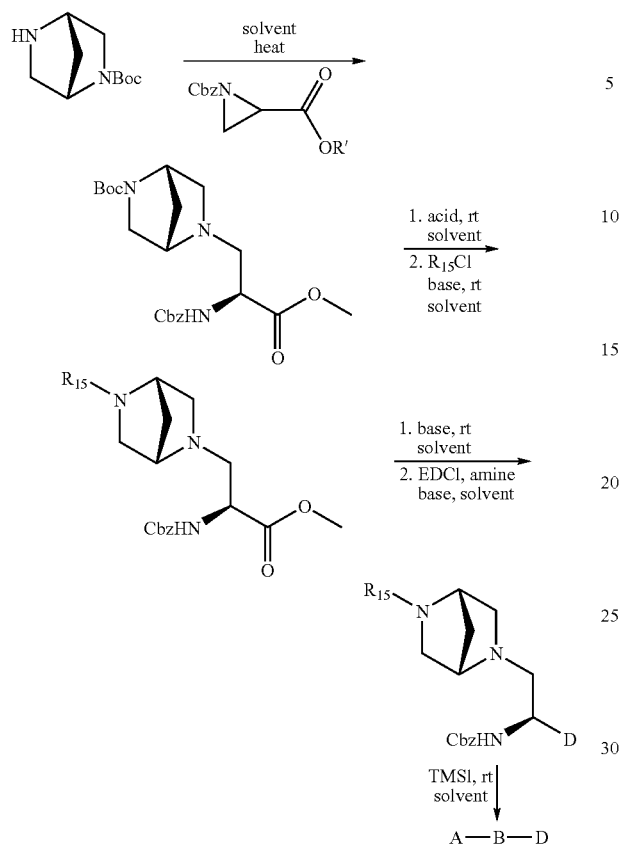

The commercially available bridged piperazine derivate is treated with a commercially available aziridine ester in an appropriate solvent to afford the desired compound after purification. After acidic removal of the Boc-protection group, the desired product reacts in presence of a base with an acid chloride or sulfonic acid chloride to yield the desired products after purification. After basic saponification, the free acids are treated with EDCI in the presence of an appropriate base and a suitable amine derivative to afford the desired compounds after purification. The Cbz-protecting group is then removed by treatment with TMSI and subsequent purification to afford the desired final compounds.

Starting with the enantiomers of the amine and aziridine derivatives above, and proceeding through the general procedures as described above, the enantiomeric piperazine derivatives can be made.

As can be seen by the generic schemes, each of the structures of "B" bonds to the "A" structures on its left side and to the "D" structures on its right side as each is depicted below.

The compound A-B-D chooses an "A" which includes the following:

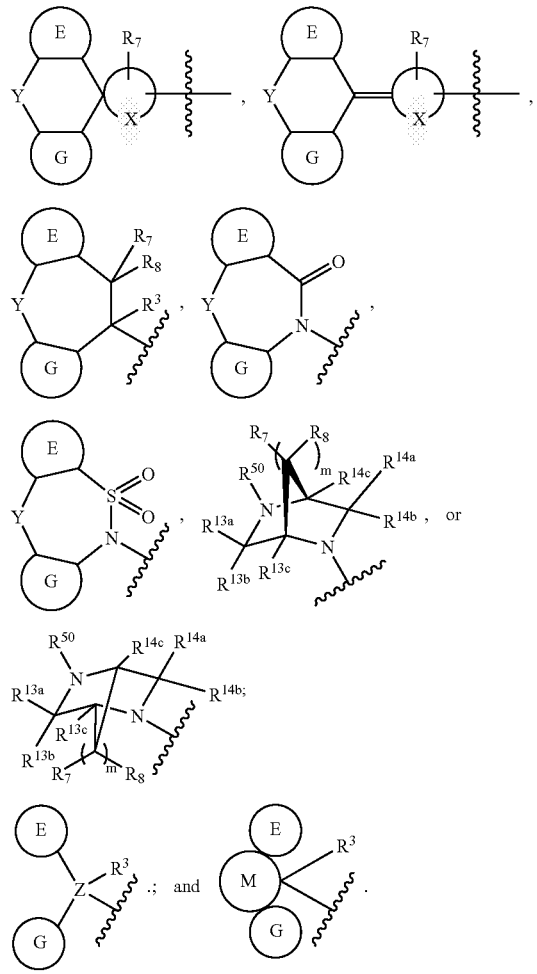

A is desirably

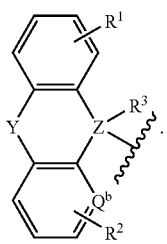

The "B" structures are chosen from:

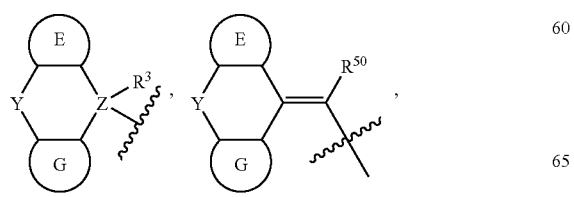

(a)

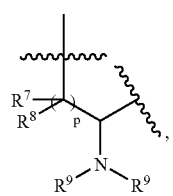

-continued

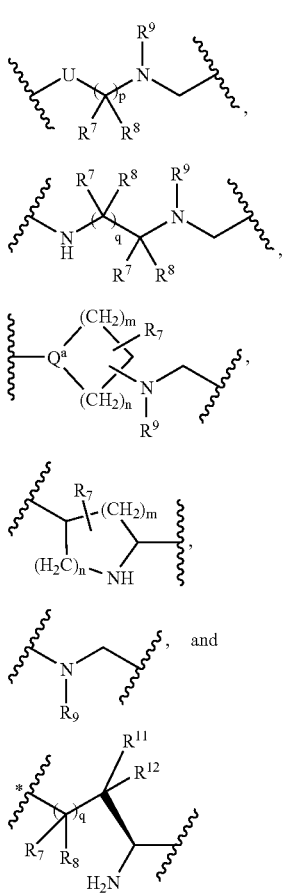

Desirably, B is one of structure (a), (b), (c), and (d). More desirably, B is structure (b)

The "D" structures are chosen from:

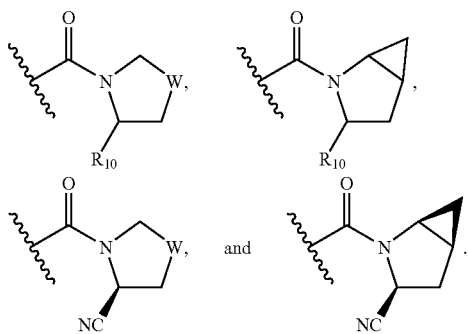

The substituents are selected as follows:

E, G, and M represent a three ring system wherein M shares two carbon atoms with each of E and G;

E and G are each independently selected from 6-membered aryl, 5-membered heteroaryl; 6-membered heteroaryl; a 5-7-membered saturated or partially saturated carbocyclic ring; and a 5-7 membered saturated or partially saturated heterocyclic ring; desirably E and G are substituted phenyl; M is a 5-7-membered saturated or partially saturated carboxylic or heterocyclic ring, or a 5-6-membered aromatic or heteroaromatic ring.

E may be substituted with one or more $R^1$ groups;

G may be substituted with one or more $R^2$ groups;

X and Y are divalent and are each independently: a bond, $CR^4R^5$, O, $NR^4$, S, S=O, $S(=O)_2$, $C(=O)$, $(C=O)N(R^4)$, $S(=O)_2N(R^4)$, $C=N-OR^4$, $-C(R^4R^5)C(R^4R^5)-$, $-C(R^4)=C(R^5)-$, $-C(R^4R^5)NR^4-$, $-C(R^4R^5)O-$, $-C(R^4R^5)S(=O)_t-$, $-(C=O)O-$, $-(C=NR^a)N(R^4)-$, $-(C=NR^a)-$, $N(C=O)NR^4NR^5$, $N(C=O)R^4$, $N(C=O)OR^4$, $NS(=O)_2NR^4NR_5$, $NS(=O)_2R^4$; or aryl, heteroaryl, cycloalkyl or heterocyclic ring, all may be optionally substituted;

$R^1$ and $R^2$ are each independently: halogen, $CF_3$, $COR^4$, $OR^4$, $NR^4R^5$, $NO_2$, $CN$, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-C($=NR^a$)NHR$^a$, $(C_0-C_6)$-alkyl-C($=NR^4$)NHR$^a$, $(C_0-C_6)$-alkyl-NR$^4$C($=NR^4$)NR$^4R^5$, $(C_0-C_6)$-alkyl-C(O)OR$^4$, $(C_0-C_6)$-alkyl-C(O)NR$^4R^5$, $(C_0-C_6)$-alkyl-C(O)—NH—CN, O—$(C_0-C_6)$-alkyl-C(O)NR$^4R^5$, $S(O)_t$—$(C_0-C_6)$-alkyl-C(O)OR$^4$, $S(O)_t$—$(C_0-C_6)$-alkyl-C(O)NR$^4R^5$, $(C_0-C_6)$-alkyl-C(O)NR$^4$—$(C_0-C_6)$-alkyl-NR$^4R^5$, $(C_0-C_6)$-alkyl-NR$^4R^5$, $(C_0-C_6)$-alkyl-NR$^4$—C(O)R$^5$, $(C_0-C_6)$-alkyl-NR$^4$—C(O)OR$^4$, $(C_0-C_6)$-alkyl-NR$^4$—C(O)—NR$^4R^5$, $(C_0-C_6)$-alkyl-NR$^4$ SO$_2$NR$^4R^5$, $(C_0-C_6)$-alkyl-NR$^4$—SO$_2$R$^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all of which may be optionally substituted. Desirably, $R^1$ and $R^2$ may be defined independently as —H, —F, —Cl, —CONR$^4R^5$, —CO$_2$H, —CN or —SO$_2$NR$^4R^5R^2$.

$R^3$ is absent or is halogen, $CF_3$, $COR^4$, $OR^4$, $NR^4R^5$, $NO_2$, $CN$, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-C($=NR^a$)NHR$^4$, $(C_0-C_6)$-alkyl-C($=NR^4$)NHR$^a$, $(C_0-C_6)$-alkyl-NR$^4$C($=NR^4$)NR$^4R^5$, $(C_0-C_6)$-alkyl-C(O)OR$^4$, $(C_0-C_6)$-alkyl-C(O)NR$^4R^5$, $(C_0-C_6)$-alkyl-C(O)—NH—CN, O—$(C_0-C_6)$-alkyl-C(O)NR$^4R^5$, $S(O)_t$—$(C_0-C_6)$-alkyl-C(O)OR$^4$, $S(O)_t$-$(C_0-C_6)$-alkyl-C(O)NR$^4R^5$, $(C_0-C_6)$-alkyl-C(O)NR$^4$—$(C_0-C_6)$-alkyl-NR$^4R^5$, $(C_0-C_6)$-alkyl-NR$^4R^5$, $(C_0-C_6)$-alkyl-NR$^4$—C(O)R$^5$, $(C_0-C_6)$-alkyl-NR$^4$—C(O)OR$^4$, $(C_0-C_6)$-alkyl-NR$^4$—C(O)—NR$^4R^5$, $(C_0-C_6)$-alkyl-NR$^4$ SO$_2$NR$^4R^5$, $(C_0-C_6)$-alkyl-NR$^4$—SO$_2$R$^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all of which may be optionally substituted. Desirably, $R^3$ is absent or is —H, —OH, —CO$_2$H, —CN, —CONR$^4R^5$, $R^5$, aryl, NH(C=O)R$^4$, NH(SO$_2$)R$^4$, heteroaryl —SO$_3$H, —PO$_3$H$_2$, —CONR$^4R^5$, $R^5$, aryl, NH(C=O)R$^4$, or NH(SO$_2$)R$^4$, and more desirably, $R^3$ is —CONR$^4R^5$ or tetrazolyl.

$R^a$ is hydrogen, CN, NO$_2$, alkyl, haloalkyl, $S(O)_tNR^4R^5$, $S(O)_tR^4$, $C(O)OR^4$, $C(O)R^4$, or $C(O)NR^4R^5$;

each occurrence of $R^4$, $R^5$, $R^{20}$ and $R^{21}$ are each independently: hydrogen, alkyl, cycloalkyl, cycloalkylalkyl, heterocycloalkyl, fluoroalkyl, heterocycloalkylalkyl, alkynyl, aryl, heteroaryl, arylalkyl, heteroarylalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl and aminoalkyl are all optionally substituted, or $R^4$ and $R^5$ when taken together with the nitrogen to which they are attached complete a 3- to 8-membered ring containing carbon atoms and may optionally contain a heteroatom selected from O, S, or $NR^{50}$ and the 3- to 8-membered ring may be optionally substituted. Desirably, $R^4$ and $R^5$ are each independently —H or alkyl.

$R^{50}$ is, in each occurrence, $R^{20}$, CN, $NO_2$, $S(O)_tNR^{20}R^{21}$, $S(O)_tR^{20}$, $C(O)OR^{20}$, $C(O)R^{20}C(=NR^a)NR^{20}R^{21}$, $C(=NR^{20})NR^{21}R^a$, $C(=NOR^{20})R^{21}$ or $C(O)NR^{20}R^{21}$;

each occurrence of $R^7$ and $R^8$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C-C_6)$-alkyl-$C(=NR^a)NHR^4$, $(C_0-C_6)$-alkyl-$C(=NR^4)NHR^a$, $(C_0-C_6)$-alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$—$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted. Desirably, $R^7$ and $R^8$ are independently H or alkyl.

$R^9$ is H or $C_{1-6}$ alkyl, desirably H.

$R^{10}$ is halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-$C(=NR^a)NHR^4$, $(C_0-C_6)$-alkyl-$C(=NR^4)NHR^a$, $(C_0-C_6)$-alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$-$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, $B(OH)_2$, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl are all optionally substituted. Desirably $R^{10}$ is CN.

$R^{11}$ and $R^{12}$ are each independently: halogen, $CF_3$, $COR^4$, $OR^4$, $NR^4R^5$, $NO_2$, CN, $SO_2OR^4$, $CO_2R^4$, $CONR^4R^5$, $CO_2H$, $SO_2NR^4R^5$, $S(O)_tR^4$, $SO_3H$, $OC(O)R^4$, $OC(O)NR^4R^5$, $NR^4C(O)R^5$, $NR^4CO_2R^5$, $(C_0-C_6)$-alkyl-$C(=NR^a)NHR^4$ $(C_0-C_6)$-alkyl-$C(=NR^4)NHR^a$ $(C_0-C_6)$- alkyl-$NR^4C(=NR^4)NR^4R^5$, $(C_0-C_6)$-alkyl-$C(O)OR^4$, $(C_0-C_6)$-alkyl-$C(O)NR^4R^5$, $(C_0-C_6)$-alkyl-$C(O)$—NH—CN, O—$(C_0-C_6)$-alkyl-$C(O)NR^4R^5$, $S(O)_t$-$(C_0-C_6)$-alkyl-$C(O)OR^4$, $S(O)_t$—$(C_0-C_6)$-alkyl-$C(O)NR^4R^5$, $(C_0-C_6)$-alkyl-$C(O)NR^4$—$(C_0-C_6)$-alkyl-$NR^4R^5$, $(C_0-C_6)$-alkyl-$NR^4R^5$, $(C_0-C_6)$-alkyl-$NR^4$—$C(O)R^5$, $(C_0-C_6)$-alkyl-$NR^4$—$C(O)OR^4$, $(C_0-C_6)$-alkyl-$NR^4$—$C(O)$—$NR^4R^5$, $(C_0-C_6)$-alkyl-$NR^4$—$SO_2NR^4R^5$, $(C_0-C_6)$-alkyl-$NR^4$—$SO_2R^4$, hydrogen, alkyl, cycloalkyl, cycloalkylalkyl, heterocycloalkyl, fluoroalkyl, heterocycloalkylalkyl, haloalkyl, alkenyl, alkynyl, aryl, heteroaryl, arylalkyl, heteroarylalkyl, alkoxyalkyl or aminoalkyl, wherein alkyl, cycloalkyl, cycloalkylalkyl, heterocycloalkyl, fluoroalkyl, heterocycloalkylalkyl, alkenyl, alkynyl, aryl, heteroaryl, arylalkyl, heteroarylalkyl, alkoxyalkyl and aminoalkyl all may be optionally substituted;

$R^{13a}$ and $R^{13b}$ are each independently $R^5$ or together are =O;

$R^{14a}$ and $R^{14b}$ are each independently $R^5$ or together are =O;

$R^{13c}$ and $R^{14c}$ are each independently $R^5$;

$Q^a$ is CH or N;

$Q^b$ is CH or N;

U is —C(O)—, —C(=$NR^4$)—, —($CR^4R^5$—)$_p$, $NR^{50}$, $S(=O)_2$, $C(=O)$, $(C=O)N(R^4)$, $N(R^4)(C=O)$, $S(=O)_2N(R^4)$, $N(R^4)S(=O)_2$, C=N—$OR^4$, —$C(R^4)$=$C(R^5)$—, —$C(R^4R^5)_pNR^5$—, $N(R^{50})C(R^4R^5)_p$—, —O—$C(R^4R^5)$—, —$C(R^4R^5)S(=O)_t$—, —(C=O) O—, —(C=$NR^a$)N($R^4$)—, —(C=$NR^a$)—, N(C=O) $NR^4$ $NR^5$, $N(C=O)R^4$, $N(C=O)OR^4$, $NS(=O)_2NR^4NR^5$, $NS(=O)_2R^4$, or an optionally substituted aryl, heteroaryl, cycloalkyl or heterocyclic ring, all of which may be optionally substituted. Desirably, U is $CH_2$.

W is —$CH_2$—, —S—, —CHF— or —$CF_2$—;

Z is C or N;

m is 1, or 2;

n is 0, 1, or 2;

p is 0 to 6;

q is 0 to 6; and t is 0, 1, or 2.

EXAMPLES

Compounds of the present invention having one or more optically active carbons can exist as racemates and racemic mixtures, diasteromeric mixtures and individual diasteromers, enatiomeric mixtures and single enantiomers, tautomers, atropisomers, and rotamers, with all isomeric forms being included in the present invention. Compounds described in this invention containing olefinic double bonds include both E and Z geometric isomers. Also included in this invention are all salt forms, polymorphs, hydrates and solvates. All of the above mentioned compounds are included within the scope of the invention.

The DPP-IV inhibition activity of the DPP-IV inhibitor compounds of the present invention may be measured using any suitable assay known in the art. A standard in vitro assay for measuring DPP-IV inhibitor activity is described.

The synthesis of DPP-IV inhibiting compounds of the invention and their biological activity assay are described in the following examples which are not intended to be limiting in any way.

Examples And Methods

All reagents and solvents were obtained from commercial sources and used without further purification. Proton ($^1$H) spectra were recorded on a 250 MHz NMR spectrometer in deuterated solvents. Chromatography was performed using Roth silica gel (Si 60, 0.06-0.2 mm) and suitable organic solvents as indicated in specific examples. For flash chromatography Roth silica gel (Si 60, 0.04-0.063 mm) was used. Thin layer chromatography (TLC) was carried out on silica gel plates with UV detection. Preparative thin layer chromatography (Prep-TLC) was conducted with 0.5 mm or 1 mm silica gel plates (Merck Si 60, $F_{254}$) and the solvents indicated in the specific examples.

Preparative Example 1

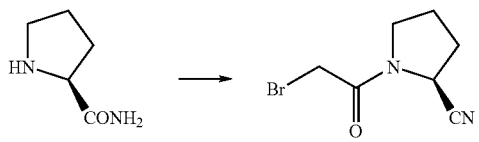

Commercially available prolinamide (5 g) was first treated with bromacetylbromide (4.2 ml) in $CH_2Cl_2$ and then with trifluoracetic acid anhydride in $CH_2Cl_2$ as described in WO 98/19998 to afford the title compound (7.85 g; 83%).

$^1$HNMR δ ($CDCl_3$) 2.05-2.40 (m, 4H), 3.51-3.70 (m, 2H), 3.80-3.85 (m, 2H), 4.70-4.86 (m, 1H).

Preparative Example 2

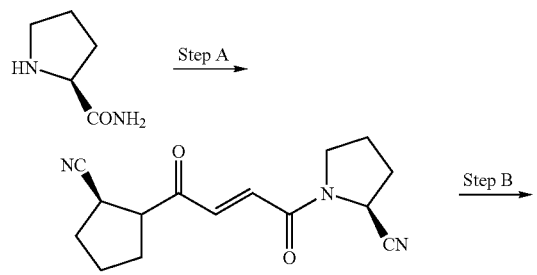

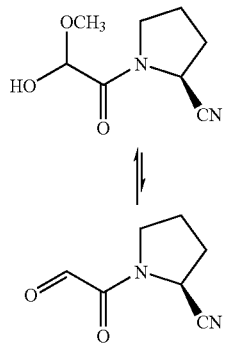

Step A

Commercially available L-prolinamide (25 g) was dissolved in $CH_2Cl_2$ (1200 ml) and triethylamine (30 ml) and 4-dimethylaminopyridine (1.9 g) added. The mixture was cooled to 0° C. and treated with fumaryl chloride (11.7 ml). The dark mixture was stirred at rt for 16 h and cooled to 0° C. TFAA (77 ml) was added dropwise under stirring and the solution allowed to warm to rt over 6 hours. The reaction mixture was stirred at rt for 1 to 2 days. Ice (500 g) was added followed by cautious addition of sat. $NaHCO_3$ (600 ml). After the evolution of gas had ceased, the organic phase was separated and washed with sat. $NaHCO_3$ (350 ml), $H_2O$ (350 ml), and brine (200 ml). The organic phase was dried over $MgSO_4$ and concentrated to afford the title compound (28.6 g; 98%).

$^1$HNMR δ ($CDCl_3$) 2.12-2.30 (m, 8H), 3.58-3.69 (m, 2H), 3.73-3.89 (m, 2H), 4.72-4.83 (m, 2H), 7.26 (s, 2H).

Step B

The title compound from Step A above (9.6 g) was dissolved in $CHCl_3$ (90 ml) and MeOH (90 ml) and cooled to −78° C. At −78° C. a slow flow of ozone (originating from an $O_2$ cylinder) was passed through the mixture for 3 h. The mixture was purged with $N_2$ and dimethylsulfide (6 ml) added. The mixture was stirred for 1 h, allowed to reach rt and concentrated. The residue was purified by chromatography on silica ($CH_2Cl_2$/MeOH, 100:0->92:8) to afford the title compound as a mixture of the aldehyde and methoxy hemiacetal in a ratio of ~1:9 (8.9 g; 69%).

$^1$HNMR δ ($D_2O$) 2.10-2.38 (m, 4H), 3.32 (s, 3H), 3.60-3.84 (m, 2H), 4.72-4.81 (m, 1H), 5.5 (s, 9/10H), 7.9 (s, 1/10H).

Preparative Example 3

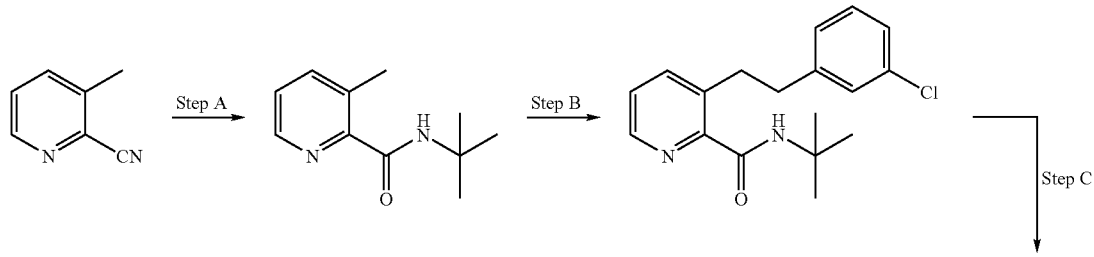

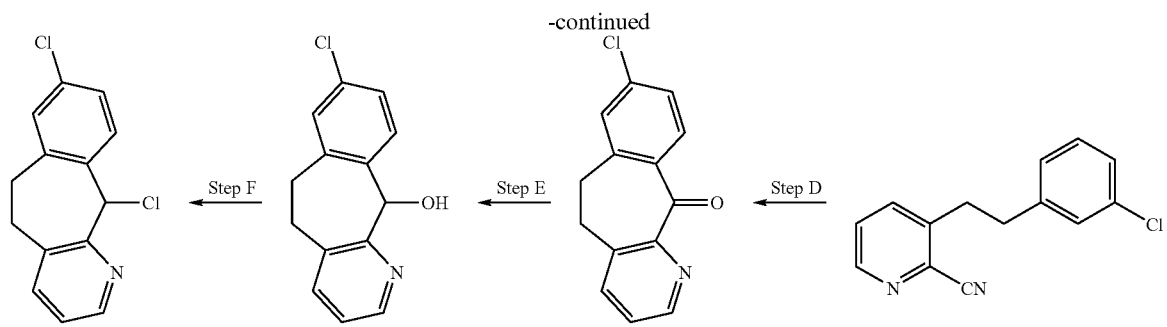

Step A

Commercially available 2-cyano-3-methylpyridine (25 g) was dissolved in t-butanol (50 ml) and stirred at 80° C. Concentrated sulphuric acid (25 ml) was slowly added over a period of 45 minutes. After complete addition of the acid stirring was continued at 80° C. for 1 h. The reaction was diluted with water (50 ml) and toluene (125 ml). The pH was adjusted to 10 with 25% aqueous ammonia (110 ml). The separated organic phase was concentrated in vacuum affording the desired product (27 g, 90%).

$^1$HNMR δ (CDCl$_3$) 1.4 (s, 9H), 2.7 (s, 3H), 7.2-7.3 (m, 1H), 7.6 (m, 1H), 8.1 (s br, 1H), 8.4 (m, 1H)

Step B

The title compound of Step A (12 g) above was dissolved in THF (150 ml) and cooled to −64° C. n-Butyllithium (1.6 M in hexane, 77 ml) was added over a period of 30 min. After addition of sodium bromide (0.6 g) stirring was continued for 30 min at −64° C. m-Chlorobenzylchloride (11 g) was added while the temperature was kept below −55° C. The mixture was stirred for 2 hours at −60° C. and for further 2 h at −10° C. Subsequently, the reaction was quenched with water (100 ml) and concentrated. The aqueous phase was extracted with chloroform (3×100 ml). The combined organic phase was dried over MgSO$_4$ and concentrated in vacuum affording the title compound (22 g; 82%).

$^1$HNMR δ (CDCl$_3$) 1.4 (s, 9H), 2.9-3.0 (m, 2H), 3.4-3.5 (m, 2H), 7.0-7.4 (m, 6H), 8.0 (s br, 1H), 8.4 (m, 1H)

Step C

The title compound of Step B (21.5 g) above was dissolved in phosphorus oxychloride (80 ml) and refluxed for 5 h. The reaction was concentrated and neutralized with 50% aqueous NaOH. The solid was separated and washed with hot isopropanol to afford the title compound (10.4 g; 63%)

$^1$HNMR δ (CDCl$_3$) 2.9-3.0 (m, 2H), 3.0-3.2 (m, 2H), 7.0-7.3 (m, 4H), 7.3-7.4 (m, 1H), 7.4-7.5 (m, 1H), 8.5-8.6 (m, 1H)

Step D

The title compound of Step C (10 g) above was dissolved in trifluorosulfonic acid (80 ml) and stirred at 60° C. for 1 h. At rt 6 N aqueous HCl (80 ml) was dropwise added. The reaction was refluxed for 1 h and subsequently, poured on ice. After neutralization with 50% aqueous NaOH the precipitate was separated, washed with water and recrystallized from isopropanol/water (3.1) affording the title compound. The mother liquor was concentrated and the residue washed with water and chloroform to afford additional title compound (9.4 g; 94%).

$^1$HNMR δ (MeOD-d$_4$) 3.3-3.4 (m, 2H), 3.4-3.5 (m, 2H), 7.5 (m, 2H), 8.1-8.2 (m, 2H), 8.7 (d, 1H), 8.9 (d, 1H)

Step E

The title compound of Step D (700 mg) above was dissolved in MeOH (10 ml) and cooled to 0° C. NaBH$_4$ (95 mg) was added in one portion. The mixture was allowed to warm to RT and stirred for 1 h. The reaction was acidified with 1 N HCl and subsequently, brought to pH 12 with 1 N NaOH. The mixture was poured in water (100 ml) and extracted with CHCl$_3$ (100 ml). The organic phase was dried over MgSO$_4$ and concentrated affording the title compound (705 mg; 100%).

$^1$HNMR δ (MeOD-d$_4$) 3.0-3.4 (m, 4H), 6.1 (s, 1H), 7.1.7.3 (m, 3H), 7.5-7.6 (m, 2H), 8.3.8.4 (m, 1H)

Step F

The title compound of step E (370 mg) above was dissolved in toluene (5 ml) and cooled to −15° C. Thionyl chloride (286 mg) was slowly added and the reaction was allowed to come to RT and run overnight. The solution was neutralized with triethylamine and directly used in the next step.

Preparative Example 4

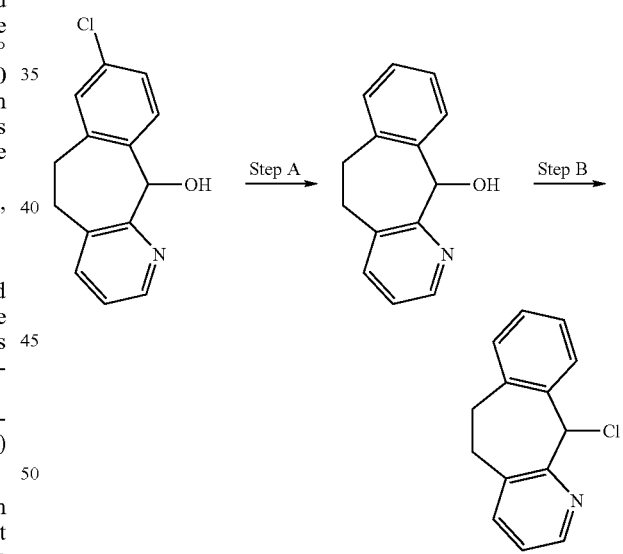

Step A

The title compound from Preparative Example 3 Step E (285 mg) was dissolved in ethanol (10 ml) and 10% Pd/C (100 mg) and ammonium formiate (916 mg) were added. The mixture was refluxed for 2 h. Subsequently, the reaction was treated with water (20 ml) and extracted twice with chloroform (50 ml). The combined organic phase was dried over MgSO$_4$ and concentrated. The residue was purified by chromatography on silica (EtOAc/cyclohexane 1:4) to afford the title compound (200 mg; 82%).

$^1$HNMR δ (MeOD-d$_4$) 2.9-3.1 (m, 2H), 3.3-3.6 (m, 2H), 6.3 (s, 1H), 7.0-7.3 (m, 4H), 7.4 (m, 1H), 7.8 (m, 1H), 8.3 (m, 1H)

Step B

The title compound of Step A (200 mg) above was dissolved in toluene (5 ml) and cooled to −15° C. Thionyl chloride (235 mg) was slowly added and the reaction was allowed to come to RT and run overnight. The solution was neutralized with triethylamine directly used.

Preparative Example 5

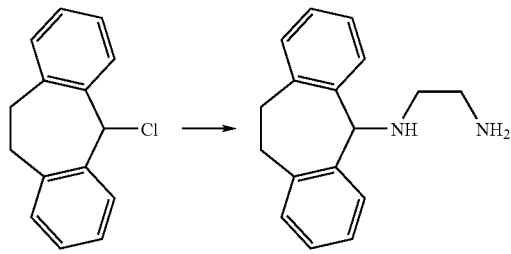

To a cooled solution (12° C.) of commercially available ethylenediamine (30 ml) was added within 5 min commercially available dibenzosuberylchloride (3.3 g). The mixture was stirred at rt for 1 h and then $K_2CO_3$ (5.8 g) was added. After an additional 30 min at rt, the mixture as filtered, the salts washed with 5 ml ethylenediamine and the filtrates concentrated. The residue was dissolved in 80 ml EtOAc, 20 ml $H_2O$ and 5 ml $NH_4OH$-solution (25%). The organic phase was separated, dried over $MgSO_4$ and concentrated to afford the title compound (3.4 g; 93%; $MH^+$=253).

Preparative Example 6-9

The title compounds from Preparative Example 6 to 9 were prepared according to the procedure described in Preparative Example 5 using the chlorides and amines as indicated in the Table below. In case the chlorides did not dissolve in the amines after 10 Min, $CH_3CN$ or THF was added until a clear solution was obtained.

| Preparative Example | Chloride | Amine | Product | 1. Yield 2. $MH^+$ |
|---|---|---|---|---|
| 6 | | $NH_4OH$ | | 1. 61% 2. $^1$H-NMR δ ($CDCl_3$) 2.0 (s, 2H), 3.10-3.24 (m, 2H), 3.31-3.45 (m, 2H), 5.43 (s, 1H), 7.10-7.19 (m, 6H), 7.36-7.41 (m, 2H) |
| 7 | | $H_2N$ $NH_2$ | | 1. 97% 2. 281 |
| 8 | | $H_2N$ $NH_2$ | | 1. 60% 2. 288 |

-continued

| Preparative Example | Chloride | Amine | Product | 1. Yield 2. MH+ |
|---|---|---|---|---|
| 9 | 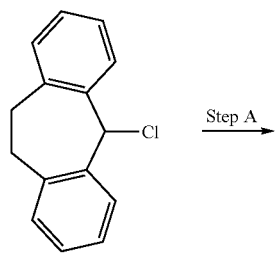 | H₂N-NH₂ | | 1. 78% 2. ¹H-NMR δ (CD₃OD) 2.6-2.8 (m, 4H), 3.0-3.2 (m, 2H), 3.3-3.6 (m, 2H), 5.2 (s, 1H), 7.1-7.2 (m, 4H), 7.3-7.4 (m, 1H), 7.5 (m, 1H), 8.2-8.3 (m, 1H) |

Preparative Example 10

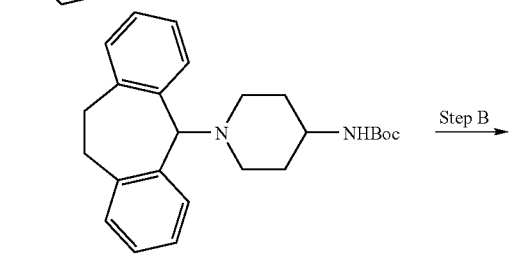

Step A

Commercially available dibenzosuberylchloride (300 mg) and 4-N-Boc-amino-piperidine (290 mg) were suspended in CH₃CN (10 ml). After 10 min K₂CO₃ (545 mg) was added and the mixture was stirred at rt for 3 h. The mixture was diluted with EtOAc (30 ml) and H₂O (15 ml), the organic phase separated, dried over MgSO₄ and concentrated to afford the title compound (460 mg; 89%; MH⁺=393).

Step B

The title compound from Step A above (460 mg) was dissolved in a solution of 4 M HCl in dioxane (20 ml). The mixture was stirred at rt for 2 h and concentrated to afford the title compound (335 mg; 97%; MH⁺=293).

Preparative Example 11-12

The title compounds from Preparative Example 11 and 12 were prepared according to the procedure described in Preparative Example 10 using the chlorides and amines as indicated in the Table below.

| Preparative Example | Chloride | Amine | Product | 1. Yield 2. MH+ |
|---|---|---|---|---|
| 11 | 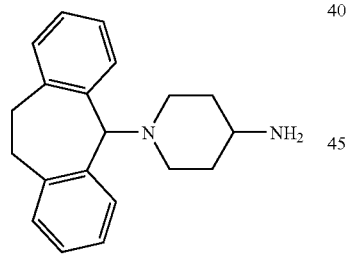 | | | 1. 64% 2. 279 |

-continued

| Preparative Example | Chloride | Amine | Product | 1. Yield 2. MH+ |
|---|---|---|---|---|
| 12 | 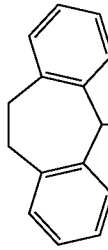 |  | 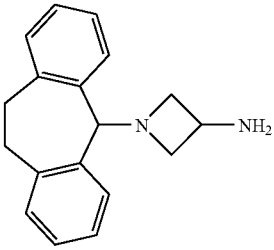 | 1. 56% 2. 265 |

Preparative Example 13

Preparative Example 14

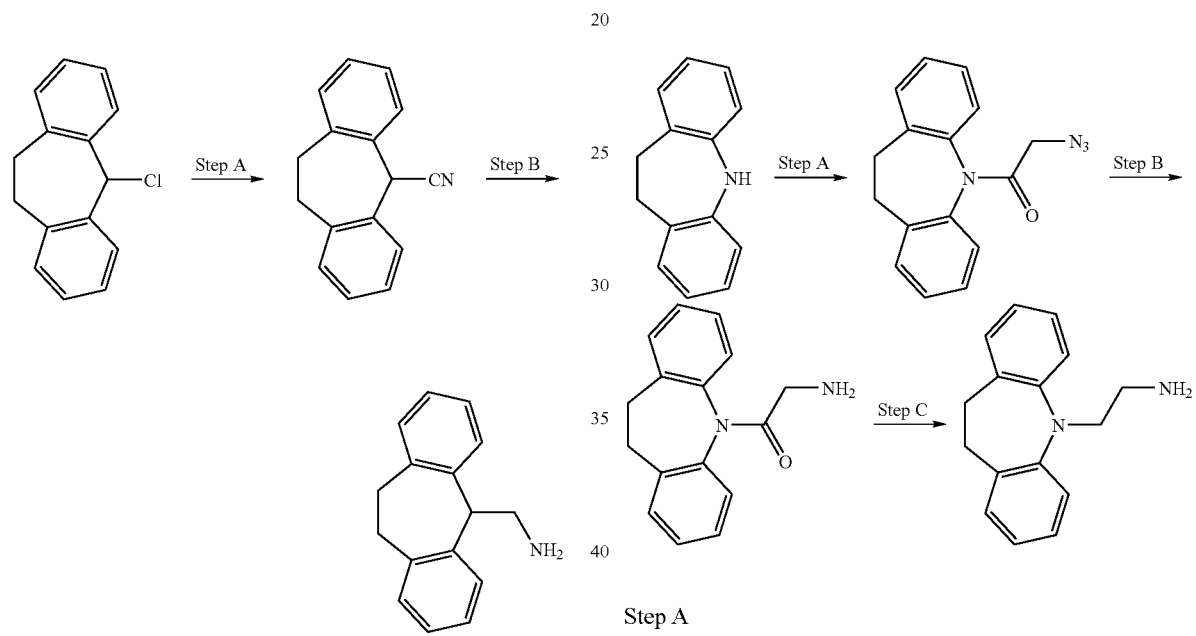

Step A

To a suspension of AgCN (4.7 g) in CH₃CN (60 ml) under nitrogen was added at rt a solution of commercially available dibenzosuberylchloride (6 g) in CH₃CN (60 ml) and benzene (10 ml). The mixture was heated at reflux for 2 h, cooled to rt and filtered. The salts were washed with 20 ml CH₃CN and the filtrates concentrated. The residue was purified by chromatography on silica (EtOAc/cyclohexane, 1:9) to afford the title compound (5 g; 87%; MNa⁺=242).

Step B

A suspension of LiAlH₄ (360 mg) in Et₂O (20 ml) was slowly treated with a solution of AlCl₃ (950 mg) in Et₂O (20 ml). The mixture was stirred at rt for 10 min and then the title compound from Step A above (1.03 g) was added within 5 min. The mixture was stirred at rt for 10 min and then refluxed for 8 h. After the addition of H₂O (20 ml) and 25% NH₄OH (6 ml), the mixture was filtered and the salts washed with H₂O (20 ml) and Et₂O (10 ml). The organic phase was separated, dried over MgSO₄ and concentrated to afford the title compound (157 mg; 15%; MH⁺=224).

Step A

To a solution of commercially available iminodibenzyl (5 g) in toluene (25 ml) was added commercially available bromoacetylbromide (4.35 ml). The mixture was heated under reflux for 2 h 30 Min, cooled and concentrated. A portion of the crude product (800 mg) was dissolved in DMA (6 ml) and treated with NaN₃ (815 mg). The mixture was heated at 60-70° C. overnight and diluted with EtOAc (30 ml) and H₂O (10 ml). The organic phase was separated, dried over MgSO₄ and concentrated. The residue was treated with EtOAc/cyclohexane (1:9) (2 ml), sonicated for 2 min and the solvents removed by syringe. The residue was dried to afford the title compound (483 mg; 69%; MH⁺=279).

Step B

The title compound from Step A above (483 mg) was dissolved in MeOH (25 ml) and 10% Pd/C (100 mg) added. The mixture was hydrogenated for 1 h, filtered and the catalyst washed with MeOH (10 ml). The filtrates were concentrated and the residue purified by chromatography on silica (CH₂Cl₂/MeOH, 9:1) to afford the title compound (415 mg; 95%; MH⁺=253).

Step C

To a suspension of LiAlH₄ (242 mg) in THF (6 ml) was added a solution of the title compound from Step B above (322 mg) in THF (6 ml). The mixture was heated under reflux for 2 h 30 min. The mixture was cooled to 0° C., quenched with H$_2$O (0.3 ml) and diluted with 15% NH$_4$OH-solution (0.3 ml) and H$_2$O (0.8 ml). The mixture was stirred at rt for 45 Min, filtered and the salts washed with THF (8 ml). The filtrates were concentrated and the residue purified by chromatography on silica (CH$_2$Cl$_2$/MeOH, 9:1) to afford the title compound (79 mg; 26%; MH$^+$=239).

Preparative Example 15

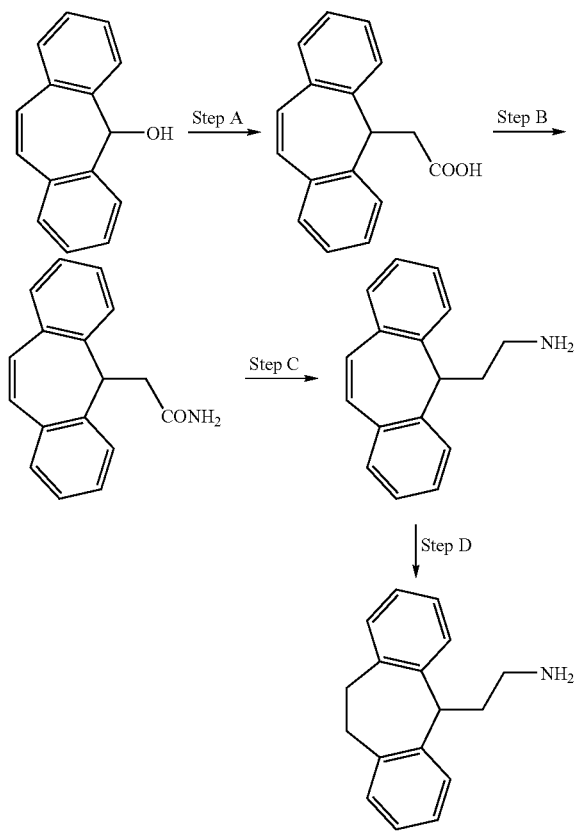

Step A

A mixture of commercially available dibenzosuberenol (1.5 g) and malonic acid (830 mg) was heated at 160-170° C. for 2 h. A mixture of H$_2$O (5 ml) and 0.1 M HCl (5 ml) was added and the mixture cooled to rt. The mixture was diluted with EtOAc (100 ml) and H$_2$O (10 ml), the organic phase separated, dried over MgSO$_4$ and concentrated. The residue was purified by chromatography on silica (CH$_2$Cl$_2$/acetone, 98:2->CH$_2$Cl$_2$/acetone, 9:1) to afford the title compound (775 mg; 43%; MNa$^+$=273).

Step B

A mixture of title compound from Step A above (775 mg) and triethylamine (0.59 ml) in THF (20 ml) was cooled to −40° C. and treated with isobutylchloroformate. After stirring at −40° C. for 1 h, the mixture was filtered and the salts washed with THF (5 ml). The filtrates were then treated at 0° C. with 25% NH$_4$OH (15 ml) for 1 h 30 min. The mixture was diluted with EtOAc (60 ml), the organic phase separated, dried over MgSO$_4$ and concentrated. The residue was treated with CHCl$_3$ (1.5 ml), the solvent removed by syringe and the residue dried to afford the title compound (677 mg; 88%; MH$^+$=250).

Step C

To a suspension of LiAlH$_4$ (513 mg) in THF (15 ml) was added a solution of the title compound from Step B above (677 mg) in THF (25 ml). The mixture was heated under reflux for 2 h. The mixture was cooled to 0° C., quenched with H$_2$O (0.65 ml) and diluted with 4 M NaOH-solution (2.5 ml) The mixture was stirred at rt for 45 Min, filtered and the salts washed with THF (15 ml). The filtrates were concentrated and the residue purified by chromatography on silica (CH$_2$Cl$_2$/MeOH, 9:1) to afford the title compound (560 mg; 88%; MH$^+$=236).

Step D

The title compound from Step C above (350 mg) was dissolved in MeOH (15 ml) and 10% Pd/C (300 mg) and 1 M HCl (1.5 ml) were added. The mixture was hydrogenated overnight, filtered and the catalyst washed with MeOH (10 ml). The filtrates were concentrated and the residue dissolved in EtOAc (30 ml) and sat. NaHCO$_3$ (10 ml). The organic phase was separated and the aqueous phase extracted with EtOAc (20 ml). The combined organic phase was dried over MgSO$_4$ and concentrated to afford the title compound (232 mg; 66%; MH$^+$=238).

Preparative Example 16

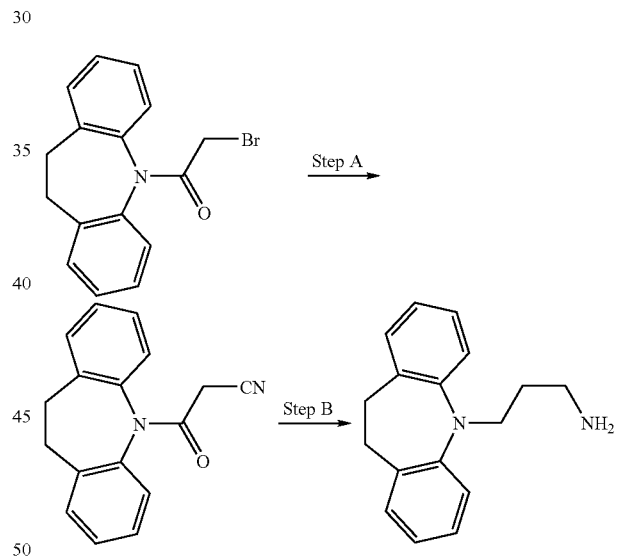

Step A

The intermediate from Preparative Example 14 Step A (1 g) was dissolved in DMA (6 ml) and treated with NaCN (368 mg). The mixture was heated at 60-70° C. overnight and diluted with EtOAc (50 ml) and H$_2$O (15 ml). The organic phase was separated, dried over MgSO$_4$ and concentrated. The residue was purified by chromatography on silica (CH$_2$Cl$_2$/acetone, 98:2) to afford the title compound (282 mg; 34%; MH$^+$=263).

Step B

To a suspension of LiAlH$_4$ (123 mg) in THF (6 ml) was added a solution of the title compound from Step A above (282 mg) in THF (6 ml). The mixture was heated at 50° C. for 2 h, cooled to 0° C. and treated with H$_2$O (0.2 ml) and 4 M NaOH (0.8 ml). The mixture was stirred at rt for 45 Min, treated with MgSO₄ and filtered. The filtrate was concentrated and the residue purified by chromatography on silica (CH₂Cl₂/MeOH, 95:5->CH₂Cl₂/MeOH, 9:1) to afford the title compound (32 mg; 12%; MH⁺=253).

Preparative Example 17

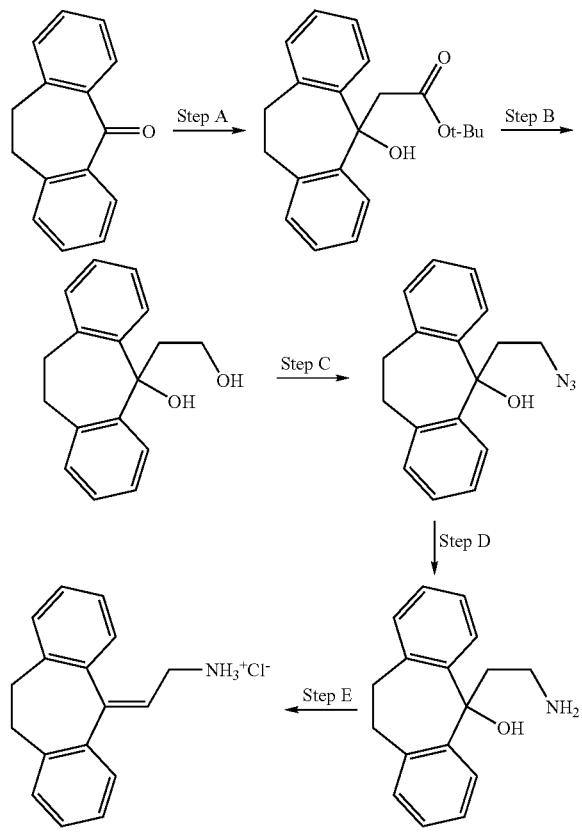

Step A

To a suspension of magnesium (701 mg) in Et₂O (7 ml) was slowly added ethylbromide (2.15 ml). After the formation of the Grignard reagent, the mixture was cooled to 5° C. and a solution of diethylamine (3 ml) in Et₂O (5 ml) was slowly added. The mixture was refluxed for 30 Min, cooled to 5° C. and treated with a mixture of commercially available dibenzosuberone (3 g) and tert-butylacetate (1.95 ml) in Et₂O (15 ml). The mixture was heated under reflux for 2 h, cooled to rt and poured onto ice-water containing an excess of NH₄Cl. The mixture was extracted with CH₂Cl₂ (3×100 ml), the organic phase dried over MgSO₄ and concentrated. The residue was purified by chromatography on silica (EtOAc/cyclohexane, 1:9) to afford the title compound (3.5 g; 75%; MNa⁺=347).

Step B

To a suspension of LiAlH₄ (346 mg) in THF (12 ml) was added a solution of the title compound from Step A above (2 g) in THF (12 ml). The mixture was heated under reflux for 2 h, cooled to 0° C. and treated 4 M NaOH (4.5 ml). The mixture was stirred at rt for 45 min and filtered. The filtrate was concentrated and the residue dissolved in EtOAc (100 ml), H₂O (10 ml) and sat. NH₄Cl (10 ml). The organic phase was separated, dried over MgSO₄ and concentrated. The residue was purified by chromatography on silica (EtOAc/cyclohexane, 3:7) to afford the title compound (937 mg; 60%; MNa⁺=277).

Step C

The title compound from Step B above (937 mg) was dissolved in benzene (1.5 ml) and pyridine (1.5 ml). The mixture was cooled to 5° C. and treated with a solution of p-tosylchloride in benzene (1.5 ml). The mixture was stirred at rt for 7 h, diluted with EtOAc (40 ml) and washed with 0.1 M HCl (10 ml), sat. NaHCO₃ (10 ml) and brine (10 ml). The organic phase was separated, dried over MgSO₄ and concentrated. The crude intermediate was dissolved in DMA (9 ml) and treated with NaN₃ (1.2 g). The mixture was heated at 70° C. overnight and the DMA removed. The residue was dissolved in EtOAc (50 ml), sat. NaHCO₃ (10 ml) and brine (10 ml). The organic phase was separated, dried over MgSO₄ and concentrated. The residue was purified by chromatography on silica (EtOAc/cyclohexane, 1:4) to afford the title compound (704 mg; 68%; MNa⁺=302).

Step D

The title compound from Step C above (200 mg) was dissolved in MeOH (8 ml) and 10% Pd/C (40 mg) added. The mixture was hydrogenated for 1 h 30 Min, filtered and the catalyst washed with MeOH (10 ml). The filtrates were concentrated to afford the title compound (175 mg; 96%; MH⁺=254).

Step E

The title compound from Step D above (75 mg) was dissolved in EtOH (1 ml) and a 4 M solution of HCl in dioxane (1 ml) added. The mixture was stirred at rt for 12 h and concentrated. The residue was dissolved in EtOAc (20 ml) and sat. NaHCO₃ (5 ml). The organic phase was separated, dried over MgSO₄ and concentrated to afford the title compound (67 mg; 96%; M⁺—NH₃=219).

Preparative Example 18

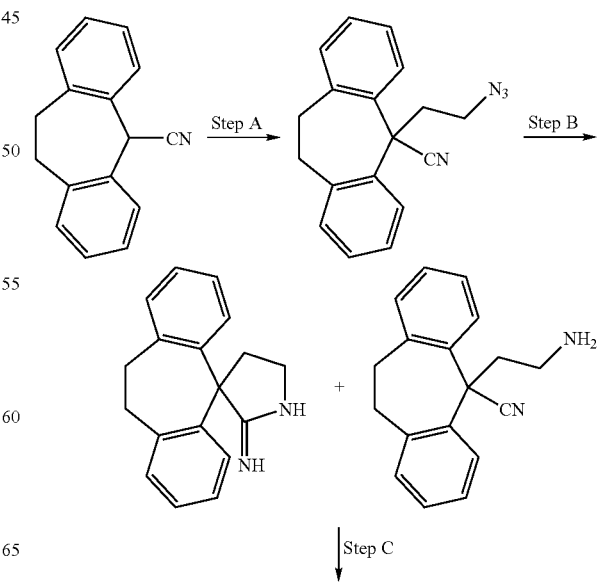

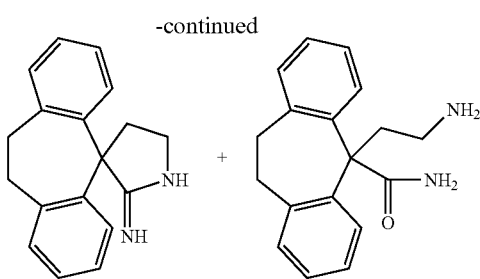

Step A

The title compound from Preparative Example 13 Step A (1.1 g) was dissolved in THF (5 ml) and added to a suspension of NaH (132 mg) in THF (5 ml). The mixture was heated under reflux for 1 h, cooled to rt and treated with 1,2-dibromoethane (0.9 ml) in THF (1 ml). The mixture was heated under reflux for 4 h, cooled to rt and filtered. The salts were washed with THF (5 ml) and the filtrates concentrated. The residue was dissolved in DMA (12 ml) and treated with NaN$_3$ (1.6 g). The mixture was heated at 60-70° C. overnight and the DMA removed. The residue was dissolved in EtOAc (40 ml) and H$_2$O (10 ml), the organic phase separated, dried over MgSO$_4$ and concentrated. The residue was purified by chromatography on silica (EtOAc/cyclohexane, 1:9) to afford the title compound (1.14 g; 78%; MH$^+$=289).

Step B

The title compound from Step A above (510 mg) was dissolved in MeOH (20 ml) and 10% Pd/C (150 mg) and 2 M HCl (0.9 ml) added. The mixture was hydrogenated for 1 h 30 Min, filtered and the catalyst washed with MeOH (10 ml). The filtrates were concentrated and the residue purified by chromatography on silica (CH$_2$Cl$_2$/MeOH, 95:5 to CH$_2$Cl$_2$/MeOH, 4:1) to afford a mixture of the title compound and the cyclic amidine (450 mg; 96%; MH$^+$=263).

Step C

The title compounds from Step B above (350 mg) were treated with 2 ml 57% H$_2$SO$_4$. The mixture was heated at 100° C. for 3 h, cooled to rt and diluted with H$_2$O (10 ml). The mixture was made alkaline (pH~11) by adding 10% NaOH and extracted with EtOAc (3×30 ml). The organic phase was dried over MgSO$_4$ and concentrated. The residue was purified by chromatography on silica (CH$_2$Cl$_2$/MeOH, 9:1 to CH$_2$Cl$_2$/MeOH (7 M NH$_3$), 9:1) to afford a mixture of the title compound and the cyclic amidine (223 mg; 60%; MH$^+$=281).

Preparative Example 19

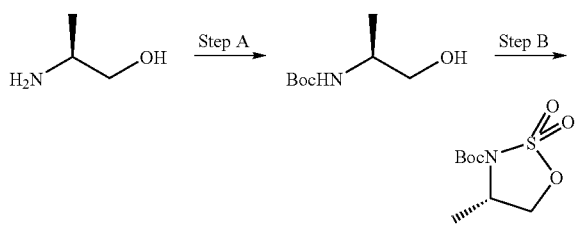

Step A

Commercially available (S)-2-aminopropan-1-ol (2.0 g) was dissolved in CH$_2$Cl$_2$ (20 ml) and Boc$_2$O (6.4 g) was added. After stirring for 4 h at room temperature the solvent was removed to afford the title compound (4.7 g, 99%).

$^1$H-NMR δ (CDCl$_3$): 1.10 (s, 3H), 1.50 (s, 9H), 2.40 (s, 1H), 3.45-3.70 (m, 2H), 3.75-3.80 (m, 1H), 4.80 (s, 1H).

Step B

Imidazole (4.1 g) was dissolved in CH$_2$Cl$_2$ (50 ml) and cooled to 0° C. Thionyl chloride (1.3 ml) dissolved in CH$_2$Cl$_2$ (10 ml) was added dropwise and the resulting suspension was allowed to warm to rt. Stirring was continued for 1 h at rt and then the mixture was cooled to −78° C. A solution of the title compound from Step A above (1.8 g) in CH$_2$Cl$_2$ (50 ml) was added over a period of 1 h and the resulting mixture was allowed to warm to rt and stirred overnight. The mixture was filtered through celite and the filter aid was washed well with CH$_2$Cl$_2$. The organic phase was diluted with CH$_2$Cl$_2$, washed with water and brine, dried over MgSO$_4$, filtered and concentrated to a volume of approx. 100 ml.

A solution of NaIO$_4$ (4.3 g) in water (100 ml) was added and the mixture was cooled to 0° C. Ru(IV)O$_2$ hydrate (150 mg) was added and the black suspension was stirred for 2 h at 0° C. It was then warmed to rt and stirred overnight. The mixture was filtered through celite and the filtrate was extracted with CH$_2$Cl$_2$. The combined organic phase was washed with brine, dried and filtered. Treatment of the filtrate with activated charcoal (2 g) for 30 min removed traces of ruthenium. The mixture was filtered again and evaporated to yield the title compound (1.5 g, 63%).

$^1$H-NMR δ (CDCl$_3$): 1.45 (s, 3H), 1.49 (s, 9H), 4.14 (dd, 1H), 4.29-4.42 (m, 1H), 4.61 (dd, 1H).

Preparative Example 20

The title compound from Preparative Example 20 was prepared according to the procedure described in Preparative Example 19 using the aminoalcohol as indicated in the Table below.

| Preparative Example | Aminoalcohol | Product | 1. Yield 2. $^1$H-NMR |
|---|---|---|---|
| 20 | ![H2N-CH(CH3)-CH2OH] | ![BocN-S(O)2-O cyclic] | 1. 69% 2. $^1$H-NMR δ (CDCl$_3$): 1.45 (s, 3H), 1.49 (s, 9H), 4.14 (dd, 1H), 4.29-4.42 (m, 1H), 4.61 (dd, 1H). |

Preparative Example 21

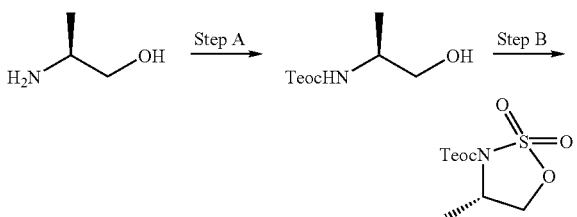

Step A

To a stirred solution of the commercially available 2-(S)-amino propanol (17.4 g) in water (200 ml) was added a solution of triethylamine (32 ml) in dioxane (200 ml). To the solution was added commercially available 1-[2-(Trimetylsilyl)ethoxy-carbonyloxy]pyrrolidin-2,5-dione (60 g). The mixture was stirred at rt overnight, then diluted with water (200 ml), acidified with 1 N HCl, and extracted with Et$_2$O (2×500 ml). The combined organic phase was washed with brine, dried over MgSO$_4$ and evaporated to afford the title compound (44.2 g; 87

$^1$H-NMR δ (CDCl$_3$): 0.02 (s, 9H), 0.90-1.05 (m, 2H), 1.20 (d, 3H), 2.80 (br s, 1H), 3.40-3.80 (m, 3H), 4.10-4.20 (m, 2H), 4.85 (s, 1H).

Step B

Imidazole (96 g) was dissolved in CH$_2$Cl$_2$ (1200 ml) and cooled to 0° C. Thionyl chloride (30.8 ml) was diluted with CH$_2$Cl$_2$ (600 ml) and added dropwise. The resulting suspension was allowed to warm to rt. Stirring was continued for 1 h at rt and then the mixture was cooled to −78° C. A solution of the title compound from Step A above (44.2 g) in CH$_2$Cl$_2$ (1200 ml) was added over a period of 1 h and the resulting mixture was allowed to warm to rt and stirred overnight. The mixture was filtered through celite, the filter aid was washed well with CH$_2$Cl$_2$. The organic phase was washed with water (2×700 ml), dried over MgSO$_4$, filtered and concentrated to a volume of approx. 1000 ml.

A solution of NaIO$_4$ (100 g) in water (1000 ml) was added and the mixture was cooled to 0° C. RuO$_2$×H$_2$O (1 g) was added and the black suspension was stirred for 2 h at 0° C. It was then warmed to rt and stirred overnight. The phases were separated and the organic phase was treated with granulated charcoal (~20 g). The mixture was stirred for approx. 1 h, filtered through celite and the filtrate was dried with MgSO$_4$, filtered and evaporated to yield the title compound (50.7 g, 89%).

$^1$H-NMR δ (CDCl$_3$): 0.02 (s, 9H), 1.00-1.15 (m, 2H), 1.50 (d, 3H), 4.15 (dd, 1H), 4.35-4.45 (m, 3H), 4.65 (dd, 1H).

Preparative Example 22-23

Following a similar procedure as that described in Preparative Example 21 but using the aminoalcohols as indicated in the Table below, the title compounds were obtained.

| Preparative Example | Aminoalcohol | Product | 1. Yield 2. $^1$H-NMR |
|---|---|---|---|
| 22 | H$_2$N-CH$_2$CH$_2$-OH | [Teoc-N,S-dioxathiazolidine] | 1. 58% 2. $^1$H-NMR δ (CDCl$_3$): 0.02 (s, 9H), 1.00-1.15 (m, 2H), 4.00-4.10 (m, 2H), 4.25-4.40 (m, 2H), 4.55-4.65 (m, 2H). |
| 23 | H$_2$N-CH(Et)-CH$_2$OH | [Teoc-N,S-dioxathiazolidine with ethyl] | 1. 32% (M + Na)$^+$ = 318 |

Preparative Example 24-46

If one were to follow a similar procedure as that described in Preparative Example 21 but using the aminoalcohols as indicated in the Table below, one would obtain the desired products.

| Preparative Example | Aminoalcohol | Product |
|---|---|---|
| 24 | H$_2$N-CH(Me)-CH$_2$OH | [Teoc-cyclic sulfamidate with methyl] |
| 25 | H$_2$N-CH(Et)-CH$_2$OH | [Teoc-cyclic sulfamidate with ethyl] |
| 26 | H$_2$N-CH(iPr)-CH$_2$OH | [Teoc-cyclic sulfamidate with isopropyl] |
| 27 | H$_2$N-CH(iPr)-CH$_2$OH (other stereo) | [Teoc-cyclic sulfamidate with isopropyl] |
| 28 | H$_2$N-CH(tBu)-CH$_2$OH | [Teoc-cyclic sulfamidate with tert-butyl] |
| 29 | H$_2$N-CH(tBu)-CH$_2$OH (other stereo) | [Teoc-cyclic sulfamidate with tert-butyl] |
| 30 | H$_2$N-CH(cyclopropyl)-CH$_2$OH | [Teoc-cyclic sulfamidate with cyclopropyl] |
| 31 | H$_2$N-CH(cyclopropyl)-CH$_2$OH (other stereo) | [Teoc-cyclic sulfamidate with cyclopropyl] |
| 32 | H$_2$N-CH(cyclobutyl)-CH$_2$OH | [Teoc-cyclic sulfamidate with cyclobutyl] |

-continued

| Preparative Example | Aminoalcohol | Product |
|---|---|---|
| 33 | cyclobutyl aminoalcohol | Teoc-protected cyclic sulfamidate with cyclobutyl |
| 34 | cyclopentyl aminoalcohol | Teoc-protected cyclic sulfamidate with cyclopentyl |
| 35 | cyclopentyl aminoalcohol | Teoc-protected cyclic sulfamidate with cyclopentyl |
| 36 | cyclohexyl aminoalcohol | Teoc-protected cyclic sulfamidate with cyclohexyl |
| 37 | cyclohexyl aminoalcohol | Teoc-protected cyclic sulfamidate with cyclohexyl |
| 38 | 4-fluorophenyl aminoalcohol | Teoc-protected cyclic sulfamidate with 4-fluorophenyl |
| 39 | 4-fluorophenyl aminoalcohol | Teoc-protected cyclic sulfamidate with 4-fluorophenyl |

-continued

| Preparative Example | Aminoalcohol | Product |
|---|---|---|
| 40 | 4-fluorobenzyl aminoalcohol | Teoc-protected cyclic sulfamidate with 4-fluorobenzyl |
| 41 | 4-fluorobenzyl aminoalcohol | Teoc-protected cyclic sulfamidate with 4-fluorobenzyl |
| 42 | 2-amino-2-methylpropanol | Teoc-protected gem-dimethyl cyclic sulfamidate |
| 43 | (1-aminocyclopropyl)methanol | Teoc-protected cyclopropane spiro sulfamidate |
| 44 | (1-aminocyclobutyl)methanol | Teoc-protected cyclobutane spiro sulfamidate |
| 45 | (1-aminocyclopentyl)methanol | Teoc-protected cyclopentane spiro sulfamidate |
| 46 | (1-aminocyclohexyl)methanol | Teoc-protected cyclohexane spiro sulfamidate |

Preparative Example 47

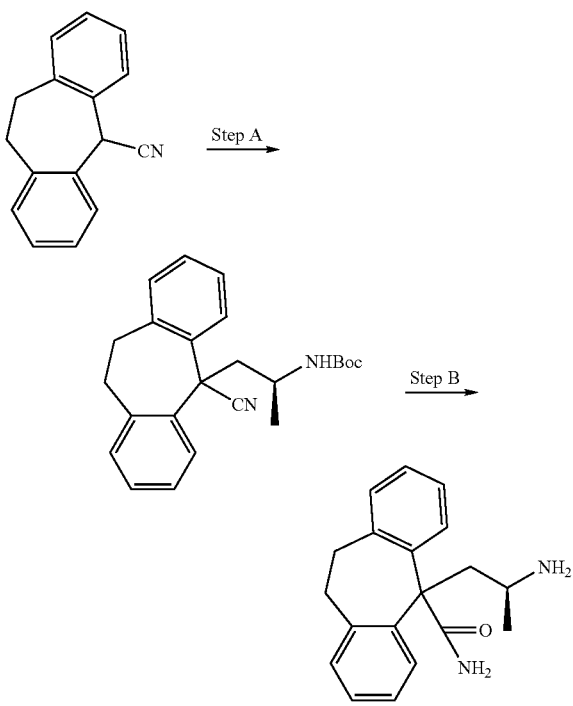

Step A

A suspension of NaH (132 mg) in THF (10 ml) was added to a solution of Preparative Example 13 Step A (1.1 g) in THF (20 ml) and heated at 60° C. for 1 h. Then the mixture was cooled to 0° C. and a solution of Preparative Example 19 (1.2 g) in THF (10 ml) was added. The suspension was heated at 60° C. for 4 h and then diluted with ethyl acetate. The organic phase was washed with water, brine and dried over $MgSO_4$. Removal of the solvents and column chromatography (EtOAc/hexane, 1:4) afford the title compound (1.7 g, 90%, $MH^+$=377).

Step B

The title compound from Step A above (1.5 g) was dissolved in 57% $H_2SO_4$ and the solution was heated at 100° C. for 2 h. The mixture was diluted with water and extracted with ethyl acetate. The organic phase was discarded and 50%-aqueous KOH solution added to the aqueous phase until pH>8. The aqueous phase was extracted with ethyl acetate (2×75 ml). The organic phase was washed with water, brine, dried over $MgSO_4$ and evaporated to afford the title compound. (600 mg, 53%).

$^1$H-NMR δ ($CDCl_3$): 0.95 (d, 3H), 1.82 (s, 2H), 2.37-2.58 (m, 2H), 2.82-2.92 (m, 1H), 3.18 (s, 4H), 5.60 (s, 2H), 7.08-7.24 (m, 6H), 7.40-7.48 (m, 2H).

Preparative Example 48

The title compound was prepared according to the procedure described in Preparative Example 47 using the sulfamidate from Preparative Example 20 as indicated in the Table below.

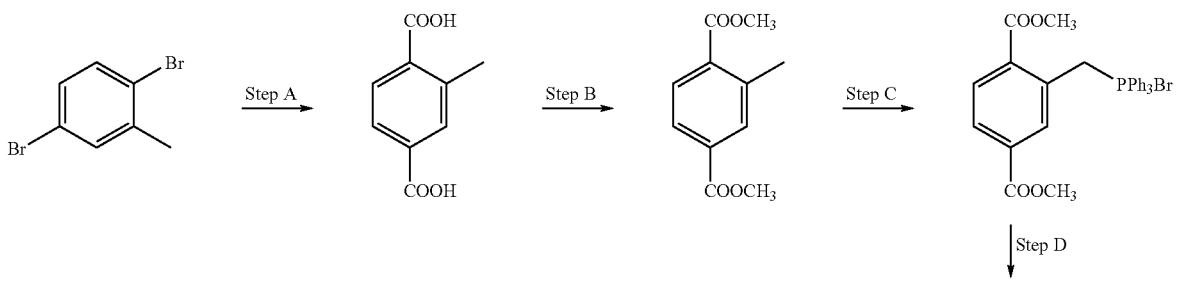

| Preparative Example | Nitrile | Sulfamidate | Product | 1. Yield 2. $^1$H-NMR |
|---|---|---|---|---|
| 48 | | | | 1. 80% 2. $^1$H-NMR δ ($CDCl_3$): 0.95 (d, 3H), 1.82 (s, 2H), 2.37-2.58 (m, 2H), 2.82-2.92 (m, 1H), 3.18 (s, 4H), 5.60 (s, 2H), 7.08-7.24 (m, 6H), 7.40-7.48 (m, 2H). |

Preparative Example 49

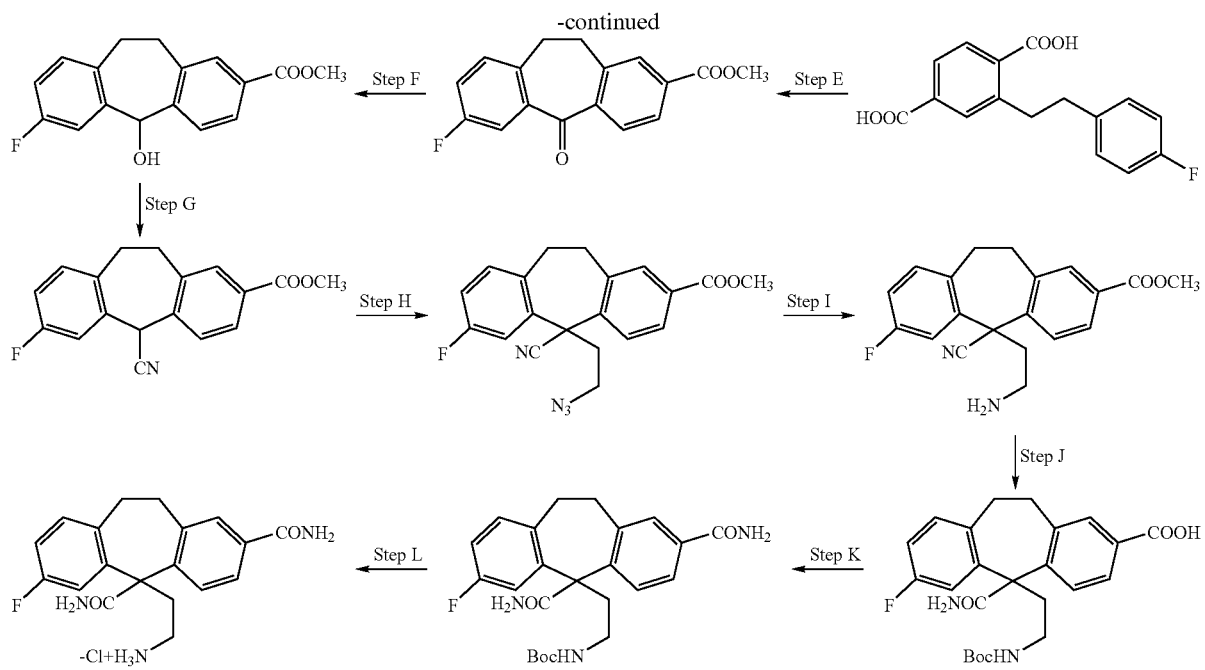

Step A

Commercially available 2,5-dibromotoluene (8.28 ml) was dissolved in hexane (90 ml) and treated with a 1.6 M solution of butyllithium in hexane (160 ml). The mixture was heated at 60° C. for 20 h, cooled to rt and poured onto a mixture of dry ice in Et$_2$O (750 ml). The mixture was allowed to warm to rt, filtered and the precipitate washed with 90 ml Et$_2$O. The precipitate was titrated with 140 ml glacial acetic acid to afford the title compound (10 g; 92%).

$^1$H-NMR δ (DMSO-d$_6$) 2.58 (s, 3H), 7.80-7.90 (m, 3H)

Step B

The title compound from Step A above (13 g) was suspended in MeOH (300 ml) and slowly treated with thionyl chloride (15.7 ml). The mixture was heated under reflux for 2 h to become a clear solution. The solvents were concentrated to afford the title compound (13.3 g; 88%; MH$^+$=209).

Step C

The title compound from Step B above (13.3 g) was dissolved in CCl$_4$ (500 ml) and commercially available N-bromosuccinimide (10.7 g) added. The mixture was heated to 80° C. and commercially available AIBN (327 mg) added. The mixture was then irradiated with a 100 W light bulb and heated at 100-105° C. for 2 h 30 min. The cooled mixture was filtered and the precipitate washed with 50 ml CCl$_4$. The filtrates were concentrated and the residue dissolved in CH$_3$CN (180 ml). The mixture was treated with triphenylphosphine (16 g) and heated under reflux for 3 h. The mixture was concentrated to ~100 ml and Et$_2$O (500 ml) added. The mixture was allowed to stand at rt for 30 Min, filtered and the precipitate washed with Et$_2$O (30 ml) to afford the title compound (20 g; 57%).

Step D

The title compound from Step C above (20 g) was suspended in CH$_3$CN (160 ml) and commercially available 4-Fluorobenzaldehyde (5.4 ml) added. The mixture was then treated with commercially available DBN (10 ml) and heated at 100° C. for 1 h. The mixture was concentrated to half its volume and poured into H$_2$O (150 ml). The mixture was extracted with EtOAc (2×150 ml), the organic phase washed with 5% HCl (2×75 ml), dried over MgSO$_4$ and concentrated. The residue was suspended in H$_2$O (240 ml) and MeOH (20 ml) and KOH (20 g) added. The mixture was heated at 100° C. for 16 h, cooled to rt and washed with CH$_2$Cl$_2$ (3×75 ml). The aqueous phase was acidified (pH~1) by adding conc. HCl, filtered, the precipitate washed with H$_2$O (20 ml) and air-dried. The residue was dissolved in MeOH (900 ml) and 10% Pd/C (1.5 g) added. The mixture was hydrogenated for 1 h, filtered, the catalyst washed with MeOH (50 ml) and concentrated to afford the title compound (8.6 g; 82%; MH$^+$=289).

Step E

The title compound from Step D above (1.44 g) was suspended in sulfolane (9 ml) and treated with polyphosphoric acid (30 g). The mixture was heated under N$_2$ at 170-175° C. for 3 h and poured onto ice-water (150 ml). The mixture was stirred at rt for 1 h, extracted with EtOAc (2×150 ml), dried over MgSO$_4$ and concentrated. The residue was dissolved in MeOH (20 ml) and treated with thionyl chloride (1 ml). The mixture was heated under reflux for 1 h and concentrated. The residue was dissolved in Et$_2$O (100 ml) and washed with sat. NaHCO$_3$ (30 ml) and brine (30 ml). The organic phase was separated, dried over MgSO$_4$ and concentrated. The residue was purified by chromatography on silica (CH$_2$Cl$_2$) to afford the title compound (960 mg; 67%; MH$^+$=285).

Step F

The title compound from Step E (1420 mg) was dissolved in CHCl$_3$ (20 ml) and MeOH (20 ml) and treated with NaBH$_4$ (230 mg). The mixture was stirred at rt for 1 h and poured onto ice-water (150 ml). The mixture was extracted with EtOAc (2×150 ml), the organic phase dried over MgSO$_4$ and concentrated to afford the title compound (1420 mg; 99%, M$^+$+Na=309).

Step G

The title compound from Step F above (1420 mg) was dissolved in THF (20 ml) and treated with thionyl chloride (0.91 ml). The mixture was stirred at rt for 16 h and concentrated without heating. The residue was dissolved in CH₃CN (17 ml) and treated with AgCN (785 mg). The mixture was heated at 90° C. for 2 h 30 Min, filtered and the salts washed with CH₃CN (40 ml). The filtrates were concentrated and the residue purified by chromatography on silica (CH₂Cl₂) to afford the title compound (1160 mg; 79%; MH⁺=296).

Step H

The title compound from Step G above (1327 mg) was dissolved in degassed THF (15 ml) and added to a suspension of NaH (119 mg) in degassed THF (5 ml). The mixture was heated at 90° C. for 1 h 15 min and cooled to rt. The mixture was then treated with 1,2-dibromoethane (0.81 ml) in THF (1 ml) and the mixture was heated at 90° C. for 4 h 30 min. The mixture was cooled to rt, diluted with 100 ml EtOAc, 10 ml brine and 10 ml sat. NH₄Cl. The organic phase was separated, dried over MgSO₄ and concentrated. The residue was dissolved in DMA (10 ml) and treated with NaN₃ (720 mg). The mixture was heated at 60° C. for 16 h and diluted with EtOAc (100 ml) and brine (15 ml). The organic phase was separated, washed with 0.1 m HCl (15 ml) and brine (15 ml). The organic phase was dried over MgSO₄, concentrated and the residue purified by chromatography on silica (EtOAc/cyclohexane, 1:4) to afford the title compound (931 mg; 57%; MH⁺=365).

Step I

The title compound from Step H above (1050 mg) was dissolved in MeOH (40 ml). The mixture was treated with concentrated HCl (0.25 ml) and 10% Pd/C (250 mg). The mixture was hydrogenated for 1 h, filtered and the catalyst washed with MeOH (20 ml). The filtrates were concentrated to afford a mixture of the title compound and the cyclic amidine in a 9:1 ratio (950 mg; 97%; MH⁺=339).

Step J

The title compounds from Step I above (950 mg) were treated with 57% H₂SO₄ (5 ml) and heated under N₂ at 90° C. for 3 h. The mixture was cooled, diluted with H₂O (80 ml) and made alkaline (pH~10) by adding 50% NaOH. The mixture was washed with EtOAc (20 ml) and the aqueous phase diluted with dioxane (40 ml). The mixture was treated with an excess of Boc₂O and stirred at rt for 16 h while the pH was kept at pH~10.0. The mixture was acidified to pH~4.0 by adding 1 M HCl and extracted with EtOAc (2×150 ml). The organic phase was dried over MgSO₄ and concentrated. The residue was purified by chromatography on silica (CH₂Cl₂/MeOH, 9:1) to elute the cyclic amidine side product, followed by CH₂Cl₂/MeOH (4:1) to afford the title compound (282 mg, 23%; MNa⁺=465).

Step K

The title compound from Step J above (135 mg) was dissolved in THF (6 ml) and triethylamine (0.056 ml). The mixture was cooled to −40° C. and treated with ethyl chloroformate (0.031 ml). The mixture was stirred at −40° C. for 1 h, diluted with 4 ml THF and treated at 0° C. with 33% aqueous ammonia solution (10 ml). The mixture was stirred at 0° C. for 1 h and then 1 h at rt. The mixture was diluted with EtOAc (80 ml) and washed with brine (25 ml), sat. NH₄Cl (25 ml and brine (25 ml). The organic phase was dried over MgSO₄ and concentrated. The residue was purified by chromatography on silica (CH₂Cl₂/MeOH, 9:1) to afford the title compound (97 mg, 72%, MNa⁺=464).

Step L

The title compound from Step K above (94 mg) was treated with 4 M solution of HCl in dioxane (2.5 ml) and the flask was agitated for 30 min. The mixture was concentrated and the residue dissolved in 5 ml H₂O. The mixture was filtered through a Millex VV (0.1 μM) filter unit and the filtrate concentrated to afford the title compound (65.8 mg, 82%, MH⁺=342).

Preparative Example 50

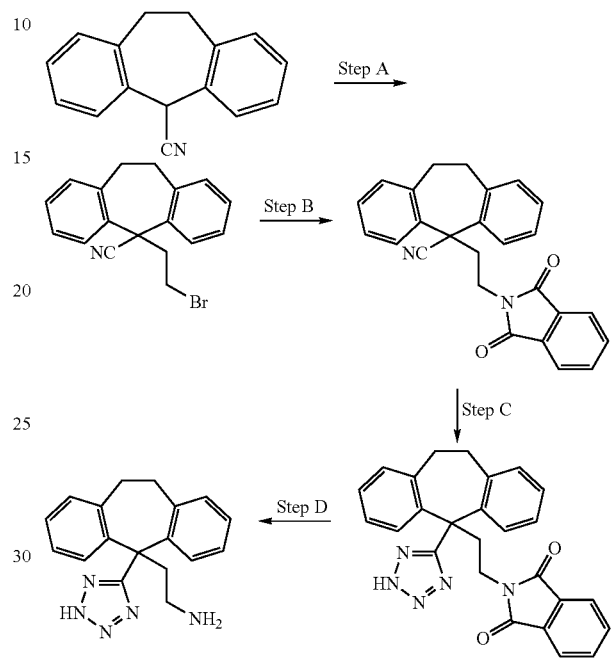

Step A

The title compound from Preparative Example 13 Step A (3.3 g) was dissolved in THF (5 ml) and slowly added to a suspension of NaH (540 mg) in THF (10 ml). The mixture was heated at reflux for 30 min, cooled to rt and treated with 1,2-dibromoethane (4 ml). The reaction was stirred at 60° C. overnight, cooled to rt and filtered. The solvent was removed affording the title compound (4.8 g; 98%)

¹HNMR δ CDCl₃ 2.9-3.2 (m, 6H), 3.2-3.4 (m, 2H), 7.1-7.3 (m, 6H), 7.9-8.0 (m, 2H)

Step B

The title compound from Step A above (1.5 g) and potassium phthalimide (13.8 g) were suspended in DMF (20 ml) and stirred at 100° C. overnight. The precipitate was removed and the reaction was concentrated in vacuum. Chromatography of the residue on silica (EtOAc/cyclohexane) afforded the title compound (1.4 g; 78%).

¹HNMR δ CDCl₃ 2.8-2.9 (m, 2H), 3.0-3.2 (m, 2H), 3.4-3.6 (m, 2H), 3.6-3.8 (m, 2H), 7.1-7.3 (m, 6H), 7.6-7.7 (m, 2H), 7.7-7.8 (m, 2H), 7.9-8.0 (m, 2H)

Step C.

The title compound from Step B above (1.40 g) was dissolved in toluene (30 ml) and treated with dibutyltin oxide (446 mg) and trimethylsilylazide (2.3 ml). The mixture was heated under a N₂ atmosphere at 90° C. overnight. Additional dibutyltin oxide (200 mg) and trimethylsilylazide (2.3 ml) were added and the reaction was continued for 24 h at 90° C. The solvent was removed and the residue was treated with EtOAc (30 ml) and 1 N HCl (30 ml) at 50° C. for 1 h. The phases were separated and the organic phase was concentrated. The residue was purified by chromatography on silica (EtOAc/cyclohexane) to afford the title compound (600 mg, 39%, MH+=436).

Step D

The title compound from Step C above (200 mg) was dissolved in ethanol (5 ml) and treated with hydrazine hydrate (100 mg) at rt. The solution was heated at 80° C. for 2 h and then stirred for 1 h at rt. The reaction was filtered and the filtrate was concentrated. The residue was treated with CHCl₃ and filtered again. The filtrate was concentrated to afford the title compound (60 mg, 43%, MH+=306).

Preparative Example 51

Step B

The title compound from Step A above (2.3 g) was dissolved in THF (50 ml). Methyl iodide (0.95 ml) and N,N-diisopropylethylamine (3.2 ml) were added. The reaction was stirred at rt for 2 h. The reaction mixture was filtered and concentrated to afford the title compound (2.3 g; 90%).

¹H-NMR δ CDCl₃ 2.6 (s, 3H), 3.9 (s, 3H), 7.0-7.2 (m, 2H), 7.6-7.7 (m, 1H)

Step C

The title compound from Step B above (8.9 g) and commercially available N-bromosuccinimide (14 g) were sus-

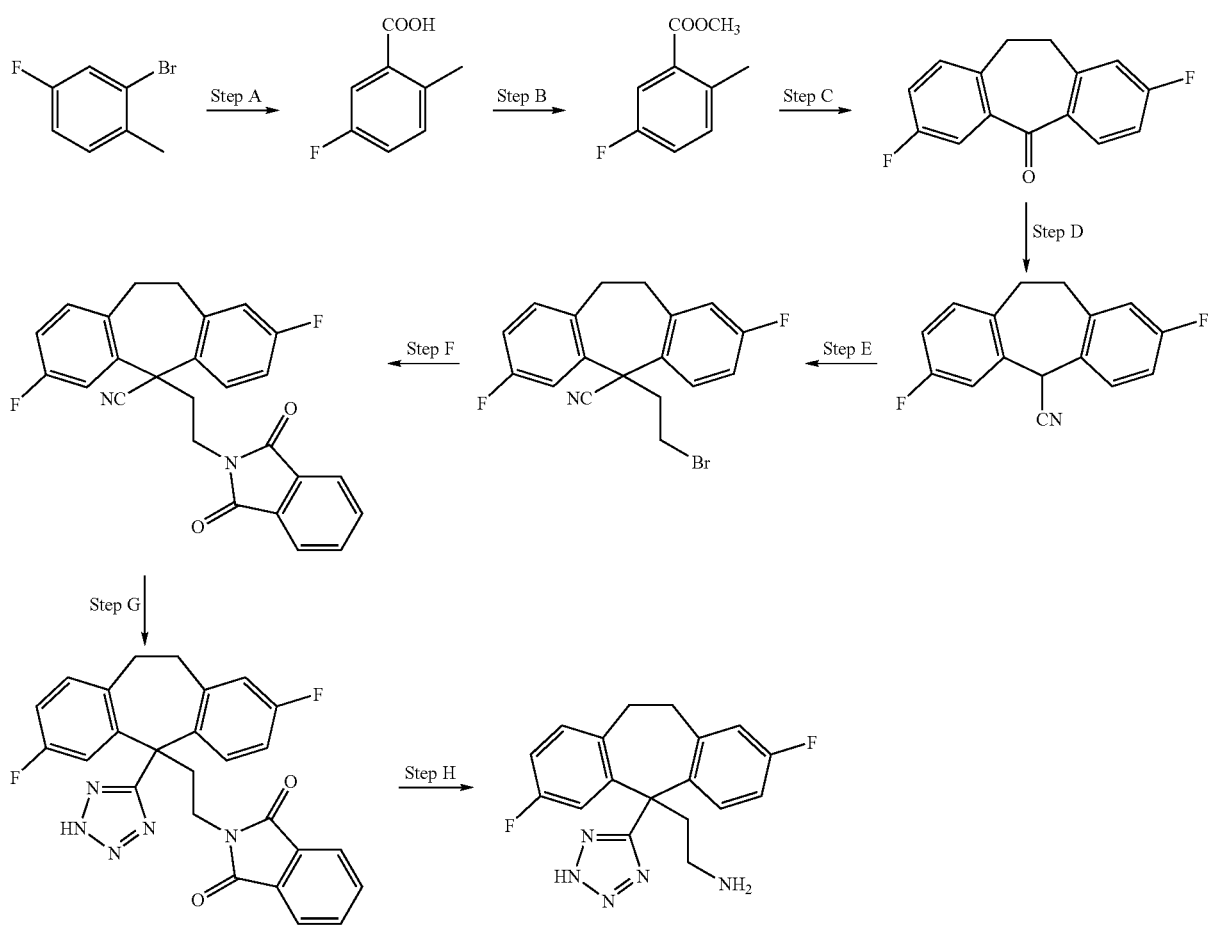

Step A

Commercially available 2-bromo-4-fluorotoluene (5 g) was diluted with diethyl ether (10 ml). About ⅓ of the resulting solution was added to magnesium turnings (761 mg) which were overlayed with Et₂O (25 ml). The remaining 2-bromo-4-fluorotoluene solution was added dropwise after the reaction started. The reaction was kept at reflux for 2 h. The Grignard reagent was poured onto a mixture of crushed dry ice in Et₂O (750 ml). The resulting mixture was allowed to warm to rt. The solvent was removed, the resulting residue was treated with EtOAc (100 ml) and extracted with aqueous 1 N HCl (100 ml). The organic phase was dried over MgSO₄, filtered and concentrated to afford the title compound (2.3 g; 56%).

¹H-NMR δ CDCl₃ 2.5 (s, 3H), 7.0-7.2 (m, 2H), 7.7 (m, 1H)

pended in CCl₄ (500 ml). The mixture was heated to 80° C. and AIBN (270 mg) added. The mixture was irradiated with a 100 W light bulb and heated at 100-105° C. for 3.5 h. The cooled mixture was filtered. The filtrate was concentrated and the residue dissolved in CH₃CN (150 ml). The mixture was treated with triphenylphosphine (14 g), heated under reflux for 3 h and then concentrated. The residue was suspended in CH₃CN (160 ml) and treated with commercially available 3-fluorobenzaldehyde (6.5 g) and DBN (13 ml). The mixture was heated under reflux for 3 h. The reaction was concentrated to half its volume and poured into H₂O (150 ml). The mixture was extracted with EtOAc (3×150 ml), the organic phase separated and concentrated. The residue was suspended in 1:1H₂O/MeOH-mixture (100 ml) and treated with KOH (30 g). The mixture was stirred at 60° C. overnight, cooled to rt and washed with CHCl₃ (3×100 ml). The aqueous phase was acidified (pH~1) by adding conc. HCl and extracted with EtOAc. The organic phase was separated and concentrated. The crude residue was suspended in sulfolane (20 ml) and treated with polyphosphoric acid (25 g). The mixture was heated under N₂ at 200° C. for 2 h, poured onto ice-water (150 ml) and stirred at rt overnight. The mixture was extracted with EtOAc and concentrated. The residue was dissolved in Et₂O and extracted with H₂O. The organic phase was separated, dried over MgSO₄ and concentrated. The residue was purified by chromatography on silica (EtOAc/Cyclohexane) to afford the title compound (4.0 g; 31%; MH⁺=245).

Step D

The title compound from Step C above (5.4 g) was dissolved in CHCl₃ (5 ml) and MeOH (30 ml) and treated with NaBH₄ (1.4 g). The mixture was stirred at rt for 1 h and concentrated. The residue was suspended in CHCl₃ (50 ml) and extracted with aqueous HCl (50 ml; pH=1). The organic phase was separated, concentrated, then resuspended in toluene and concentrated again. The residue was dissolved in toluene (50 ml). SOCl₂ (3.94 ml) was added at 0° C. The reaction was stirred overnight at RT. The solvent was removed and the remaining material was suspended in toluene and concentrated. The residue was dissolved in CH₃CN (50 ml) and treated with AgCN (2.96 g). The mixture was heated at reflux for 2 h and then stirred at 60° C. overnight. The mixture was filtered and the filtrate concentrated. The residue was purified by chromatography on silica (EtOAc/Cyclohexane) to afford the title compound (4.4 g; 78%).

$^1$H-NMR δ CDCl₃ 3.1-3.2 (m, 4H), 5.3 (s, 1H), 6.7-6.9 (m, 3H), 7.0-7.2 (m, 2H), 7.4 (m, 1H)

Step E

The title compound from Step D above (1.5 g) was dissolved in THF (5 ml) and slowly added at rt to a suspension of NaH (212 mg) in THF (10 ml). The mixture was heated at 60° C. for 30 min, then cooled to 0° C. and treated with 1,2-dibromoethane (2.3 ml). The reaction was stirred at 60° C. for 3 h, cooled to rt and filtered. The filtrate was concentrated to afford the title compound (2.1 g; 99%).

$^1$H-NMR δ CDCl₃ 2.8-3.0 (m, 4H), 3.0-3.2 (m, 2H), 3.2-3.4 (m, 2H), 6.8-7.2 (m, 4H), 7.6 (m, 1H), 7.8-7.9 (m, 1H)

Step F

The title compound from Step E above (2.1 g) and potassium phthalimide (5.4 g) were suspended in DMF (30 ml) and stirred at 60° C. overnight. The solvent was removed and the residue dissolved in CHCl₃, filtrated and concentrated. The residue was purified by chromatography on silica (EtOAc/cyclohexane) to afford the title compound (1.91 g; 76%)

$^1$HNMR δ CDCl₃ 2.8-3.2 (m, 4H), 3.4-3.6 (m, 2H), 3.7-3.9 (m, 2H), 6.8-7.0 (m, 3H), 7.1-7.2 (m, 1H), 7.7-8.0 (m, 6H)

Step G

The title compound from Step F (1.90 g) was dissolved in toluene (20 ml) and treated with dibutyltin oxide (553 mg) and trimethylsilylazide (3.7 ml). The mixture was heated under a N₂ atmosphere at 90° C. for 4 d. The reaction was quenched with aqueous 1 N HCl (20 ml) and stirred for 1 h at 50° C. The phases were separated, the aqueous phase was extracted with toluene and the combined organic phase concentrated. The residue was purified by chromatography on silica (EtOAc/cyclohexane) to afford the title compound (600 mg, 33%, MH⁺=472).

Step H

The title compound from Step G above (300 mg) was dissolved in ethanol (5 ml) and treated with hydrazine hydrate (127 mg). The solution was stirred at 80° C. for 2 h and subsequently stirred for 1 h at rt. The solvent was removed and the residue treated with 1 N HCl (20 ml) and CHCl₃ (10 ml). The aqueous phase was separated, filtered and concentrated affording the title compound (240 mg, 100% MH⁺=342).

Preparative Example 52

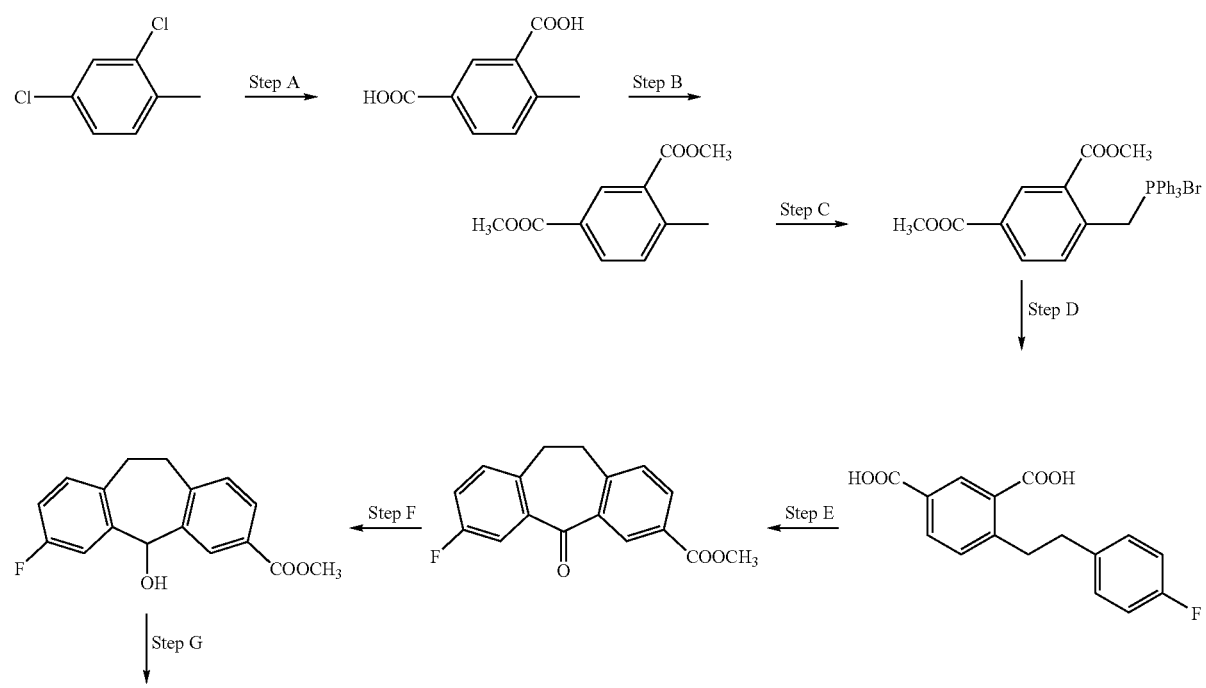

-continued

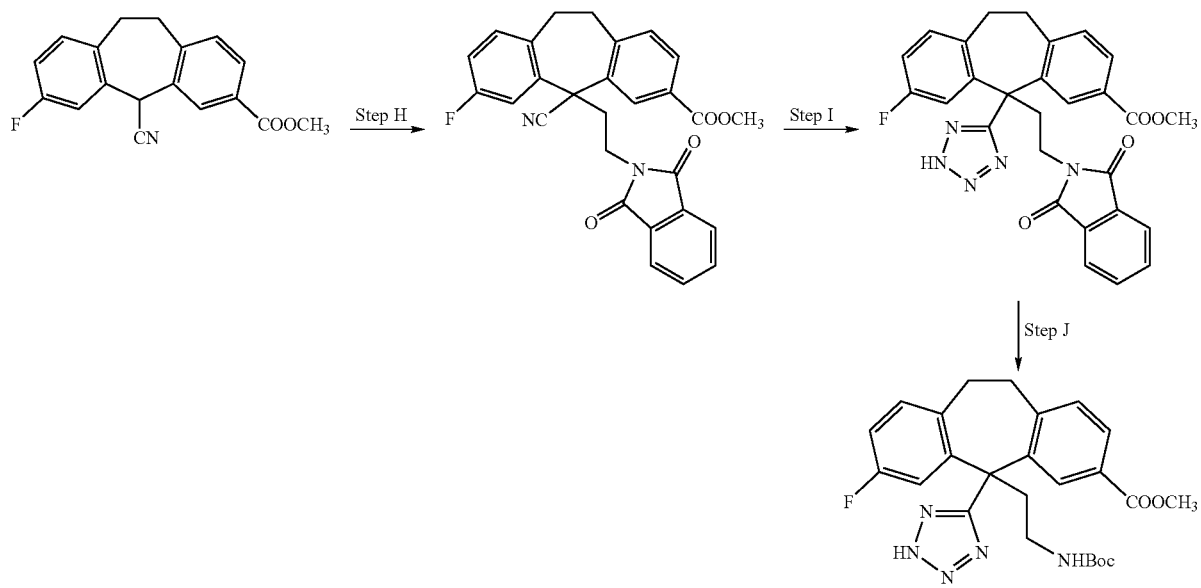

Step J

Step A

Commercially available 2,4-dichlorotoluene (24.6 g) and dry copper(I) cyanide (50 g) in N-methylpyrrolidone (130 ml) were heated under reflux (200-216° C.) for 4 d. While hot (110° C.), the mixture was poured into a flask containing 33% aq. $NH_4OH$ solution (390 ml) and toluene (100 ml) and stirred to break up the lumps. After the mixture was cooled to rt, $Et_2O$ (100 ml) was added and filtered through cloth. The precipitate was washed (2×100 ml $Et_2O/CHCl_3$ 1:1). The dark filtrate was poured into a separatory funnel and the phases were separated with the aid of additional $Et_2O$ (100 ml). The aqueous phase was extracted with $Et_2O/CHCl_3$ 1:1 (2×100 ml). The combined organic phases were washed with 10% $NH_4OH$ solution (4×110 ml, until the basic phase was no longer blue), with $H_2O$ (100 ml), and brine (100 ml). The organic phase was separated, dried over $MgSO_4$ and concentrated. The residue was mixed with NaOH (24.8 g) and diethylene glycol (275 ml) was added together with a few drops of $H_2O$. The mixture was heated at 215-220° C. overnight. The cooled mixture was diluted with $H_2O$ (220 ml) and acidified to pH 1 with 10% aq. HCl. The suspension was filtered and the precipitate washed with 0.1 N HCl (50 ml). The solid was crystallised from glacial acetic acid to afford the title compound (18.4 g, 78%; $MH^+$=181).

Step B

Following a similar procedure as that described in Preparative Example 49 Step B, the title compound from Step A above (22.1 g) was reacted to afford the title compound (30.0 g, 100%).

$^1$H-NMR ($CDCl_3$) δ: 2.65 (s, 3H), 3.91 (s, 3H), 3.92 (s, 3H), 7.32 (d, 1H), 8.04 (dd, 1H), 8.56 (d, 1H).

Step C

Following a similar procedure as that described in Preparative Example 49 Step C, the title compound from Step B above (30.0 g) was reacted. Differing from the cited example, the final mixture was allowed to stand over the weekend to form the precipitate. After filtration, the crude title compound was obtained (38.0 g, 100%; $[M-Br]^+$=469).

Step D

Following a similar procedure as that described in Preparative Example 49 Step D, the title compound from Step C above (38.0 g) was reacted. Differing from the cited example, the hydrogenation was run for 2 days. (29.2 g, 77%; $MH^+$=289).

Step E

Following a similar procedure as that described in Preparative Example 49 Step E, the title compound from Step D above (4.32 g) was reacted and the title compound obtained (1.77 g, 41%; $MH^+$=285).

Step F

Following a similar procedure as that described in Preparative Example 49 Step F, the title compound from Step E above (2.39 g) was reacted and the title compound obtained (2.45 g, 100%; $MNa^+$=309).

Step G

Following a similar procedure as that described in Preparative Example 49 Step G, the title compound from Step F above (3.07 g) was reacted and the title compound was obtained (2.17 g, 69%; $MH^+$=296).

Step H

The title compound from Step G above (2.17 g) was dissolved in THF (30 ml) and added to a suspension of NaH (250 mg) in THF (9 ml). The mixture was heated at 90° C. for 1 h 15 min and cooled to rt. The mixture was then treated with 1,2-dibromoethane (1.6 ml) in THF (3.7 ml) and the mixture was heated at 90° C. for 4 h 30 min. The mixture was cooled to rt, diluted with 200 ml EtOAc, 20 ml brine and 20 ml sat. $NH_4Cl$. The organic phase was separated, dried over $MgSO_4$ and the residue purified by chromatography on silica ($CH_2Cl_2$) to afford the bromoethyl intermediate (1.42 g, 50%; $[MNH_4]^+$=419) and starting material (636 mg, 24%). The bromoethyl compound (1.42 g) was dissolved in anhydrous DMF (18 ml) and treated with potassium phthalimide (1.96 g). The suspension was stirred at 80° C. overnight. The solvent was removed and the residue partitioned between EtOAc (50 ml), H₂O (50 ml) and brine (50 ml). The aqueous phase was extracted with EtOAc (2×50 ml) and the combined organic phase dried over MgSO₄ and concentrated. The residue was purified by chromatography on silica (CH₂Cl₂/MeOH) to afford the title compound (1525 mg; 92%; MH⁺=469).

Step I

The title compound from Step H above (1475 mg) was dissolved in anhydrous toluene (25 ml) and treated with dibutyltin oxide (784 mg) and trimethylsilylazide (8.3 ml). The mixture was heated under a N₂ atmosphere at 90° C. for 3 days. The solvent was removed, the residue dissolved in MeOH (10 ml) and concentrated. The residue was partitioned between EtOAc (100 ml) and 10%. NaHCO₃ (100 ml). The aqueous phase was extracted with EtOAc (2×70 ml) and the combined organic phase dried over MgSO₄ and concentrated. The residue was purified by chromatography on silica (CH₂Cl₂/MeOH) to afford the title compound (1216 mg, 75%, MH⁺=512).

Step J

The title compound from Step I above (1216 mg) was dissolved in anhydrous MeOH (14 ml) and Et₃N (0.66 ml). The mixture was cooled to 5° C. and N,N'-dimethylaminopropylamine (0.71 ml) added. The mixture was stirred at rt for 25 h and subsequently evaporated, toluene (10 ml) added, evaporated again and dried in HV. The residue was dissolved in dioxane (8 ml) and H₂O (8 ml). To the slightly turbid solution was added Boc₂O (2.6 g) and Et₃N (1.2 ml) and the mixture was stirred at rt overnight. After evaporation of the solvent, H₂O (20 ml) was added and the solution acidified to pH~4.0 by adding 1 M HCl and the aqueous solution extracted with EtOAc (3×50 ml). The combined organic phase was washed with brine (15 ml), separated, dried over MgSO₄ and concentrated. The residue was purified by chromatography on silica (CH₂Cl₂MeOH) to afford the title compound (567 mg, 50%, MNa⁺=504).

Preparative Example 53

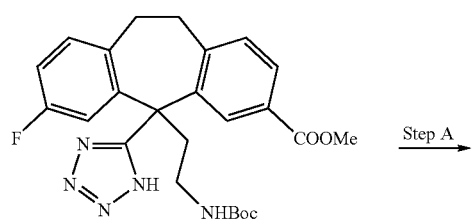

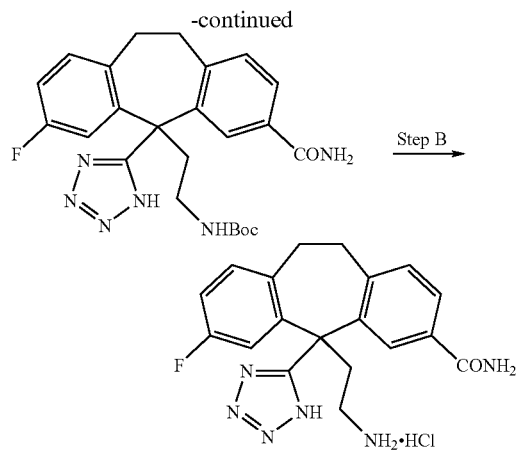

Step A

The title compound from Preparative Example 52 (215 mg) was dissolved in THF (4 ml) and 33% NH₄OH solution (40 ml) was added. The solution was stirred in a closed vessel at 80° C. overnight. The reaction mixture was allowed to cool to rt and subsequently evaporated to dryness. The crude product, which consisted of a mixture of the amide (MNa⁺=489) and the free acid (MNa⁺=490), was dissolved in anhydrous THF (8.5 ml) and triethylamine (0.28 ml) added. The ensuing precipitate was dissolved by adding anhydrous CH₃CN (6 ml). The mixture was cooled to −40° C. and ethylchloroformate (0.17 ml) was slowly added. The mixture was stirred at −25° C. for 1 h and allowed to warm to 0° C. At 0° C. 7 M NH₃/MeOH-solution (10 ml) was added and the mixture was stirred at 0° C. for 30 min and for 1 h at rt. The mixture was concentrated and the residue dissolved in H₂O (14 ml) and THF (3 ml). The pH was adjusted to pH~4.0 by adding 0.1 N HCl and the aqueous phase—after addition of brine (10 ml)—extracted with EtOAc containing 10% THF (4×33 ml) and CH₂Cl₂ containing 10% THF (1×25 ml)). The combined organic phase was washed with brine (15 ml), dried over MgSO₄ and concentrated to afford the title compound (241 mg; 100%, MNa⁺=489).

Step B

The title compound from Step A above (240 mg) was suspended/dissolved in CH₂Cl₂/MeOH 4:1 (5 ml) and a 4 M solution of HCl in dioxane (7 ml) added after which a clear solution was obtained. The mixture was stirred at rt for 3 h and concentrated. The residue was partitioned between EtOAc containing 10% THF (25 ml) and 0.01 N HCl (25 ml). The organic phase was extracted with H₂O (25 ml) and 0.01 N HCl (25 ml). The combined aqueous phase was concentrated to afford the title compound (162 mg, 90%, MH⁺=367).

Preparative Example 54

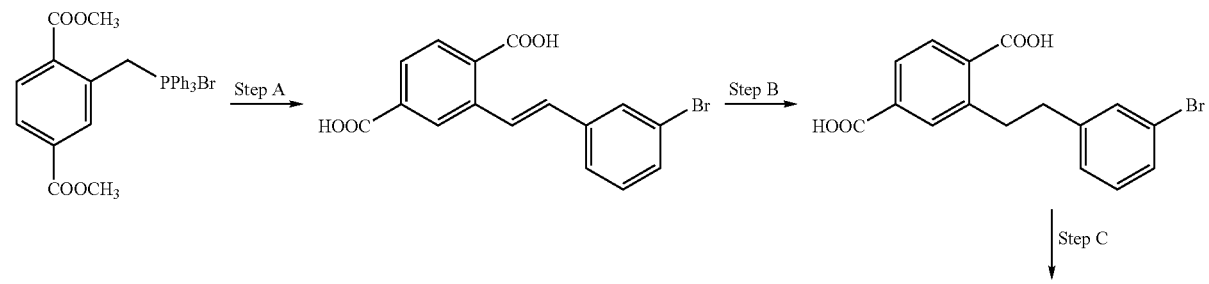

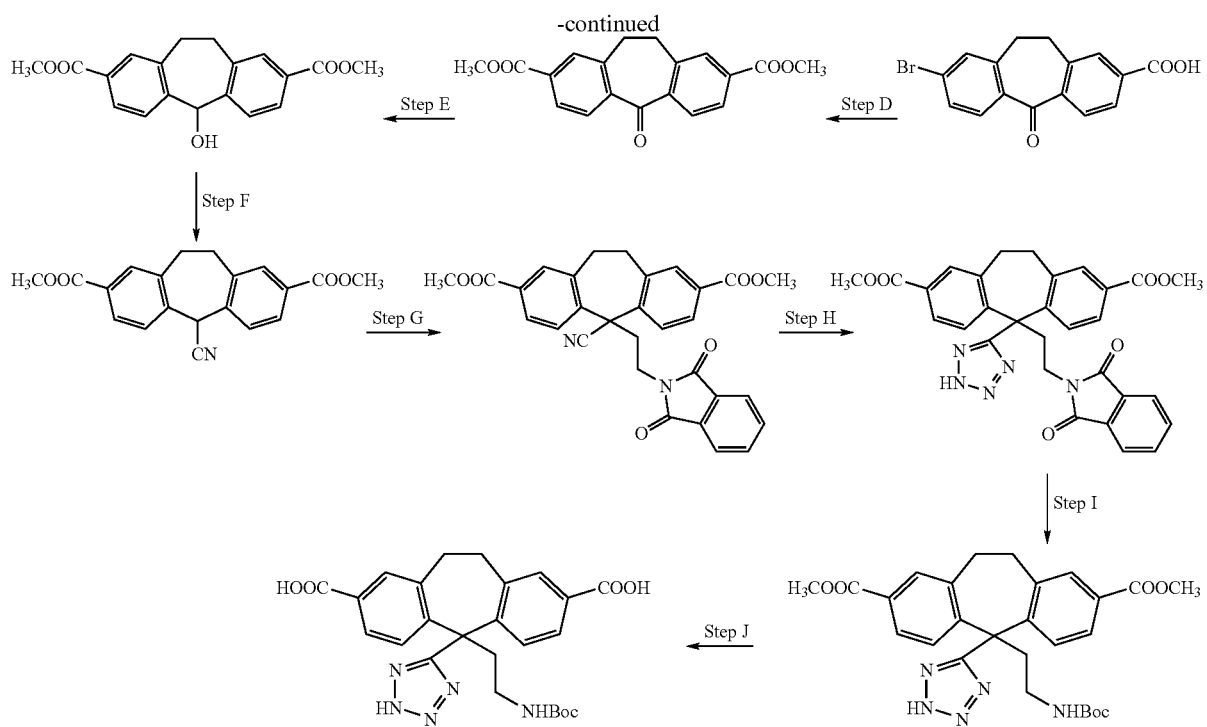

Step A

The title compound from Preparative Example 49 Step C (47.6 g) was suspended in $CH_3CN$ (350 ml) and commercially available 3-bromobenzaldehyde (13.9 ml) added. After the addition of DBN (24 ml), the mixture was heated at 100° C. for 1 h. The mixture was cooled and the precipitate collected by filtration to afford the trans-olefin (7.5 g). The mother liquor was concentrated to half its volume and poured into $H_2O$ (300 ml). The mixture was extracted with EtOAc (2×300 ml), the organic phase washed with 5% HCl (2×80 ml), dried over $MgSO_4$ and concentrated. To this residue was added the trans olefin from above and the mixture was suspended in $H_2O$ (500 ml), MeOH (60 ml) and dioxane (60 ml). After the addition of KOH (47 g), the mixture was heated at 60° C. for 16 h, cooled to rt and washed with $CH_2Cl_2$ (3×100 ml). The aqueous phase was made acidic (pH~1) by adding conc. HCl, filtered, the precipitate washed with $H_2O$ (150 ml) and air-dried to afford the title compound as a mixture of cis/trans-olefins (26.5 g; 88%; $MH^+$=347).

Step B

The title compound from Step A above (6 g) was dissolved in MeOH (450 ml) and EtOAc (150 ml). After the addition of a suspension of 5% Pt/C (2.5 g) in 10% HCl (5 ml) and MeOH (10 ml), the mixture was hydrogenated for 6 h. The mixture was filtered, the catalyst washed with MeOH (60 ml) and the filtrates evaporated to afford the title compound (5.5 g, 91%).

$^1$HNMR δ (DMSO-$d_6$) δ 2.81-2.90 (m, 2H), 3.13-3.27 (m, 2H), 7.23-7.32 (m, 2H), 7.39-7.45 (m, 1H), 7.51 (s, 1H), 7.85-7.95 (m, 3H)

Step C

The title compound from Step B above (4 g) was suspended in sulfolane (9 ml) and treated with polyphosphoric acid (30 g). The mixture was heated under $N_2$ at 175-180° C. for 2 h 30 min and poured into ice-water (250 ml). The mixture was stirred at rt overnight and the precipitate collected by filtration to afford the crude title compound (3.56 g; 94%; $MH^+$=331).

Step D

The title compound from Step C above (3.5 g) was dissolved in N-methyl pyrrolidone (25 ml) and CuCN (900 mg) added. The mixture was heated at 200° C. for 8 h, cooled to rt and diluted with $H_2O$ (200 ml) and 1 M HCl (50 ml). The mixture was extracted with EtOAc (3×100 ml) and the combined organic phase washed with $H_2O$ (100 ml) and brine (100 ml). The organic phase was dried over $MgSO_4$ and evaporated. The residue was dissolved in dioxane (50 ml) and conc. HCl (50 ml) added. The mixture was heated at 90° C. for 18 h and the solvents evaporated. The residue was suspended in MeOH (75 ml), treated with $SOCl_2$ (1.5 ml) and heated under reflux for 1 h 30 min. The mixture was concentrated to half its volume, diluted with $Et_2O$ (300 ml) and washed with sat. $NaHCO_3$ (80 ml) and brine (80 ml). The organic phase was separated, dried over $MgSO_4$ and evaporated. The residue was purified by chromatography on silica (EtOAc/hexane, 1:4) to afford the title compound (1040 mg; 27%; $MH^+$=325).

Step E

The title compound from Step D above (1040 mg) was dissolved in $CHCl_3$ (15 ml) and MeOH (15 ml) and the $NaBH_4$ (150 mg) added. The mixture was stirred at rt for 1 h, diluted with ice water (80 ml) and extracted with EtOAc (2×100 ml). The organic phase was dried over $MgSO_4$ and concentrated. The residue was purified by chromatography on silica ($CH_2Cl_2$/acetone, 98:2->$CH_2Cl_2$/acetone, 95:5) to afford the title compound (817 mg, 78%, $MNa^+$=349).

Step F

The title compound from Step E above (817 mg) was dissolved in THF (10 ml) and treated with $SOCl_2$ (0.46 ml). The mixture was stirred at rt overnight and the solvents evaporated. The residue was dissolved in $CH_3CN$ (10 ml) and benzene (5 ml) and added to a suspension of AgCN (406 mg) in $CH_3CN$ (10 ml). The mixture was heated at 90° C. for 5 h, filtered and the salts washed with $CH_3CN$ (10 ml). The filtrates were evaporated and the residue purified by chromatography on silica ($CH_2Cl_2$/acetone, 98:2) to afford the title compound (572 mg, 68%, $MH^+$=336).

Step G

The title compound from Step F above (676 mg) was suspended in THF (20 ml) and DMF (5 ml) and treated under a N₂ atmosphere with NaH (106 mg). The mixture was heated at ~95° C. for 75 Min, cooled to rt and treated with a solution of 1,2-dibromoethane (0.7 ml) in THF (3 ml). The mixture was then heated at 95° C. for 10 h, cooled to rt and treated with sat. NH₄Cl (15 ml) and EtOAc (100 ml). The organic phase was separated, washed with brine (15 ml), dried over MgSO₄ and concentrated. The residue was dissolved in DMA (8 ml) and treated with potassium phthalimide (554 mg). The mixture was heated at 60° C. overnight, the solvent removed and the residue dissolved in EtOAc (50 ml) and H₂O (15 ml). The organic phase was separated, washed with brine (15 ml) and concentrated. The residue was purified by chromatography on silica (CH₂Cl₂/acetone, 98:2) to afford the title compound (740 mg, 72%, MNH₄⁺=526).

Step H

The title compound from Step G above (600 mg) was suspended in toluene (5 ml) and treated with dibutyltin oxide (138 mg) and trimethylsilylazide (1.45 ml). The mixture was heated under a N₂ atmosphere at 90-95° C. for 3 d and the solvent evaporated. The residue was suspended in MeOH (10 ml) and the solvent evaporated. The residue was dissolved in EtOAc (30 ml) water (10 ml). The organic phase was separated, dried over MgSO₄ and concentrated. The residue was purified by chromatography on silica (CH₂Cl₂/MeOH, 95:5) to afford the title compound (415 mg, 68%, MH⁺=552).

Step I

The title compound from Step H above (415 mg) was dissolved in MeOH (6 ml) and triethylamine (0.23 ml). The mixture was cooled to 0° C. and 3-dimethylaminopropylamine (0.23 ml) added. The mixture was stirred at 0° C. for 10 min and at rt overnight. The mixture was concentrated, dissolved in MeOH (10 ml), again concentrated and dried in HV. The residue was dissolved in dioxane (5 ml) and H₂O (5 ml) and the pH adjusted to pH=8-9 by adding 1 M KOH. The mixture was then treated with Boc2O (870 mg) and stirred overnight. The mixture was adjusted to pH=4 by adding 1 M HCl and diluted with EtOAc (150 ml). The organic phase was separated and the aqueous phase extracted with EtOAc (2×75 ml). The combined organic phase was dried over MgSO₄ and concentrated. The residue was purified by chromatography on silica gel (CH₂Cl₂/MeOH, 95:5->4:1) to afford the title compound (227 mg, 58%, MH+=522).

Step J

The title compound from Step I above (227 mg) was dissolved in dioxane (10 ml) and 1 M KOH (3.75 ml) added. The mixture was stirred at rt overnight and the pH adjusted to pH=4 by adding 1 M HCl. The mixture was extracted with EtOAc, containing 10% THF (2×150 ml). The organic phase was separated, dried over MgSO₄ and concentrated to afford the title compound (177 mg, 82%; MH⁺=494).

Preparative Example 55

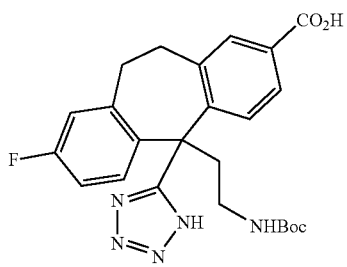

If one were to follow a similar procedure as described in Preparative Example 54, but using 3-fluorobenzaldehyde in Step A and omitting Step D, one would obtain the desired compound.

Preparative Example 56

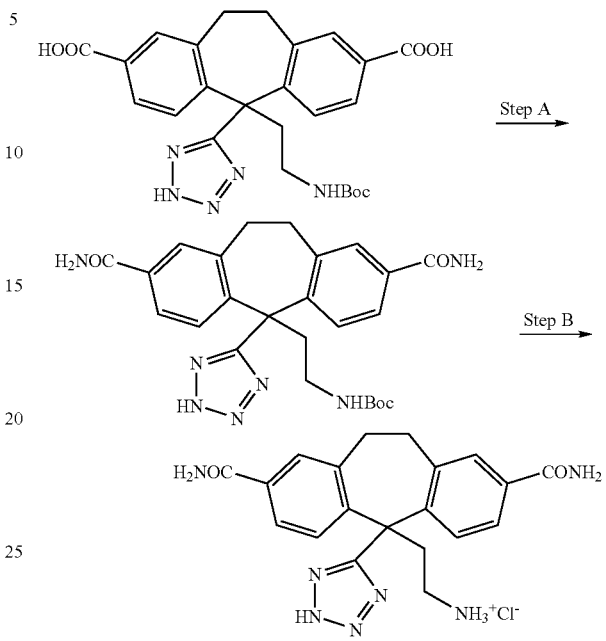

Step A

The title compound from Preparative Example 54 (177 mg) was dissolved in THF (6 ml) and triethylamine (0.2 ml) added. The precipitate was dissolved/suspended by adding CH₃CN (3 ml). The mixture was cooled to −40° C. and ethylchloroformate (0.1 ml) was slowly added. The mixture was stirred at −25° C. for 1 h and allowed to warm to 0° C. At 0° C. 7 M NH₃/MeOH-solution (7 ml) was added and the mixture was stirred at 0° C. for 30 min and 1 h at rt. The mixture was concentrated and the residue dissolved in H₂O (10 ml) and THF (2 ml). The pH was adjusted to pH~4.0 by adding 100 mM HCl and the aqueous phase extracted with EtOAc (4×30 ml) containing 10% THF. The organic phase was dried over MgSO₄ and concentrated to afford the title compound (110 mg; 62%, MNa⁺=514).

Step B

The title compound from Step A above (103 mg) was dissolved in THF (2 ml) and a 4 M solution of HCl in dioxane (5 ml) added. The mixture was stirred at rt for 2 h and concentrated. The residue was dissolved in H₂O (20 ml) and washed with EtOAc (2×8 ml). The aqueous phase was concentrated, the residue dissolved in 50 mM HCl (6 ml) and filtered through a Millex VV (0.1 μM) filter unit. The filtrate was concentrated to afford the title compound (90 mg, 94%, MH⁺=392).

Preparative Example 57

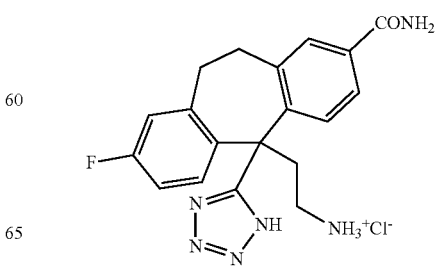

If one were to follow a similar procedure as described in Preparative Example 56, but using the title compound from Preparative Example 55, one would obtain the desired compound.

Preparative Example 58

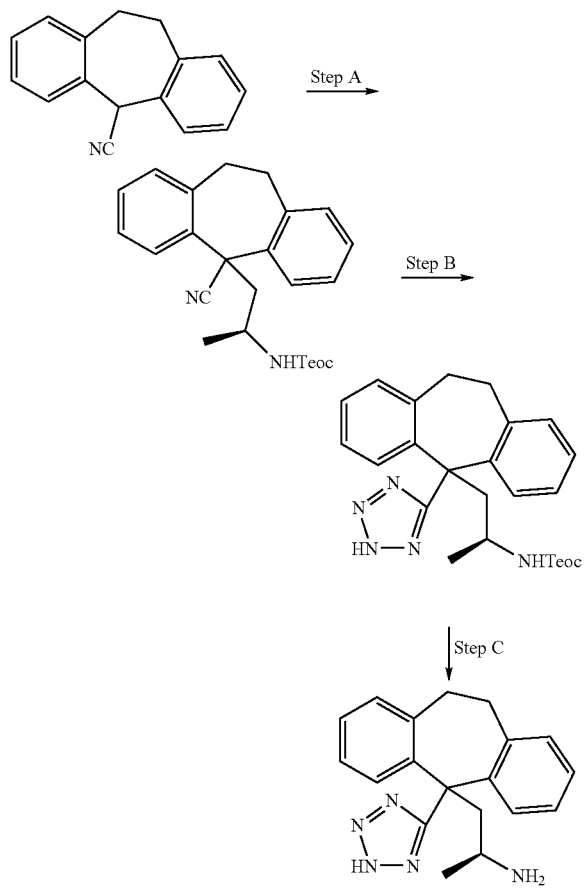

Step A

A suspension of NaH (66 mg) in THF (10 ml) was added to a solution of the title compound from Preparative Example 13 Step A (0.57 g) in THF (20 ml) and heated at 65° C. for 1 h. Then the mixture was cooled to 0° C. and a solution of Preparative Example 21 (0.74 g) in THF (10 ml) was added. The suspension was heated at 65° C. for 5 h and then diluted with ethyl acetate. The organic phase was washed with water, brine and dried over MgSO$_4$. Removal of the solvents and column chromatography (EtOAc/hexane, 1:4) afford the title compound (630 mg, 58%, MH$^+$=421).

Step B

The title compound from Step A above (632 mg) was dissolved in DMF (10 ml) and treated with NaN$_3$ (1.2 g) and NH$_4$Cl (963 mg). The mixture was heated under a N$_2$ atmosphere at 110° C. for 3 d and the solvent evaporated. Column chromatography (CH$_2$Cl$_2$/MeOH, 9:1) afford the title compound (350 mg, 51%, MH$^+$=464).

Step C

The title compound from Step B above (350 mg) was dissolved in THF (10 ml) and treated with TBAF.3H$_2$O. The mixture was stirred at rt for 4 h and the solvent evaporated. Preparative TLC using CH$_2$Cl$_2$/MeOH (4:1) afford the title compound (121 mg, 50%, MH$^+$=320).

Preparative Example 59

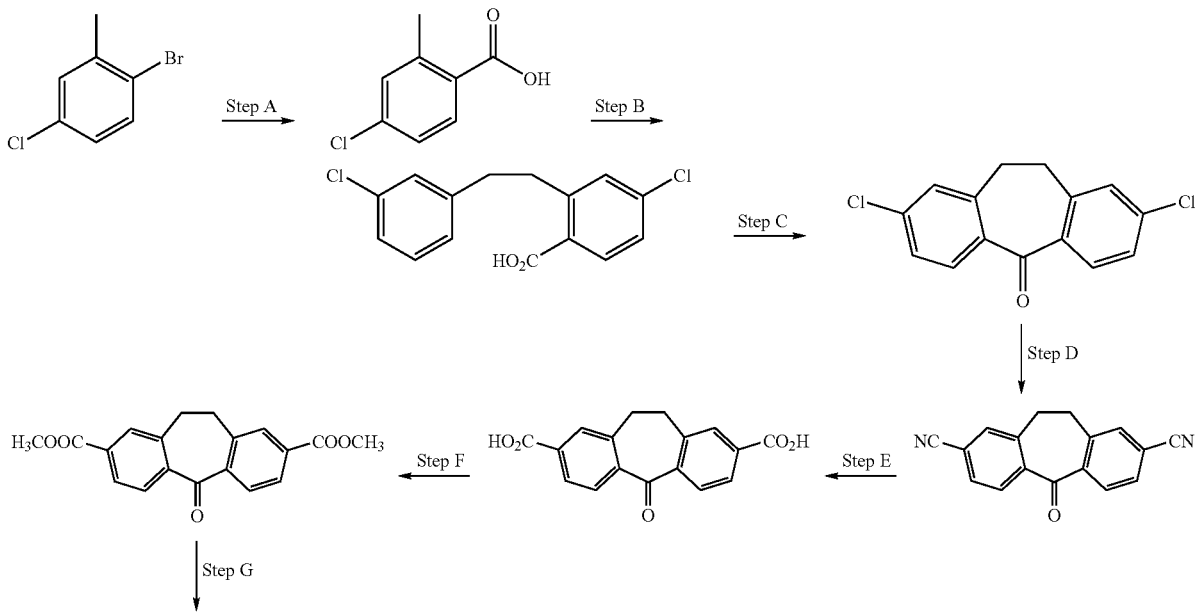

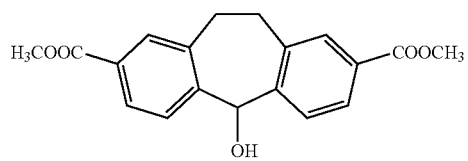 Step H → 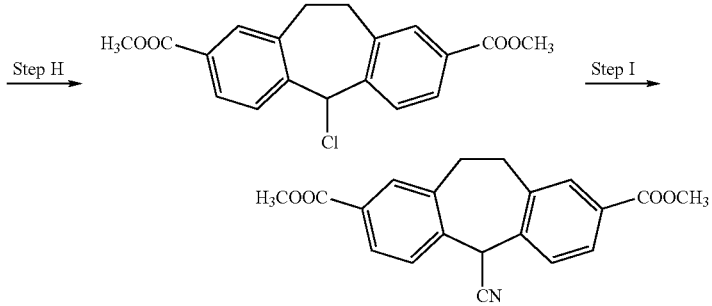 Step I →

Step A

Commercially available 2-Brom-5-chlor-toluene (123 g) was diluted with Et$_2$O (70 ml) and 10% of this solution was added to a mixture of Mg (15.2 g) and iodine (3 crystals) in Et$_2$O (250 ml). After the Grignard reaction had started, the remaining starting material was added at such a rate to maintain gentle reflux. After the complete addition of the starting material, the mixture was heated at 60° C. oil-bath temperature for 45 Min. The mixture was then cooled to rt and poured onto a mixture of dry-ice in Et$_2$O (1800 ml). The mixture was allowed to warm to rt over a period of 2 h and the solvent removed. The residue was dissolved with EtOAc (1200 ml) and washed with 3 N HCl (3×1000 ml). The organic phase was separated, dried over MgSO$_4$, filtered and concentrated to afford the title compound (94.3 g, 92%)

$^1$HNMR δ (DMSO-d$_6$) 2.51 (s, 3H), 7.33 (dd, 1H), 7.39 (d, 1H), 7.81 (d, 1H), 12.9 (br-s, 1H)

Step B

The title compound from Step A above (47 g) was dissolved in THF (500 ml) and the mixture cooled to −60° C. At −60° C. a 1.3 M solution of sec-BuLi (455 ml) in hexane was slowly added as to keep the internal temperature below −30° C. The precipitate began to dissolve after the addition of more than half of the sec-BuLi solution. After the complete addition of sec-BuLi, the deep red solution was stirred at −50° C. for 1 h. The anion solution was then transferred via canula to a cooled (−40° C.) solution of commercially available 3-chlor-benzylbromide (62.3 g) in THF (150 ml). The addition of the anion was at such a rate as to maintain −40° C. during the addition. After the addition of the anion was completed, the mixture was stirred at −40° C. for 1 h and was then allowed to warm to rt over a period of 3 h. The reaction was quenched by adding 2 M NaOH (1000 ml) and the THF removed in vacuo. The remaining solution was extracted with cyclohexane (2×500 ml) and the aqueous phase acidified to Ph=1 by adding conc. HCl. The mixture was extracted with EtOAc (3×400 ml), the organic phase dried over MgSO$_4$, filtered and concentrated to afford the title compound (71 g, 87%).

$^1$HNMR δ (acetone-d$_6$) 2.83-2.91 (m, 2H), 3.22-3.31 (m, 2H), 7.13-7.40 (m, 6H), 7.98 (d, 1H).

Step C

The title compound from Step B above (71 g) was suspended in sulfolane (250 ml) and PPA (700 g) added. The mixture was stirred with a mechanical stirrer and heated at 170° C. oil-bath temperature for 9 h. The hot mixture (~120° C.) was then poured onto crushed-ice (4000 g) and stirred overnight. The precipitate was allowed to settle for 30 Min and the aqueous phase decanted. The residue was dissolved in Et$_2$O (1500 ml) and washed with 1 M NaOH (2×500 ml). The organic phase was dried over MgSO4, filtered and concentrated to afford the title compound (50 g, 75%).

$^1$HNMR δ (CDCl$_3$) 3.16 (s, 4H), 7.23 (d, 2H), 7.32 (dd, 2H), 8.0 (d, 2H)

Step D

The title compound from Step C above (25 g) was dissolved in toluene (160 ml) and added to a mixture of KCN (11.7 g), dipiperidinomethane (7.26 ml), sulfolane (2 ml) and 1,4-Bis-(diphenylphosphino)-butane (6 g). The mixture was degassed by sonication under a stream of nitrogen and then palladium(II)-acetate (1.6 g) was added. The mixture was then heated in a sealed glass reaction vessel at 160° C. oil-bath temperature for 18 h. The mixture was cooled to rt, diluted with CH$_2$Cl$_2$ (800 ml) and washed with H$_2$O (300 ml) and brine (300 ml). The organic phase was separated, dried over MgSO$_4$, filtered and concentrated. The residue was diluted with EtOAc (90 ml) and sonicated. The suspension was then treated with cyclohexane (400 ml) and allowed to stand for 30 Min. The precipitate was collected by filtration and air-dried to afford the title compound (18 g, 77%, MH$^+$=259).

Step E

The title compound from Step D above (18 g) was suspended in EtOH (75 ml) and H$_2$O (20 ml) and the KOH (19.3 g) added. The mixture was heated at 100° C. oil-bath temperature for 12 h, concentrated and the residue dissolved in H$_2$O (500 ml). The aqueous phase was acidified to pH=1 by adding conc. HCl and the precipitate collected by filtration and air-dried to afford the title compound (19.5 g, 95%, MH$^+$=297).

Step F

The title compound from Step E above (19.5 g) was suspended in MeOH (600 ml) and treated with thionyl chloride (29 ml). The mixture was then heated at 90° C. oil-bath temperature for 3 h, the hot mixture filtered and concentrated. The residue was dissolved in CH$_2$Cl$_2$ (800 l) and washed with sat. NaHCO$_3$ (200 ml). The organic phase was separated, dried over MgSO4, filtered and concentrated to afford the title compound (18.8 g, 88%, MH$^+$=325).

Step G

The title compound from Step F above (18.8 g) was dissolved in CHCl$_3$ (250 ml) and MeOH (250 ml). The mixture was then treated with NaBH$_4$ (2.47 g) in small portions. After the complete addition of the reducing agent, the mixture was stirred at rt for 1 h. The mixture was poured into ice-water (800 ml), the organic phase separated and the aqueous phase extracted with EtOAc (300 ml). The combined organic phase was dried over MgSO$_4$, filtered and concentrated. The residue was purified by chromatography on silica (CH$_2$Cl$_2$ to CH$_2$Cl$_2$/acetone, 98:2 to CH$_2$Cl$_2$/acetone, 95:5) to afford the title compound (11.9 g, 63%, MNa$^+$=349).

Step H

The title compound from Step G above (11.9 g) was dissolved in THF (150 ml) and the mixture cooled to 0° C. At 0° C. thionyl chloride (6.5 ml) was added and the mixture was allowed to warm to rt overnight. The solvent was then removed in vacuo to afford the crude title compound.

$^1$HNMR δ (CDCl$_3$) 2.93-3.05 (m, 2H), 3.70-3.80 (m, 2H), 3.90 (s, 6H), 6.10 (s, 1H), 7.40 (d, 2H), 7.78-7.86 (m, 4H).

Step I

The title compound from Step H above was dissolved in CH$_3$CN (300 ml) and benzene (95 ml). After the addition of AgCN (5.9 g) the mixture was heated at 95° C. oil-bath temperature for 2 h 45 Min. The mixture was filtered while hot and the salts washed with CH$_2$Cl$_2$ (100 ml). The filtrate was concentrated and the residue purified by chromatography on silica (CH$_2$Cl$_2$/acetone, 98:2) to afford the title compound (11.3 g, 92%, MH$^+$=336).

Preparative Example 60

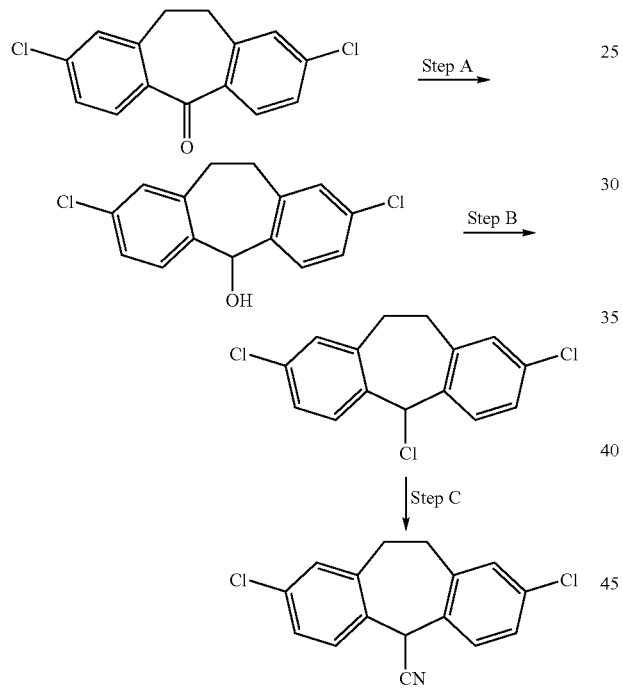

Step A

The title compound from Preparative Example 59 Step C (9.5 g) was dissolved in CHCl$_3$ (100 ml) and MeOH (60 ml) at 0° C. The mixture was then treated with NaBH$_4$ (1.64 g) in small portions. After the complete addition of the reducing agent, the mixture was stirred at rt for 3 h. Water (50 ml) was added and the mixture was concentrated to half of its volume and extracted with EtOAc (2×150 ml). The combined organic layers were washed with water (50 ml), brine (50 ml), dried over MgSO$_4$ and concentrated. The crude product was used without further purification (9 g, 90%, MNa$^+$=301).

Step B

The crude title compound from Step A above (9 g) was dissolved in THF (100 ml) and the mixture was cooled to 0° C. At 0° C. thionyl chloride (7.1 ml) was added and the mixture was allowed to warm to rt overnight. The solvent was then removed in vacuo to afford the title compound (9.2 g).

Step C

The title compound from Step B above (9.2 g) was dissolved in CH$_3$CN (180 ml) and benzene (60 ml). After the addition of solid AgCN (5.2 g) the mixture was heated at 90° C. oil-bath temperature for 2.5 h. The mixture was filtered while hot through celite and the salts washed with CH$_2$Cl$_2$ (200 ml). The filtrate was concentrated to give the crude title compound (8.66 g, 93%, MH$^+$=288).

Preparative Example 61

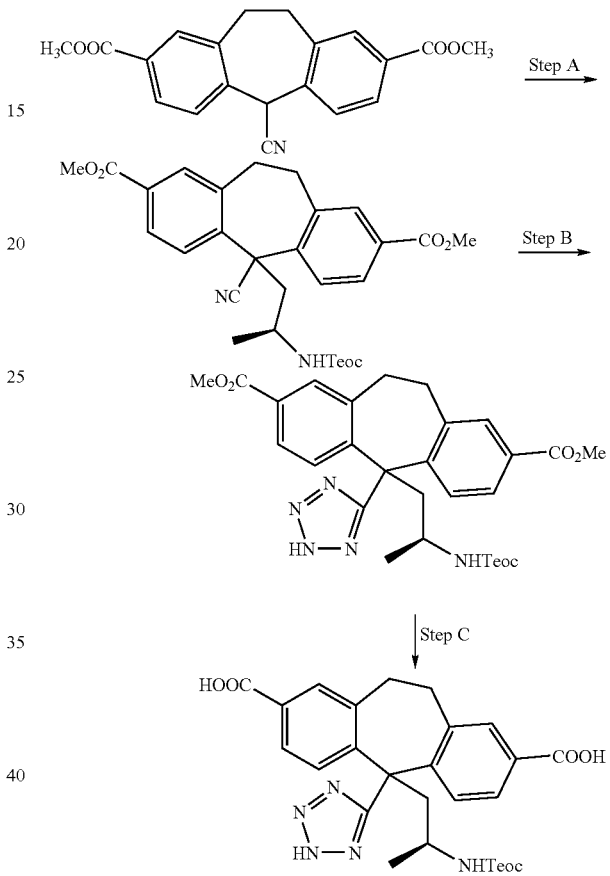

Step A

The title compound from Preparative Example 59 (3.8 g) was suspended in THF (50 ml) and DMF (35 ml). The mixture was treated under a N$_2$ atmosphere with NaH (408 mg) and the mixture was heated at ~95° C. oil-bath temperature for 90 Min, cooled to rt and treated with the title compound from Preparative Example 21 (4.78 g). The mixture was then heated at 90-95° C. for 4 h, cooled to rt and quenched with sat. NH$_4$Cl (75 ml) and brine (90 ml). The organic phase was separated and the aqueous layer extracted with EtOAc (2×50 ml). The combined organic phase was dried over MgSO$_4$ and concentrated. The residue was purified by chromatography on silica (CH$_2$Cl$_2$/MeOH, 95:5) to afford the title compound (5 g, 82%, MH$^+$=537).

Step B

The title compound from Step A above (5 g) was dissolved in DMA (90 ml) and treated with NaN$_3$ (5.9 g) and NH$_4$Cl (4.8 g). The mixture was heated under a N$_2$ atmosphere at 100-105° C. for 50 h. The cooled mixture concentrated and the residue dissolved in EtOAc (600 ml) and H$_2$O (200 ml). The aqueous layer was acidified to pH=4 by adding 1 M HCl and the organic phase separated. The aqueous phase was extracted with EtOAc (2×80 ml) and the combined organic extracts washed with 100 mM HCl (200 ml) and brine (200 ml). The organic phase was separated, dried over MgSO$_4$, filtered and concentrated. The residue was purified by chromatography on silica (CH$_2$Cl$_2$/MeOH 9:1->4:1) to afford the title compound (4 g, 74%, MH$^+$=580).

Step C

The title compound from Step B above (4 g) was dissolved in dioxane (153 ml). After the addition of 1 M KOH (42.5 ml), the mixture was stirred at rt overnight. The mixture was concentrated and then 43 ml 1 M HCl added. The precipitate was dissolved in EtOAc (100 ml) and H$_2$O (100 ml) and the organic phase separated. The aqueous phase was extracted with EtOAc (100 ml) and the organic phase combined. The solvent was then removed to afford the title compound (3.9 g, quant., MH$^+$=552).

Preparative Example 62-64

Following a similar procedure as that described in Preparative Example 61 but using the sulfamidates and compounds from the Preparative Examples as indicated in the Table below, the title compounds were obtained.

| Preparative Example | Preparative Example | Sulfamidate | Title compound | MH$^+$ |
|---|---|---|---|---|
| 62 | 59 | [structure] | [structure] | 538 |
| 63 | 59 | [structure] | [structure] | 566 |
| 64 | 60 | [structure] | [structure] | 475 |

Preparative Example 65

If one were to treat the title compound from Preparative Example 59 according to the procedures described in Preparative Example 61, but using the sulfamidate as indicated in the table below, one would obtain the title compound.

| Preparative Example | Preparative Example | Sulfamidate | Title compound |
|---|---|---|---|
| 65 | 59 | [structure] | [structure] |

Preparative Example 66

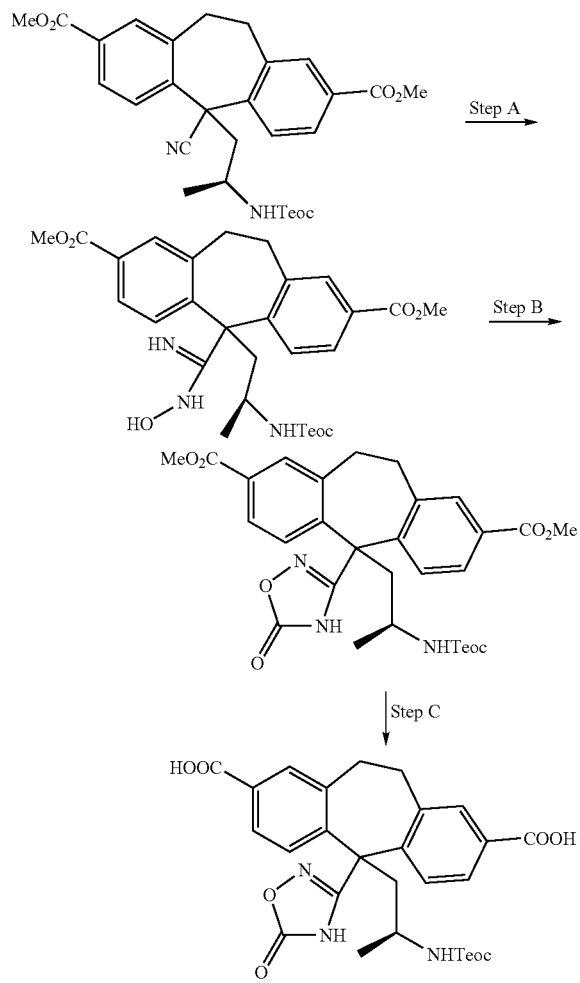

Step A

The title compound from Preparative Example 61 Step A (1000 mg) was suspended in MeOH (10 ml) and hydroxylamine hydrochloride (517 mg) and a 5.5 M solution of sodium methoxide in MeOH (1.4 ml) added. The mixture was heated in a pressure bottle at 110° C. for 12 h and then the solvent removed. The residue was purified by chromatography on silica (cyclohexane/EtOAc 1:3->1:1) to afford the title compound (210 mg, 20%, MH$^+$=570).

Step B

The title compound from Step A above (180 mg) was dissolved in MeOH (10 ml) and sodium methoxide (233 mg) and diethyl carbonate (1130 mg) added. The mixture was heated at 110° C. in a pressure bottle overnight. The solvent was removed and the residue purified by chromatography on silica (CHCl$_3$) to afford the title compound (110 mg, 58%, M$^+$-27=568).

Step C

The title compound from Step B above (110 mg) was dissolved in THF (25 ml) and treated with 1M KOH (6 ml). After stirring at rt overnight, 1M HCl (2.8 ml) was added and the solvents removed to afford the crude title compound (105 mg, quant., M$^+$-27=540).

Preparative Example 67

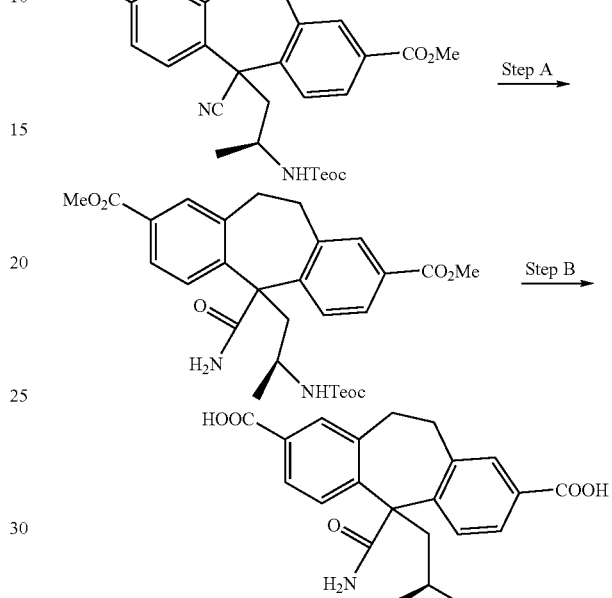

Step A

Hydroxylamine hydrochloride (401 mg) was suspended in anhydrous MeOH (14 ml) and a 5.5 M solution of sodium methoxide in MeOH (0.946 ml) added. This mixture was stirred at rt for 45 min and the title compound from Preparative Example 61 Step A (1400 mg) was added. The resulting mixture was heated in a closed vessel at 100° C. overnight and subsequently allowed to cool down to rt. Due to incomplete conversion, hydroxylamine hydrochloride (401 mg) and a 5.5 M solution of sodium methoxide in MeOH (0.946 ml) were added and the mixture was heated again at 100° C. for 20 h. After cooling down to rt, the salts were filtered off and washed with EtOAc (15 ml) and CHCl$_3$ (15 ml). The united organic phases were evaporated and the residue purified by chromatography on silica (cyclohexane/EtOAc 8:2->6:4) to afford the title compound from Preparative Example 66 Step A (300 mg, 20%, MH$^+$=570) and the title compound (1130 g, 74%, MNa$^+$=577).

Step B

The title compound from Step A above (1380 g) was dissolved in THF (30 ml) and treated with 1M KOH (9 ml). After stirring at rt overnight, 1M KOH (9 ml) was added and stirring continued for 22 h. The reaction mixture was acidified with 4 M HCl to pH 2-3, extracted with EtOAc/THF 10/1 (4×40 ml) and the combined organic extracts washed with brine (20 ml). The organic phase was separated, dried over MgSO$_4$, filtered and concentrated to afford the title compound (1220 mg, quant., M$^+$-27=499, MNa$^+$=549).

Preparative Example 68

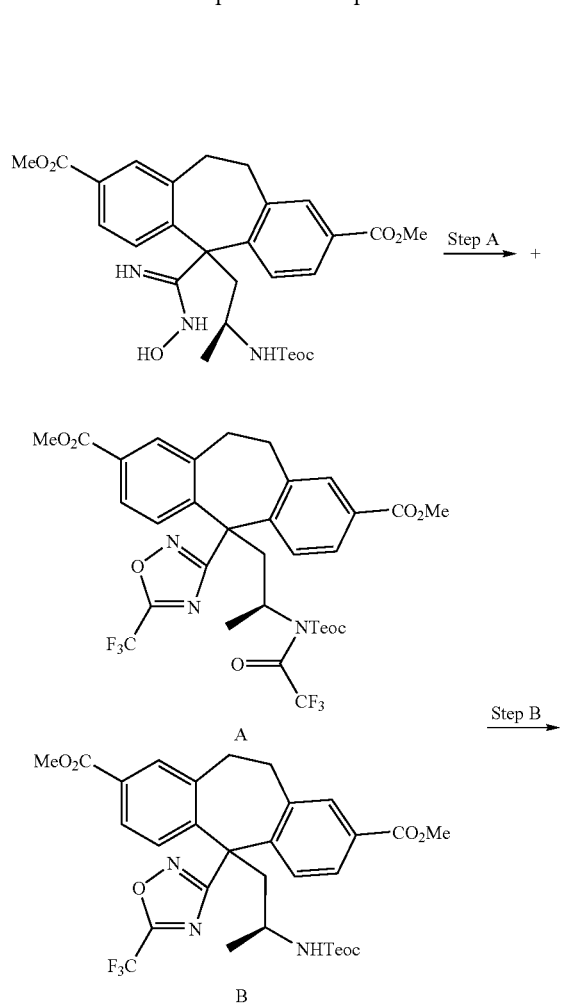

Step A

The N-hydroxyamidine product from Preparative Example 66 Step A (300 mg) was dissolved in anhydrous dichloromethane (5 ml), the solution cooled down to 0° C. and triethylamine (147 µl) and trifluoroacetic anhydride (103 µl) added. The reaction mixture was stirred at rt overnight. Due to incomplete conversion, triethylamine (221 µl) and trifluoroacetic anhydride (155 µl) were added at 0° C. and stirring was continued at rt for 3 d. Dichloromethane (9 ml) and water (10 ml) were added to the stirred mixture. After 5 min, the separated organic phase was washed with brine (5 ml), dried over MgSO$_4$, filtered and concentrated. The residue was purified by chromatography on silica (cyclohexane/EtOAc 8:2->7:3) to afford the title compounds A (2.67 mg, 68%, MNa$^+$=766) and B (36 mg, 10%, MNa$^+$=670).

Step B

The title compounds A (267 mg; MNa$^+$=766) and B (36 mg, MNa$^+$=670) from Step A above were dissolved in dioxane (11 ml) and water added (11 ml). The resulting suspension was treated with 1M NaOH (3.6 ml). After stirring at rt overnight, the reaction mixture was acidified with 1M HCl to pH 2-3, extracted with EtOAc (4×40 ml) and the combined organic phases dried over MgSO$_4$, filtered and concentrated to afford the title compound (282 mg, quant., MNa$^+$=642).

Preparative Example 69

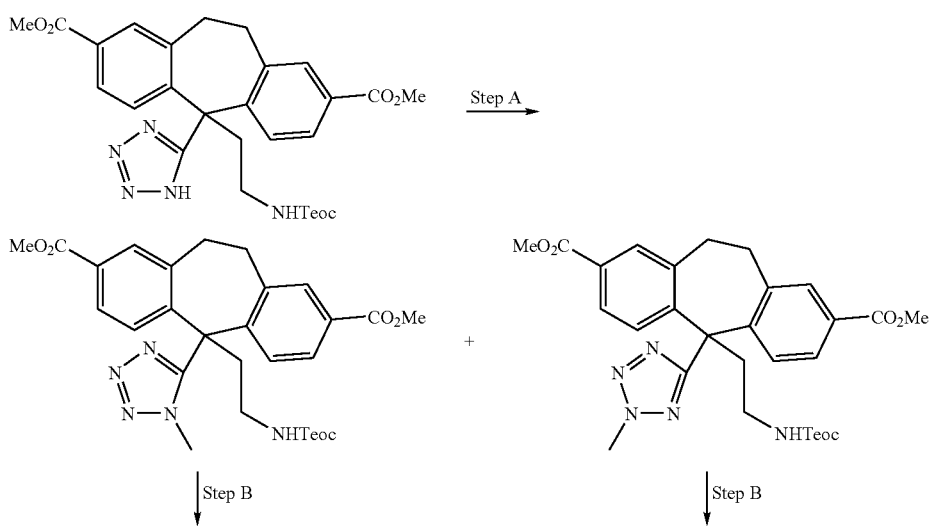

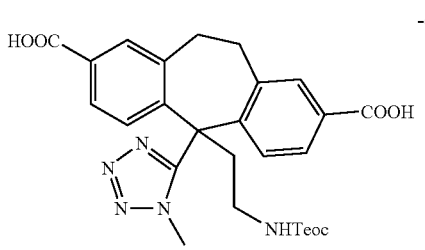
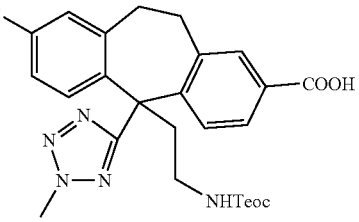

Step A

To the title compound of Preparative Example 61 Step A (500 mg) in anhydrous DMF (10 ml) was added $K_2CO_3$ (123 mg). After cooling down to 0° C., methyl iodide (75 µl) was added dropwise to the stirred mixture. After 10 min, the mixture was allowed to rt and stirred overnight. The reaction mixture was cooled down to 0° C., diluted with acidified saturated aq. NaCl solution (pH 2-3) and added to stirred EtOAc (150 ml). The separated organic phase was washed with brine (2×25 ml), dried over $MgSO_4$, filtered and concentrated. The residue was purified by chromatography on silica (cyclohexane/EtOAc 8:2->7:3) to afford the title compounds: the 1-Me-tetrazole (170 mg, 33%, $MH^+$=580) and the 2-Me-tetrazole (163 mg, 32%, $MH^+$=580).

Step B

The title compounds from Step A above (170 mg of the 1-Me-tetrazole and 163 mg of the 2-Me-tetrazole) were separately dissolved in dioxane (5.5 ml) and treated with 1M KOH (1.5 ml) each. After stirring at rt for 3 h, the reaction mixtures were concentrated to ⅓ of their volumes and the pH adjusted to 3 with 1M HCl. The resulting aq. suspension was extracted with EtOAc (3×25 ml) and the combined organic phases dried over $MgSO_4$, filtered and concentrated to afford the title compounds: the 1-Me-tetrazole (171 mg, quant., $M^+$-27=524) and the 2-Me-tetrazole (172 mg, quant., $M^+$-27=524).

Preparative Example 70

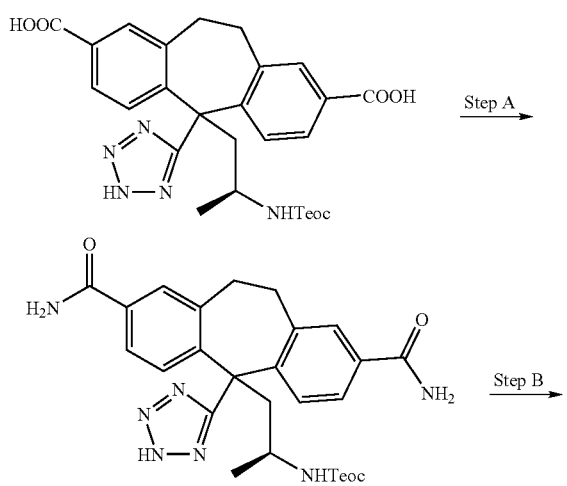

Step A

The title compound from Preparative Example 61 (2 g) was dissolved in THF (75 ml) and $CH_3CN$ (75 ml) and triethylamine (4 ml) added. The mixture was cooled to −40° C. and ethylchloroformate (2.3 ml) was slowly added. The mixture was stirred at −25° C. for 1 h, filtered and the salts washed with 35 ml THF. The filtrate was placed in a cooling bath (−20° C.) and a 33%-solution of $NH_4OH$ (30 ml) was added. The mixture was stirred at −20° C. for 30 min and 15 min at rt. Since LC-MS indicated that the conversion was not complete, the mixture was concentrated. The reaction was repeated using the same reaction conditions. After the second run LC-MS indicated that the reaction was completed. The mixture was concentrated to afford the crude title compound together with salts from the reaction ($MNa^+$=572).

Step B

The crude title compound from Step A above was suspended in $CHCl_3$ (25 ml) and the mixture cooled to 0° C. At 0° C. TFA (25 ml) was added and stirring at 0° C. was continued for 2 h. The mixture was concentrated and the residue dissolved in $H_2O$ (15 ml). The pH was adjusted to pH=7.0 by adding 10% NaOH and the neutral solution loaded onto a RP-column (Merck; silica gel 60 RP-18, 40-63 µM). The column was washed with $H_2O$ to remove the salts, followed by $CH_3CN/H_2O$ (1:1) to elute the title compound (1.3 g, 88%, $MH^+$=406).

Preparative Example 71-87

Treating the compounds from the Preparative Examples with the amines as indicated in the Table below, according to a modified procedure as described in Preparative Example 70, the title compounds were obtained as HCl-salts:

Modifications:
Step A The crude mixture from Step A was dissolved in $H_2O$ and the pH adjusted to pH=4.0 by adding 1 M HCl. The mixture was then extracted with EtOAc, the organic phase separated, dried over $MgSO_4$, filtered and the solvents removed.

Step B The residue after removal of the Teoc protecting group was diluted with 1M HCl and the aqueous phase washed with EtOAc. Concentration of the aqueous phase afforded the title compound as HCl-salt.

| Preparative Example | Preparative Example | Amines | Title compound | MH⁺ |
|---|---|---|---|---|
| 71 | 61 | H-N(Me)-Me | | 462 |
| 72 | 61 | Me-NH₂ | | 434 |
| 73 | 61 | Et-NH₂ | | 462 |
| 74 | 61 | iPr-NH₂ | | 490 |
| 75 | 61 | azetidine (HN⟨) | | 486 |

| Preparative Example | Preparative Example | Amines | Title compound | MH+ |
|---|---|---|---|---|
| 76 | 61 | morpholine | | 546 |
| 77 | 62 | CH₃NH₂ | | 420 |
| 78 | 62 | (CH₃)₂NH | | 447 |
| 79 | 63 | NH₃ | | 420 |
| 80 | 66 | (CH₃)₂NH | | 478 |

-continued

| Preparative Example | Preparative Example | Amines | Title compound | MH+ |
|---|---|---|---|---|
| 81 | 67 | (structure) | (structure) | 437 |
| 82 | 68 | (structure) | (structure) | 530 |
| 83 | 69 1-Me-tetrazole | (structure) | (structure) | 406 |
| 84 | 69 1-Me-tetrazole | (structure) | (structure) | 406 |
| 85 | 61 Step B | none | (structure) | 436 |

| Preparative Example | Preparative Example | Amines | Title compound | MH+ |
|---|---|---|---|---|
| 86 | 61 | none | 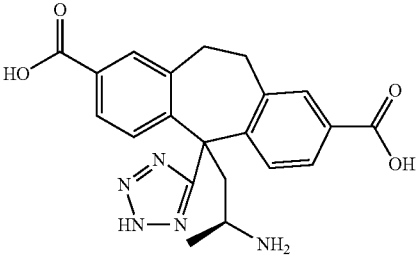 | 408 |
| 87 | 64 | none | 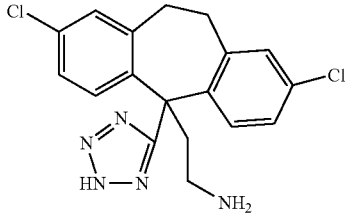 | 374 |
Preparative Example 88
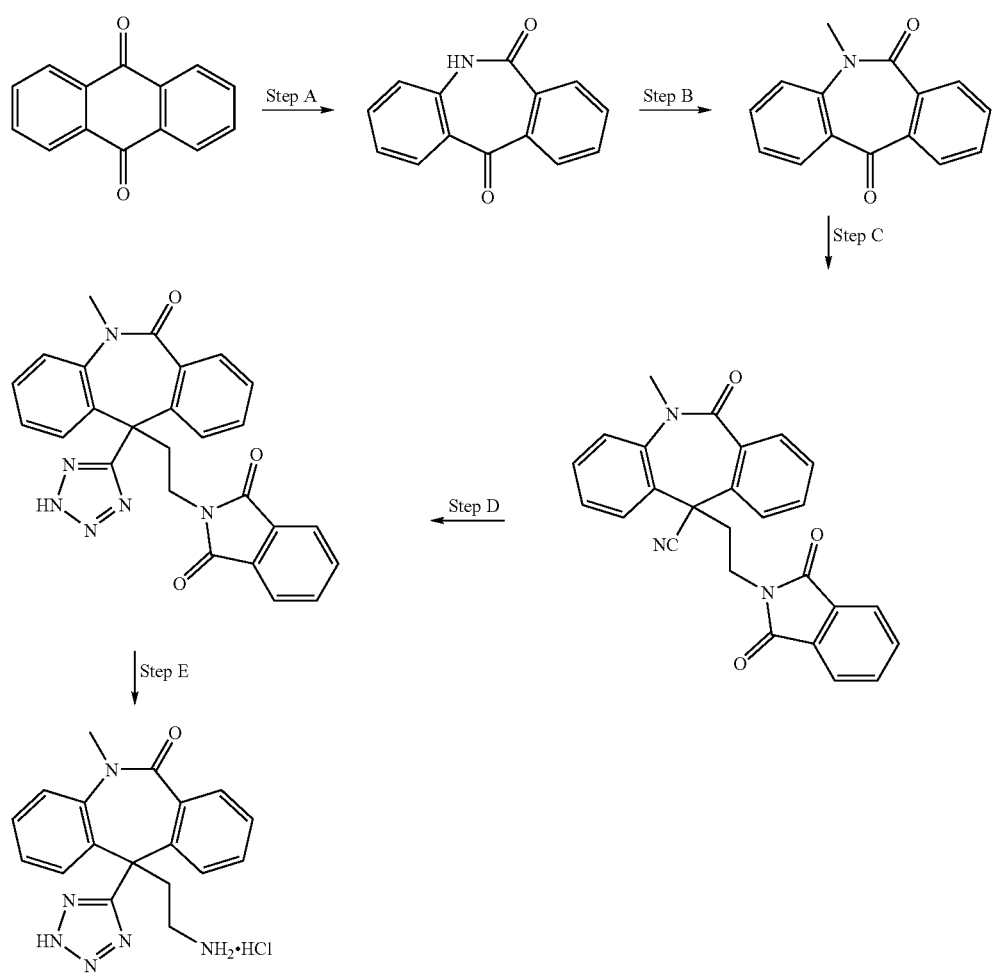

Step A

Commercially available anthraquinone (8.0 g) was suspended in CHCl$_3$ (100 ml) and conc. H$_2$SO$_4$ (20 ml) was added. The resulting biphasic system was rapidly stirred and NaN$_3$ (3.1 g) was added in portions at rt. The mixture was stirred for 1 h at rt and at 30-40° C. (water bath) for another 3 h. After the addition of ice water (80 ml), the precipitate was collected by filtration and dried to afford the title compound (8.40 g; 97%; MH$^+$=224).

Step B

The title compound from Step A above (8.0 g) was dissolved in DMSO (140 ml) under N$_2$ at 10° C. After the addition of KOtBu (5.7 g), the mixture was stirred for 15 min at that temperature. After the addition of CH$_3$I (4.2 ml), the mixture was allowed to warm to rt and stirred for 2 h. After the addition of 1 M HCl (130 ml) and EtOAc (100 ml), the organic phase was separated and the aqueous phase extracted with EtOAc (2×50 ml). The combined organic phase was washed with H$_2$O (50 ml), brine (50 ml), dried over MgSO$_4$ and concentrated. The residue was purified by chromatography on silica (EtOAc/cyclohexane) to afford the title compound (4.88 g; 61%; MH$^+$=238).

Step C

Tosylmethyl isocyanide was dissolved in DMSO (10 ml) under N$_2$ at 10° C. and KOtBu (1.36 g) was added. The mixture was stirred for 5 min and MeOH (0.173 ml) was added. The title compound from Step B above (0.8 g) was immediately added to the mixture. After 10 min dibromoethane (1.51 ml) was added and stirring was continued for 1 h at rt. The mixture was diluted with EtOAc (10 ml) and sat. NH$_4$Cl (30 ml) was added. The organic phase was separated and the aqueous phase was extracted with EtOAc (2×50 ml). The combined organic phase was washed with H$_2$O (50 ml), brine (50 ml), dried over MgSO$_4$ and concentrated. The residue was dissolved in DMF (40 ml) and potassium phthalimide (3.13 g) added. The resulting mixture was heated to 60° C. for 3 h and concentrated. The residue was suspended in CHCl$_3$ and filtered. The filtrate was concentrated and the residue purified by chromatography on silica (EtOAc/cyclohexane) to afford the title compound (612 mg; 43%; MH$^+$=422).

Step D

The title compound from Step C above (0.6 g) was dissolved in toluene (30 ml) under N$_2$ and dibutyltin oxide (1.68 g) and trimethylsilyazide (8.9 ml) were added. The mixture was then heated at 75° C. for 24 h. The mixture was concentrated, the residue suspended in EtOAc (40 ml) and 1 M HCl (40 ml) and stirred for 2 h at rt. MeOH (10 ml) was added and the organic phase was separated. The aqueous phase was extracted with EtOAc (3×20 ml) and the combined organic phase was washed with brine (20 ml), dried over MgSO$_4$ and evaporated. The residue was purified by chromatography on silica (MeOH/CH$_2$Cl$_2$) to afford the title compound (565 mg; 84%; MH$^+$=465).

Step E

The title compound from Step D above (0.22 g) was dissolved in EtOH (7 ml) and CHCl$_3$ (3 ml) and the mixture was heated to 80° C. Hydrazine monohydrate (0.108 g) was added and the mixture was stirred at 80° C. for 1 h. The mixture was allowed to cool to rt within 1 h. The precipitate was removed by filtration and washed with EtOH. The filtrate was concentrated and dissolved in CHCl$_3$ (20 ml) and 1 M HCl (10 ml). The aqueous phase was separated, filtered and evaporated to afford the title compound (85 mg; 48%; MH$^+$=335).

Preparative Example 89

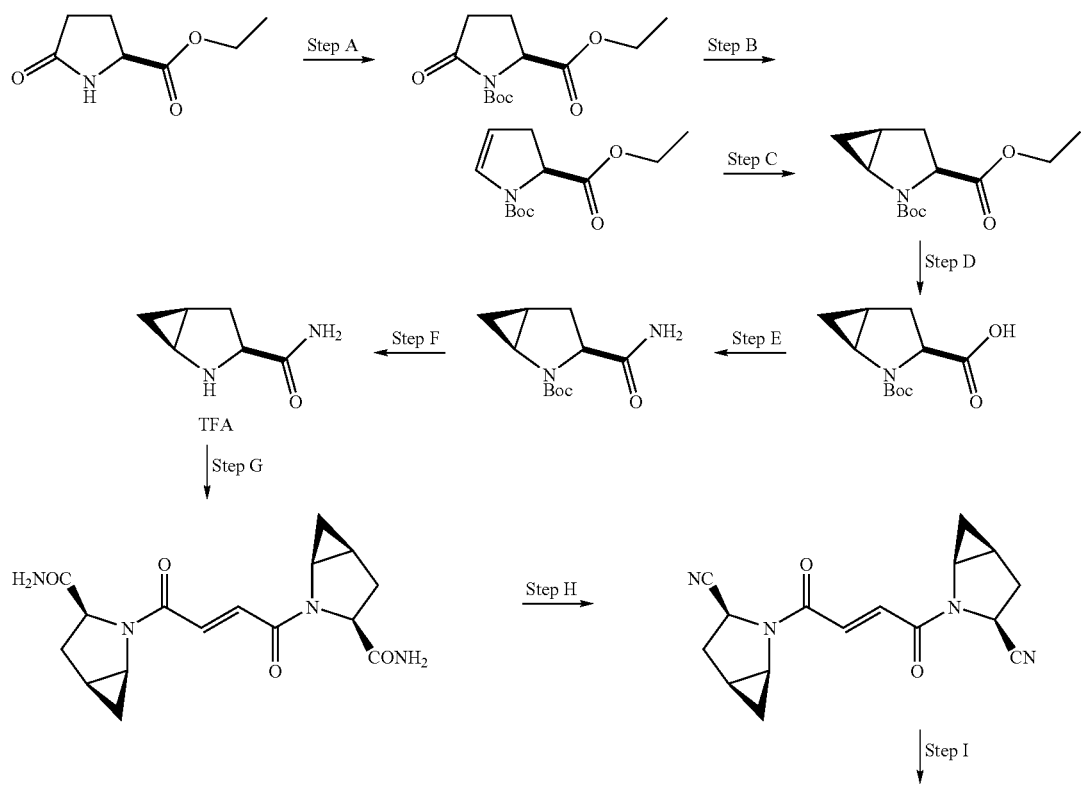

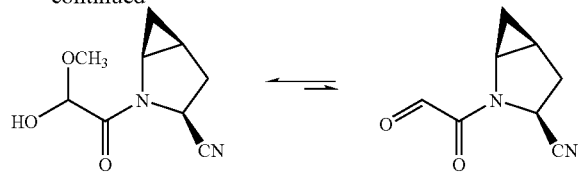

Step A

To a solution of the commercially available L-pyroglutamic acid ethylester (15.7 g) in methylene chloride (90 ml) was sequentially added at rt di-tert-butyldicarbonate (24 g) and a catalytic amount of DMAP (120 mg). After stirring for 6 h at rt the reaction mixture was quenched with saturated brine and extracted with methylene chloride. (3×30 ml). The organic phase was dried over MgSO$_4$, concentrated and the residue purified by flash chromatography on silica (CH$_2$Cl$_2$) to afford the title compound (16.3 g, 63%, MNa$^+$=280).

Step B

A solution of the title compound from Step A above (16.3 g) in toluene (100 ml) was cooled to −78° C. and triethylborohydride (67 ml of a 1.0 M solution in THF) was added dropwise over 90 minutes. After 3 h, 2,6 lutidine (43 ml) was added dropwise followed by DMAP (20 mg). To this mixture was added TFAA (11 ml) and the reaction was allowed to come to ambient temperature over 2 h. The mixture was diluted with ethyl acetate and water and the organics were washed with 3 N HCl, water, aqueous bicarbonate and brine. The organic phase was dried over MgSO$_4$, filtered and concentrated. The residue was purified by chromatography on silica (cyclohexane/EtOAc 5:1) to afford the title compound (10.9 g, 72%, MNa$^+$=264).

Step C

A solution of the title compound from Step B above (3.5 g) in 1,2 dichloroethane (75 ml) was cooled to −15° C. and Et$_2$Zn (25 mL of a 1.0 M solution in THF) was added dropwise. To this mixture was added drop wise ClCH$_2$I (4.5 ml) over 30 minutes. After stirring for 18 h at −15° C. the mixture was quenched with saturated aqueous bicarbonate and the solvent was evaporated and the reaction was taken up in ethyl acetate and washed with brine. The organic phase was dried over MgSO$_4$, filtered and concentrated. The residue was purified by chromatography on silica (cyclohexane/EtOAc 4:1) to afford the diastereomerically pure title compound (1.5 g, 41%, MNa$^+$=278).

Step D

A solution of the title compound from Step C above (1.4 g) in MeOH (40 ml) and THF (20 ml) was treated with 1 N LiOH (10 ml) and stirred overnight at rt. The reaction mixture was acidified to pH 4.5 with 2 N HCl and stirred for 15 min at rt. The mixture was then extracted with EtOAc, the organic phase washed with brine, dried over MgSO$_4$ and evaporated to afford the title compound (1.2 g, 96%, MNa$^+$=250).

Step E

To a solution of the title compound from Step D above (1.2 g) in THF (20 ml) was added at −15° C. 4-methylmorpholine (710 μl) and then isobutyl chloroformate (780 μl) over 5 minutes and stirred then for 30 minutes. The reaction mixture was cooled to −30° C. and treated with a solution of NH$_3$ in dioxane (25 ml, 0.5 M in dioxane). The reaction mixture was stirred for 30 minutes, warmed to rt and stirred overnight. The reaction mixture was acidified to pH 4.5 with 10% aqueous citric acid and extracted with ether (3×50 ml). The organic phase was dried over MgSO$_4$, filtered and concentrated. The residue was purified by chromatography on silica (cyclohexane/EtOAc 1:10) to afford the title compound (1.0 g, 84%, MNa$^+$=248).

Step F

To a stirred solution o of the title compound from Step E above (0.9 g) in methylene chloride (5 ml) was sequentially added at 0° C. TFA (5 ml). After stirring for 12 h at 0° C. the reaction mixture was concentrated under reduced pressure to afford the title compound (0.9 g, 100%, MH$^+$=127).

Step G

The title compound from Step F above (450 mg) was dissolved in CH$_2$Cl$_2$ (12 ml) and triethylamine (0.4 ml). The mixture was cooled to 0° C. and DMAP (25 mg) was added followed by fumarylchloride (0.099 ml). The mixture was stirred at 0° C. and allowed to warm to rt overnight. The mixture was concentrated to afford the crude title compound (MH$^+$=333).

Step H

To a cooled (0° C.) solution of DMF (4 ml) was carefully added oxalylchloride (0.32 ml). After the addition was completed, the mixture was stirred at 0° C. for 5 min. Then pyridine (0.6 ml) was added followed by a solution of the crude title compound from Step G above in DMF (2 ml) and CH$_2$Cl$_2$ (4 ml). The mixture was then stirred at 0° C. for 2 h. The mixture was concentrated and the residue partitioned between EtOAc (50 ml) and brine (25 ml). The organic phase was separated and the aqueous phase extracted with EtOAc (2×25 ml). The combined organic phase was dried over MgSO$_4$, filtered and concentrated. The residue was purified by chromatography on silica (CH$_2$Cl$_2$/MeOH, 95:5) to afford the title compound (250 mg, 92%, MH$^+$=297).

Step I

The title compound from Step H above (328 mg) was dissolved in CHCl$_3$ (3 ml) and MeOH (3 ml). The mixture was then treated with ozone according to Preparative Example 2 Step C to afford the title compound (350 mg, 80%, MH$^+$=165 (aldehyde); MH$^+$=219 (hemiacetal)).

Preparative Example 90

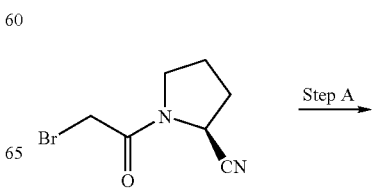

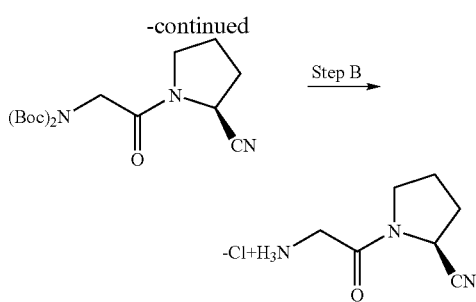

Step A

To a stirred solution of potassium hydroxide (1.2 g) in ethanol (10 mL) was sequentially added at rt the commercial available bis(tert.-butyldicarbonyl)amine (4.5 g). After stirring for 1 h at rt the reaction mixture was quenched with ether and the precipitate was filtered and washed with ether (3×10 mL) to afford the title compound (3.4 g)

Step B

The title compound from Step A above (95 mg) was dissolved in CHCl$_3$ (2.25 ml) and 1,3-dimethoxybenzene (0.18 ml) added. To the mixture was then added TFA (0.75 ml) and the mixture was stirred at rt for 1 h 30 min. The mixture was concentrated, dissolved in CH$_3$CN (3 ml) and concentrated again. The residue was dissolved in 100 mM HCl (3 ml) and EtOAc (3 ml). The aqueous phase was separated, washed with EtOAc (2 ml) and concentrated. The residue was suspended in CH$_3$CN (1.5 ml), sonicated for 1 min and the CH$_3$CN removed by syringe. The residue was then dried in HV to afford the title compound (42 mg, 84%, MH$^+$=154).

Step A

To a solution of the commercial available Boc-Fmoc-protected amino acid (1.05 g) in methanol (25 ml) was added diethyl amine (1.5 ml). After stirring for 2.5 h at room temperature the reaction mixture was concentrated, and the residue was dissolved in water (50 ml) and Et$_2$O (50 ml). The organic phase was extracted with water (3×50 ml) and the combined aqueous extracts were concentrated. The residue was used for the next step without any further purification.

Step B

To a solution of the title compound from Step A above (530 mg) and 3-fluorobenzaldehyde (245 µl) in 15 ml of methanol was added NaBH$_3$CN (150 mg), and the mixture was stirred at 25° C. overnight. The mixture was concentrated, and the residue was dissolved in EtOAc (50 ml). The organic layer was extracted with water (3×50 ml) and the combined aqueous extracts were concentrated. The residue was used for the next step without any further purification.

Step C

To a stirring solution of the title compound from Step B above (760 mg) in DMF (20 ml) was added HOBt (470 mg) followed by EDCI (670 mg) and DMAP (30 mg). N-methyl morpholine (440 µl) was added and stirring was continued at rt overnight. The solvent was removed in vacuo, the residue diluted with EtOAc and then washed with saturated aqueous NaHCO$_3$. The organic phase was dried over MgSO$_4$, concentrated and the residue purified by flash chromatography on silica (CH$_2$Cl$_2$/acetone, 9:1) to afford the title compound (430 mg, 60% over 3 steps, MH$^+$=321).

Step D

The title compound from Step C above (760 mg) was dissolved in EtOAc (6 ml) and a solution of 4 M HCl in dioxane (6 ml) was added. After 2 h the mixture was triturated with aqueous NaHCO$_3$ to pH 7.5 and stirred for 15 min at rt. After evaporation of the solvent, the crude product was puri-

Preparative Example 91

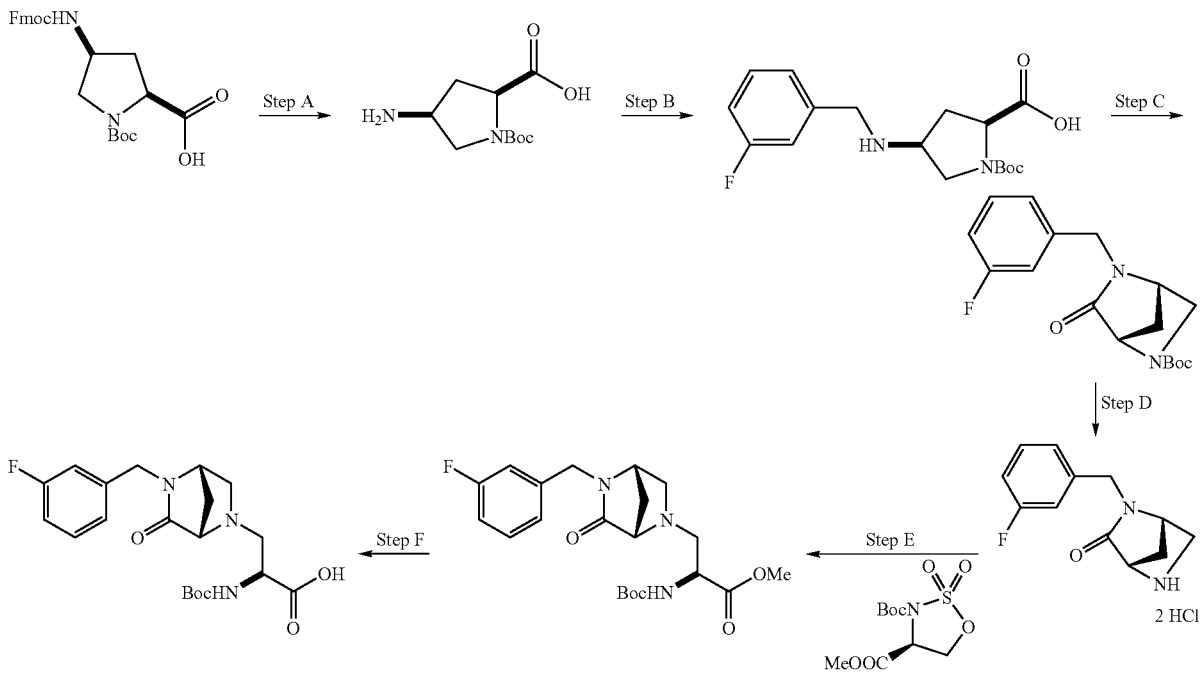

fied by flash chromatography on silica (CH₂Cl₂MeOH, 9:1) to afford the title compound (420 mg, 80%, MH⁺=221).

Step E

To a solution of the title compound from Step D above (85 mg) in THF (5 ml) was added triethylamine (80 µl) and the mixture was stirred for 1 h at 50° C. Then the sulfamidate (240 mg.), prepared according to WO 03/037327, was added in one portion at −15° C. and the mixture was stirred at ambient temperature over 2 d. After the addition of 1 M NH₄HCO₃ solution (5 ml), the mixture was stirred for 30 min. Then an excess saturated NaHCO₃ solution was added and stirring was continued for another 15 min. The mixture was then partitioned between EtOAc and water and the aqueous phase extracted with EtOAc. The combined organic phase was dried over MgSO₄ and concentrated in vacuo. The residue was purified by column chromatography on silica (CH₂Cl₂/acetone, 9:1) to afford the title compound (135 mg, 79%, MH⁺=422).

Step F

A solution of the title compound from Step E above (135 mg) in MeOH (2.5 ml) and THF (5 ml) was treated with 1 N LiOH (1.5 ml) and stirred overnight at rt. The reaction mixture was acidified to pH 4.5 with 2 N HCl and stirred for 15 min at rt. The mixture was then extracted with EtOAc, the organic phase washed with brine, dried over MgSO₄ and evaporated to afford the title compound (125 mg, 96%, MH⁺=408).

Preparative Example 92

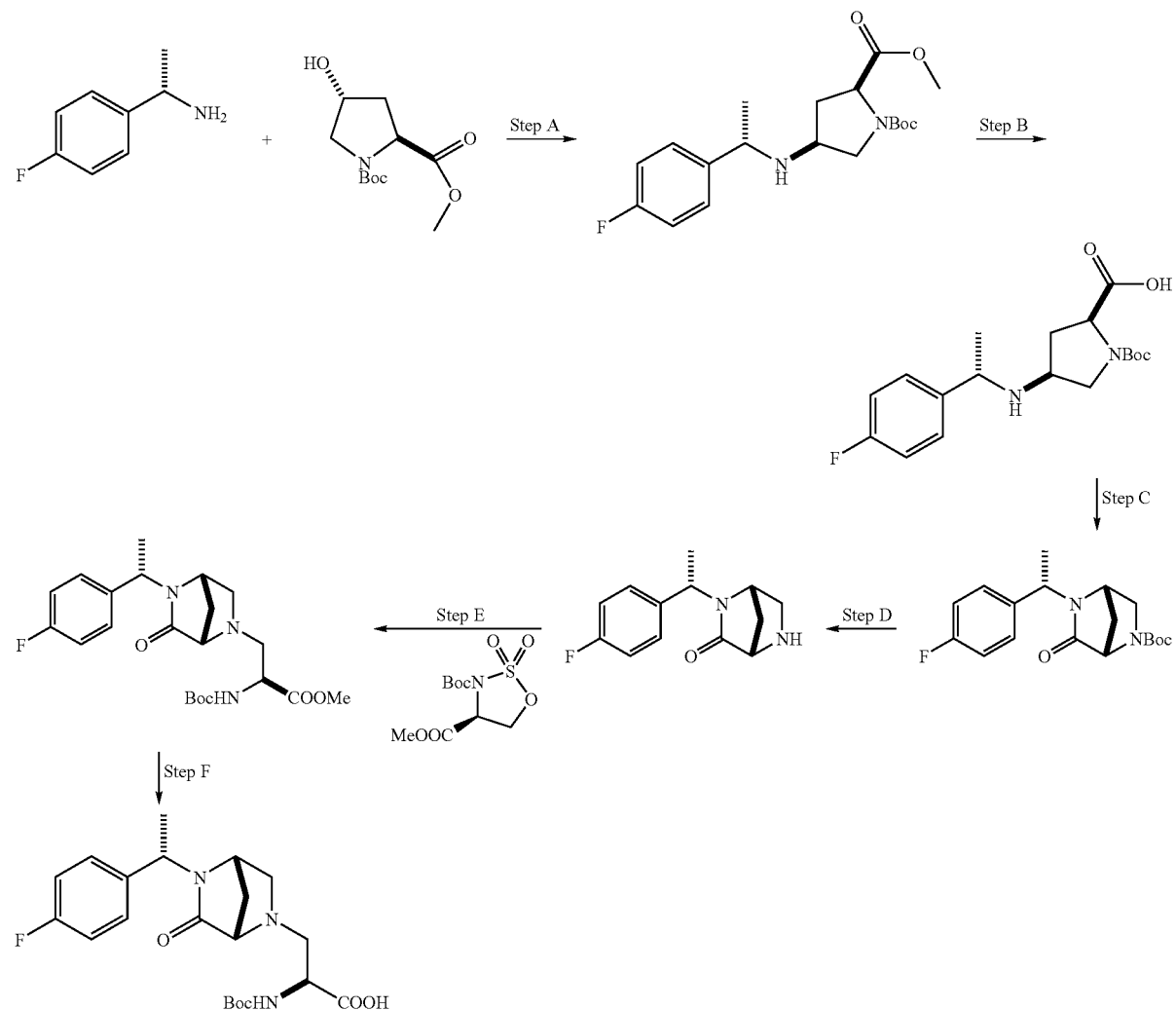

Step A

A solution of commercially available N-Boc-trans-4-hydroxyl-L-proline ester (2.93 g) in CH₂Cl₂ (20 ml) was cooled to −30° C. and treated with DIEA (4.8 ml). After the addition of triflic anhydride (2.2 ml), the mixture was stirred at −30° C. for 60 min and then treated with a solution of the commercially available amine in CH₂Cl₂ (20 ml). The mixture was allowed to warm to rt overnight. The mixture was diluted with CH₂Cl₂ (20 ml), washed with 0.5 M Na₂CO₃ (2×50 ml) and brine (50 ml). The organic phase was dried over MgSO₄ and concentrated to leave a residue, which was purified by chromatography on silica (CH₂Cl₂/acetone, 4:1) to afford the title compound (2.22 g, 75%, MH⁺=367).

Step B

A solution of the title compound from Step A above (700 mg) in MeOH (24 ml) and THF (12 ml) was treated with 1 N LiOH (6 ml) and stirred overnight at rt. The reaction mixture was acidified to pH 4.5 with 1 N HCl and stirred for 15 min at rt. The mixture was then extracted with EtOAc, the organic phase washed with brine, dried over MgSO$_4$ and evaporated to afford the title compound (665 mg, 95%, MH$^+$=353).

Step C

To a stirring solution of the title compound from Step B above (665 mg) in DMF (15 ml) was added HOBt (390 mg) followed by EDCI (560 mg) and DMAP (30 mg). N-methyl morpholine (420 μl) was added and stirring was continued at rt overnight. The solvent was removed in vacuo, the residue diluted with EtOAc and then washed with saturated aqueous NaHCO$_3$. The organic phase was dried over MgSO$_4$, concentrated and the residue purified by flash chromatography on silica (CH$_2$Cl$_2$/acetone, 9:1) to afford the title compound (556 mg, 87%, MH$^+$=335).

Step D

The title compound from Step C above (760 mg) was dissolved in EtOAc (4 ml) and a solution of 4 M HCl in dioxane (4 ml) was added. After 2 h the mixture was triturated with aqueous NaHCO$_3$ to pH 7.5 and stirred for 15 min at rt. After evaporation of the solvent, the crude residue was purified by flash chromatography on silica (CH$_2$Cl$_2$/MeOH, 9:1) to afford the title compound (300 mg, 77%, MH$^+$=235).

Step E

To a solution of the title compound from Step D above (290 mg) in THF (5 ml) was added triethyl amine (280 μl) and the mixture was stirred for 1 h at 50° C. Then the sulfamidate (590 mg.), prepared according to WO 03/037327, was added in one portion at −15° C. and the mixture was stirred at ambient temperature over 2 d. After the addition of 1 M NH$_4$HCO$_3$ solution (5 ml), the mixture was stirred for 30 min. Then an excess saturated NaHCO$_3$ solution was added and stirring was continued for another 15 min. The mixture was then partitioned between EtOAc and water and the aqueous phase extracted with EtOAc. The combined organic phase was dried over MgSO$_4$ and concentrated in vacuo. The residue was purified by column chromatography on silica (CH$_2$Cl$_2$/acetone, 4:1) to afford the title compound (163 mg, 30%, MH$^+$=436).

Step F

A solution of the title compound from Step E above (163 mg) in MeOH (2.5 ml) and THF (5 ml) was treated with 1 N LiOH (1.5 ml) and stirred overnight at rt. The reaction mixture was acidified to pH 4.5 with 2 N HCl and stirred for 15 min at rt. The mixture was then extracted with EtOAc, the organic phase washed with brine, dried over MgSO$_4$ and evaporated to afford the title compound (140 mg, 96%, MH$^+$=422).

Preparative Example 93

Step A

To a stirring solution of the title compound from Preparative Example 91 (25 mg) in DMF (3 ml) was added HOBt (15 mg), followed by EDCI (20 mg) and DMAP (3 mg). Commercially available (S)-Pyrrolidine-2-carbonitrile hydrochloride (15 mg) was added after 1 h, followed by N-methyl morpholine (20 μl). The mixture was stirred at rt overnight, the solvent removed in vacuo, and the residue was diluted with EtOAc. The mixture was washed with saturated aqueous NaHCO$_3$, separated, dried over MgSO$_4$ and concentrated. The residue was purified by flash chromatography on silica (CH$_2$Cl$_2$/acetone, 9:1) to afford the title compound (17 mg, 59%, MH$^+$=486).

Step B

To a stirring solution of the title compound Preparative Example 91 (125 mg) in DMF (5 ml) was HOBt (46 mg), followed by EDCI (65 mg) and DMAP (5 mg). After 1 h commercially available L-proline amide (68 mg) and N-methyl morpholine (100 μl) were added and stirring was continued at rt overnight. The solvent was removed in vacuo, the residue diluted with EtOAc and washed with saturated aqueous NaHCO$_3$. The organic phase was separated, dried over MgSO$_4$ and concentrated. The residue was purified by flash chromatography on silica (CH$_2$Cl$_2$/acetone, 4:1) to afford the title compound (137 mg; 88%; MH$^+$=504).

Step C

To a solution of the title compound from Step B above (137 mg) in pyridine (7 ml) was added imidazole (41 mg). At −30° C. POCl$_3$ (102 μl) was slowly added to the mixture and the mixture was allowed to reach rt over a period of 1 h. Then the solvent was removed and the residue diluted with 1 N HCl and Et$_2$O. The organic phase was separated, dried over MgSO$_4$ and evaporated. The residue was purified by column chromatography on silica (CH$_2$Cl$_2$/acetone, 4:1) to afford the title compound (72 mg, 55%, MH$^+$=486).

Preparative Example 94-108

Following a similar procedure as that described in Preparative Examples 92 and 93, except using the amines and amides as indicated in the Table below, the following compound were prepared. For Preparative Examples 105 and 106 the conversion of the nitrile to the carboxamide with subsequent saponification of the ester moiety was done according to Preparative Example 91 Step F with 3M Na$_2$CO$_3$ and H$_2$O$_2$.

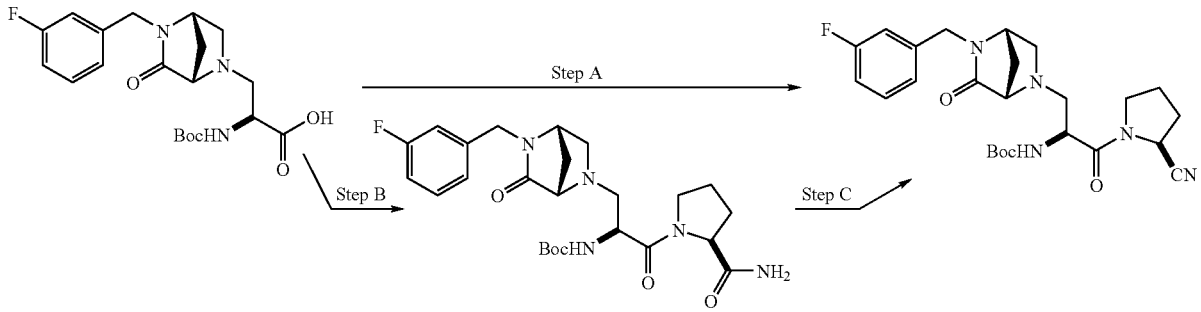

| Preparative Example | Amide | Amine | Product | 1. Yield 2. MH+ |
|---|---|---|---|---|
| 94 | | | | 1. 55% 2. 498 |
| 95 | | | | 1. 90% 2. 537 |
| 96 | | | | 1. 71% 2. 493 |
| 97 | | | | 1. 70% 2. 504 |
| 98 | | | | 1. 73% 2. 516 |
| 99 | | | | 1. 65% 2. 493 |

-continued

| Preparative Example | Amide | Amine | Product | 1. Yield 2. MH+ |
|---|---|---|---|---|
| 100 | | | | 1. 54% 2. 505 |
| 101 | | | | 1. 78% 2. 493 |
| 102 | | | | 1. 56% 2. 500 |
| 103 | | | | 1. 65% 2. 512 |
| 104 | | | | 1. 71% 2. 514 |
| 105 | | | | 1. 68% 2. 511 |

| Preparative Example | Amide | Amine | Product | 1. Yield 2. MH+ |
|---|---|---|---|---|
| 106 | | | | 1. 56% 2. 511 |
| 107 | | | | 1. 62% 2. 526 |
| 108 | | | | 1. 2. |

Preparative Example 109

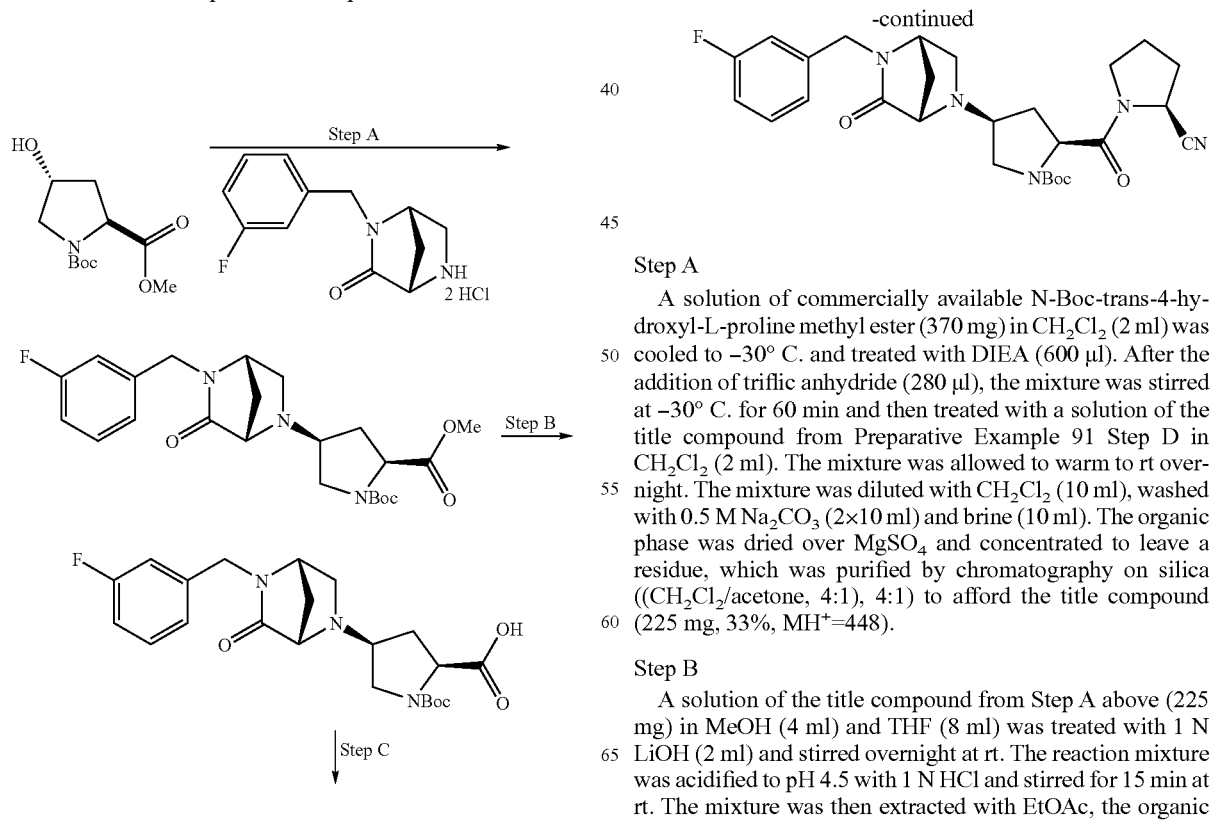

Step A

A solution of commercially available N-Boc-trans-4-hydroxyl-L-proline methyl ester (370 mg) in CH$_2$Cl$_2$ (2 ml) was cooled to −30° C. and treated with DIEA (600 μl). After the addition of triflic anhydride (280 μl), the mixture was stirred at −30° C. for 60 min and then treated with a solution of the title compound from Preparative Example 91 Step D in CH$_2$Cl$_2$ (2 ml). The mixture was allowed to warm to rt overnight. The mixture was diluted with CH$_2$Cl$_2$ (10 ml), washed with 0.5 M Na$_2$CO$_3$ (2×10 ml) and brine (10 ml). The organic phase was dried over MgSO$_4$ and concentrated to leave a residue, which was purified by chromatography on silica ((CH$_2$Cl$_2$/acetone, 4:1), 4:1) to afford the title compound (225 mg, 33%, MH$^+$=448).

Step B

A solution of the title compound from Step A above (225 mg) in MeOH (4 ml) and THF (8 ml) was treated with 1 N LiOH (2 ml) and stirred overnight at rt. The reaction mixture was acidified to pH 4.5 with 1 N HCl and stirred for 15 min at rt. The mixture was then extracted with EtOAc, the organic phase washed with brine, dried over MgSO$_4$ and evaporated to afford the title compound (91 mg, 40%, MH$^+$=434).

Step C

To a stirring solution of the title compound from Step B above (91 mg) in DMF (3 ml) was added HOBt (40 mg), followed by EDCI (60 mg) and DMAP (10 mg). Commercially available (S)-Pyrrolidine-2-carbonitrile hydrochloride (35 mg) was added after 1 h, followed by N-methyl morpholine (66 µl). The mixture was stirred at rt overnight, the solvent removed in vacuo, and the residue was diluted with EtOAc. The mixture was washed with saturated aqueous NaHCO$_3$, separated, dried over MgSO$_4$ and concentrated. The residue was purified by flash chromatography on silica (CH$_2$Cl$_2$/acetone, 1:1) to afford the title compound (50 mg, 47%, MH$^+$=512).

Preparative Example 110

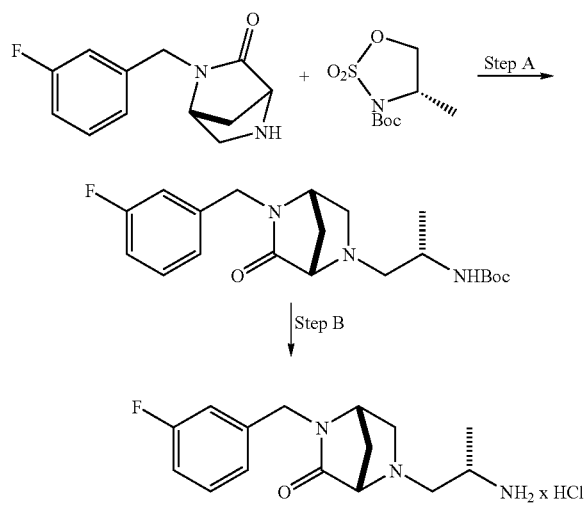

Step A

The title compound from Preparative Example 91 Step D (305 mg) was dissolved in THF (2 ml) was added triethyl amine (63 µl) and the mixture was stirred for 1 h at 50° C. Then the title compound from Preparative Example 19 (100 mg) was added in one portion at −15° C. and the mixture was stirred at ambient temperature overnight. After the addition of 1 M NH$_4$HCO$_3$ solution (5 ml), the mixture was stirred for 30 min. Then an excess saturated NaHCO$_3$ solution was added and stirring was continued for another 15 min. The mixture was then partitioned between EtOAc and water and the aqueous phase extracted with EtOAc. The combined organic phase was dried over MgSO$_4$ and concentrated in vacuo. The residue was purified by column chromatography on silica (CH$_2$Cl$_2$/acetone, 4:1) to afford the title compound (58 mg, 57%, MH$^+$=378).

Step B

The title compound from Step A above (58 mg) was dissolved in EtOAc (2 ml) and a solution of 4 M HCl in dioxane (2 ml) was added. After 2 h the mixture was evaporated to afford the title compound (48 mg, quant., MH$^+$=278).

Preparative Example 111

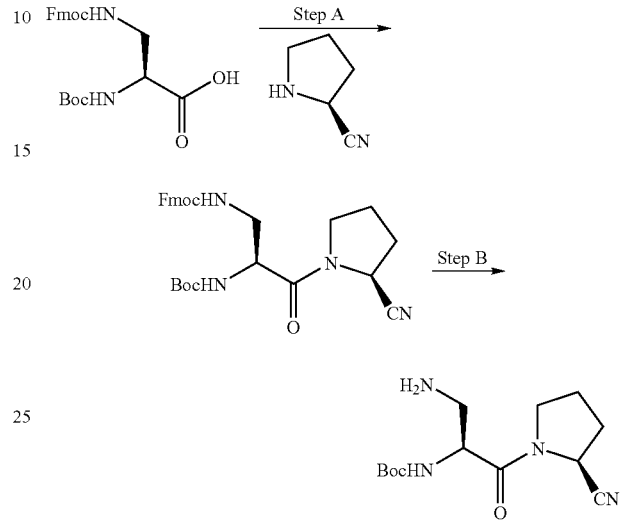

Step A

Commercially available N-cyclohexylcarbodiimde-N'-methyl polystyrene resin (1.9 g) was suspended in 5 ml dichloromethane and agitated for 5 Min. The commercially available amino acid (468 mg) and amine (86 mg), prepared from the commercially available hydrochloride by adding 1 eq. pyridine, were dissolved in 1.5 ml dimethylformamide and added to the above resin. The mixture was agitated for 16 h, filtered and the resin washed with 2×5 ml dichloromethane and 5 ml methanol. The combined filtrates were concentrated and the residue purified by flash chromatography (silica, CH$_2$Cl$_2$/MeOH, 9:1) to afford the title compound (500 mg; 91%).

$^1$H-NMR (CDCl$_3$): δ 1.45 (9H,s), 2.05-2.30 (4H, m), 3.25-3.40 (1H, m), 3.50-3.70 (2H, m), 3.80-3.90 (1H, m), 4.15-4.25 (1H, m), 4.30-4.40 (2H, m), 4.55-4.65 (1H, m), 4.70-4.80 (1H, m), 5.50-5.60 (2H, m), 7.25-7.40 (4H, m), 7.55-7.65 (2H, m), 7.70-7.80 (2H, m).

Step B

The title compound from Step A above (500 mg) was dissolved in dichloromethane (10 ml) and treated with diethylamine (10 ml). After 2 h the mixture was concentrated and the residue was purified by flash chromatography (silica, CH$_2$Cl$_2$/MeOH, 4:1) to afford the title compound (224 mg; 80%).

$^1$H-NMR (CDCl$_3$): δ 1.45 (9H,s), 1.70 (2H,s), 2.05-2.30 (4H, m), 2.95-3.05 (2H, m), 3.70-3.85 (2H, m), 4.35-4.50 (1H, m), 4.75-4.85 (1H, m), 5.50-5.60 (1H, m).

Preparative Example 112

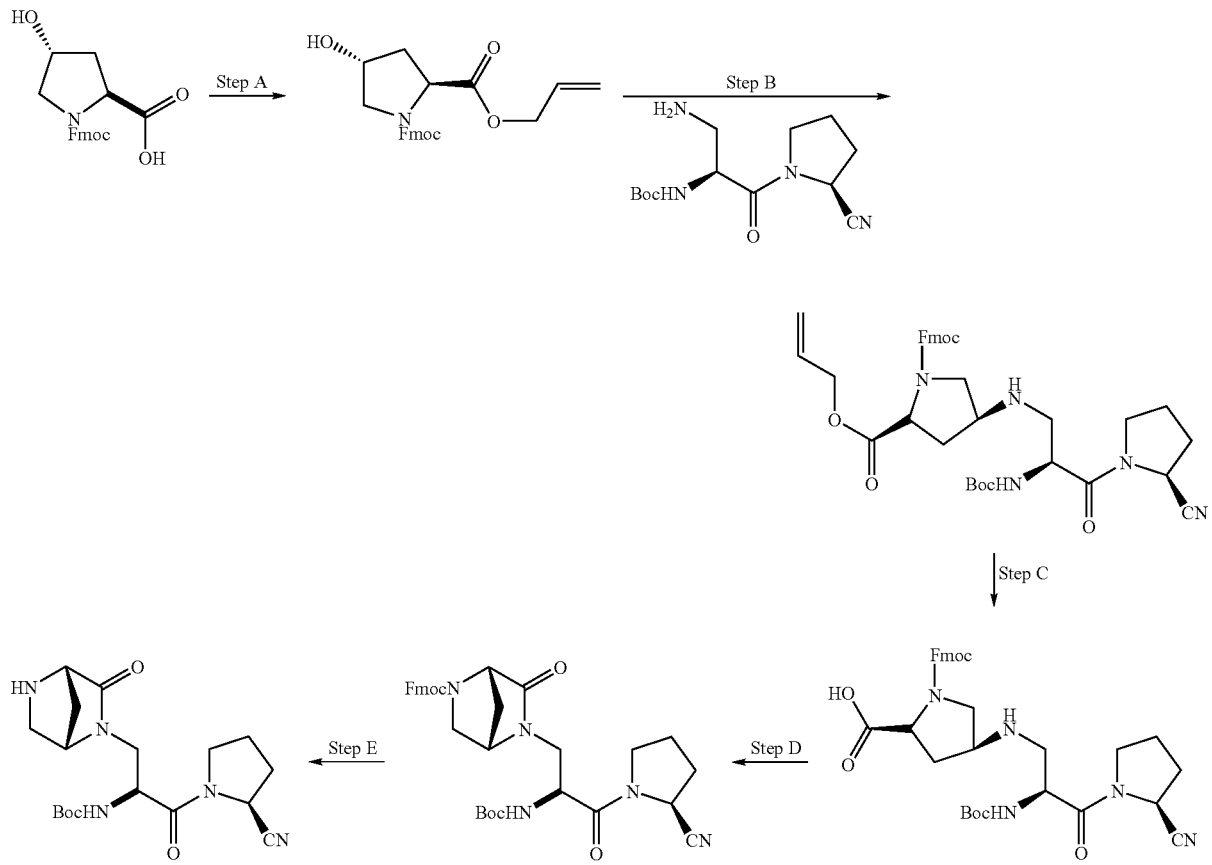

Step A

A solution of commercially available N-Fmoc-trans-4-hydroxyl-L-proline (4.5 g) in aqueous ethanol (80%, 45 ml) was titrated with a solution of $Cs_2CO_3$ (2.3 g) in water (18 ml) to pH 7. The solvents were evaporated and the residue dried in vacuo. The caesium salt was suspended in dry DMF (45 ml), cooled to 0° C. and treated with allyl bromide (11.5 ml) by dropwise addition over 10 min. After 30 min the solution was allowed to reach rt and stirring was continued for another 3 h. The reaction mixture was filtered and concentrated. The residue was purified by chromatography on silica (EtOAc/cyclohexane) to afford the title compound (4.5 g, 90%, $MH^+$=394).

Step B

The title compound from Step A above (2.5 g) in $CH_2Cl_2$ (60 ml) was cooled to −30° C. and treated with DIEA (2.5 ml). After the addition of triflic anhydride (1.2 ml), the mixture was stirred at −30° C. for 60 min and then treated with a solution of Preparative Example 84 (1.17 g) in $CH_2Cl_2$ (15 ml). The mixture was allowed to warm to 0° C., stirred at 0° C. for 12 h and refluxed for additional 4 h. The mixture was diluted with $CH_2Cl_2$ (50 ml), washed with 0.5 M $Na_2CO_3$ (2×25 ml) and brine (25 ml). The organic phase was dried over $MgSO_4$ and concentrated to leave a residue, which was purified by chromatography on silica (EtOAc/cyclohexane, 7:3) to afford the title compound (1.41 g, 50%, $MH^+$=658).

Step C

To the title compound from Step B above (1.8 g) in THF (120 ml) was added dimedone (1.27 g) and $Pd(PPh_3)_4$ (422 mg). The reaction mixture was stirred at room temperature for 19 h. Following removal of the solvent under reduced pressure, chromatography on silica ($CH_2Cl_2$/MeOH 9:1) afforded the title compound (1.42 g, 84%, $MH^+$=618).

Step D

To a solution of the title compound from Step C above (1.42 g) in $CH_2Cl_2$ (70 ml) was added HOBT (405 mg) followed by EDCI (575 mg) and N-methyl-morpholine (0.33 ml). After being stirred at ambient temperature for 24 h, the solvent was evaporated to give a viscous residue, which was partitioned between EtOAc and ammonium acetate buffer (pH 6). The aqueous phase was extracted with ethyl acetate (3×100 ml) and the combined organic phase dried over $MgSO_4$ and concentrated to afford the title compound (1.35 g, $MNH_4^+$=617).

Step E

To a solution of the title compound from Step D above (1.35 g) in acetonitrile (100 ml) was added diethyl amine (10 ml). After stirring for 2.5 h at rt, the reaction mixture was concentrated. The residue was purified by chromatography on silica ($CH_2Cl_2$/MeOH, 9:1) to afford the title compound (712 mg; 85%, $MH^+$=378).

Preparative Example 113

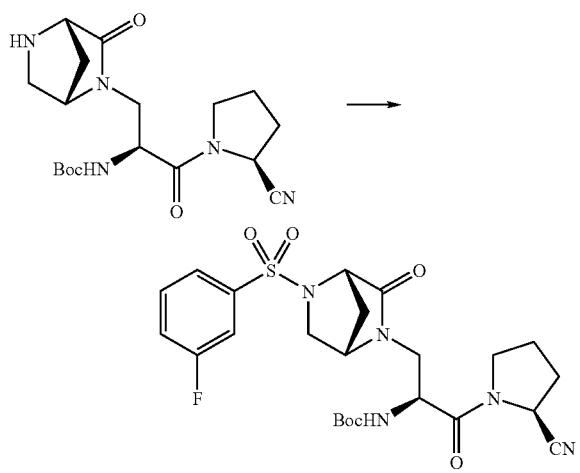

To a solution of the title compound from Preparative Example 112 (13 mg) in $CH_2Cl_2$ (0.8 ml) was added piperidino methyl polystyrene resin (65 mg) and 3-fluorobenzene-1-sulfonyl chloride (5.5 µl). After shaking at rt for 3 h, tris-(2-aminoethyl)amine polystyrene resin (30 mg) was added and agitated for additional 1 h at rt. The mixture was filtered, the resin washed with $CH_2Cl_2$ (5 ml) and methanol (1 ml) and the combined filtrates evaporated. Purification by chromatography on silica ($CH_2Cl_2$/MeOH 9:1) afforded the title compound (13 mg, 71%, $MNH_4^+$=553).

Preparative Example 114-116

Following a similar procedure as that described in Preparative Example 113, except using the sulfonic acid chlorides as indicated in the Table below, the following compounds were prepared.

| Preparative Example | Sulfonic acid chloride | Product | 1. Yield 2. $MH^+$ |
|---|---|---|---|
| 114 | | | 1. 69 2. 541 ($MNH_4^+$) |
| 115 | | | 1. 92 2. 546 ($MNa^+$) |
| 116 | | | 1. 89 2. 604 ($MNa^+$) |

Preparative Example 117-119

Following a similar procedure as that described in Preparative Example 113, except using the acid chlorides as indicated in the Table below, the following compounds were prepared.

| Preparative Example | Acid chloride | Product | 1. Yield 2. MH+ |
|---|---|---|---|
| 117 | | | 1. 100 2. 488 (MH+) |
| 118 | | | 1. 49 2. 519 (MNH4+) |
| 119 | | | 1. 70 2. 506 (MNa+) |

Preparative Example 120

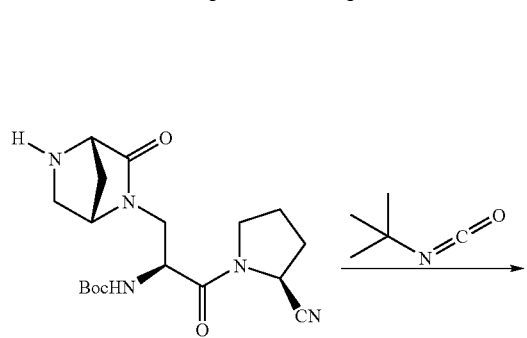

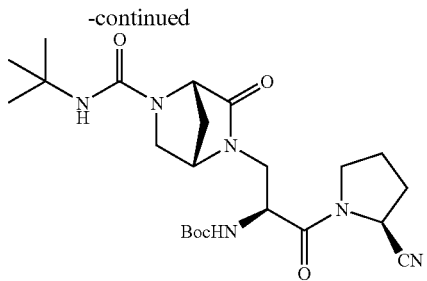

-continued

To a solution of the title compound from Preparative Example 112 (20 mg) in CH$_2$Cl$_2$ (0.8 ml) was added tert.-butyl isocyanate (5.8 mg). After stirring at room temperature for 3 h the solvent was evaporated. Purification by chromatography (CH$_2$Cl$_2$/acetone 1:1) afford the title compound (16 mg, 63%, MH+=477).

Preparative Example 121

Following a similar procedure as that described in Preparative Example 120, except using the isocyanate as indicated in the Table below, the following compound was prepared.

| Preparative Example | Isocyanate | Product | 1. Yield 2. MH+ |
|---|---|---|---|
| 121 | | | 1. 69 2. 592 (MNH$_4^+$) |

Preparative Example 122

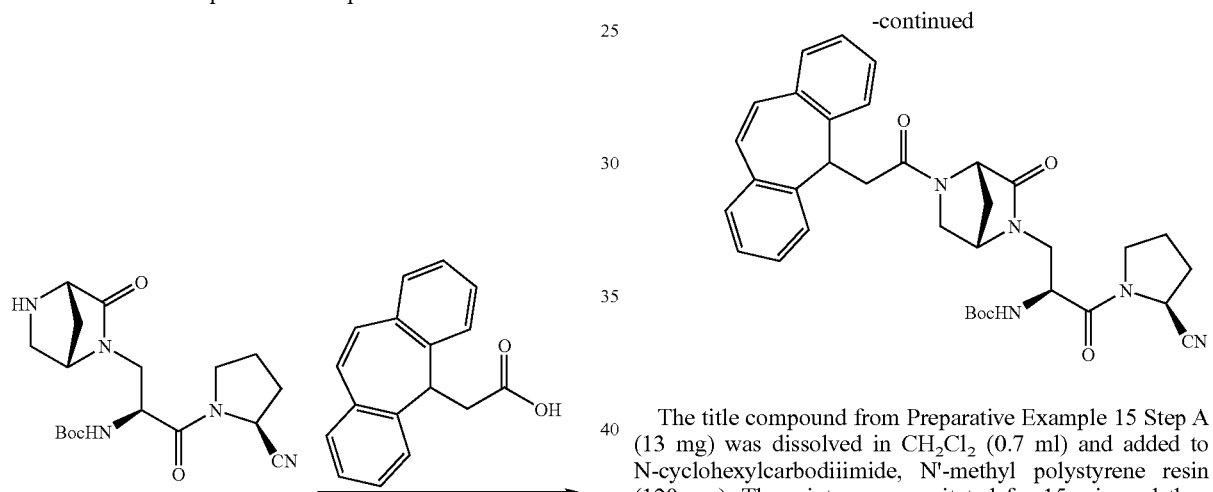

The title compound from Preparative Example 15 Step A (13 mg) was dissolved in CH$_2$Cl$_2$ (0.7 ml) and added to N-cyclohexylcarbodiimide, N'-methyl polystyrene resin (120 mg). The mixture was agitated for 15 min and then treated with a solution of the title compound from Preparative Example 112 (0.54 ml, 7.5 mM CH$_2$Cl$_2$). After shaking at rt for 12 h, the mixture was filtered and the resin washed with CH$_2$Cl$_2$ (5 ml). The filtrates were concentrated in vacuo to afford the title compound (30 mg, 95%, MNa$^+$=632).

Preparative Example 123

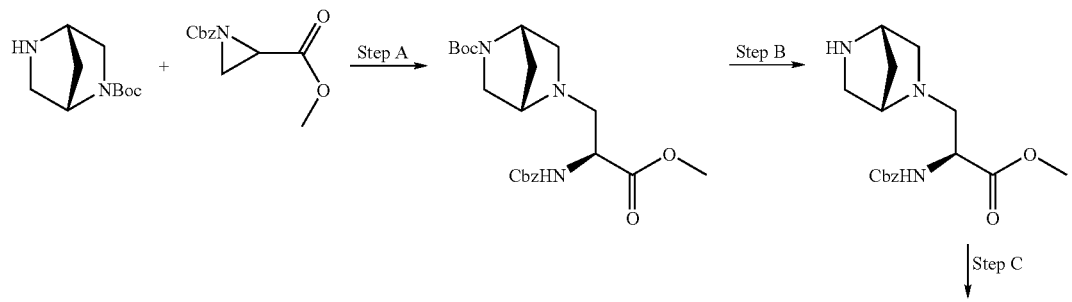

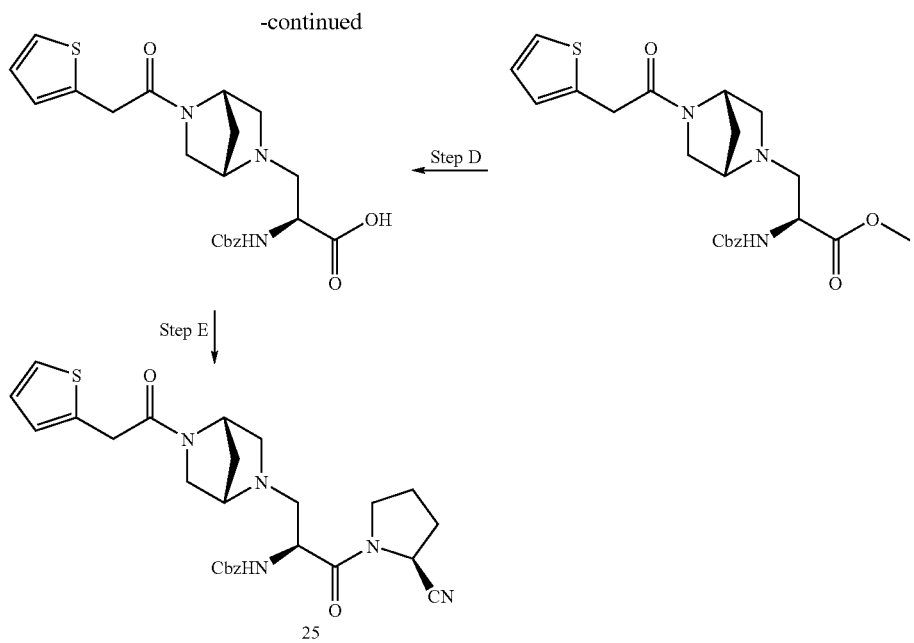

Step A

Commercially available 2,5-diaza-bicyclo[2.2.1]heptane-2-carboxylic acid tert-butyl ester (400 mg) and aziridine-1,2-dicarboxylic acid 1-benzyl ester 2-methyl ester (431 mg) were dissolved in toluene (5 ml). The mixture was stirred at rt overnight and then for 5 h at 80° C. The solvent was removed and the residue purified by chromatography on silica ($CH_2Cl_2$/acetone 9:1) to afford the title compound (468 mg, 58%, $MH^+$=434).

Step B

The title compound from Step A above (245 mg) was dissolved in dioxane (5 ml) and a solution of 4 M HCl in dioxane (5 ml) was added. The mixture was stirred for 2 h at rt and the solvents removed to afford the title compound (208 mg, 100%, $MH^+$=334).

Step C

To the title compound from Step B above (130 mg) were added $CH_2Cl_2$ (10 ml) and pyridine (1 ml). After the addition of commercially available thiophen-2-yl-acetyl chloride (61 mg) the reaction mixture was stirred at rt overnight. The solvent was removed and the residue purified by chromatography on silica ($CH_2Cl_2$/acetone 9:1) to afford the title compound (90 mg, 57%, $MH^+$=458).

Step D

The title compound from Step C above (130 mg) was dissolved in THF (4 ml) and methanol (2 ml). After the addition of 1 M aqueous LiOH-solution (1 ml), the mixture was stirred for 4 h at rt. The solvents were removed and the residue dissolved in water and acidified with 1 M HCl to pH~4. The mixture was extracted with EtOAc, the organic phase washed with brine, dried over $MgSO_4$ and concentrated to yield the title compound (75 mg, 86%, $MH^+$=444).

Step E

The title compound from Step D above (75 mg) was dissolved in DMF (5 ml). After the addition of EDCI (38 mg), HOBt (27 mg), N-methylmorpholine (0.15 ml) and DMAP (10 mol %), the mixture was stirred for 1 h at rt. Then commercially available 2-(S)-cyanopyrrolidine hydrochloride was added and the mixture was stirred overnight at rt. The solvent was removed and the residue dissolved in EtOAc, washed with brine, dried over $MgSO_4$, and concentrated. The residue was purified by chromatography on silica (cyclohexane/EtOAc, 7:3) to afford the title compound (27 mg, 30%, $MH^+$=522).

Preparative Example 124-125

Following a similar procedure as that described in Preparative Example 123, except using the piperazine derivatives and sulfonic acid chlorides as indicated in the Table below, the following compounds were prepared.

| Example | Piperazine derivative | Sulfonic Acid chloride | Product | 1. Yield 2. $MH^+$ |
|---|---|---|---|---|
| 124 | (structure) | (structure) | (structure) | 1. 73% 2. 556 |

| Example | Piperazine derivative | Sulfonic Acid chloride | Product | 1. Yield 2. MH+ |
|---|---|---|---|---|
| 125 | (3-fluorophenyl piperazine bicyclic) | none | (product structure) | 1. 27% 2. 492 |

Preparative Examples 126-129 have been intentionally excluded.

Preparative Example 130

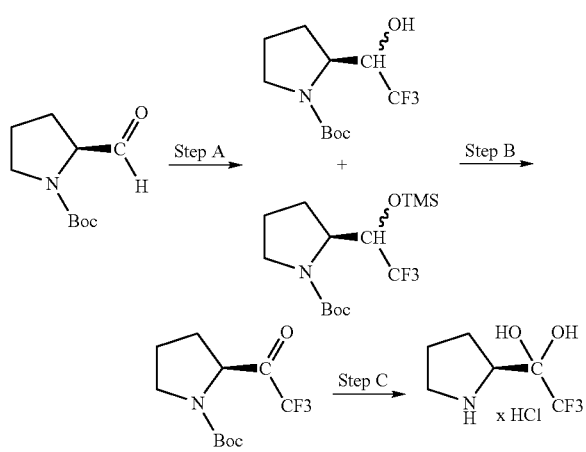

Step A

Commercially available 2-formyl-pyrrolidine-1-carboxylic acid tert-butyl ester (330 mg) in anhydrous THF (5 ml) was cooled to 0° C. and trimethyl-trifluoromethylsilane (300 μl) added, followed by addition of tetrabutylammoniumfluoride (60 μl; 1 M in THF). The reaction mixture was allowed to warm to rt and then stirred for 1 h. After dilution with diethyl ether, the organic phase was washed with brine and the aqueous phase extracted with diethyl ether. The combined organic phases were dried ($MgSO_4$) and evaporated to afford the title compounds as a 1:1 mixture of alcohol and TMS ether (490 mg, 97%, [MH-Boc]+=242 (TMS ether); [MH-Boc]+=170 (alcohol)).

Step B

The title compounds from Step A above (721 mg) in dichloromethane (5 ml) were added to Dess Martin periodinane (2.32 g) in dichloromethane (15 ml) with stirring. Trifluoroacetic acid (410 μl) was added dropwise and the turbid reaction mixture stirred for 17 h at rt, after which it was directly coated on silica and purified by column chromatography (silica, cyclohexane/EtOAc 90:10->80:20) to afford the title compound (301 mg, 45%, [MH-Boc]+=168).

Step C

To the title compound from Step B above (106 mg) in dioxane (500 μl) was added 4 M HCl in dioxane (500 μl) and the resulting mixture stirred for 16 h at rt. Diethyl ether was added (2 ml) and the suspension filtered. The precipitate was dried and the title compound obtained as its HCl salt (81 mg, 91%, MH+=186).

Preparative Examples 131-199 have been intentionally excluded.

Preparative Example 200-294

If one were to follow a similar procedure as that described in Preparative Example Preparative Example 44, except using the sulfamidates as indicated in the Table below of Preparative Example 61, one would obtain the title compounds, listed in the Table in the "product" column.

| Preparative Example | Preparative Example Sulfamidate | Product |
|---|---|---|
| 200 | 24 | (product structure with tetrazole, amide groups) |

-continued
| Preparative Example | Preparative Example Sulfamidate | Product |
|---|---|---|
| 201 | 25 | 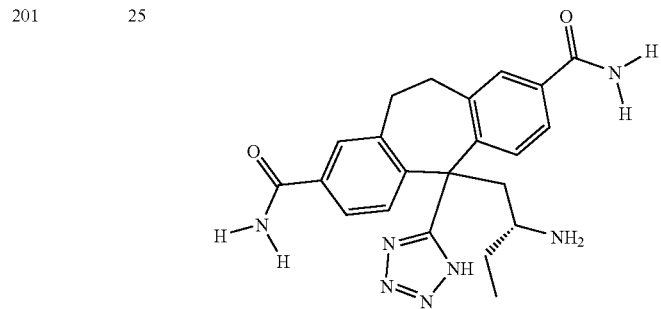 |
| 202 | 26 | 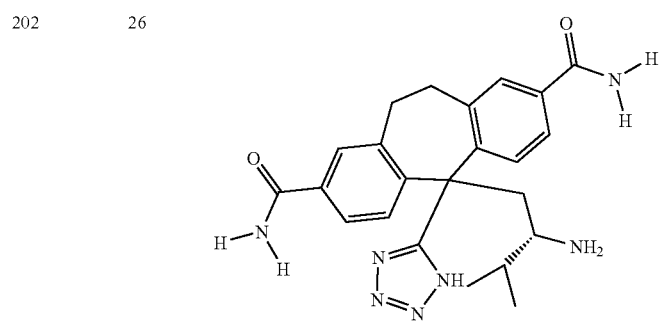 |
| 203 | 27 | 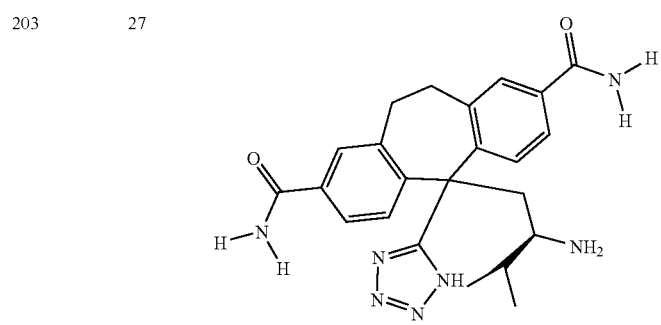 |
| 204 | 28 | 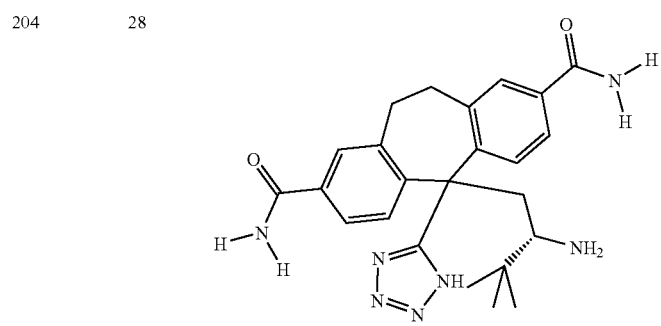 |

-continued
| Preparative Example | Preparative Example Sulfamidate | Product |
|---|---|---|
| 205 | 29 | 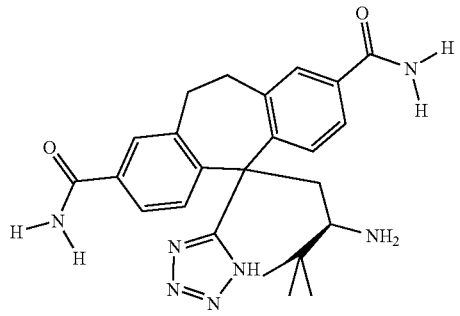 |
| 206 | 30 | 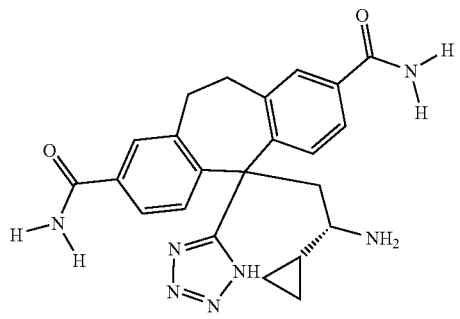 |
| 207 | 31 | 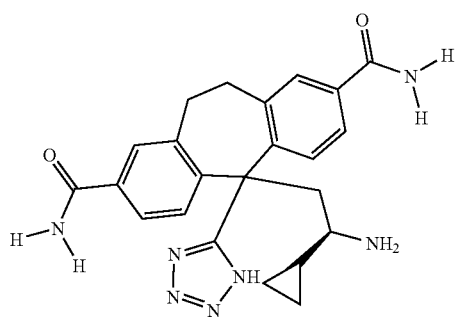 |
| 208 | 32 | 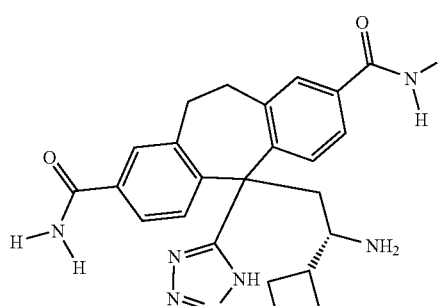 |

-continued
| Preparative Example | Preparative Example Sulfamidate | Product |
|---|---|---|
| 209 | 33 | 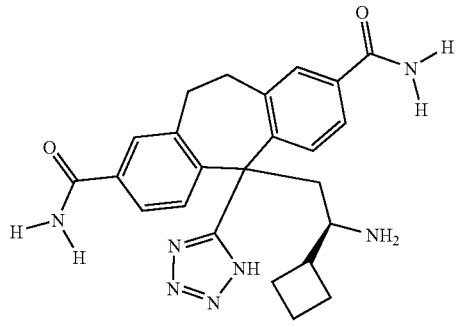 |
| 210 | 34 | 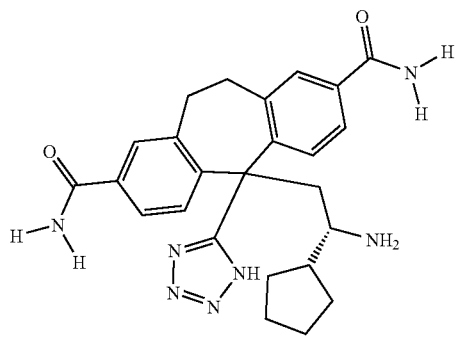 |
| 211 | 35 | 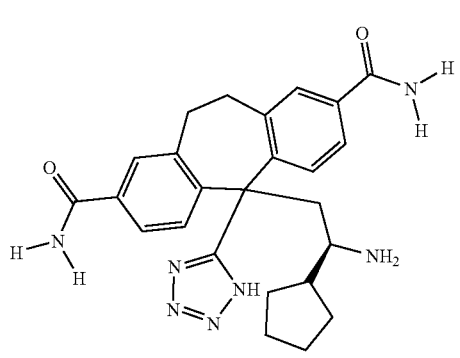 |
| 212 | 36 | 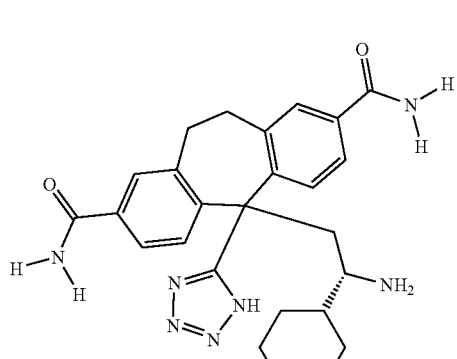 |

-continued
| Preparative Example | Preparative Example Sulfamidate | Product |
|---|---|---|
| 213 | 37 | 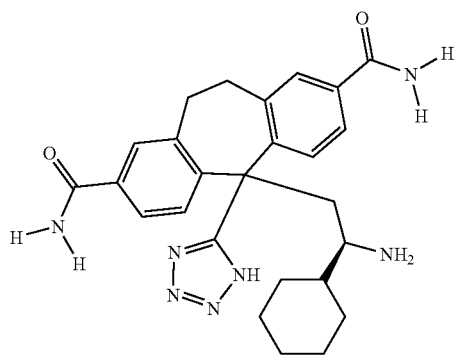 |
| 214 | 38 | 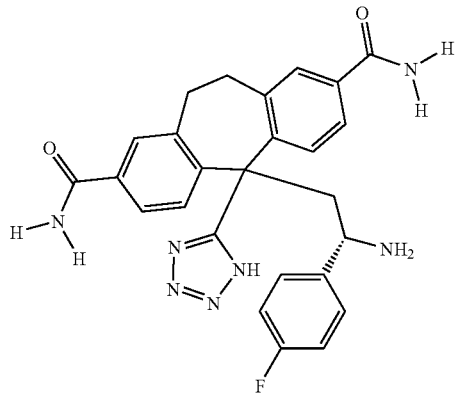 |
| 215 | 39 | 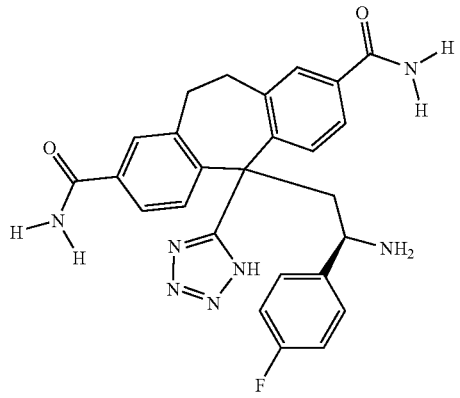 |
| 216 | 40 | 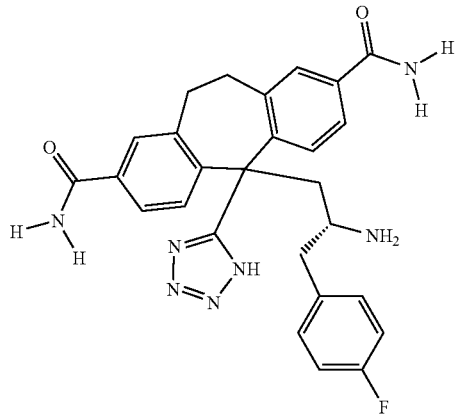 |

-continued
| Preparative Example | Preparative Example Sulfamidate | Product |
|---|---|---|
| 217 | 41 | 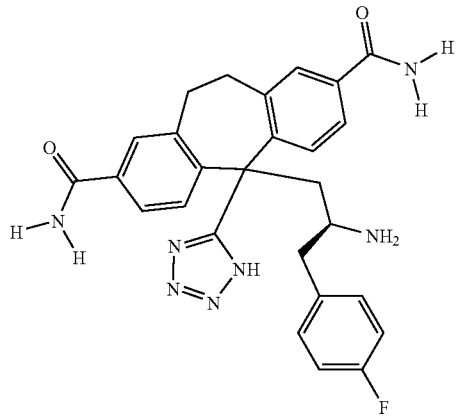 |
| 218 | 42 | 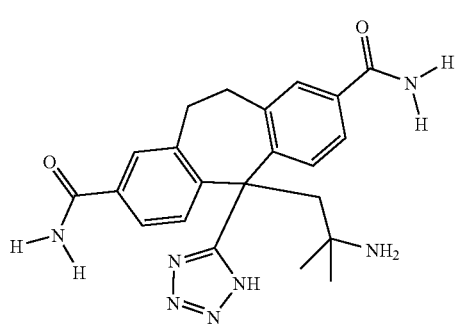 |
| 219 | 43 | 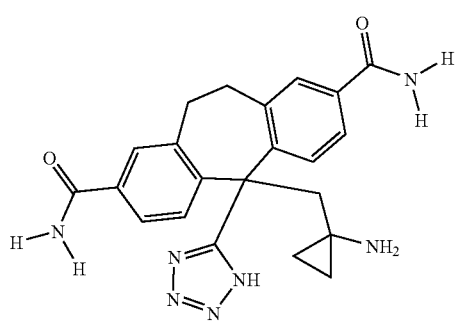 |
| 220 | 44 | 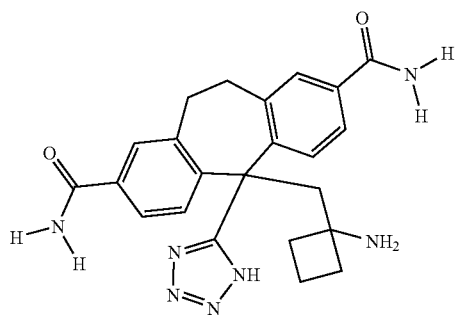 |

-continued
| Preparative Example | Preparative Example Sulfamidate | Product |
|---|---|---|
| 221 | 45 | 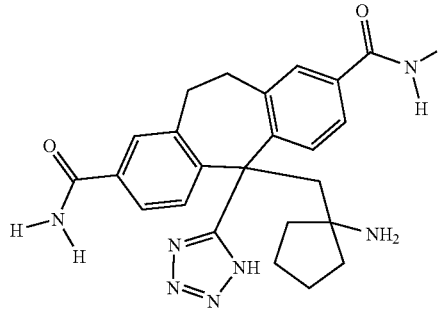 |
| 222 | 46 | 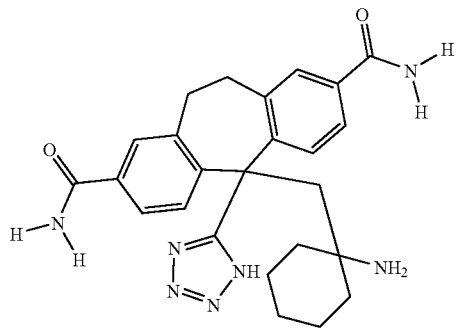 |
| 223 | 24 | 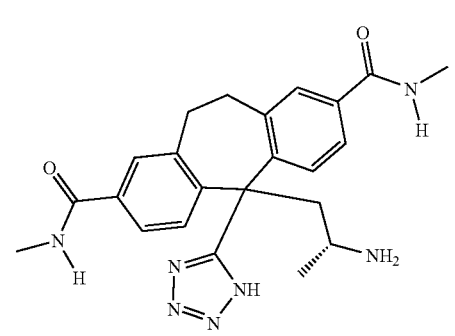 |
| 224 | 23 | 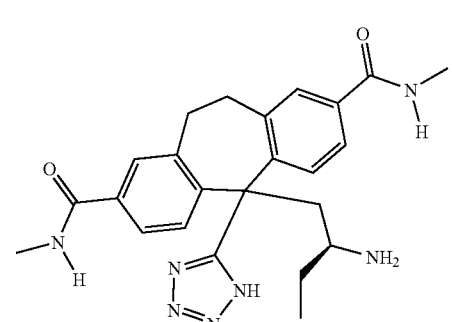 |

-continued

| Preparative Example | Preparative Example Sulfamidate | Product |
|---|---|---|
| 225 | 25 | |
| 226 | 26 | |
| 227 | 27 | |
| 228 | 28 | |

-continued
| Preparative Example | Preparative Example Sulfamidate | Product |
|---|---|---|
| 229 | 29 | 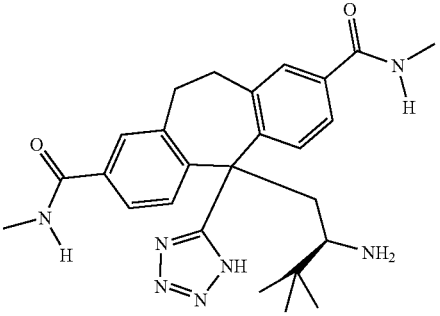 |
| 230 | 30 | 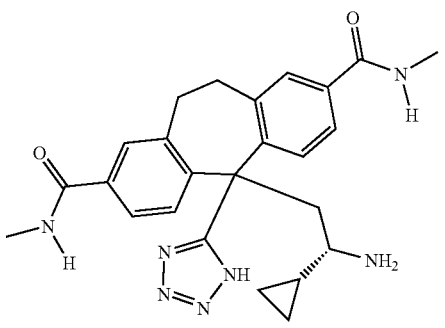 |
| 231 | 31 | 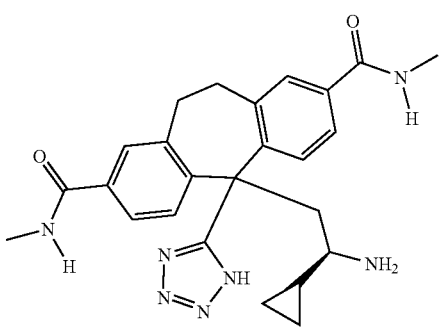 |
| 232 | 32 | 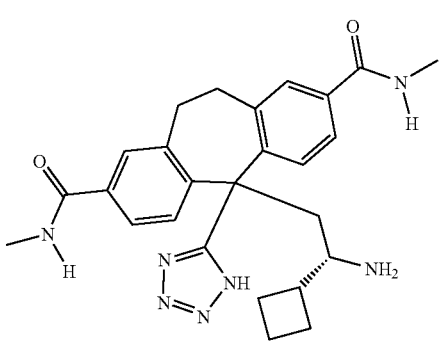 |

-continued

| Preparative Example | Preparative Example Sulfamidate | Product |
|---|---|---|
| 233 | 33 | |
| 234 | 34 | |
| 235 | 35 | |
| 236 | 36 | |

-continued

| Preparative Example | Preparative Example Sulfamidate | Product |
|---|---|---|
| 237 | 37 | |
| 238 | 38 | |
| 239 | 39 | |
| 240 | 40 | |

| Preparative Example | Preparative Example Sulfamidate | Product |
|---|---|---|
| 241 | 41 | 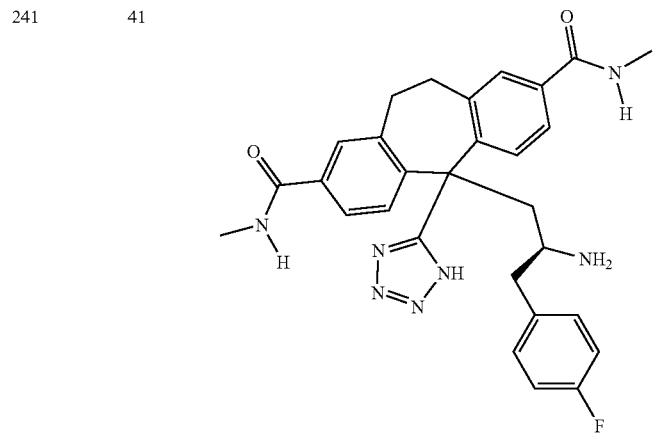 |
| 242 | 42 | 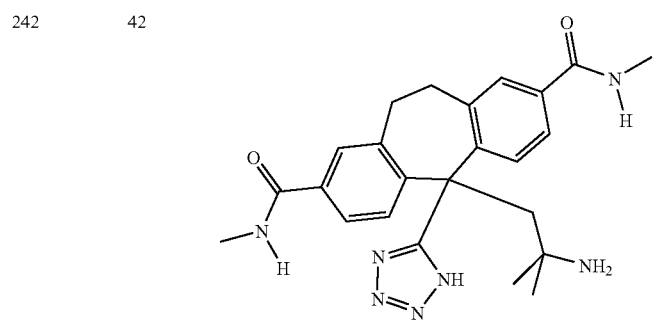 |
| 243 | 43 | 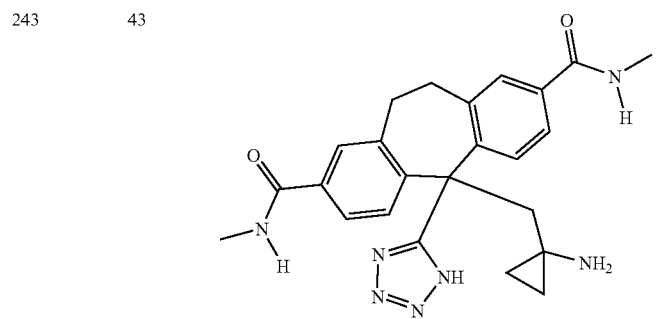 |
| 244 | 44 | 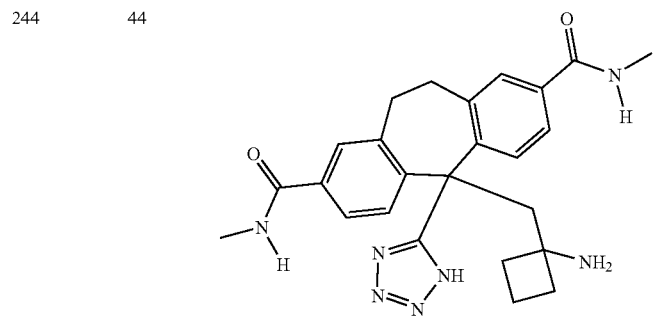 |

-continued

| Preparative Example | Preparative Example Sulfamidate | Product |
|---|---|---|
| 245 | 45 | |
| 246 | 46 | |
| 247 | 24 | |
| 248 | 23 | |

-continued

| Preparative Example | Preparative Example Sulfamidate | Product |
|---|---|---|
| 249 | 25 | |
| 250 | 26 | |
| 251 | 27 | |
| 252 | 28 | |

|  |  |  |
| --- | --- | --- |
| Preparative Example | Preparative Example Sulfamidate | Product |
| 253 | 29 | |
| 254 | 30 | |
| 255 | 31 | |
| 256 | 32 | |

-continued
| Preparative Example | Preparative Example Sulfamidate | Product |
|---|---|---|
| 257 | 33 | 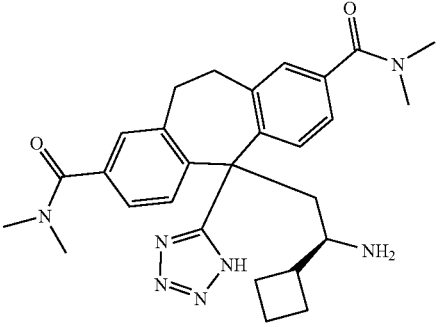 |
| 258 | 34 | 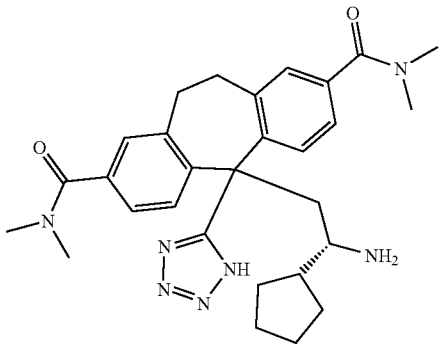 |
| 259 | 35 | 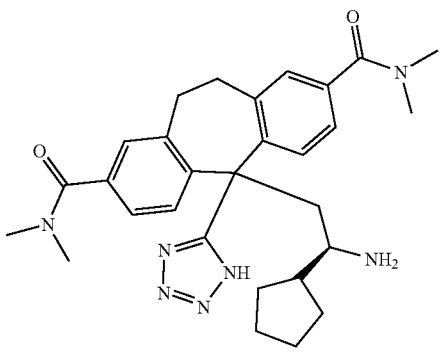 |
| 260 | 36 | 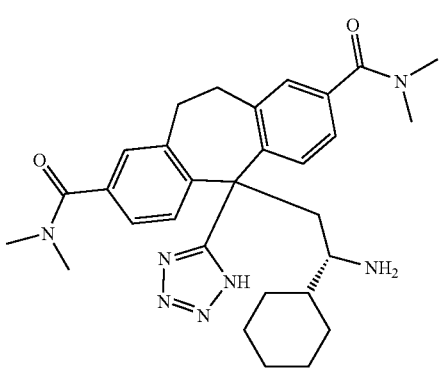 |

-continued

| Preparative Example | Preparative Example Sulfamidate | Product |
|---|---|---|
| 261 | 37 | |
| 262 | 38 | |
| 263 | 39 | |
| 264 | 40 | |

-continued
| Preparative Example | Preparative Example Sulfamidate | Product |
|---|---|---|
| 265 | 41 | 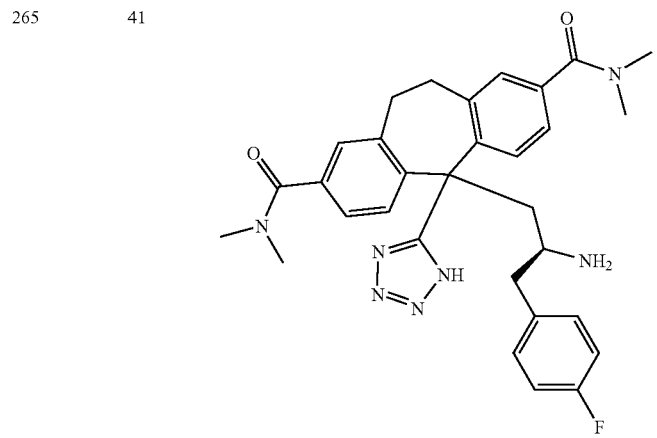 |
| 266 | 42 | 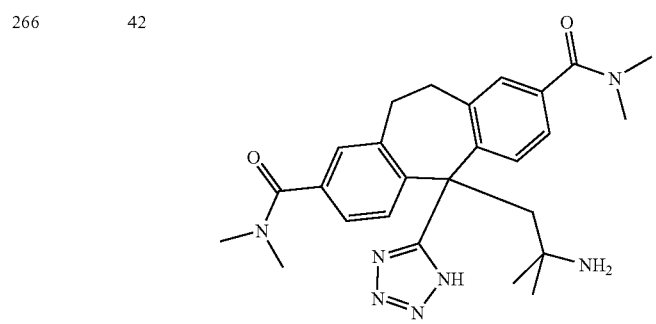 |
| 267 | 43 | 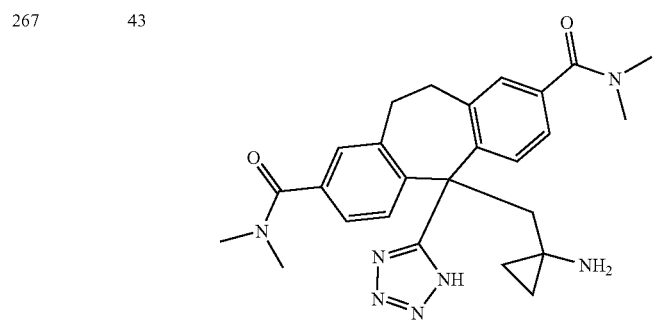 |
| 268 | 44 | 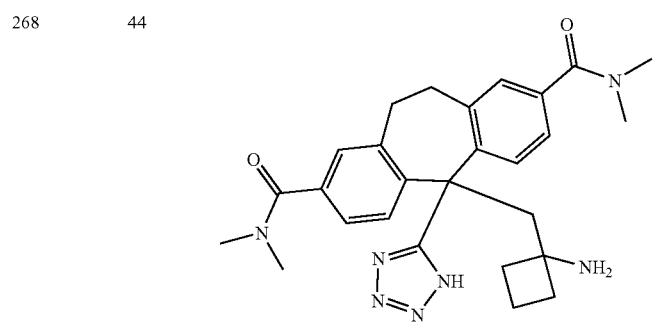 |

-continued
| Preparative Example | Preparative Example Sulfamidate | Product |
|---|---|---|
| 269 | 45 | 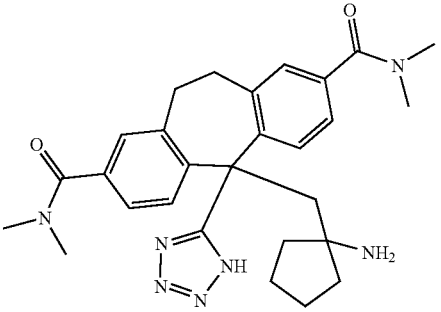 |
| 270 | 46 | 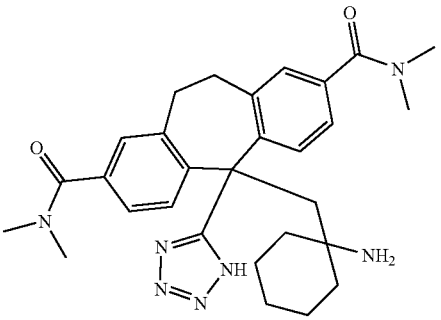 |
| 271 | 24 | 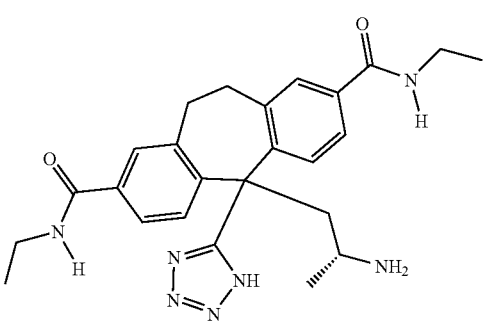 |
| 272 | 23 | 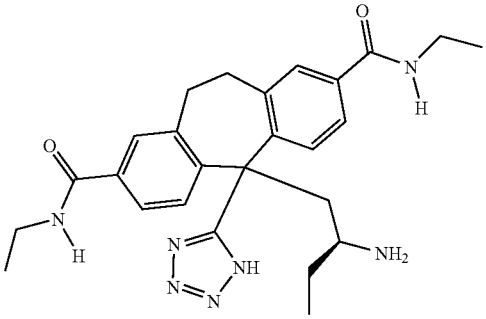 |

-continued
| Preparative Example | Preparative Example Sulfamidate | Product |
|---|---|---|
| 273 | 25 | 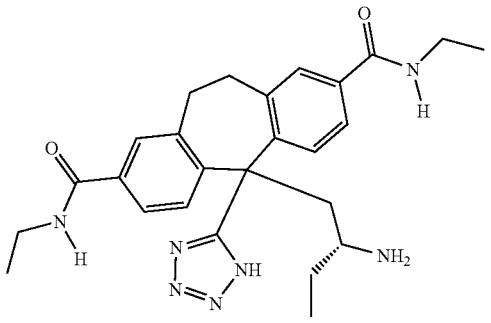 |
| 274 | 26 | 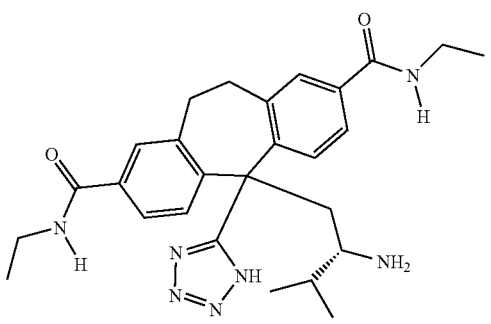 |
| 275 | 27 | 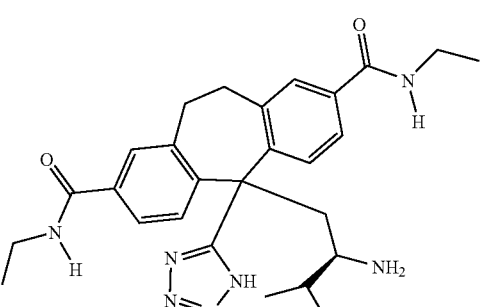 |
| 276 | 28 | 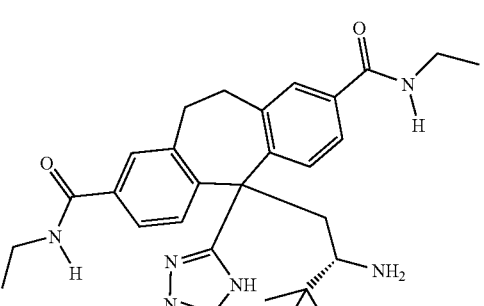 |

-continued

| Preparative Example | Preparative Example Sulfamidate | Product |
|---|---|---|
| 277 | 29 | |
| 278 | 30 | |
| 279 | 31 | |
| 280 | 32 | |

-continued

| Preparative Example | Preparative Example Sulfamidate | Product |
|---|---|---|
| 281 | 33 | |
| 282 | 34 | |
| 283 | 35 | |
| 284 | 36 | |

-continued
| Preparative Example | Preparative Example Sulfamidate | Product |
|---|---|---|
| 285 | 37 | 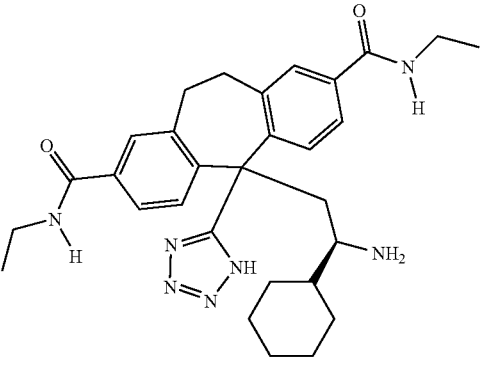 |
| 286 | 38 | 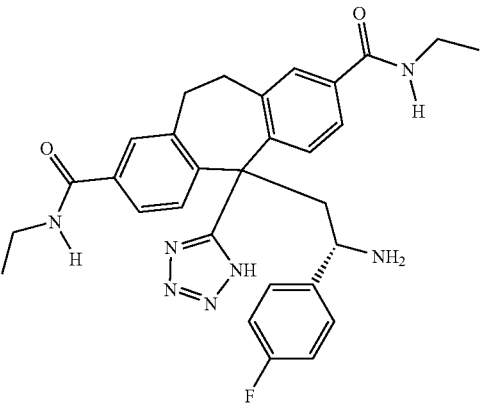 |
| 287 | 39 | 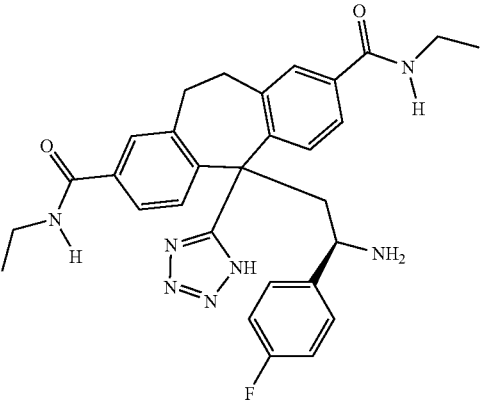 |

-continued
| Preparative Example | Preparative Example Sulfamidate | Product |
|---|---|---|
| 288 | 40 | 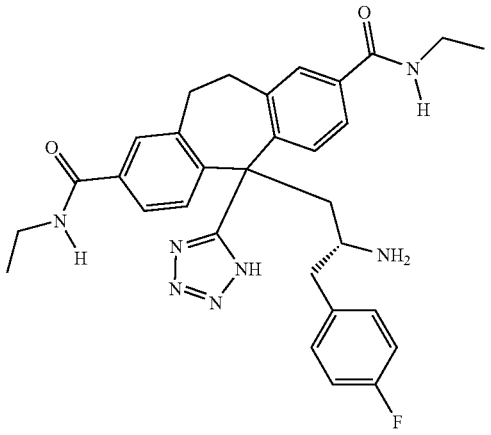 |
| 289 | 41 | 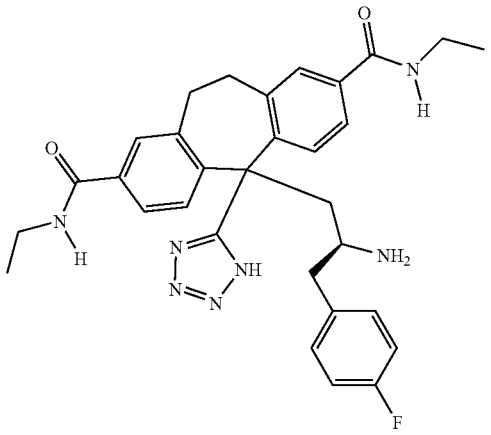 |
| 290 | 42 | 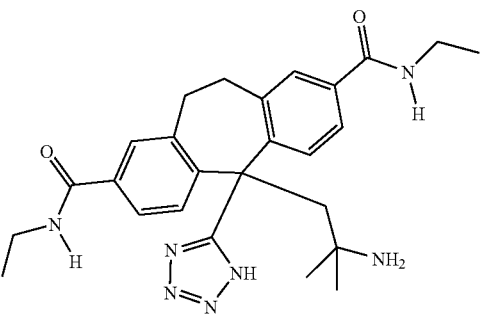 |
| 291 | 43 | 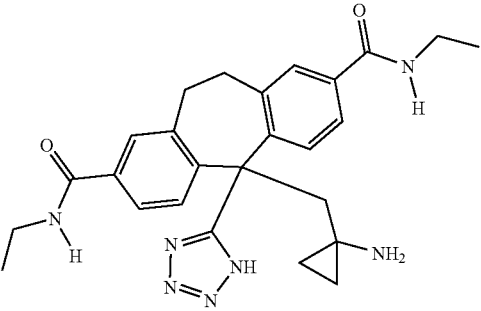 |

-continued
| Preparative Example | Preparative Example Sulfamidate | Product |
|---|---|---|
| 292 | 44 | 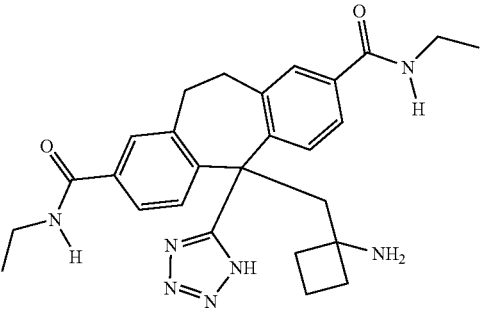 |
| 293 | 45 | 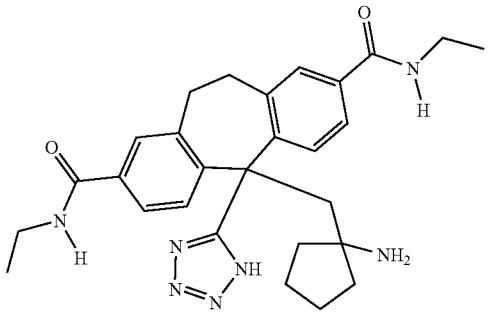 |
| 294 | 46 | 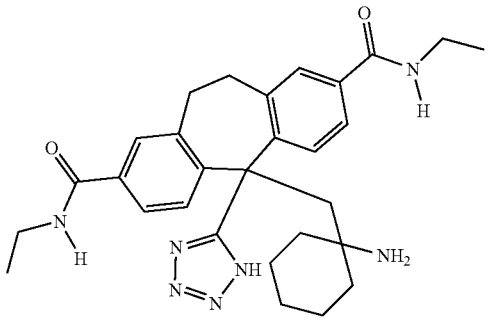 |
Examples 295-299 have been intentionally excluded.
Preparative Example 300
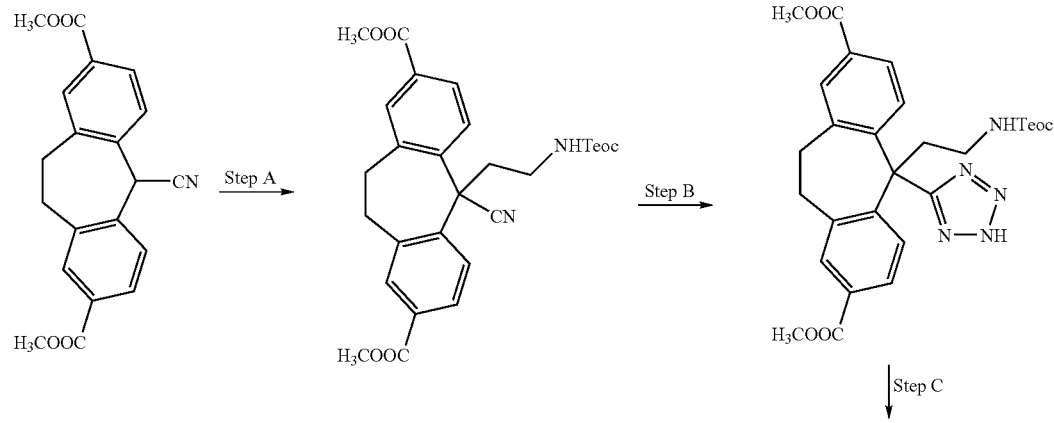

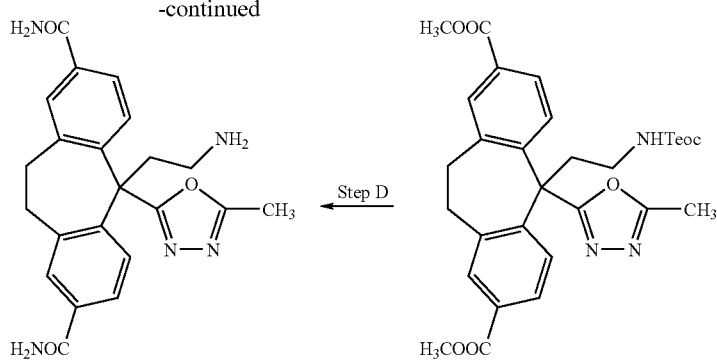

Step A

If one were to treat the compound from Preparative Example 59 with the sulfimidate from Preparative Example 22 according to the procedure described in Preparative Example 61 Step A, one would obtain the title compound.

Step B

If one were to treat the title compound from Step A above with NaN₃ as described in Preparative Example 61 Step B, one would obtain the title compound.

Step C

If one were to treat the title compound from Step B above with acetic acid anhydride in pyridine at 100° C. for 2 h one would obtain, after the removal of the pyridine under reduced pressure and after column chromatography, the title compound.

Step D

If one were to treat the title compound from Step A above according to the procedures described in Preparative Example 70 one would obtain the title compound.

Preparative Example 301-335

If one were to follow a similar procedure as that described in Preparative Example 300, except using the appropriate intermediate from the Preparative Examples and anhydrides or acid chlorides and amines as indicated in the Table below, one would obtain the desired amine product.

| Preparative Example | Preparative Example | Acid Chloride/Anhydride | Amine | Product |
|---|---|---|---|---|
| 301 | 300 | propionic anhydride | NH₃ | [tricyclic product with ethyl-oxadiazole, two H₂NOC groups, and CH₂CH₂NH₂ chain] |
| 302 | 300 | isobutyryl chloride | NH₃ | [tricyclic product with isopropyl-oxadiazole, two H₂NOC groups, and CH₂CH₂NH₂ chain] |

-continued
| Preparative Example | Preparative Example | Acid Chloride/ Anhydride | Amine | Product |
|---|---|---|---|---|
| 303 | 300 | 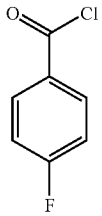 | NH$_3$ | 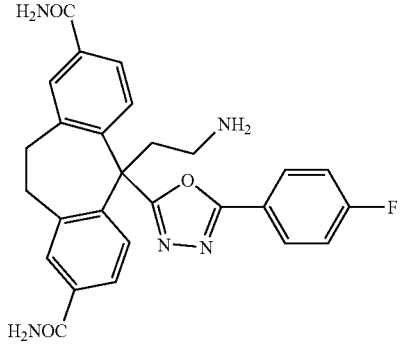 |
| 304 | 61 | 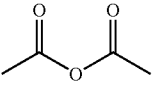 | NH$_3$ | 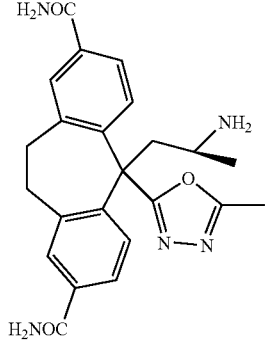 |
| 305 | 61 | 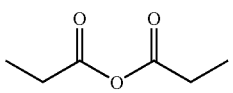 | NH$_3$ | 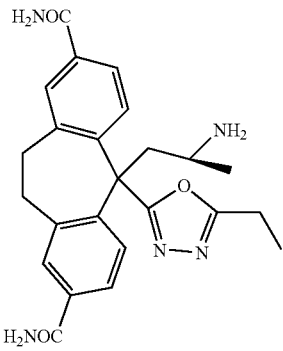 |
| 306 | 61 | 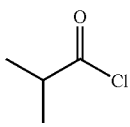 | NH$_3$ | 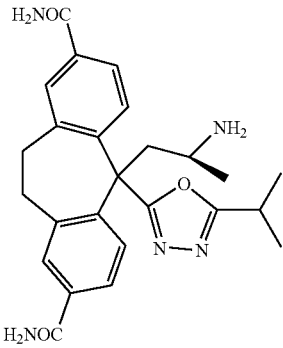 |

-continued
| Preparative Example | Preparative Example | Acid Chloride/ Anhydride | Amine | Product |
|---|---|---|---|---|
| 307 | 61 | 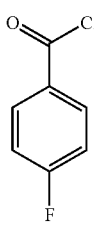 | NH$_3$ | 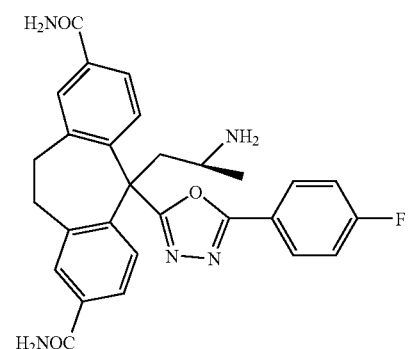 |
| 308 | 65 | 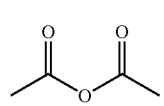 | NH$_3$ | 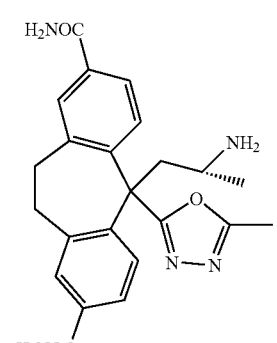 |
| 309 | 65 | 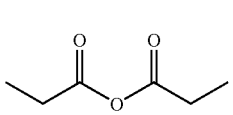 | NH$_3$ | 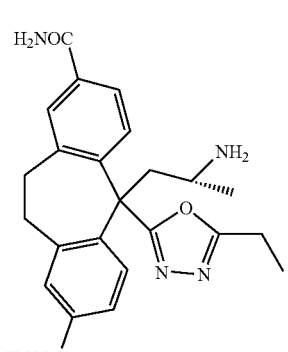 |
| 310 | 65 | 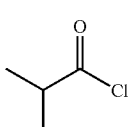 | NH$_3$ | 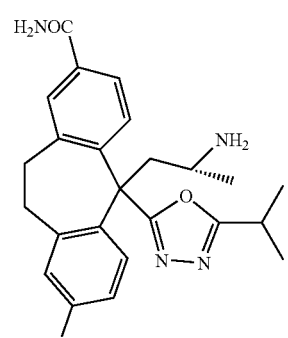 |

-continued
| Preparative Example | Preparative Example | Acid Chloride/ Anhydride | Amine | Product |
|---|---|---|---|---|
| 311 | 65 | 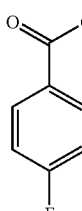 | NH₃ | 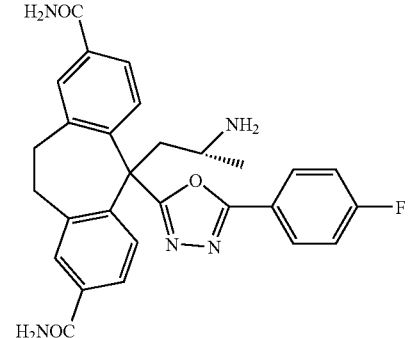 |
| 312 | 300 | 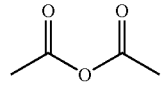 | CH₃NH₂ | 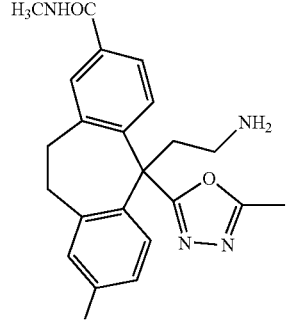 |
| 313 | 300 | 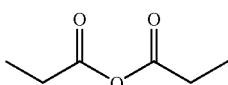 | CH₃NH₂ | 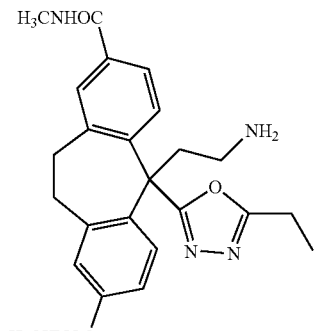 |
| 314 | 300 | 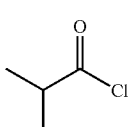 | CH₃NH₂ | 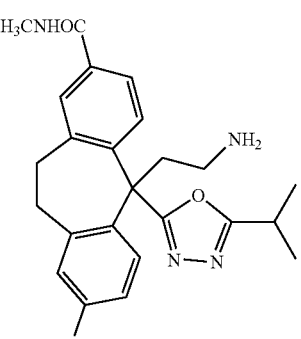 |

-continued

| Preparative Example | Preparative Example | Acid Chloride/ Anhydride | Amine | Product |
| --- | --- | --- | --- | --- |
| 315 | 300 | 4-fluorobenzoyl chloride | CH₃NH₂ | (product structure with 5-(4-fluorophenyl)-1,3,4-oxadiazole) |
| 316 | 61 | acetic anhydride | CH₃NH₂ | (product structure with 5-methyl-1,3,4-oxadiazole) |
| 317 | 61 | propionic anhydride | CH₃NH₂ | (product structure with 5-ethyl-1,3,4-oxadiazole) |
| 318 | 61 | isobutyryl chloride | CH₃NH₂ | (product structure with 5-isopropyl-1,3,4-oxadiazole) |

-continued

| Preparative Example | Preparative Example | Acid Chloride/ Anhydride | Amine | Product |
|---|---|---|---|---|
| 319 | 61 | 4-fluorobenzoyl chloride | CH₃NH₂ | (structure with 5-(4-fluorophenyl)-1,3,4-oxadiazole) |
| 320 | 65 | acetic anhydride | CH₃NH₂ | (structure with 5-methyl-1,3,4-oxadiazole) |
| 321 | 65 | propionic anhydride | CH₃NH₂ | (structure with 5-ethyl-1,3,4-oxadiazole) |
| 322 | 65 | isobutyryl chloride | CH₃NH₂ | (structure with 5-isopropyl-1,3,4-oxadiazole) |

-continued

| Preparative Example | Preparative Example | Acid Chloride/ Anhydride | Amine | Product |
|---|---|---|---|---|
| 323 | 65 | 4-fluorobenzoyl chloride | CH₃NH₂ | (product structure with H₃CNHOC, NH₂, oxadiazole-4-fluorophenyl, H₃CHNOC) |
| 324 | 300 | acetic anhydride | (CH₃)₂NH | (product with (H₃C)₂NOC groups, NH₂, 5-methyl-1,3,4-oxadiazole) |
| 325 | 300 | propionic anhydride | (CH₃)₂NH | (product with (H₃C)₂NOC groups, NH₂, 5-ethyl-1,3,4-oxadiazole) |
| 326 | 300 | isobutyryl chloride | (CH₃)₂NH | (product with (H₃C)₂NOC groups, NH₂, 5-isopropyl-1,3,4-oxadiazole) |

-continued
| Preparative Example | Preparative Example | Acid Chloride/ Anhydride | Amine | Product |
|---|---|---|---|---|
| 327 | 300 | 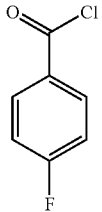 | (CH₃)₂NH | 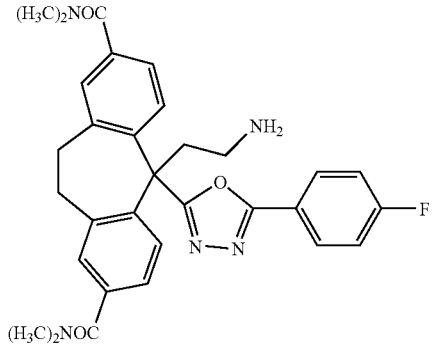 |
| 328 | 61 | 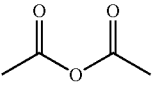 | (CH₂)₂NH | 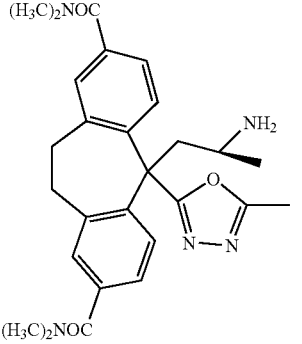 |
| 329 | 61 | 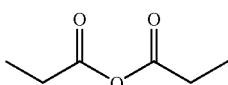 | (CH₃)₂NH | 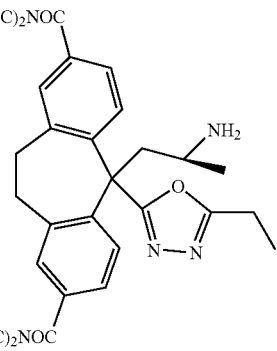 |
| 330 | 61 | 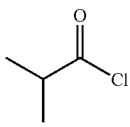 | (CH₃)₂NH | 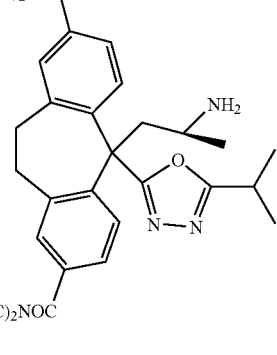 |

-continued
| Preparative Example | Preparative Example | Acid Chloride/ Anhydride | Amine | Product |
| --- | --- | --- | --- | --- |
| 331 | 61 | 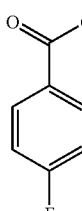 | (CH₃)₂NH | 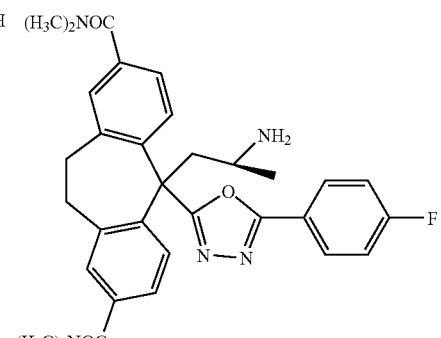 |
| 332 | 65 | 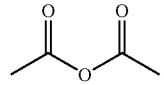 | (CH₃)₂NH | 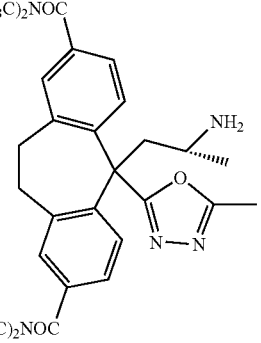 |
| 333 | 65 | 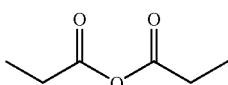 | (CH₃)₂NH | 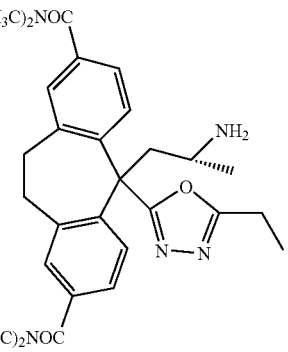 |
| 334 | 65 | 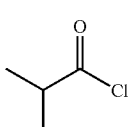 | (CH₃)₂NH | 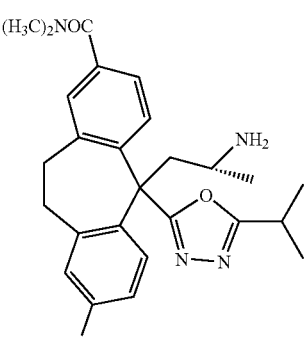 |

-continued

| Preparative Example | Preparative Example | Acid Chloride/ Anhydride | Amine | Product |
|---|---|---|---|---|
| 335 | 65 | 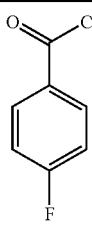 | (CH$_3$)$_2$NH | 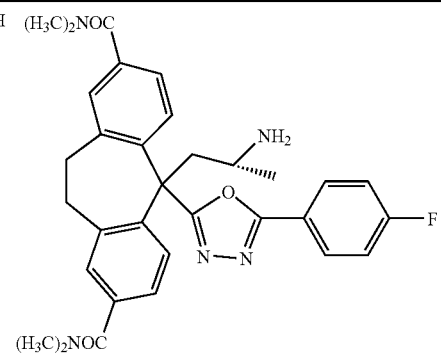 |

Example numbers 336-399 were intentionally excluded.

Preparative Example 400-434

If one were to follow a similar procedure as that described in Preparative Example 66, using the appropriate intermediate from the Preparative Examples and hydroxylamine hydrochlorides and amines as indicated in the Table below and treat the products according to Preparative Example 70, one would obtain the desired amine product.

| Preparative Example | Preparative Example | Hydroxylamine hydrochloride | Amine | Product |
|---|---|---|---|---|
| 400 | 300 | H$_2$N–OH | NH$_3$ | 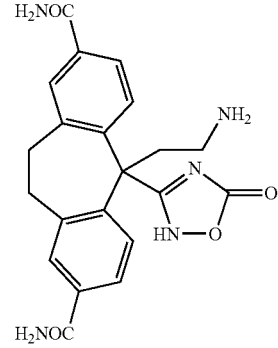 |
| 401 | 300 | CH$_3$NH–OH | NH$_3$ | 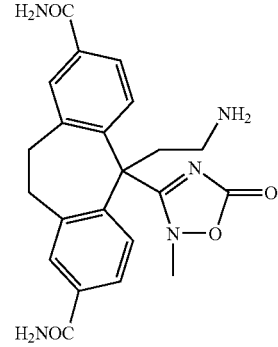 |

-continued

| Preparative Example | Preparative Example | Hydroxylamine hydrochloride | Amine | Product |
|---|---|---|---|---|
| 402 | 300 | NHOH-cyclohexyl | NH₃ | (structure) |
| 403 | 300 | iPr-NH-OH | NH₃ | (structure) |
| 404 | 61 | H₂N-OH | NH₃ | (structure) |
| 405 | 61 | MeNH-OH | NH₃ | (structure) |

-continued
| Preparative Example | Preparative Example | Hydroxylamine hydrochloride | Amine | Product |
|---|---|---|---|---|
| 406 | 61 | NHOH-cyclohexyl | NH₃ | 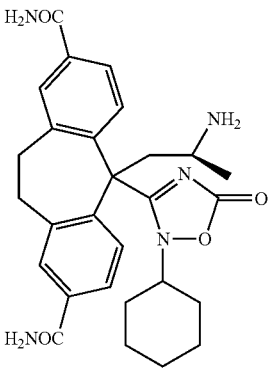 |
| 407 | 61 | iPr-NH-OH | NH₃ | 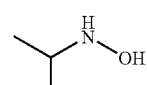 |
| 408 | 65 | H₂N-OH | NH₃ | 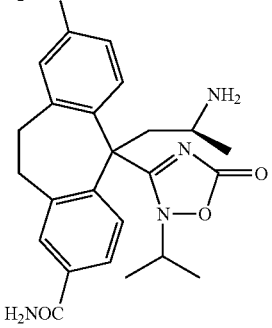 |
| 409 | 65 | MeNH-OH | NH₃ | 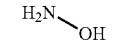 |

| Preparative Example | Preparative Example | Hydroxylamine hydrochloride | Amine | Product |
|---|---|---|---|---|
| 410 | 65 | 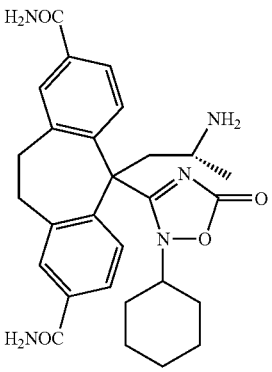 NHOH (cyclohexyl) | NH₃ | 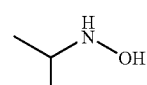 |
| 411 | 65 | 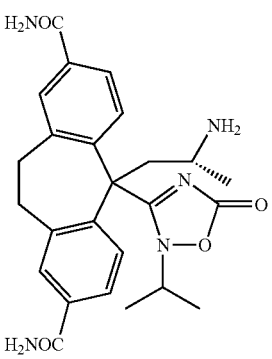 isopropyl-N(H)-OH | NH₃ | 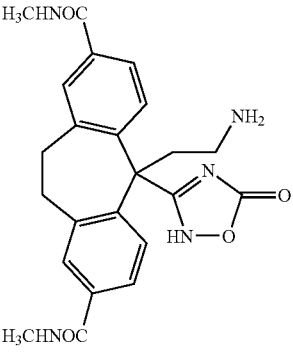 |
| 412 | 300 | H₂N-OH | CH₃NH₂ | 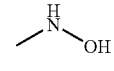 |
| 413 | 300 | CH₃-N(H)-OH | CH₃NH₂ | 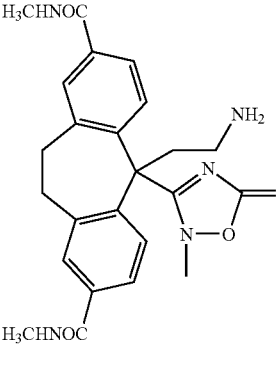 |

-continued
| Preparative Example | Preparative Example | Hydroxylamine hydrochloride | Amine | Product |
|---|---|---|---|---|
| 414 | 300 | 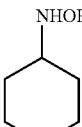 NHOH (cyclohexyl) | CH₃NH₂ | 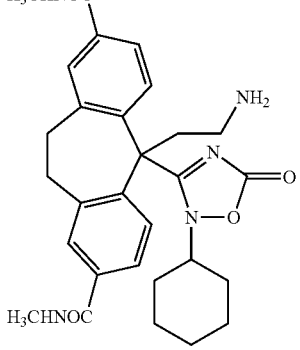 |
| 415 | 300 | 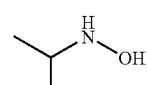 iPrNH-OH | CH₃NH₂ | 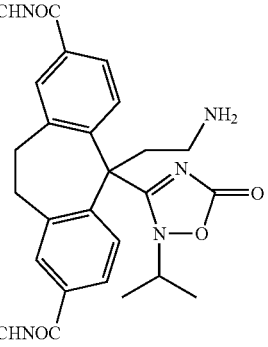 |
| 416 | 61 | H₂N-OH | CH₃NH₂ | 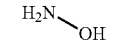 |
| 417 | 61 |  CH₃NH-OH | CH₃NH₂ | 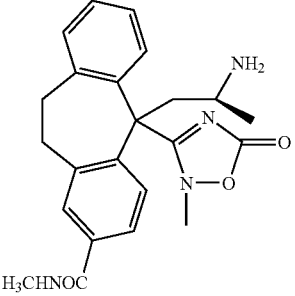 |

-continued
| Preparative Example | Preparative Example | Hydroxylamine hydrochloride | Amine | Product |
|---|---|---|---|---|
| 418 | 61 | 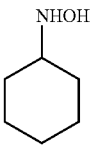 | CH₃NH₂ | 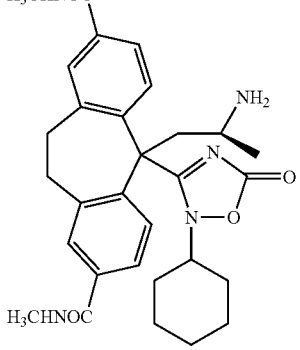 |
| 419 | 61 | 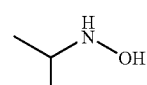 | CH₃NH₂ | 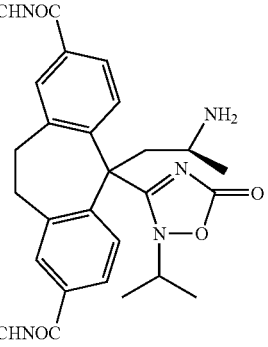 |
| 420 | 65 | 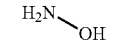 | CH₃NH₂ | 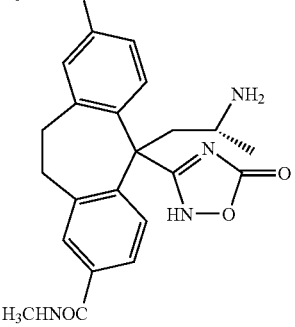 |
| 421 | 65 |  | CH₃NH₂ | 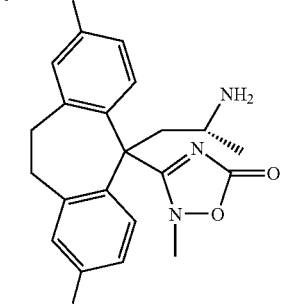 |

-continued

| Preparative Example | Preparative Example | Hydroxylamine hydrochloride | Amine | Product |
|---|---|---|---|---|
| 422 | 65 | NHOH-cyclohexyl | CH₃NH₂ | (structure) |
| 423 | 65 | iPr-NH-OH | CH₃NH₂ | (structure) |
| 424 | 300 | H₂N-OH | (CH₃)₂NH | (structure) |
| 425 | 300 | CH₃-NH-OH | (CH₃)₂NH | (structure) |

-continued

| Preparative Example | Preparative Example | Hydroxylamine hydrochloride | Amine | Product |
|---|---|---|---|---|
| 426 | 300 | NHOH-cyclohexyl | (CH₃)₂NH | (H₃C)₂NOC-[tricyclic]-CH₂CH₂NH₂, oxadiazolone N-cyclohexyl, (H₃C)₂NOC |
| 427 | 300 | isopropyl-N(H)-OH | (CH₃)₂NH | (H₃C)₂NOC-[tricyclic]-CH₂CH₂NH₂, oxadiazolone N-isopropyl, (H₃C)₂NOC |
| 428 | 61 | CH₃-N(H)-OH | (CH₃)₂NH | (H₃C)₂NOC-[tricyclic]-CH(CH₃)CH₂NH₂, oxadiazolone N-methyl, (H₃C)₂NOC |
| 429 | 61 | NHOH-cyclohexyl | (CH₃)₂NH | (H₃C)₂NOC-[tricyclic]-CH(CH₃)CH₂NH₂, oxadiazolone N-cyclohexyl, (H₃C)₂NOC |

-continued

| Preparative Example | Preparative Example | Hydroxylamine hydrochloride | Amine | Product |
|---|---|---|---|---|
| 430 | 61 | isopropyl-NH(H)-OH | (CH$_3$)$_2$NH | (structure with N-isopropyl oxadiazolone) |
| 431 | 65 | H$_2$N-OH | (CH$_3$)$_2$NH | (structure with NH oxadiazolone) |
| 432 | 65 | CH$_3$-NH(H)-OH | (CH$_3$)$_2$NH | (structure with N-methyl oxadiazolone) |
| 433 | 65 | cyclohexyl-NHOH | (CH$_3$)$_2$NH | (structure with N-cyclohexyl oxadiazolone) |

-continued
| Preparative Example | Preparative Example | Hydroxylamine hydrochloride | Amine | Product |
|---|---|---|---|---|
| 434 | 65 | 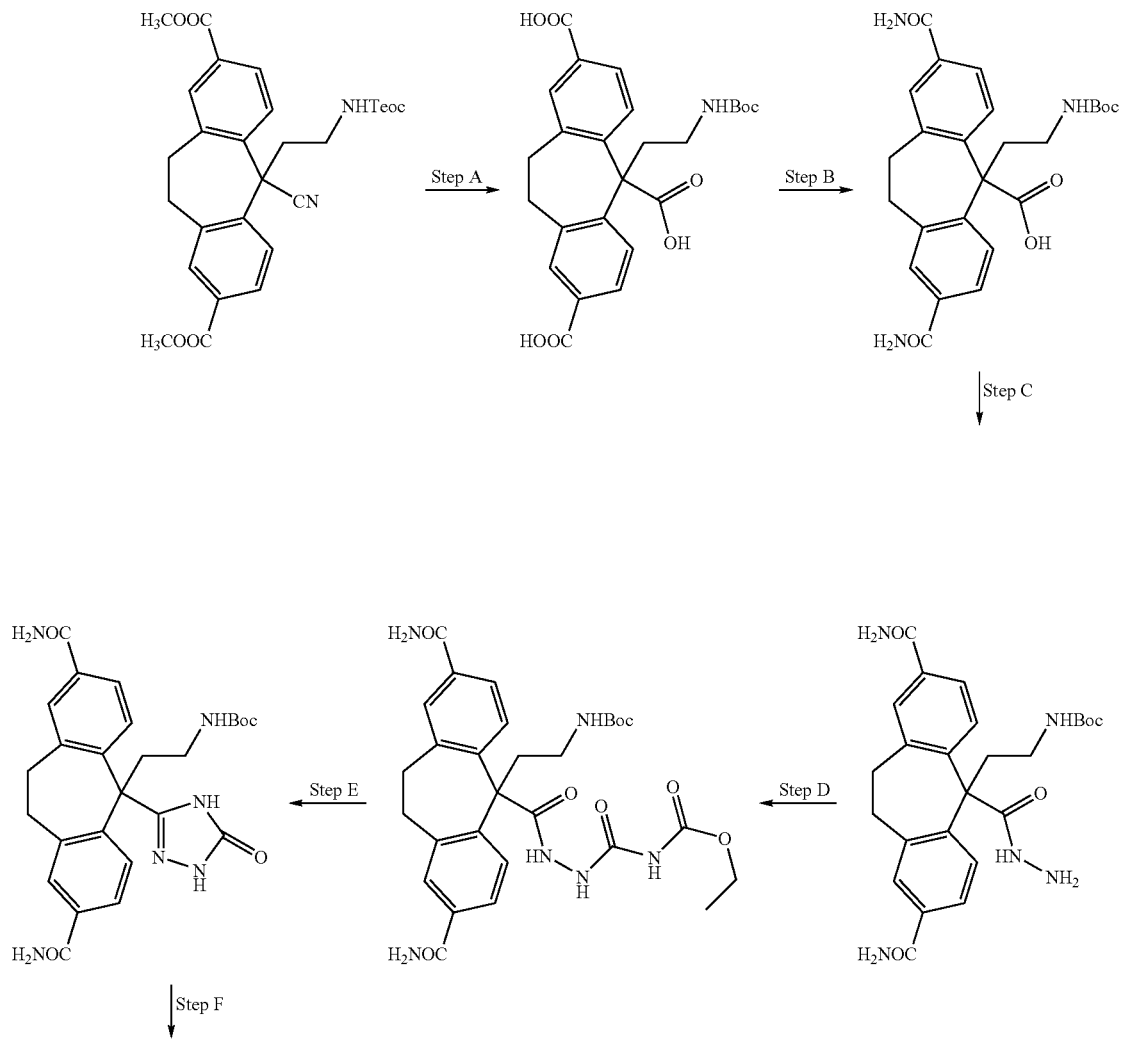 | (CH₃)₂NH | |
Example numbers 435-499 were intentionally excluded.
Preparative Example 500

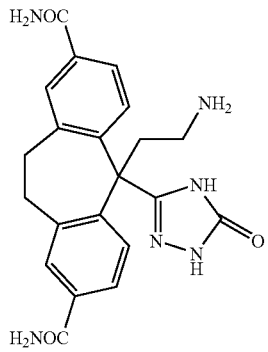

Step A

If one were to treat the compound from Preparative Example 300 Step A with conc. HCl in acetic acid according to the procedure described in Preparative Example 49 Step J, one would obtain the title compound.

Step B

If one were to treat the title compound from Step A above according to the procedure described in Preparative Example 70 Step A, one would obtain the title compound.

Step C

If one were to treat the title compound from Step B above according to the procedure described in Preparative Example 70 Step A but using hydrazine instead of an amine, one would obtain the title compound.

Step D

If one were to stir the title compound from Step C above with 1 eq. ethyl isocyanate in DMA one would obtain after removing of DMA and the title compound.

Step E

If one were to treat the title compound from Step D above with a 2% aqueous NaOH at 100° C. for several hours one would obtain after neutralisation, precipitation and recrystallisation from ethanol the title compound.

Step F

If one were to treat the title compound from Step E above according to the procedure described in Preparative Example 70 Step B, one would obtain the title compound.

Preparative Example 501-535

If one were to follow a similar procedure as that described in Preparative Example 500, except using the appropriate intermediate from the Preparative Examples and hydrazines and amines as indicated in the Table below, one would obtain the desired amine product.

| Preparative Example | Preparative Example | Hydrazine | Amine | Product |
|---|---|---|---|---|
| 501 | 300 | H-N(CH3)-NH2 | NH3 | (structure) |

-continued

| Preparative Example | Preparative Example | Hydrazine | Amine | Product |
|---|---|---|---|---|
| 502 | 300 | 4-fluorophenylhydrazine | NH₃ | (structure) |
| 503 | 300 | isopropylhydrazine | NH₃ | (structure) |
| 504 | 61 | N₂H₄ | NH₃ | (structure) |
| 505 | 61 | methylhydrazine | NH₃ | (structure) |

-continued
| Preparative Example | Preparative Example | Hydrazine | Amine | Product |
|---|---|---|---|---|
| 506 | 61 | 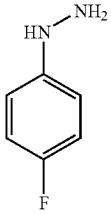 | $NH_3$ | 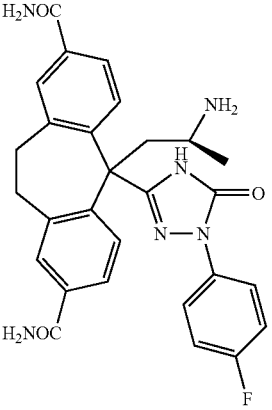 |
| 507 | 61 | 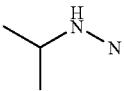 | $NH_3$ | 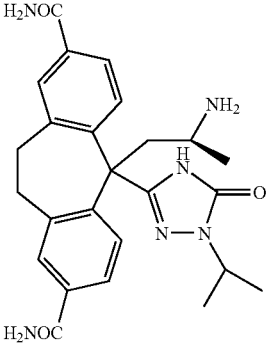 |
| 508 | 65 | $N_2H_4$ | $NH_3$ | 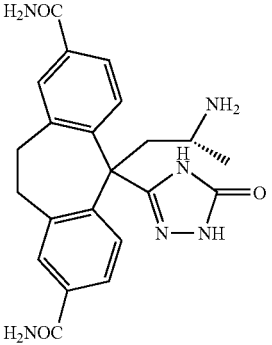 |
| 509 | 65 | 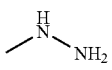 | $NH_3$ | 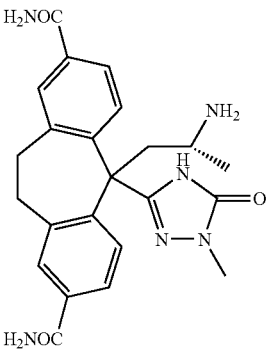 |

-continued

| Preparative Example | Preparative Example | Hydrazine | Amine | Product |
|---|---|---|---|---|
| 510 | 65 | 4-fluorophenylhydrazine | NH₃ | (structure) |
| 511 | 65 | isopropylhydrazine | NH₃ | (structure) |
| 512 | 300 | N₂H₄ | CH₃NH₂ | (structure) |
| 513 | 300 | methylhydrazine | CH₃NH₂ | (structure) |

| Preparative Example | Preparative Example | Hydrazine | Amine | Product |
|---|---|---|---|---|
| 514 | 300 | 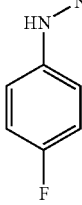 | CH$_3$NH$_2$ | 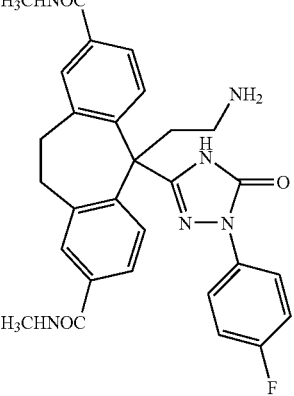 |
| 515 | 300 | 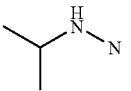 | CH$_3$NH$_2$ | 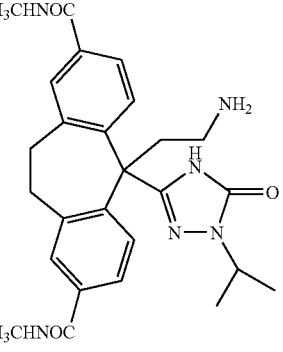 |
| 516 | 61 | N$_2$H$_4$ | CH$_3$NH$_2$ | 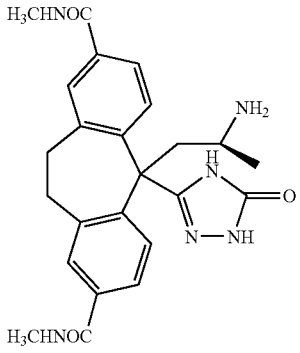 |
| 517 | 61 | 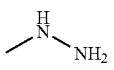 | CH$_3$NH$_2$ | 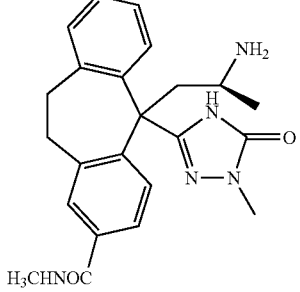 |

-continued

| Preparative Example | Preparative Example | Hydrazine | Amine | Product |
|---|---|---|---|---|
| 518 | 61 | HN-NH₂ with 4-fluorophenyl | CH₃NH₂ | (structure shown) |
| 519 | 61 | isopropyl-NH-NH₂ | CH₃NH₂ | (structure shown) |
| 520 | 65 | N₂H₄ | CH₃NH₂ | (structure shown) |
| 521 | 65 | CH₃-NH-NH₂ | CH₃NH₂ | (structure shown) |

-continued

| Preparative Example | Preparative Example | Hydrazine | Amine | Product |
|---|---|---|---|---|
| 522 | 65 | HN-NH2 (4-fluorophenyl) | CH3NH2 | (structure) |
| 523 | 65 | iPr-NH-NH2 | CH3NH2 | (structure) |
| 524 | 300 | N2H4 | (CH3)2NH | (structure) |
| 525 | 300 | CH3-NH-NH2 | (CH3)2NH | (structure) |

-continued

| Preparative Example | Preparative Example | Hydrazine | Amine | Product |
|---|---|---|---|---|
| 526 | 300 | 4-fluorophenylhydrazine | (CH₃)₂NH | (structure) |
| 527 | 300 | isopropylhydrazine | (CH₃)₂NH | (structure) |
| 528 | 61 | N₂H₄ | (CH₃)₂NH | (structure) |
| 529 | 61 | methylhydrazine | (CH₃)₂NH | (structure) |

-continued

| Preparative Example | Preparative Example | Hydrazine | Amine | Product |
|---|---|---|---|---|
| 530 | 61 | 4-fluorophenylhydrazine | $(CH_3)_2NH$ | |
| 531 | 61 | isopropylhydrazine | $(CH_3)_2NH$ | |
| 532 | 65 | $N_2H_4$ | $(CH_3)_2NH$ | |
| 533 | 65 | methylhydrazine | $(CH_3)_2NH$ | |

-continued
| Preparative Example | Preparative Example | Hydrazine | Amine | Product |
|---|---|---|---|---|
| 534 | 65 | HN-NH₂ with 4-fluorophenyl | $(CH_3)_2NH$ | $(H_3C)_2NOC$ tricyclic with $NH_2$ and triazolone bearing 4-fluorophenyl, $(H_3C)_2NOC$ |
| 535 | 65 | isopropyl-NH-NH₂ | $(CH_3)_2NH$ | $(H_3C)_2NOC$ tricyclic with $NH_2$ and N-isopropyl triazolone, $(H_3C)_2NOC$ |
Example numbers 536-599 were intentionally excluded.
Preparative Example 600
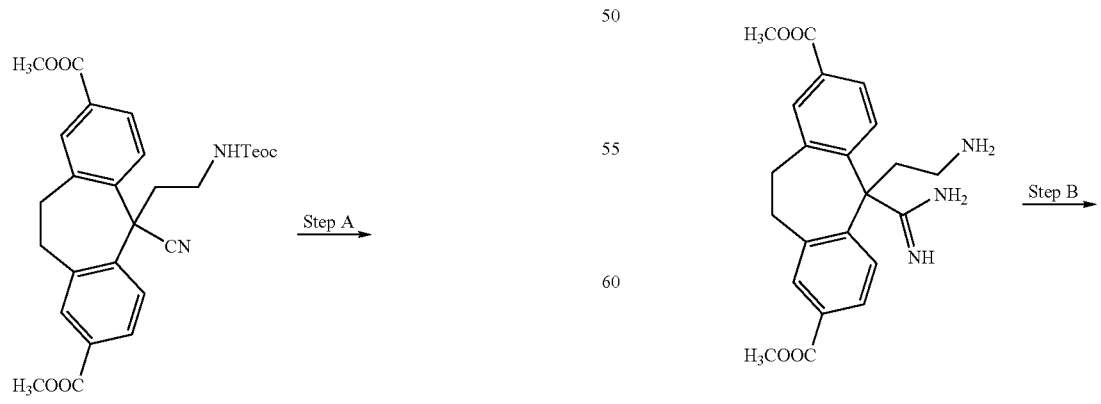
Step A → Step B

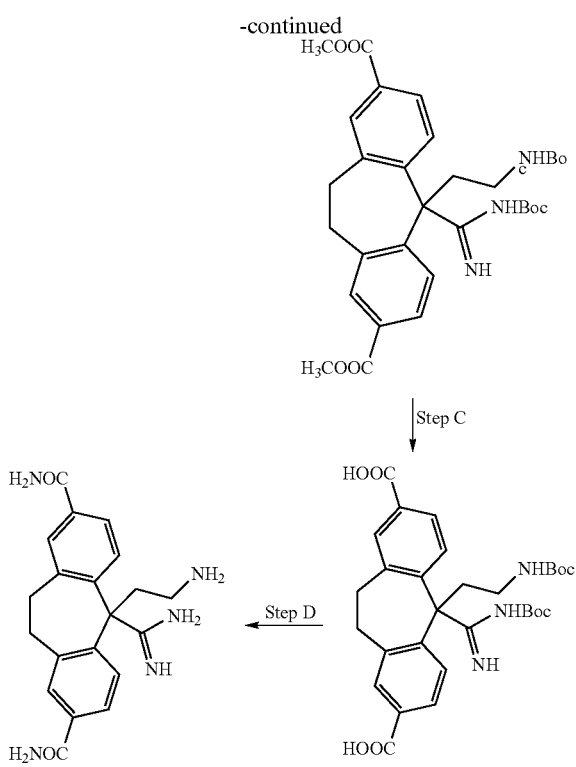

Step A

If one were to treat the intermediate from Preparative Example 300 Step A with dry HCl gas in EtOH/CHCl$_3$ at 0° C. and set aside for 10 days, one would obtain after removal of the solvents the imidate hydrochloride. If one were to treat the imidate hydrochloride with NH$_3$ in dry EtOH and heat it to reflux for 7 h, one would obtain, after filtration and evaporation of the filtrate followed by recrystallization, the title compound.

Step B

If one were to treat the title compound from Step A above with Boc$_2$O according to the procedure described in Preparative Example 49 Step J but without the acid treatment, one would obtain the title compound.

Step C

If one were to treat the title compound from Step B above according to Preparative Example 61 Step C, one would obtain the title compound.

Step D

If one were to treat the title compound from Step C above according to the procedures described in Preparative Example 70, one would obtain the title compound.

Preparative Example 601-635

If one were to follow a similar procedure as that described in Preparative Example 600 except using the amines and appropriate intermediate from the Preparative Examples as indicated in the Table below, one would obtain the desired amine product.

| Preparative Example | Preparative Example | Amine Step A | Amine Step B | Product |
|---|---|---|---|---|
| 601 | 300 | CH$_3$NH$_2$ | NH$_3$ | 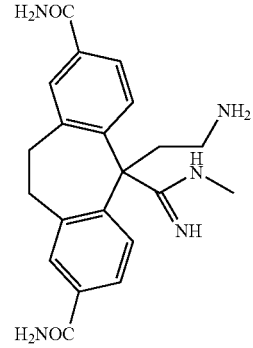 |
| 602 | 300 |  | NH$_3$ | 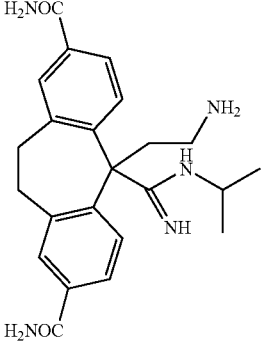 |

-continued

| Preparative Example | Preparative Example | Amine Step A | Amine Step B | Product |
|---|---|---|---|---|
| 603 | 300 | 4-fluoroaniline (NH₂-C₆H₄-F) | NH₃ | (structure) |
| 604 | 61 | NH₃ | NH₃ | (structure) |
| 605 | 61 | CH₃NH₂ | NH₃ | (structure) |
| 606 | 61 | isopropylamine | NH₃ | (structure) |

-continued

| Preparative Example | Preparative Example | Amine Step A | Amine Step B | Product |
|---|---|---|---|---|
| 607 | 61 | 4-fluoroaniline | NH₃ | tricyclic diamide with 4-fluorophenyl amidine and chiral aminopropyl group |
| 608 | 65 | NH₃ | NH₃ | tricyclic diamide with amidine and chiral aminopropyl group |
| 609 | 65 | CH₃NH₂ | NH₃ | tricyclic diamide with N-methyl amidine and chiral aminopropyl group |
| 610 | 65 | isopropylamine | NH₃ | tricyclic diamide with N-isopropyl amidine and chiral aminopropyl group |

-continued

| Preparative Example | Preparative Example | Amine Step A | Amine Step B | Product |
|---|---|---|---|---|
| 611 | 65 | 4-fluoroaniline (NH₂) | NH₃ | (structure with two H₂NOC groups on tricyclic system, CH(CH₃)NH₂ side chain, amidine NH linked to 4-fluorophenyl) |
| 612 | 300 | NH₃ | CH₃NH₂ | (tricyclic bis-H₃CHNOC substituted, with CH₂CH₂NH₂ and C(=NH)NH₂ groups) |
| 613 | 300 | CH₃NH₂ | CH₃NH₂ | (tricyclic bis-H₃CHNOC substituted, with CH₂CH₂NH₂ and C(=NH)NHCH₃ groups) |
| 614 | 300 | iPrNH₂ | CH₃NH₂ | (tricyclic bis-H₃CHNOC substituted, with CH₂CH₂NH₂ and C(=NH)NHiPr groups) |

-continued

| Preparative Example | Preparative Example | Amine Step A | Amine Step B | Product |
|---|---|---|---|---|
| 615 | 300 | NH$_2$-C$_6$H$_4$-F (4-fluoroaniline) | CH$_3$NH$_2$ | (structure shown) |
| 616 | 61 | NH$_3$ | CH$_3$NH$_2$ | (structure shown) |
| 617 | 61 | CH$_3$NH$_2$ | CH$_3$NH$_2$ | (structure shown) |
| 618 | 61 | NH$_2$-CH(CH$_3$)$_2$ (isopropylamine) | CH$_3$NH$_2$ | (structure shown) |

-continued
| Preparative Example | Preparative Example | Amine Step A | Amine Step B | Product |
|---|---|---|---|---|
| 619 | 61 | NH₂–C₆H₄–F (4-fluoroaniline) | CH₃NH₂ | 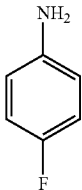 |
| 620 | 65 | NH₃ | CH₃NH₂ | 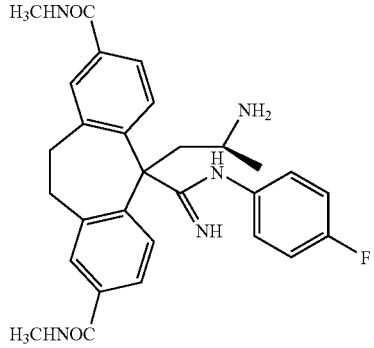 |
| 621 | 65 | CH₃NH₂ | CH₃NH₂ |  |
| 622 | 65 | NH₂–CH(CH₃)₂ (isopropylamine) | CH₃NH₂ |  |

-continued

| Preparative Example | Preparative Example | Amine Step A | Amine Step B | Product |
|---|---|---|---|---|
| 623 | 65 | NH₂–C₆H₄–F (4-fluoroaniline) | CH₃NH₂ | H₃CHNOC-substituted tricyclic with –CH₂–CH(NH₂)CH₃ and –C(=NH)NH–C₆H₄–F side chain; second ring bears H₃CHNOC |
| 624 | 300 | NH₃ | (CH₃)₂NH | (H₃C)₂NOC-substituted tricyclic with –CH₂CH₂NH₂ and –C(=NH)NH₂; second ring bears (H₃C)₂NOC |
| 625 | 300 | CH₃NH₂ | (CH₃)₂NH | (H₃C)₂NOC-substituted tricyclic with –CH₂CH₂NH₂ and –C(=NH)NHCH₃; second ring bears (H₃C)₂NOC |
| 626 | 300 | NH₂–CH(CH₃)₂ (isopropylamine) | (CH₃)₂NH | (H₃C)₂NOC-substituted tricyclic with –CH₂CH₂NH₂ and –C(=NH)NH-iPr; second ring bears (H₃C)₂NOC |

-continued
| Preparative Example | Preparative Example | Amine Step A | Amine Step B | Product |
|---|---|---|---|---|
| 627 | 300 | NH2-C6H4-F (4-fluoroaniline) | (CH3)2NH | 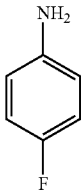 |
| 628 | 61 | NH3 | (CH3)2NH | 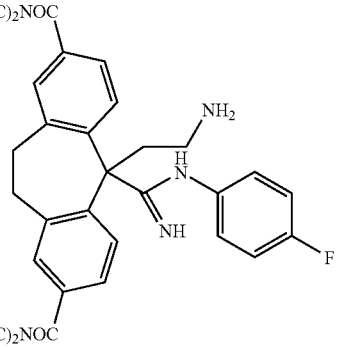 |
| 629 | 61 | CH3NH2 | (CH3)2NH | 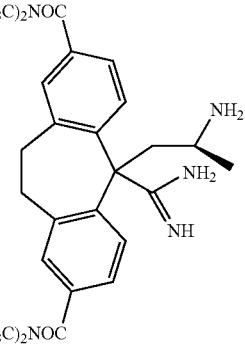 |
| 630 | 61 | NH2-CH(CH3)2 (isopropylamine) | (CH3)2NH | 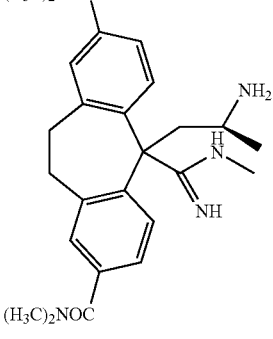 |

-continued
| Preparative Example | Preparative Example | Amine Step A | Amine Step B | Product |
|---|---|---|---|---|
| 631 | 61 | NH₂-C₆H₄-F (4-fluoroaniline) | (CH₃)₂NH | 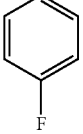 |
| 632 | 65 | NH₃ | (CH₃)₂NH | 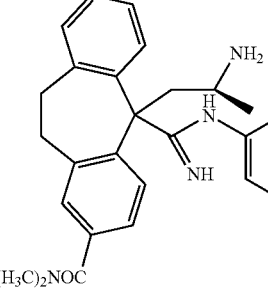 |
| 633 | 65 | CH₃NH₂ | (CH₃)₂NH |  |
| 634 | 65 | NH₂-iPr (isopropylamine) | (CH₃)₂NH |  |

-continued

| Preparative Example | Preparative Example | Amine Step A | Amine Step B | Product |
|---|---|---|---|---|
| 635 | 65 | NH₂ (4-F-C₆H₄) | (CH₃)₂NH | 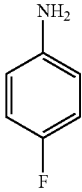 |

Example numbers 636-679 were intentionally excluded.

Preparative Example 680-687

If one were to follow a similar procedure as that described in Preparative Example 67 and 70, except using the appropriate intermediate from the Preparative Examples and amines as indicated in the Table below, one would obtain the desired amine product.

| Preparative Example | Preparative Example | Amine | Product |
|---|---|---|---|
| 680 | 300 | NH₃ | 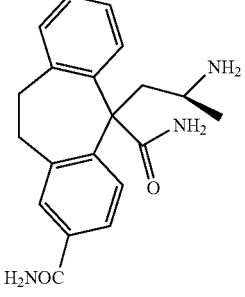 |
| 681 | 61 | NH₃ | |

-continued

| Preparative Example | Preparative Example | Amine | Product |
|---|---|---|---|
| 682 | 65 | NH₃ | 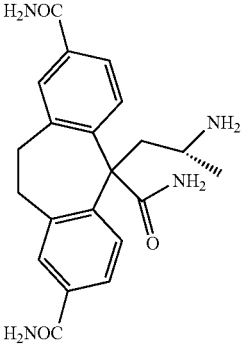 |
| 683 | 300 | CH₃NH₂ | 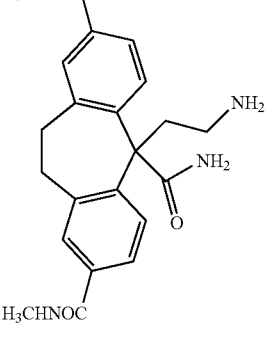 |

-continued
| Preparative Example | Preparative Example | Amine | Product |
|---|---|---|---|
| 684 | 61 | CH$_3$NH$_2$ | 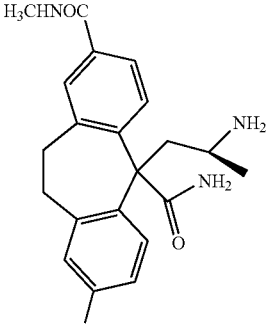 |
| 685 | 65 | CH$_3$NH$_2$ | |
-continued
| Preparative Example | Preparative Example | Amine | Product |
|---|---|---|---|
| 686 | 300 | (CH$_3$)$_2$NH | |
| 687 | 65 | (CH$_3$)$_2$NH | |
Example numbers 688-699 were intentionally excluded.
Preparative Example 700
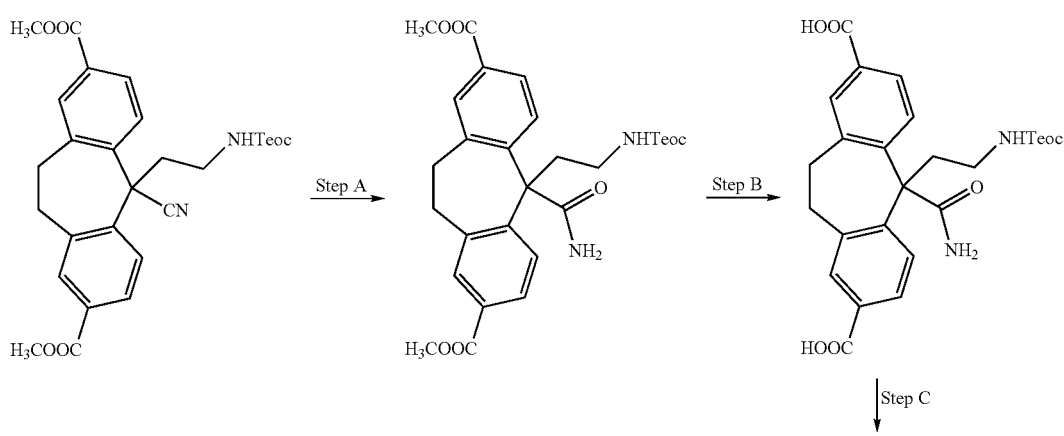

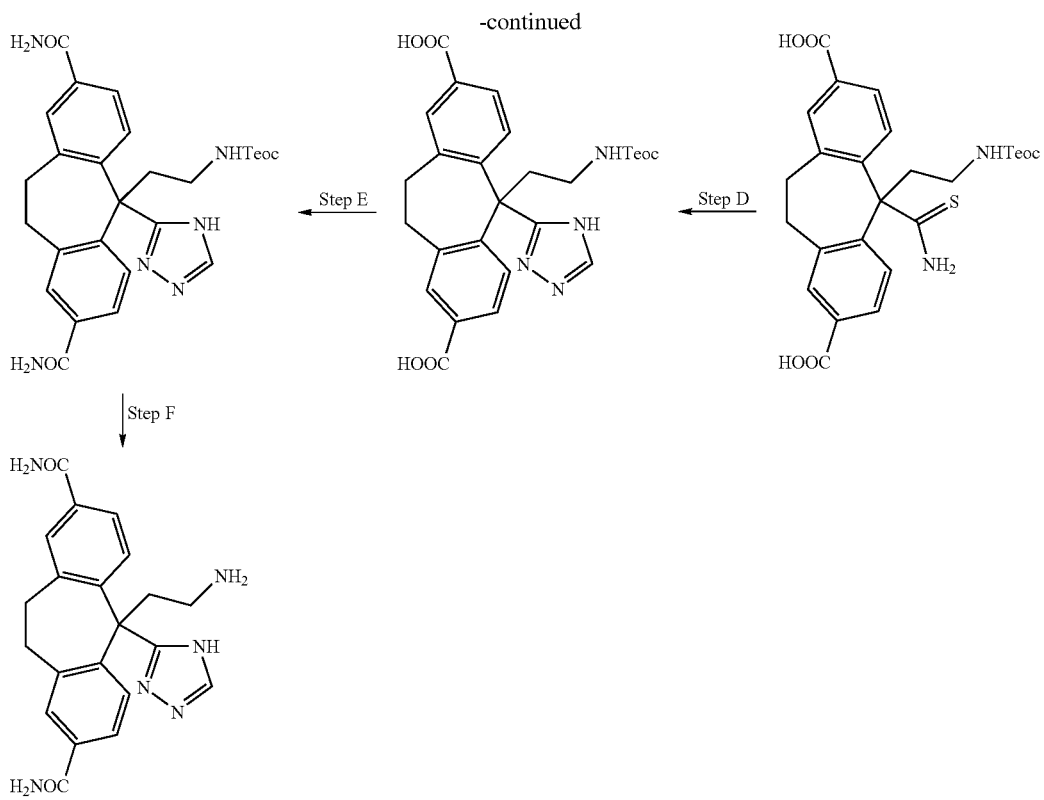

Step A

If one were to treat the compound from Preparative Example 300 Step A with hydroxylamine hydrochloride and base according to Preparative Example 67 Step A, one would obtain the title compound.

Step B

If one were to treat the title compound from Step A above according to Preparative Example 67 Step B, one would obtain the title compound.

Step C

If one were to treat the title compound from step B above with Lawesson's Reagent in toluene and heat the mixture to reflux for 4 h, one would obtain after column chromatography the title compound.

Step D

If one were to treat the title compound from Step C above with formic acid hydrazide (Pellizzari-Synthesis), one would obtain the title compound.

Step E

If one were to treat the title compound from Step D above according to the procedures described in Preparative Example 70, one would obtain the title compound.

Preparative Example 701-735

If one were to follow a similar procedure as that described in Preparative Example 700, except using the appropriate intermediate from the Preparative Examples, acid hydrazides and amines as indicated in the Table below, one would obtain the desired amine product.

| Preparative Example | Preparative Example | Acid hydrazide | Amine | Product |
| --- | --- | --- | --- | --- |
| 701 | 300 | ![](o-acetyl hydrazide) | $NH_3$ | ![](product structure) |

-continued

| Preparative Example | Preparative Example | Acid hydrazide | Amine | Product |
|---|---|---|---|---|
| 702 | 300 | 4-fluorobenzohydrazide | NH₃ | (structure) |
| 703 | 300 | isobutyrohydrazide | NH₃ | (structure) |
| 704 | 61 | formohydrazide | NH₃ | (structure) |
| 705 | 61 | acetohydrazide | NH₃ | (structure) |

-continued

| Preparative Example | Preparative Example | Acid hydrazide | Amine | Product |
|---|---|---|---|---|
| 706 | 61 | 4-fluorobenzoyl hydrazide | NH₃ | (structure) |
| 707 | 61 | isobutyryl hydrazide | NH₃ | (structure) |
| 708 | 65 | formyl hydrazide | NH₃ | (structure) |
| 709 | 65 | acetyl hydrazide | NH₃ | (structure) |

-continued

| Preparative Example | Preparative Example | Acid hydrazide | Amine | Product |
|---|---|---|---|---|
| 710 | 65 | 4-fluorobenzoic acid hydrazide (O=C(NHNH₂)-C₆H₄-F) | NH₃ | [structure with dibenzosuberane core, two H₂NOC groups, triazole with 4-fluorophenyl, and CH(NH₂)CH₃ side chain] |
| 711 | 65 | isobutyric acid hydrazide (O=C(NHNH₂)-CH(CH₃)₂) | NH₃ | [structure with dibenzosuberane core, two H₂NOC groups, triazole with isopropyl, and CH(NH₂)CH₃ side chain] |
| 712 | 300 | formic acid hydrazide (H-C(=O)-NHNH₂) | CH₃NH₂ | [structure with dibenzosuberane core, two H₃CHNOC groups, unsubstituted triazole, and CH₂CH₂NH₂ side chain] |
| 713 | 300 | acetic acid hydrazide (CH₃-C(=O)-NHNH₂) | CH₃NH₂ | [structure with dibenzosuberane core, two H₃CHNOC groups, methyl-triazole, and CH₂CH₂NH₂ side chain] |

-continued

| Preparative Example | Preparative Example | Acid hydrazide | Amine | Product |
|---|---|---|---|---|
| 714 | 300 | 4-fluorobenzoic acid hydrazide | CH$_3$NH$_2$ | (structure with 4-fluorophenyl triazole) |
| 715 | 300 | isobutyric acid hydrazide | CH$_3$NH$_2$ | (structure with isopropyl triazole) |
| 716 | 61 | formic acid hydrazide | CH$_3$NH | (structure with unsubstituted triazole) |
| 717 | 61 | acetic acid hydrazide | CH$_3$NH$_2$ | (structure with methyl triazole) |

-continued

| Preparative Example | Preparative Example | Acid hydrazide | Amine | Product |
|---|---|---|---|---|
| 718 | 61 | 4-fluorobenzoic acid hydrazide | CH₃NH₂ | (structure) |
| 719 | 61 | isobutyric acid hydrazide | CH₃NH₂ | (structure) |
| 720 | 65 | formic acid hydrazide | CH₃NH₂ | (structure) |
| 721 | 65 | acetic acid hydrazide | CH₃NH₂ | (structure) |

| Preparative Example | Preparative Example | Acid hydrazide | Amine | Product |
|---|---|---|---|---|
| 722 | 65 | 4-fluorobenzoic acid hydrazide | CH₃NH₂ | (structure) |
| 723 | 65 | isobutyric acid hydrazide | CH₃NH₂ | (structure) |
| 724 | 300 | formic acid hydrazide | (CH₃)₂NH | (structure) |
| 725 | 300 | acetic acid hydrazide | (CH₃)₂NH | (structure) |

-continued

| Preparative Example | Preparative Example | Acid hydrazide | Amine | Product |
|---|---|---|---|---|
| 726 | 300 | 4-fluorobenzoic acid hydrazide | (CH₃)₂NH | (see structure) |
| 727 | 300 | isobutyric acid hydrazide | (CH₃)₂NH | (see structure) |
| 728 | 61 | formic acid hydrazide | (CH₃)₂NH | (see structure) |
| 729 | 61 | acetic acid hydrazide | (CH₃)₂NH | (see structure) |

-continued

| Preparative Example | Preparative Example | Acid hydrazide | Amine | Product |
|---|---|---|---|---|
| 730 | 61 | 4-fluorobenzoyl hydrazide | (CH₃)₂NH | |
| 731 | 61 | isobutyryl hydrazide | (CH₃)₂NH | |
| 732 | 65 | formyl hydrazide | (CH₃)₂NH | |
| 733 | 65 | acetyl hydrazide | (CH₃)₂NH | |

-continued

| Preparative Example | Preparative Example | Acid hydrazide | Amine | Product |
|---|---|---|---|---|
| 734 | 65 | 4-fluorobenzoyl hydrazide | (CH$_3$)$_2$NH | (structure shown) |
| 735 | 65 | isobutyryl hydrazide | (CH$_3$)$_2$NH | (structure shown) |

Example numbers 736-779 were intentionally excluded.

Preparative Example 780

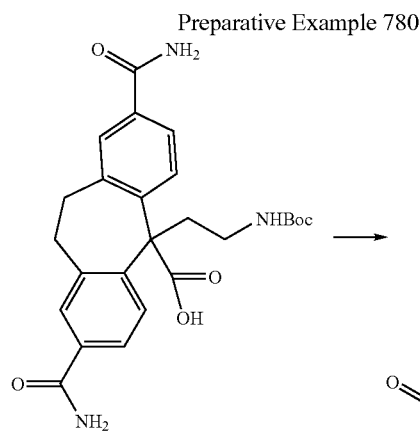

If one were to treat the starting material, which was obtained by treating the title compound from Preparative Example 300 Step A according to the procedures described in Preparative Example 500 Step A-C, according to the procedure described in Preparative Example 70 Step B, one would obtain the title compound.

Preparative Example 781-788

If one were to follow a similar procedure as that described in Preparative Example 780, except using the appropriate intermediate from the Preparative Examples and amines as indicated in the Table below, one would obtain the desired amine product.

| Preparative Example | Preparative Example | Amine | Product |
|---|---|---|---|
| 781 | 61 | NH$_3$ | (structure shown) |

-continued
| Preparative Example | Preparative Example | Amine | Product |
|---|---|---|---|
| 782 | 65 | NH₃ | 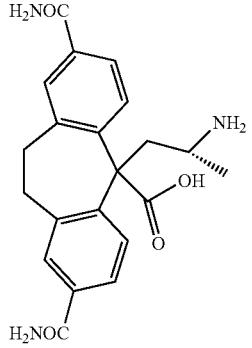 |
| 783 | 300 | CH₃NH₂ | 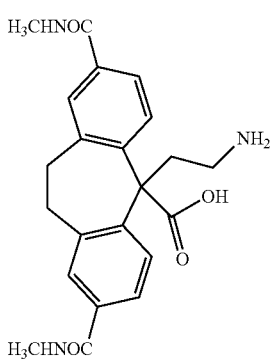 |
| 784 | 61 | CH₃NH₂ | 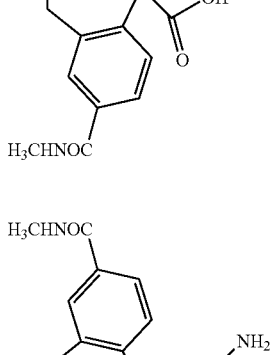 |
| 785 | 65 | CH₃NH₂ | 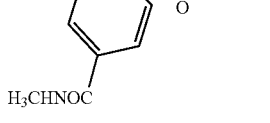 |
-continued
| Preparative Example | Preparative Example | Amine | Product |
|---|---|---|---|
| 786 | 300 | (CH₃)₂NH | 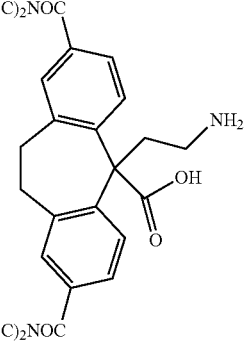 |
| 787 | 61 | (CH₃)₂NH | |
| 788 | 65 | (CH₃)₂NH | |
Example numbers 789-799 were intentionally excluded.

Preparative Example 800

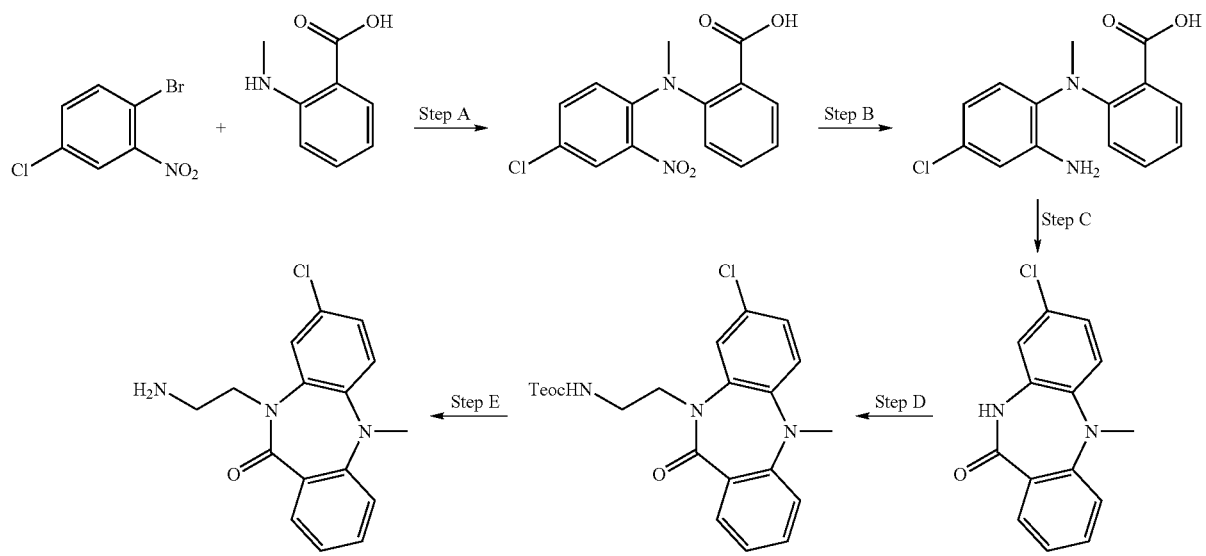

Step A
If one were to treat commercial available N methyl anthranilic acid with 2 eq. of 2-bromo-5-chloronitrobenzene, 10 eq. of potassium carbonate and a catalytic amount of copper powder in 3-methylbutan-1-ol under reflux for several hours one would obtain, after removing of the volatile compound by steam distillation, acidification of the residue with 2 M HCl, precipitation and recrystallisation of the precipitate from ethanol, the title compound.

Step B
If one were to treat the title compound from Step A above with 7 eq. of sodium dithionite in 2 M aqueous ammonia at 80° C. one would obtain, after filtration, acidification of the filtrate with glacial acetic acid to pH 4, precipitation and recrystallisation from methanol, the title compound.

Step C
If one were to reflux the title compound from Step B above in xylene under Dean Stark conditions one would obtain, after evaporation of the solvent, washing of the residue with 2 M aqueous ammonia and recrystallisation from acetone, the title compound.

Step D
If one were to treat the title compound from Step C above with the sulfamidate from Preparative Example 22 according to Preparative Example 61 Step A one would obtain the title compound.

Step E
If one were to treat the title compound from Step A above with TFA as described in Preparative Example 70 Step B, one would obtain the title compound.

Preparative Example 801-805

If one were to follow a similar procedure as that described in Preparative Example 800, except using the diazepines and sulfamidates as indicated in the Table below, one would obtain the desired amine product.

| Preparative Example | Diazepine | Sulfamidate | Product |
|---|---|---|---|
| 801 | ![Cl-diazepine] | 22 | ![Cl-diazepine-ethylamine] |

-continued
| Preparative Example | Diazepine | Sulfamidate | Product |
|---|---|---|---|
| 802 | 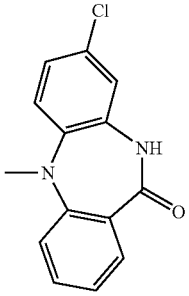 | 21 | 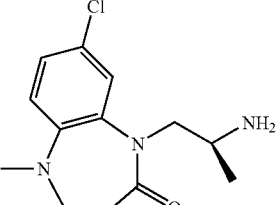 |
| 803 | 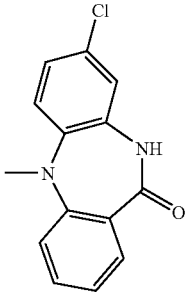 | 24 | 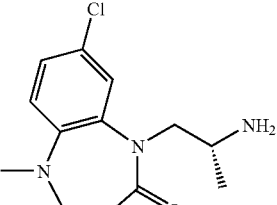 |
| 804 | 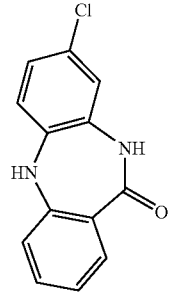 | 21 | 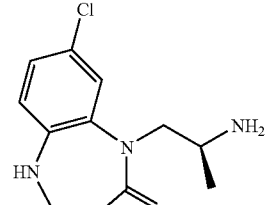 |
| 805 | 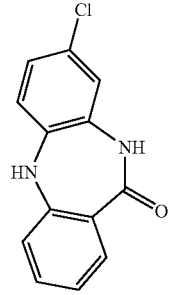 | 24 | 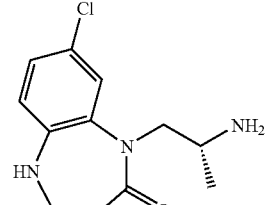 |
Examples 806-809 have been intentionally excluded.
Preparative Example 810
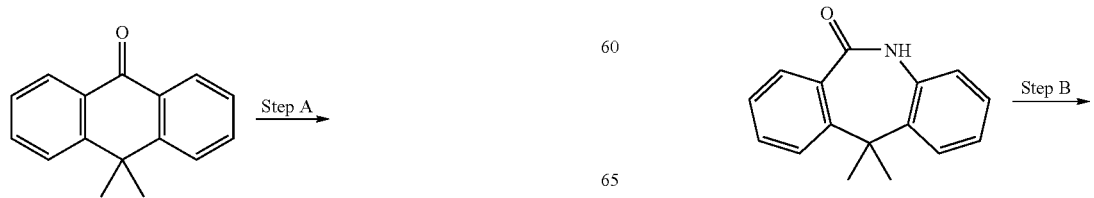

-continued

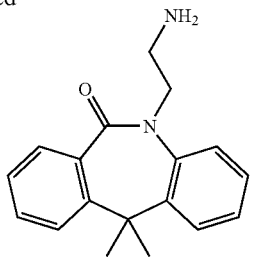

Step A

If one were to treat commercially available 10,10-dimethyl-10H-anthracen-9-one and concentrated sulphuric acid in chloroform in a flask equipped with reflux condenser with sodium azide at room temperature, followed by heating this mixture at 50° C. and subsequently pouring it on crushed ice followed by neutralization with conc. aqueous ammonia, separation and evaporation of the organic phase, one would obtain the title compound.

Step B

If one were to treat the title compound from Step A above with the sulfamidate from Preparative Example 22 as described in Preparative Example 800, one would obtain the title compound.

Preparative Example 811-812

If one were to follow a similar procedure as described in Preparative Example 810, except using the azepines and sulfamidates as indicated in the able below, one would obtain the desired amine product.

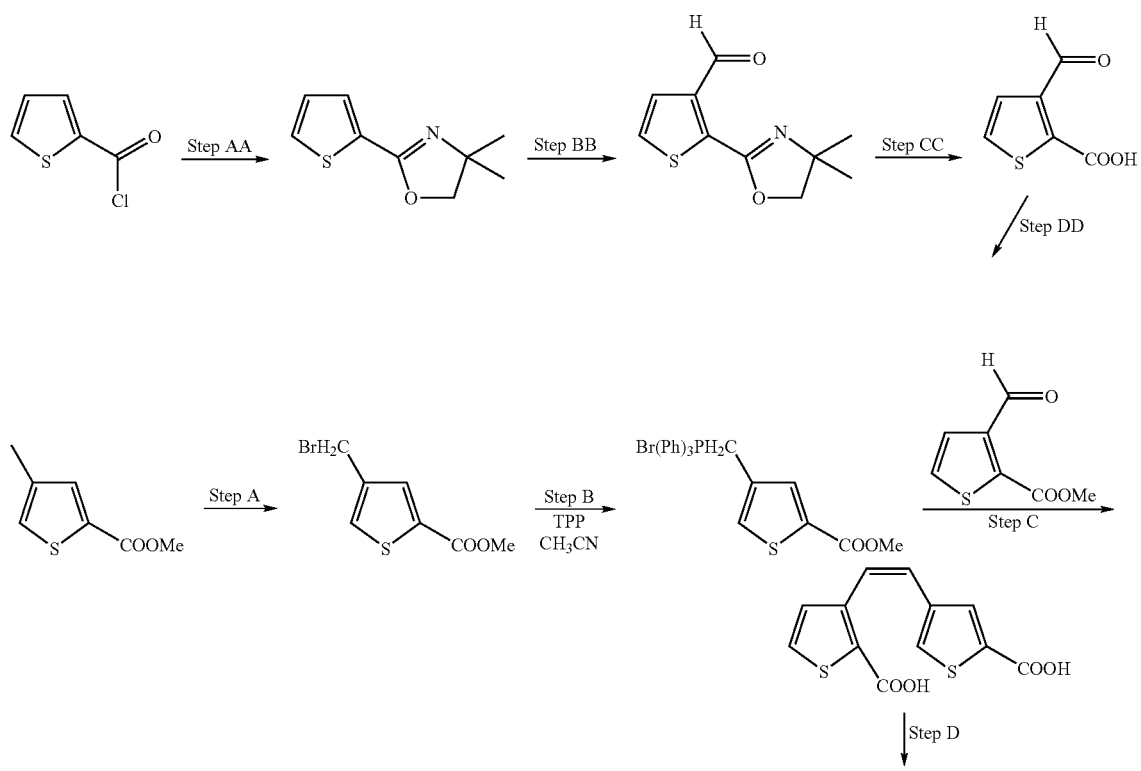

Examples 813-829 have been intentionally excluded.

Preparative Example 830

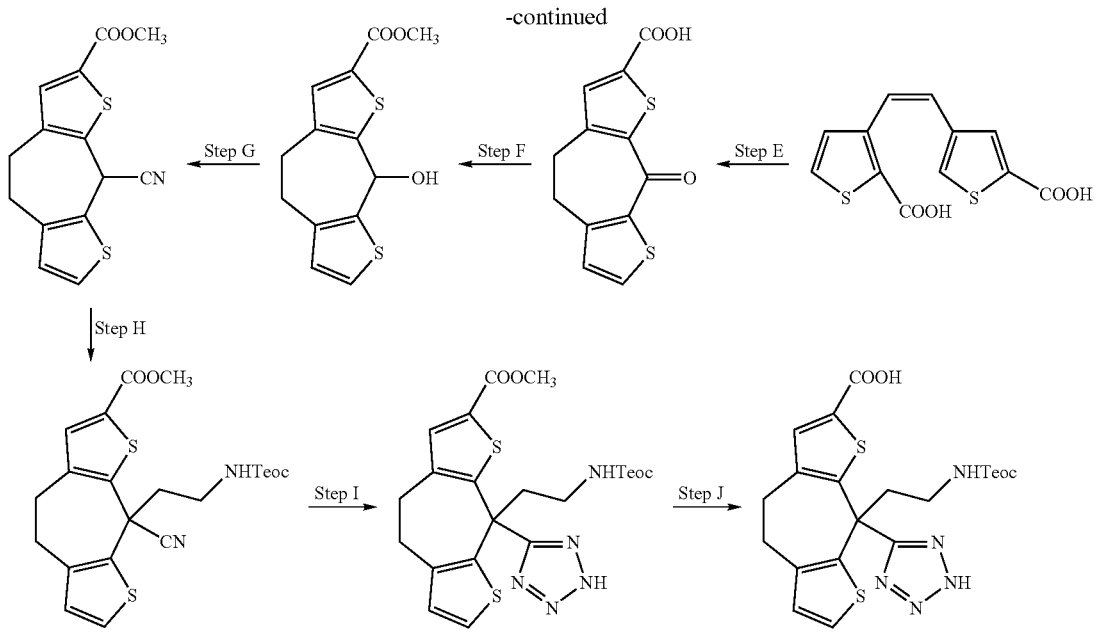

Step AA

If one were to add a solution of commercially available 2-amino-2-methyl-1-propanol in methylene chloride to a solution of commercially available 2-thiophenecarboxyl chloride in methylene chloride dropwise while maintaining the temperature below 20° C., subsequently stir the mixture at room temperature for 2 h and wash with water, dry the organic layer (MgSO$_4$) and evaporate, suspend the residue in toluene and add thionyl chloride dropwise with stirring while maintaining the temperature below 30° C., subsequently continue the stirring overnight, evaporate the toluene, dissolve the residue in water, basify with 1 N aqueous NaOH and extract with ether, then, after drying (MgSO$_4$) and evaporation of the solvent, followed by distillation, one would obtain the title compound.

Step BB

If one were to add commercial -nBuLi in hexane to the title compound from Step AA above in ether at −78° C., stir the mixture under argon for 0.25 h, add DMF, allow the mixture to slowly warm to room temperature and leave the mixture at this temperature for 18 h, subsequently add water and ether, separate the organic solution, wash with water, brine and dry the solution (MgSO$_4$), then, after evaporation of the solvent, followed by chromatographic purification, one would obtain the title compound.

Step CC

If one were to boil the title compound from Step BB above under reflux with 4M aqueous hydrochloric acid under argon atmosphere for 14 h, saturate the cooled solution with NaCl, extract repeatedly with ethyl acetate, dry the combined organic extracts (MgSO$_4$), then, after evaporation of the solvent, followed by recrystallization from ethyl acetate/hexane, one would obtain the title compound.

Step DD

If one were to treat the title compound from Step CC above in methanol dropwise with an ethereal solution of diazomethane at −15° C., followed by careful removal of all volatiles, then one would obtain the title compound.

Step A

If one were to add commercially available methyl 4-methylthiophene-2-carboxylate to N-bromosuccinimide, benzoyl peroxide and tetrachloromethane and would heat the mixture under reflux for 4 h followed by filtration and evaporation of the solvent, one would obtain the title compound.

Step B

If one were to treat the title compound from Step A above with triphenylphosphine according to Preparative Example 51 Step C, one would obtain the title compound.

Step C

If one were to treat the title compound from Step B above with the thiophene aldehyde from Step DD as described in Preparative Example 54 Step A, one would obtain the title compound.

Step D

If one were to treat a suspension of the title compound from Step C above, hydroiodic acid and red phosphorus at 140° C. for 18 h, followed by cooling and pouring the reaction mixture into an ice/water mixture, subsequent filtration, washing of the precipitate with water, dissolving the precipitate in refluxing conc. ammonia and subsequent filtration, acidification of the filtrate with conc. aqueous hydrochloric acid and extraction of the aqueous phase with dichloromethane, washing of the organic phase with water and drying (MgSO$_4$) followed by evaporation of the solvent, one would obtain the title compound.

Step E

If one were to treat a suspension of the title compound from Step D above with polyphosphoric acid at 170° C., followed by cooling to 30° C., pouring into water, extraction with diethyl ether, washing with 1N aqueous sodium hydroxide solution and drying (MgSO$_4$) followed by evaporation of the solvent, one would obtain the title compound.

Step F

If one were to treat the title compound from Step E above as described in Preparative Example 59 Step G, one would obtain the title compound.

Step G

If one were to treat the title compound from Step F above as described in Preparative Example 59 Step H and Step I, one would obtain the title compound.

Step H

If one were to treat the title compound from Step G above with the compound from Preparative Example 22 as described in Preparative Example 61 Step A, one would obtain the title compound.

Step I

If one were to treat the title compound from Step H above as described in Preparative Example 61 Step B, one would obtain the title compound.

Step J

If one were to treat the title compound from Step I above as described in Preparative Example 61 Step C, one would obtain the title compound.

Preparative Example 831

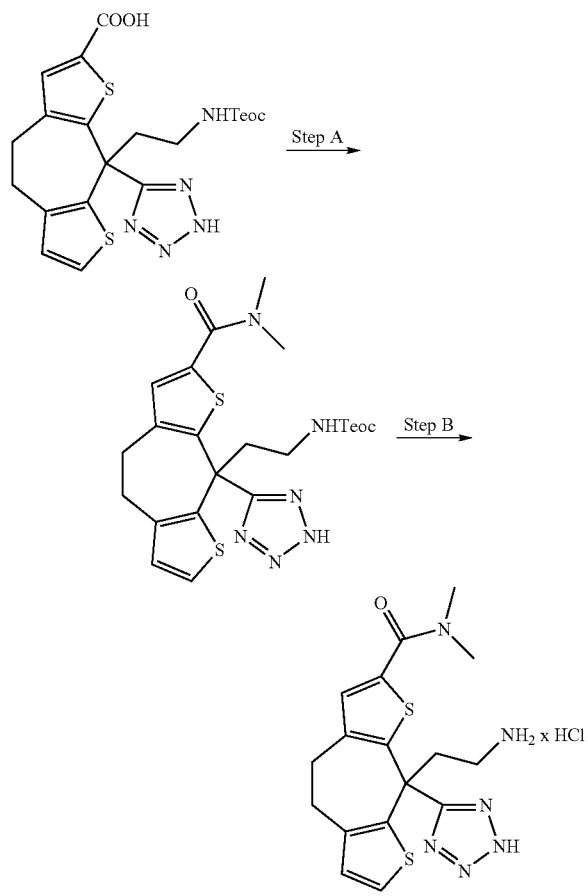

Step A

If one were to treat the title compound from Preparative Example 830 as described in Preparative Example 71 Step A, one would obtain the title compound.

Step B

If one were to treat the title compound from Step A above as described in Preparative Example 71 Step B, one would obtain the title compound.

Preparative Example 832-839

If one were to follow a similar procedure as that described in Preparative Example 830, except using the sulfamidates in Step H, and treat the product obtained according to Preparative Example 831 with the amine as indicated in the table below, one would obtain the desired title compound as HCl salts.

| Preparative Example | Sulfamidate | Amine | Title compound |
|---|---|---|---|
| 831 | 21 | NH₃ | (structure) |
| 832 | 24 | NH₃ | (structure) |
| 833 | 22 | NH₃ | (structure) |
| 834 | 21 | CH₃NH₂ | (structure) |

| Preparative Example | Sulfamidate | Amine | Title compound |
|---|---|---|---|
| 835 | 24 | CH₃NH₂ | 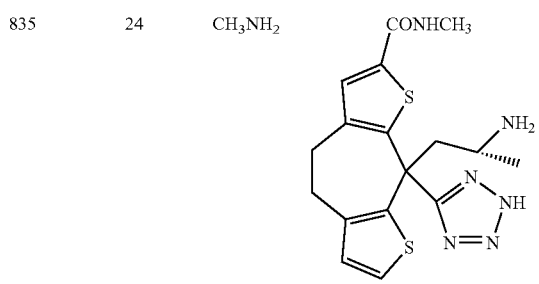 |
| 836 | 22 | CH₃NH₂ | 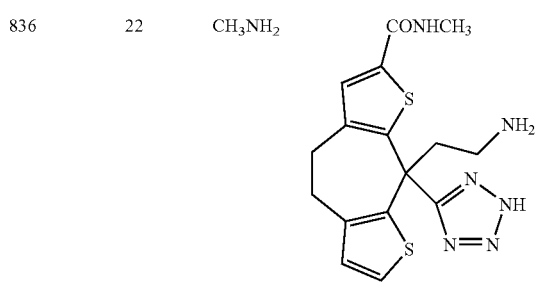 |
| Preparative Example | Sulfamidate | Amine | Title compound |
|---|---|---|---|
| 837 | 24 | (CH₃)₂NH | |
| 838 | 22 | (CH₃)₂NH | |
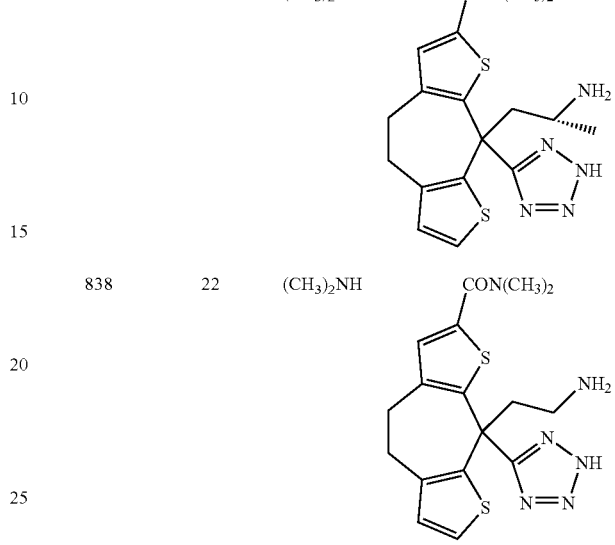
Examples 839 to 849 have been intentionally excluded.
Preparative Example 850
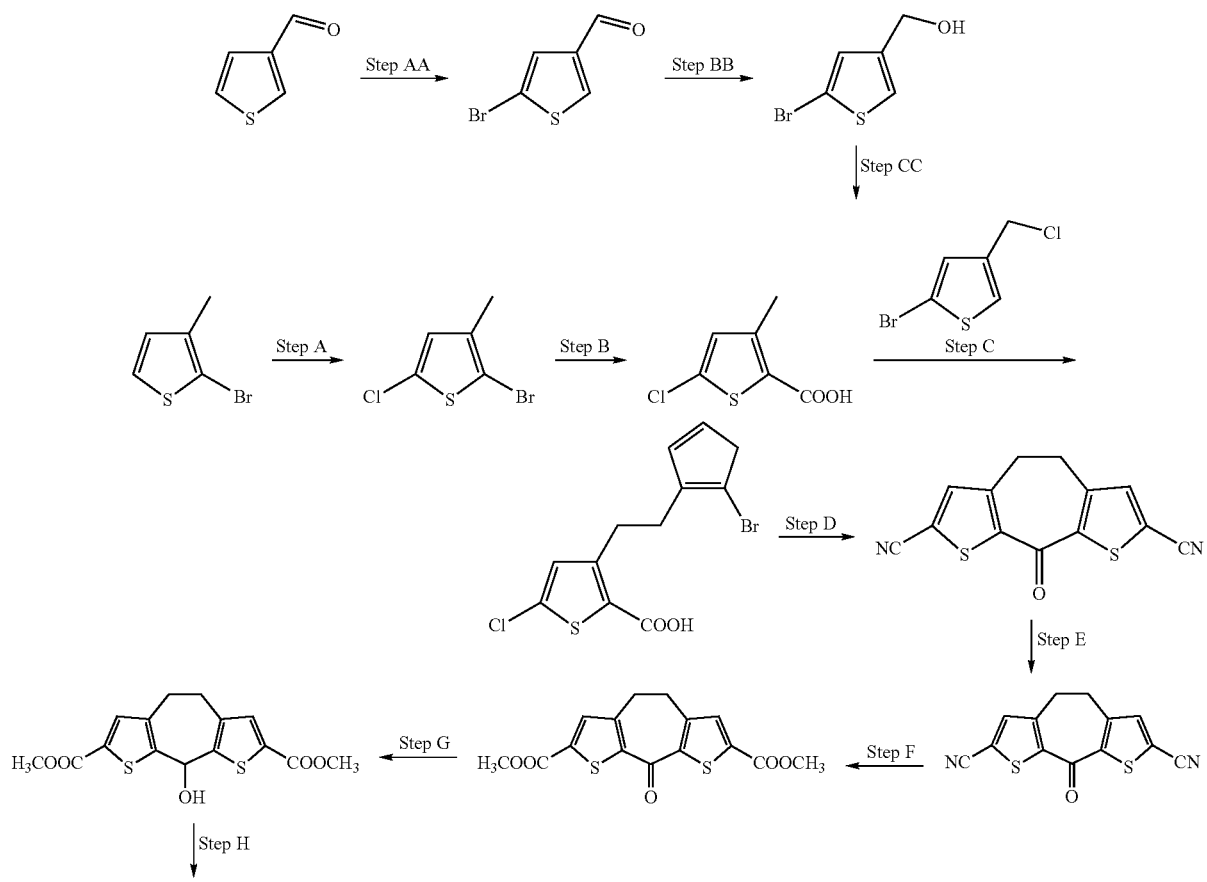

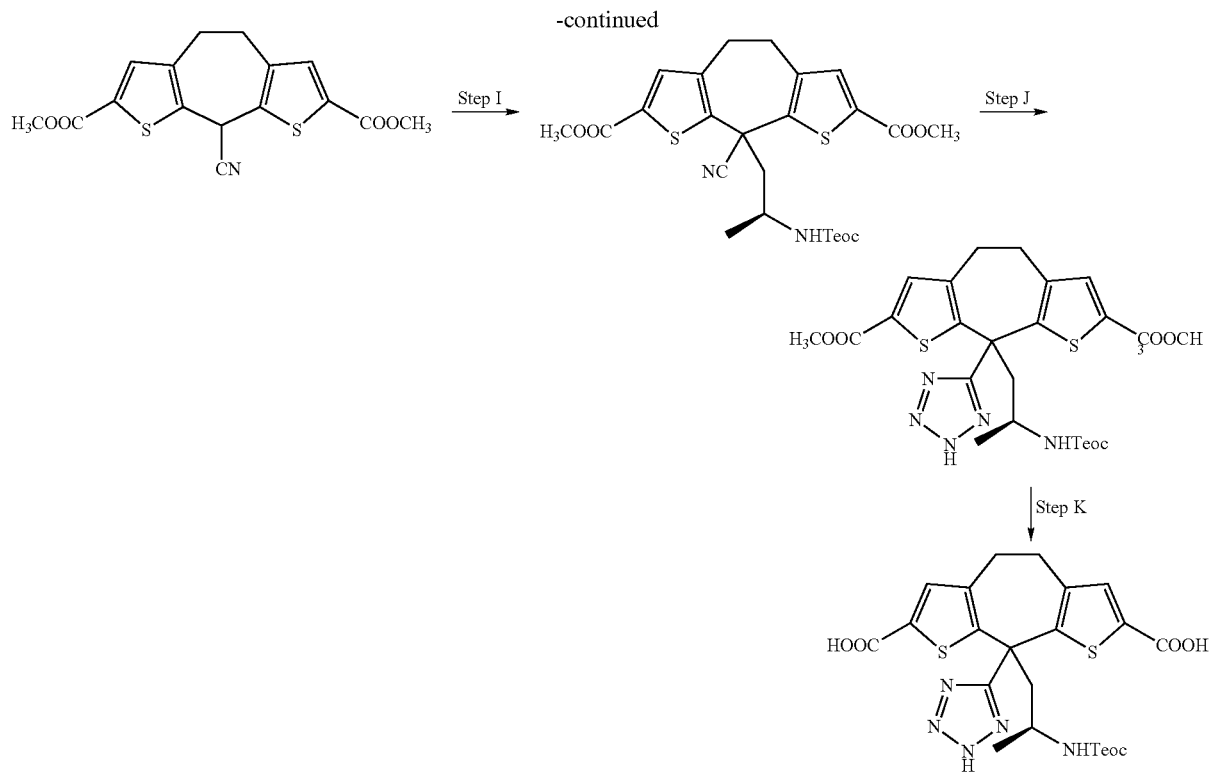

Step AA

If one were to treat commercially available thiophene-3-carbaldehyde with bromine and aluminium trichloride in dichloromethane and heat the reaction mixture for 2 h, subsequently pouring it into water, followed by extraction with ether, washing of the organic phase successively with aqueous 1N NaOH solution and water until neutral, then, after drying (MgSO$_4$) and evaporation of the solvent, followed by distillation, one would obtain the title compound.

Step BB

If one were to treat a solution of the title compound from Step AA above in tetrahydrofuran with NaBH$_4$ for 1 h and quench the reaction by the addition of saturated aqueous ammonium chloride solution followed by dilution with ethyl acetate, separation of the organic layer, washing with H$_2$O and brine, then, after drying (MgSO$_4$) and evaporation of the solvent, one would obtain the title compound.

Step CC

If one were to treat a solution of the title compound from Step BB above in chloroform with thionyl chloride at room temperature for 4 h, subsequently pouring it into water, followed by extraction with chloroform, washing of the organic phase with water, then, after drying (MgSO$_4$) and evaporation of the solvent, one would obtain the title compound.

Step A

If one were to treat commercially available 2-bromo-3-methylthiophene in acetic acid with N-chlorosuccinimide and stir the reaction mixture for about 2 h, then refluxing it for 1 h, subsequently pouring it into water, followed by extraction with ether, washing of the organic phase successively with aqueous 1N NaOH solution and water until neutral, then, after drying (MgSO$_4$) and evaporation of the solvent, followed by distillation, one would obtain the title compound.

Step B

If one were to treat the title compound from Step A above as described in Preparative Example 59 Step A, one would obtain the title compound.

Step C

If one were to treat the title compound from Step B above with the title compound from Step CC above, as described in Preparative Example 59 Step B, one would obtain the title compound.

Step D

If one were to treat the title compound from Step C above as described in Preparative Example 59 Step C, one would obtain the title compound.

Step E

If one were to treat the title compound from Step D above as described in Preparative Example 59 Step D, one would obtain the title compound.

Step F

If one were to treat the title compound from Step E above as described in Preparative Example 59 Step E and Step F, one would obtain the title compound.

Step G

If one were to treat the title compound from Step F above as described in Preparative Example 59 Step G, one would obtain the title compound.

Step H

If one were to treat the title compound from Step G above as described in Preparative Example 59 Step H and Step I, one would obtain the title compound.

Step I

If one were to treat the title compound from Step H above as described in Preparative Example 61 Step A, one would obtain the title compound.

Step J

If one were to treat the title compound from Step I above as described in Preparative Example 61 Step B, one would obtain the title compound.

Step K

If one were to treat the title compound from Step J above as described in Preparative Example 61 Step C, one would obtain the title compound.

Preparative Example 851

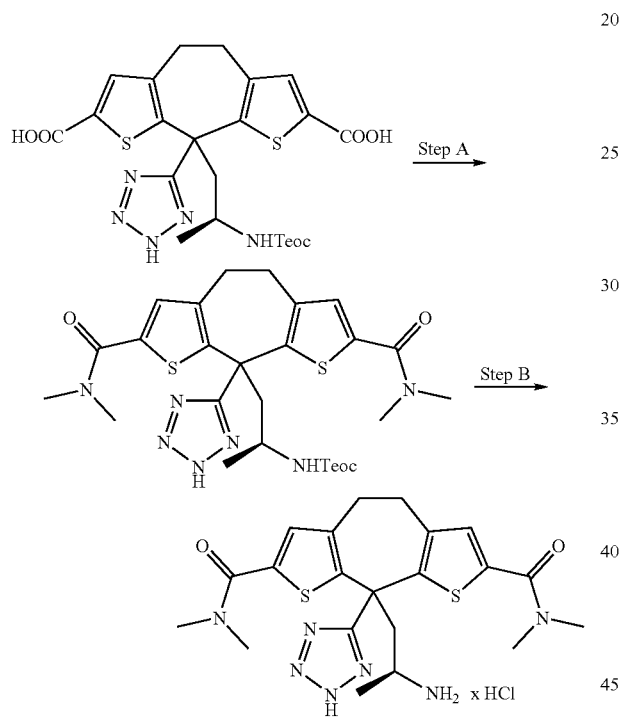

Step A

If one were to treat the title compound from Preparative Example 851 as described in Preparative Example 71 Step A one would obtain the title compound.

Step B

If one were to treat the title compound from Step A above as described in Preparative Example 71 Step B, one would obtain the title compound.

Preparative Example 852-859

If one were to follow a similar procedure as that described in Preparative Example 850, except using the sulfamidates in Step I, and treat the product obtained according to Preparative Example 851 with the amine as indicated in the table below, one would obtain the desired title compound as HCl salt.

| Preparative Example | Sulfamidate | Amine | Title Compound |
|---|---|---|---|
| 852 | 21 | $NH_3$ | 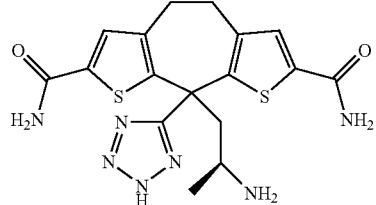 |
| 853 | 24 | $NH_3$ | 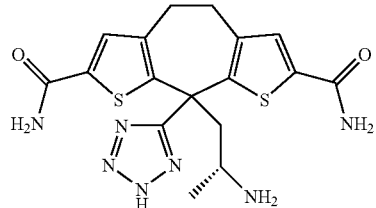 |
| 854 | 22 | $NH_3$ | 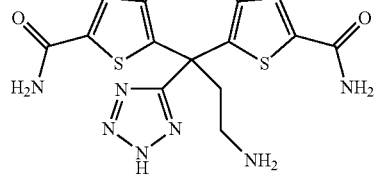 |
| 855 | 21 | $CH_3NH_2$ | 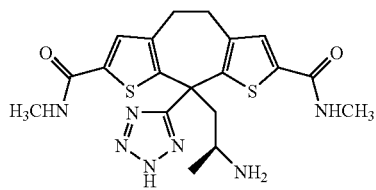 |
| 856 | 24 | $CH_3NH_2$ | 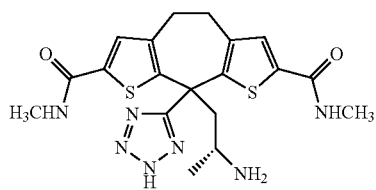 |

-continued
| Preparative Example | Sulfamidate | Amine | Title Compound |
|---|---|---|---|
| 857 | 22 | CH$_3$NH$_2$ | 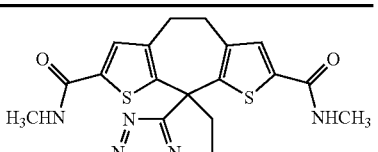 |
| 858 | 24 | (CH$_3$)$_2$NH | 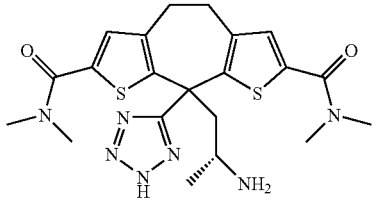 |
-continued
| Preparative Example | Sulfamidate | Amine | Title Compound |
|---|---|---|---|
| 859 | 22 | (CH$_3$)$_2$NH | 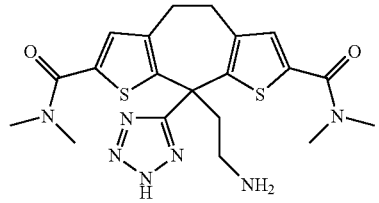 |
Examples 860-899 have been intentionally excluded.
Preparative Example 900
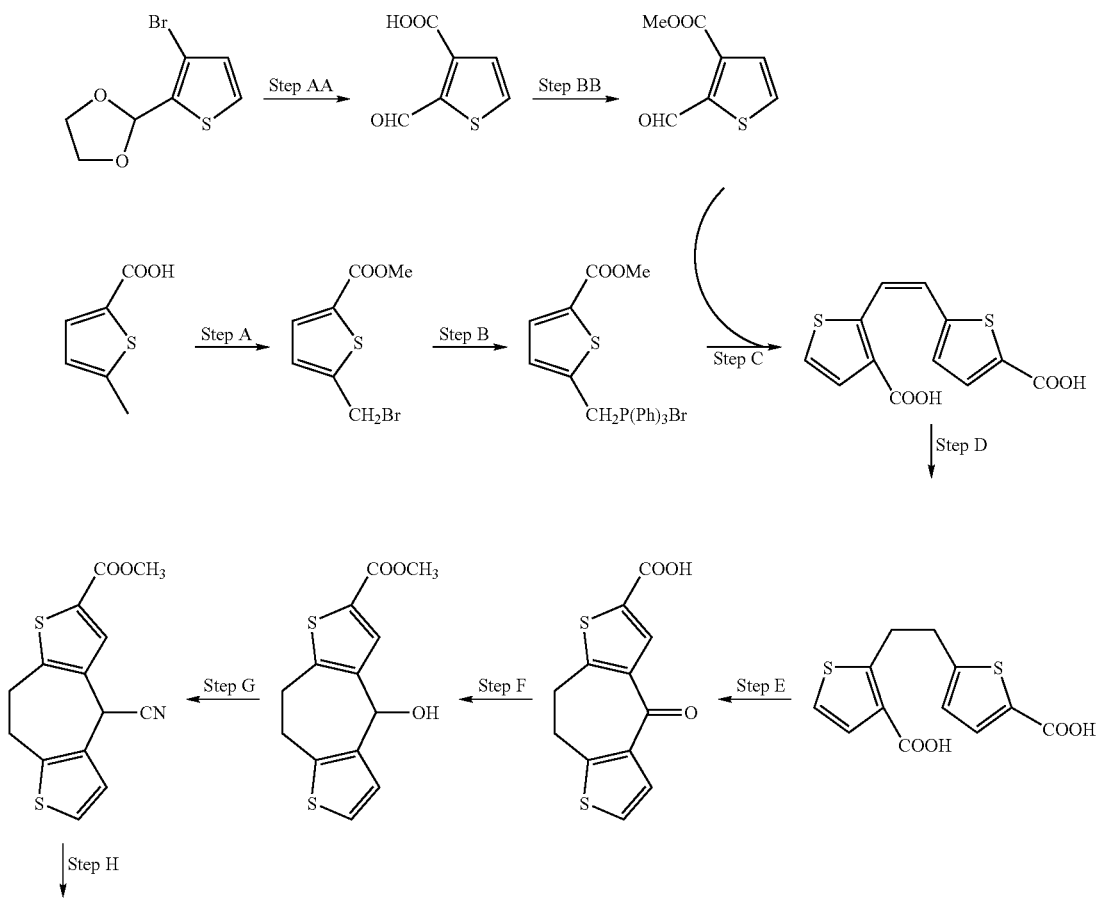

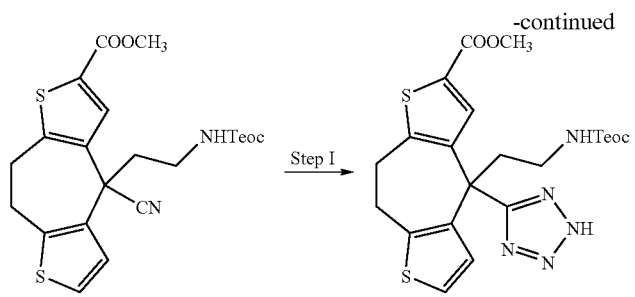
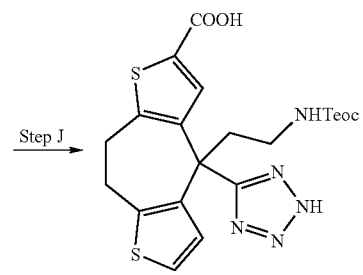

Step AA

If one were to add a solution of commercially available 2-(3bromo-2-thienyl)-1,3-dioxolane in dry diethylether with stirring to 1.05 N butyl lithium in diethylether at −70° C., followed by addition of the mixture to solid $CO_2$ covered with diethylether. Hydrolysis, followed by extraction with diluted aqueous sodium hydroxide, acidification, then extraction with diethylether afford the title compound.

Step BB

If one were to add $H_2SO_4$ and methanol to a solution of the title compound from step AA above in dichloroethane, one would obtain the title compound.

Step A

If one were to treat a solution of commercially available 5-methylthiophene-2-carboxylic acid in benzene and methanol at 0° C. dropwise with 2.0 M trimethylsilyldiazo-methane in hexanes, one would obtain the methyl ester. If one were to treat a solution of that ester intermediate in $CCl_4$ with NBS and 2,2'-azobisisobutyronitrile (AIBN) and heat the solution to reflux for 2 h, followed by cooling down to room temperature, filtration and concentration in vacuo one would obtain the title compound.

Step B

If one were to treat the title compound from Step A above with triphenylphosphine according to Preparative Example 49 Step C, one would obtain the title compound.

Step C

If one were to treat the title compound from Step B above with the title compound from Step BB above as described in Preparative Example 54 Step A, one would obtain the title compound.

Step D

If one were to heat a mixture of the title compound from Step C, red phosphorous and hydroiodic acid in acetic acid at 110° C. for 1 h, one would obtain a solution after filtration of the hot mixture. After cooling to room temperature and pouring in ice water one would obtain the title compound by suction.

Step E

If one were to heat a mixture of the title compound from Step D above and polyphosphoric acid at 115° C. for 1.5 h one would obtain a mixture, which was poured on ice. After extraction with Ether washing the organic phases with water, drying ($MgSO_4$) and removing of the solvent one would obtain the title compound.

Step F

If one were to treat the title compound from Step E above as described in Preparative Example 59 Step G, one would obtain the title compound.

Step G

If one were to treat the title compound from Step F above as described in Preparative Example 59 Step H and Step I, one would obtain the title compound.

Step H

If one were to treat the title compound from Step G above with the compound from Preparative Example 22 as described in Preparative Example 61 Step A, one would obtain the title compound.

Step I

If one were to treat the title compound from Step H above as described in Preparative Example 61 Step B, one would obtain the title compound.

Step J

If one were to treat the title compound from Step I above as described in Preparative Example 61 Step C, one would obtain the title compound.

Preparative Example 901

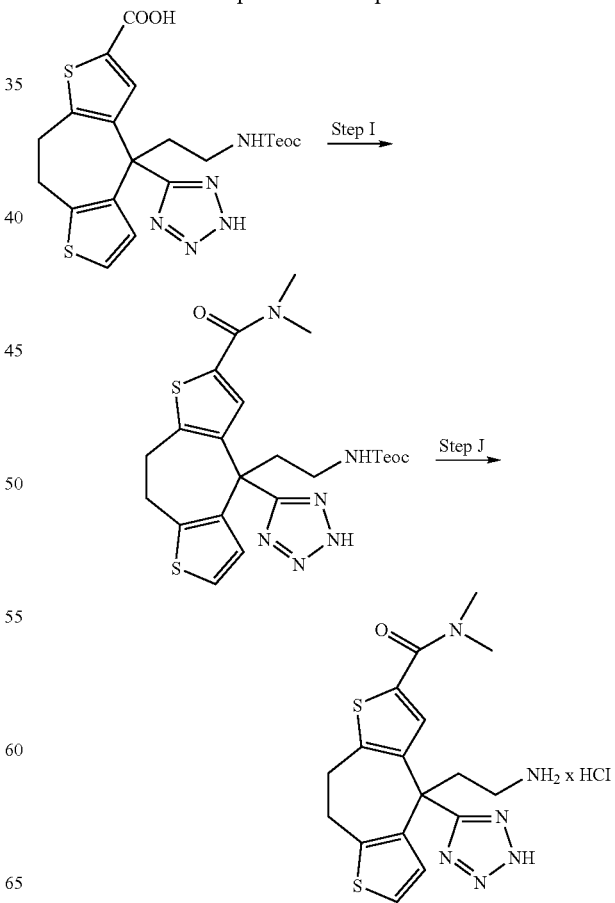

Step A

If one were to treat the title compound from Preparative Example 900 as described in Preparative Example 71 Step A, one would obtain the title compound.

Step B

If one were to treat the title compound from Step A above as described in Preparative Example 71 Step B, one would obtain the title compound.

Preparative Example 902-909

If one were to follow a similar procedure as that described in Preparative Example 900, except using the sulfamidates in Step H, and treat the product obtained according to Preparative Example 901 with the amines as indicated in the table below, one would obtain the desired title compound as HCl salt.

| Preparative Example | Sulfamidate | Amine | Title compound |
|---|---|---|---|
| 902 | 21 | NH₃ | 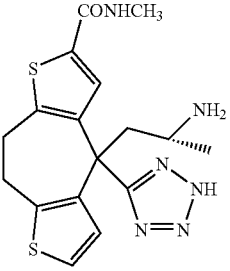 |
| 903 | 24 | NH₃ | |
| 904 | 22 | NH₃ | |
| 905 | 21 | CH₃NH₂ | |
| 906 | 24 | CH₃NH₂ | 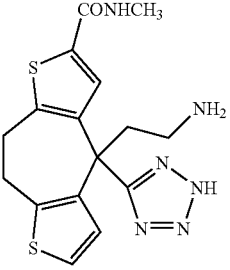 |
| 907 | 22 | CH₃NH₂ | |
| 908 | 24 | (CH₃)₂NH | 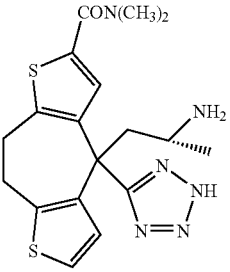 |
| 909 | 22 | (CH₃)₂NH | 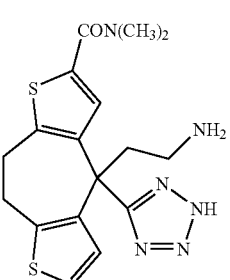 |

Examples 910-919 have been intentionally excluded.

Preparative Example 920

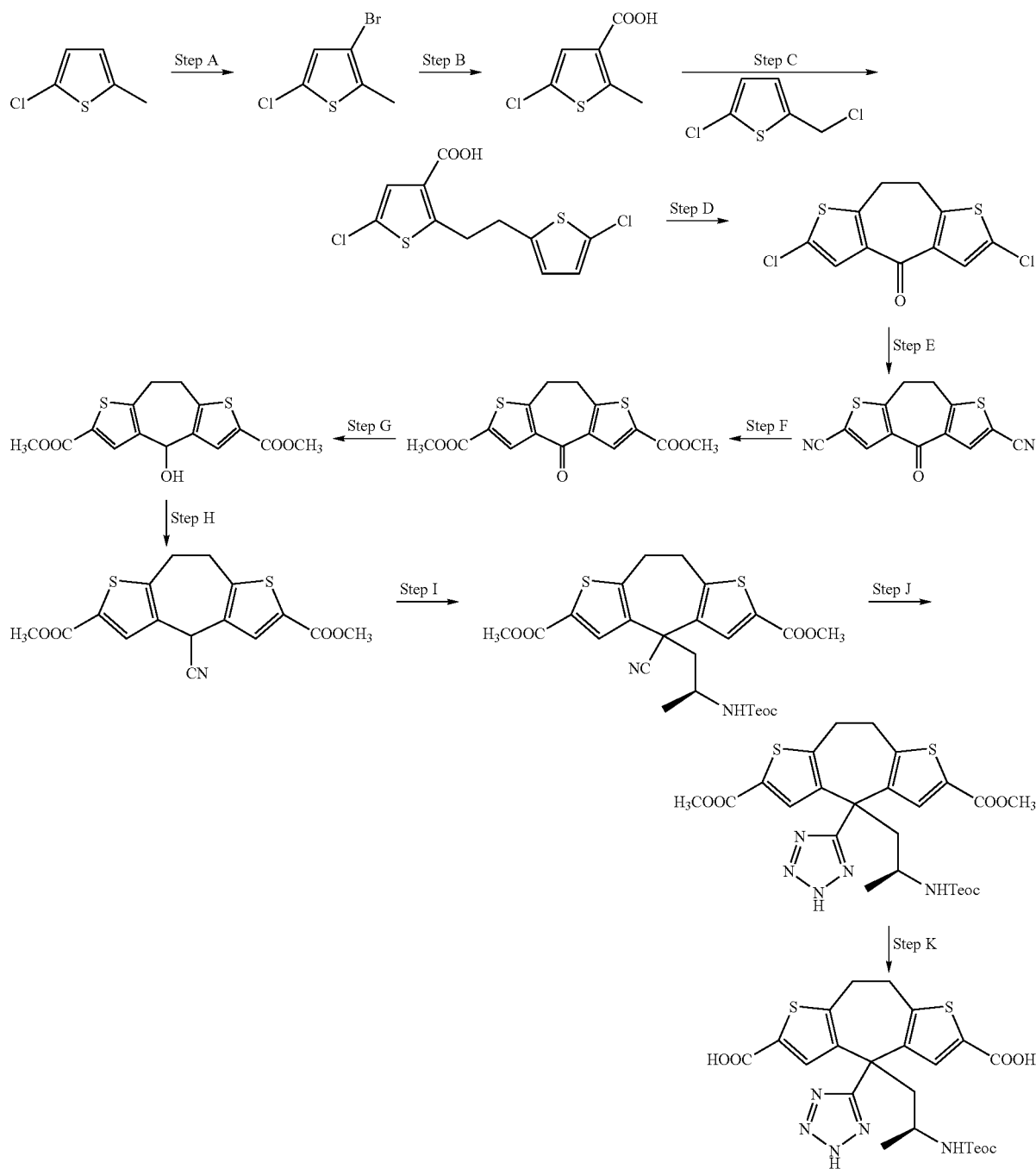

Step A

If one were to add a solution of bromine in CHCl$_3$ slowly to an ice-cooled solution of commercially available 2-chloro-5-methylthiophene in CHCl$_3$ one would obtain a reaction mixture which was stirred for 2 h at room temperature, and subsequently poured into H$_2$O. If one were to extract than the mixture with dichloromethane combine the organic extracts dry filter and evaporate the solvent, one would obtain a yellow/brown oil.

Step B

If one were to treat the title compound from Step A above as described in Preparative Example 59 Step A, one would obtain the title compound.

Step C

If one were to treat the title compound from Step B above with commercially available 2-chloro-5-chloromethyl-thiophene as described in Preparative Example 59 Step B, one would obtain the title compound.

315

Step D
If one were to treat the title compound from Step C above as described in Preparative Example 59 Step C, one would obtain the title compound.

Step E
If one were to treat the title compound from Step D above as described in Preparative Example 59 Step D, one would obtain the title compound.

Step F
If one were to treat the title compound from Step E above as described in Preparative Example 59 Step E and Step F, one would obtain the title compound.

Step G
If one were to treat the title compound from Step F above as described in Preparative Example 59 Step G, one would obtain the title compound.

Step G
If one were to treat the title compound from Step G above as described in Preparative Example 59 Step H and Step I, one would obtain the title compound.

Step I
If one were to treat the title compound from Step H above as described in Preparative Example 61 Step A, one would obtain the title compound.

Step J
If one were to treat the title compound from Step I above as described in Preparative Example 61 Step B, one would obtain the title compound.

Step K
If one were to treat the title compound from Step J above as described in Preparative Example 61 Step C, one would obtain the title compound.

Preparative Example 921

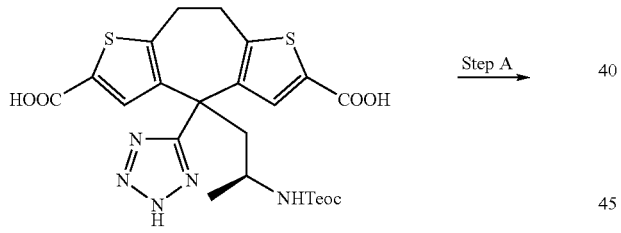

316

-continued

Step A
If one were to treat the title compound from Preparative Example 920 as described in Preparative Example 71 Step A one would obtain the title compound.

Step B
If one were to treat the title compound from Step A above as described in Preparative Example 71 Step B, one would obtain the title compound.

Preparative Example 922-929

If one were to follow a similar procedure as that described in Preparative Example 920, except using the sulfamidates in Step I, and treat the product obtained according to Preparative Example 921 with the amine as indicated in the table below, one would obtain the desired title compound as HCl salt.

| Preparative Example | Sulfamidate | Amine | Title compound |
|---|---|---|---|
| 922 | 21 | NH₃ | |

-continued

| Preparative Example | Sulfamidate | Amine | Title compound |
|---|---|---|---|
| 923 | 24 | NH₃ | |
| 924 | 22 | NH₃ | |
| 925 | 21 | CH₃NH₂ | |
| 926 | 24 | CH₃NH₂ | |
| 927 | 22 | CH₃NH₂ | |
| 928 | 24 | (CH₃)₂NH | |

| Preparative Example | Sulfamidate | Amine | Title compound |
|---|---|---|---|
| 929 | 22 | (CH₃)₂NH | *(structure)* |

Examples 930-999 have been intentionally excluded.

Preparative Example 1000-1209

If one were to follow similar procedure as described in Preparative Examples 92 and 93, except using the amides and amines as indicated in the Table below, the following title compound would be obtained.

| Prep Example | Amide | Amines | Title compound |
|---|---|---|---|
| 1000 | *(structure)* | *(structure)* | *(structure)* |
| 1001 | *(structure)* | *(structure)* | *(structure)* |
| 1002 | *(structure)* | *(structure)* | *(structure)* |
| 1003 | *(structure)* | *(structure)* | *(structure)* |

-continued

| Prep Example | Amide | Amines | Title compound |
|---|---|---|---|
| 1004 | | | |
| 1005 | | | |
| 1006 | | | |
| 1007 | | | |
| 1008 | | | |
| 1009 | | | |

-continued

| Prep Example | Amide | Amines | Title compound |
| --- | --- | --- | --- |
| 1010 | | | |
| 1011 | | | |
| 1012 | | | |
| 1013 | | | |
| 1014 | | | |
| 1015 | | | |

-continued

| Prep Example | Amide | Amines | Title compound |
|---|---|---|---|
| 1016 | | | |
| 1017 | | | |
| 1018 | | | |
| 1019 | | | |
| 1020 | | | |
| 1021 | | | |

-continued

| Prep Example | Amide | Amines | Title compound |
|---|---|---|---|
| 1022 | prolinamide | 1-(3-sulfamoylphenyl)ethylamine | |
| 1023 | prolinamide | 1-(3-(N-methylsulfamoyl)phenyl)ethylamine | |
| 1024 | prolinamide | 1-(3-(N,N-dimethylsulfamoyl)phenyl)ethylamine | |
| 1025 | prolinamide | 1-(4-fluorophenyl)propylamine | |
| 1026 | prolinamide | 1-(4-fluorophenyl)-2-methylpropylamine | |
| 1027 | prolinamide | 1-(4-fluorophenyl)-2,2-dimethylpropylamine | |

-continued
| Prep Example | Amide | Amines | Title compound |
|---|---|---|---|
| 1028 | 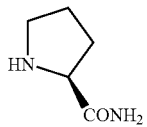 | 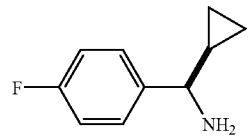 | 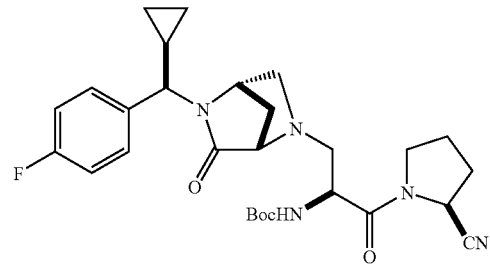 |
| 1029 | 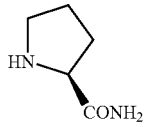 | 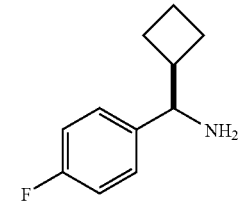 | 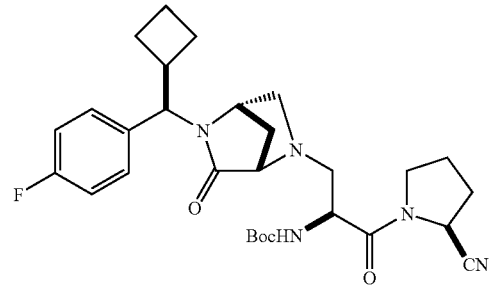 |
| 1030 | 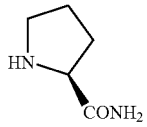 | 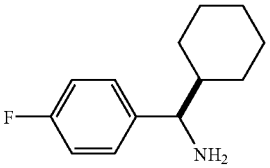 | 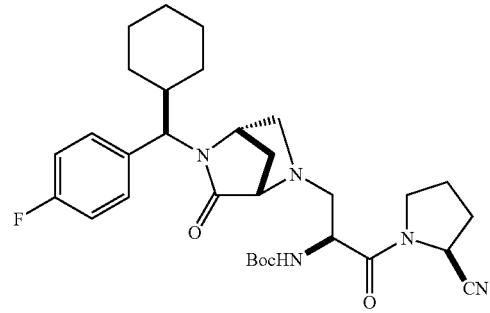 |
| 1031 | 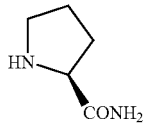 | 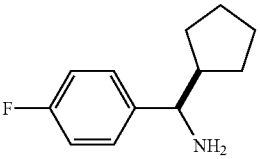 | 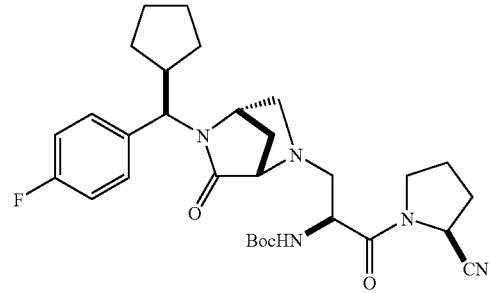 |
| 1032 | 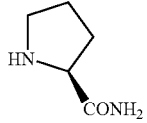 | 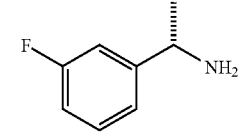 | 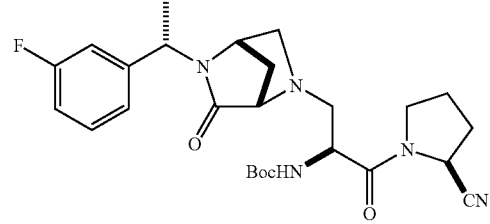 |

-continued

| Prep Example | Amide | Amines | Title compound |
|---|---|---|---|
| 1033 | | | |
| 1034 | | | |
| 1035 | | | |
| 1036 | | | |
| 1037 | | | |
| 1038 | | | |

-continued

| Prep Example | Amide | Amines | Title compound |
|---|---|---|---|
| 1039 | | | |
| 1040 | | | |
| 1041 | | | |
| 1042 | | | |
| 1043 | | | |
| 1044 | | | |

-continued

| Prep Example | Amide | Amines | Title compound |
|---|---|---|---|
| 1045 | | | |
| 1046 | | | |
| 1047 | | | |
| 1048 | | | |
| 1049 | | | |
| 1050 | | | |

-continued

| Prep Example | Amide | Amines | Title compound |
|---|---|---|---|
| 1051 | | | |
| 1052 | | | |
| 1053 | | | |
| 1054 | | | |
| 1055 | | | |
| 1056 | | | |

-continued

| Prep Example | Amide | Amines | Title compound |
|---|---|---|---|
| 1057 | | | |
| 1058 | | | |
| 1059 | | | |
| 1060 | | | |
| 1061 | | | |

-continued
| Prep Example | Amide | Amines | Title compound |
|---|---|---|---|
| 1062 | 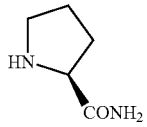 | 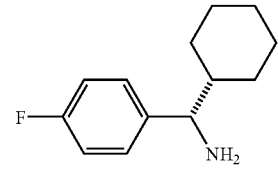 | 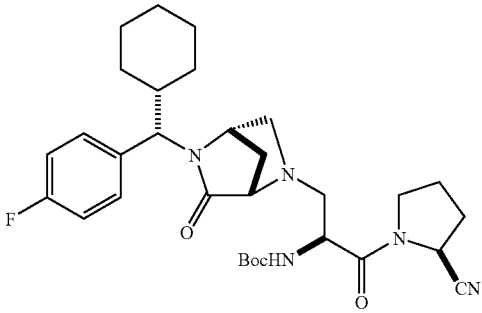 |
| 1063 | 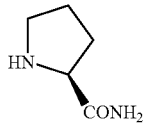 | 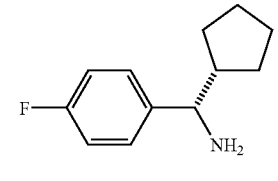 | 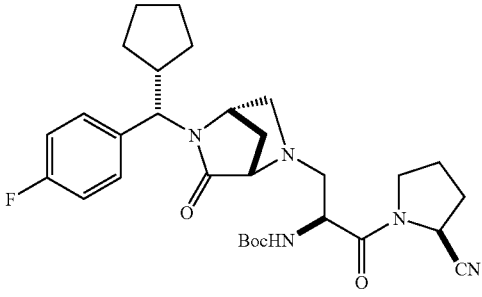 |
| 1064 | 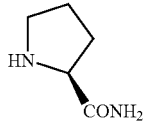 | 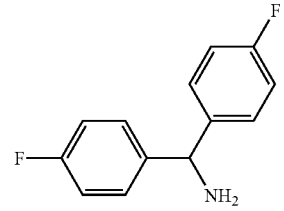 | 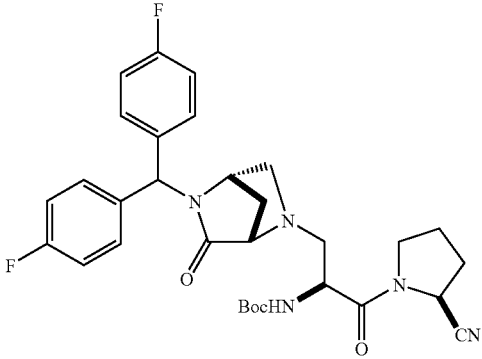 |
| 1065 | 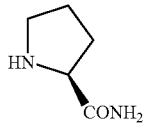 | 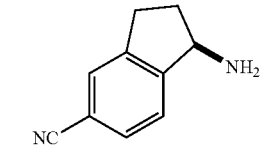 | 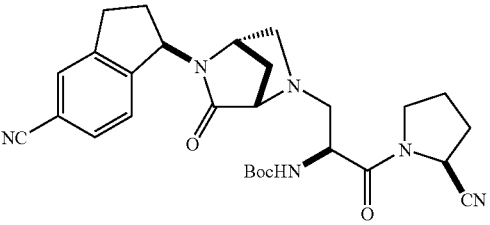 |
| 1066 | 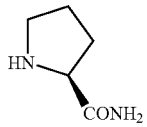 | 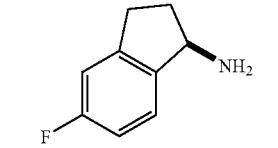 | 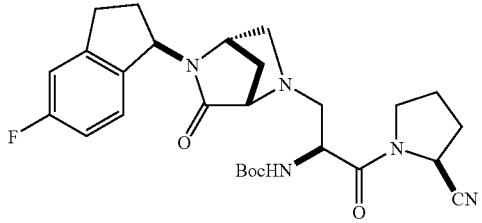 |

-continued

| Prep Example | Amide | Amines | Title compound |
|---|---|---|---|
| 1067 | | | |
| 1068 | | | |
| 1069 | | | |
| 1070 | | | |
| 1071 | | | |
| 1072 | | | |

-continued

| Prep Example | Amide | Amines | Title compound |
|---|---|---|---|
| 1073 | | | |
| 1074 | | | |
| 1075 | | | |
| 1076 | | | |
| 1077 | | | |
| 1078 | | | |

-continued

| Prep Example | Amide | Amines | Title compound |
|---|---|---|---|
| 1079 | | | |
| 1080 | | | |
| 1081 | | | |
| 1082 | | | |
| 1083 | | | |
| 1084 | | | |

-continued
| Prep Example | Amide | Amines | Title compound |
|---|---|---|---|
| 1085 | 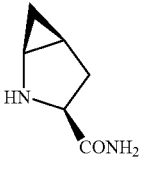 | 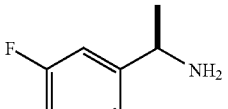 | 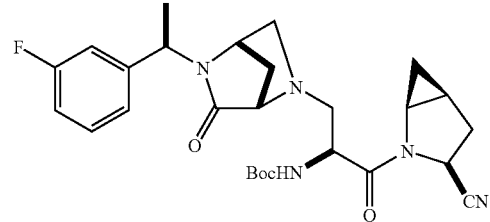 |
| 1086 | 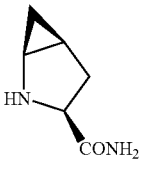 | 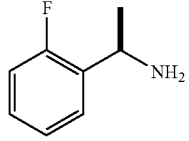 | 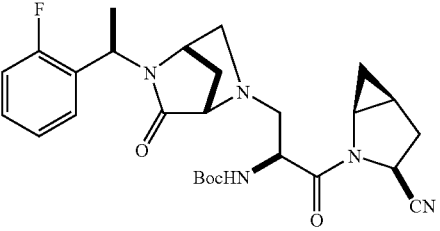 |
| 1087 |  | 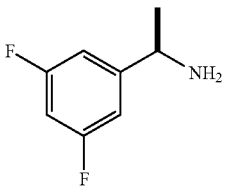 | 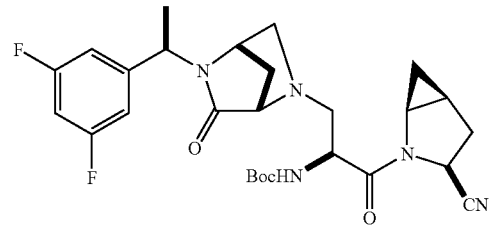 |
| 1088 |  | 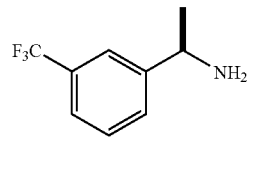 | 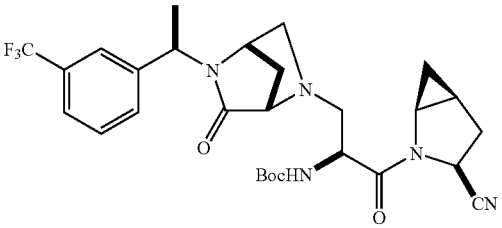 |
| 1089 |  | 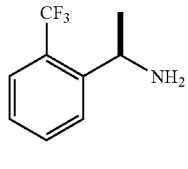 | 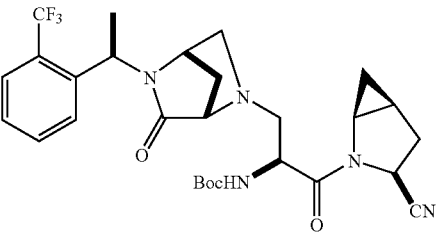 |
| 1090 |  | 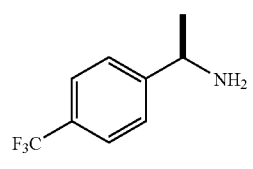 | 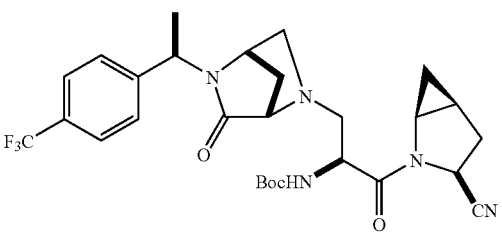 |

-continued

| Prep Example | Amide | Amines | Title compound |
|---|---|---|---|
| 1091 | | | |
| 1092 | | | |
| 1093 | | | |
| 1094 | | | |
| 1095 | | | |
| 1096 | | | |

-continued

| Prep Example | Amide | Amines | Title compound |
|---|---|---|---|
| 1097 | | | |
| 1098 | | | |
| 1099 | | | |
| 1100 | | | |
| 1101 | | | |
| 1102 | | | |

-continued

| Prep Example | Amide | Amines | Title compound |
|---|---|---|---|
| 1103 | | | |
| 1104 | | | |
| 1105 | | | |
| 1106 | | | |
| 1107 | | | |
| 1108 | | | |

-continued

| Prep Example | Amide | Amines | Title compound |
|---|---|---|---|
| 1109 | | | |
| 1110 | | | |
| 1111 | | | |
| 1112 | | | |
| 1113 | | | |

-continued
| Prep Example | Amide | Amines | Title compound |
|---|---|---|---|
| 1114 | 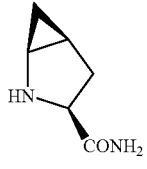 | 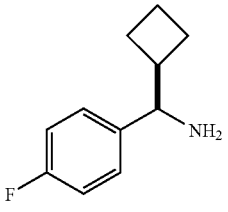 | 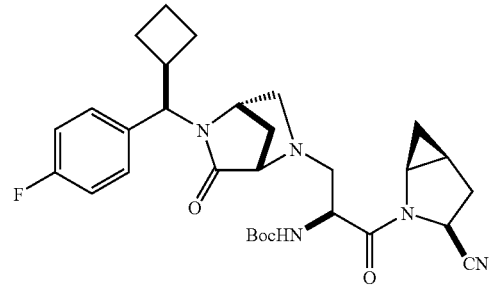 |
| 1115 | 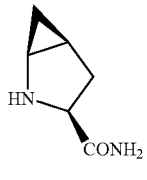 | 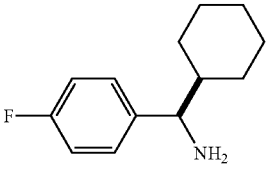 | 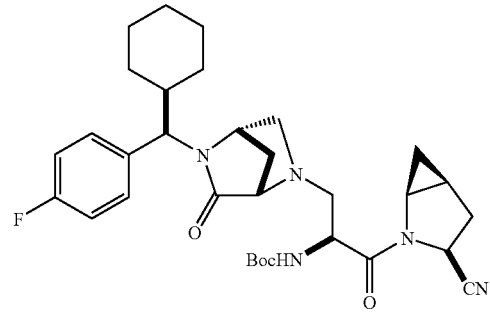 |
| 1116 | 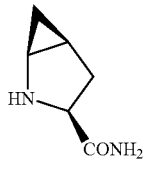 | 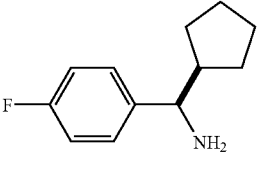 | 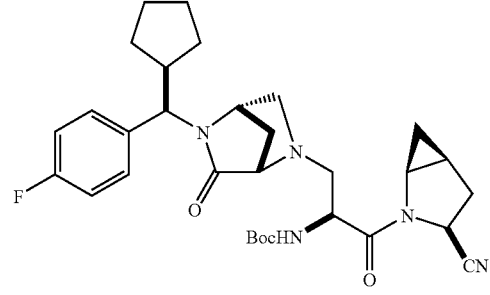 |
| 1117 | 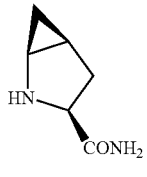 | 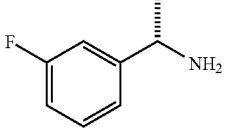 | 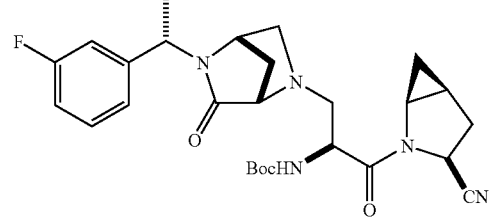 |
| 1118 | 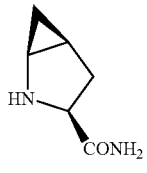 | 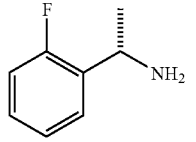 | 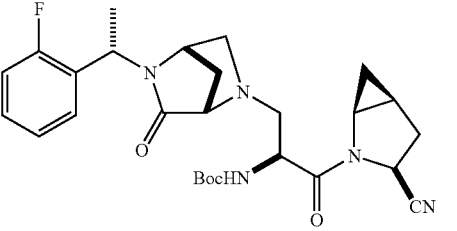 |

US 7,553,861 B2
361                                                                                         362
-continued
| Prep Example | Amide | Amines | Title compound |
|---|---|---|---|
| 1119 | 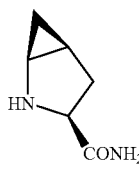 | 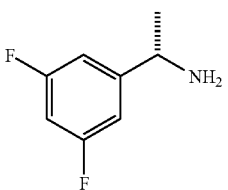 | 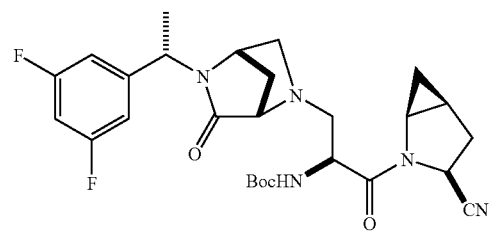 |
| 1120 | 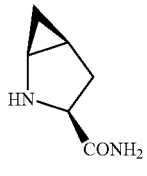 | 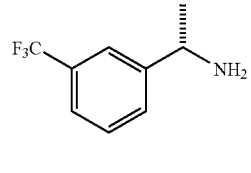 | 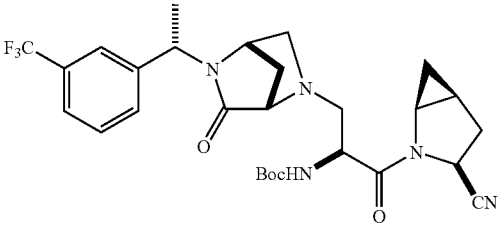 |
| 1121 | 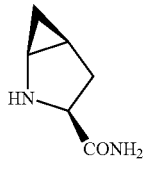 | 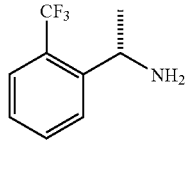 | 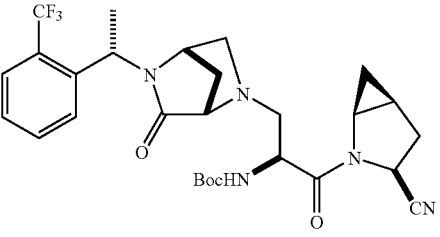 |
| 1122 |  | 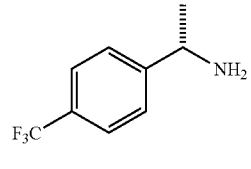 | 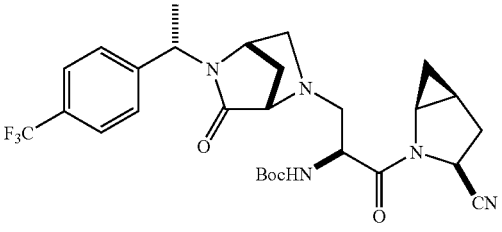 |
| 1123 | 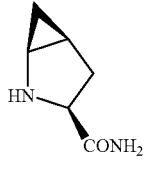 | 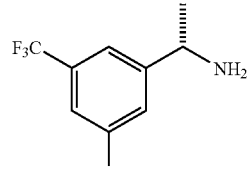 | 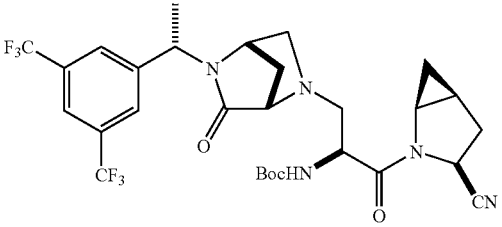 |
| 1124 | 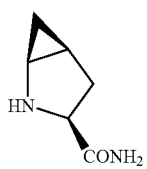 | 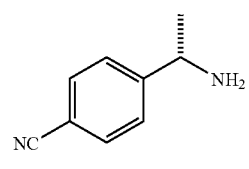 | 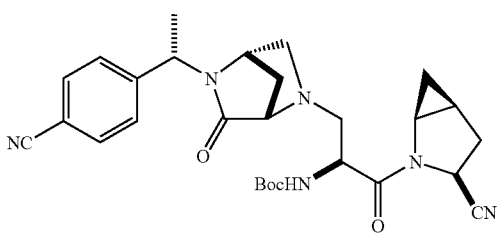 |

-continued

| Prep Example | Amide | Amines | Title compound |
|---|---|---|---|
| 1125 | | | |
| 1126 | | | |
| 1127 | | | |
| 1128 | | | |
| 1129 | | | |
| 1130 | | | |

-continued

| Prep Example | Amide | Amines | Title compound |
|---|---|---|---|
| 1131 | | | |
| 1132 | | | |
| 1133 | | | |
| 1134 | | | |
| 1135 | | | |
| 1136 | | | |

-continued

| Prep Example | Amide | Amines | Title compound |
|---|---|---|---|
| 1137 | | | |
| 1138 | | | |
| 1139 | | | |
| 1140 | | | |
| 1141 | | | |
| 1142 | | | |

| Prep Example | Amide | Amines | Title compound |
|---|---|---|---|
| 1143 | | | |
| 1144 | | | |
| 1145 | | | |
| 1146 | | | |
| 1147 | | | |

US 7,553,861 B2
371                                                                 372
-continued
| Prep Example | Amide | Amines | Title compound |
|---|---|---|---|
| 1148 | 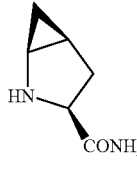 | 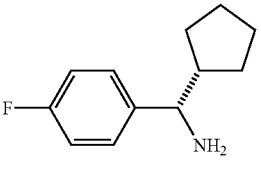 | 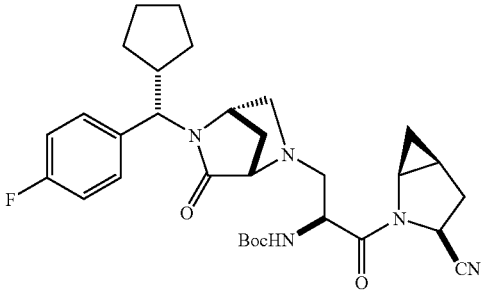 |
| 1149 | 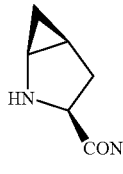 | 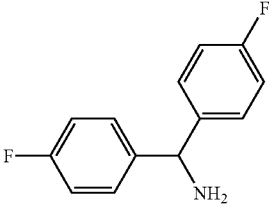 | 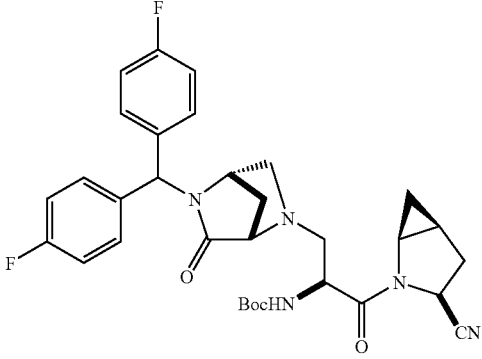 |
| 1150 |  | 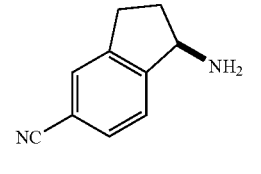 | 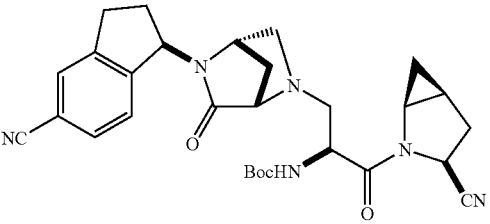 |
| 1151 |  | 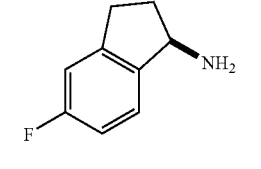 | 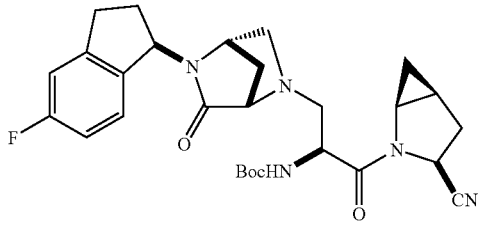 |
| 1152 | 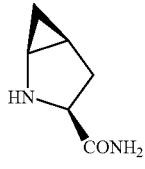 | 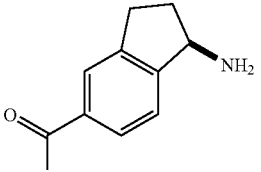 | 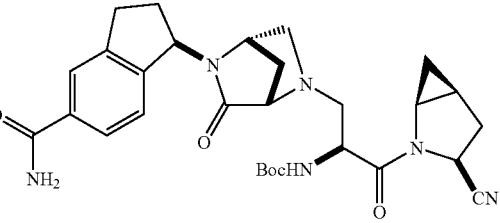 |

-continued

| Prep Example | Amide | Amines | Title compound |
|---|---|---|---|
| 1153 | | | |
| 1154 | | | |
| 1155 | | | |
| 1156 | | | |
| 1157 | | | |
| 1158 | | | |

-continued

| Prep Example | Amide | Amines | Title compound |
|---|---|---|---|
| 1159 | | | |
| 1160 | | | |
| 1161 | | | |
| 1162 | | | |
| 1163 | | | |
| 1164 | | | |

| Prep Example | Amide | Amines | Title compound |
|---|---|---|---|
| 1165 | | | |
| 1166 | | | |
| 1167 | | | |
| 1168 | | | |
| 1169 | | | |
| 1170 | | | |

-continued
| Prep Example | Amide | Amines | Title compound |
|---|---|---|---|
| 1171 | 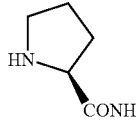 | 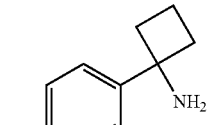 | 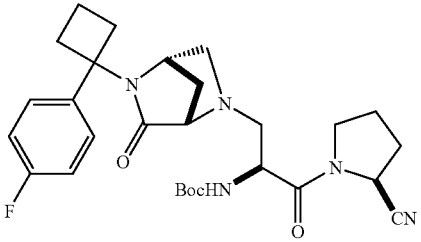 |
| 1172 | 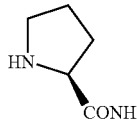 | 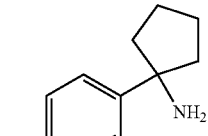 | 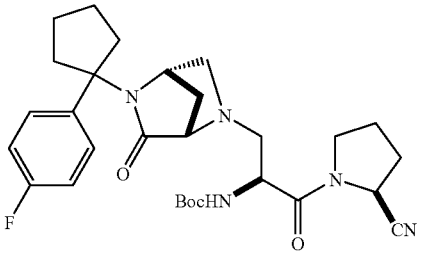 |
| 1173 |  | 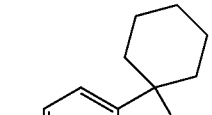 | 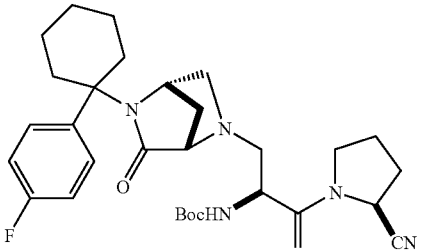 |
| 1174 | 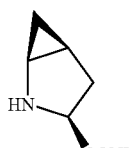 | 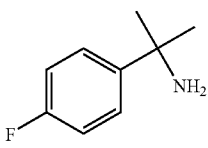 | 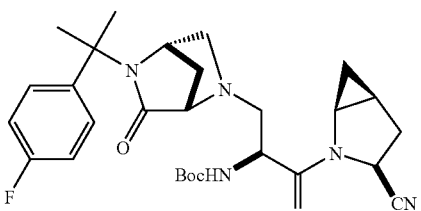 |
| 1175 |  | 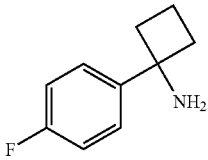 | 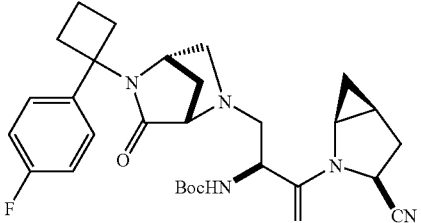 |
| 1176 |  | 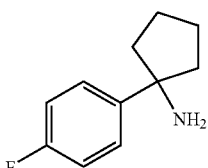 | 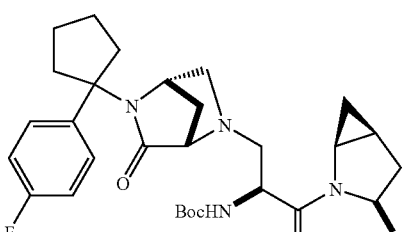 |

-continued
| Prep Example | Amide | Amines | Title compound |
|---|---|---|---|
| 1177 | 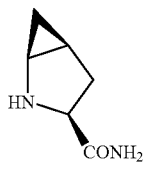 | 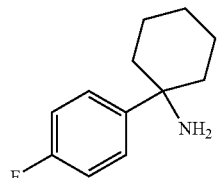 | 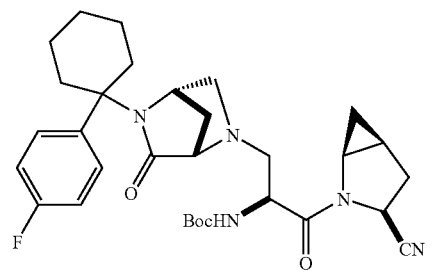 |
| 1178 | 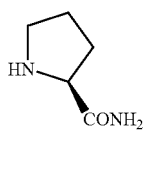 | 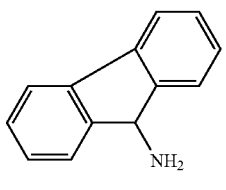 | 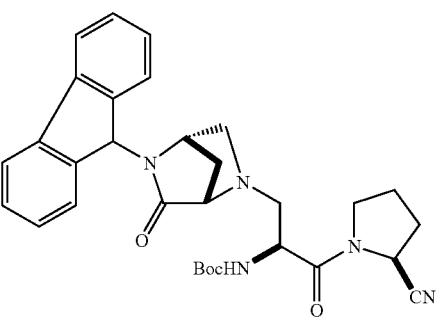 |
| 1179 | 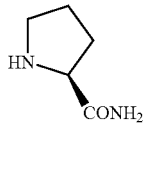 | 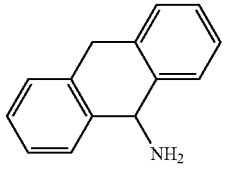 | 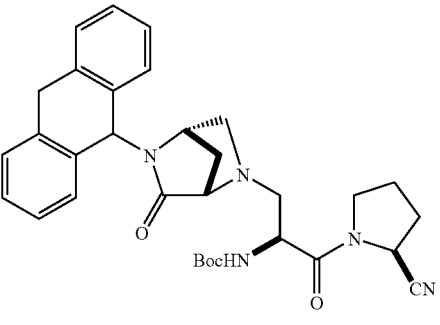 |
| 1180 | 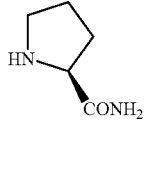 | 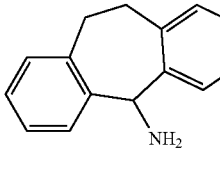 | 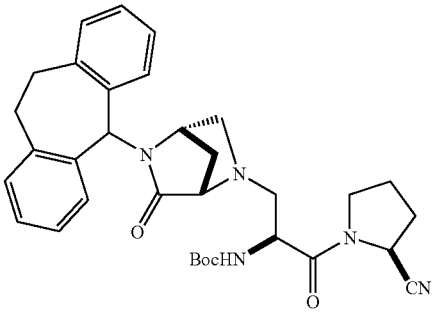 |
| 1181 | 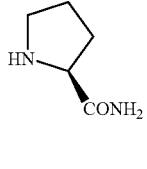 | 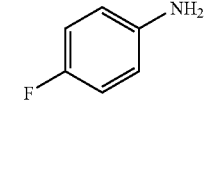 | 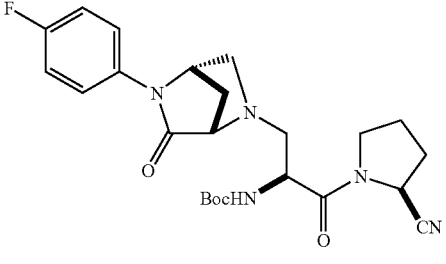 |

-continued

| Prep Example | Amide | Amines | Title compound |
|---|---|---|---|
| 1182 | | | |
| 1183 | | | |
| 1184 | | | |
| 1185 | | | |
| 1186 | | | |

-continued

| Prep Example | Amide | Amines | Title compound |
|---|---|---|---|
| 1187 | | | |
| 1188 | | | |
| 1189 | | | |
| 1190 | | | |
| 1191 | | | |

-continued
| Prep Example | Amide | Amines | Title compound |
|---|---|---|---|
| 1192 | 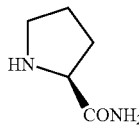 | 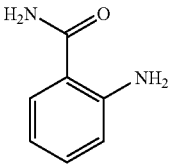 | 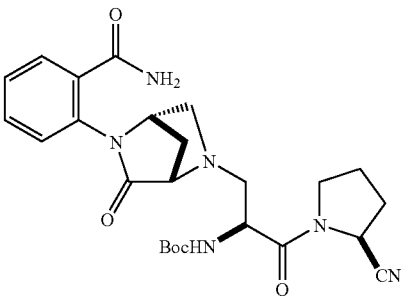 |
| 1193 | 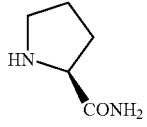 | 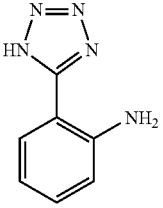 | 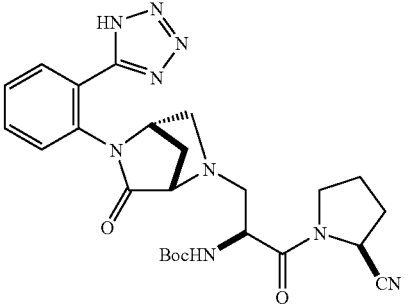 |
| 1194 | 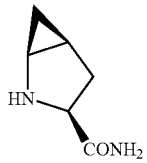 | 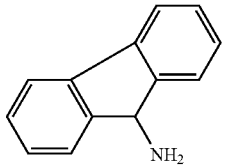 | 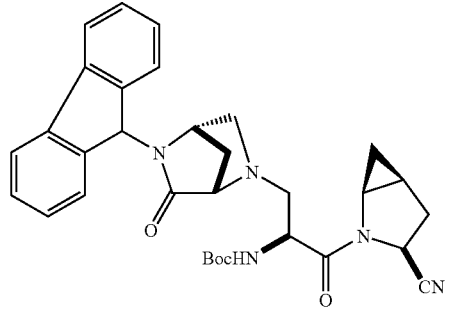 |
| 1195 |  | 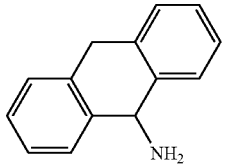 | 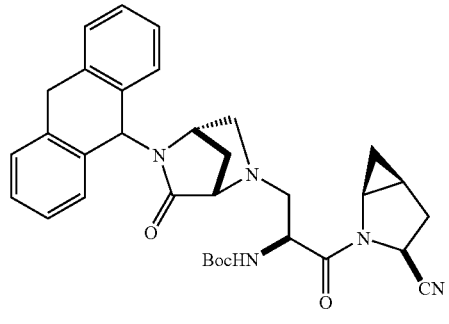 |

| Prep Example | Amide | Amines | Title compound |
|---|---|---|---|
| 1196 | 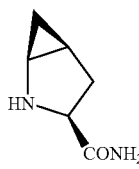 | 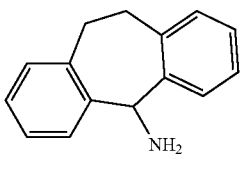 | 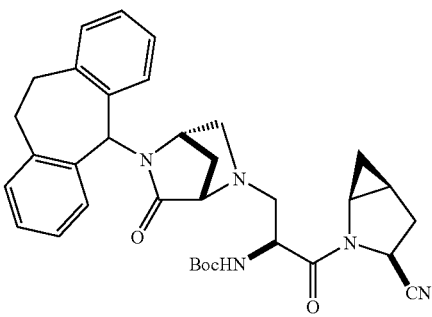 |
| 1197 | 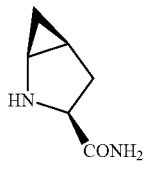 | 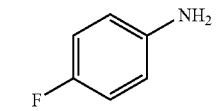 | 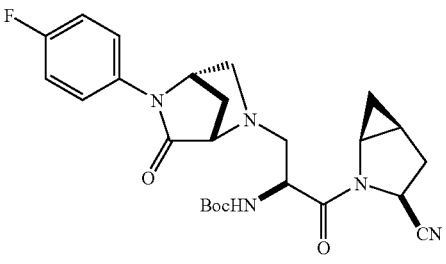 |
| 1198 | 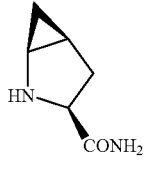 | 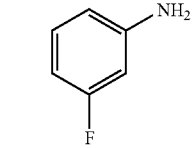 | 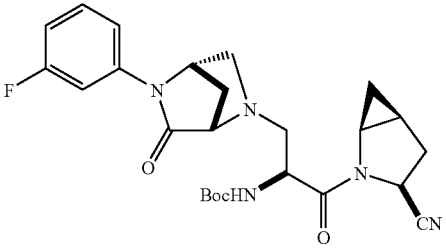 |
| 1199 | 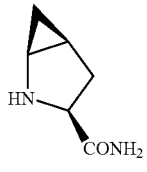 |  | 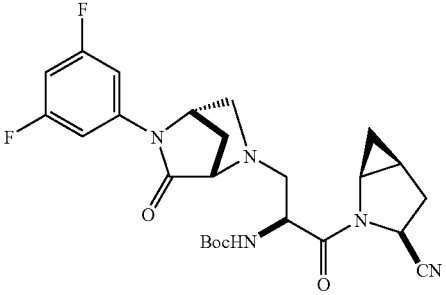 |
| 1200 | 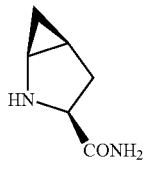 | 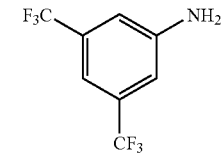 | 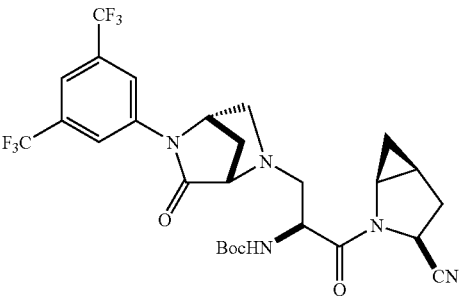 |

-continued

| Prep Example | Amide | Amines | Title compound |
|---|---|---|---|
| 1201 | | | |
| 1202 | | | |
| 1203 | | | |
| 1204 | | | |
| 1205 | | | |

Examples 1210-1299 have been intentionally excluded.
Preparative Example 1300
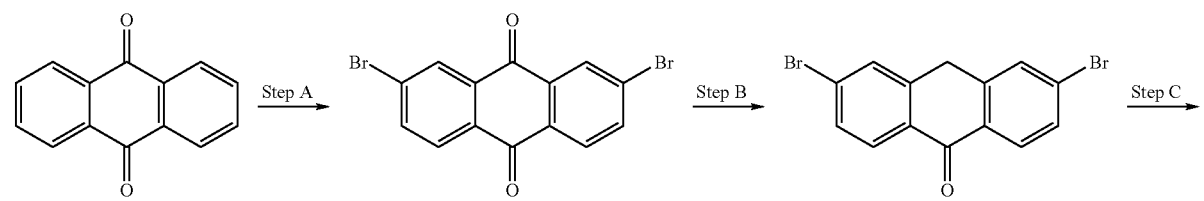

-continued

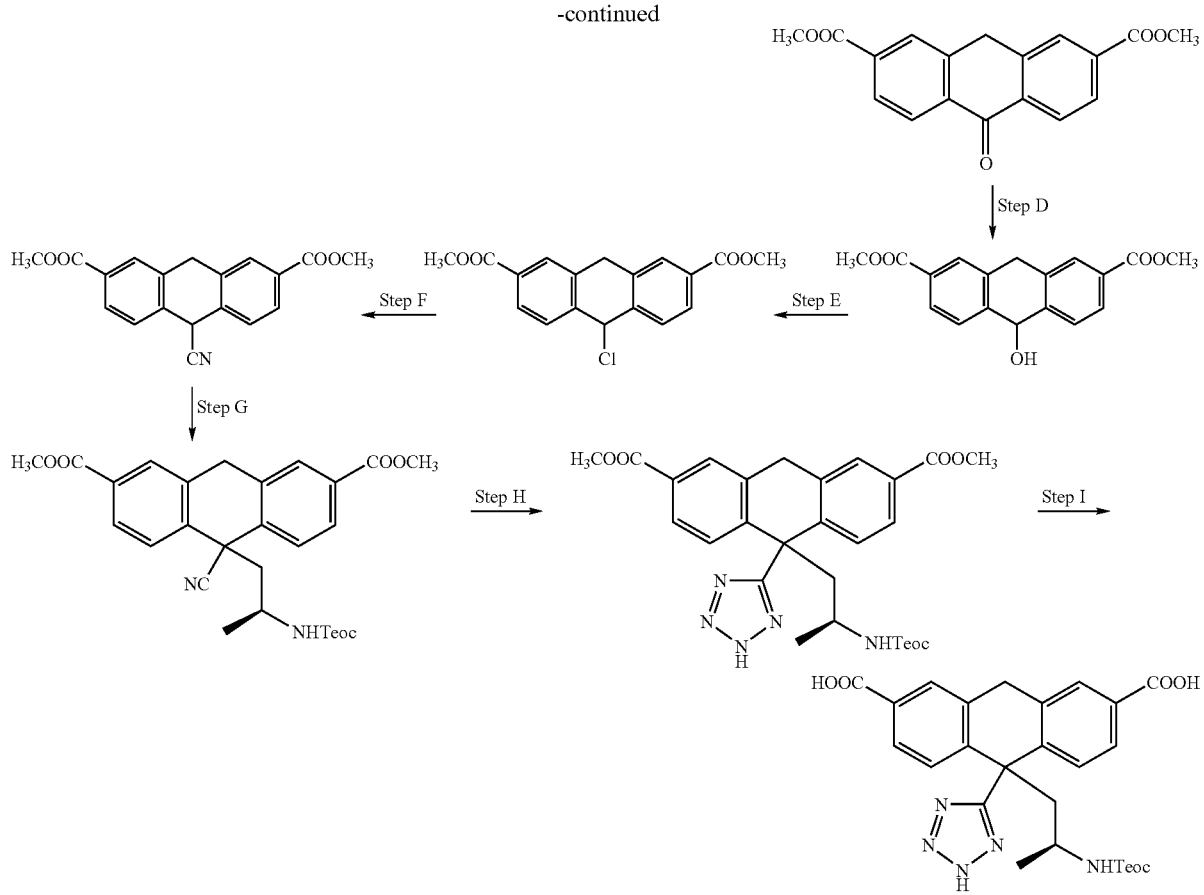

Step A
If one were to treat commercially available anthraquinone with 1.5-2 equivalents of bromine and some iodine at 160° C., and then treat the mixture with aqueous sodium hydroxide at reflux, one would obtain the title compound, after crystallisation from glacial acetic acid.

Step B
If one were to treat the title compound from Step A above with hot concentrated $H_2SO_4$, treat the obtained solution with Al powder at rt and stir the mixture at rt for 3 h, one would obtain the title compound, after aqueous workup and chromatography on silica gel.

Step C
If one were to treat the title compound from Step B above as described in Preparative Example 59 Step D, Step E and Step F, one would obtain the title compound.

Step D
If one were to treat the title compound from Step C above as described in Preparative Example 59 Step G, one would obtain the title compound.

Step E
If one were to treat the title compound from Step D above as described in Preparative Example 59 Step H, one would obtain the title compound.

Step F
If one were to treat the title compound from Step E above as described in Preparative Example 59 Step I, one would obtain the title compound.

Step G
If one were to treat the title compound from Step F above as described in Preparative Example 61 Step A, one would obtain the title compound.

Step H
If one were to treat the title compound from Step G above as described in Preparative Example 61 Step B, one would obtain the title compound.

Step I
If one were to treat the title compound from Step H above as described in Preparative Example 61 Step C, one would obtain the title compound.

Preparative Example 1301

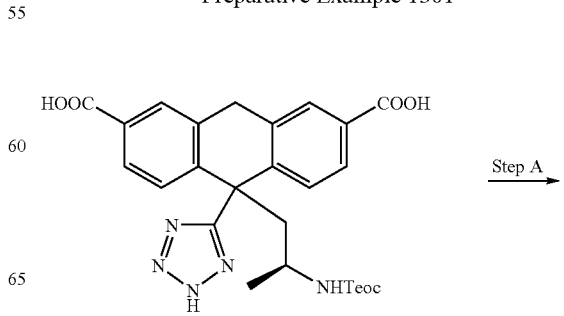

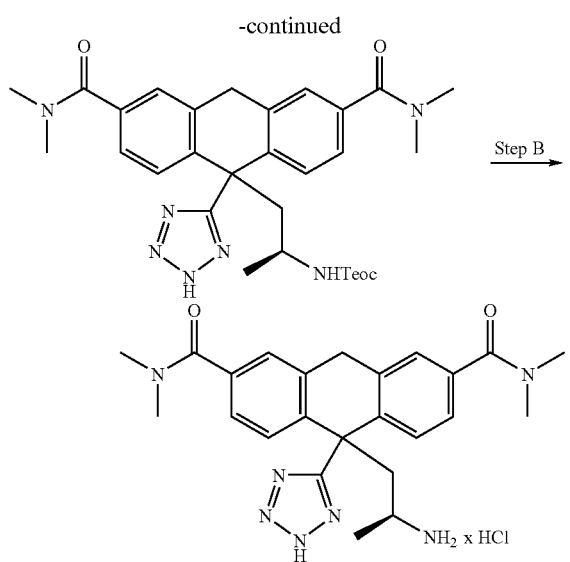

Step A

If one were to treat the title compound from Preparative Example 1300 as described in Preparative Example 71 Step A one would obtain the title compound.

Step B

If one were to treat the title compound from Step A above as described in Preparative Example 71 Step B, one would obtain the title compound.

Preparative Example 1302-1309

If one were to follow a similar procedure as that described in Preparative Example 1300, except using the sulfamidates in Step G, and treat the product obtained according to Preparative Example 1301 with the amine as indicated in the table below, one would obtain the desired title compound as HCl salt.

| Preparative Example | Sulfamidate | Amine | Title compound |
|---|---|---|---|
| 1302 | 21 | $NH_3$ | |
| 1303 | 24 | $NH_3$ | |
| 1304 | 22 | $NH_3$ | |

-continued

| Preparative Example | Sulfamidate | Amine | Title compound |
|---|---|---|---|
| 1305 | 21 | CH₃NH₂ | |
| 1306 | 24 | CH₃NH₂ | |
| 1307 | 22 | CH₃NH₂ | |
| 1308 | 24 | (CH₃)₂NH | |
| 1309 | 22 | (CH₃)₂NH | |

Examples 1310-1349 have been intentionally excluded.

Preparative Example 1350

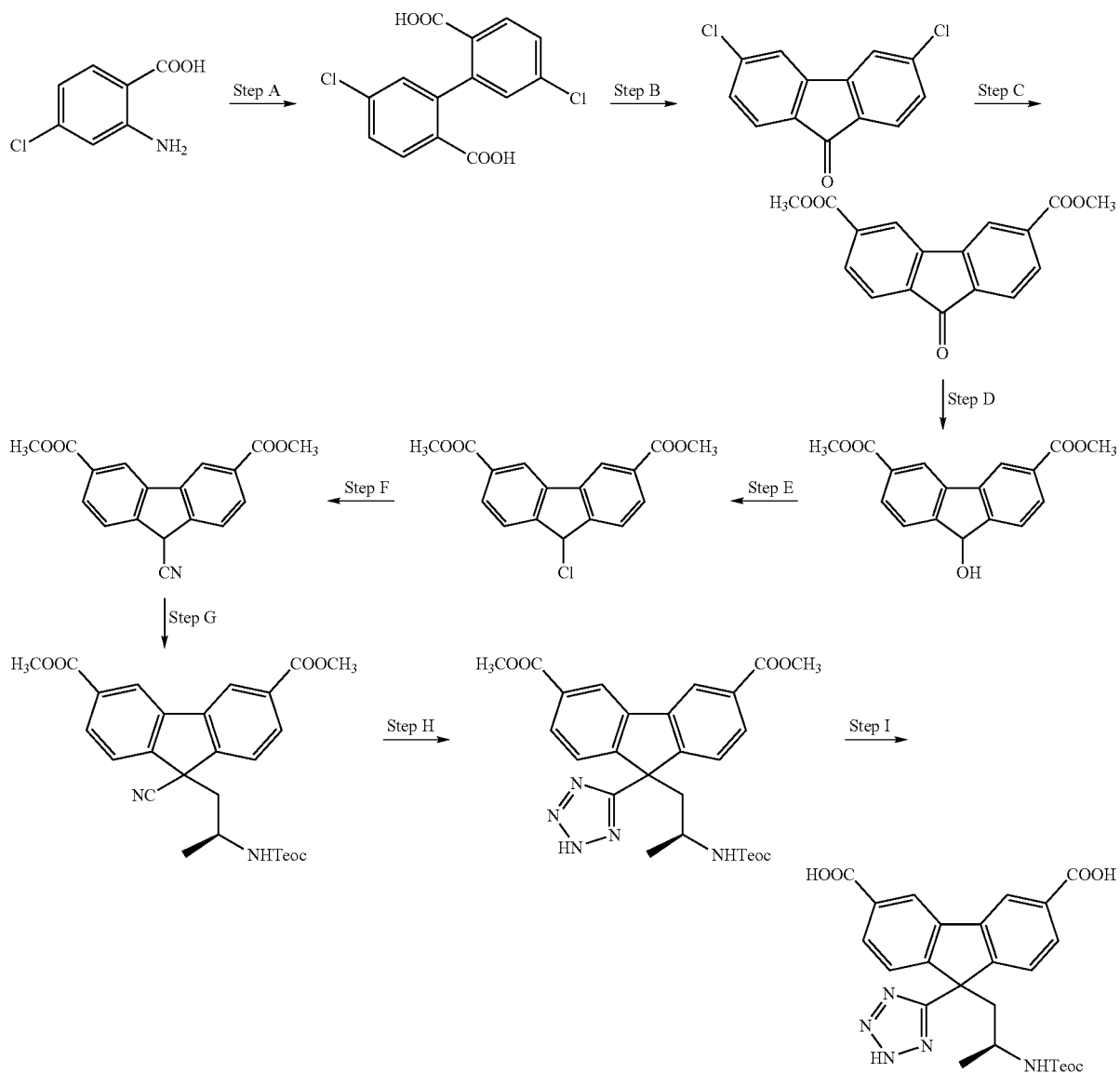

Step A

If one were to treat a solution of commercially available 4-chloroanthranilic acid in water and concentrated hydrochloric acid at 0° C. with a solution of sodium nitrate in water over 45 min and stir the resulting mixture at 0° C. for 1 h, one would obtain the diazonium salt solution after filtration. If one were to treat a solution of commercially available hydroxylamine hydrochloride in water at 10° C. with an aqueous solution of sodium hydroxide and carefully pour the mixture into an aqueous solution of hydrated copper(II) sulfate and concentrated ammonia solution, one would obtain a blue solution after filtration. If one were to carefully add the diazonium salt solution from above to the blue solution over a period of 1 h and then heat the mixture at reflux, followed by the addition of concentrated hydrochloric acid, one would obtain a precipitate after 3 h. If one were to collect the precipitate by filtration, wash it with water and dissolved it in a solution of sodium bicarbonate, one would obtain a clear solution after treatment with charcoal and filtration. If one were to add an excess of 6 M aqueous hydrochloric acid and collect the precipitate, one would obtain the title compound after crystallisation from EtOH.

Step B

If one were to treat the title compound of Step A above at 400° C. for twenty-five minutes and then sublime the mixture at 250° C. under a pressure of 2 mm, one would obtain the title compound after crystallization from benzene.

Step C

If one were to treat the title compound from Step B above as described in Preparative Example 59 Step D, Step E and Step F, one would obtain the title compound.

Step D

If one were to treat the title compound from Step C above as described in Preparative Example 59 Step G, one would obtain the title compound.

403

Step E
If one were to treat the title compound from Step D above as described in Preparative Example 59 Step H, one would obtain the title compound.

Step F
If one were to treat the title compound from Step E above as described in Preparative Example 59 Step I, one would obtain the title compound.

Step G
If one were to treat the title compound from Step F above as described in Preparative Example 61 Step A, one would obtain the title compound.

Step H
If one were to treat the title compound from Step G above as described in Preparative Example 61 Step B, one would obtain the title compound.

Step I
If one were to treat the title compound from Step H above as described in Preparative Example 61 Step C, one would obtain the title compound.

Preparative Example 1351

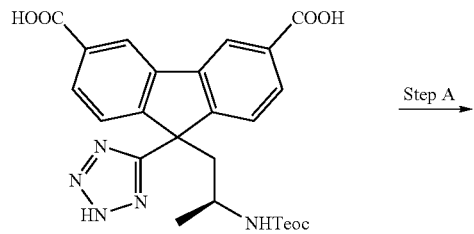

404

-continued

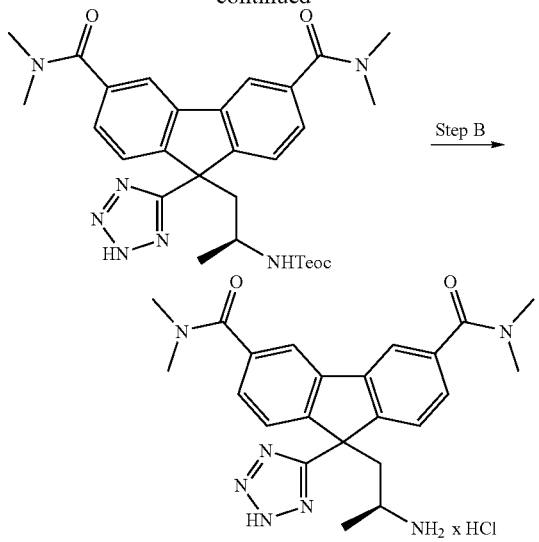

Step A
If one were to treat the title compound from Preparative Example 1350 as described in Preparative Example 71 Step A one would obtain the title compound.

Step B
If one were to treat the title compound from Step A above as described in Preparative Example 71 Step B, one would obtain the title compound.

Preparative Example 1352-1359

If one were to follow a similar procedure as that described in Preparative Example 1350, except using the sulfamidates in Step G, and treat the product obtained according to Preparative Example 1351 with the amine as indicated in the table below, one would obtain the desired title compound as HCl salt.

| Preparative Example | Sulfamidate | Amine | Title compound |
|---|---|---|---|
| 1352 | 21 | $NH_3$ | (structure shown) |
| 1353 | 24 | $NH_3$ | (structure shown) |

-continued

| Preparative Example | Sulfamidate | Amine | Title compound |
|---|---|---|---|
| 1354 | 22 | NH₃ | 9-(2-aminoethyl)-9-(1H-tetrazol-5-yl)-fluorene-2,7-dicarboxamide |
| 1355 | 21 | CH₃NH₂ | 9-[(2R)-2-aminopropyl]-N,N'-dimethyl-9-(1H-tetrazol-5-yl)-fluorene-2,7-dicarboxamide |
| 1356 | 24 | CH₃NH₂ | 9-[(2S)-2-aminopropyl]-N,N'-dimethyl-9-(1H-tetrazol-5-yl)-fluorene-2,7-dicarboxamide |
| 1357 | 22 | CH₃NH₂ | 9-(2-aminoethyl)-N,N'-dimethyl-9-(1H-tetrazol-5-yl)-fluorene-2,7-dicarboxamide |
| 1358 | 24 | (CH₃)₂NH | 9-[(2S)-2-aminopropyl]-N,N,N',N'-tetramethyl-9-(1H-tetrazol-5-yl)-fluorene-2,7-dicarboxamide |

| Preparative Example | Sulfamidate | Amine | Title compound |
|---|---|---|---|
| 1359 | 22 | (CH₃)₂NH | |

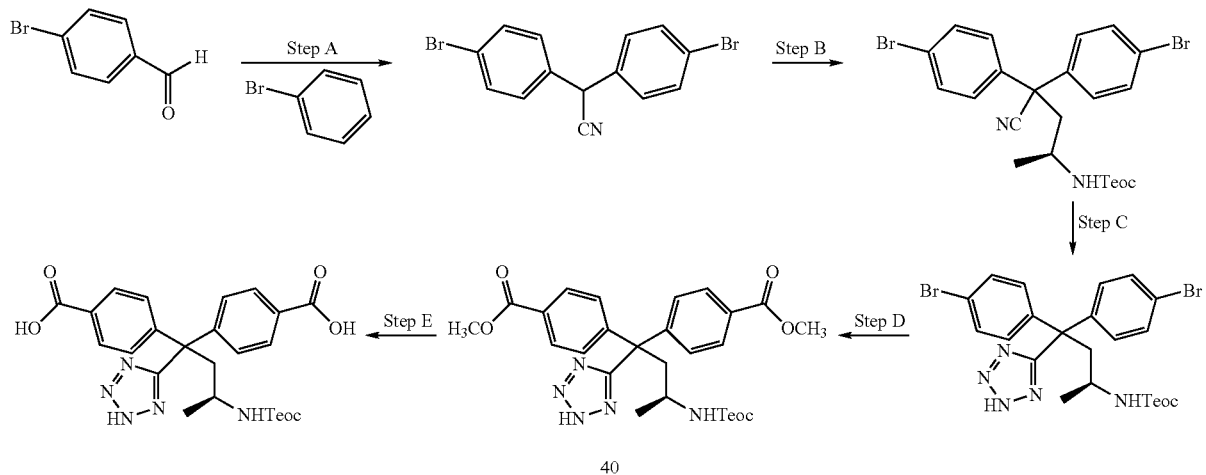

Examples 1360-1399 have been intentionally excluded.

Preparative Example 1400

Step A

If one were to treat commercially available 4-bromo benzaldehyde dissolved in ether at 0° C. over a period of two hours portion-wise with KCN and concentrated HCl and maintain the temperature of the reaction below 10° C., followed by stirring for 1 h after complete addition, while permitting the temperature to rise to 15° C., subsequently the resultant two-phase system is filtered off and washed with ether, separating the combined organic solutions one would obtain the intermediate after washing with saturated aqueous sodium bisulfide, drying over $MgSO_4$, and concentrating in vacuo. If one were to dilute the residue with benzene and slowly add this mixture over a period of one hour to concentrated $H_2SO_4$, which would maintained under stirring in an ice bath at a temperature below 15° C. until completion of the addition, followed by stirring for an additional hour, allowing the mixture to warm to room temperature one would obtain after pouring the reaction mixture onto ice and the mixture is being extracted with benzene, the title compound.

Step B

If one were to treat the title compound from Step A above as described in Preparative Example 61 Step A, one would obtain the title compound.

Step C

If one were to treat the title compound from Step B above as described in Preparative Example 61 Step B, one would obtain the title compound.

Step D

If one were to treat the title compound from Step C above as described in Preparative Example 59 Step D, Step E and Step F, one would obtain the title compound.

Step E

If one were to treat the title compound from Step D above as described in Preparative Example 61 Step C, one would obtain the title compound.

Preparative Example 1401

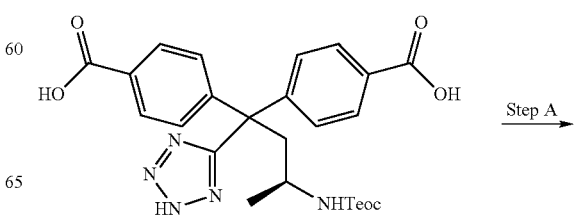

Step A

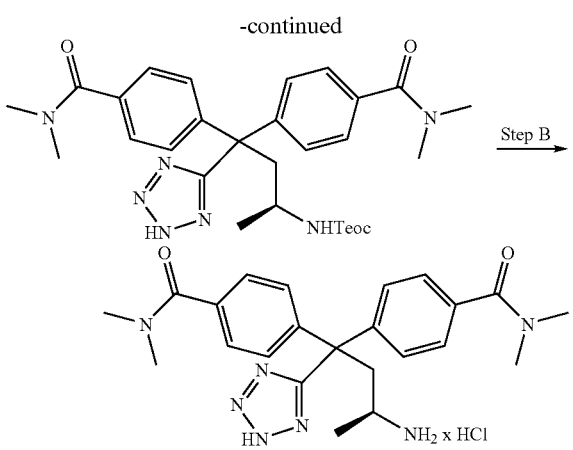

Step A

If one were to treat the title compound from Preparative Example 1400 as described in Preparative Example 71 Step A one would obtain the title compound.

Step B

If one were to treat the title compound from Step A above as described in Preparative Example 71 Step B, one would obtain the title compound.

Preparative Example 1402-1409

If one were to follow a similar procedure as that described in Preparative Example 1400, except using the sulfamidates in Step B, and treat the product obtained according to Preparative Example 1401 with the amine as indicated in the table below, one would obtain the desired title compound as HCl salt.

| Preparative Example | Sulfamidate | Amine | Title compound |
|---|---|---|---|
| 1402 | 21 | NH₃ | 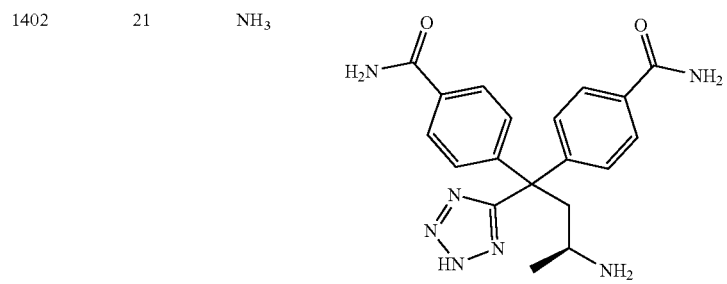 |
| 1403 | 24 | NH₃ | 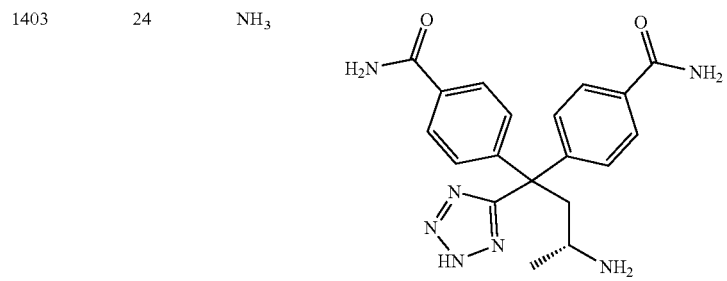 |
| 1404 | 22 | NH₃ | 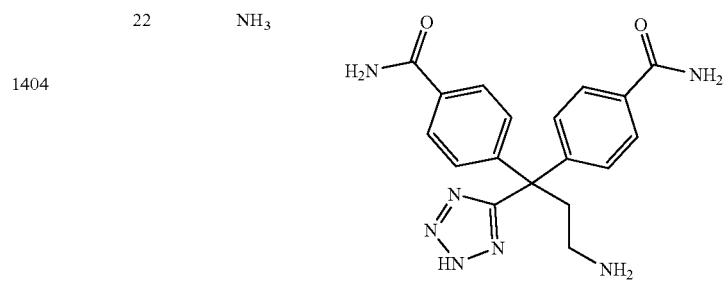 |

-continued

| Preparative Example | Sulfamidate | Amine | Title compound |
|---|---|---|---|
| 1405 | 21 | CH₃NH₂ | |
| 1406 | 24 | CH₃NH₂ | |
| 1407 | 22 | CH₃NH₂ | |
| 1408 | 24 | (CH₃)₂NH | |
| 1409 | 22 | (CH₃)₂NH | |

Examples 1410-1449 have been intentionally excluded.

Preparative Example 1450

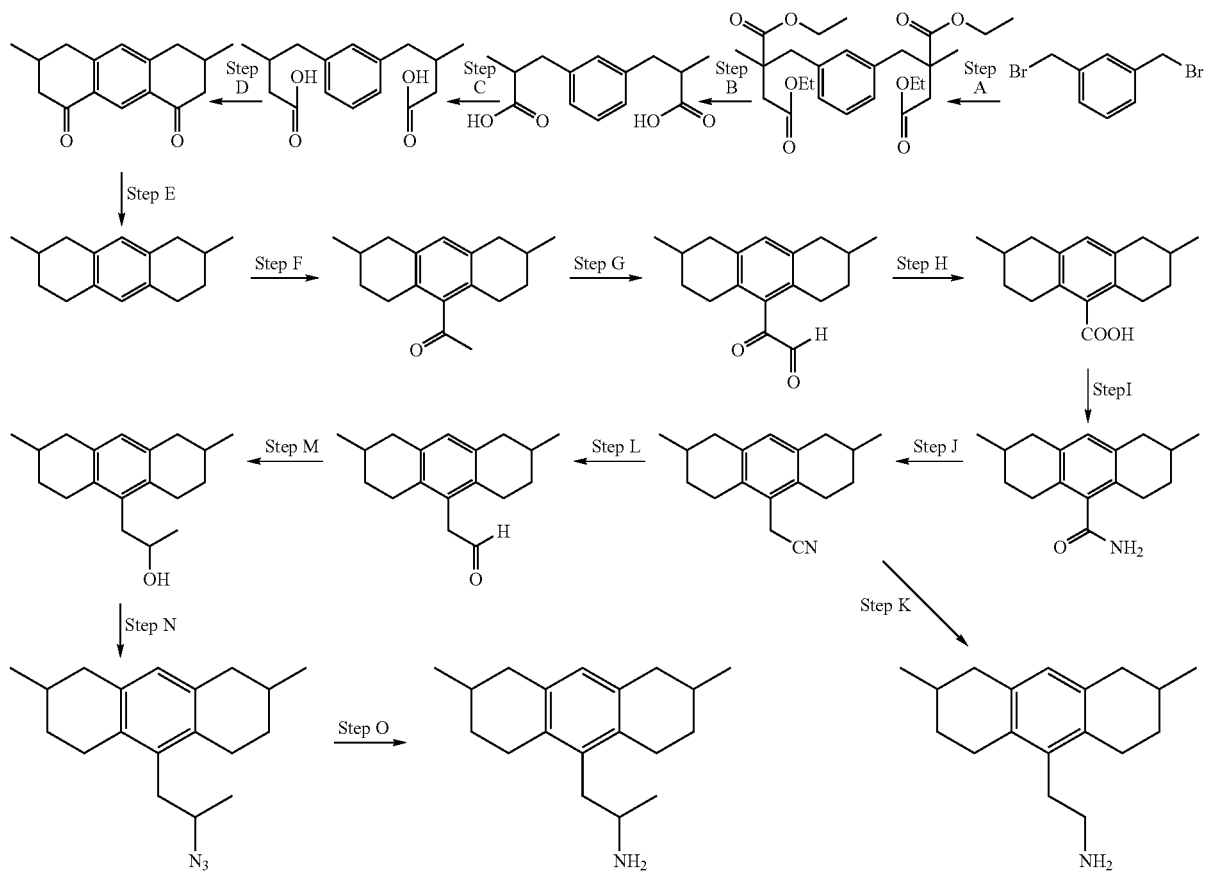

Step A

If one were to add commercially available diethylmethylmalonate to a solution of sodium ethoxide in EtOH, and then add a solution of α,α'-dibromo-m-xylene in benzene to the above solution solution and boil the mixture at reflux for 1 h, one would obtain the title compound after distillation and crystallisation.

Step B

If one were to treat the title compound from Step A above with aqueous-ethanolic potassium hydroxide, one would obtain the crude tetracarboxylic acid. If one were to decarboxylate the crude tetracarboxylic acid at 210° C., one would obtain the title compound.

Step C

If one were to convert the title compound from Step B above to its bis-acid chloride with thionyl chloride in benzene and treat the bis-acid chloride with a solution of diazomethane in ether, one would obtain the diazoketone intermediate after 12 h and evaporation of the solvents. If one were to treat the diazoketone with benzyl alcohol-γ-collidine (1:1) in an oil-bath maintained at 180° C. for 10 Min, one would obtain the crude title compound. If one were to treat the crude title compound with MeOH and HCl, one would obtain the dimethylester. If one were to treat the diemthylester with KOH in EtOH, one would obtain the title compound.

Step D

If one were to treat the title compound from Step C above with phosphorus pentachloride in benzene for 1 h and warm the mixture on a steam-bath for 5 min, one would obtain the crude bis-acid chloride. If one were to dissolve the bis-acid chloride in nitrobenzene, add a solution of aluminium chloride in nitrobenzene at 0° C. and then allow the mixture to stand at rt for 6 h, one would obtain the title compound, after removal of the nitrobenzene by steam distillation and crystallisation of the residue with EtOH.

Step E

If one were to treat the title compound from Step D above with hydrazine hydrate and potassium hydroxide in diethylene glycol for 4 h at 180° C., followed by purification by chromatography on alumina one would obtain the title compound.

Step F

If one were to treat the title compound from Step E with 10 eq. of aluminium chloride by adding the compound to the reagent in tetrachloroethane at low temperature, add dropwise 2.0 eq. of acetic anhydride to the mixture, pour onto ice and hydrochloric acid and extract with an appropriate solvent, wash with water, evaporate, recrystallize from methanol, one would obtain the title compound.

Step G

If one were to treat the title compound from Step F above with selenium dioxide in water and dioxane and refluxed for 4 h, followed by removal of precipitated selenium one would obtain after recrystallizaiton the title compound.

Step H

If one were to treat the title compound from Step G above with hydrogen peroxide and drop wise with 10% NaOH in ethanol at 80° C., followed by dilution with water, treatment with norite, filtration and acidifying with HCl, one would obtain after recrystallization the title compound.

Step I

If one were to treat the title compound from Step H above as described in Preparative Example 70 Step A, one would obtain the title compound Step J If one were to treat the title compound from Step I above as described in Preparative Example 93 Step C, one would obtain the title compound.

Step K

If one were to treat the title compound from Step J above as described in Preparative Example 13 Step B, one would obtain the title compound.

Step L

If one were to treat the title compound from Step K above with diisobutylaluminium hydride in $CH_2Cl_2$ at −78° C., add 10% aq AcOH, extract with ether:hexane, wash with $H_2O$, sat. aq $NaHCO_3$, and brine, dry over $Na_2SO_4$, evaporate, purify the crude product through chromatography on silica gel, one would obtain the title compound.

Step M

If one were to treat the title compound from Step L above with 1.2 eq. commercially available methylmagnesium bromide in $Et_2O$ at room temperature, heat the mixture to reflux, add ice and half concentrated hydrochlorid acid, extract with $Et_2O$, wash the organic layer with $H_2O$, sat. aq $NaHCO_3$, and brine, dry over $Na_2SO_4$, evaporate, purify the crude product through chromatography on silica gel, one would obtain the title compound.

Step N

If one were to treat the title compound from Step M above with methylsulfonyl chloride and triethylamine in $CH_2Cl_2$ at 0° C., evaporate, add water and ethyl acetate to the residue, extract with ethyl acetate, wash the organic layer with $H_2O$, sat. aq $NaHCO_3$, and brine, dry over $Na_2SO_4$, evaporate and then the obtained intermediate with $NaN_3$ in DMA as described in Preparative Example 17 Step C, one would obtain the title compound.

Step O

If one were to treat the title compound from Step N above as described in Preparative Example 17 Step D, one would obtain the title compound.

Preparative Example 1451

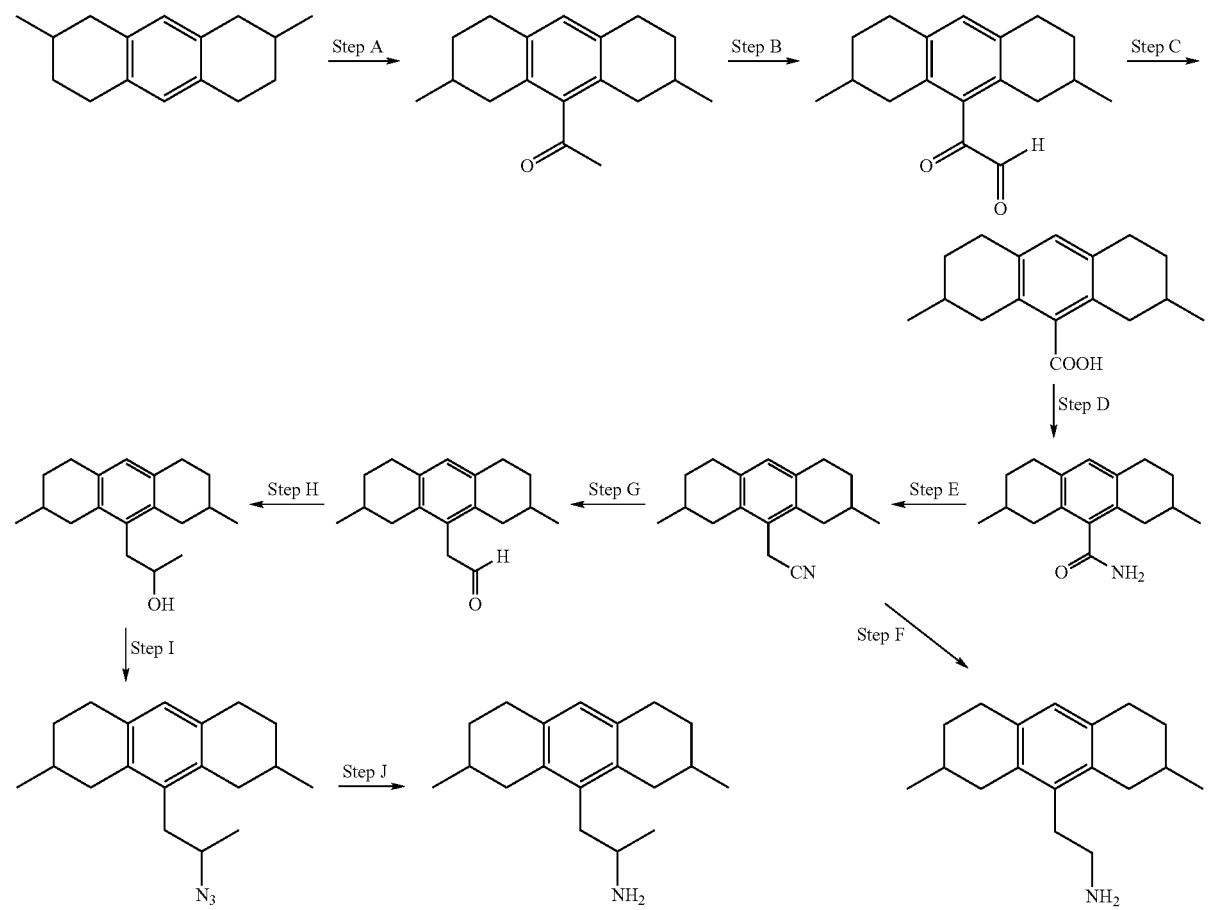

Step A

If one were to treat the title compound from Preparative Example 1450 Step E with 10 eq. of aluminium chloride by adding the compound to the reagent in tetrachloroethane at low temperature, add dropwise 2.0 eq. of acetic anhydride to the mixture, pour onto ice and hydrochloric acid and extract with an appropriate solvent, wash with water, evaporate, recrystallize from methanol, one would obtain the title compound.

Step B

If one were to treat the title compound from Step F above with selenium dioxide in water and dioxane and refluxed for 4 h, followed by removal of precipitated selenium one would obtain after recrystallizaiton the title compound.

Step C

If one were to treat the title compound from Step G above with hydrogen peroxide and drop wise with 10% NaOH in ethanol at 80° C., followed by dilution with water, treatment with norite, filtration and acidifying with HCl, one would obtain after recrystallization the title compound.

Step D

If one were to treat the title compound from Step H above as described in Preparative Example 70 Step A, one would obtain the title compound Step E If one were to treat the title compound from Step I above as described in Preparative Example 93 Step C, one would obtain the title compound.

Step F

If one were to treat the title compound from Step J above as described in Preparative Example 13 Step B, one would obtain the title compound.

Step G

If one were to treat the title compound from Step K above with diisobutylaluminium hydride in $CH_2Cl_2$ at −78° C., add 10% aq AcOH, extract with ether:hexane, wash with $H_2O$, sat. aq $NaHCO_3$, and brine, dry over $Na_2SO_4$, evaporate, purify the crude product through chromatography on silica gel, one would obtain the title compound.

Step H

If one were to treat the title compound from Step L above with 1.2 eq. commercially available methylmagnesium bromide in $Et_2O$ at room temperature, heat the mixture to reflux, add ice and half concentrated hydrochlorid acid, extract with $Et_2O$, wash the organic layer with $H_2O$, sat. aq $NaHCO_3$, and brine, dry over $Na_2SO_4$, evaporate, purify the crude product through chromatography on silica gel, one would obtain the title compound.

Step I

If one were to treat the title compound from Step M above with methylsulfonyl chloride and triethylamine in $CH_2Cl_2$ at 0° C., evaporate, add water and ethyl acetate to the residue, extract with ethyl acetate, wash the organic layer with $H_2O$, sat. aq $NaHCO_3$, and brine, dry over $Na_2SO_4$, evaporate and then the obtained intermediate with $NaN_3$ in DMA as described in Preparative Example 17 Step C, one would obtain the title compound.

Step J

If one were to treat the title compound from Step N above as described in Preparative Example 17 Step D, one would obtain the title compound.

Preparative Example 1452

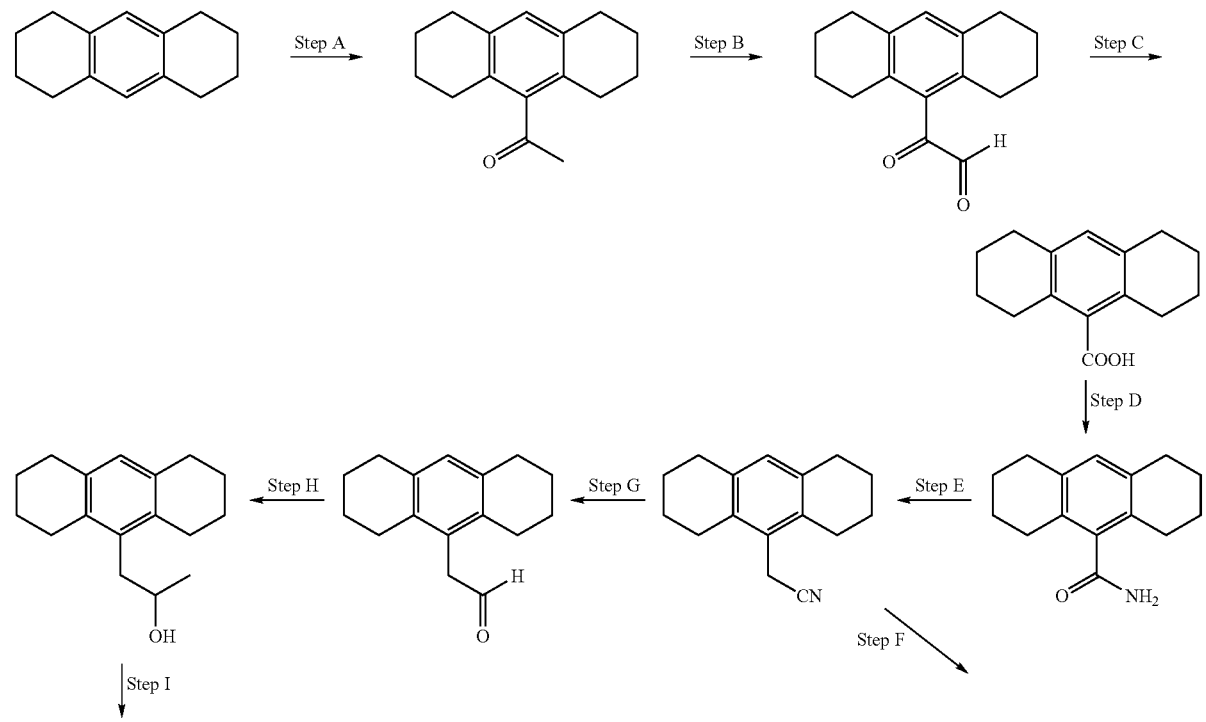

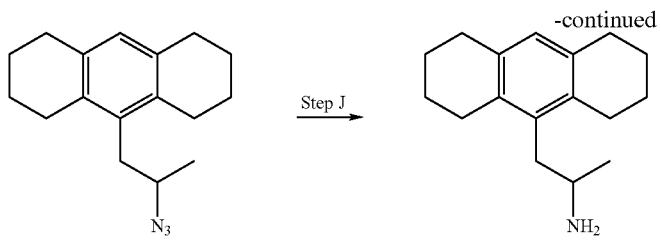 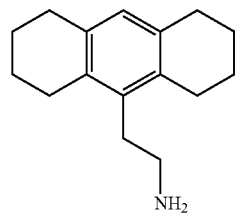

Step A

If one were to treat commercially available 1,2,3,4,5,6,7,8-octahydro-anthracene with 10 eq. of aluminium chloride by adding the compound to the reagent in tetrachloroethane at low temperature, add dropwise 2.0 eq. of acetic anhydride to the mixture, pour onto ice and hydrochloric acid and extract with an appropriate solvent, wash with water, evaporate, recrystallize from methanol, one would obtain the title compound.

Step B

If one were to treat the title compound from Step A above with selenium dioxide in water and dioxane and refluxed for 4 h, followed by removal of precipitated selenium one would obtain after recrystallization the title compound.

Step C

If one were to treat the title compound from Step B above with hydrogen peroxide and drop wise with 10% NaOH in ethanol at 80° C., followed by dilution with water, treatment with norite, filtration and acidifying with HCl, one would obtain after recrystallization the title compound.

Step D

If one were to treat the title compound from Step C above as described in Preparative Example 70 Step A, one would obtain the title compound Step E If one were to treat the title compound from Step D above as described in Preparative Example 93 Step C, one would obtain the title compound.

Step F

If one were to treat the title compound from Step E above as described in Preparative Example 13 Step B, one would obtain the title compound.

Step G

If one were to treat the title compound from Step F above with diisobutylaluminium hydride in $CH_2Cl_2$ at −78° C., add 10% aq AcOH, extract with ether:hexane, wash with $H_2O$, sat. aq $NaHCO_3$, and brine, dry over $Na_2SO_4$, evaporate, purify the crude product through chromatography on silica gel, one would obtain the title compound.

Step H

If one were to treat the title compound from Step G above with 1.2 eq. commercially available methylmagnesium bromide in $Et_2O$ at room temperature, heat the mixture to reflux, add ice and half concentrated hydrochlorid acid, extract with $Et_2O$, wash the organic layer with $H_2O$, sat. aq $NaHCO_3$, and brine, dry over $Na_2SO_4$, evaporate, purify the crude product through chromatography on silica gel, one would obtain the title compound.

Step I

If one were to treat the title compound from Step H above with methylsulfonyl chloride and triethylamine in $CH_2Cl_2$ at 0° C., evaporate, add water and ethyl acetate to the residue, extract with ethyl acetate, wash the organic layer with $H_2O$, sat. aq $NaHCO_3$, and brine, dry over $Na_2SO_4$, evaporate and then the obtained intermediate with $NaN_3$ in DMA as described in Preparative Example 17 Step C, one would obtain the title compound.

Step J

If one were to treat the title compound from Step I above as described in Preparative Example 17 Step D, one would obtain the title compound.

Preparative Example 1453

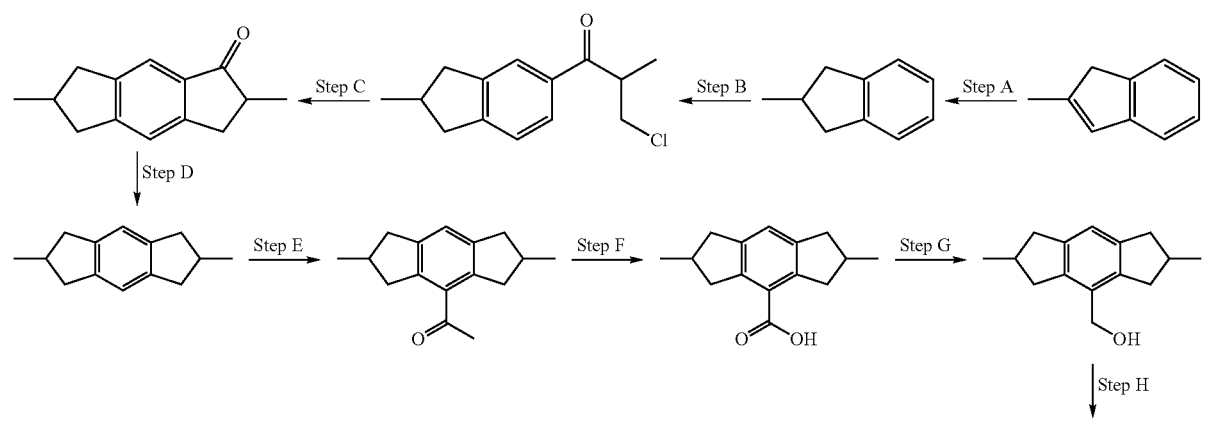

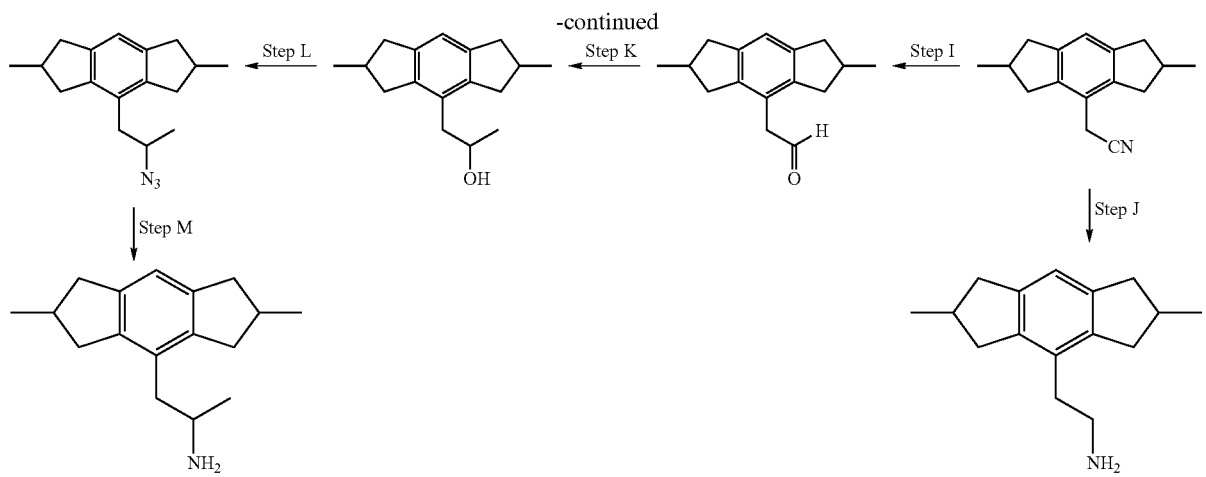

Step A

If one were to treat commercially available 2-methyl-1H-indene and with 0.01 eq of platinum oxide in tetrahydrofuran and hydrogenate at 20-30 psi for 10-15 h at room temperature, filter the mixture through a pad of Celite, purify the crude product through chromatography on silica gel, one would obtain the title compound.

Step B

If one were to treat the title compound from Step A above with 1.0 eq. of 3-chloro-2-methyl-propionyl chloride and 3.0 eq. of aluminum chloride in nitromethane at room temperature, decompose the mixture with ice and hydrochloric acid, dilute with water, filter, dissolve the solid in benzene and wash with dilute hydrochloric acid, evaporate, purify with a Soxhlet extractor, one would obtain the title compound.

Step C

If one were to treat the title compound from Step B above with concentrated sulphuric acid by adding the compound in small portions to the acid at low temperature, heat on the steam-bath, pour onto ice and extract with benzene and water, evaporate, distillate at reduced pressure, recrystallize from petroleum ether, sublimate, one would obtain the title compound.

Step D

If one were to treat the title compound from Step C above with amalgamated zinc, water, acetic acid, toluene, hydrochloric acid, separate the organic layer, evaporate, distillate at reduced pressure, recrystallize, one would obtain the title compound.

Step E

If one were to treat the title compound from Step D with 10 eq. of aluminium chloride by adding the compound to the reagent in tetrachloroethane at low temperature, add dropwise 2.0 eq. of acetic anhydride to the mixture, pour onto ice and hydrochloric acid and extract with an appropriate solvent, wash with water, evaporate, recrystallize from methanol, one would obtain the title compound.

Step F

If one were to treat the title compound from Step E with an aqueous solution of potassium hypochlorite prepared from bleaching powder in methanol, separate the precipitate formed by filtration, acidify the filtrate, separate the precipitate formed by filtration, recrystallize from methanol, one would obtain the title compound.

Step G

If one were to treat the title compound from Step F above as described in Preparative Example 70 Step A, one would obtain the title compound Step H If one were to treat the title compound from Step G above as described in Preparative Example 93 Step C, one would obtain the title compound.

Step I

If one were to treat the title compound from Step H above with diisobutylaluminium hydride in $CH_2Cl_2$ at $-78°$ C., add 10% aq AcOH, extract with ether:hexane, wash with $H_2O$, sat. aq $NaHCO_3$, and brine, dry over $Na_2SO_4$, evaporate, purify the crude product through chromatography on silica gel, one would obtain the title compound.

Step J

If one were to treat the title compound from Step H above as described in Preparative Example 13 Step B, one would obtain the title compound.

Step K

If one were to treat the title compound from Step I above with 1.2 eq. commercially available methylmagnesium bromide in $Et_2O$ at room temperature, heat the mixture to reflux, add ice and half concentrated hydrochlorid acid, extract with $Et_2O$, wash the organic layer with $H_2O$, sat. aq $NaHCO_3$, and brine, dry over $Na_2SO_4$, evaporate, purify the crude product through chromatography on silica gel, one would obtain the title compound.

Step L

If one were to treat the title compound from Step K above with methylsulfonyl chloride and triethylamine in $CH_2Cl_2$ at $0°$ C., evaporate, add water and ethyl acetate to the residue, extract with ethyl acetate, wash the organic layer with $H_2O$, sat. aq $NaHCO_3$, and brine, dry over $Na_2SO_4$, evaporate and then the obtained intermediate with $NaN_3$ in DMA as described in Preparative Example 17 Step C, one would obtain the title compound.

Step M

If one were to treat the title compound from Step L above as described in Preparative Example 17 Step D, one would obtain the title compound.

Preparative Example 1454

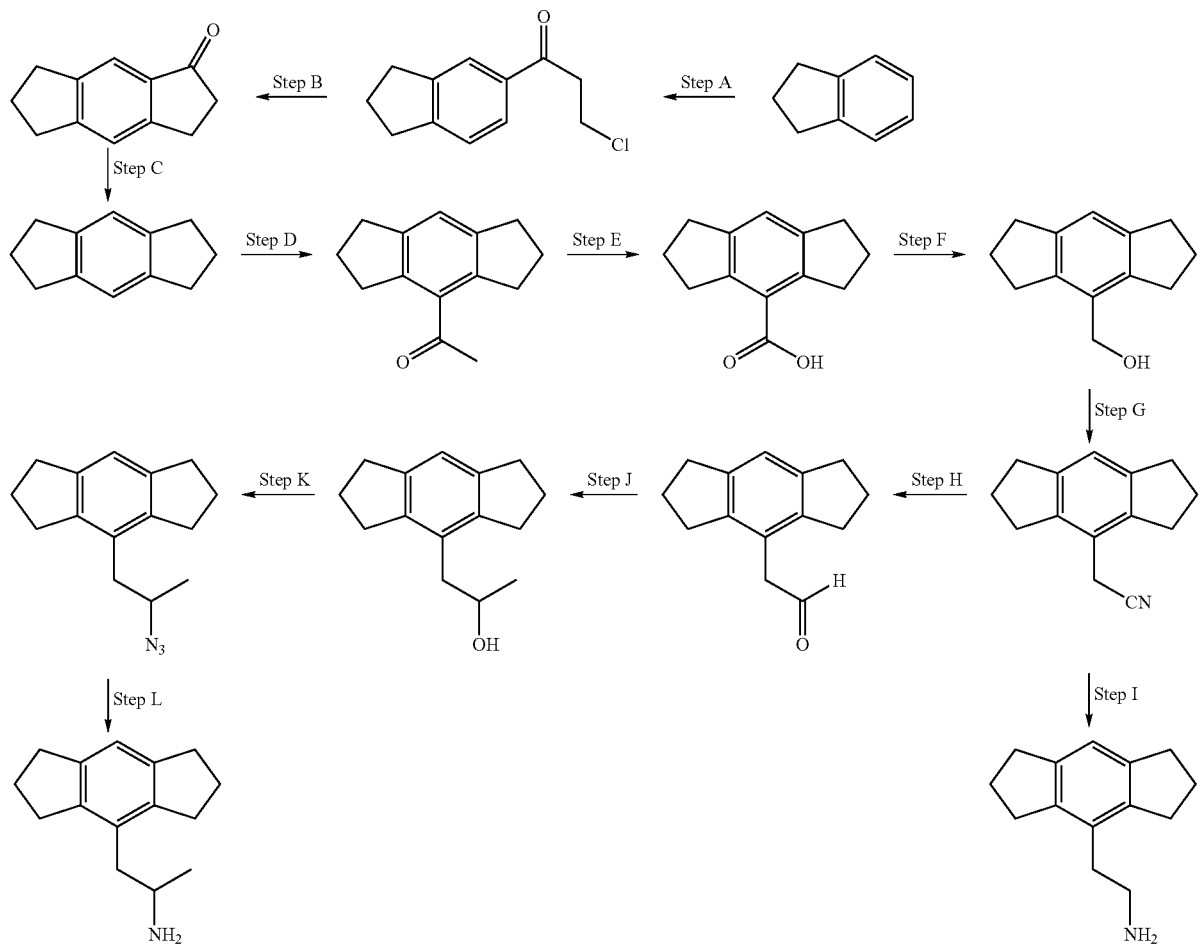

Step A

If one were to treat commercially available indane with 1.0 eq. of 3-chloro-propionyl chloride and 3.0 eq. of aluminum chloride in nitromethane at room temperature, decompose the mixture with ice and hydrochloric acid, dilute with water, filter, dissolve the solid in benzene and wash with dilute hydrochloric acid, evaporate, purify with a Soxhlet extractor, one would obtain the title compound.

Step B

If one were to treat the title compound from Step A above with concentrated sulphuric acid by adding the compound in small portions to the acid at low temperature, heat on the steam-bath, pour onto ice and extract with benzene and water, evaporate, distillate at reduced pressure, recrystallize from petroleum ether, sublimate, one would obtain the title compound.

Step C

If one were to treat the title compound from Step B above with amalgamated zinc, water, acetic acid, toluene, hydrochloric acid, separate the organic layer, evaporate, distillate at reduced pressure, recrystallize, one would obtain the title compound.

Step D

If one were to treat the title compound from Step D with 10 eq. of aluminium chloride by adding the compound to the reagent in tetrachloroethane at low temperature, add dropwise 2.0 eq. of acetic anhydride to the mixture, pour onto ice and hydrochloric acid and extract with an appropriate solvent, wash with water, evaporate, recrystallize from methanol, one would obtain the title compound.

Step E

If one were to treat the title compound from Step D with an aqueous solution of potassium hypochlorite prepared from bleaching powder in methanol, separate the precipitate formed by filtration, acidify the filtrate, separate the precipitate formed by filtration, recrystallize from methanol, one would obtain the title compound.

Step F

If one were to treat the title compound from Step E above as described in Preparative Example 70 Step A, one would obtain the title compound Step G If one were to treat the title compound from Step F above as described in Preparative Example 93 Step C, one would obtain the title compound.

Step H

If one were to treat the title compound from Step G above with diisobutylaluminium hydride in $CH_2Cl_2$ at −78° C., add 10% aq AcOH, extract with ether:hexane, wash with $H_2O$, sat. aq $NaHCO_3$, and brine, dry over $Na_2SO_4$, evaporate, purify the crude product through chromatography on silica gel, one would obtain the title compound.

Step I

If one were to treat the title compound from Step G above as described in Preparative Example 13 Step B, one would obtain the title compound.

Step J

If one were to treat the title compound from Step H above with 1.2 eq. commercially available methylmagnesium bromide in $Et_2O$ at room temperature, heat the mixture to reflux, add ice and half concentrated hydrochloride acid, extract with $Et_2O$, wash the organic layer with $H_2O$, sat. aq $NaHCO_3$, and brine, dry over $Na_2SO_4$, evaporate, purify the crude product through chromatography on silica gel, one would obtain the title compound.

Step K

If one were to treat the title compound from Step J above with methylsulfonyl chloride and triethylamine in $CH_2Cl_2$ at 0° C., evaporate, add water and ethyl acetate to the residue, extract with ethyl acetate, wash the organic layer with $H_2O$, sat. aq $NaHCO_3$, and brine, dry over $Na_2SO_4$, evaporate and then the obtained intermediate with $NaN_3$ in DMA as described in Preparative Example 17 Step C, one would obtain the title compound.

Step L

If one were to treat the title compound from Step K above as described in Preparative Example 17 Step D, one would obtain the title compound.

Examples 1455-1499 have been intentionally excluded.

Preparative Example 1500 lowed by aqueous workup and column chromatography the title compound.

Step C

If one were to treat the title compound from Step B above with methanesulfonyl chloride in pyridine at 0° C. for 24 h, one would obtain after pouring into an ice/water mixture followed by extraction with benzene and subsequently washing the organic phase with water, cold 5% sulphuric acid, water, 2% sodium bicarbonate solution, brine and finally evaporation to dryness, the methansulfonate intermediate. If one were to treat the methansulfonate intermediate with $LiAlH_4$ in THF and heat to reflux for 24 h, one would obtain after removal of the solvent, followed by aqueous workup the alcohol intermediate.

If one were to treat the alcohol intermediate with $CrO_3$ in pyridine at 40° C. for 9 h, one would obtain after pouring into water, followed by extraction with $CCl_4$ and subsequently drying the organic phase and evaporating to dryness, followed by column chromatography and crystallization the alkene intermediate. If one were to treat the alkene intermediate with Pd/C in ethanol at 10 bar $H_2$ and room temperature, separate the crude product from the reaction mixture and then the obtained intermediate with $CrO_3$ in aqueous acetic acid and water, neutralize the mixture, extract with $Et_2O$, recrystallize from $THF/CH_2Cl_2$, one would obtain the title compound.

Step D

If one were to treat the title compound from Step C above as described in Preparative Example 59 Step G, one would obtain the title compound.

Step E

If one were to treat the title compound from Step D above as described in Preparative Example 59 Step H, one would obtain the title compound.

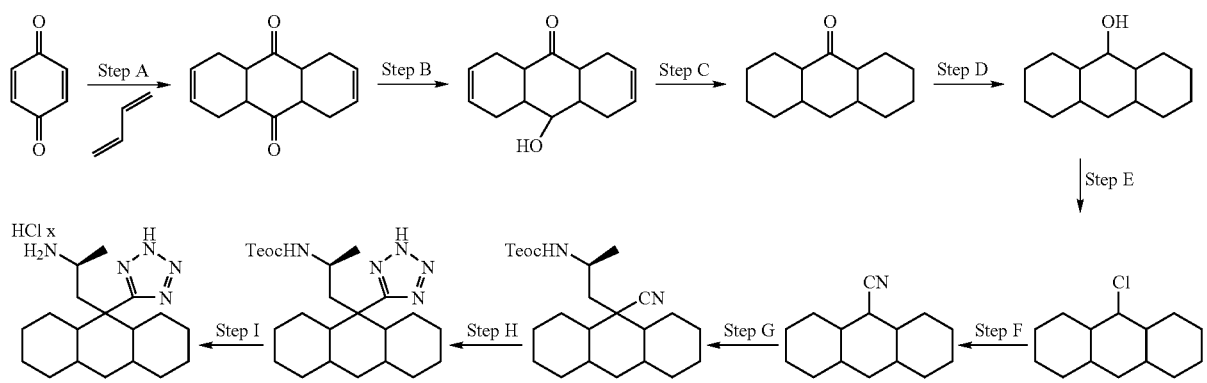

Step A

If one were to treat commercially available 1,4-benzoquinone with buta-1,3-diene in benzene at 100° C. in an autoclave, separate the precipitate, wash it with methanol, one would obtain the title compound.

Step B

If one were to treat the title compound from Step A above with $LiAlH_4$ in THF at rt for 15 min and then heat to reflux for 50 min, one would obtain after removal of the solvent, fol- Step F If one were to treat the title compound from Step E with NaCN in 90% ethanol under reflux, add water, extract with $CHCl_3$, wash the organic layer with 5% sulphuric acid, sat. aq $NaHCO_3$, water, brine, dry over $Na_2SO_4$, distillate, one would obtain the title compound.

Step G

If one were to treat the title compound from Step F above as described in Preparative Example 61 Step A, one would obtain the title compound.

Step H

If one were to treat the title compound from Step G above as described in Preparative Example 61 Step B, one would obtain the title compound.

Step I

If one were to treat the title compound from Step H above as described in Preparative Example 70 Step B, one would obtain the title compound.

Preparative Example 1501-1502

If one were to follow a similar procedure as that described in Preparative Example 1500, except using the sulfamidates in Step G, one would obtain the desired title compound as HCl salt.

| Preparative Example | Sulfamidate | Title compound |
|---|---|---|
| 1501 | 22 | 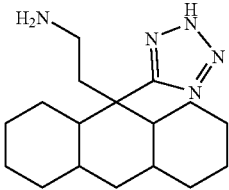 |
| 1502 | 24 | 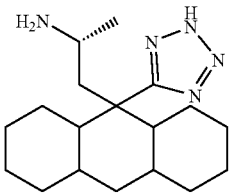 |

Example 1

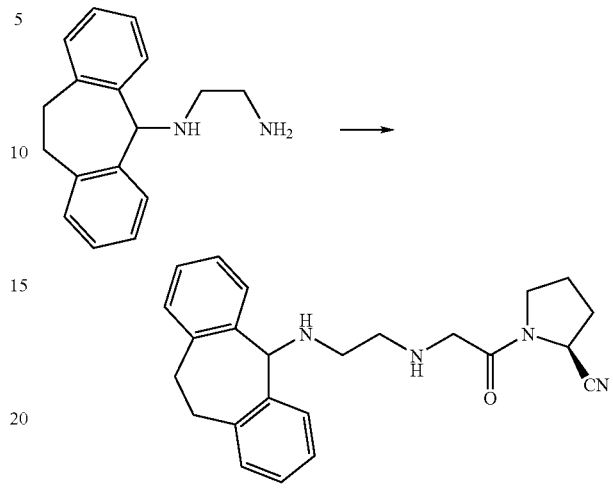

The title compound from Preparative Example 5 (378 mg) and 419 mg $K_2CO_3$ were suspended in 3 ml THF and cooled to 0° C. A solution of Preparative Example 1 (109 mg) in 1 ml THF was slowly added and the reaction mixture stirred at 0° C. for 2 h and then at rt overnight. The mixture was diluted with 30 ml EtOAc and 10 ml $H_2O$, the organic phase separated, dried over $MgSO_4$ and concentrated. The residue was purified by chromatography on silica ($CH_2Cl_2$/MeOH, 4:1) to afford the title compound (66 mg; 39%; MH$^+$=389).

Example 2-14

Following a similar procedure as that described in Example 1, except using the compounds from the Preparative Examples indicated in the Table below, the following compounds were prepared.

| Example | Compound Preparative Example | Compound Preparative Example | Product | 1. Yield 2. MH$^+$ |
|---|---|---|---|---|
| 2 | 1 | 6 | 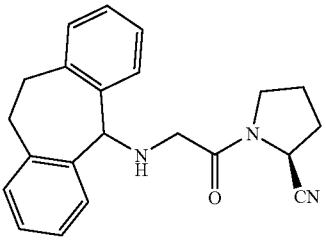 | 1. 17% 2. 346 |
| 3 | 1 | 7 | 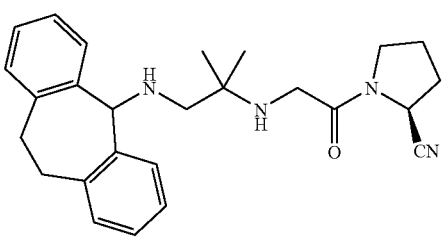 | 1. 8% 2. 417 |

|Example|Compound Preparative Example|Compound Preparative Example|Product|1. Yield 2. MH+|
|---|---|---|---|---|
|4|1|13| |1. 19% 2. 360|
|5|1|14 Step B| |1. 18% 2. 389|
|6|1|14| |1. 15% 2. 375|
|7|1|15 Step C| |1. 8% 2. 372|
|8|1|15| |1. 8% 2. 374|
|9|1|16| |1. 16% 2. 389|

| Example | Compound Preparative Example | Compound Preparative Example | Product | 1. Yield 2. MH+ |
|---------|------------------------------|------------------------------|---------|-----------------|
| 10 | 1 | 17 Step D | | 1. 7% 2. 390 |
| 11 | 1 | 17 | | 1. 8% 2. 372 |
| 12 | 1 | 10 | | 1. 16% 2. 429 |
| 13 | 1 | 11 | | 1. 19% 2. 415 |
| 14 | 1 | 12 | | 1. 19% 2. 401 |

Example 15

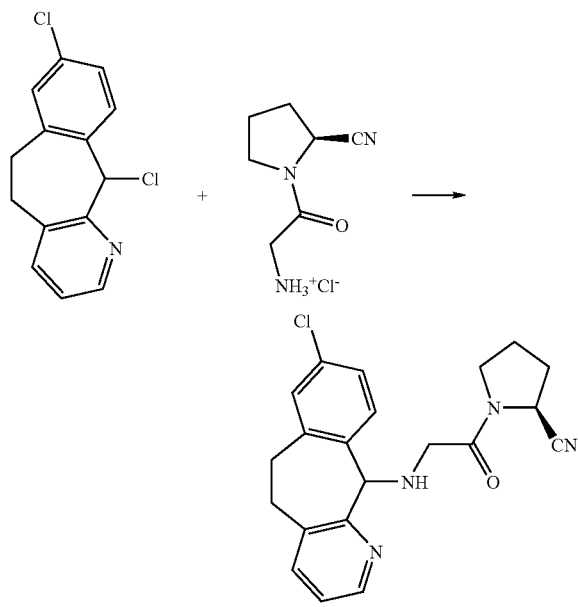

An aliquot of the title compound of Preparative Example 3 was taken and the solvent removed. The residue (67 mg) was dissolved in DMF (2 ml) and triethylamine (0.1 ml). The title compound from Preparative Example 90 (71 mg) was added and the mixture was stirred at 60° C. for 2 h. The solvent was removed and the residue was purified by preparative TLC (CHCl$_3$/MeOH (+0.1% Triethylamine), 4:1) to afford the title compound (12 mg; 13%; MH$^+$=381).

Example 16

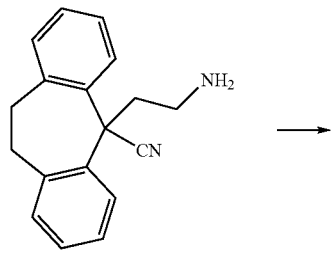

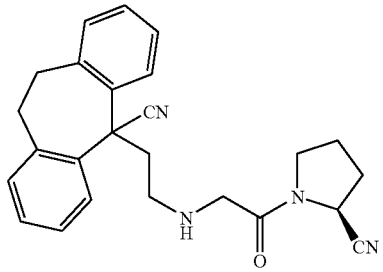

The title compound from Preparative Example 18 Step B (100 mg) and Preparative Example 2 (68 mg) were dissolved in 2 ml EtOH and 1 ml H$_2$O. The pH of the solution was adjusted to pH~6 by adding 0.1 M HCl-solution and the mixture was stirred at rt for 10 min. After the addition of NaCNBH$_3$ (24 mg) the pH was maintained at pH~6 by the addition of 0.1 M HCl and the mixture was stirred at rt overnigth. The mixture was diluted with 30 ml EtOAc and 15 ml sat. NaHCO$_3$/brine (1:1), the organic phase separated, dried over MgSO$_4$ and concentrated. The residue was purified by Prep TLC (CH$_2$Cl$_2$/MeOH, 95:5) to afford the title compound (25.9 mg; 17%; MH$^+$=399).

Example 17-47

Following a similar procedure as described in Example 16 by dissolving the amine in a EtOH/H$_2$O— or MeOH/H$_2$O-mixture and adjusting the pH to pH~6-8 by either 0.1 M HCl, 3 M NaOAc or 1 M NaOH, except using the compounds from the Preparative Examples indicated in the Table below, the following compounds were prepared. In case the reaction was not completed after 24 h as judged by HPLC, additional aldehyde from Preparative Example 2 or 89 and NaCNBH$_3$ were added, and the reaction was continued for another 1-3 days.

For the products obtained, the following purification methods were employed:
Method A: chromatography on silica using CH$_2$Cl$_2$/MeOH-mixtures; or
Method B: product was precipitated from the reaction mixture by adding 1 M HCl to pH 1-3 and the precipitate washed with MeOH; or
Method C: reaction mixture was concentrated to half its volume and the crude product purified by reverse phase HPLC (21.5×250 mm, Phenomenex, Luna C-18 (2), 5 µM; flow=15 ml/min or 10×250 mm, Phenomenex, Luna C-18 (2), 5 µM; flow=3 ml/min) using acetonitrile (solvent B; 0.1% formic acid) and H$_2$O (solvent A; 0.1% formic acid) as eluents and a suitable gradient, ramping solvent B from 0% to 100% over a period of 18 min.

| Example | Compound Preparative Example | Compound Preparative Example | Purification Method | Product | 1. Yield 2. MH$^+$ |
|---|---|---|---|---|---|
| 17 | 2 | 18 | A | 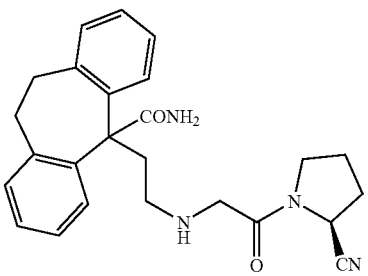 | 1. 17% 2. 417 |

-continued

| Example | Compound Preparative Example | Compound Preparative Example | Purification Method | Product | 1. Yield 2. MH⁺ |
|---|---|---|---|---|---|
| 18 | 2 | 47 | A | | 1. 41% 2. 431 |
| 19 | 2 | 48 | A | | 1. 18% 2. 431 |
| 20 | 2 | 8 | A | | 1. 25% 2. 424 |
| 21 | 2 | 9 | A | | 1. 18% 2. 390 |
| 22 | 2 | 49 | A | | 1. 21% 2. 478 |

-continued

| Example | Compound Preparative Example | Compound Preparative Example | Purification Method | Product | 1. Yield 2. MH+ |
|---|---|---|---|---|---|
| 23 | 2 | 50 | B | | 1. 30% 2. 442 |
| 24 | 2 | 51 | B | | 1. 5% 2. 478 |
| 25 | 2 | 87 | B | | 1. 46% 2. 510 |
| 26 | 2 | 110 | A | | 1. 15% 2. 414 |
| 27 | 2 | 70 | C | | 1. 36% 2. 542 |

-continued

| Example | Compound Preparative Example | Compound Preparative Example | Purification Method | Product | 1. Yield 2. MH+ |
|---|---|---|---|---|---|
| 28 | 2 | 72 | C | | 1. 14% 2. 570 |
| 29 | 2 | 71 | C | | 1. 38% 2. 598 |
| 30 | 2 | 73 | C | | 1. 21% 2. 598 |

-continued

| Example | Compound Preparative Example | Compound Preparative Example | Purification Method | Product | 1. Yield 2. MH+ |
|---|---|---|---|---|---|
| 31 | 2 | 74 | C | | 1. 8% 2. 626 |
| 32 | 2 | 75 | C | | 1. 58% 2. 622 |
| 33 | 2 | 76 | C | | 1. 9% 2. 682 |

-continued

| Example | Compound Preparative Example | Compound Preparative Example | Purification Method | Product | 1. Yield 2. MH+ |
|---|---|---|---|---|---|
| 34 | 2 | 56 | C | | 1. 11% 2. 528 |
| 35 | 2 | 77 | C | | 1. 7% 2. 556 |
| 36 | 2 | 78 | C | | 1. 10% 2. 584 |

-continued
| Example | Compound Preparative Example | Compound Preparative Example | Purification Method | Product | 1. Yield 2. MH+ |
|---|---|---|---|---|---|
| 37 | 2 | 79 | C | 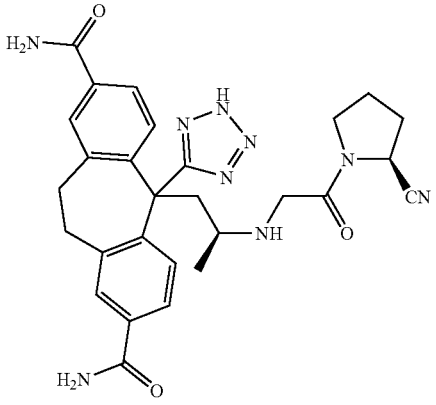 | 1. 12% 2. 556 |
| 38 | 2 | 80 | C | 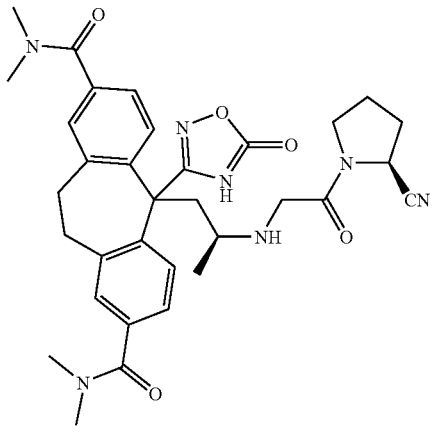 | 1. 43% 2. 614 |
| 39 | 2 | 81 | C | 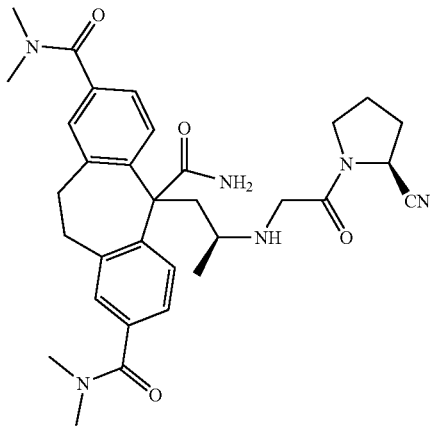 | 1. 2% 2. 573 |

-continued
| Example | Compound Preparative Example | Compound Preparative Example | Purification Method | Product | 1. Yield 2. MH+ |
|---|---|---|---|---|---|
| 40 | 2 | 82 | C | 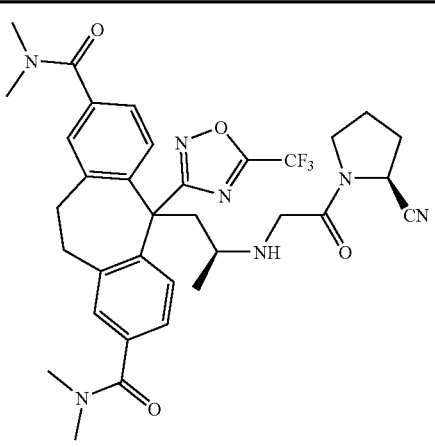 | 1. 26% 2. 666 |
| 41 | 2 | 83 | C | 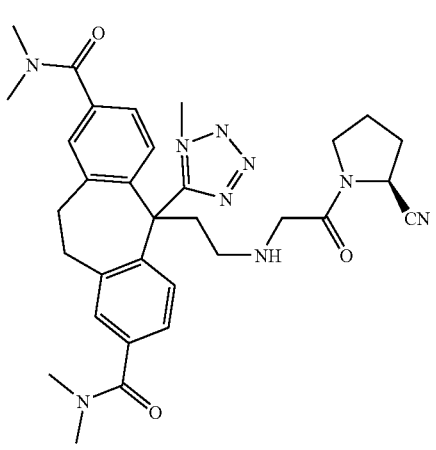 | 1. 12% 2. 542 |
| 42 | 2 | 84 | C | 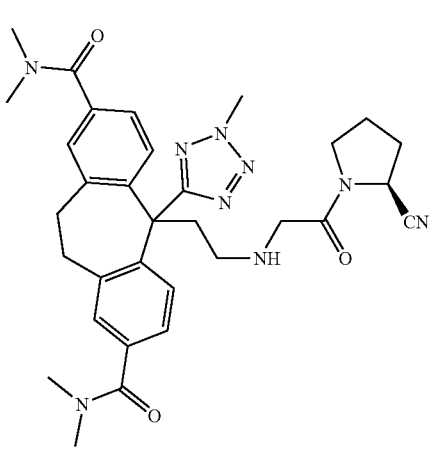 | 1. 10% 2. 542 |

-continued
| Example | Compound Preparative Example | Compound Preparative Example | Purification Method | Product | 1. Yield 2. MH+ |
|---|---|---|---|---|---|
| 43 | 2 | 85 | C | 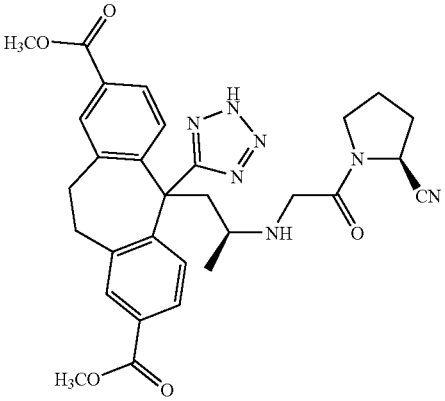 | 1. 60% 2. 572 |
| 44 | 2 | 86 | C | 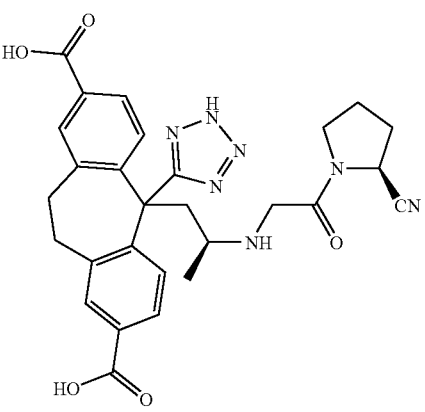 | 1. 28% 2. 544 |
| 45 | 2 | 52 | C | 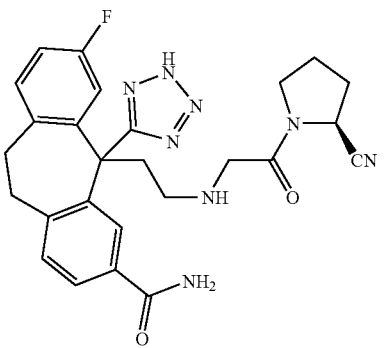 | 1. 14% 2. 503 |
| 46 | 2 | 88 | C | 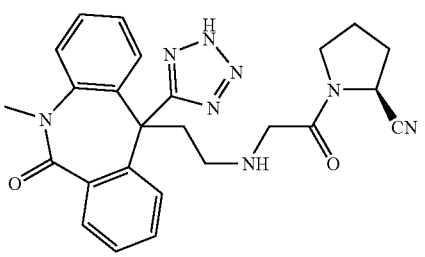 | 1. 2% 2. 471 |

-continued

| Example | Compound Preparative Example | Compound Preparative Example | Purification Method | Product | 1. Yield 2. MH+ |
|---|---|---|---|---|---|
| 47 | 89 | 56 | C | | 1. 9% 2. 540 |

Example 48

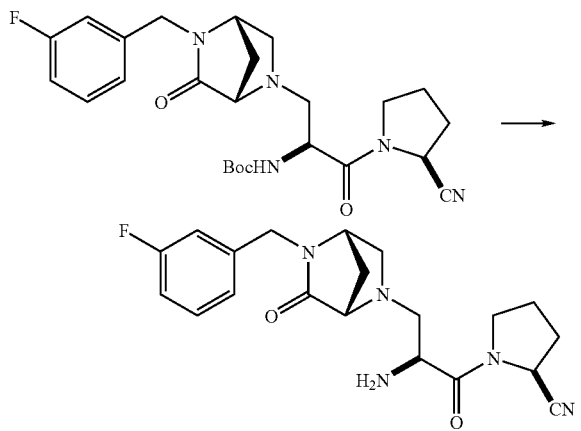

The title compound from Preparative Example 93 (16 mg) was dissolved in a mixture of $H_2O$ (3 ml) and a solution of 4 M HCl in dioxane (3 ml). After 20 h the reaction mixture was diluted with toluene. The organic layer was evaporated to afford the title compound (14 mg; 99%; MH+=386).

Example 49-64

Following a similar procedure as that described in Example 48, except using the compounds from the Preparative Examples indicated in the Table below, the following compound was prepared.

| Example | Compound Preparative Example | Product | 1. Yield 2. MH+ |
|---|---|---|---|
| 49 | 95 | | 1. 77% 2. 436 |

-continued
| Example | Compound Preparative Example | Product | 1. Yield 2. MH+ |
|---|---|---|---|
| 50 | 96 | 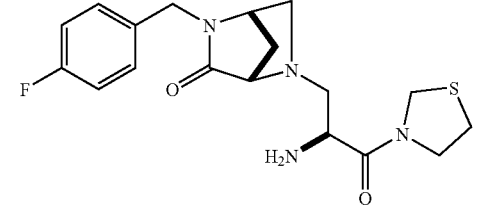 | 1. 92% 2. 393 |
| 51 | 97 | 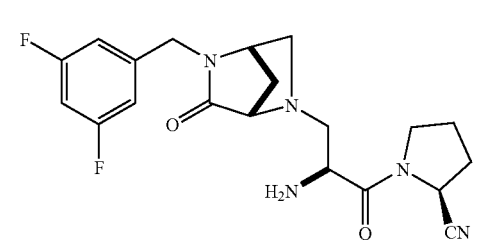 | 1. 89% 2. 404 |
| 52 | 98 | 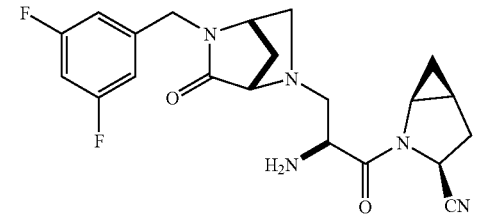 | 1. 96% 2. 416 |
| 53 | 99 |  | 1. 57% 2. 393 |
| 54 | 100 | 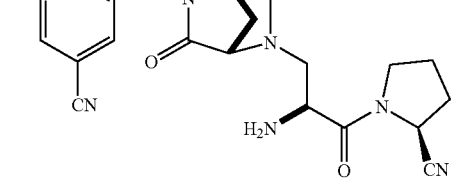 | 1. 95% 2. 404 |
| 55 | 101 | 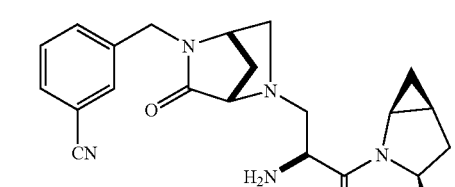 | 1. 93% 2. 393 |

-continued

| Example | Compound Preparative Example | Product | 1. Yield 2. MH+ |
|---|---|---|---|
| 56 | 102 | | 1. 98% 2. 400 |
| 57 | 108 | | 1. 96% 2. 400 |
| 58 | 103 | | 1. 95% 2. 412 |
| 59 | 104 | | 1. 95% 2. 414 |
| 60 | 105 | | 1. 92% 2. 411 |

457

-continued

| Example | Compound Preparative Example | Product | 1. Yield 2. MH+ |
|---|---|---|---|
| 61 | 106 | | 1. 95% 2. 411 |
| 62 | 107 | | 1. 81% 2. 426 |
| 63 | 109 | | 1. 85% 2. 412 |
| 64 | 94 | | 1. 95% 2. 398 |

Example 65

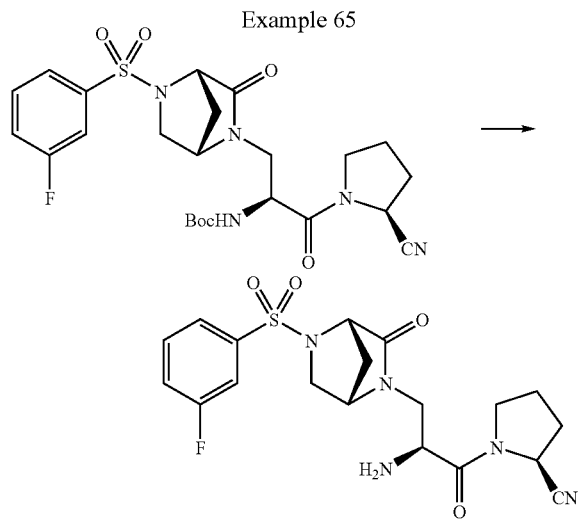

The title compound from Preparative Example 113 (13 mg) was treated with 4 M HCl in dioxane as described in Example 47 to afford the title compound (11.2 mg, 98%, MH+=436).

Example 66-75

Following a similar procedure as that described in Example 65, except using the compounds from the Preparative Examples indicated in the Table below, the following compounds were prepared.

| Example | Compound Preparative Example | Product | 1. Yield 2. MH+ |
|---|---|---|---|
| 66 | 114 | | 1. 100 2. 424 |
| 67 | 115 | | 1. 33 2. 424 |
| 68 | 116 | | 1. 40 2. 482 |
| 69 | 117 | | 1. 85 2. 388 |
| 70 | 118 | | 1. 96 2. 402 |

| Example | Compound Preparative Example | Product | 1. Yield 2. MH+ |
|---|---|---|---|
| 71 | 119 | | 1. 84 2. 384 |
| 72 | 122 | | 1. 30 2. 510 |
| 73 | 112 Step D | | 1. 50 2. 500 |
| 74 | 121 | | 1. 97 2. 475 |
| 75 | 120 | | 1. 100 2. 377 |

Example 76

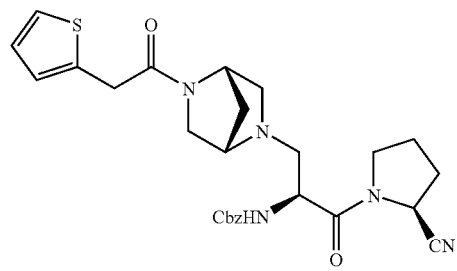

The title compound from Preparative Example 123 (27 mg) was dissolved in dichloromethane (2 ml) and trimethylsilyl iodine (21 mg) was added. The mixture was stirred for 1 h at room temperature. After removal of the solvent the residue was purified by preparative TLC to afford the desired compound (CHCl$_3$/MeOH, 4 mg, 20%, MH$^+$=388).

Examples 77-78

Following a similar procedure as that described in Example 76, except using the compounds from the Preparative Examples as indicated in the Table below, the following compounds were prepared.

| Example | Preparative Example | Product | 1. Yield 2. MH$^+$ |
|---|---|---|---|
| 77 | 124 | | 1. 10% 2. 422 |
| 78 | 125 | | 1. 11% 2. 358 |

Examples 79-99 have been intentionally excluded.

Example 100-184

If one were to follow the procedures outlined in Preparative Example 71 and Examples 28 or 29 but using the amines, carboxylic acids and aldehydes from the Preparative Examples as indicated in the Table below, one would obtain the indicated Product.

| Example # | Amine | Carboxylic Acid | Aldehyde | Product |
|---|---|---|---|---|
| 100 | | Prep Ex 62 | Prep Ex 2 | |

-continued

| Example # | Amine | Carboxylic Acid | Aldehyde | Product |
|---|---|---|---|---|
| 101 | pyrrolidine | Prep Ex 62 | Prep Ex 2 | |
| 102 | piperidine | Prep Ex 62 | Prep Ex 2 | |
| 103 | ethylamine | Prep Ex 62 | Prep Ex 2 | |
| 104 | isopropylamine | Prep Ex 62 | Prep Ex 2 | |

-continued
| Example # | Amine | Carboxylic Acid | Aldehyde | Product |
|---|---|---|---|---|
| 105 |  | Prep Ex 62 | Prep Ex 2 | 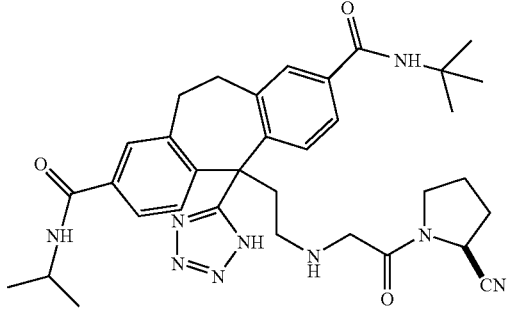 |
| 106 | 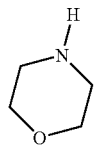 | Prep Ex 62 | Prep Ex 2 | 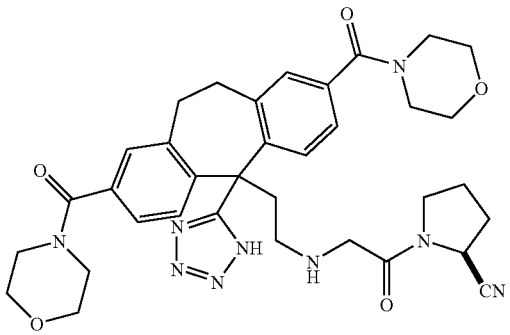 |
| 107 | 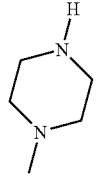 | Prep Ex 62 | Prep Ex 2 | 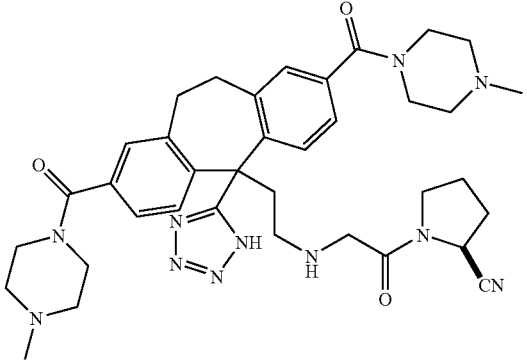 |
| 108 | 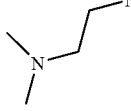 | Prep Ex 62 | Prep Ex 2 | 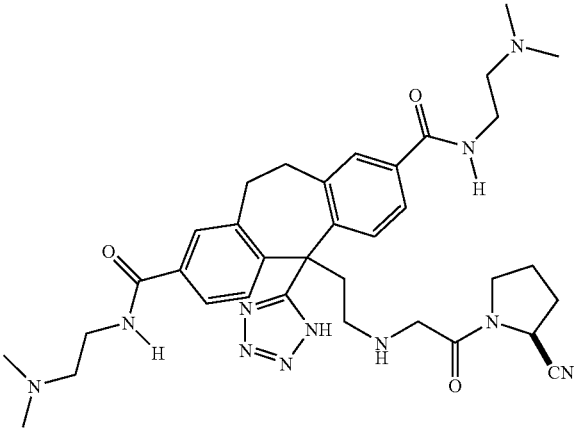 |

-continued

| Example # | Amine | Carboxylic Acid | Aldehyde | Product |
|---|---|---|---|---|
| 109 | HO-C(Me)₂-CH₂-NH₂ | Prep Ex 62 | Prep Ex 2 | (structure) |
| 110 | NH₃ | Prep Ex 55 | Prep Ex 2 | (structure) |
| 111 | MeNH₂ | Prep Ex 55 | Prep Ex 2 | (structure) |
| 112 | (Me)₂NH | Prep Ex 55 | Prep Ex 2 | (structure) |

-continued

| Example # | Amine | Carboxylic Acid | Aldehyde | Product |
|---|---|---|---|---|
| 113 | azetidine | Prep Ex 55 | Prep Ex 2 | |
| 114 | pyrrolidine | Prep Ex 55 | Prep Ex 2 | |
| 115 | piperidine | Prep Ex 55 | Prep Ex 2 | |
| 116 | H₂N-ethyl | Prep Ex 55 | Prep Ex 2 | |

-continued
| Example # | Amine | Carboxylic Acid | Aldehyde | Product |
|---|---|---|---|---|
| 117 | 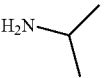 | Prep Ex 55 | Prep Ex 2 | 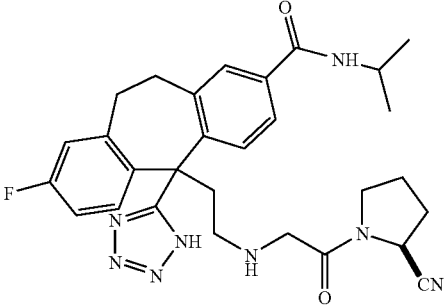 |
| 118 | 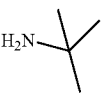 | Prep Ex 55 | Prep Ex 2 | 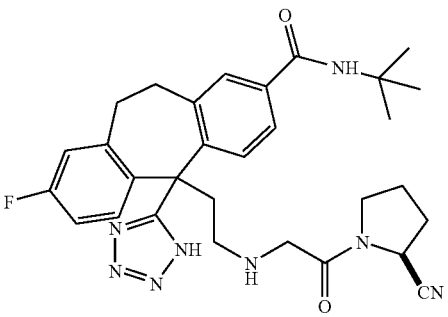 |
| 119 | 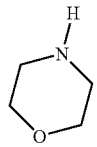 | Prep Ex 55 | Prep Ex 2 | 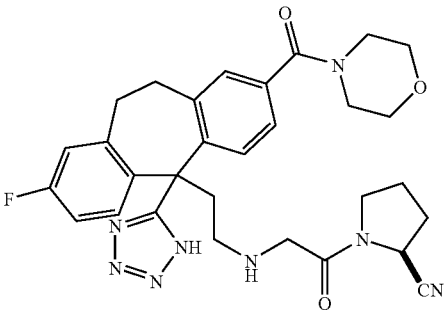 |
| 120 | 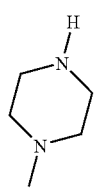 | Prep Ex 55 | Prep Ex 2 | 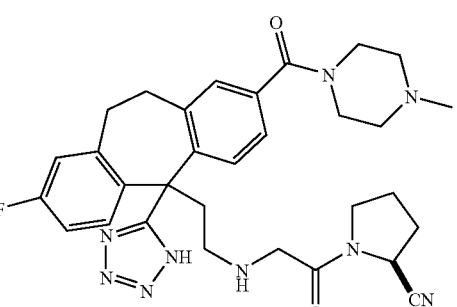 |

-continued

| Example # | Amine | Carboxylic Acid | Aldehyde | Product |
|---|---|---|---|---|
| 121 | (CH3)2N-CH2CH2-NH2 | Prep Ex 55 | Prep Ex 2 | |
| 122 | HO-C(CH3)2-CH2-NH2 | Prep Ex 55 | Prep Ex 2 | |
| 123 | azetidine | Prep Ex 65 | Prep Ex 2 | |
| 124 | pyrrolidine | Prep Ex 65 | Prep Ex 2 | |

-continued

| Example # | Amine | Carboxylic Acid | Aldehyde | Product |
|---|---|---|---|---|
| 125 | piperidine (NH) | Prep Ex 65 | Prep Ex 2 | (structure) |
| 126 | H₂N-iPr | Prep Ex 65 | Prep Ex 2 | (structure) |
| 127 | H₂N-tBu | Prep Ex 65 | Prep Ex 2 | (structure) |
| 128 | morpholine (NH) | Prep Ex 65 | Prep Ex 2 | (structure) |

-continued

| Example # | Amine | Carboxylic Acid | Aldehyde | Product |
|---|---|---|---|---|
| 129 | (1-methylpiperazine) | Prep Ex 65 | Prep Ex 2 | |
| 130 | (N,N-dimethylethylenediamine) | Prep Ex 65 | Prep Ex 2 | |
| 131 | (1-amino-2-methyl-2-propanol) | Prep Ex 65 | Prep Ex 2 | |
| 132 | (tert-butylamine) | Prep Ex 61 | Prep Ex 2 | |

-continued
| Example # | Amine | Carboxylic Acid | Aldehyde | Product |
|---|---|---|---|---|
| 133 | 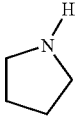 | Prep Ex 61 | Prep Ex 2 | 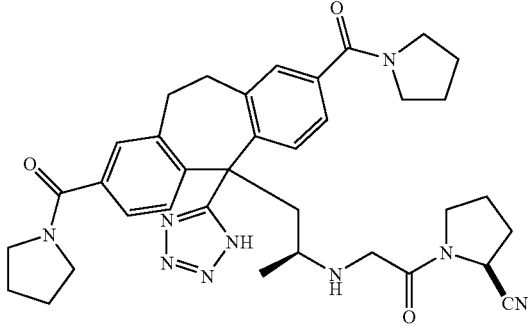 |
| 134 | 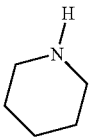 | Prep Ex 61 | Prep Ex 2 | 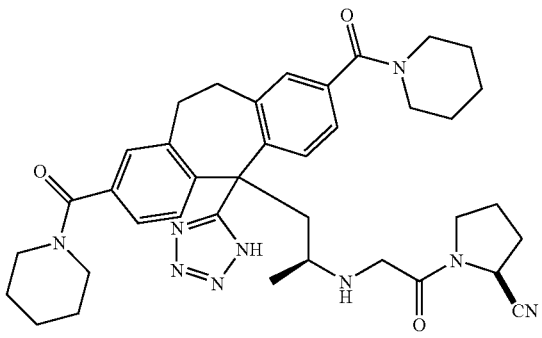 |
| 135 | 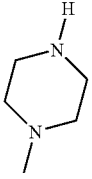 | Prep Ex 61 | Prep Ex 2 | 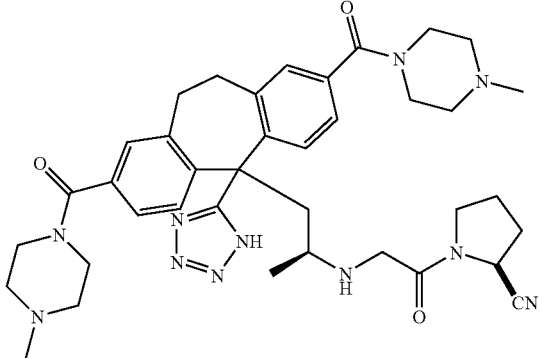 |
| 136 | 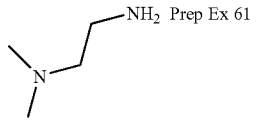 | Prep Ex 61 | Prep Ex 2 | 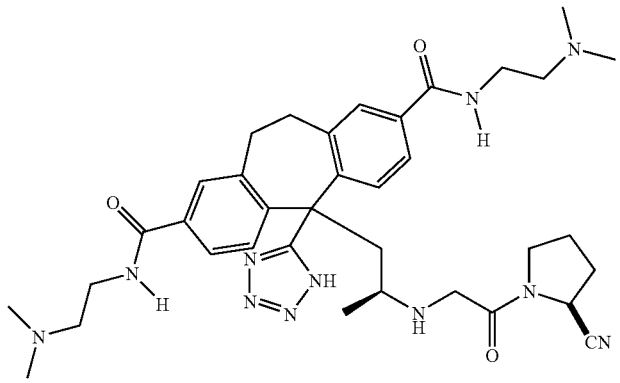 |

-continued
| Example # | Amine | Carboxylic Acid | Aldehyde | Product |
|---|---|---|---|---|
| 137 | 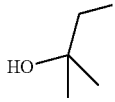 | Prep Ex 61 | Prep Ex 2 | 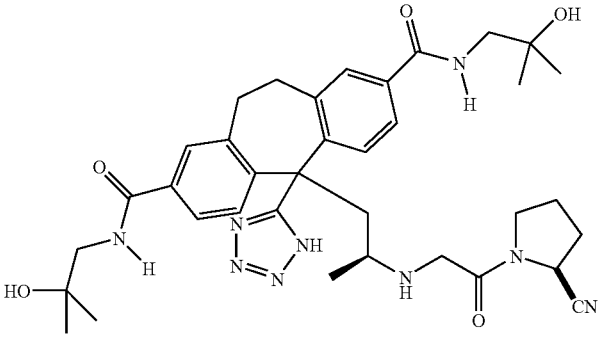 |
| 138 | MeNH$_2$ | Prep Ex 62 | Prep Ex 89 | 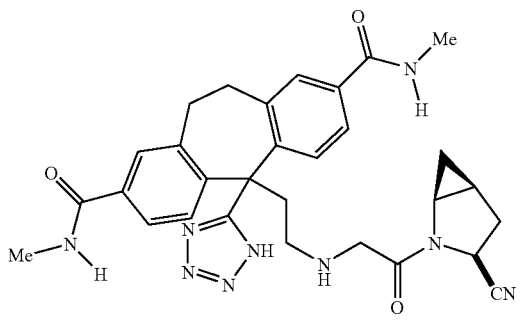 |
| 139 | (Me)$_2$NH | Prep Ex 62 | Prep Ex 89 | 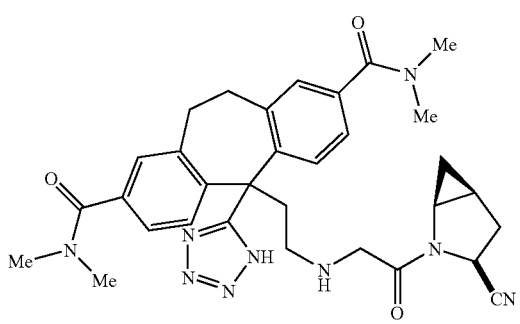 |
| 140 | 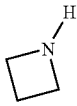 | Prep Ex 62 | Prep Ex 89 | 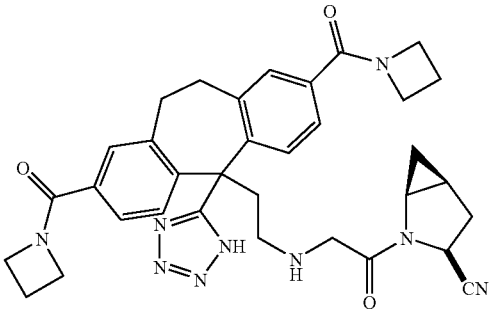 |

-continued

| Example # | Amine | Carboxylic Acid | Aldehyde | Product |
|---|---|---|---|---|
| 141 | pyrrolidine | Prep Ex 62 | Prep Ex 89 | |
| 142 | piperidine | Prep Ex 62 | Prep Ex 89 | |
| 143 | ethylamine | Prep Ex 62 | Prep Ex 89 | |
| 144 | isopropylamine | Prep Ex 62 | Prep Ex 89 | |

-continued
| Example # | Amine | Carboxylic Acid | Aldehyde | Product |
|---|---|---|---|---|
| 145 |  | Prep Ex 62 | Prep Ex 89 | 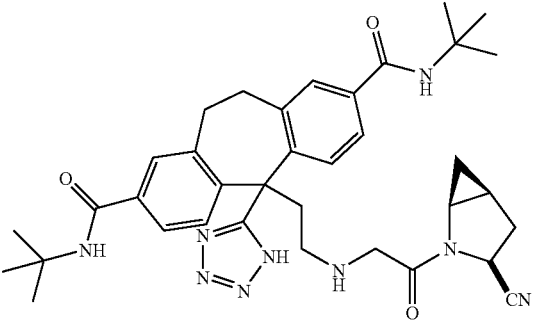 |
| 146 | 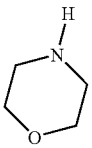 | Prep Ex 62 | Prep Ex 89 | 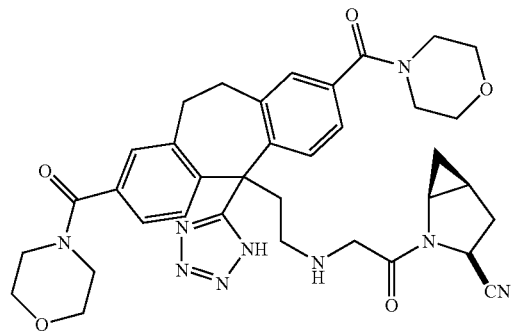 |
| 147 | 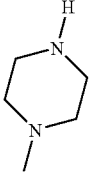 | Prep Ex 62 | Prep Ex 89 | 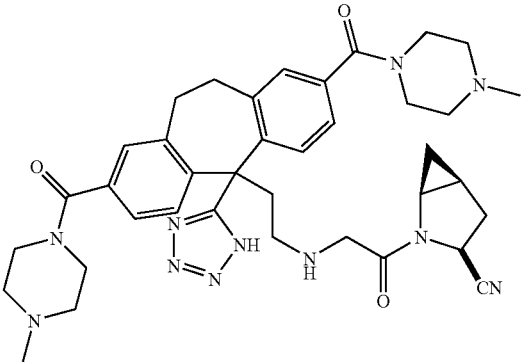 |
| 148 |  | Prep Ex 62 | Prep Ex 89 | 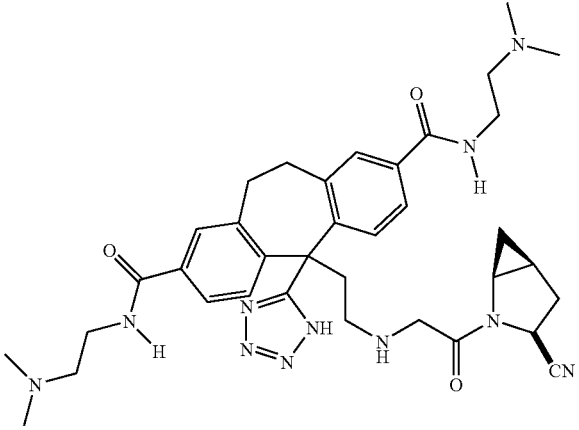 |

-continued
| Example # | Amine | Carboxylic Acid | Aldehyde | Product |
|---|---|---|---|---|
| 149 | ![HOCH2C(CH3)2CH2NH2] | Prep Ex 62 | Prep Ex 89 | 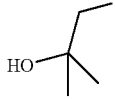 |
| 150 | NH3 | Prep Ex 55 | Prep Ex 89 | 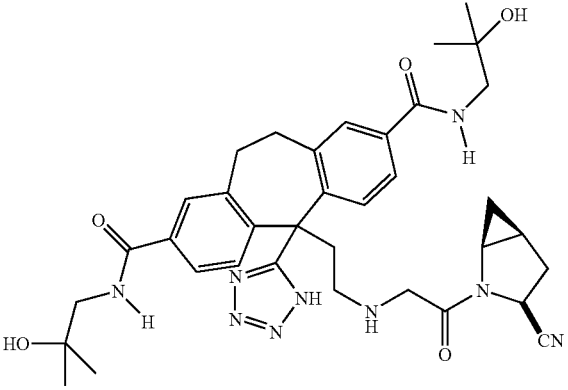 |
| 151 | MeNH2 | Prep Ex 55 | Prep Ex 89 |  |
| 152 | (Me)2NH | Prep Ex 55 | Prep Ex 89 |  |

-continued

| Example # | Amine | Carboxylic Acid | Aldehyde | Product |
|---|---|---|---|---|
| 153 | azetidine | Prep Ex 55 | Prep Ex 89 | |
| 154 | pyrrolidine | Prep Ex 55 | Prep Ex 89 | |
| 155 | piperidine | Prep Ex 55 | Prep Ex 89 | |
| 156 | ethylamine | Prep Ex 55 | Prep Ex 89 | |

-continued

| Example # | Amine | Carboxylic Acid | Aldehyde | Product |
|---|---|---|---|---|
| 157 | H₂N-iPr | Prep Ex 55 | Prep Ex 89 | |
| 158 | H₂N-tBu | Prep Ex 55 | Prep Ex 89 | |
| 159 | morpholine | Prep Ex 55 | Prep Ex 89 | |
| 160 | N-methylpiperazine | Prep Ex 55 | Prep Ex 89 | |

-continued

| Example # | Amine | Carboxylic Acid | Aldehyde | Product |
|---|---|---|---|---|
| 161 | (CH3)2N-CH2CH2-NH2 | Prep Ex 55 | Prep Ex 89 | |
| 162 | HO-C(CH3)2-CH2-NH2 | Prep Ex 55 | Prep Ex 89 | |
| 163 | azetidine | Prep Ex 65 | Prep Ex 89 | |
| 164 | pyrrolidine | Prep Ex 65 | Prep Ex 89 | |

-continued

| Example # | Amine | Carboxylic Acid | Aldehyde | Product |
|---|---|---|---|---|
| 165 | piperidine | Prep Ex 65 | Prep Ex 89 | |
| 166 | isopropylamine | Prep Ex 65 | Prep Ex 89 | |
| 167 | tert-butylamine | Prep Ex 65 | Prep Ex 89 | |
| 168 | morpholine | Prep Ex 65 | Prep Ex 89 | |

-continued

| Example # | Amine | Carboxylic Acid | Aldehyde | Product |
|---|---|---|---|---|
| 169 | 1-methylpiperazine | Prep Ex 65 | Prep Ex 89 | |
| 170 | N,N-dimethylethylenediamine | Prep Ex 65 | Prep Ex 89 | |
| 171 | 1-amino-2-methyl-2-propanol | Prep Ex 65 | Prep Ex 89 | |
| 172 | NH₃ | Prep Ex 61 | Prep Ex 89 | |

-continued

| Example # | Amine | Carboxylic Acid | Aldehyde | Product |
|---|---|---|---|---|
| 173 | MeNH₂ | Prep Ex 61 | Prep Ex 89 | |
| 174 | (Me)₂NH | Prep Ex 61 | Prep Ex 89 | |
| 175 | azetidine | Prep Ex 61 | Prep Ex 89 | |
| 176 | pyrrolidine | Prep Ex 61 | Prep Ex 89 | |

-continued

| Example # | Amine | Carboxylic Acid | Aldehyde | Product |
|---|---|---|---|---|
| 177 | piperidine | Prep Ex 61 | Prep Ex 89 | |
| 178 | H₂N-Et | Prep Ex 61 | Prep Ex 89 | |
| 179 | H₂N-iPr | Prep Ex 61 | Prep Ex 89 | |
| 180 | H₂N-tBu | Prep Ex 61 | Prep Ex 89 | |

-continued

| Example # | Amine | Carboxylic Acid | Aldehyde | Product |
|---|---|---|---|---|
| 181 | morpholine | Prep Ex 61 | Prep Ex 89 | |
| 182 | 1-methylpiperazine | Prep Ex 61 | Prep Ex 89 | |
| 183 | N,N-dimethylethylenediamine | Prep Ex 61 | Prep Ex 89 | |
| 184 | 1-amino-2-methyl-2-propanol | Prep Ex 61 | Prep Ex 89 | |

Examples 185-199 have been intentionally excluded.

Example 200-389
If one were to follow the procedures outlined in Examples 28 or 29 except using the compounds from the Preparative Examples as indicated in the Table below, one would obtain the indicated Product.
| Example | Preparative Example | Preparative Example | Product |
|---|---|---|---|
| 200 | 200 | 2 | 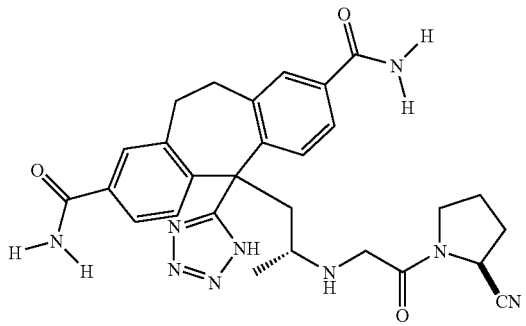 |
| 201 | 201 | 2 | 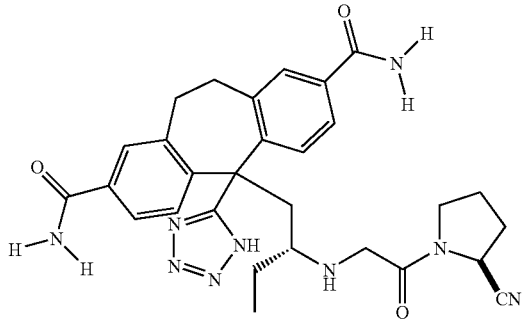 |
| 202 | 202 | 2 | 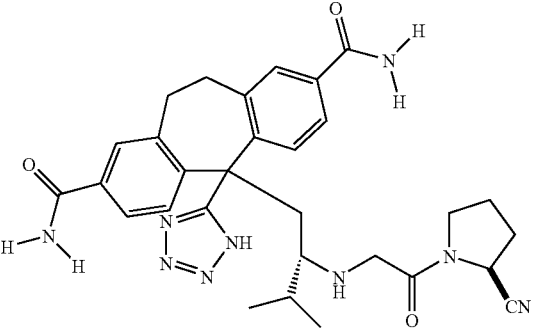 |
| 203 | 203 | 2 | 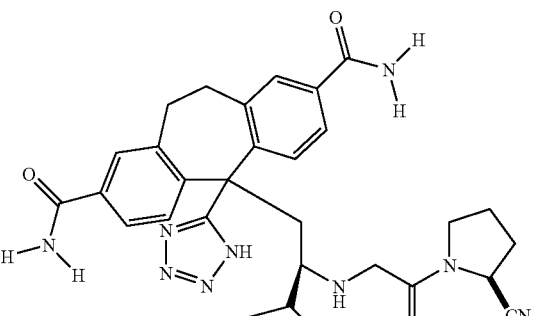 |

-continued
| Example | Preparative Example | Preparative Example | Product |
|---|---|---|---|
| 204 | 204 | 2 | 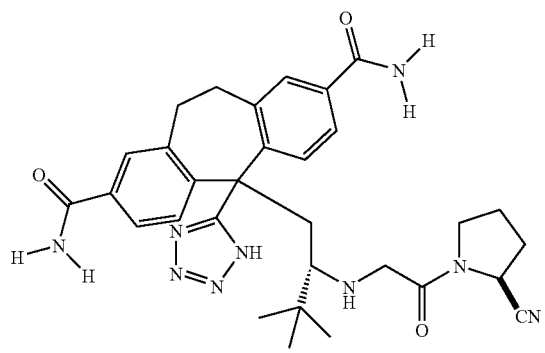 |
| 205 | 205 | 2 | 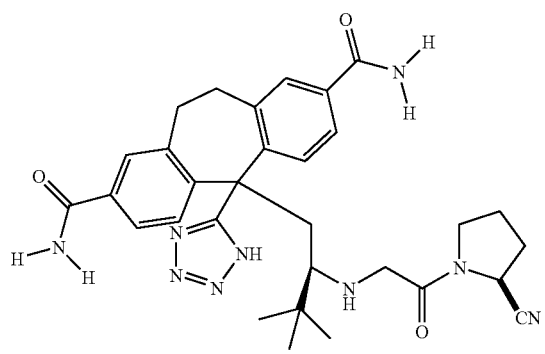 |
| 206 | 206 | 2 | 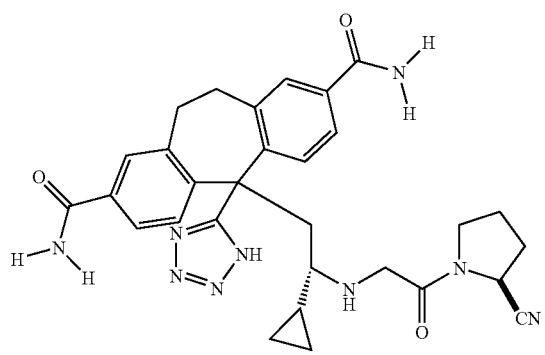 |
| 207 | 207 | 2 | 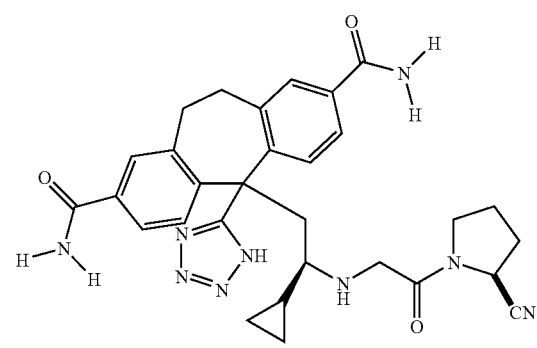 |

-continued
| Example | Preparative Example | Preparative Example | Product |
|---------|---------------------|---------------------|---------|
| 208 | 208 | 2 | 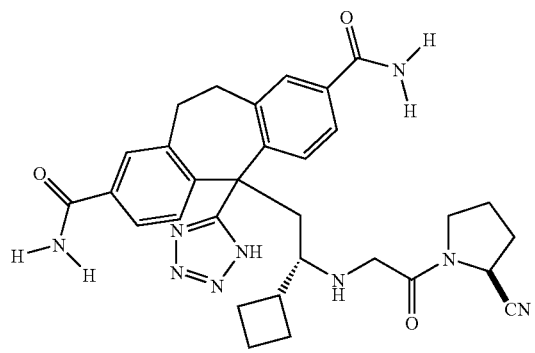 |
| 209 | 209 | 2 | 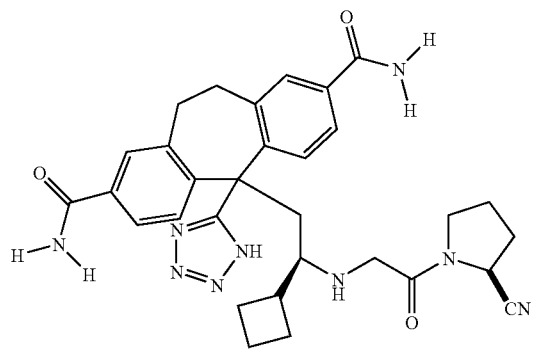 |
| 210 | 210 | 2 | 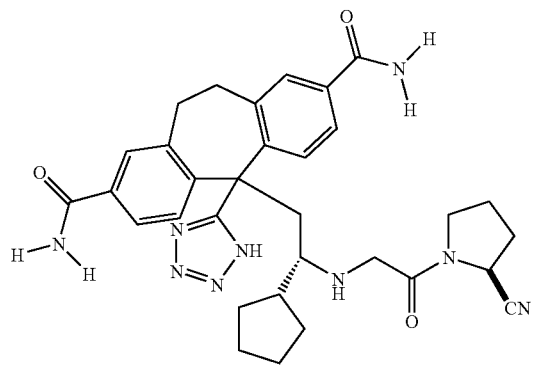 |
| 211 | 211 | 2 | 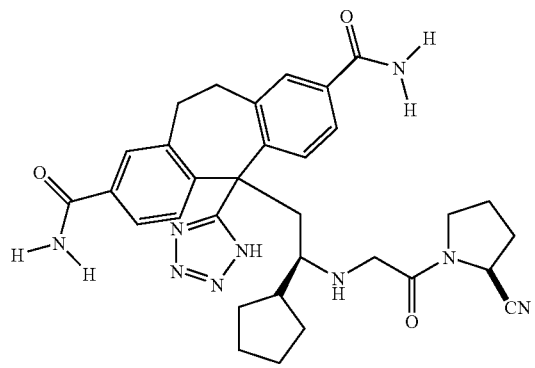 |

| Example | Preparative Example | Preparative Example | Product |
|---|---|---|---|
| 212 | 212 | 2 | 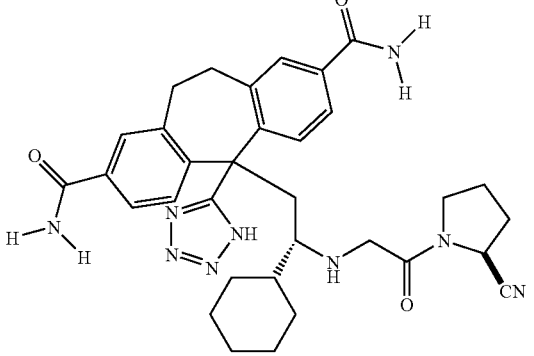 |
| 213 | 213 | 2 | 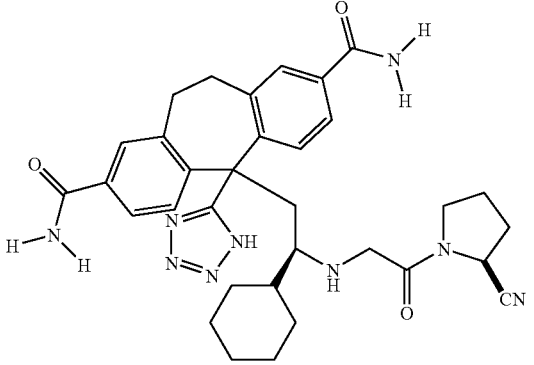 |
| 214 | 214 | 2 | 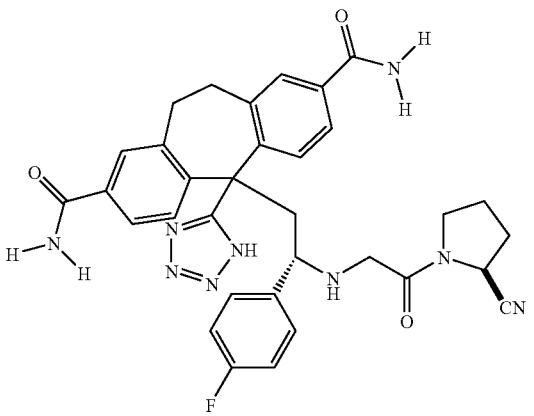 |
| 215 | 215 | 2 | 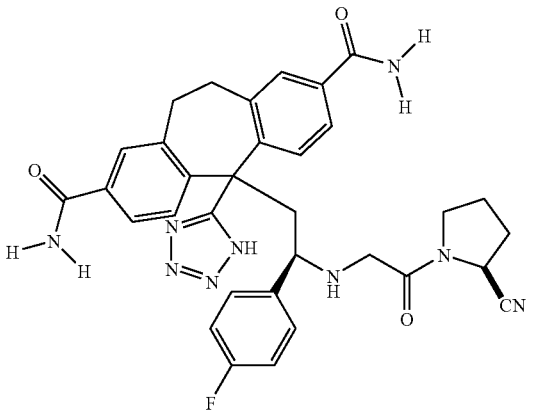 |

-continued

| Example | Preparative Example | Preparative Example | Product |
|---|---|---|---|
| 216 | 216 | 2 | |
| 217 | 217 | 2 | |
| 218 | 218 | 2 | |
| 219 | 219 | 2 | |

| Example | Preparative Example | Preparative Example | Product |
|---|---|---|---|
| 220 | 220 | 2 | 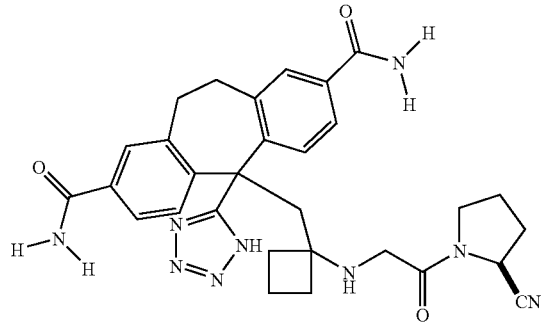 |
| 221 | 221 | 2 | 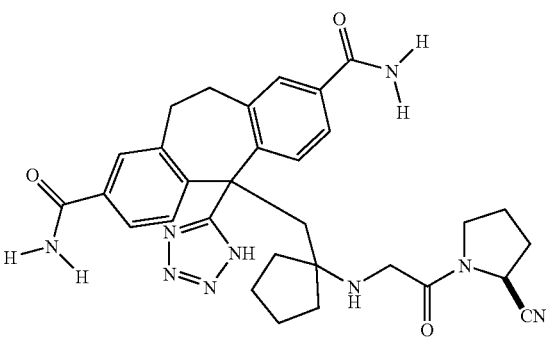 |
| 222 | 222 | 2 | 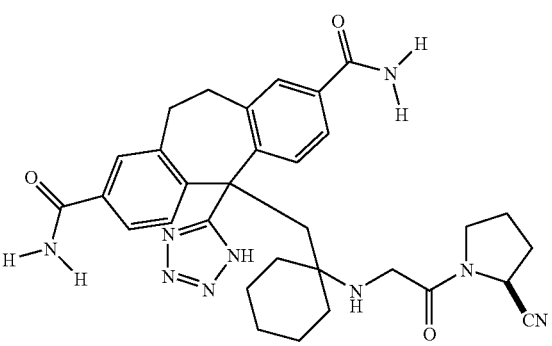 |
| 223 | 223 | 2 | 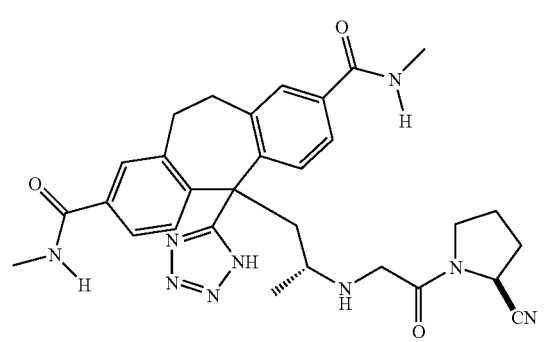 |

-continued
| Example | Preparative Example | Preparative Example | Product |
|---|---|---|---|
| 224 | 224 | 2 | 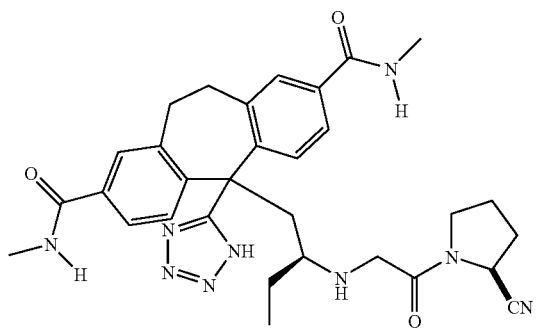 |
| 225 | 225 | 2 | 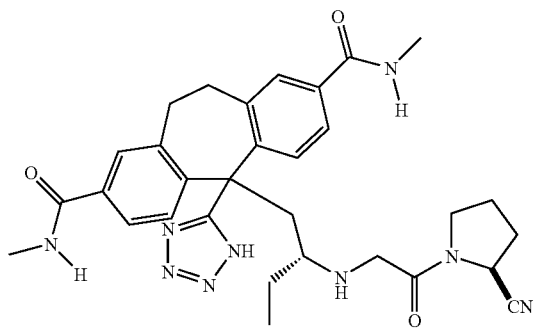 |
| 226 | 226 | 2 | 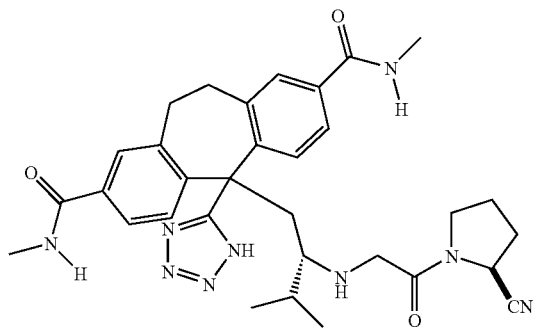 |
| 227 | 227 | 2 | 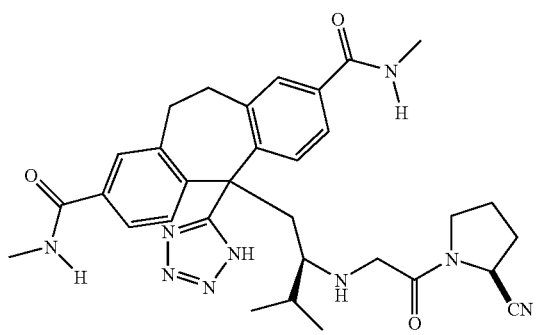 |

-continued
| Example | Preparative Example | Preparative Example | Product |
|---|---|---|---|
| 228 | 228 | 2 | 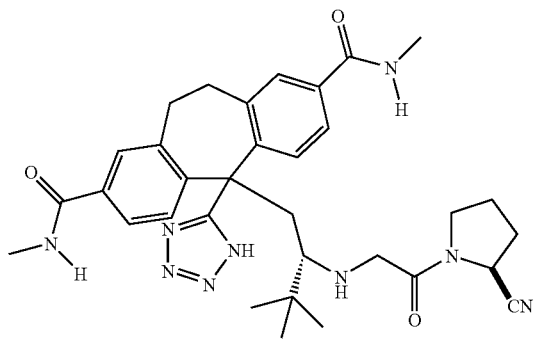 |
| 229 | 229 | 2 | 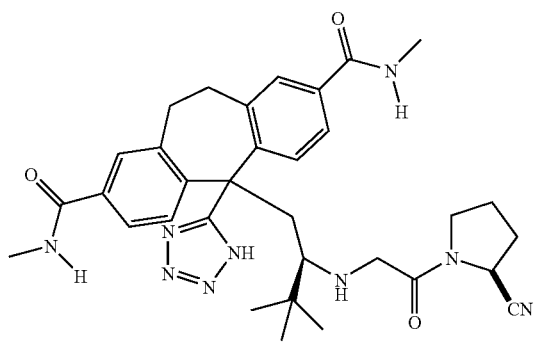 |
| 230 | 230 | 2 | 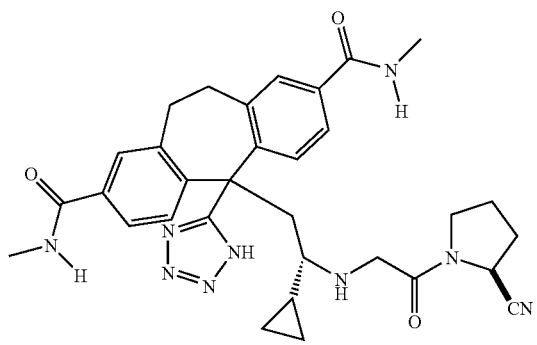 |
| 231 | 231 | 2 | 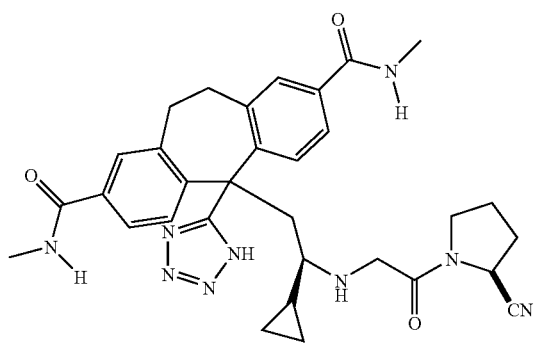 |

-continued
| Example | Preparative Example | Preparative Example | Product |
|---|---|---|---|
| 232 | 232 | 2 | 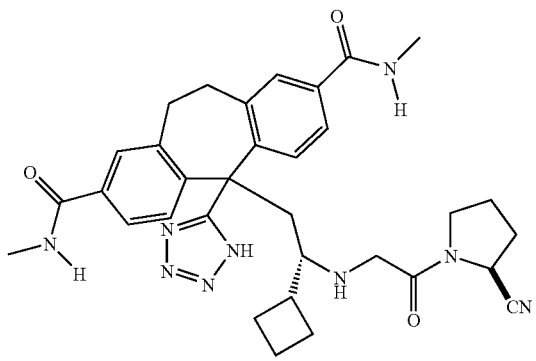 |
| 233 | 233 | 2 | 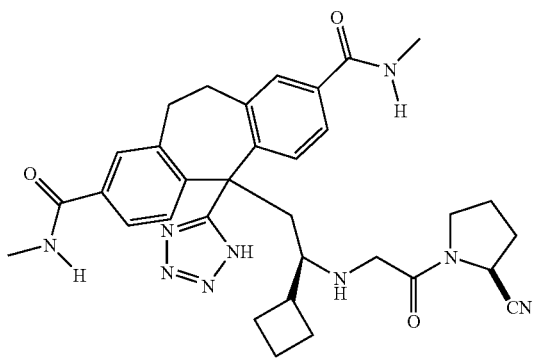 |
| 234 | 234 | 2 | 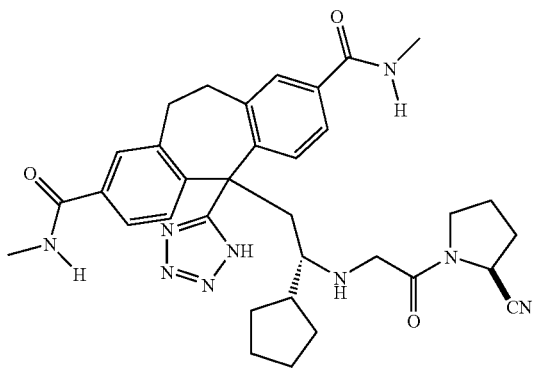 |
| 235 | 235 | 2 | 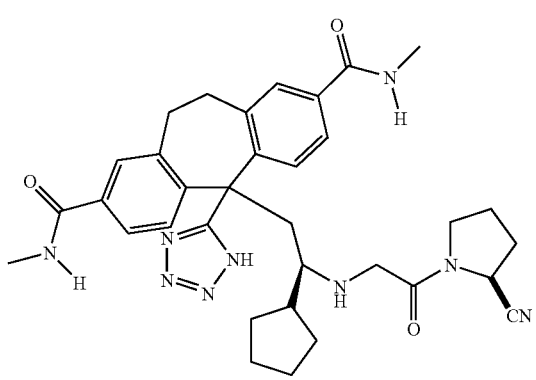 |

| Example | Preparative Example | Preparative Example | Product |
|---|---|---|---|
| 236 | 236 | 2 | 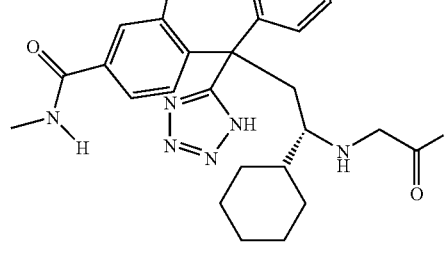 |
| 237 | 237 | 2 | 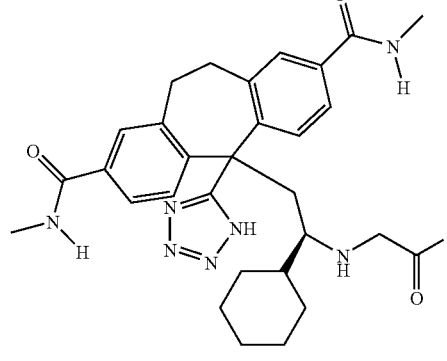 |
| 238 | 238 | 2 | 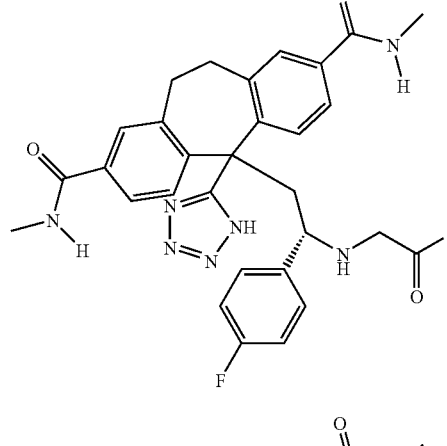 |
| 239 | 239 | 2 | 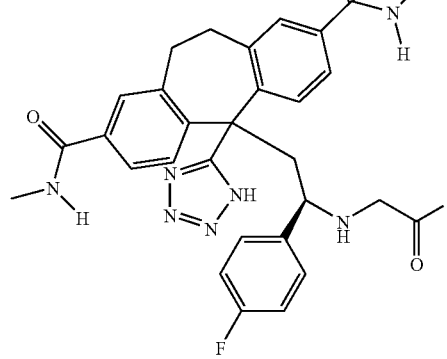 |

| Example | Preparative Example | Preparative Example | Product |
|---|---|---|---|
| 240 | 240 | 2 | 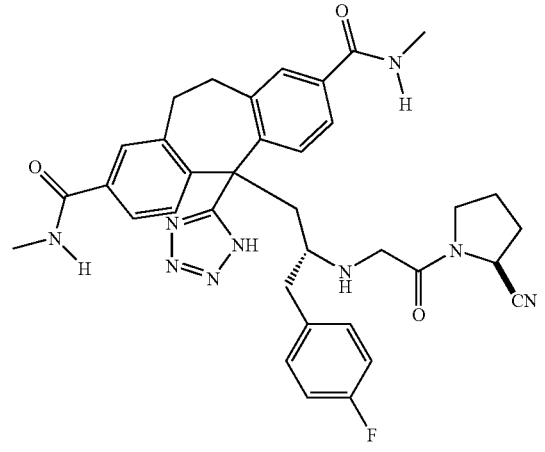 |
| 241 | 241 | 2 | 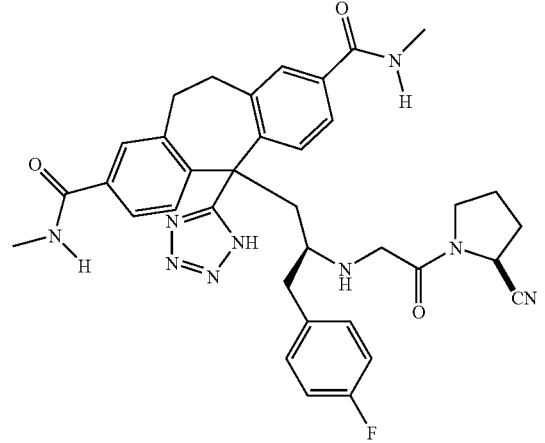 |
| 242 | 242 | 2 | 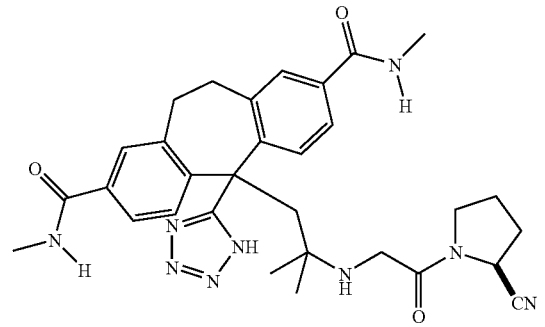 |
| 243 | 243 | 2 | 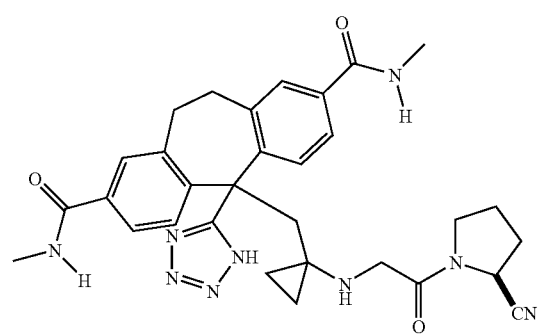 |

| Example | Preparative Example | Preparative Example | Product |
|---|---|---|---|
| 244 | 244 | 2 | 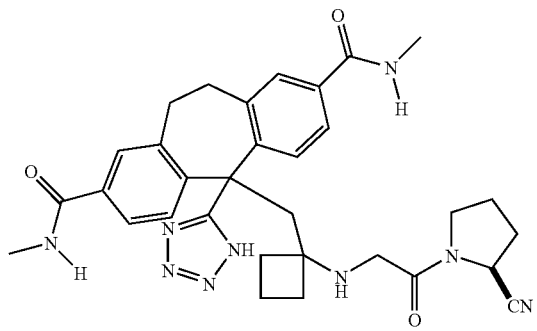 |
| 245 | 245 | 2 | 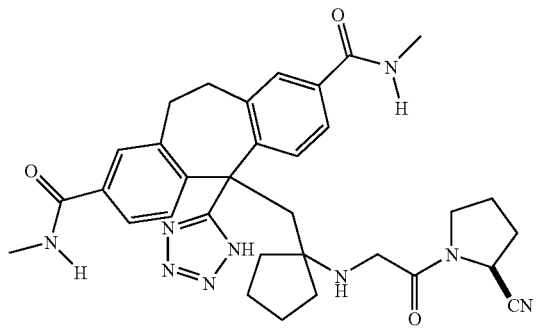 |
| 246 | 246 | 2 | 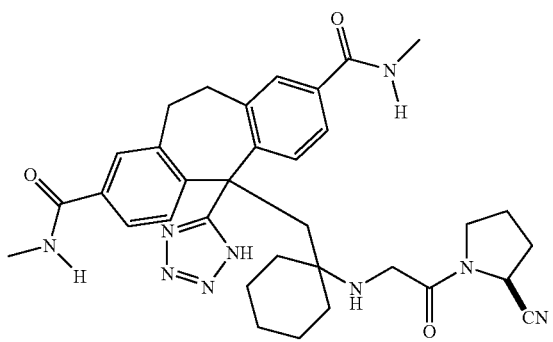 |
| 247 | 247 | 2 | 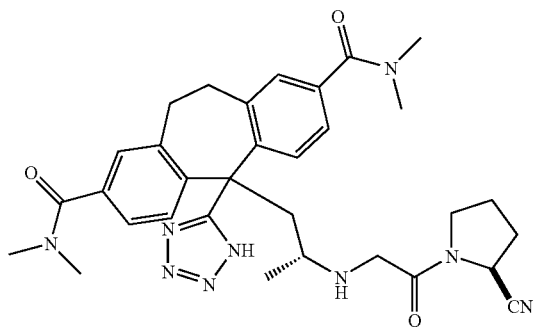 |

-continued
| Example | Preparative Example | Preparative Example | Product |
| --- | --- | --- | --- |
| 248 | 248 | 2 | 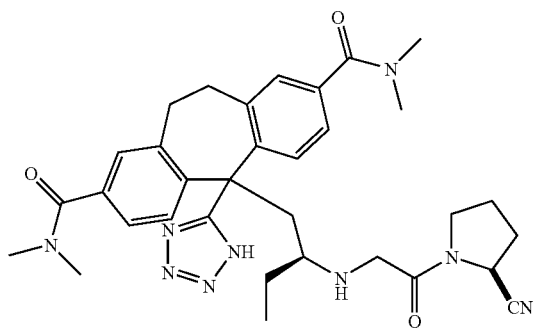 |
| 249 | 249 | 2 | 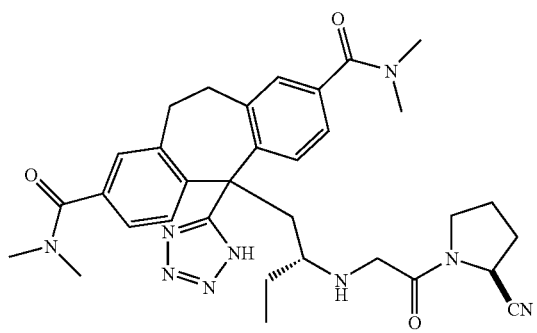 |
| 250 | 250 | 2 | 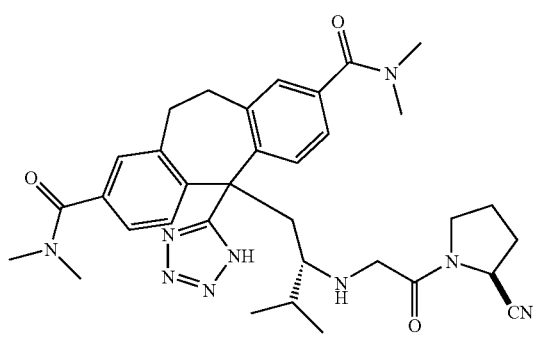 |
| 251 | 251 | 2 | 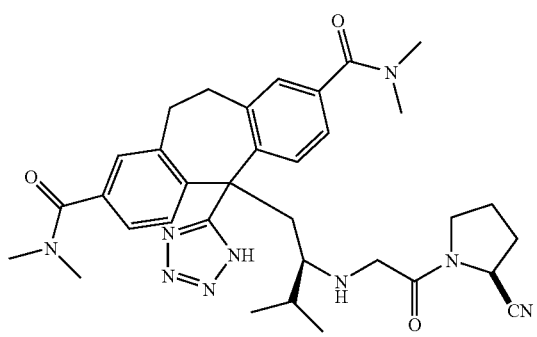 |

| Example | Preparative Example | Preparative Example | Product |
|---|---|---|---|
| 252 | 252 | 2 | |
| 253 | 253 | 2 | |
| 254 | 254 | 2 | |
| 255 | 255 | 2 | |

-continued
| Example | Preparative Example | Preparative Example | Product |
|---|---|---|---|
| 256 | 256 | 2 | 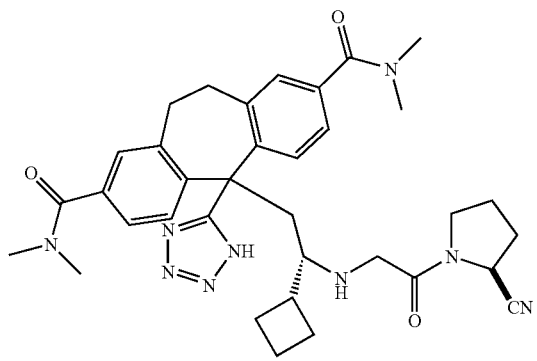 |
| 257 | 257 | 2 | 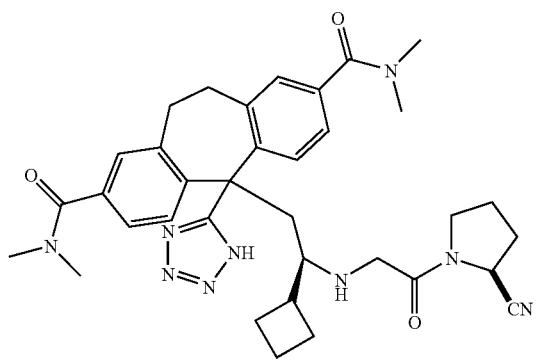 |
| 258 | 258 | 2 | 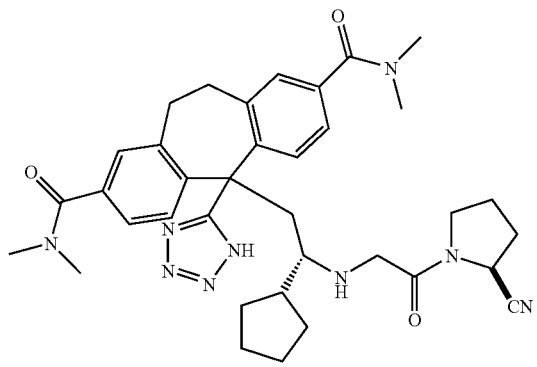 |
| 259 | 259 | 2 | 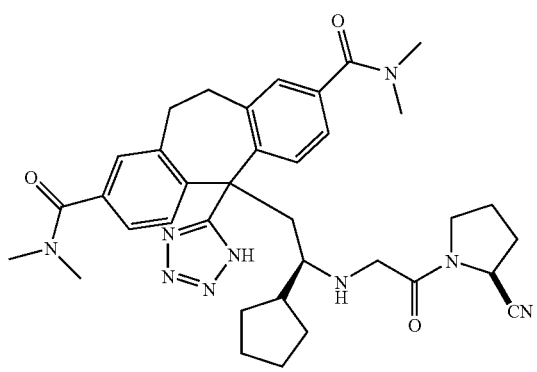 |

| Example | Preparative Example | Preparative Example | Product |
|---|---|---|---|
| 260 | 260 | 2 | 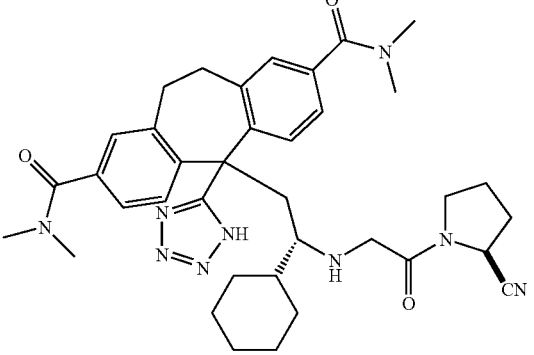 |
| 261 | 261 | 2 | 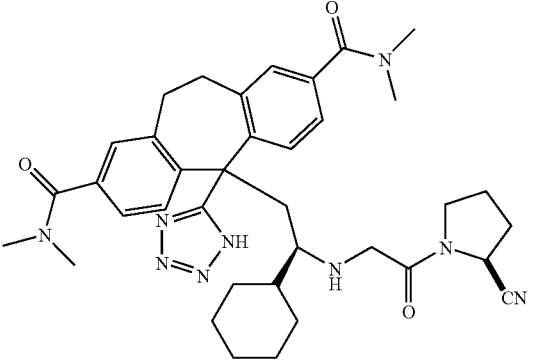 |
| 262 | 262 | 2 | 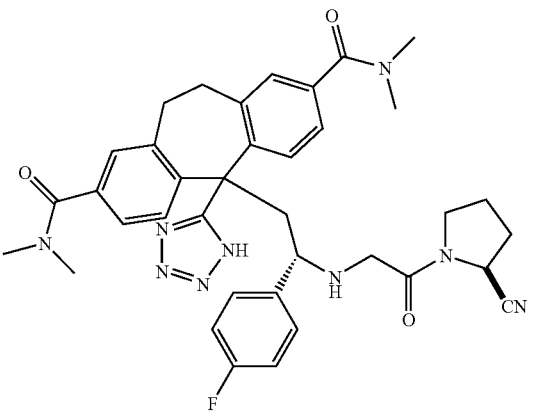 |
| 263 | 263 | 2 | 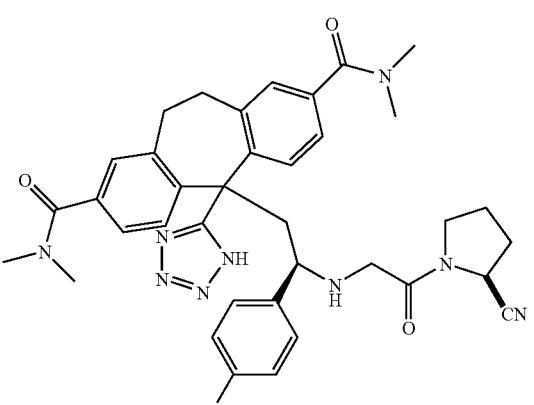 |

| Example | Preparative Example | Preparative Example | Product |
|---|---|---|---|
| 264 | 264 | 2 | 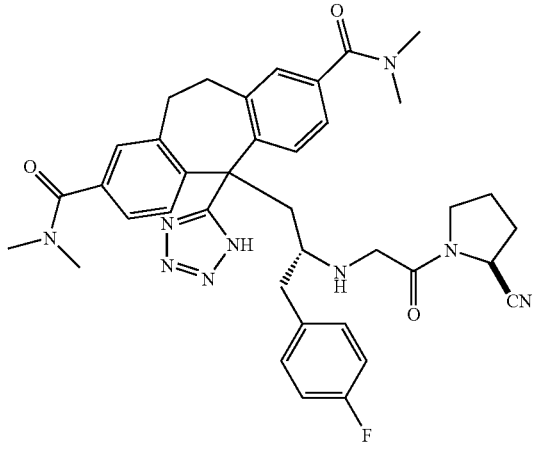 |
| 265 | 265 | 2 | 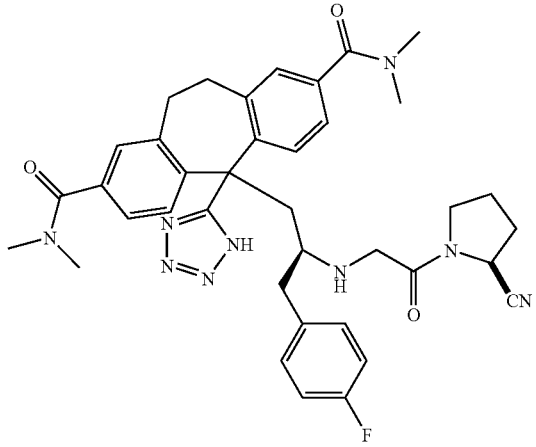 |
| 266 | 266 | 2 | 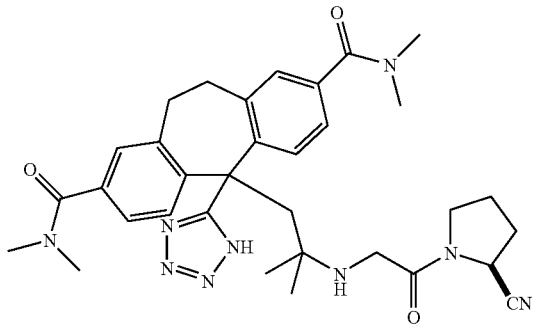 |
| 267 | 267 | 2 | 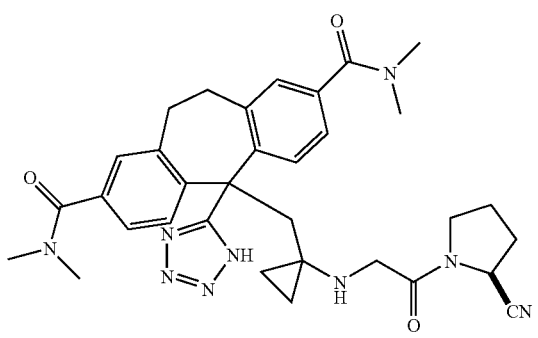 |

-continued
| Example | Preparative Example | Preparative Example | Product |
|---|---|---|---|
| 268 | 268 | 2 | 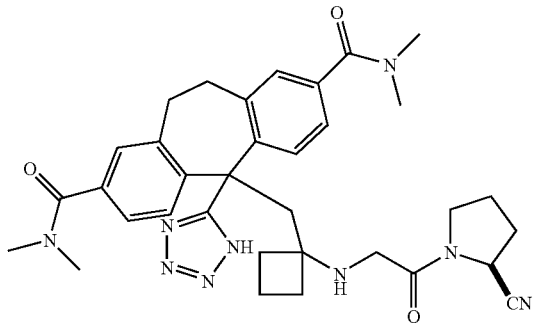 |
| 269 | 269 | 2 | 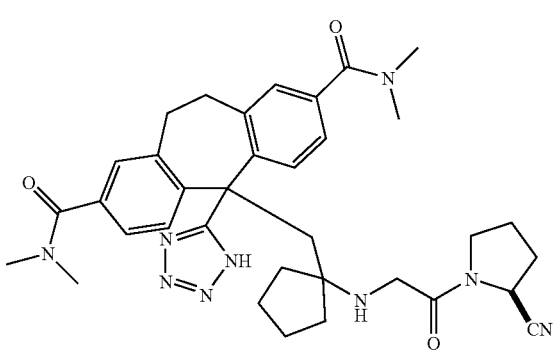 |
| 270 | 270 | 2 | 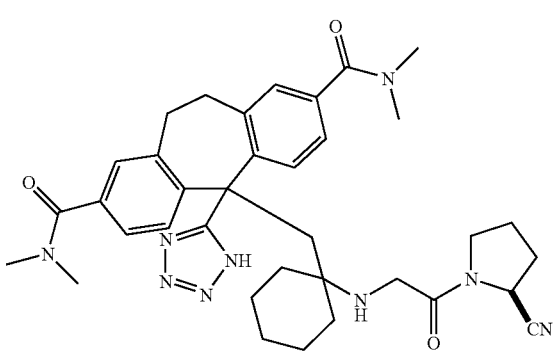 |
| 271 | 271 | 2 | 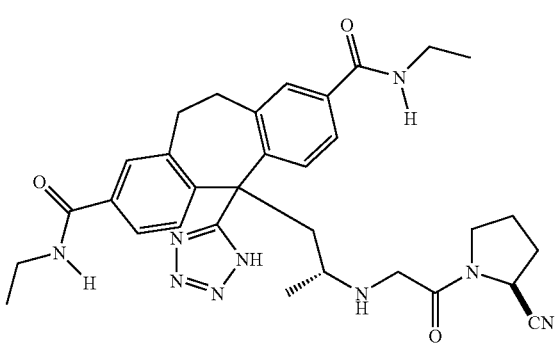 |

-continued

| Example | Preparative Example | Preparative Example | Product |
|---------|---------------------|---------------------|---------|
| 272 | 272 | 2 | |
| 273 | 273 | 2 | |
| 274 | 274 | 2 | |
| 275 | 275 | 2 | |

-continued
| Example | Preparative Example | Preparative Example | Product |
|---|---|---|---|
| 276 | 276 | 2 | 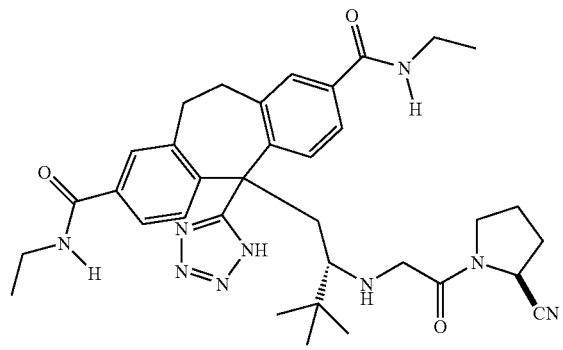 |
| 277 | 277 | 2 | 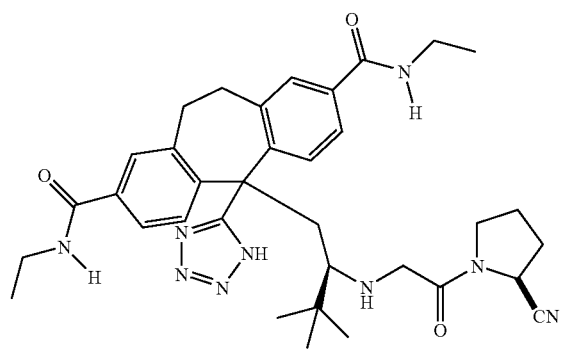 |
| 278 | 278 | 2 | 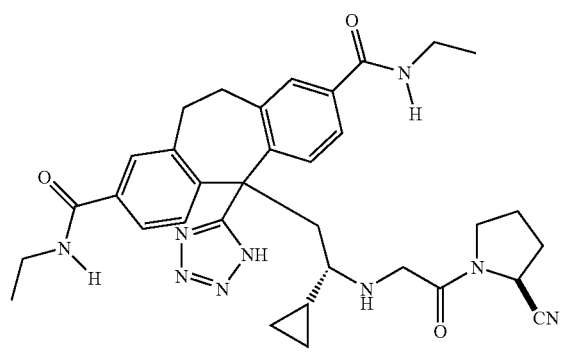 |
| 279 | 279 | 2 | 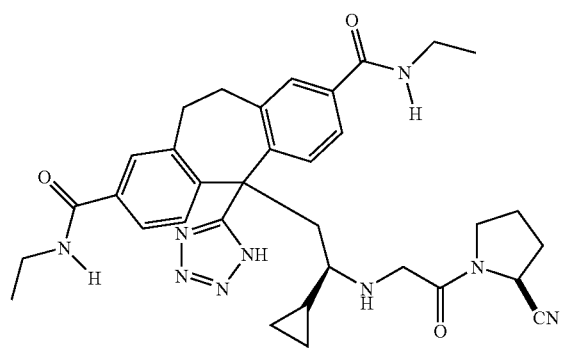 |

-continued
| Example | Preparative Example | Preparative Example | Product |
|---|---|---|---|
| 280 | 280 | 2 | 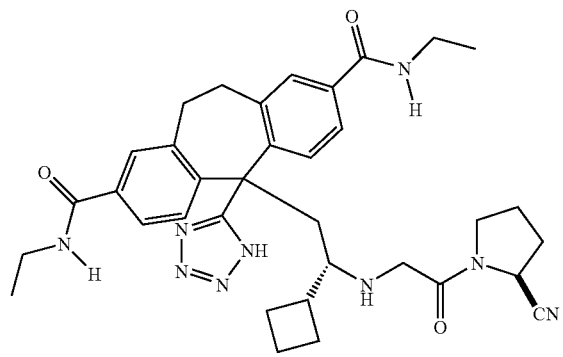 |
| 281 | 281 | 2 | 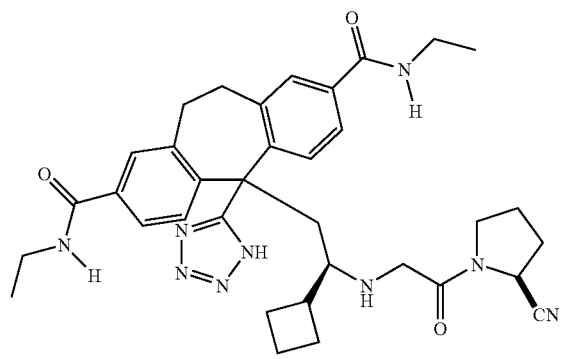 |
| 282 | 282 | 2 | 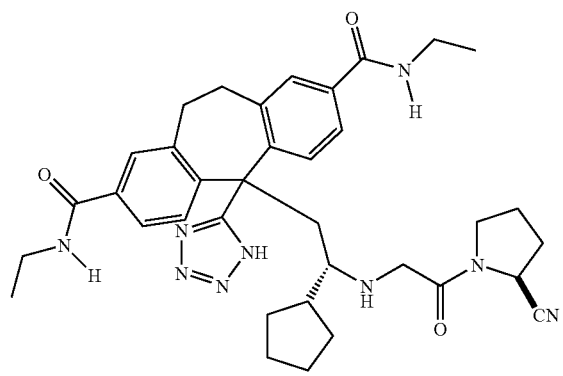 |
| 283 | 283 | 2 | 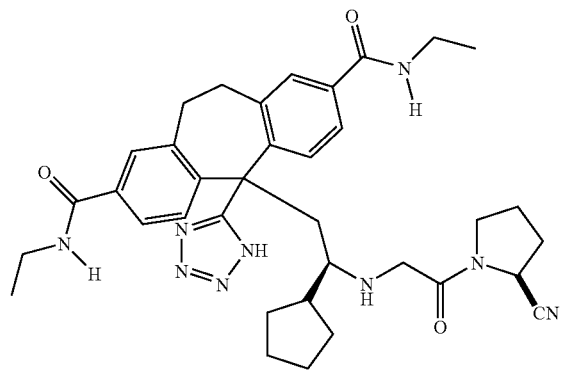 |

-continued

| Example | Preparative Example | Preparative Example | Product |
|---|---|---|---|
| 284 | 284 | 2 | |
| 285 | 285 | 2 | |
| 286 | 286 | 2 | |
| 287 | 287 | 2 | |

| Example | Preparative Example | Preparative Example | Product |
|---|---|---|---|
| 288 | 288 | 2 | 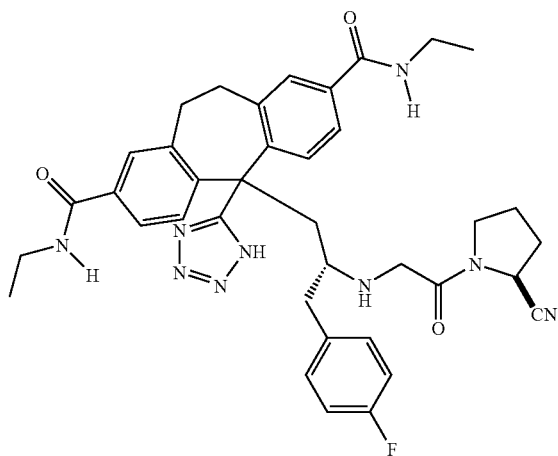 |
| 289 | 289 | 2 | 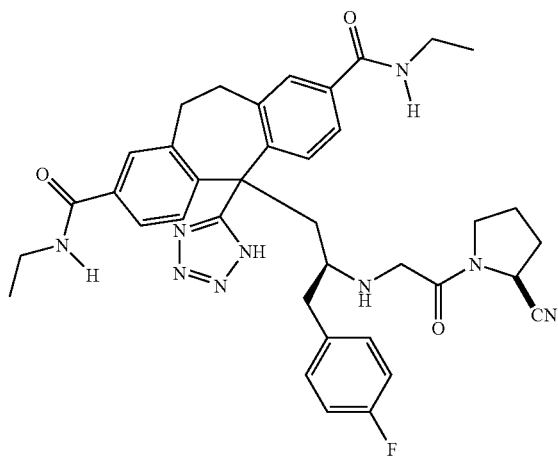 |
| 290 | 290 | 2 | 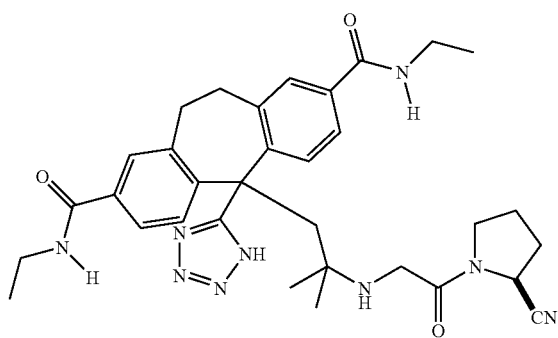 |

-continued
| Example | Preparative Example | Preparative Example | Product |
|---|---|---|---|
| 291 | 291 | 2 | 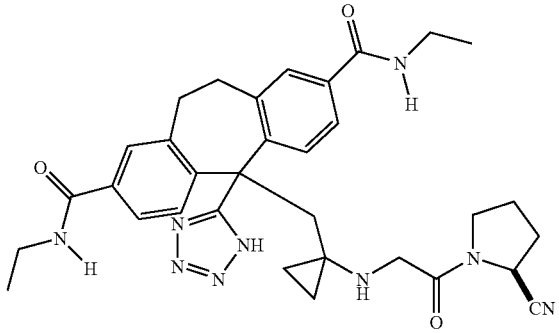 |
| 292 | 292 | 2 | 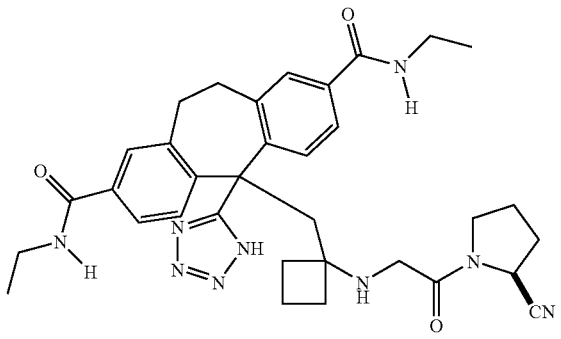 |
| 293 | 293 | 2 | 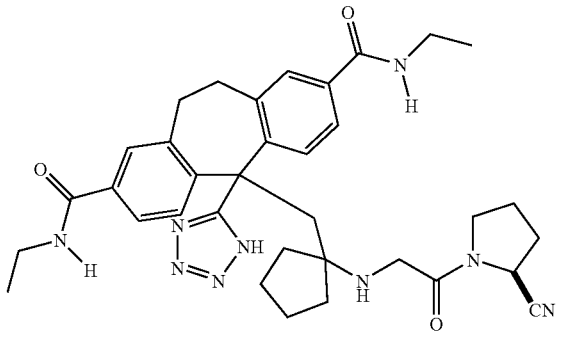 |
| 294 | 294 | 2 | 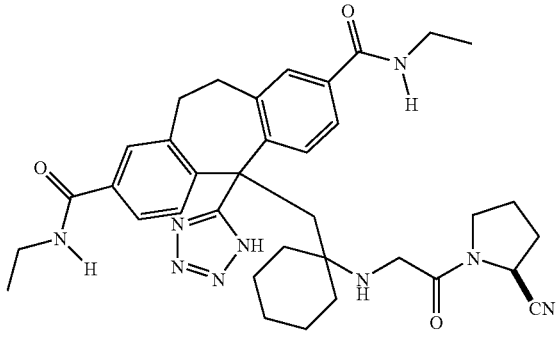 |

| Example | Preparative Example | Preparative Example | Product |
|---|---|---|---|
| 295 | 200 | 89 | |
| 296 | 201 | 89 | |
| 297 | 202 | 89 | |
| 298 | 203 | 89 | |

-continued
| Example | Preparative Example | Preparative Example | Product |
|---------|---------------------|---------------------|---------|
| 299 | 204 | 89 | 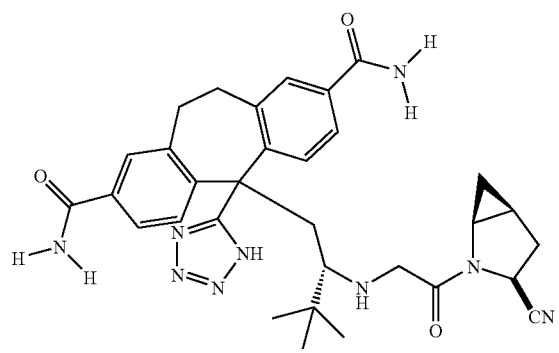 |
| 300 | 205 | 89 | 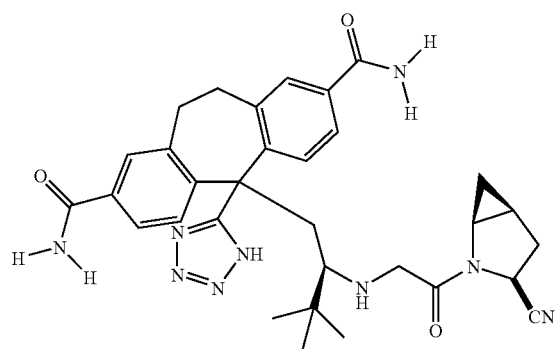 |
| 301 | 206 | 89 | 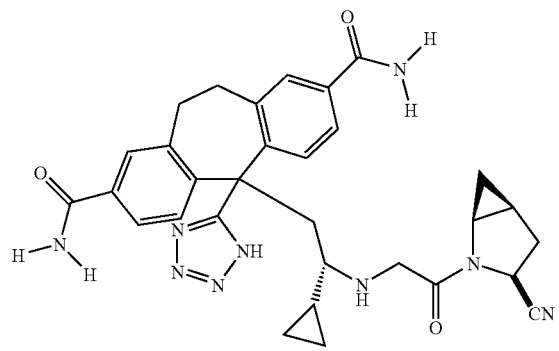 |
| 302 | 207 | 89 | 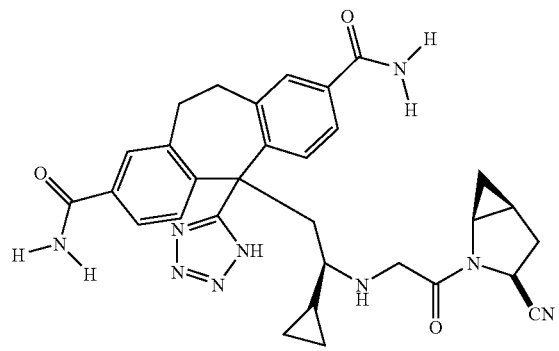 |

-continued
| Example | Preparative Example | Preparative Example | Product |
|---|---|---|---|
| 303 | 208 | 89 | 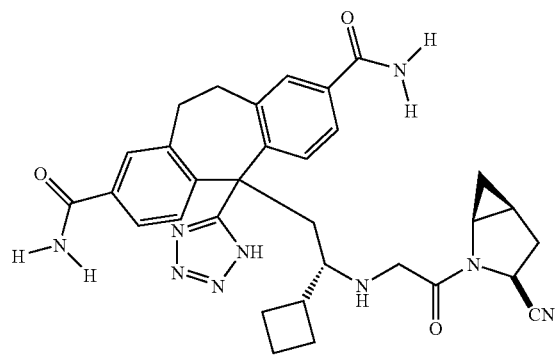 |
| 304 | 209 | 89 | 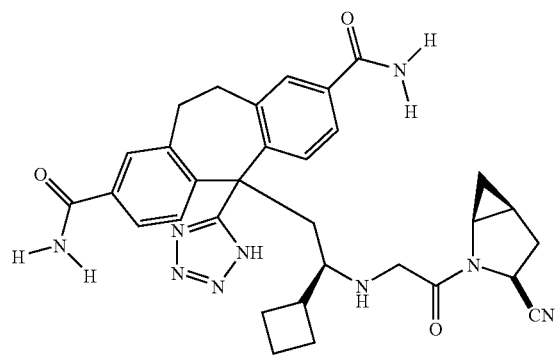 |
| 305 | 210 | 89 | 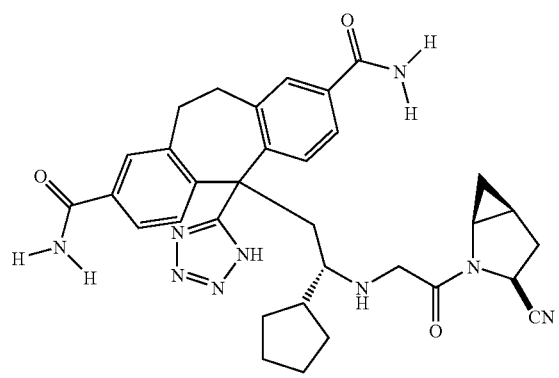 |
| 306 | 211 | 89 | 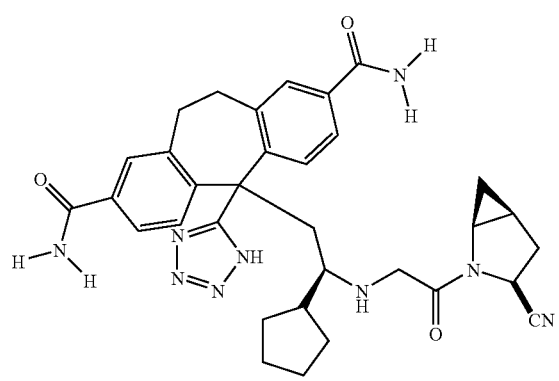 |

| Example | Preparative Example | Preparative Example | Product |
|---|---|---|---|
| 307 | 212 | 89 | 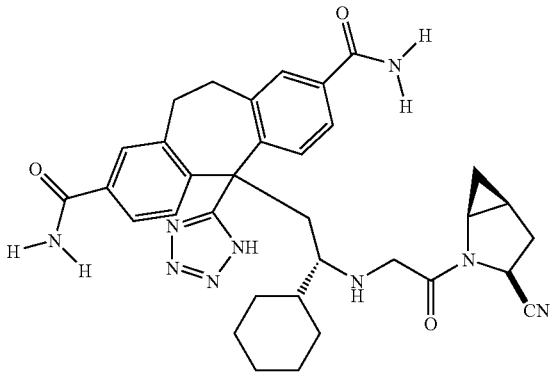 |
| 308 | 213 | 89 | 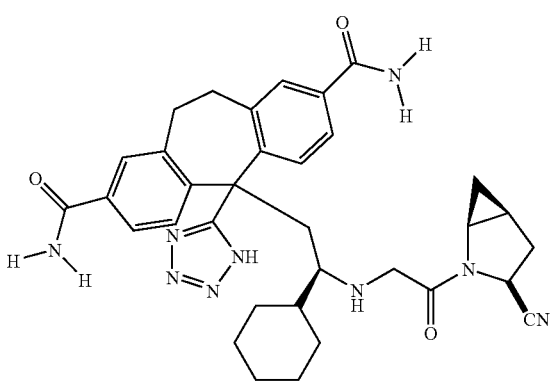 |
| 309 | 214 | 89 | 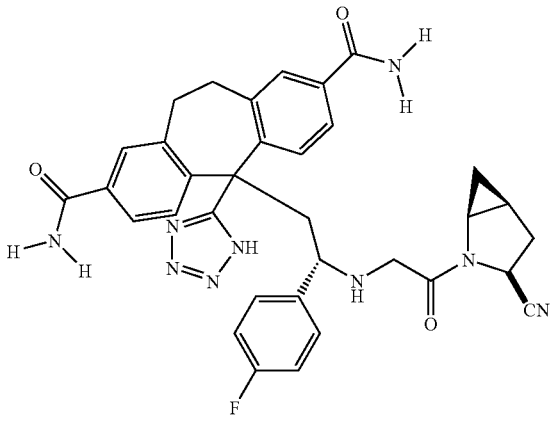 |
| 310 | 215 | 89 | 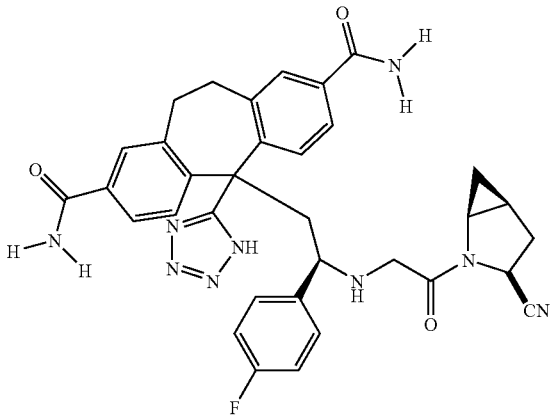 |

-continued
| Example | Preparative Example | Preparative Example | Product |
|---|---|---|---|
| 311 | 216 | 89 | 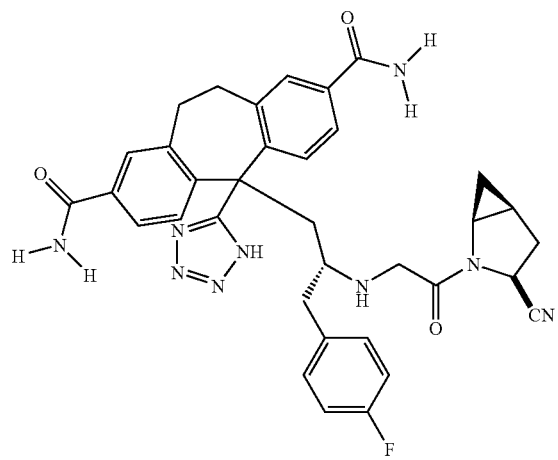 |
| 312 | 217 | 89 | 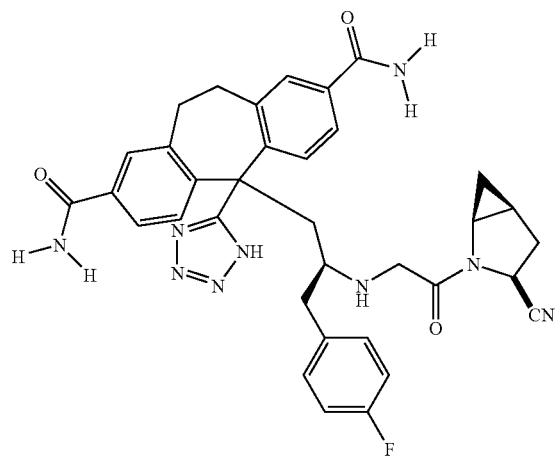 |
| 313 | 218 | 89 | 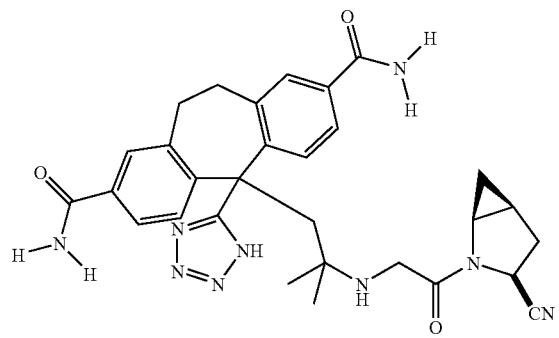 |

| Example | Preparative Example | Preparative Example | Product |
|---|---|---|---|
| 314 | 219 | 89 | 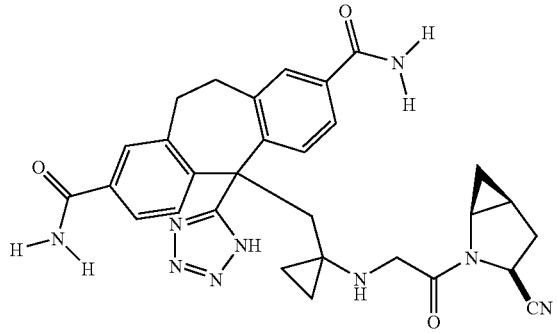 |
| 315 | 220 | 89 | 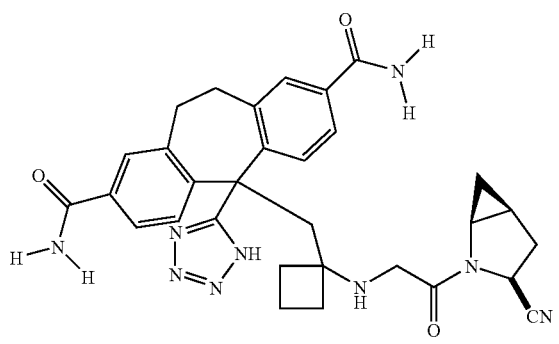 |
| 316 | 221 | 89 | 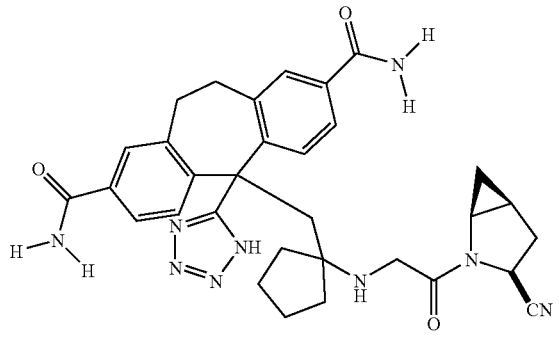 |
| 317 | 222 | 89 | 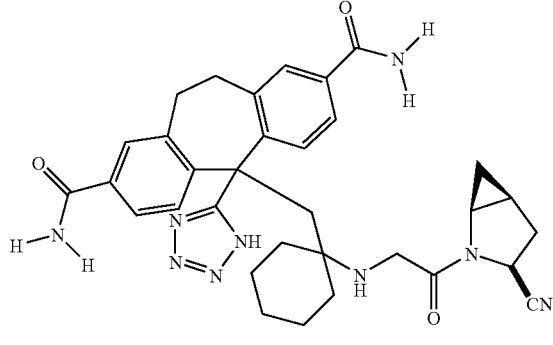 |

-continued
| Example | Preparative Example | Preparative Example | Product |
|---|---|---|---|
| 318 | 223 | 89 | 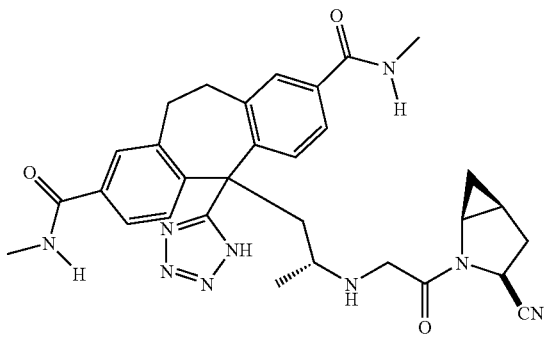 |
| 319 | 224 | 89 | 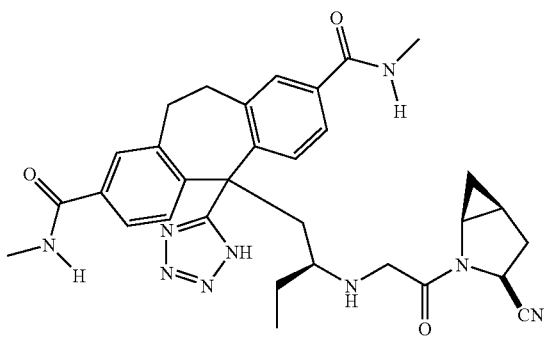 |
| 320 | 225 | 89 | 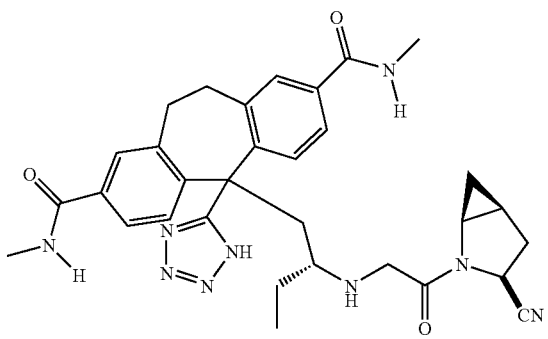 |
| 321 | 226 | 89 | 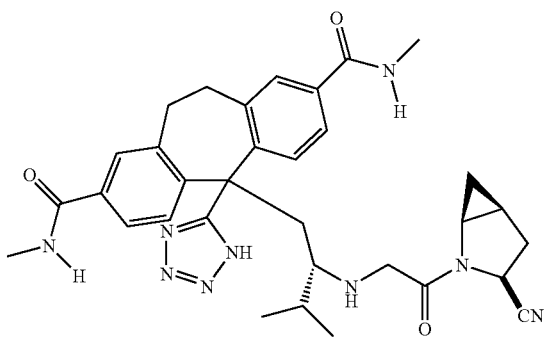 |

| Example | Preparative Example | Preparative Example | Product |
|---|---|---|---|
| 322 | 227 | 89 | 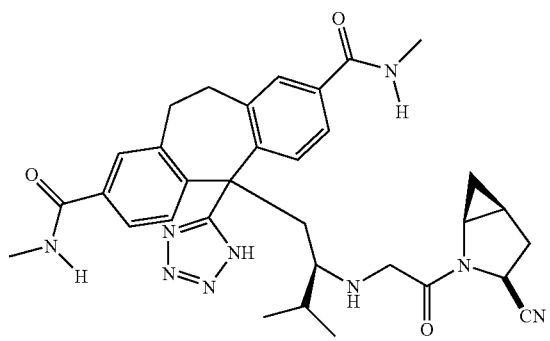 |
| 323 | 228 | 89 | 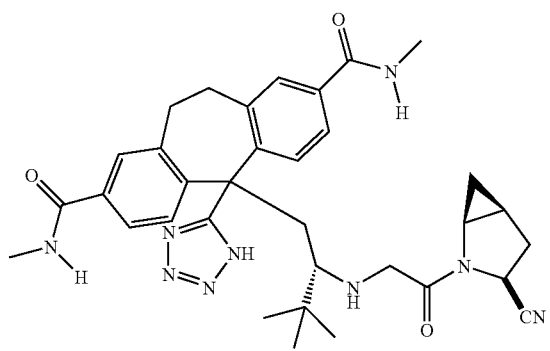 |
| 324 | 229 | 89 | 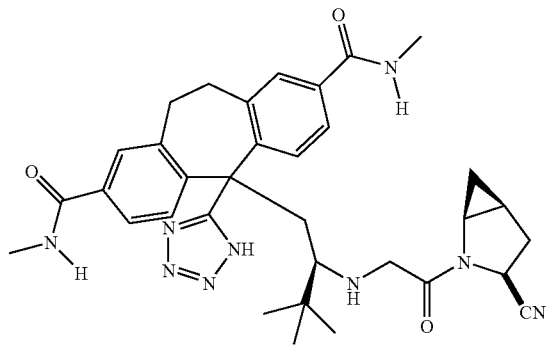 |
| 325 | 230 | 89 | 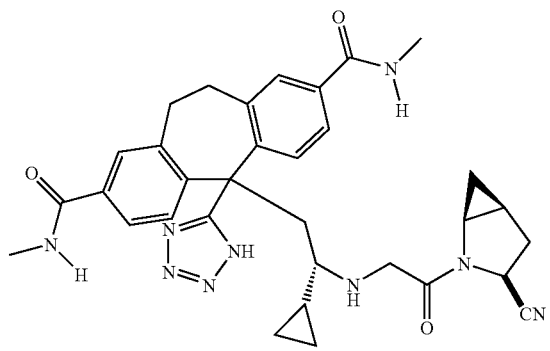 |

-continued
| Example | Preparative Example | Preparative Example | Product |
|---|---|---|---|
| 326 | 231 | 89 | 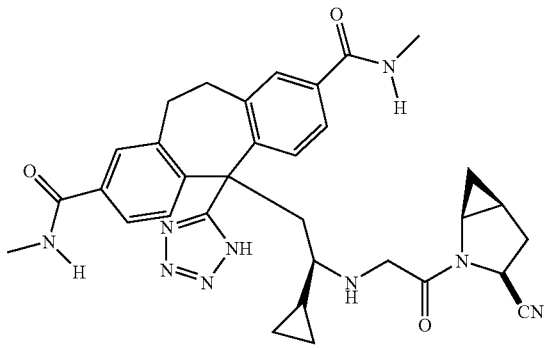 |
| 327 | 232 | 89 | 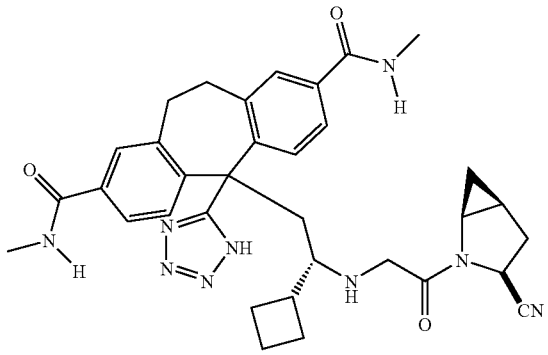 |
| 328 | 233 | 89 | 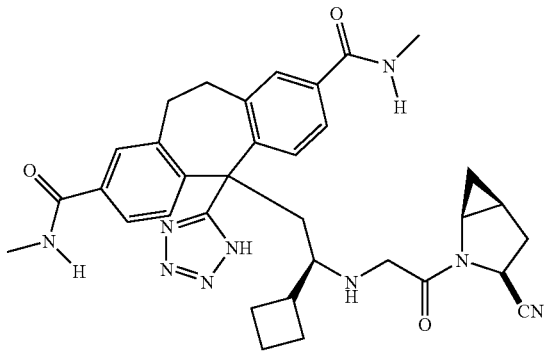 |
| 329 | 234 | 89 | 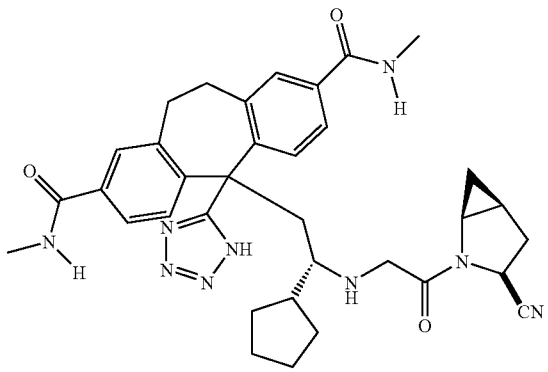 |

| Example | Preparative Example | Preparative Example | Product |
| --- | --- | --- | --- |
| 330 | 235 | 89 | |
| 331 | 236 | 89 | |
| 332 | 237 | 89 | |
| 333 | 238 | 89 | |

-continued
| Example | Preparative Example | Preparative Example | Product |
|---|---|---|---|
| 334 | 239 | 89 | 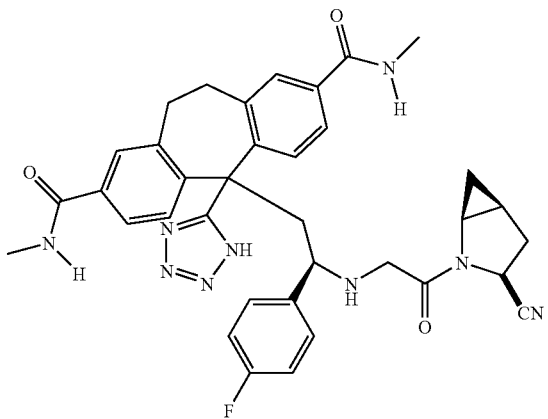 |
| 335 | 240 | 89 | 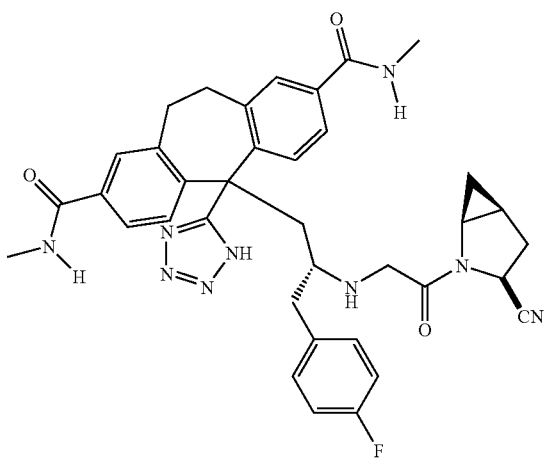 |
| 336 | 241 | 89 | 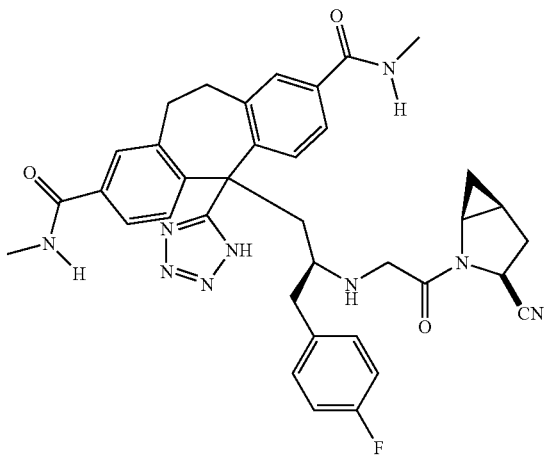 |

-continued
| Example | Preparative Example | Preparative Example | Product |
|---|---|---|---|
| 337 | 242 | 89 | 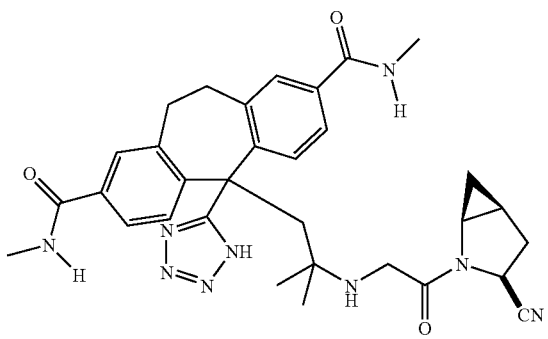 |
| 338 | 243 | 89 | 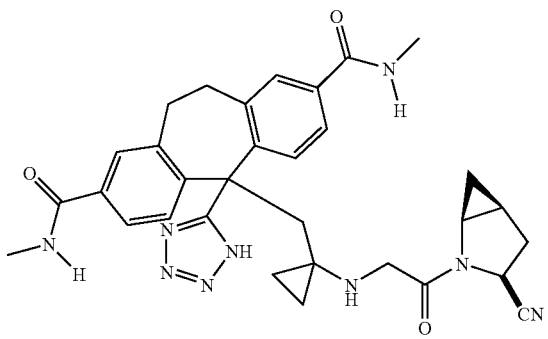 |
| 339 | 244 | 89 | 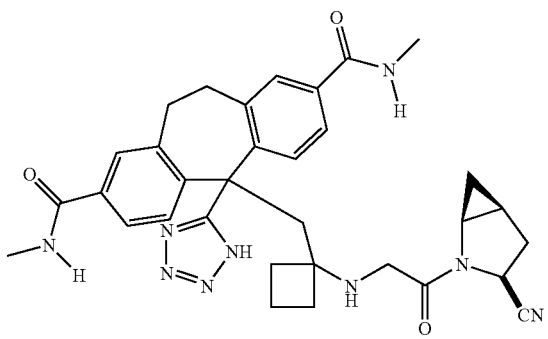 |
| 340 | 245 | 89 | 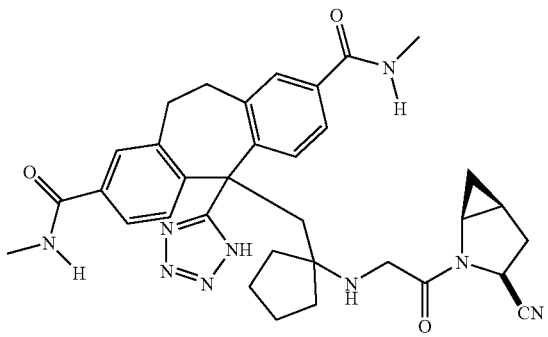 |

-continued
| Example | Preparative Example | Preparative Example | Product |
|---|---|---|---|
| 341 | 246 | 89 | 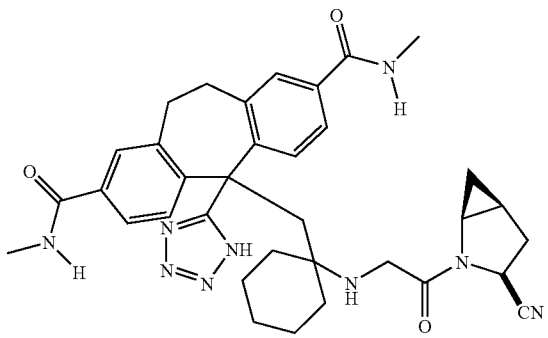 |
| 342 | 247 | 89 | 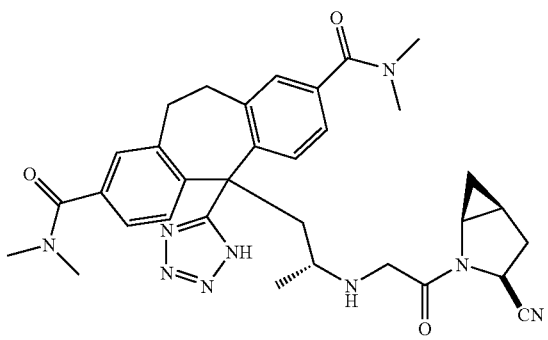 |
| 343 | 248 | 89 | 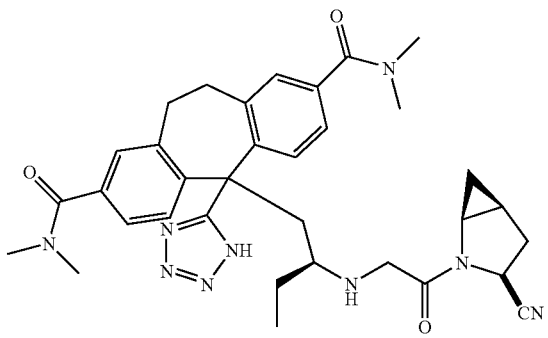 |
| 344 | 249 | 89 | 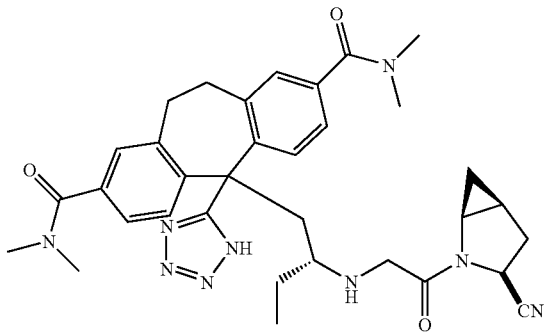 |

| Example | Preparative Example | Preparative Example | Product |
|---|---|---|---|
| 345 | 250 | 89 | 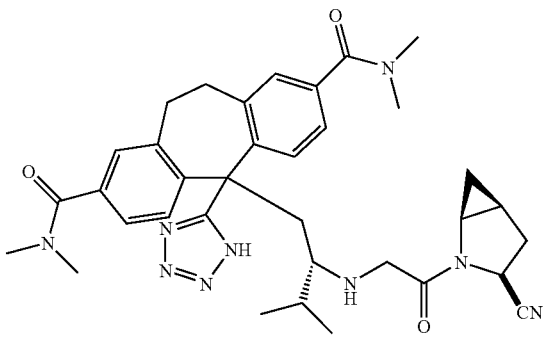 |
| 346 | 251 | 89 | 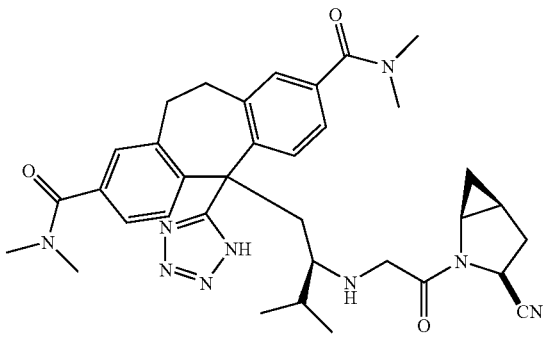 |
| 347 | 252 | 89 | 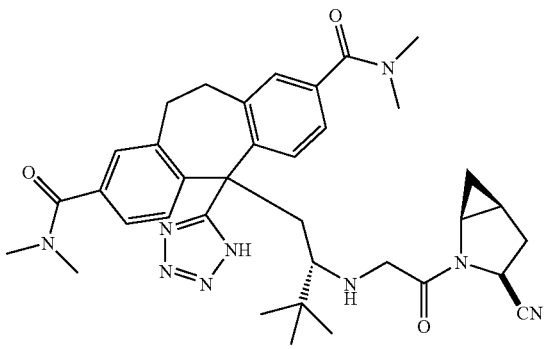 |
| 348 | 253 | 89 | 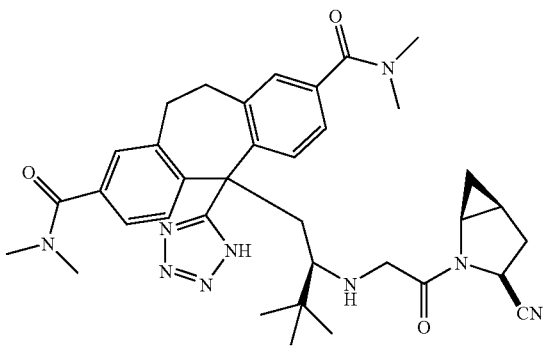 |

-continued
| Example | Preparative Example | Preparative Example | Product |
|---|---|---|---|
| 349 | 254 | 89 | 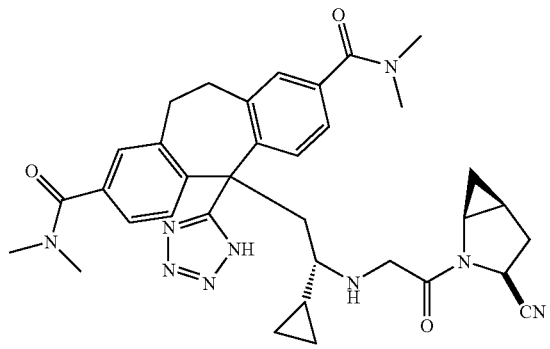 |
| 350 | 255 | 89 | 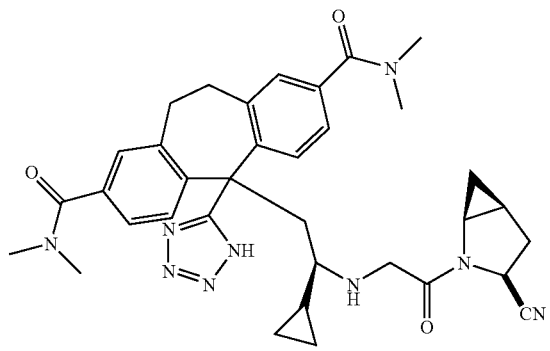 |
| 351 | 256 | 89 | 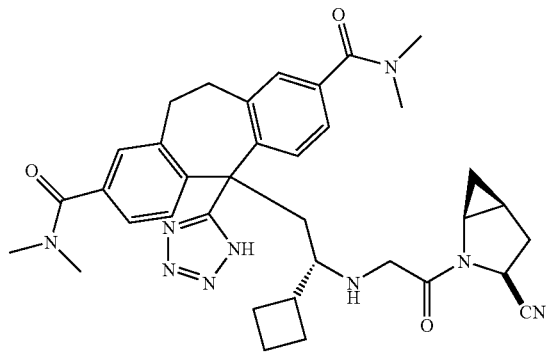 |
| 352 | 257 | 89 | 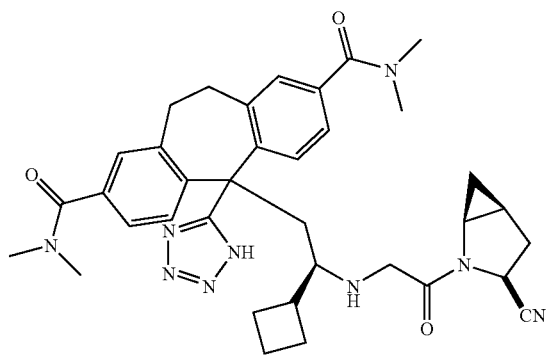 |

| Example | Preparative Example | Preparative Example | Product |
|---|---|---|---|
| 353 | 258 | 89 | 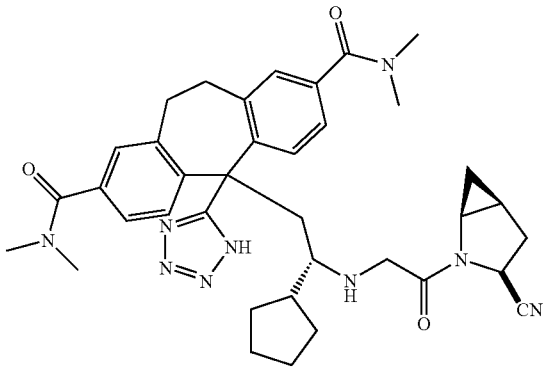 |
| 354 | 259 | 89 | 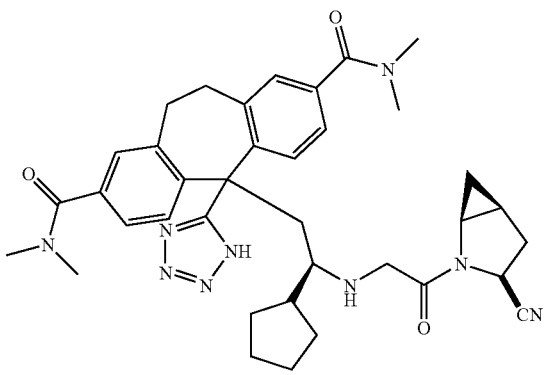 |
| 355 | 260 | 89 | 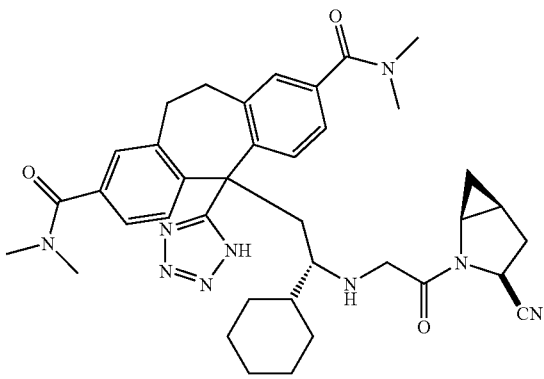 |
| 356 | 261 | 89 | 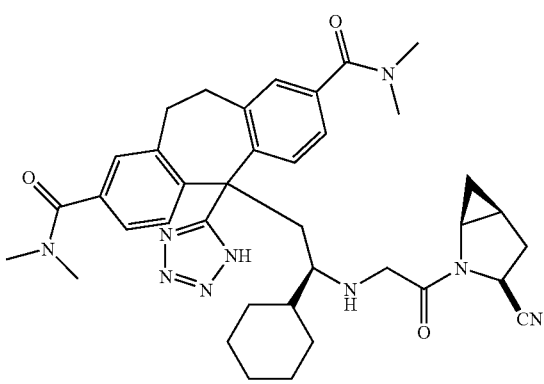 |

| Example | Preparative Example | Preparative Example | Product |
|---|---|---|---|
| 357 | 262 | 89 | 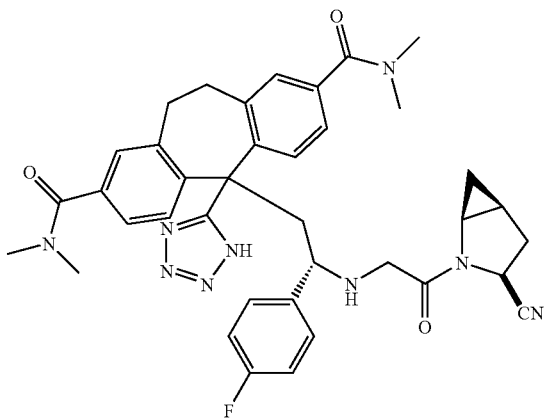 |
| 358 | 263 | 89 | 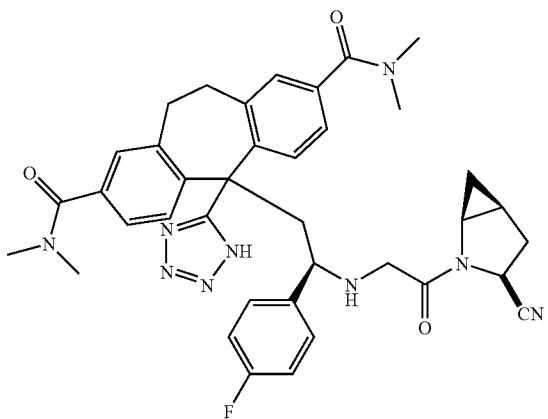 |
| 359 | 264 | 89 | 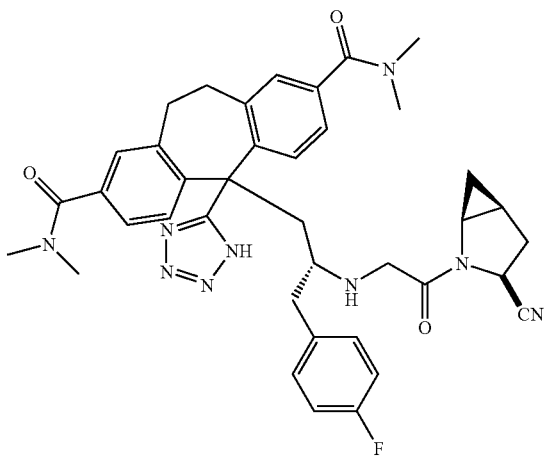 |

-continued
| Example | Preparative Example | Preparative Example | Product |
|---|---|---|---|
| 360 | 265 | 89 | 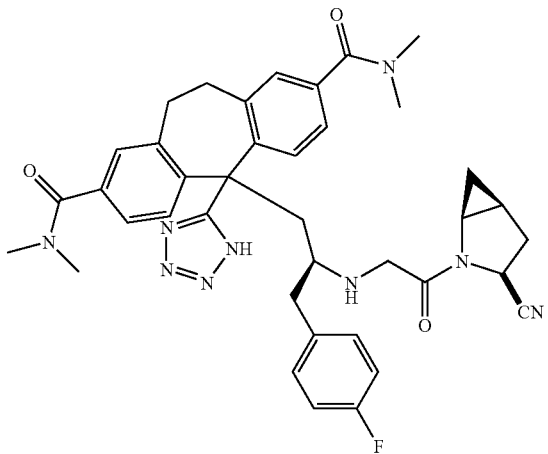 |
| 361 | 266 | 89 | 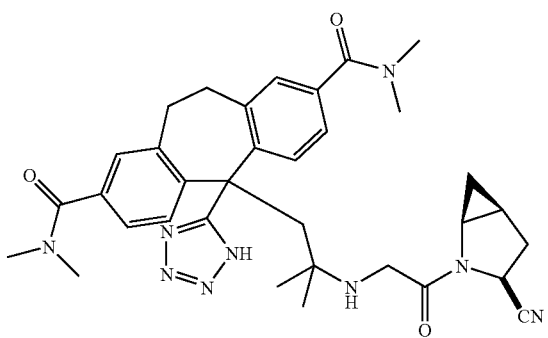 |
| 362 | 267 | 89 | 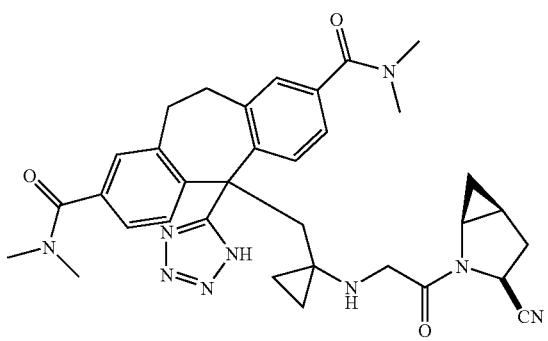 |
| 363 | 268 | 89 | 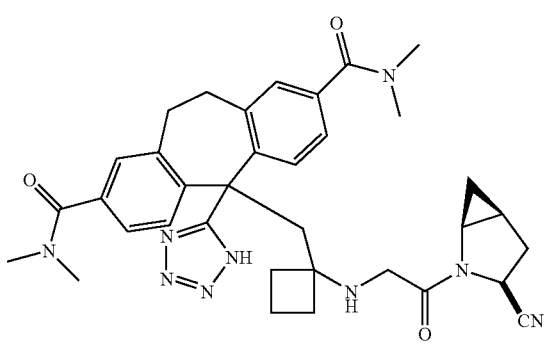 |

-continued
| Example | Preparative Example | Preparative Example | Product |
|---|---|---|---|
| 364 | 269 | 89 | 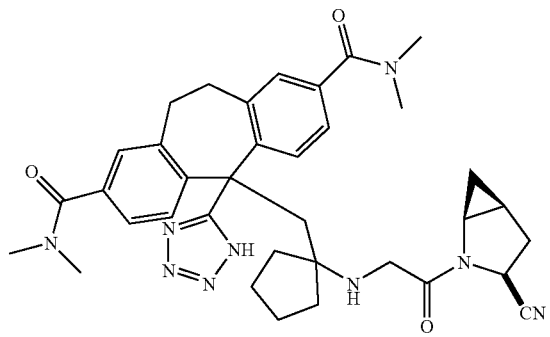 |
| 365 | 270 | 89 | 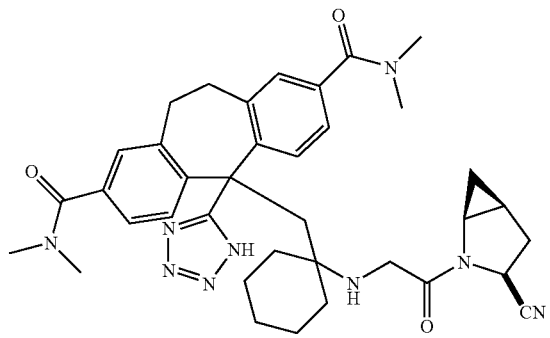 |
| 366 | 271 | 89 | 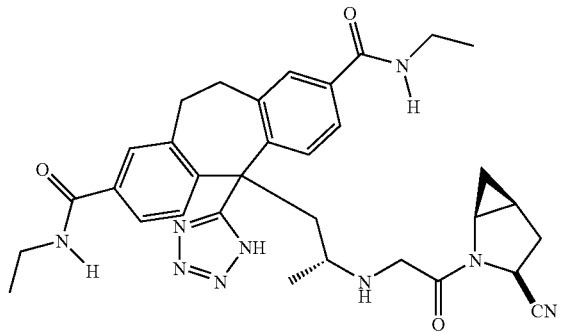 |
| 367 | 272 | 89 | 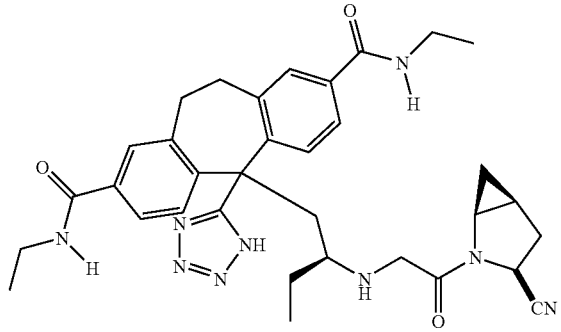 |

-continued
| Example | Preparative Example | Preparative Example | Product |
|---|---|---|---|
| 368 | 273 | 89 | 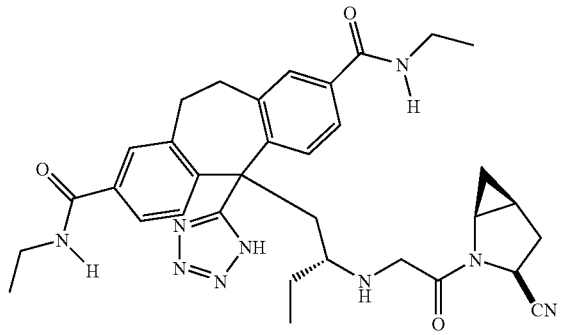 |
| 369 | 274 | 89 | 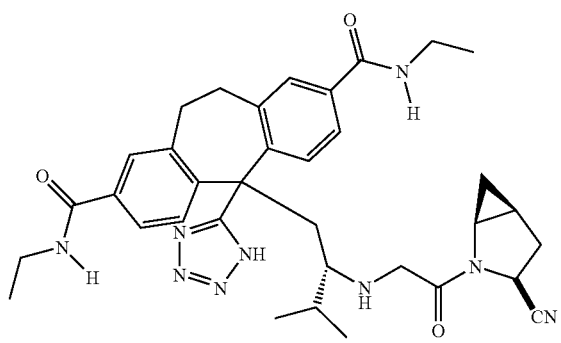 |
| 370 | 275 | 89 | 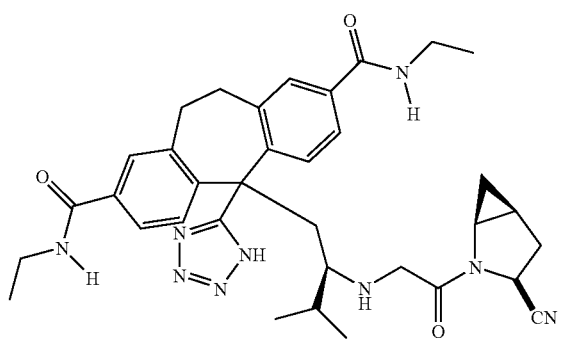 |
| 371 | 276 | 89 | 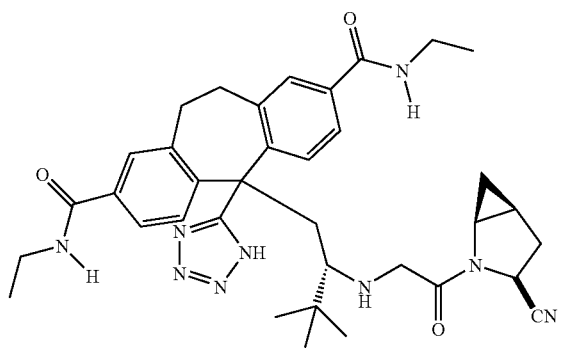 |

| Example | Preparative Example | Preparative Example | Product |
|---|---|---|---|
| 372 | 277 | 89 | 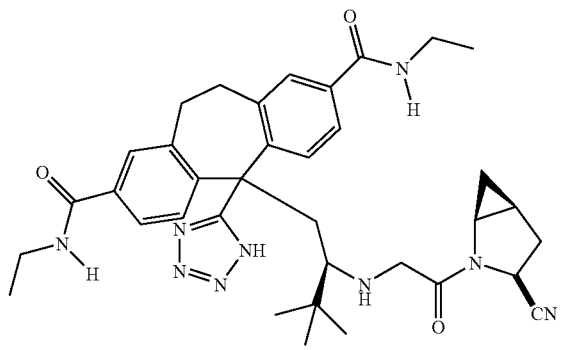 |
| 373 | 278 | 89 | 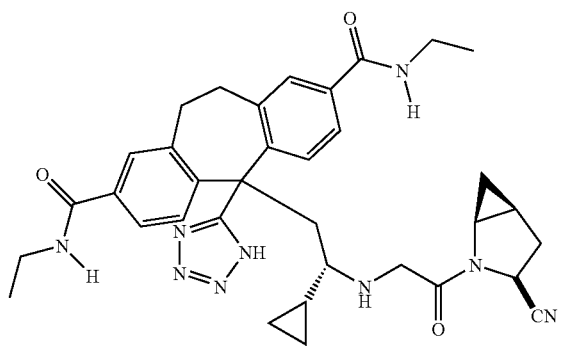 |
| 374 | 279 | 89 | 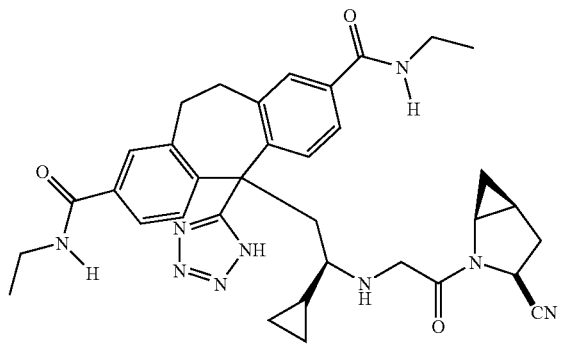 |
| 375 | 280 | 89 | 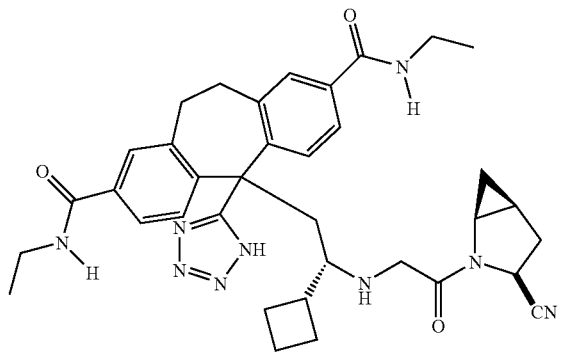 |

-continued
| Example | Preparative Example | Preparative Example | Product |
|---|---|---|---|
| 376 | 281 | 89 | 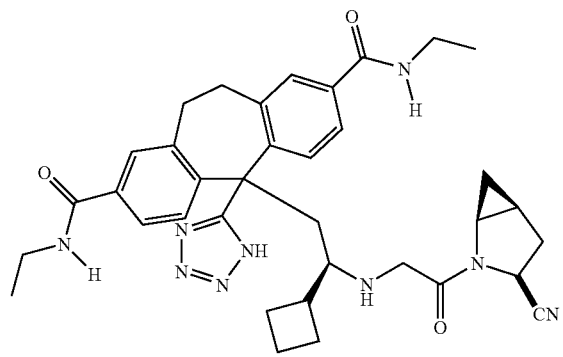 |
| 377 | 282 | 89 | 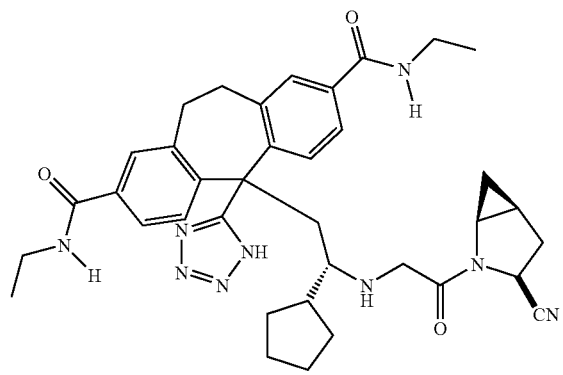 |
| 378 | 283 | 89 | 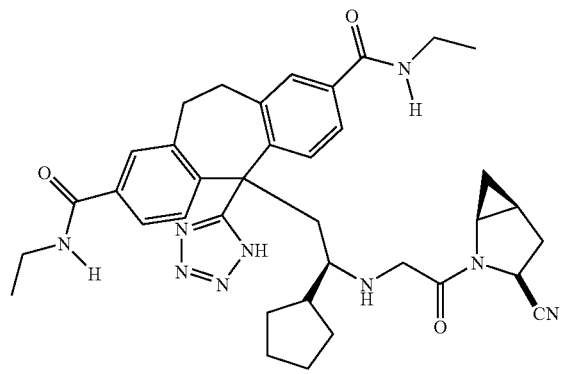 |
| 379 | 284 | 89 | 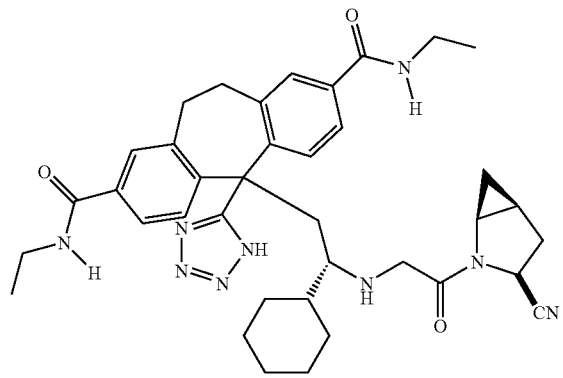 |

| Example | Preparative Example | Preparative Example | Product |
|---|---|---|---|
| 380 | 285 | 89 | 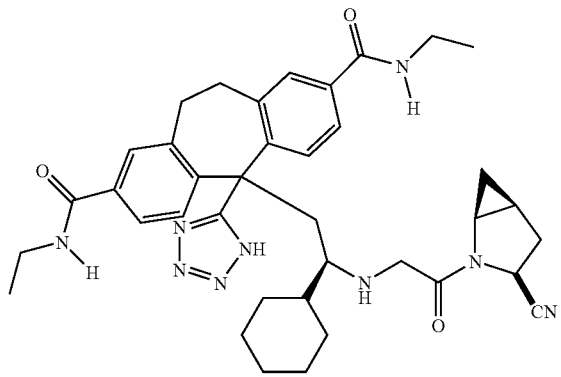 |
| 381 | 286 | 89 | 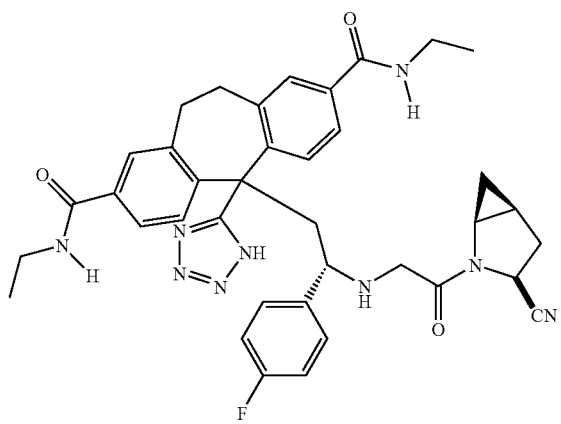 |
| 382 | 287 | 89 | 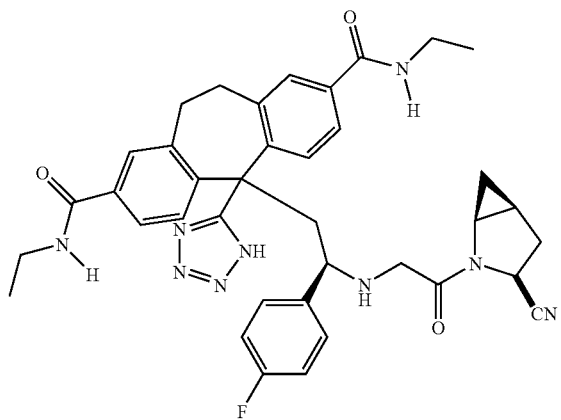 |

-continued
| Example | Preparative Example | Preparative Example | Product |
|---|---|---|---|
| 383 | 288 | 89 | 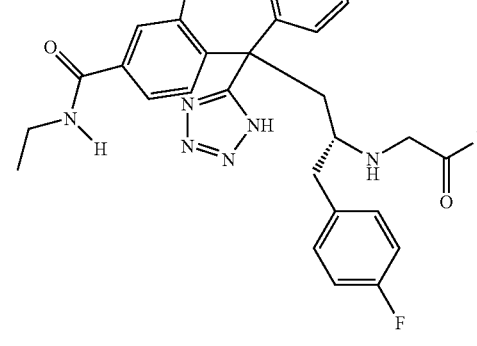 |
| 384 | 289 | 89 | 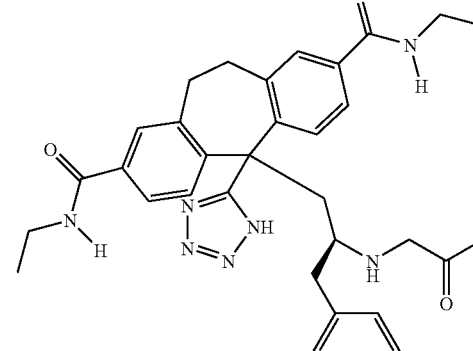 |
| 385 | 290 | 89 | 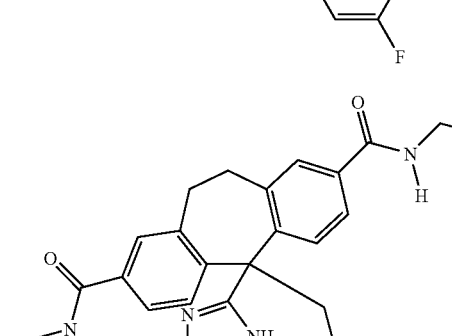 |
| 386 | 291 | 89 | 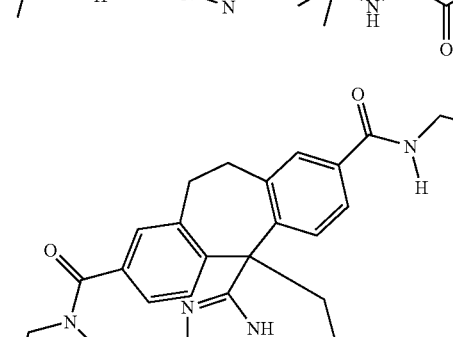 |

-continued
| Example | Preparative Example | Preparative Example | Product |
|---|---|---|---|
| 387 | 292 | 89 | 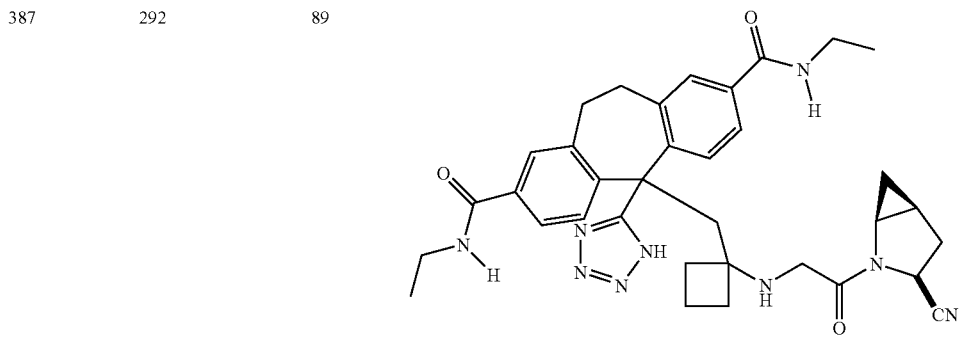 |
| 388 | 293 | 89 | 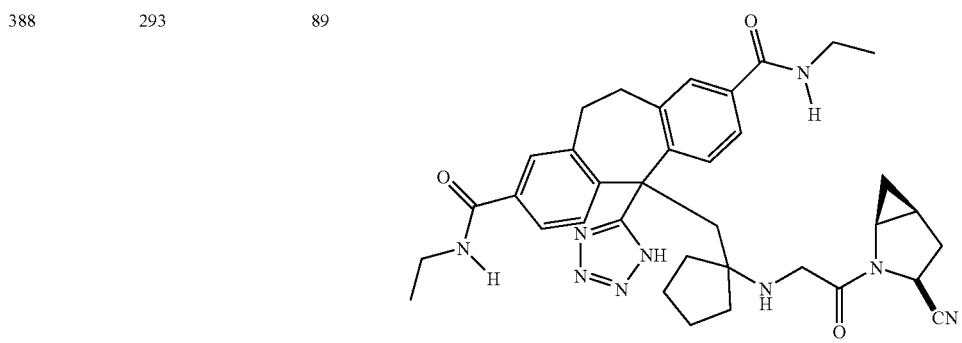 |
| 389 | 294 | 89 | 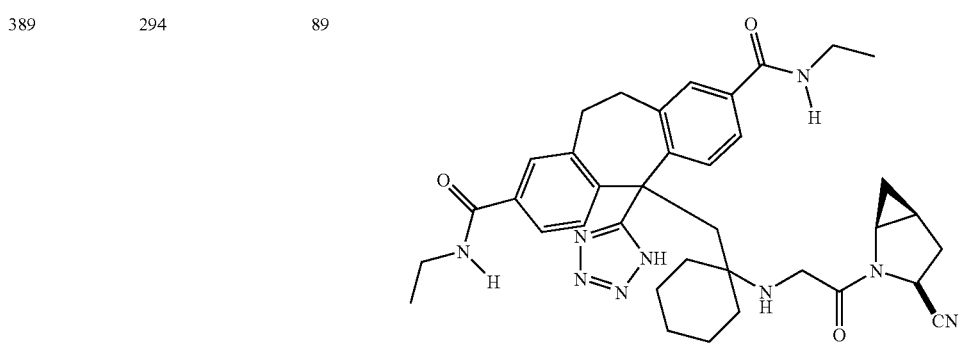 |
Examples 390-399 have been intentionally excluded.

Example 400-595
If one were to follow the procedures outlined in Examples 28 or 29 except using the compounds from the Preparative Examples as indicated in the Table below, one would obtain the indicated Product.
| Example | Preparative Example | Preparative Example | Product |
|---|---|---|---|
| 400 | 300 | 2 | 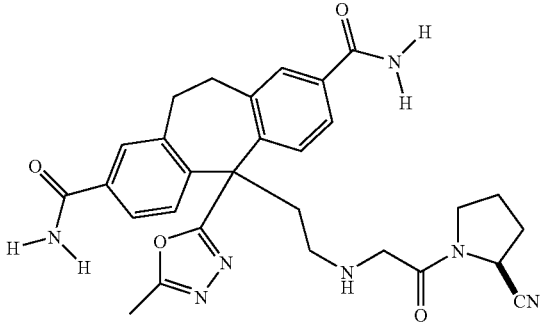 |
| 401 | 301 | 2 | 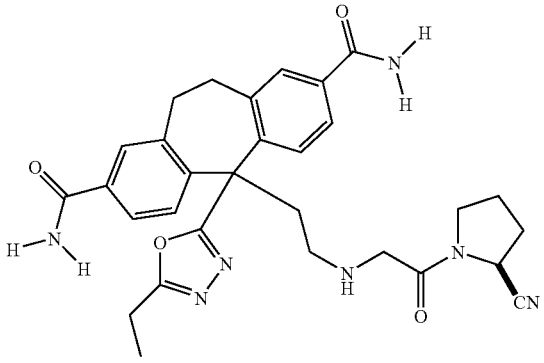 |
| 402 | 302 | 2 | 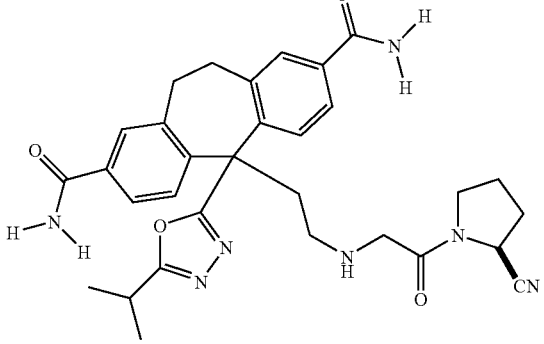 |

| Example | Preparative Example | Preparative Example | Product |
|---|---|---|---|
| 403 | 303 | 2 | |
| 404 | 304 | 2 | |
| 405 | 305 | 2 | |
| 406 | 306 | 2 | |

-continued
| Example | Preparative Example | Preparative Example | Product |
|---|---|---|---|
| 407 | 307 | 2 | 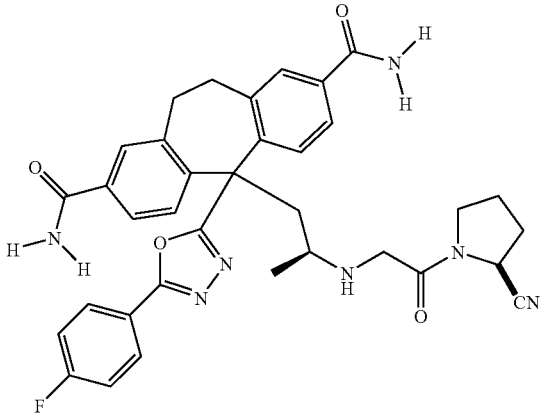 |
| 408 | 308 | 2 | 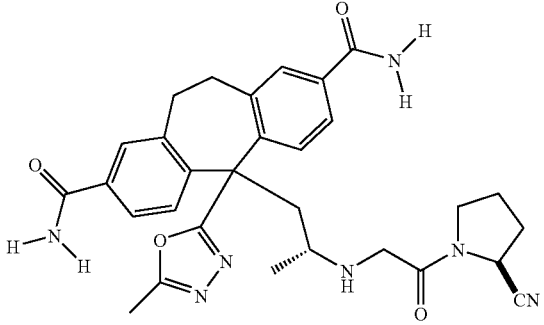 |
| 409 | 309 | 2 | 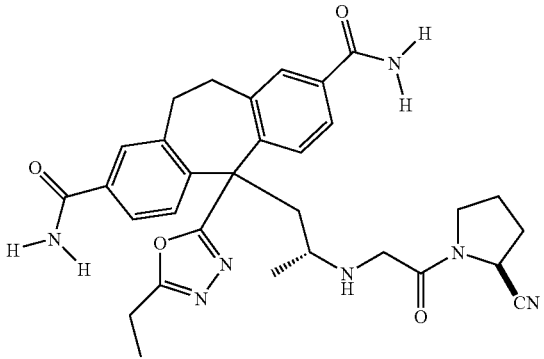 |
| 410 | 310 | 2 | 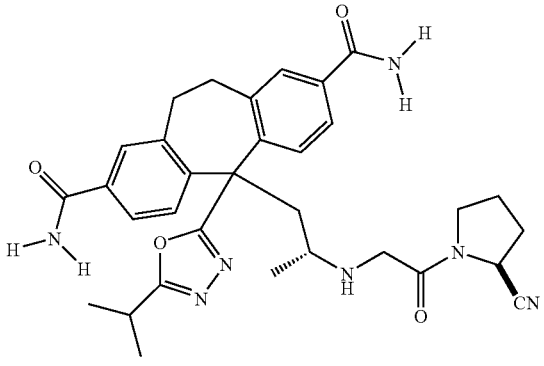 |

-continued

| Example | Preparative Example | Preparative Example | Product |
|---|---|---|---|
| 411 | 311 | 2 | |
| 412 | 312 | 2 | |
| 413 | 313 | 2 | |
| 414 | 314 | 2 | |

-continued

| Example | Preparative Example | Preparative Example | Product |
|---------|---------------------|---------------------|---------|
| 415 | 315 | 2 | |
| 416 | 316 | 2 | |
| 417 | 317 | 2 | |
| 418 | 318 | 2 | |

| Example | Preparative Example | Preparative Example | Product |
|---|---|---|---|
| 419 | 319 | 2 | 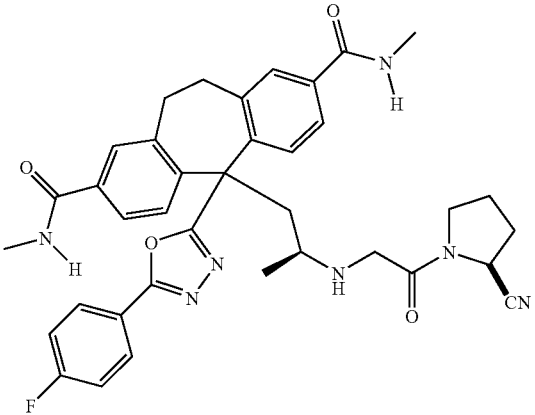 |
| 420 | 320 | 2 | 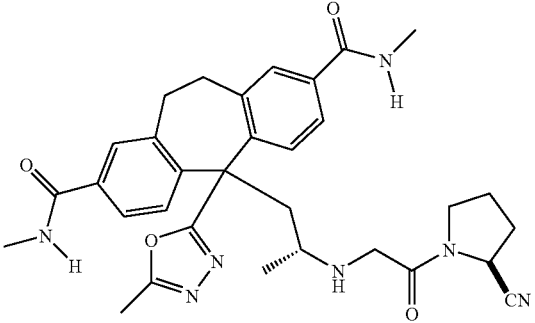 |
| 421 | 321 | 2 | 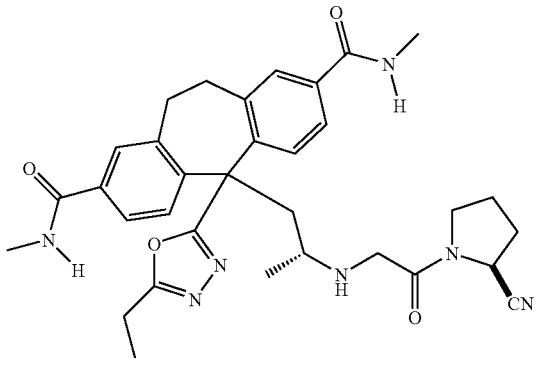 |
| 422 | 322 | 2 | 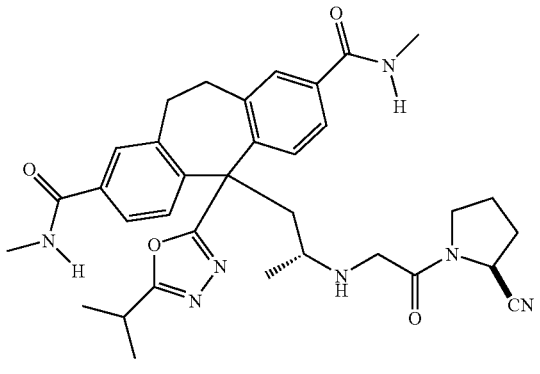 |

-continued

| Example | Preparative Example | Preparative Example | Product |
|---------|---------------------|---------------------|---------|
| 423 | 323 | 2 | |
| 424 | 324 | 2 | |
| 425 | 325 | 2 | |
| 426 | 326 | 2 | |

-continued

| Example | Preparative Example | Preparative Example | Product |
|---|---|---|---|
| 427 | 327 | 2 | |
| 428 | 328 | 2 | |
| 429 | 329 | 2 | |
| 430 | 330 | 2 | |

-continued
| Example | Preparative Example | Preparative Example | Product |
|---|---|---|---|
| 431 | 331 | 2 | 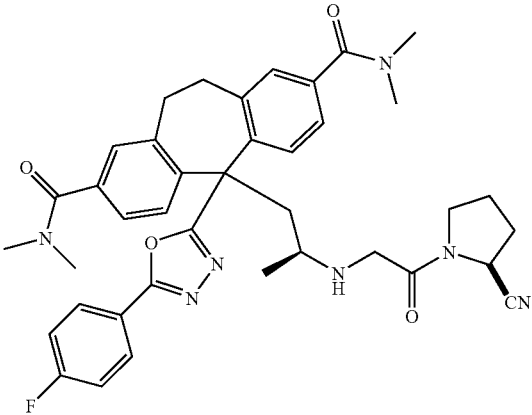 |
| 432 | 332 | 2 | 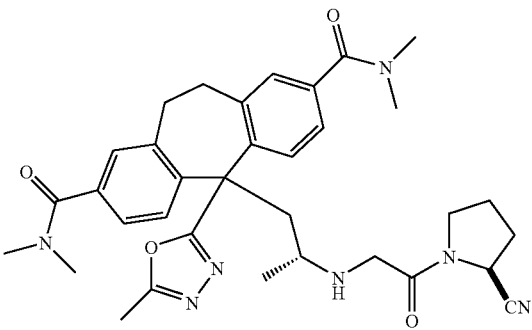 |
| 433 | 333 | 2 | 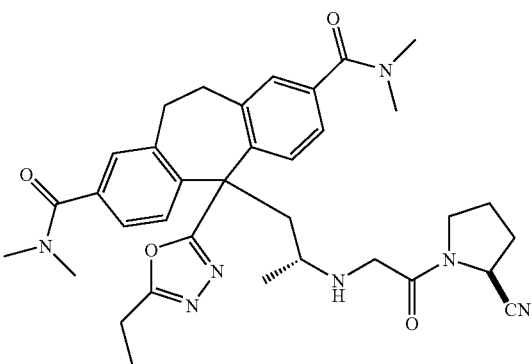 |
| 434 | 334 | 2 | 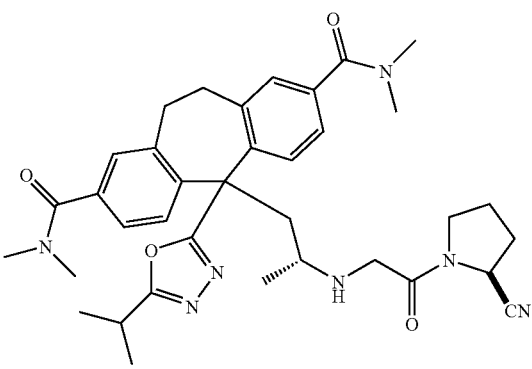 |

-continued
| Example | Preparative Example | Preparative Example | Product |
|---|---|---|---|
| 435 | 335 | 2 | 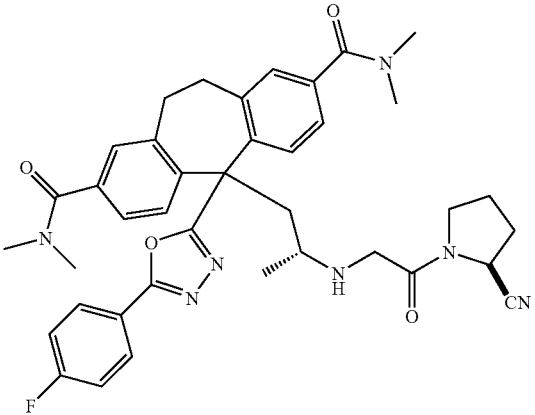 |
| 436 | 400 | 2 | 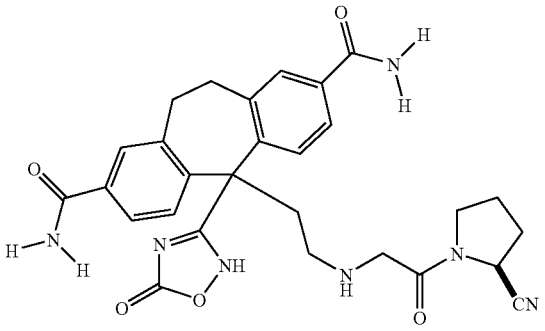 |
| 437 | 401 | 2 | 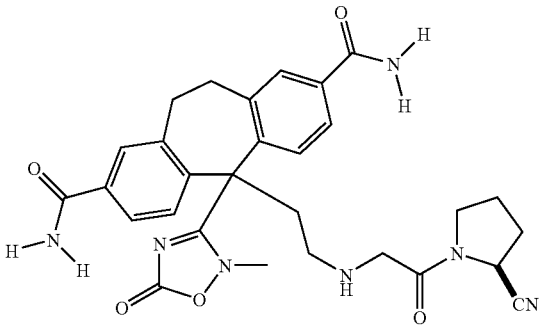 |
| 438 | 402 | 2 | 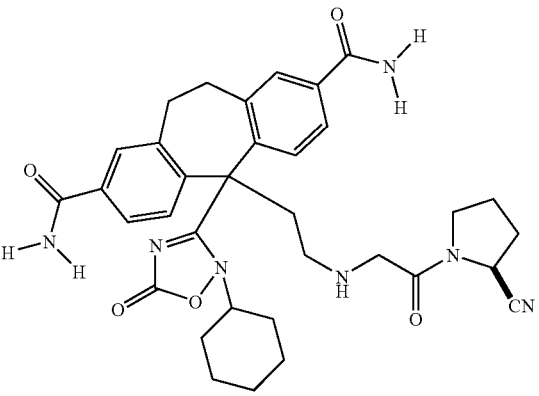 |

-continued
| Example | Preparative Example | Preparative Example | Product |
|---|---|---|---|
| 439 | 403 | 2 | 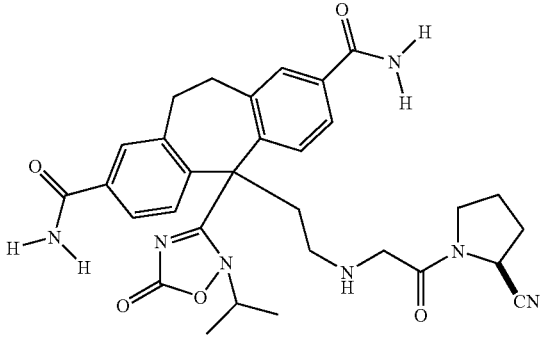 |
| 440 | 404 | 2 | 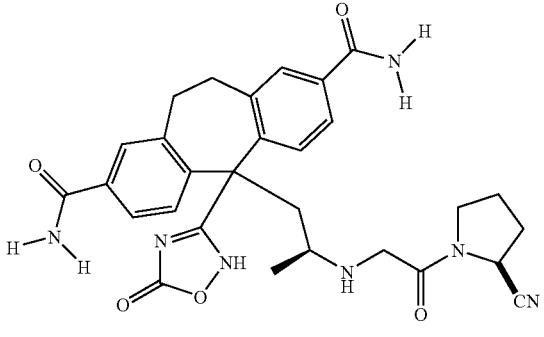 |
| 441 | 405 | 2 | 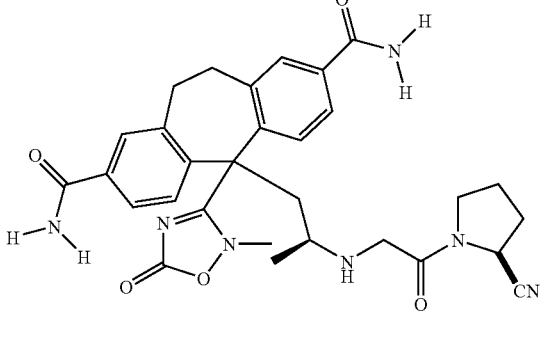 |
| 442 | 406 | 2 | 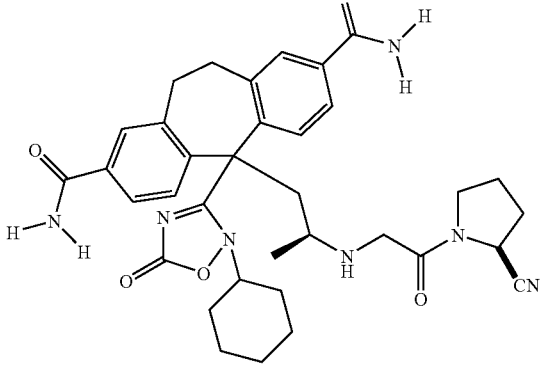 |

-continued
| Example | Preparative Example | Preparative Example | Product |
|---|---|---|---|
| 443 | 407 | 2 | 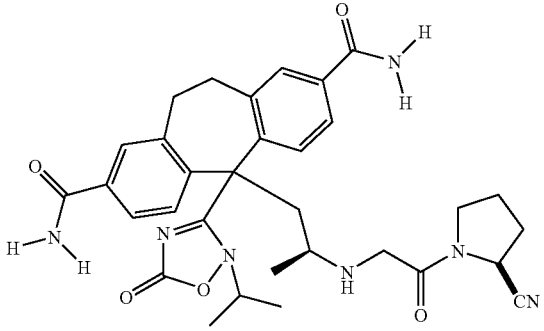 |
| 444 | 408 | 2 | 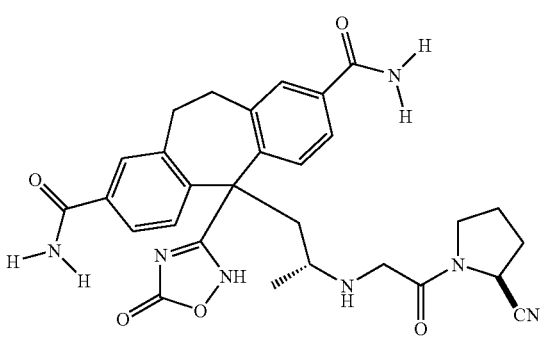 |
| 445 | 409 | 2 | 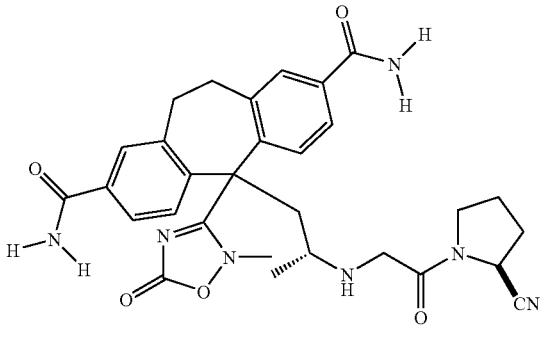 |
| 446 | 410 | 2 | 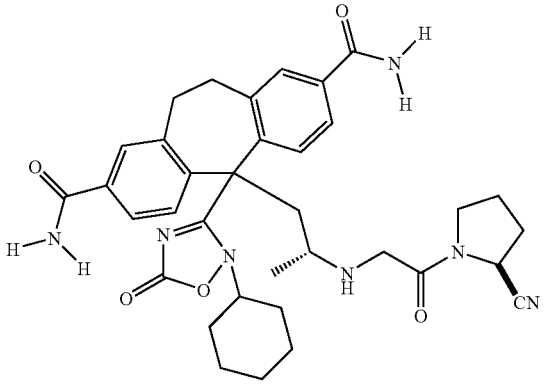 |

-continued
| Example | Preparative Example | Preparative Example | Product |
|---------|---------------------|---------------------|---------|
| 447 | 411 | 2 | 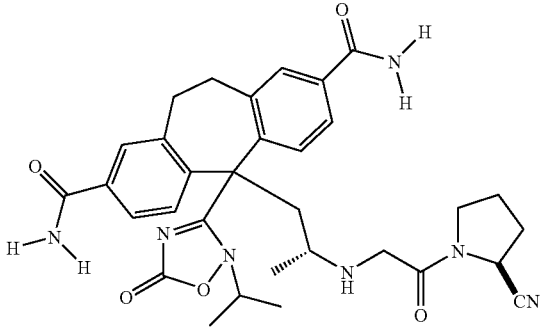 |
| 448 | 412 | 2 | 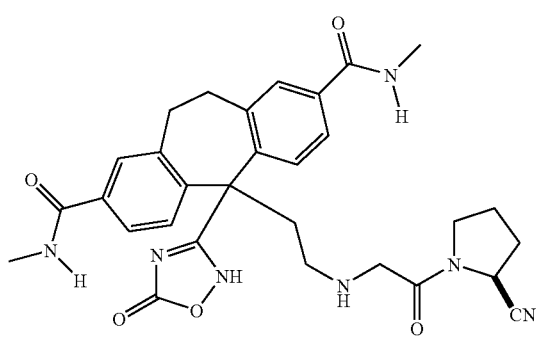 |
| 449 | 413 | 2 | 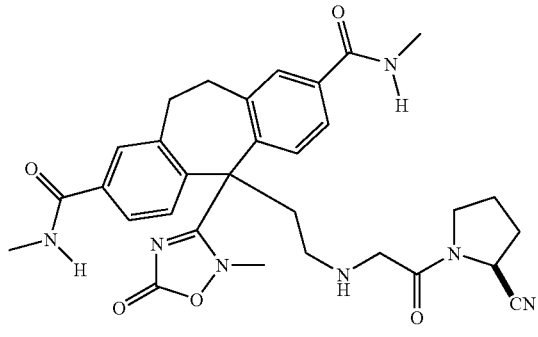 |
| 450 | 414 | 2 | 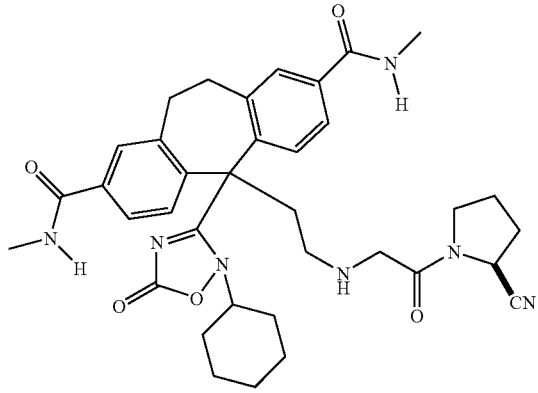 |

-continued

| Example | Preparative Example | Preparative Example | Product |
|---------|---------------------|---------------------|---------|
| 451 | 415 | 2 | |
| 452 | 416 | 2 | |
| 453 | 417 | 2 | |
| 454 | 418 | 2 | |

-continued
| Example | Preparative Example | Preparative Example | Product |
|---|---|---|---|
| 455 | 419 | 2 | 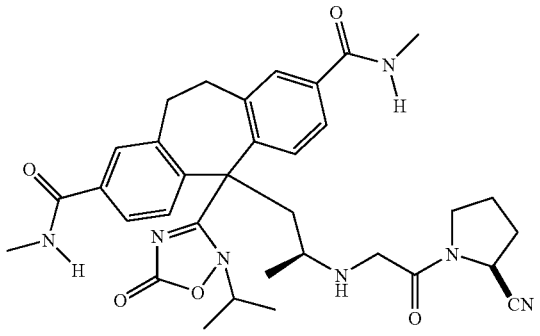 |
| 456 | 420 | 2 | 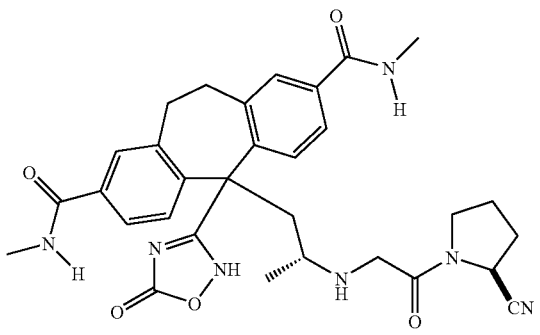 |
| 457 | 421 | 2 | 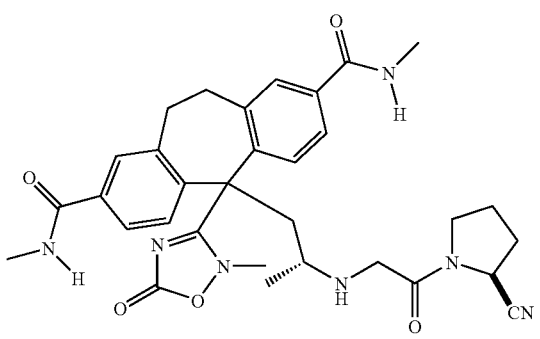 |
| 458 | 422 | 2 | 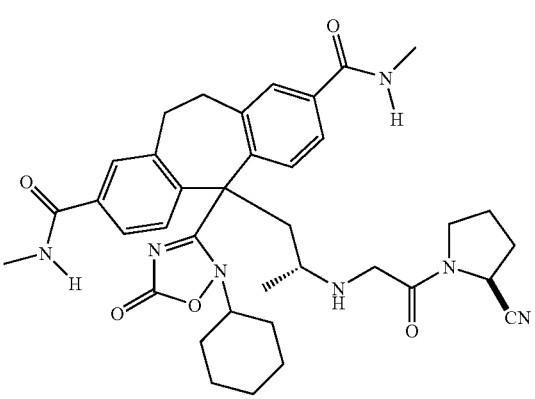 |

-continued
| Example | Preparative Example | Preparative Example | Product |
|---|---|---|---|
| 459 | 423 | 2 | 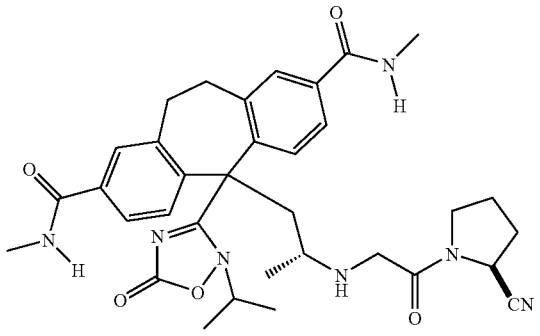 |
| 460 | 424 | 2 | 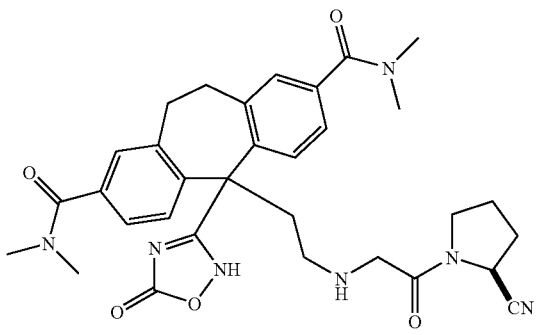 |
| 461 | 425 | 2 | 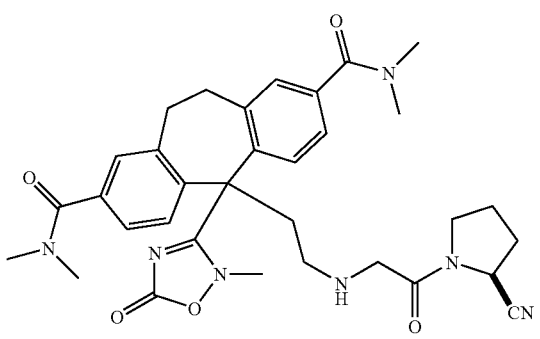 |
| 462 | 426 | 2 | 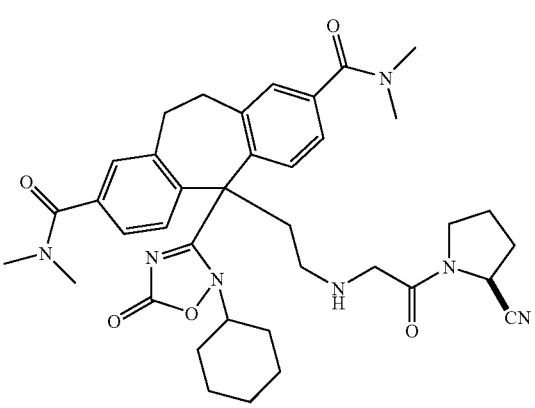 |

-continued
| Example | Preparative Example | Preparative Example | Product |
|---|---|---|---|
| 463 | 427 | 2 | 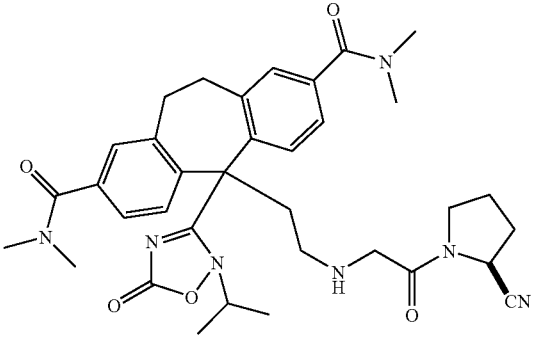 |
| 464 | 428 | 2 | 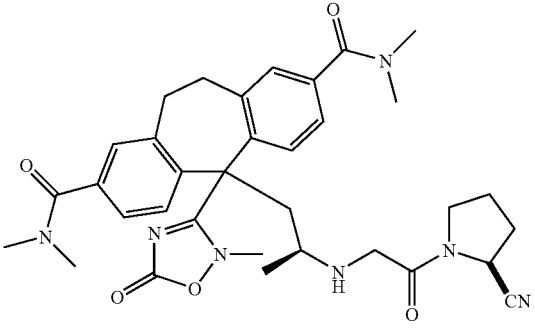 |
| 465 | 429 | 2 | 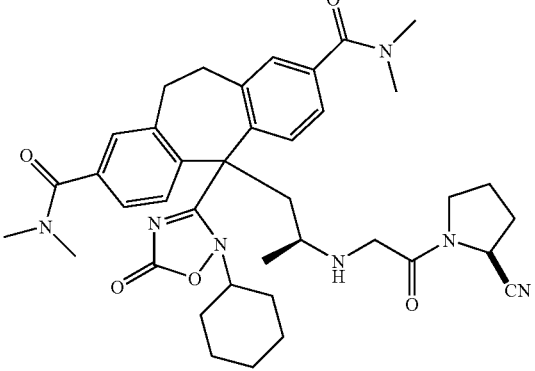 |
| 466 | 430 | 2 | 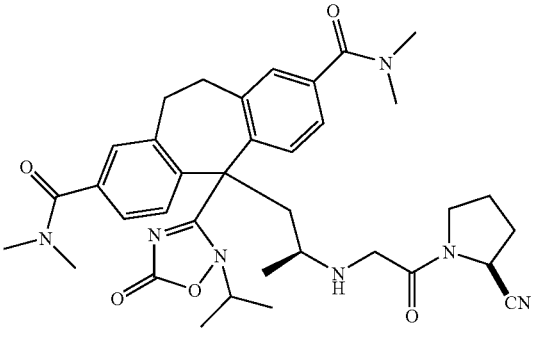 |

-continued

| Example | Preparative Example | Preparative Example | Product |
|---|---|---|---|
| 467 | 431 | 2 | |
| 468 | 432 | 2 | |
| 469 | 433 | 2 | |
| 470 | 434 | 2 | |

-continued
| Example | Preparative Example | Preparative Example | Product |
|---|---|---|---|
| 471 | 500 | 2 | 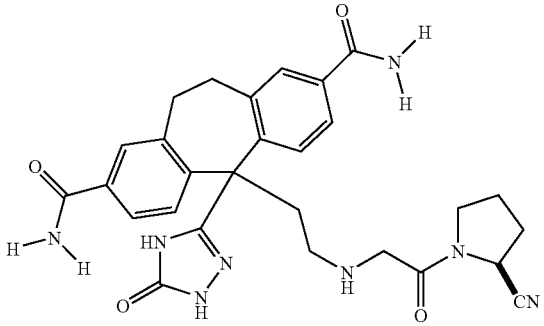 |
| 472 | 501 | 2 | 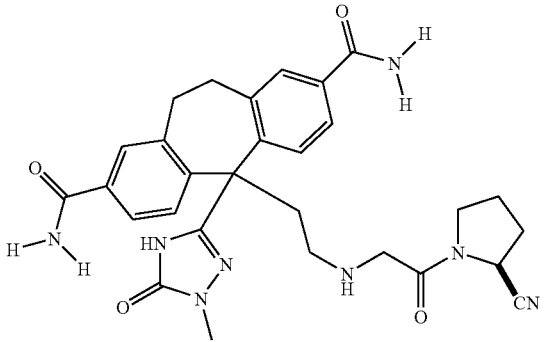 |
| 473 | 502 | 2 | 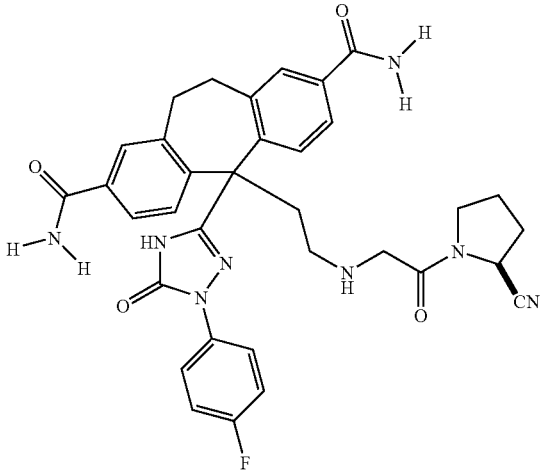 |
| 474 | 503 | 2 | 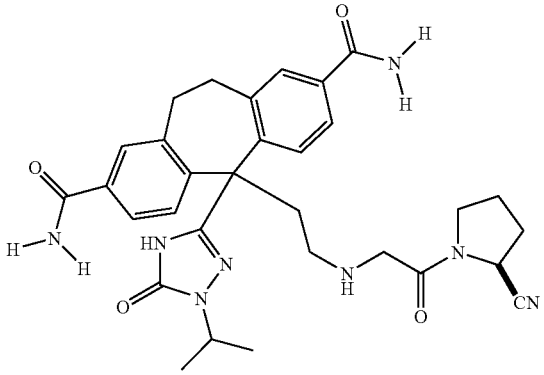 |

-continued
| Example | Preparative Example | Preparative Example | Product |
|---------|--------------------|--------------------|---------|
| 475 | 504 | 2 | 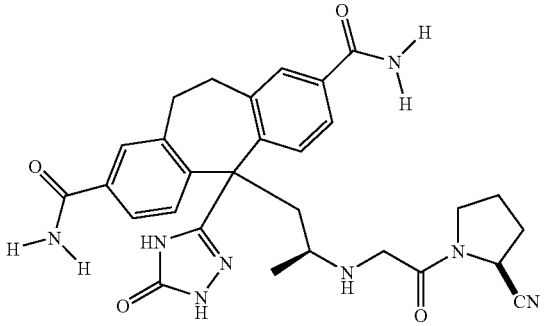 |
| 476 | 505 | 2 | 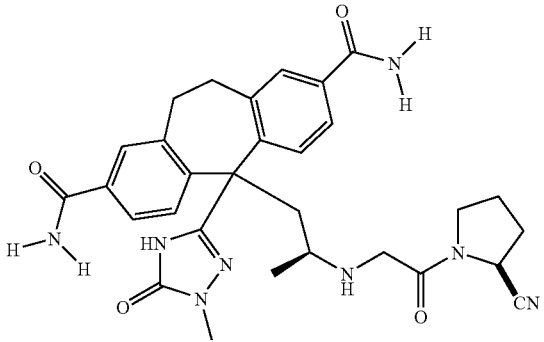 |
| 477 | 506 | 2 | 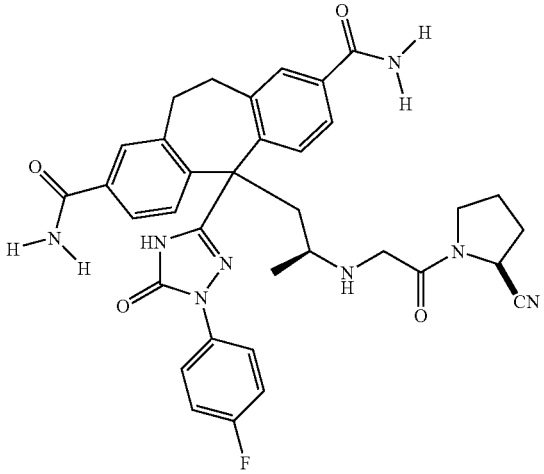 |
| 478 | 507 | 2 | 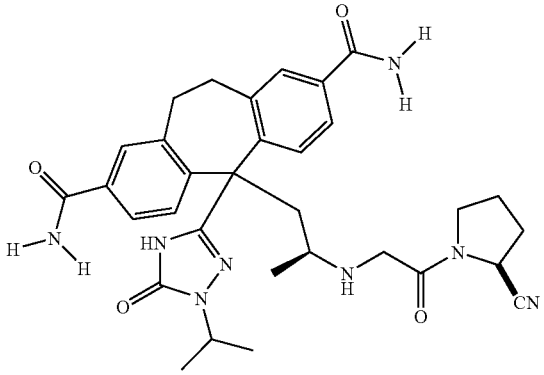 |

| Example | Preparative Example | Preparative Example | Product |
|---|---|---|---|
| 479 | 508 | 2 | |
| 480 | 509 | 2 | |
| 481 | 510 | 2 | |
| 482 | 511 | 2 | |

| Example | Preparative Example | Preparative Example | Product |
|---|---|---|---|
| 483 | 512 | 2 | 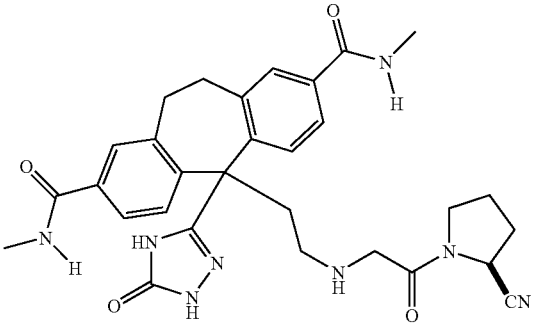 |
| 484 | 513 | 2 | 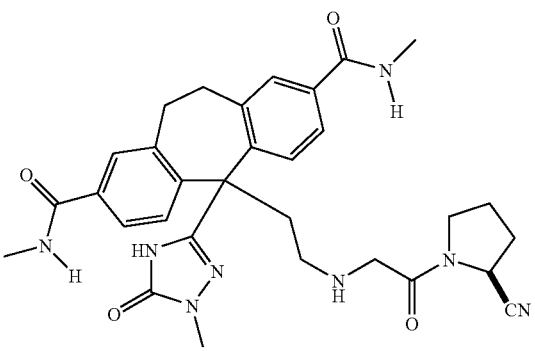 |
| 485 | 514 | 2 | 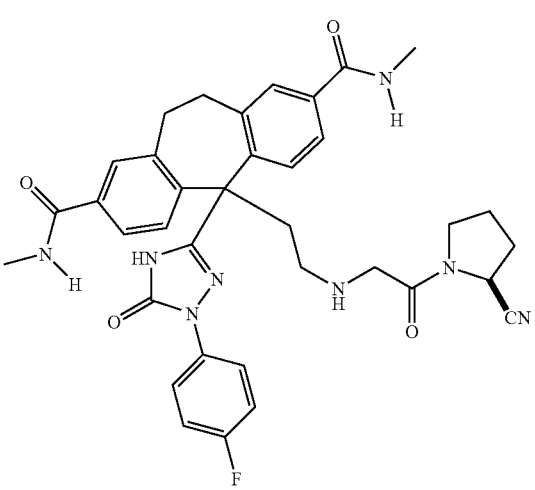 |
| 486 | 515 | 2 | 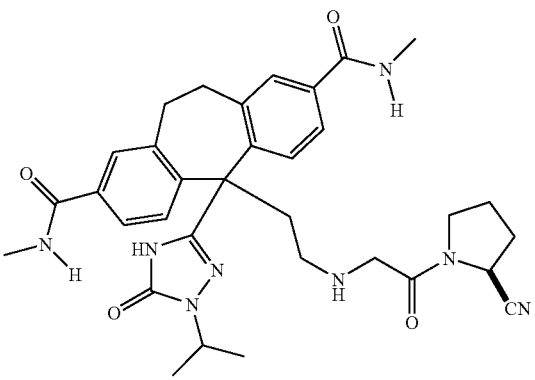 |

-continued
| Example | Preparative Example | Preparative Example | Product |
|---------|--------------------|--------------------|---------|
| 487 | 516 | 2 | 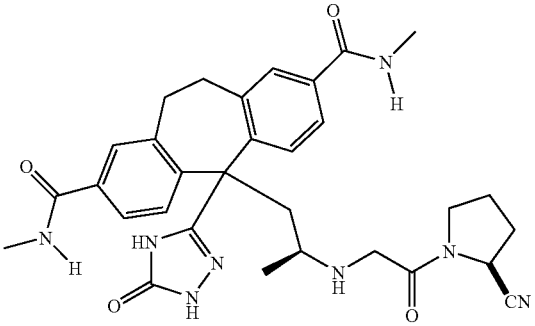 |
| 488 | 517 | 2 | 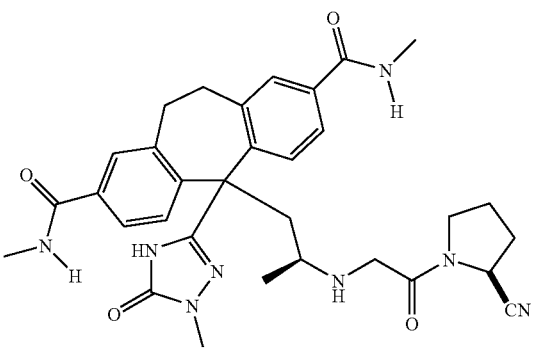 |
| 489 | 518 | 2 | 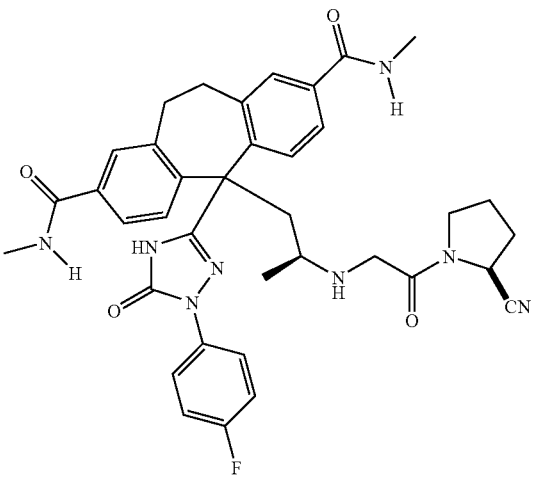 |
| 490 | 519 | 2 | 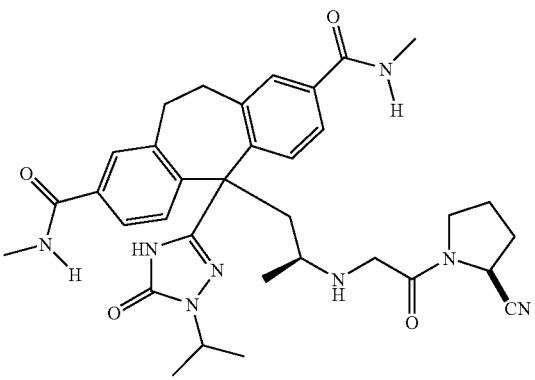 |

| Example | Preparative Example | Preparative Example | Product |
|---|---|---|---|
| 491 | 520 | 2 | 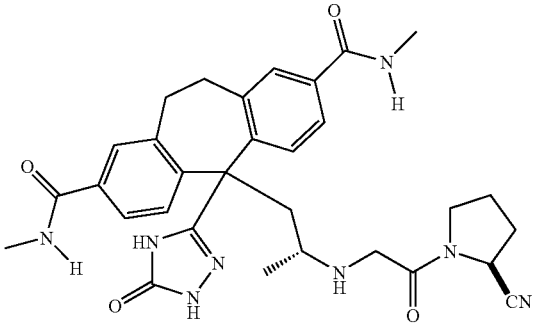 |
| 492 | 521 | 2 | 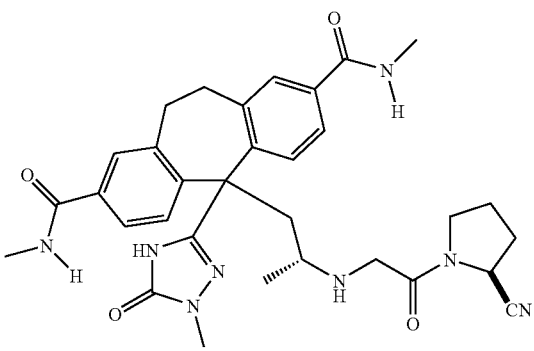 |
| 493 | 522 | 2 | 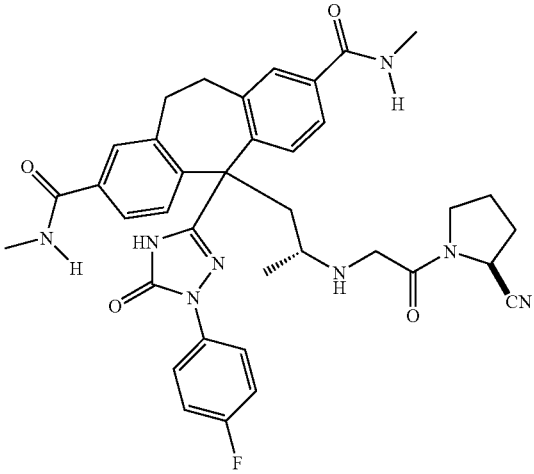 |
| 494 | 523 | 2 | 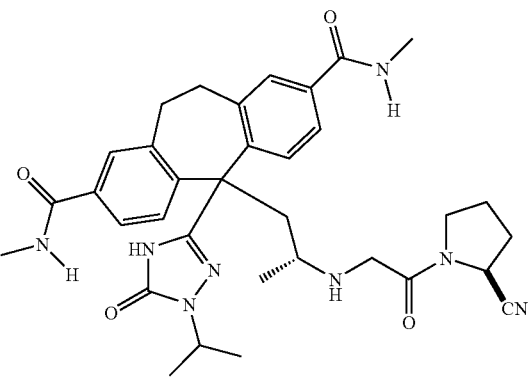 |

| Example | Preparative Example | Preparative Example | Product |
|---|---|---|---|
| 495 | 524 | 2 | 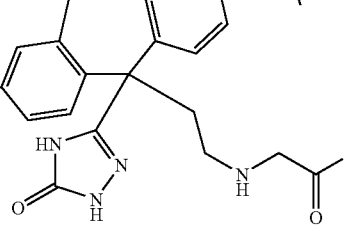 |
| 496 | 525 | 2 | 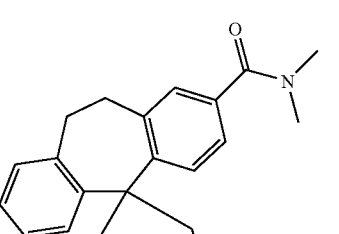 |
| 497 | 526 | 2 | 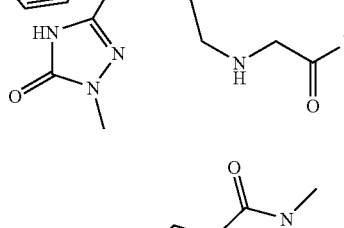 |
| 498 | 527 | 2 | 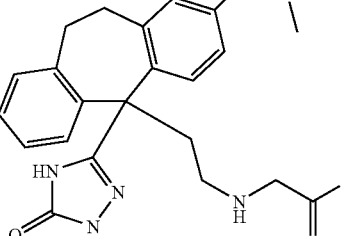 |

| Example | Preparative Example | Preparative Example | Product |
|---|---|---|---|
| 499 | 528 | 2 | 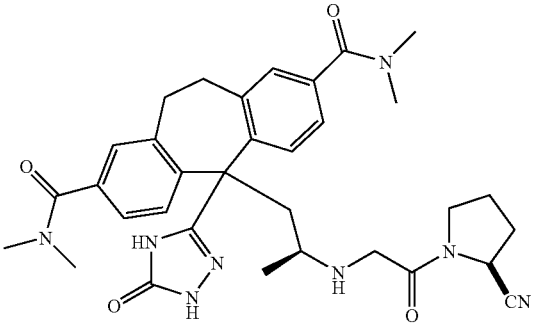 |
| 500 | 529 | 2 | 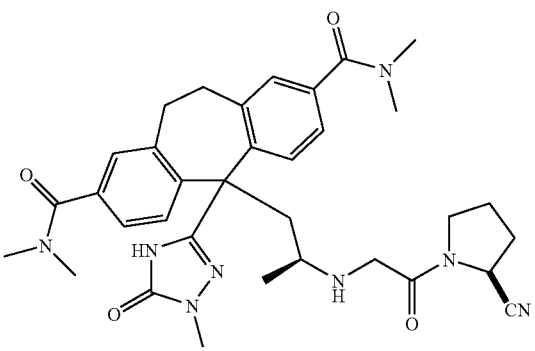 |
| 501 | 530 | 2 | 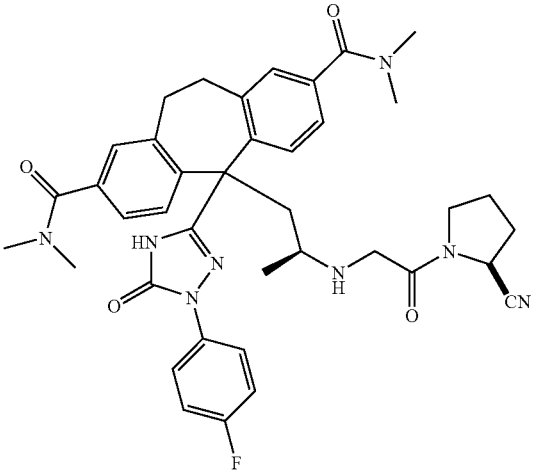 |
| 502 | 531 | 2 | 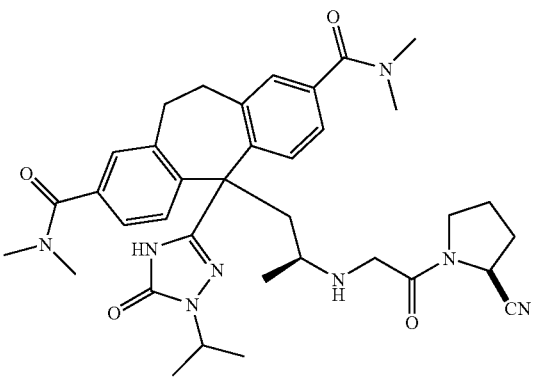 |

| Example | Preparative Example | Preparative Example | Product |
|---|---|---|---|
| 503 | 532 | 2 | 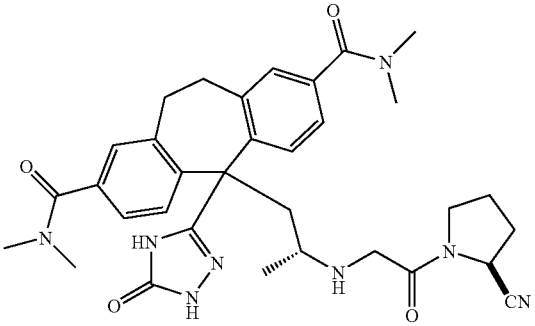 |
| 504 | 533 | 2 | 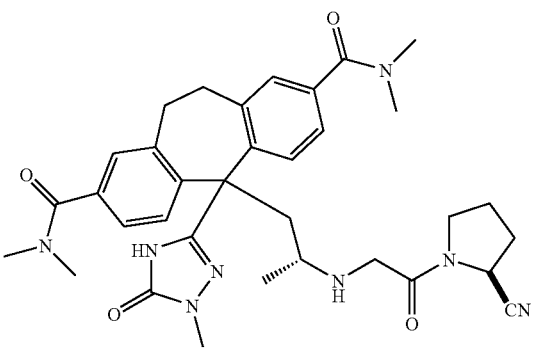 |
| 505 | 534 | 2 | 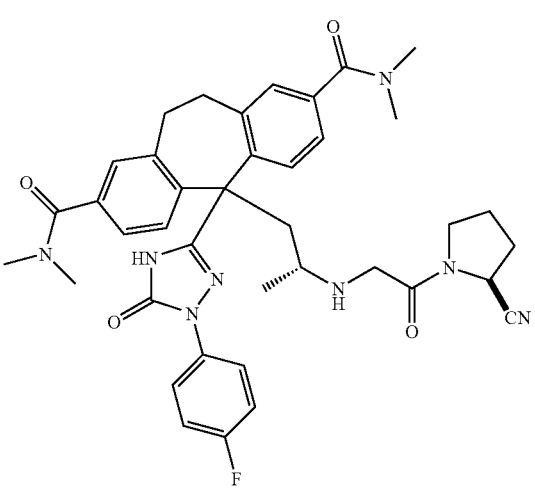 |
| 506 | 535 | 2 | 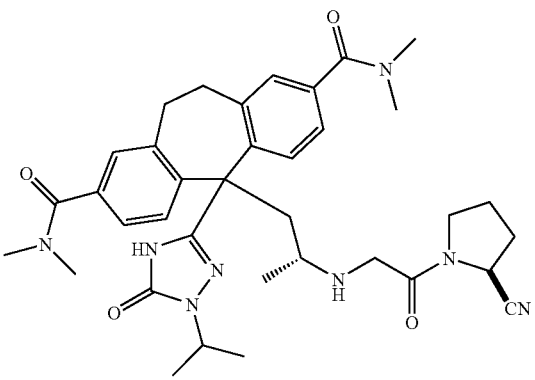 |

| Example | Preparative Example | Preparative Example | Product |
|---|---|---|---|
| 507 | 600 | 2 | |
| 508 | 601 | 2 | |
| 509 | 602 | 2 | |
| 510 | 603 | 2 | |

-continued

| Example | Preparative Example | Preparative Example | Product |
|---|---|---|---|
| 511 | 604 | 2 | |
| 512 | 605 | 2 | |
| 513 | 606 | 2 | |
| 514 | 607 | 2 | |

| Example | Preparative Example | Preparative Example | Product |
| --- | --- | --- | --- |
| 515 | 608 | 2 | 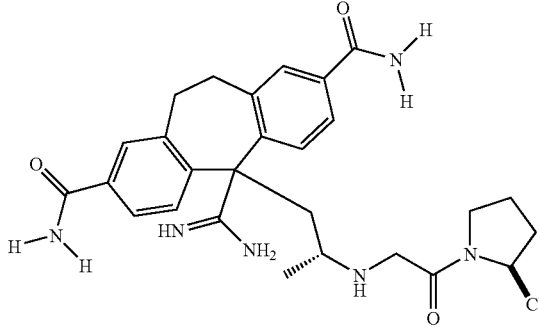 |
| 516 | 609 | 2 | 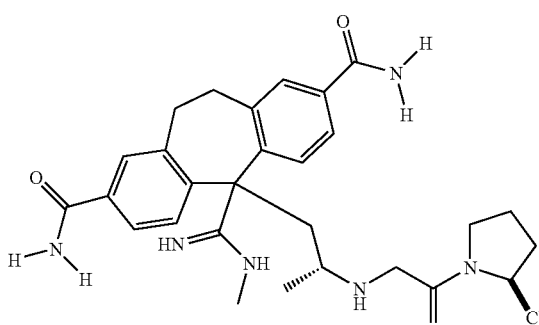 |
| 517 | 610 | 2 | 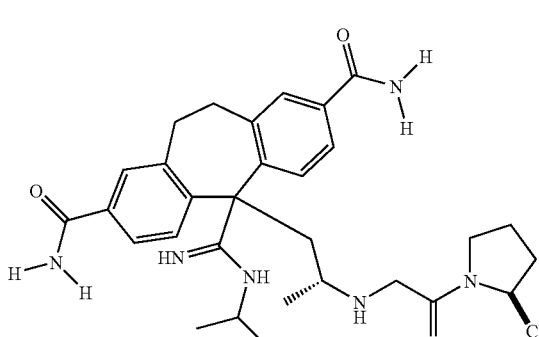 |
| 518 | 611 | 2 | 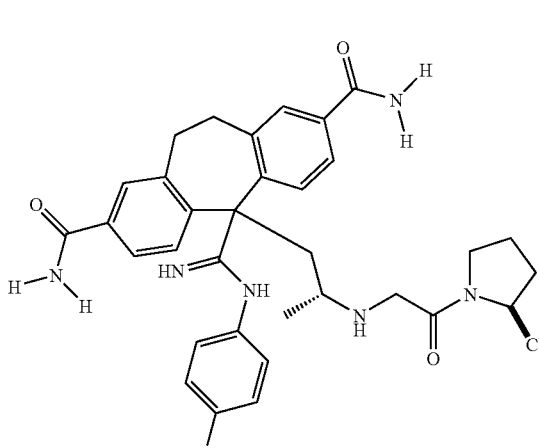 |

-continued
| Example | Preparative Example | Preparative Example | Product |
|---|---|---|---|
| 519 | 612 | 2 | 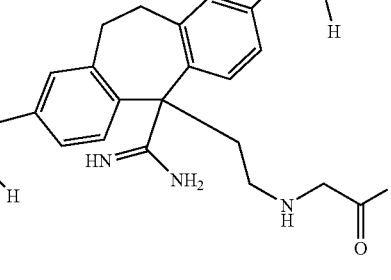 |
| 520 | 613 | 2 | 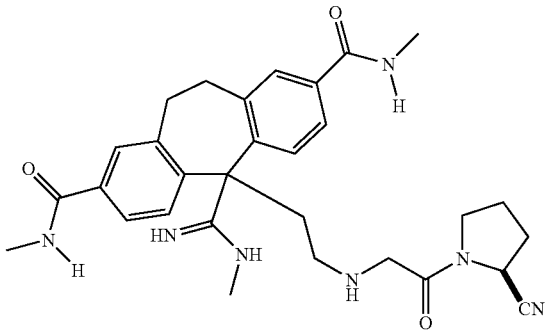 |
| 521 | 614 | 2 | 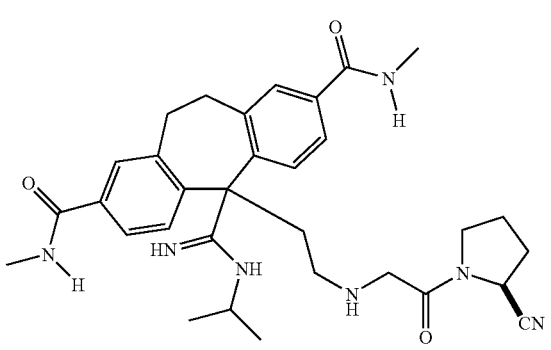 |
| 522 | 615 | 2 | 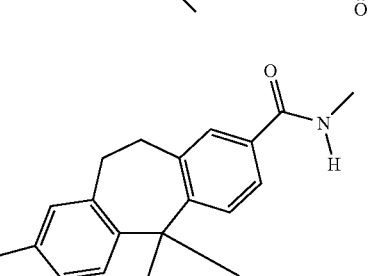 |

-continued

| Example | Preparative Example | Preparative Example | Product |
|---|---|---|---|
| 523 | 616 | 2 | |
| 524 | 617 | 2 | |
| 525 | 618 | 2 | |
| 526 | 619 | 2 | |

| Example | Preparative Example | Preparative Example | Product |
|---|---|---|---|
| 527 | 620 | 2 | 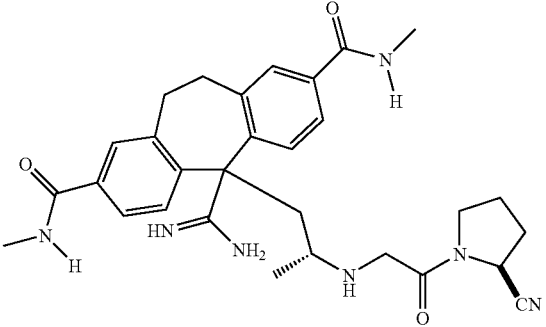 |
| 528 | 621 | 2 | 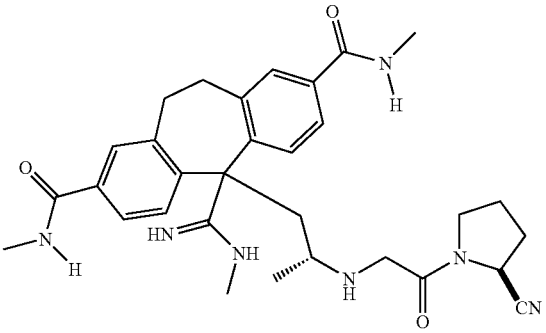 |
| 529 | 622 | 2 | 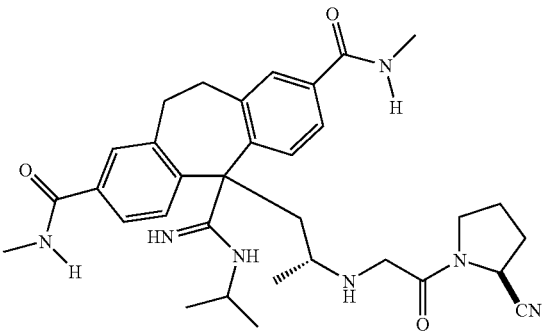 |
| 530 | 623 | 2 | 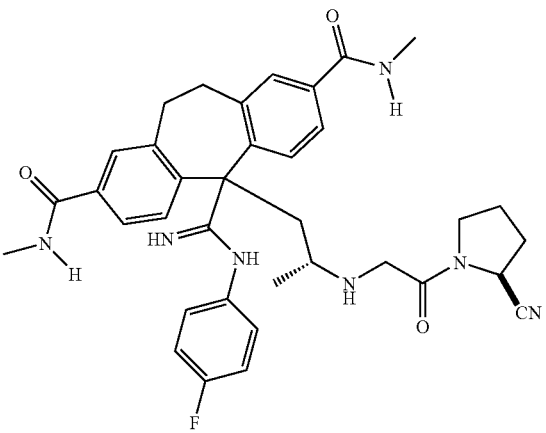 |

-continued

| Example | Preparative Example | Preparative Example | Product |
|---|---|---|---|
| 531 | 624 | 2 | |
| 532 | 625 | 2 | |
| 533 | 626 | 2 | |
| 534 | 627 | 2 | |

| Example | Preparative Example | Preparative Example | Product |
|---|---|---|---|
| 535 | 628 | 2 | |
| 536 | 629 | 2 | |
| 537 | 630 | 2 | |
| 538 | 631 | 2 | |

-continued

| Example | Preparative Example | Preparative Example | Product |
|---------|---------------------|---------------------|---------|
| 539 | 632 | 2 | |
| 540 | 633 | 2 | |
| 541 | 634 | 2 | |
| 542 | 635 | 2 | |

-continued
| Example | Preparative Example | Preparative Example | Product |
|---------|---------------------|---------------------|---------|
| 543 | 680 | 2 | 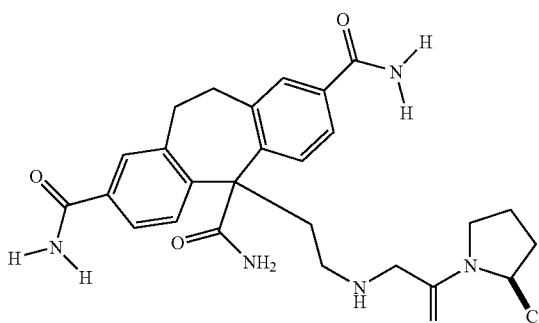 |
| 544 | 681 | 2 | 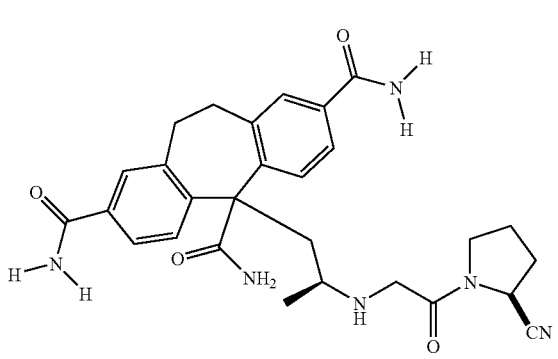 |
| 545 | 682 | 2 | 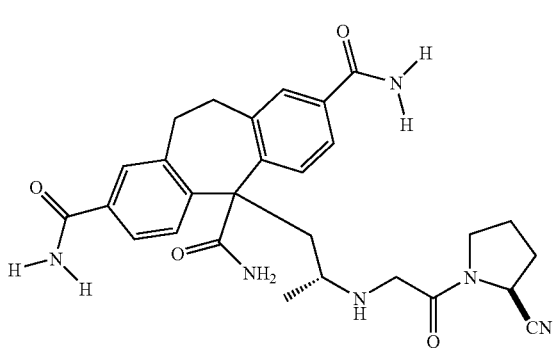 |
| 546 | 683 | 2 | 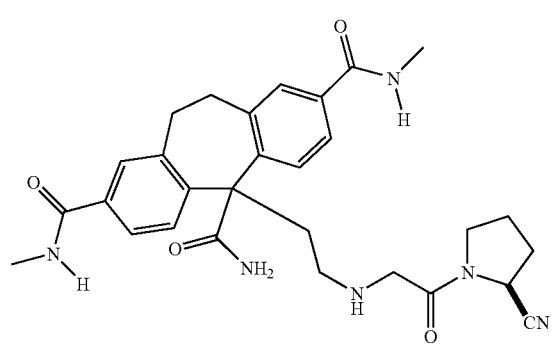 |

| Example | Preparative Example | Preparative Example | Product |
|---|---|---|---|
| 547 | 684 | 2 | |
| 548 | 685 | 2 | |
| 549 | 686 | 2 | |
| 550 | 687 | 2 | |

| Example | Preparative Example | Preparative Example | Product |
|---|---|---|---|
| 551 | 700 | 2 | 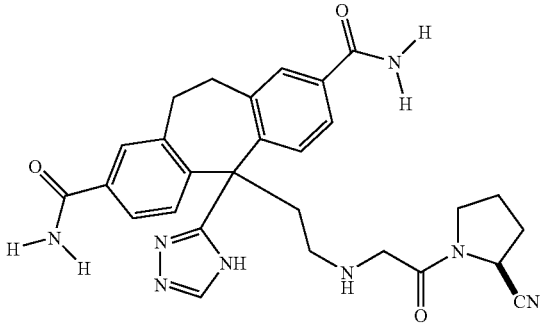 |
| 552 | 701 | 2 | 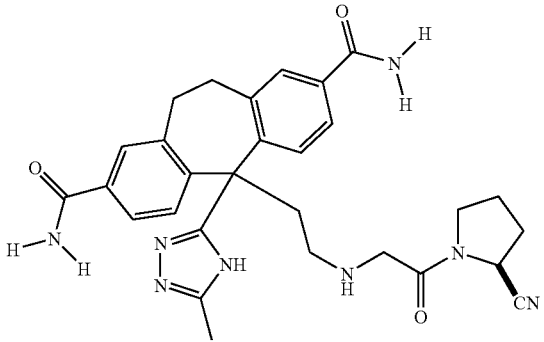 |
| 553 | 702 | 2 | 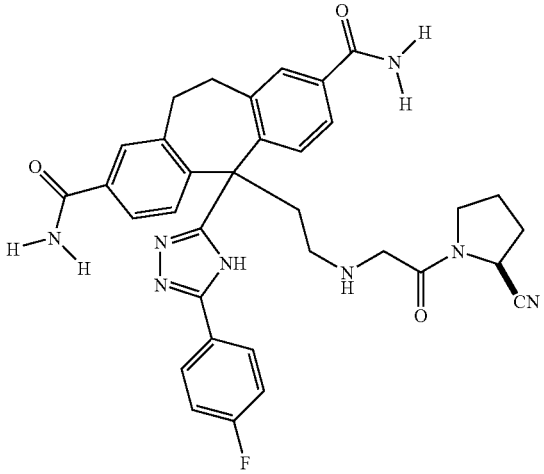 |
| 554 | 703 | 2 | 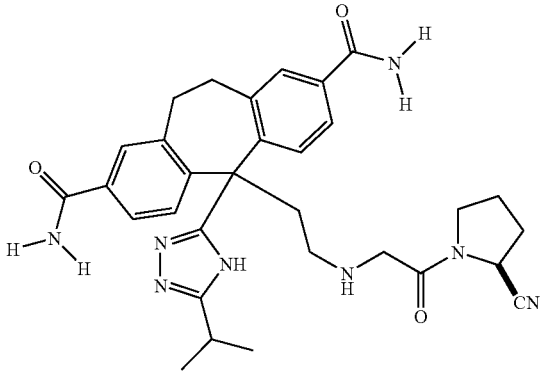 |

-continued

| Example | Preparative Example | Preparative Example | Product |
|---|---|---|---|
| 555 | 704 | 2 | |
| 556 | 705 | 2 | |
| 557 | 706 | 2 | |
| 558 | 707 | 2 | |

-continued

| Example | Preparative Example | Preparative Example | Product |
|---|---|---|---|
| 559 | 708 | 2 | |
| 560 | 709 | 2 | |
| 561 | 710 | 2 | |
| 562 | 711 | 2 | |

| Example | Preparative Example | Preparative Example | Product |
|---|---|---|---|
| 563 | 712 | 2 | |
| 564 | 713 | 2 | |
| 565 | 714 | 2 | |
| 566 | 715 | 2 | |

-continued
| Example | Preparative Example | Preparative Example | Product |
|---|---|---|---|
| 567 | 716 | 2 | 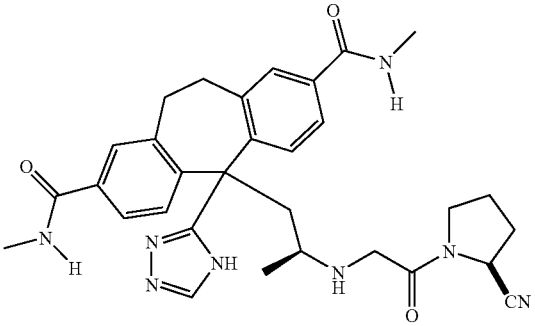 |
| 568 | 717 | 2 | 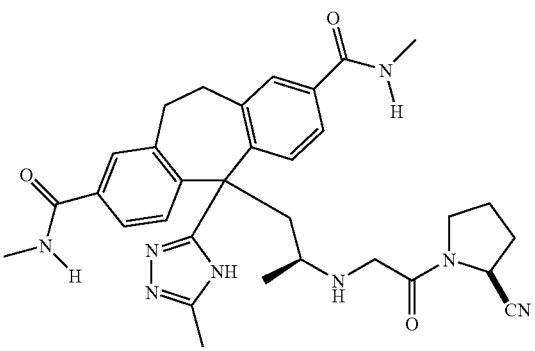 |
| 569 | 718 | 2 | 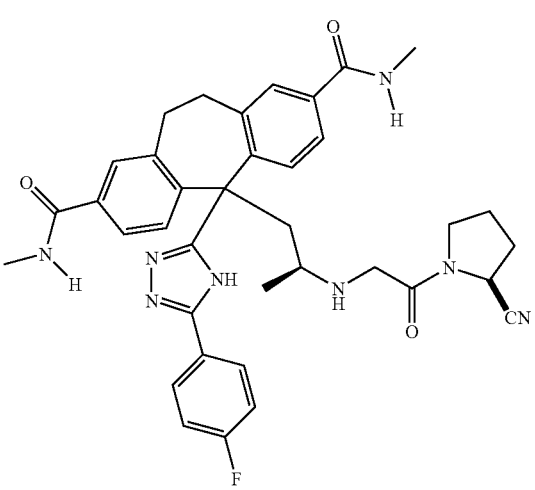 |
| 570 | 719 | 2 | 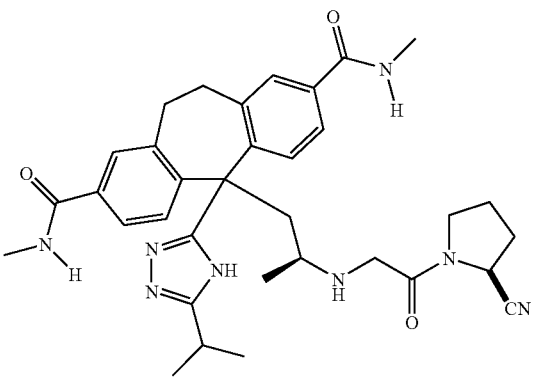 |

-continued

| Example | Preparative Example | Preparative Example | Product |
|---|---|---|---|
| 571 | 720 | 2 | |
| 572 | 721 | 2 | |
| 573 | 722 | 2 | |
| 574 | 723 | 2 | |

-continued

| Example | Preparative Example | Preparative Example | Product |
|---|---|---|---|
| 575 | 724 | 2 | |
| 576 | 725 | 2 | |
| 577 | 726 | 2 | |
| 578 | 727 | 2 | |

| Example | Preparative Example | Preparative Example | Product |
|---|---|---|---|
| 579 | 728 | 2 | |
| 580 | 729 | 2 | |
| 581 | 730 | 2 | |
| 582 | 731 | 2 | |

-continued

| Example | Preparative Example | Preparative Example | Product |
|---------|---------------------|---------------------|---------|
| 583 | 732 | 2 | |
| 584 | 733 | 2 | |
| 585 | 734 | 2 | |
| 586 | 735 | 2 | |

-continued

| Example | Preparative Example | Preparative Example | Product |
|---------|---------------------|---------------------|---------|
| 587 | 780 | 2 | |
| 588 | 781 | 2 | |
| 589 | 782 | 2 | |
| 590 | 783 | 2 | |

|Example|Preparative Example|Preparative Example|Product|
|---|---|---|---|
|591|784|2||
|592|785|2||
|593|786|2||
|594|787|2||

-continued

| Example | Preparative Example | Preparative Example | Product |
|---------|---------------------|---------------------|---------|
| 595 | 788 | 2 | 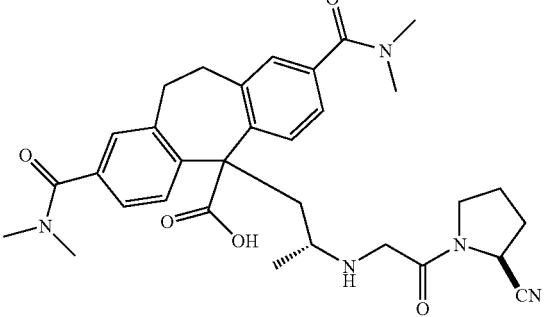 |

Examples 596-599 have been intentionally excluded.

Example 600-795

If one were to follow the procedures outlined in Examples 28 or 29 except using the compounds from the Preparative Examples as indicated in the Table below, one would obtain the indicated Product.

| Example | Preparative Example | Preparative Example | Product |
|---------|---------------------|---------------------|---------|
| 600 | 336 | 89 | 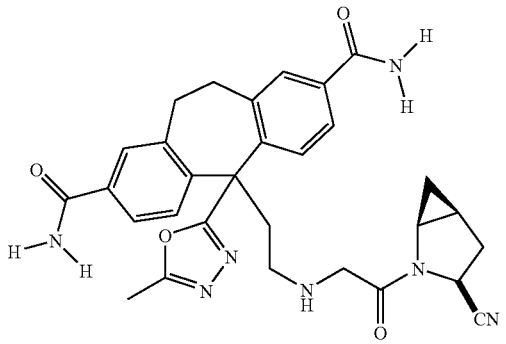 |
| 601 | 337 | 89 | 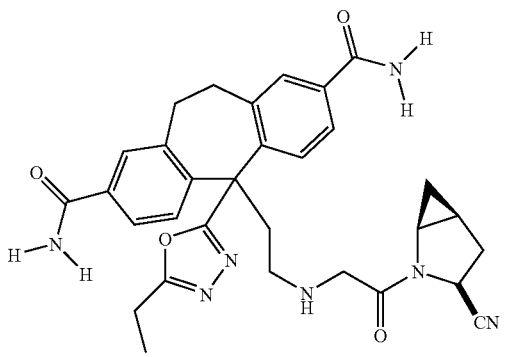 |

-continued

| Example | Preparative Example | Preparative Example | Product |
|---|---|---|---|
| 602 | 338 | 89 | |
| 603 | 339 | 89 | |
| 604 | 340 | 89 | |
| 605 | 341 | 89 | |

-continued

| Example | Preparative Example | Preparative Example | Product |
|---|---|---|---|
| 606 | 342 | 89 | |
| 607 | 343 | 89 | |
| 608 | 344 | 89 | |
| 609 | 345 | 89 | |

-continued

| Example | Preparative Example | Preparative Example | Product |
|---------|---------------------|---------------------|---------|
| 610 | 346 | 89 | |
| 611 | 347 | 89 | |
| 612 | 348 | 89 | |
| 613 | 349 | 89 | |

-continued
| Example | Preparative Example | Preparative Example | Product |
|---|---|---|---|
| 614 | 350 | 89 | 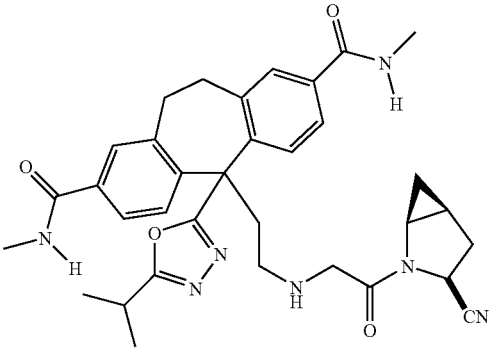 |
| 615 | 351 | 89 | 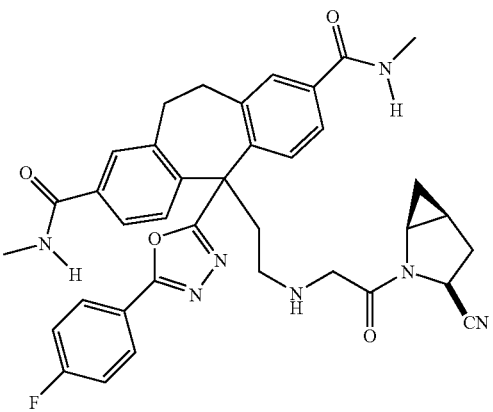 |
| 616 | 352 | 89 | 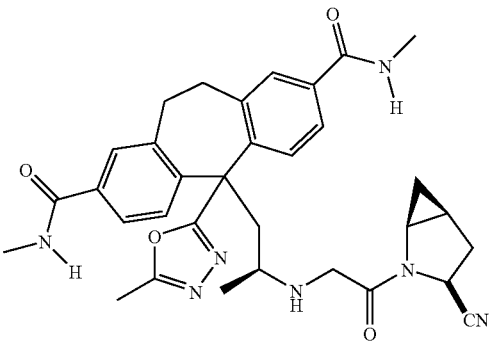 |
| 617 | 353 | 89 | 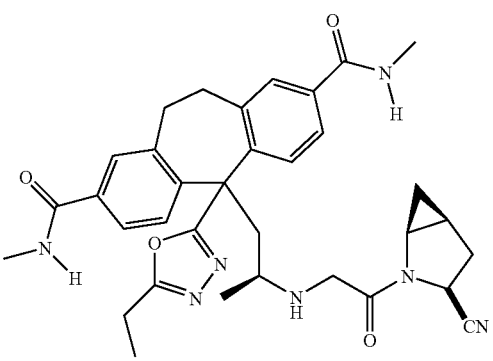 |

-continued

| Example | Preparative Example | Preparative Example | Product |
|---|---|---|---|
| 618 | 354 | 89 | |
| 619 | 355 | 89 | |
| 620 | 356 | 89 | |
| 621 | 357 | 89 | |

| Example | Preparative Example | Preparative Example | Product |
|---|---|---|---|
| 622 | 358 | 89 | 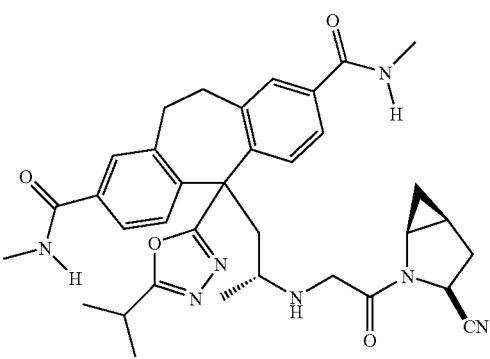 |
| 623 | 359 | 89 | 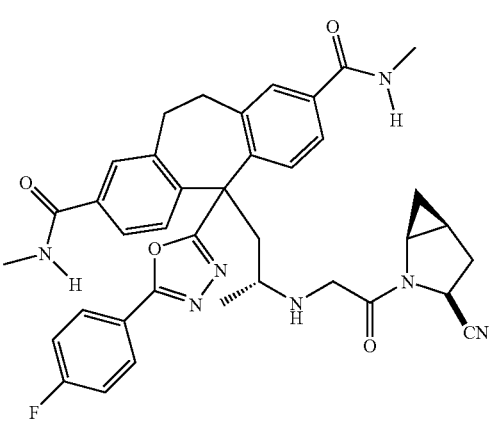 |
| 624 | 360 | 89 | 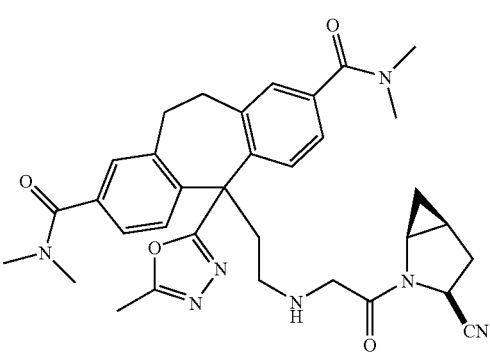 |
| 625 | 361 | 89 | 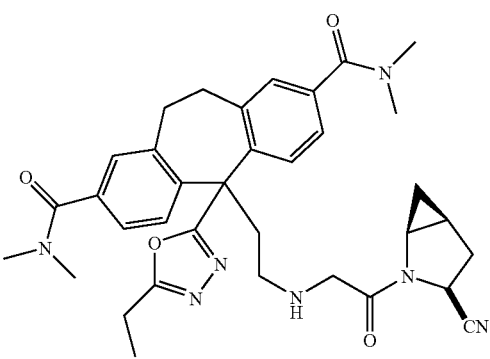 |

| Example | Preparative Example | Preparative Example | Product |
|---|---|---|---|
| 626 | 362 | 89 | |
| 627 | 363 | 89 | |
| 628 | 364 | 89 | |
| 629 | 365 | 89 | |

-continued
| Example | Preparative Example | Preparative Example | Product |
|---|---|---|---|
| 630 | 366 | 89 | 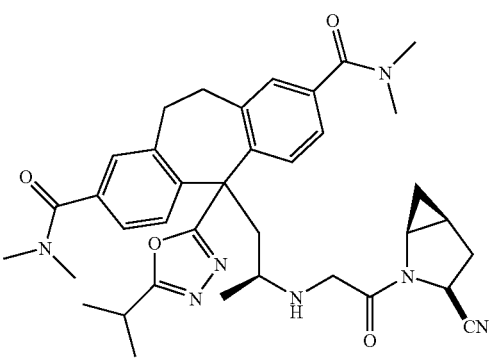 |
| 631 | 367 | 89 | 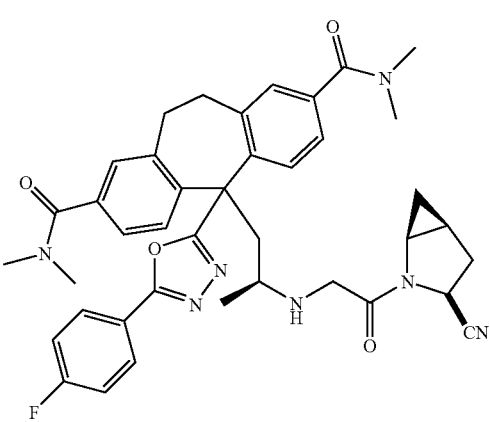 |
| 632 | 368 | 89 | 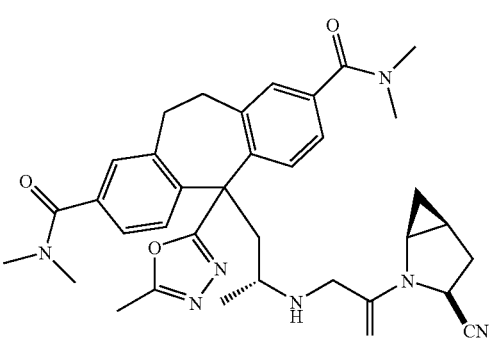 |
| 633 | 369 | 89 | 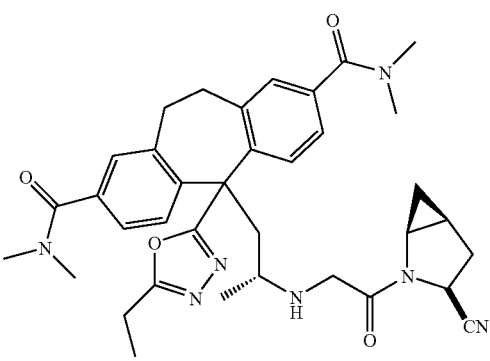 |

-continued

| Example | Preparative Example | Preparative Example | Product |
|---|---|---|---|
| 634 | 370 | 89 | |
| 635 | 371 | 89 | |
| 636 | 435 | 89 | |
| 637 | 436 | 89 | |

-continued
| Example | Preparative Example | Preparative Example | Product |
| --- | --- | --- | --- |
| 638 | 437 | 89 | 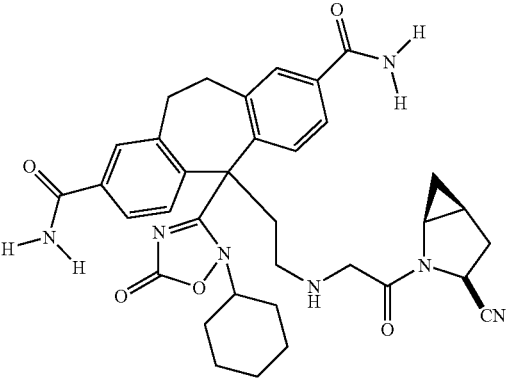 |
| 639 | 438 | 89 | 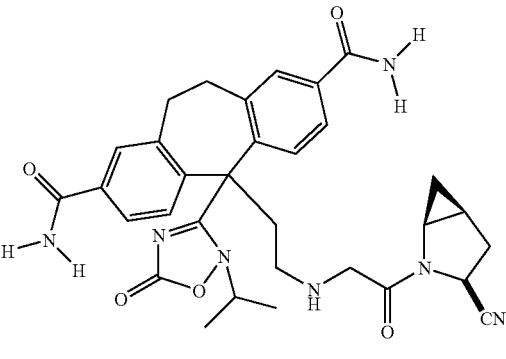 |
| 640 | 439 | 89 | 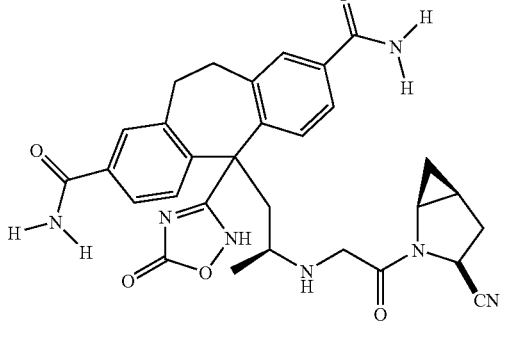 |
| 641 | 440 | 89 | 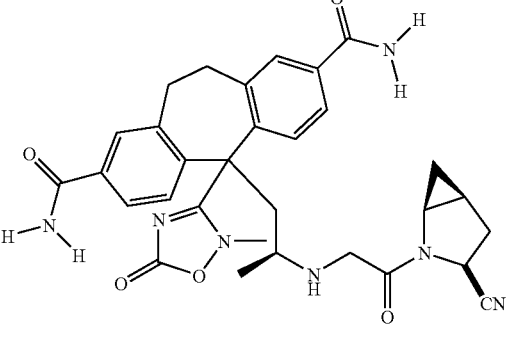 |

-continued

| Example | Preparative Example | Preparative Example | Product |
|---------|--------------------|--------------------|---------|
| 642 | 441 | 89 | |
| 643 | 442 | 89 | |
| 644 | 443 | 89 | |
| 645 | 444 | 89 | |

-continued

| Example | Preparative Example | Preparative Example | Product |
|---|---|---|---|
| 646 | 445 | 89 | |
| 647 | 446 | 89 | |
| 648 | 447 | 89 | |
| 649 | 448 | 89 | |

-continued

| Example | Preparative Example | Preparative Example | Product |
|---|---|---|---|
| 650 | 449 | 89 | |
| 651 | 450 | 89 | |
| 652 | 451 | 89 | |
| 653 | 452 | 89 | |

-continued

| Example | Preparative Example | Preparative Example | Product |
|---------|---------------------|---------------------|---------|
| 654 | 453 | 89 | |
| 655 | 454 | 89 | |
| 656 | 455 | 89 | |
| 657 | 456 | 89 | |

-continued

| Example | Preparative Example | Preparative Example | Product |
|---------|---------------------|---------------------|---------|
| 658 | 457 | 89 | |
| 659 | 458 | 89 | |
| 660 | 459 | 89 | |
| 661 | 460 | 89 | |

| Example | Preparative Example | Preparative Example | Product |
|---------|---------------------|---------------------|---------|
| 662 | 461 | 89 | |
| 663 | 462 | 89 | |
| 664 | 463 | 89 | |
| 665 | 464 | 89 | |

-continued

| Example | Preparative Example | Preparative Example | Product |
|---------|--------------------|--------------------|---------|
| 666 | 465 | 89 | |
| 667 | 466 | 89 | |
| 668 | 467 | 89 | |
| 669 | 468 | 89 | |

-continued
| Example | Preparative Example | Preparative Example | Product |
|---|---|---|---|
| 670 | 469 | 89 | 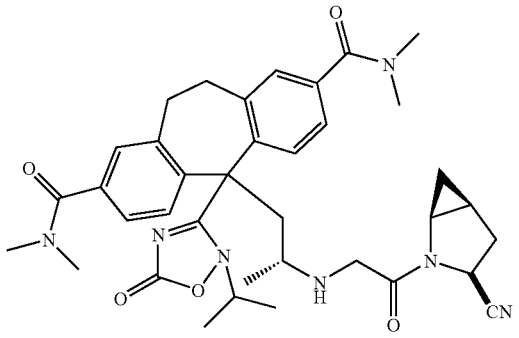 |
| 671 | 536 | 89 | 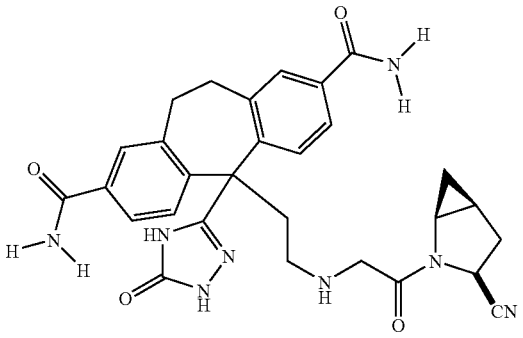 |
| 672 | 537 | 89 | 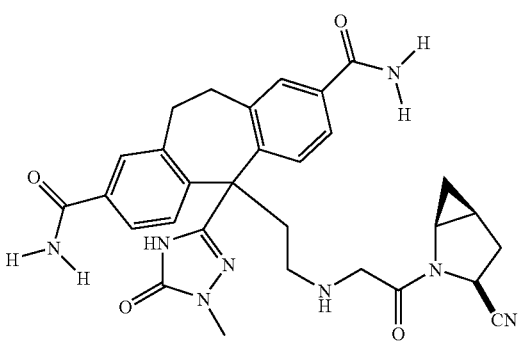 |
| 673 | 538 | 89 | 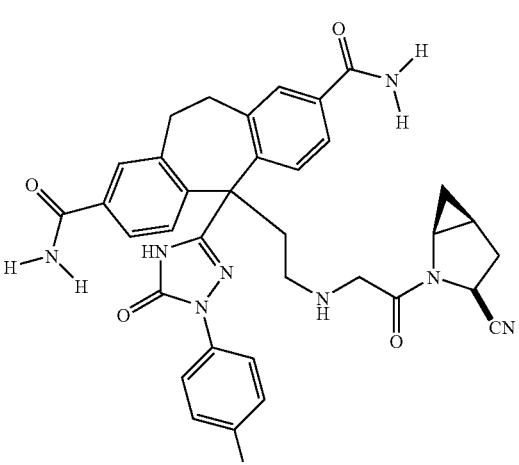 |

-continued
| Example | Preparative Example | Preparative Example | Product |
|---|---|---|---|
| 674 | 539 | 89 | 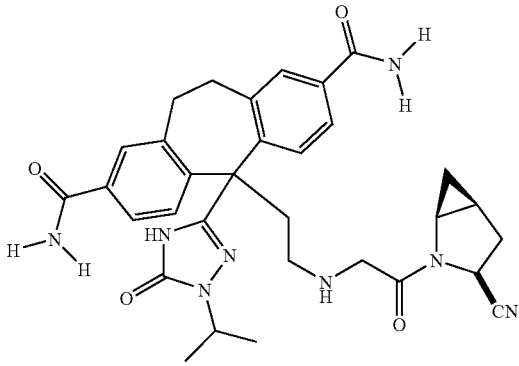 |
| 675 | 540 | 89 | 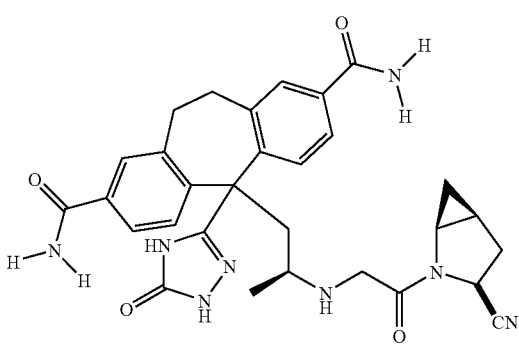 |
| 676 | 541 | 89 | 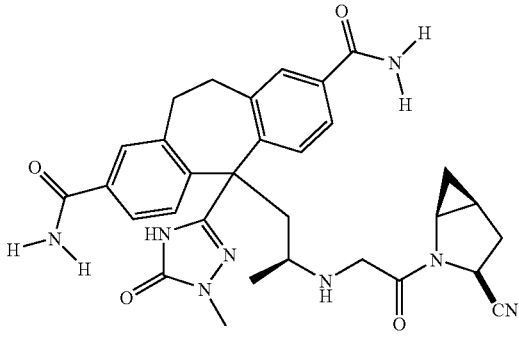 |
| 677 | 542 | 89 | 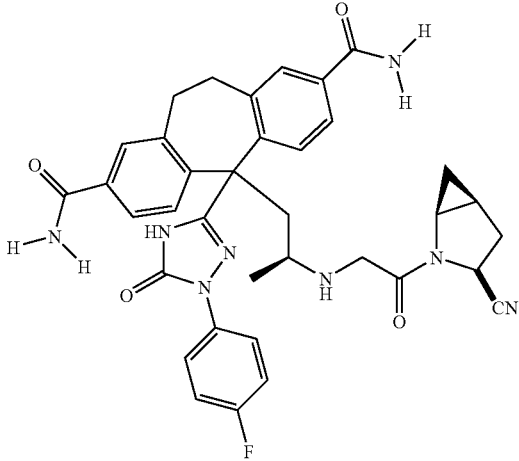 |

-continued
| Example | Preparative Example | Preparative Example | Product |
|---|---|---|---|
| 678 | 543 | 89 | 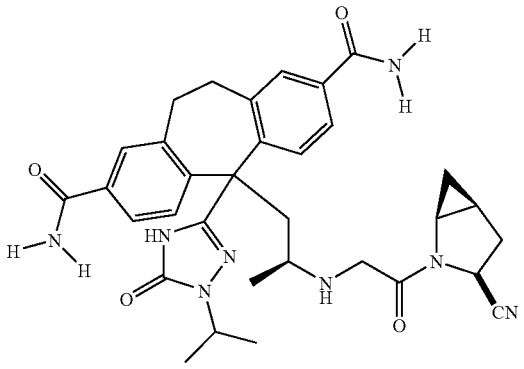 |
| 679 | 544 | 89 | 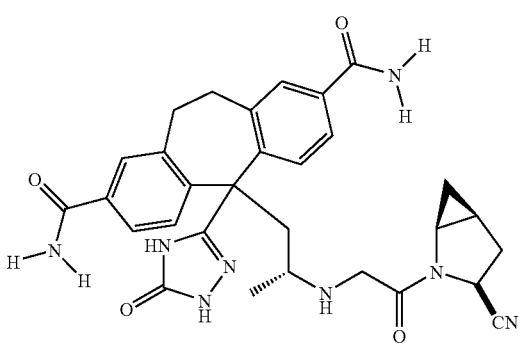 |
| 680 | 545 | 89 | 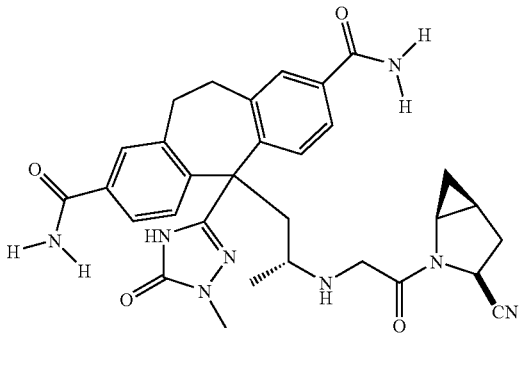 |
| 681 | 546 | 89 | 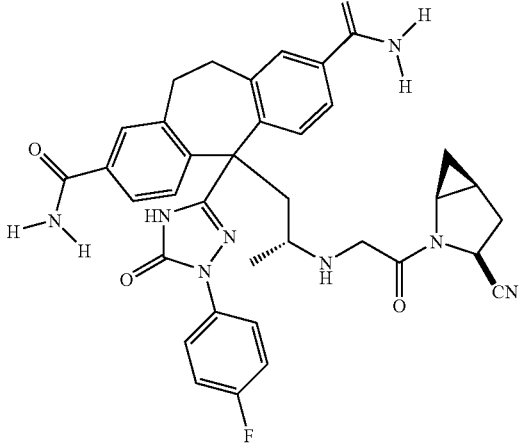 |

-continued
| Example | Preparative Example | Preparative Example | Product |
|---------|--------------------|--------------------|---------|
| 682 | 547 | 89 | 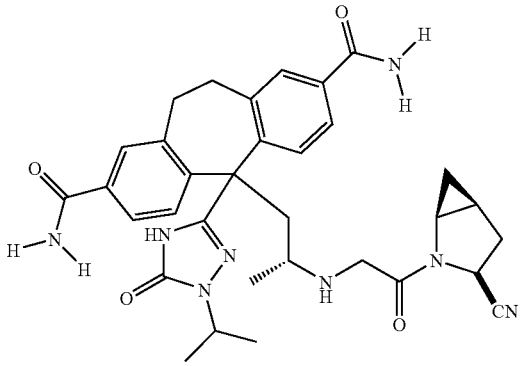 |
| 683 | 548 | 89 | 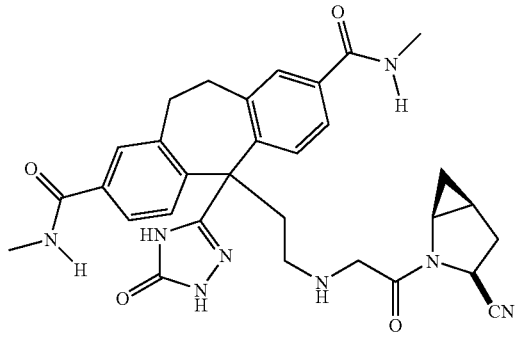 |
| 684 | 549 | 89 | 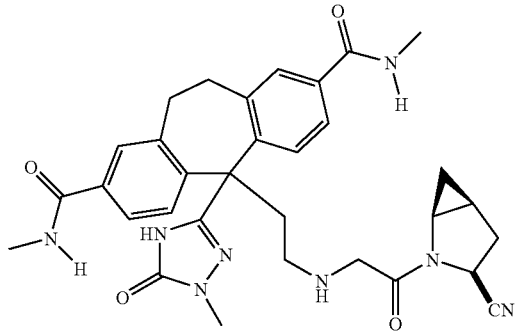 |
| 685 | 550 | 89 | 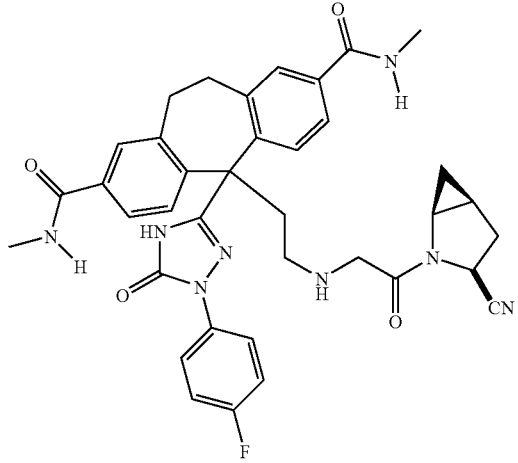 |

-continued
| Example | Preparative Example | Preparative Example | Product |
|---|---|---|---|
| 686 | 551 | 89 | 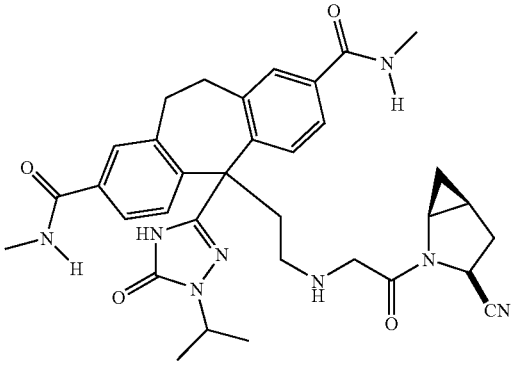 |
| 687 | 552 | 89 | 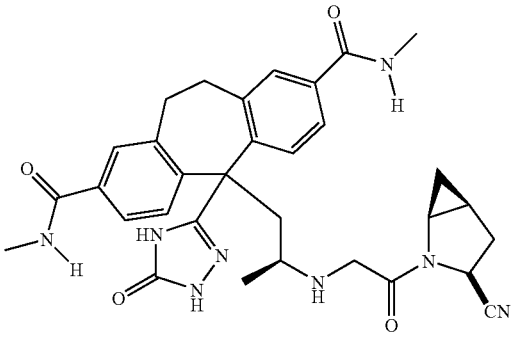 |
| 688 | 553 | 89 | 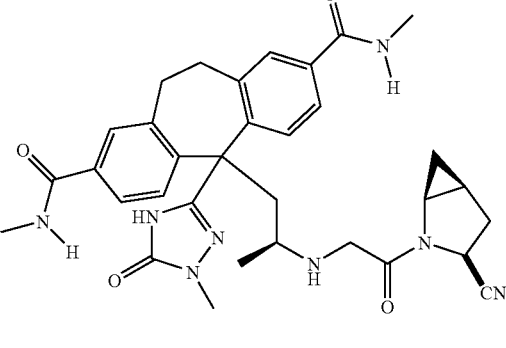 |
| 689 | 554 | 89 | 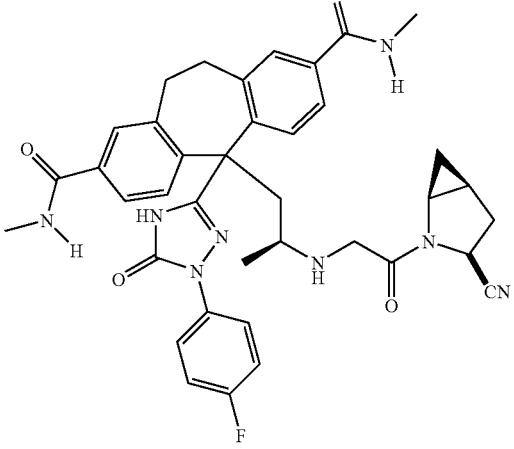 |

-continued
| Example | Preparative Example | Preparative Example | Product |
|---------|--------------------|--------------------|---------|
| 690 | 555 | 89 | 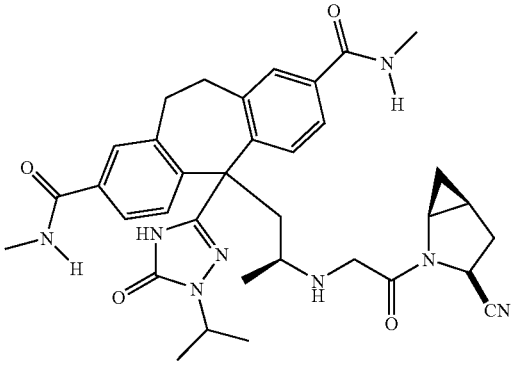 |
| 691 | 556 | 89 | 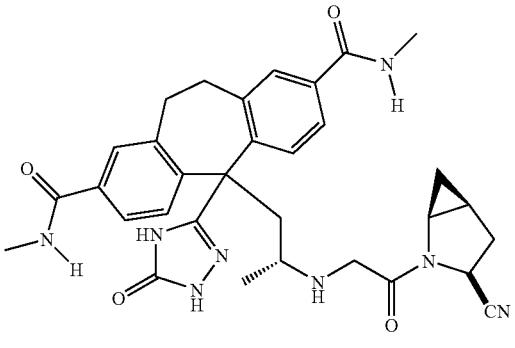 |
| 692 | 557 | 89 | 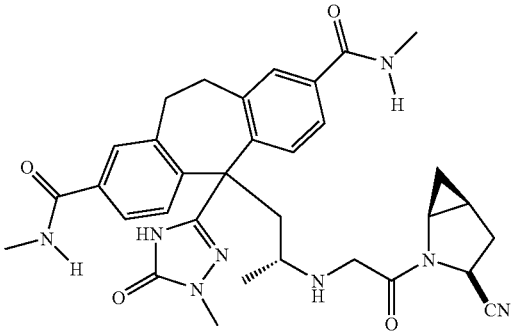 |
| 693 | 558 | 89 | 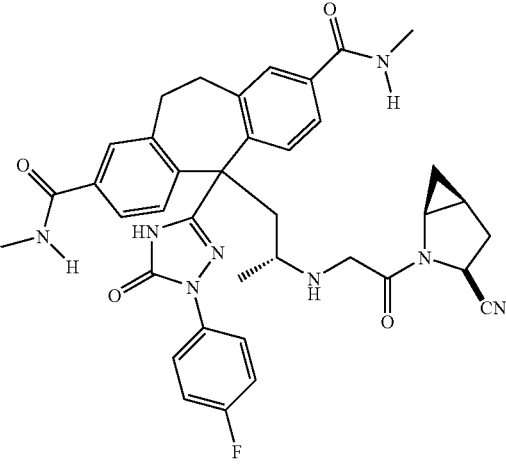 |

-continued
| Example | Preparative Example | Preparative Example | Product |
|---|---|---|---|
| 694 | 559 | 89 | 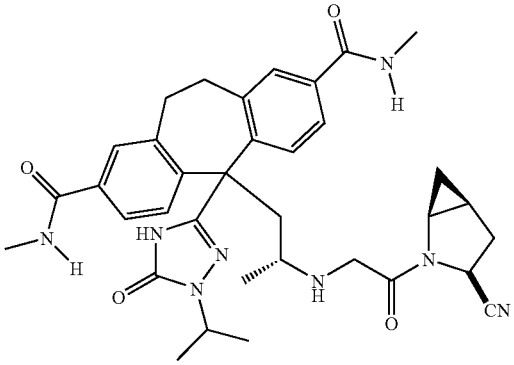 |
| 695 | 560 | 89 | 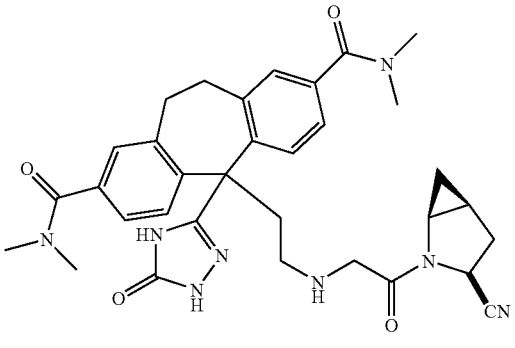 |
| 696 | 561 | 89 | 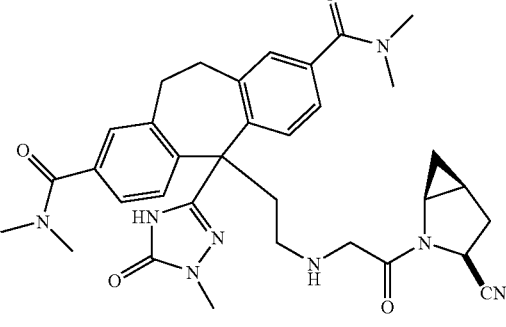 |
| 697 | 562 | 89 | 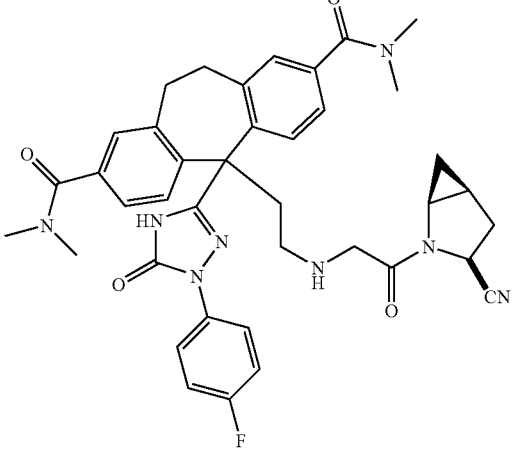 |

-continued
| Example | Preparative Example | Preparative Example | Product |
|---|---|---|---|
| 698 | 563 | 89 | 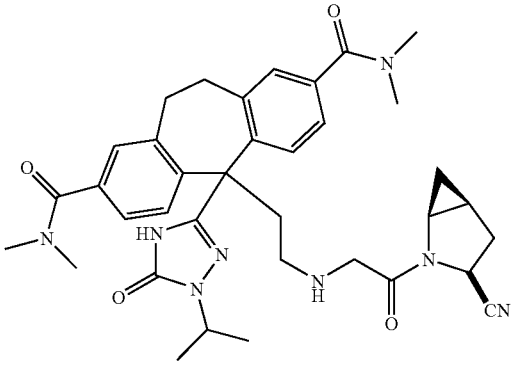 |
| 699 | 564 | 89 | 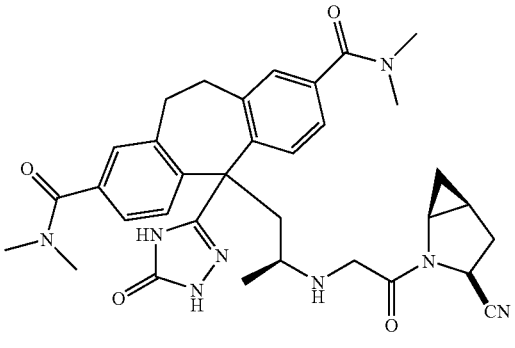 |
| 700 | 565 | 89 | 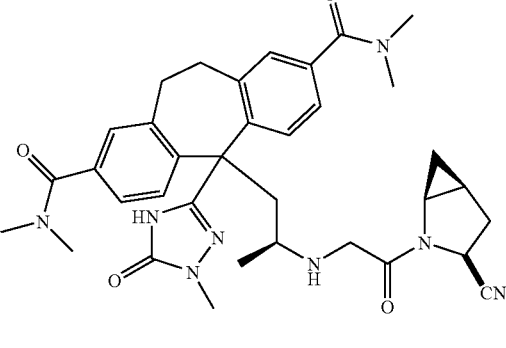 |
| 701 | 566 | 89 | 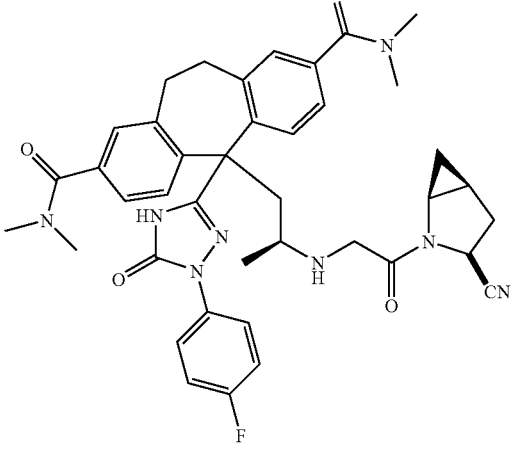 |

-continued
| Example | Preparative Example | Preparative Example | Product |
|---|---|---|---|
| 702 | 567 | 89 | 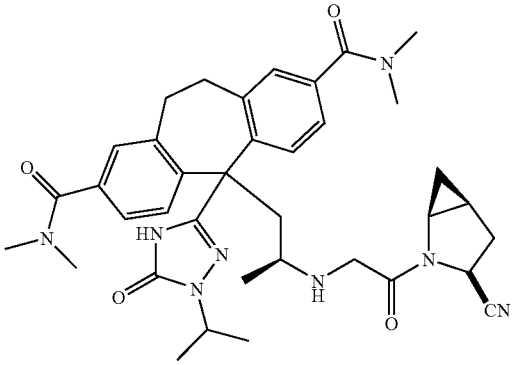 |
| 703 | 568 | 89 | 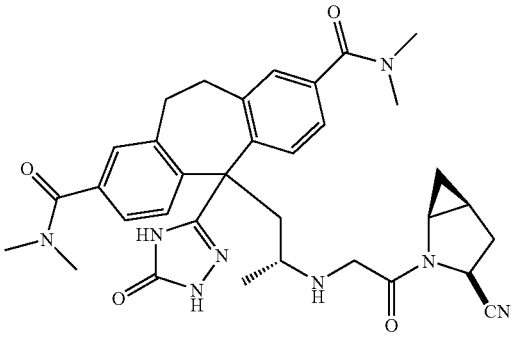 |
| 704 | 569 | 89 | 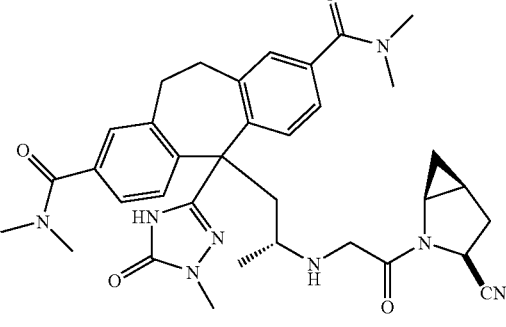 |
| 705 | 570 | 89 | 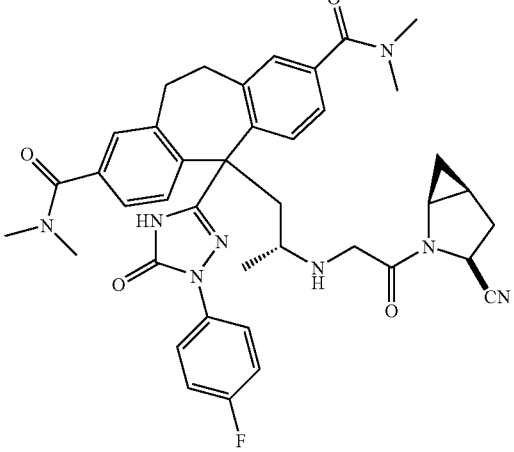 |

-continued

| Example | Preparative Example | Preparative Example | Product |
|---------|---------------------|---------------------|---------|
| 706 | 571 | 89 | |
| 707 | 636 | 89 | |
| 708 | 637 | 89 | |
| 709 | 638 | 89 | |

-continued
| Example | Preparative Example | Preparative Example | Product |
|---|---|---|---|
| 710 | 639 | 89 | 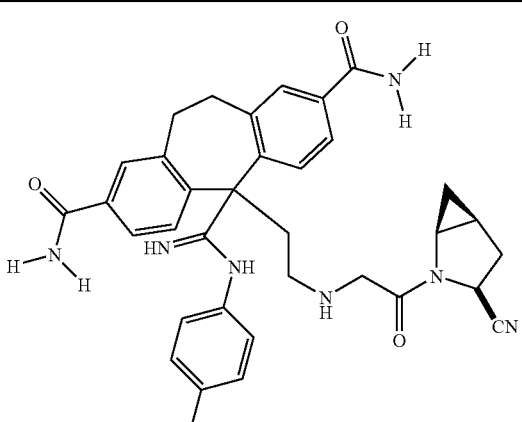 |
| 711 | 640 | 89 | 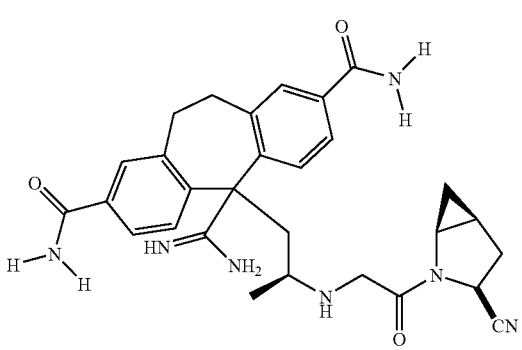 |
| 712 | 641 | 89 | 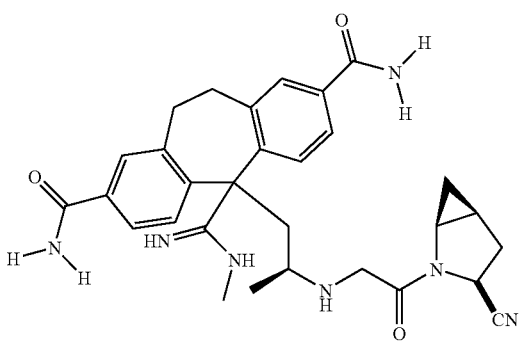 |
| 713 | 642 | 89 | 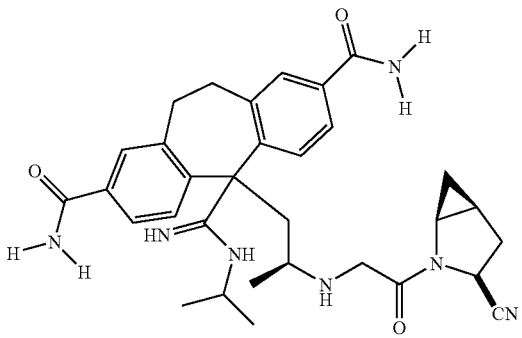 |

-continued
| Example | Preparative Example | Preparative Example | Product |
|---|---|---|---|
| 714 | 643 | 89 | 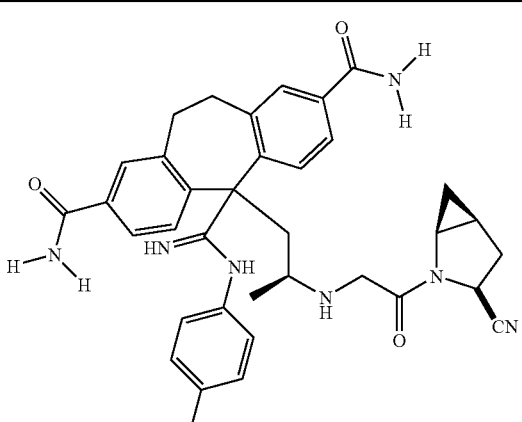 |
| 715 | 644 | 89 | 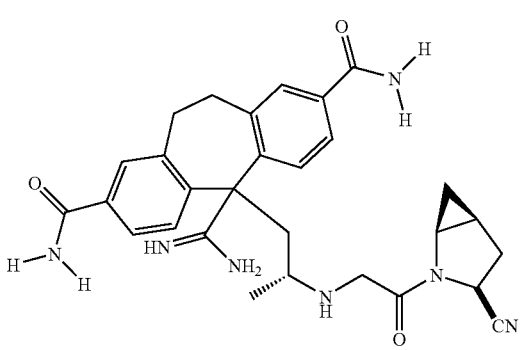 |
| 716 | 645 | 89 | 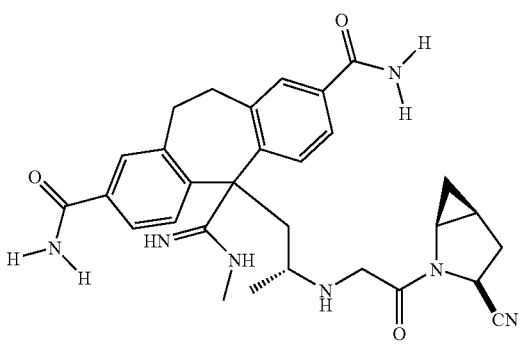 |
| 717 | 646 | 89 | 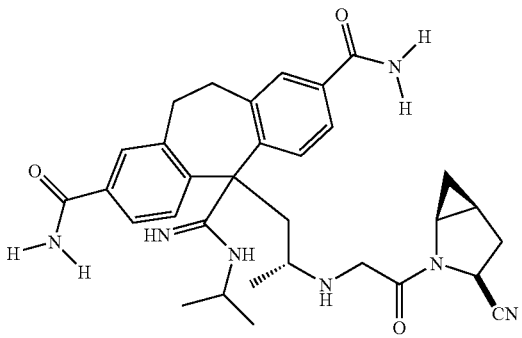 |

-continued
| Example | Preparative Example | Preparative Example | Product |
|---|---|---|---|
| 718 | 647 | 89 | 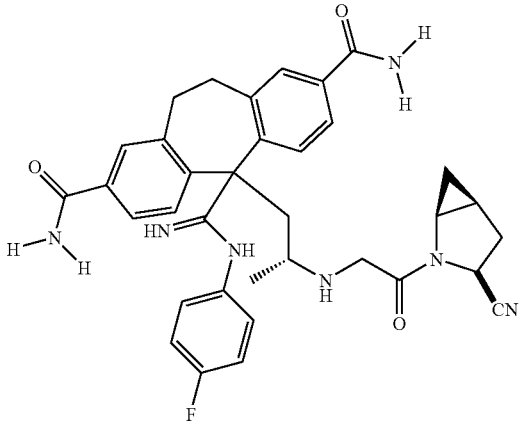 |
| 719 | 648 | 89 | 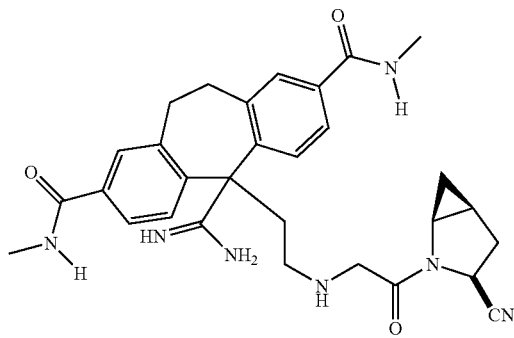 |
| 720 | 649 | 89 | 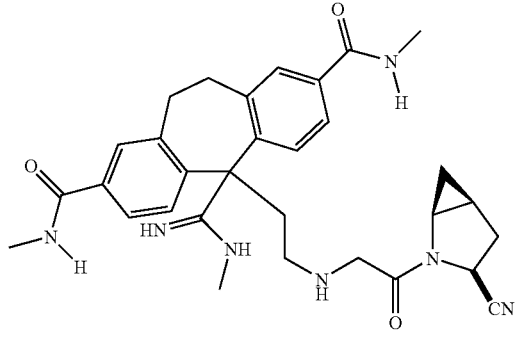 |
| 721 | 650 | 89 | 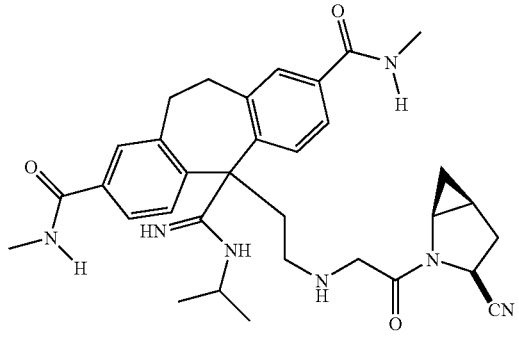 |

-continued

| Example | Preparative Example | Preparative Example | Product |
|---|---|---|---|
| 722 | 651 | 89 | |
| 723 | 652 | 89 | |
| 724 | 653 | 89 | |
| 725 | 654 | 89 | |

-continued

| Example | Preparative Example | Preparative Example | Product |
|---|---|---|---|
| 726 | 655 | 89 | |
| 727 | 656 | 89 | |
| 728 | 657 | 89 | |
| 729 | 658 | 89 | |

| Example | Preparative Example | Preparative Example | Product |
|---------|---------------------|---------------------|---------|
| 730 | 659 | 89 | |
| 731 | 660 | 89 | |
| 732 | 661 | 89 | |
| 733 | 662 | 89 | |

-continued
| Example | Preparative Example | Preparative Example | Product |
|---|---|---|---|
| 734 | 663 | 89 | 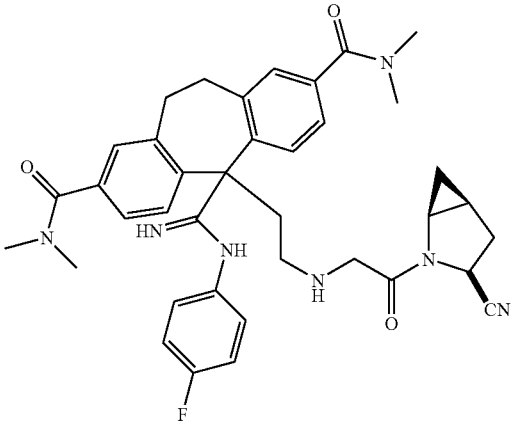 |
| 735 | 664 | 89 | 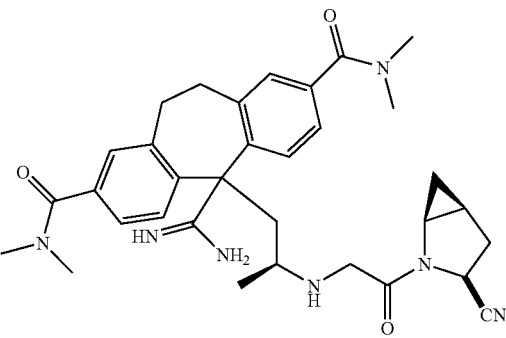 |
| 736 | 665 | 89 | 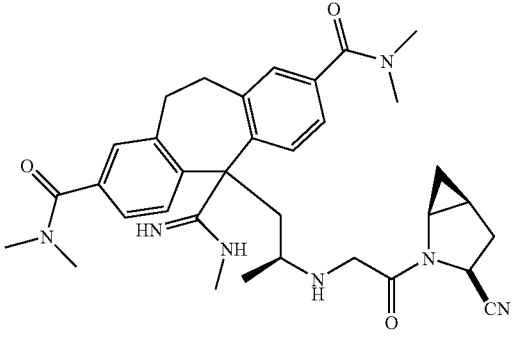 |
| 737 | 666 | 89 | 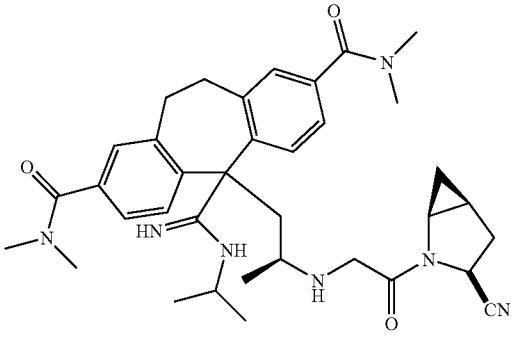 |

-continued

| Example | Preparative Example | Preparative Example | Product |
|---------|--------------------|--------------------|---------|
| 738 | 667 | 89 | |
| 739 | 668 | 89 | |
| 740 | 669 | 89 | |
| 741 | 670 | 89 | |

| Example | Preparative Example | Preparative Example | Product |
|---|---|---|---|
| 742 | 671 | 89 | |
| 743 | 688 | 89 | |
| 744 | 689 | 89 | |
| 745 | 690 | 89 | |

-continued
| Example | Preparative Example | Preparative Example | Product |
|---|---|---|---|
| 746 | 691 | 89 | 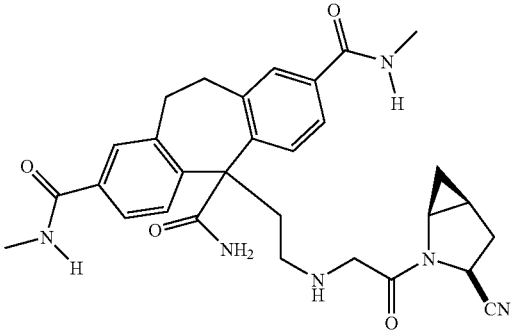 |
| 747 | 692 | 89 | 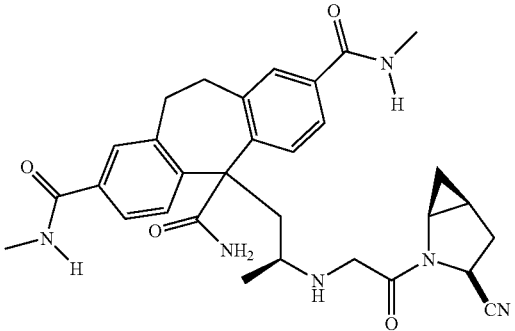 |
| 748 | 693 | 89 | 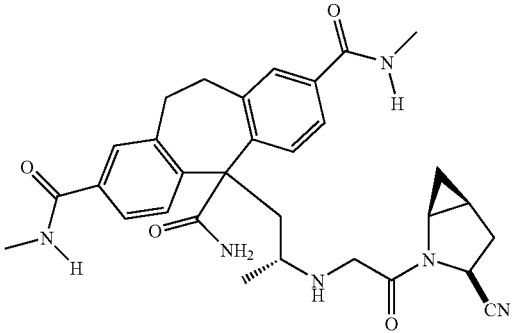 |
| 749 | 694 | 89 | 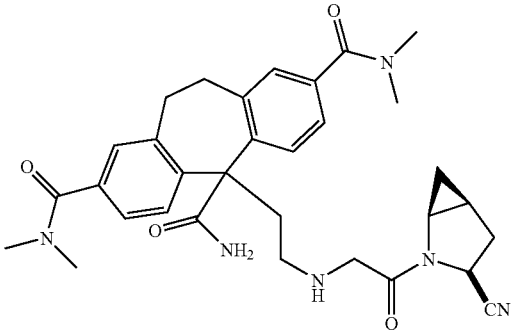 |

-continued

| Example | Preparative Example | Preparative Example | Product |
|---|---|---|---|
| 750 | 695 | 89 | |
| 751 | 736 | 89 | |
| 752 | 737 | 89 | |
| 753 | 738 | 89 | |

|Example|Preparative Example|Preparative Example|Product|
|---|---|---|---|
|754|739|89|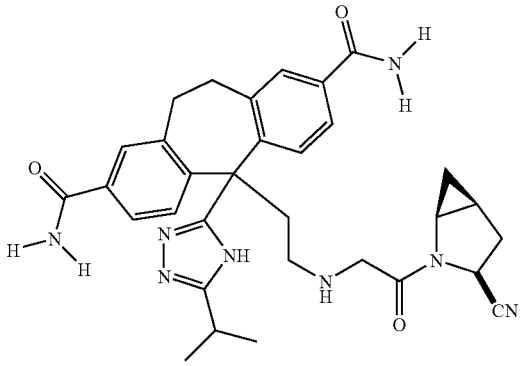|
|755|740|89|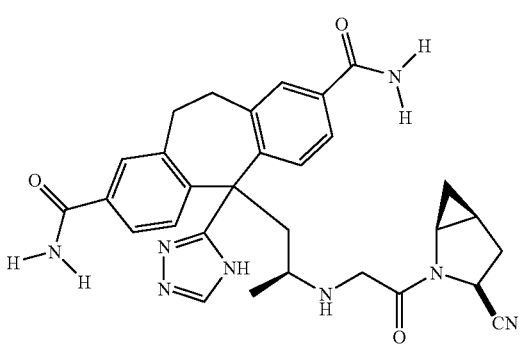|
|756|741|89|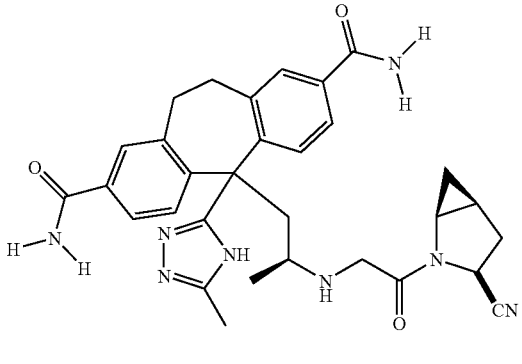|
|757|742|89|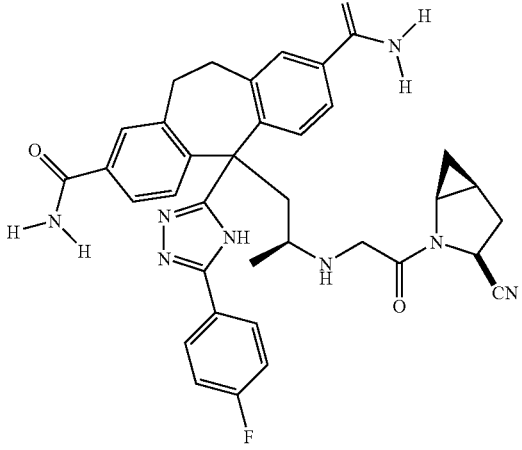|

-continued
| Example | Preparative Example | Preparative Example | Product |
|---|---|---|---|
| 758 | 743 | 89 | 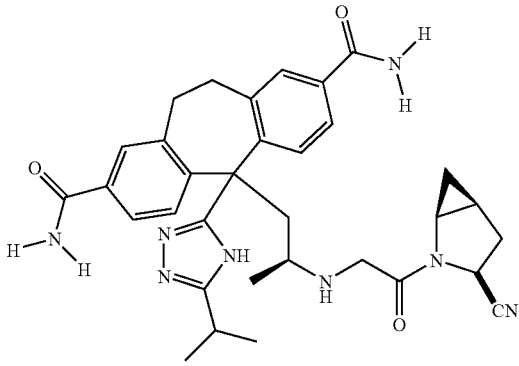 |
| 759 | 744 | 89 | 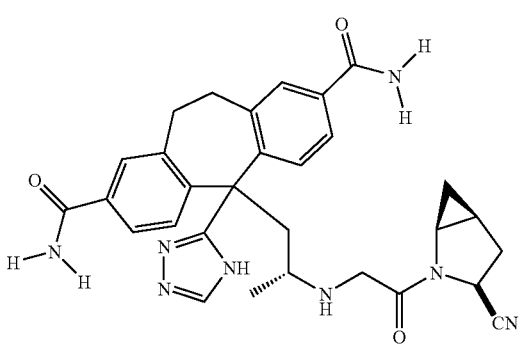 |
| 760 | 745 | 89 | 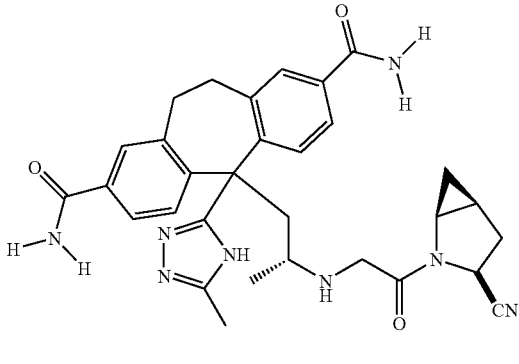 |
| 761 | 746 | 89 | 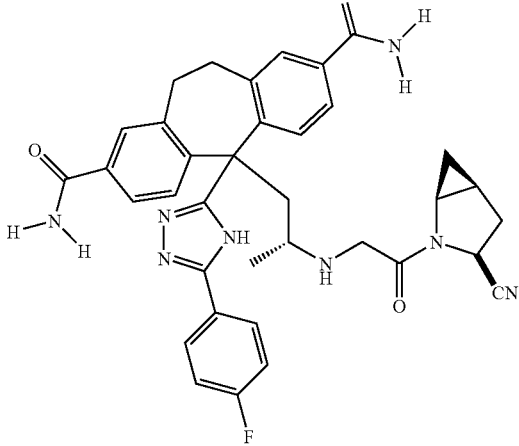 |

-continued
| Example | Preparative Example | Preparative Example | Product |
|---|---|---|---|
| 762 | 747 | 89 | 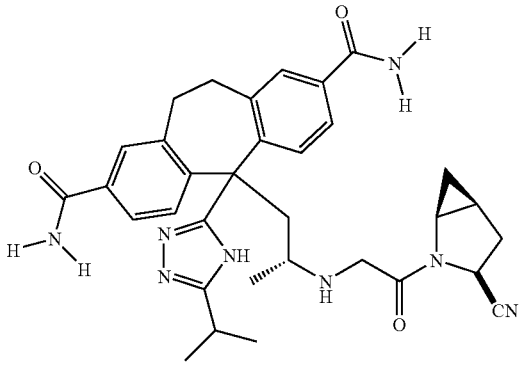 |
| 763 | 748 | 89 | 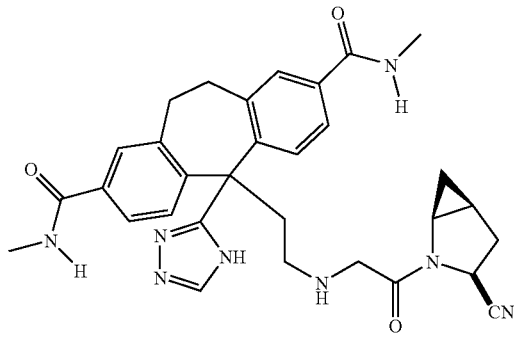 |
| 764 | 749 | 89 | 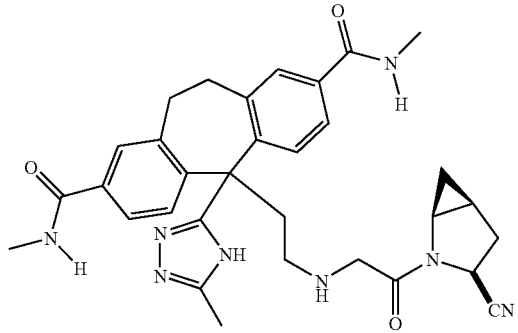 |
| 765 | 750 | 89 | 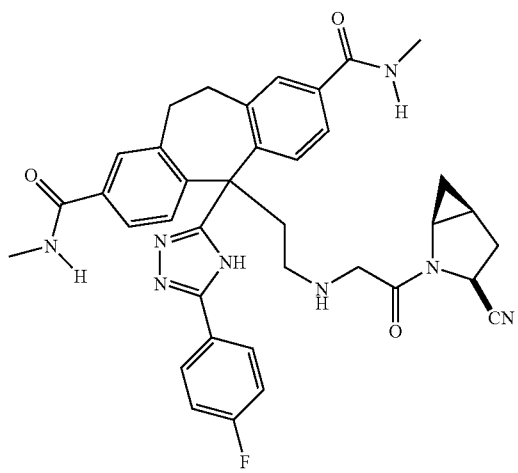 |

-continued
| Example | Preparative Example | Preparative Example | Product |
|---|---|---|---|
| 766 | 751 | 89 | 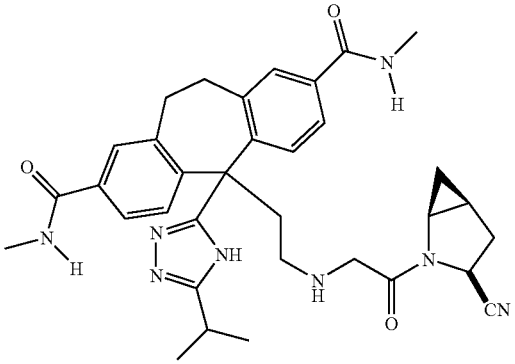 |
| 767 | 752 | 89 | 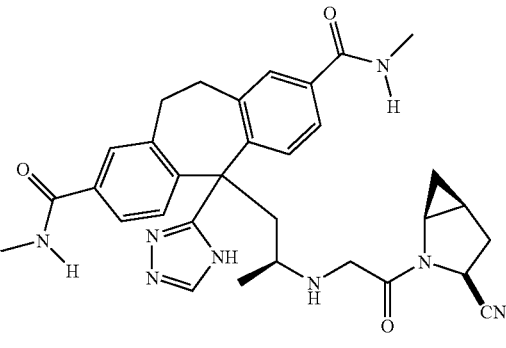 |
| 768 | 753 | 89 | 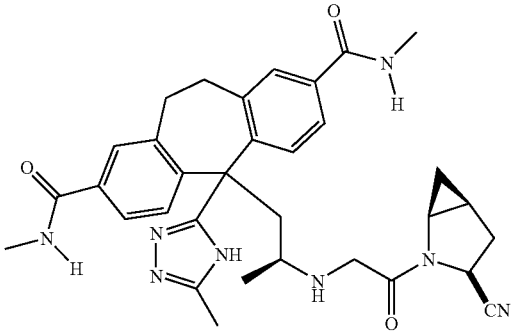 |
| 769 | 754 | 89 | 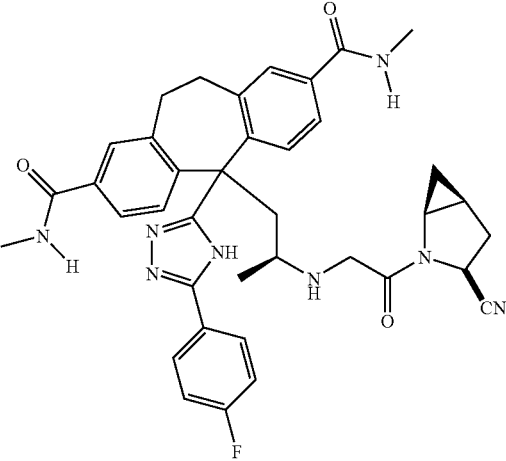 |

-continued
| Example | Preparative Example | Preparative Example | Product |
|---|---|---|---|
| 770 | 755 | 89 | 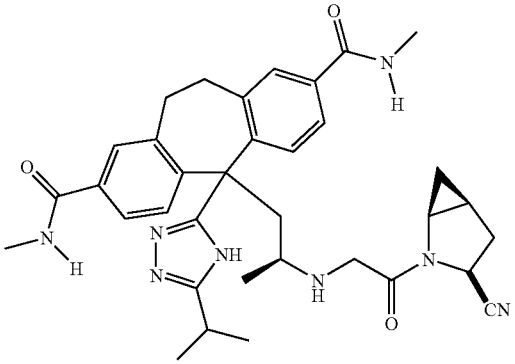 |
| 771 | 756 | 89 | 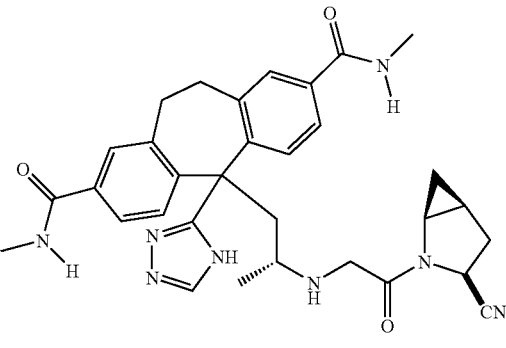 |
| 772 | 757 | 89 | 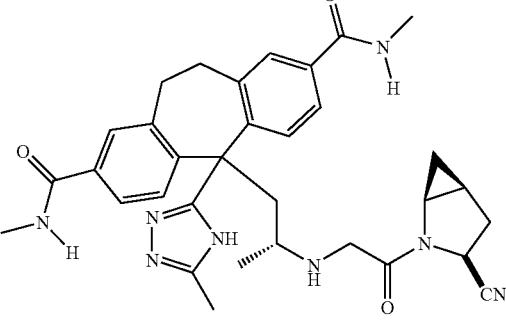 |
| 773 | 758 | 89 | 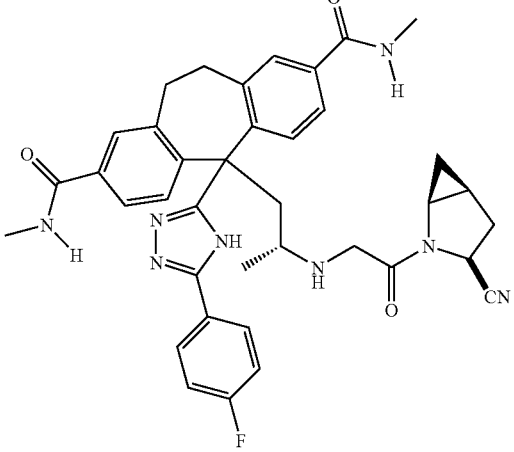 |

-continued
| Example | Preparative Example | Preparative Example | Product |
|---------|--------------------|--------------------|---------|
| 774 | 759 | 89 | 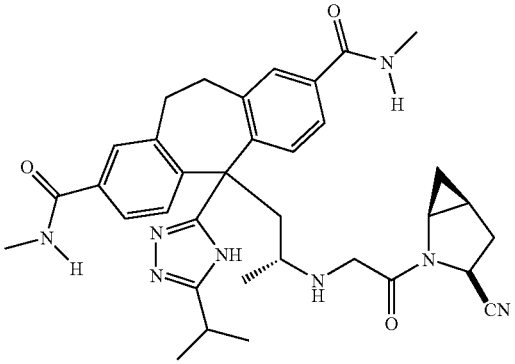 |
| 775 | 760 | 89 | 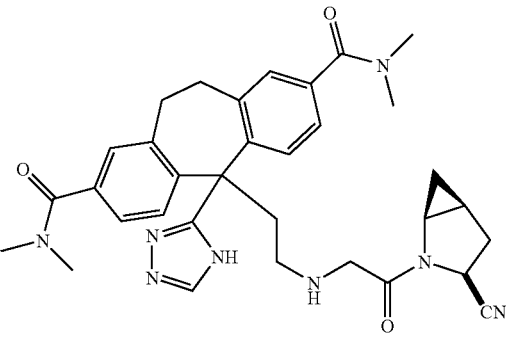 |
| 776 | 761 | 89 | 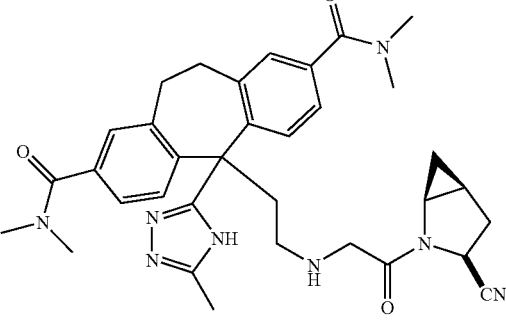 |
| 777 | 762 | 89 | 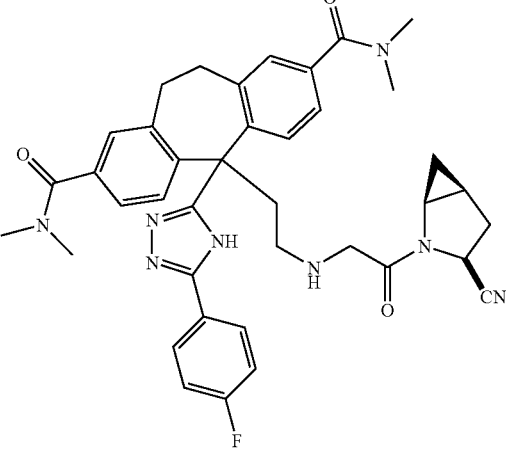 |

-continued
| Example | Preparative Example | Preparative Example | Product |
|---|---|---|---|
| 778 | 763 | 89 | 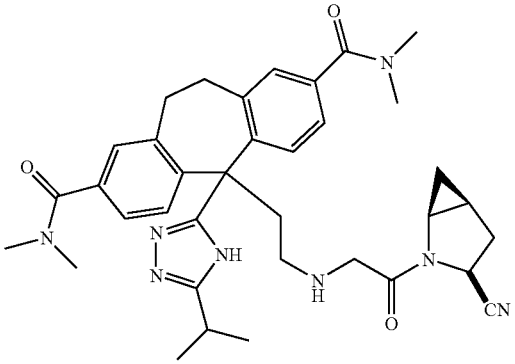 |
| 779 | 764 | 89 | 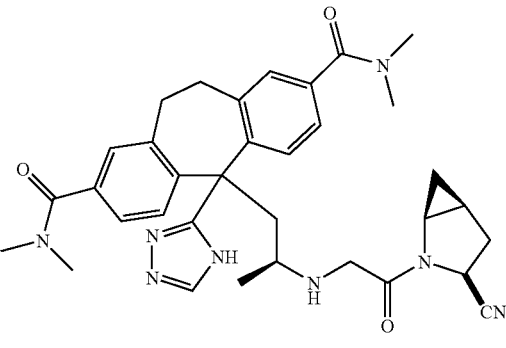 |
| 780 | 765 | 89 | 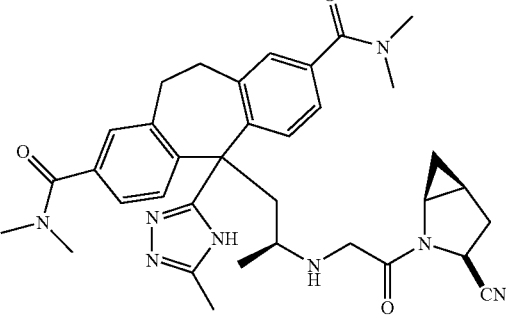 |
| 781 | 766 | 89 | 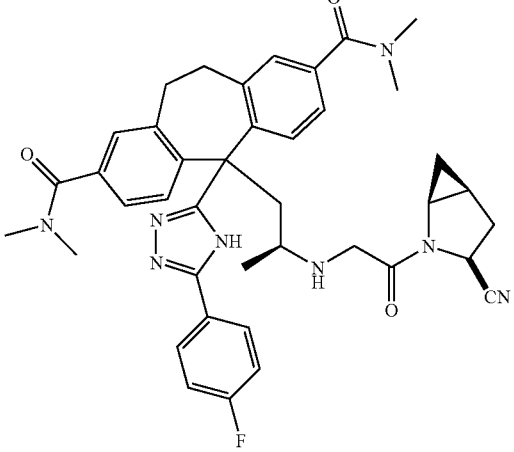 |

-continued
| Example | Preparative Example | Preparative Example | Product |
|---|---|---|---|
| 782 | 767 | 89 | 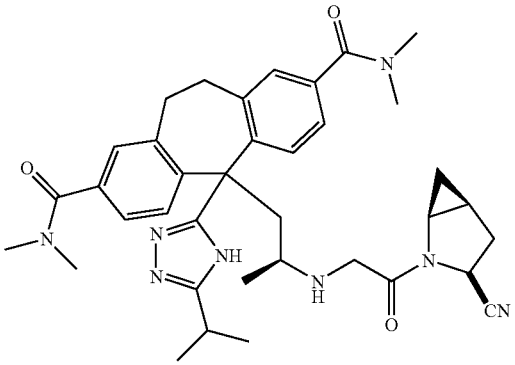 |
| 783 | 768 | 89 | 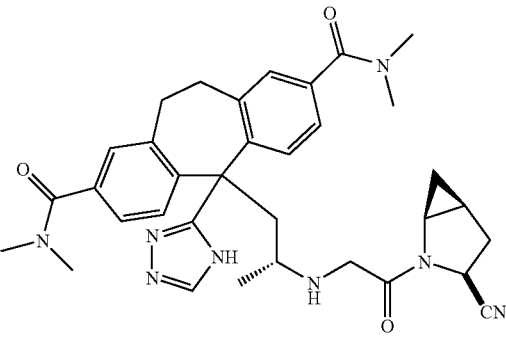 |
| 784 | 769 | 89 | 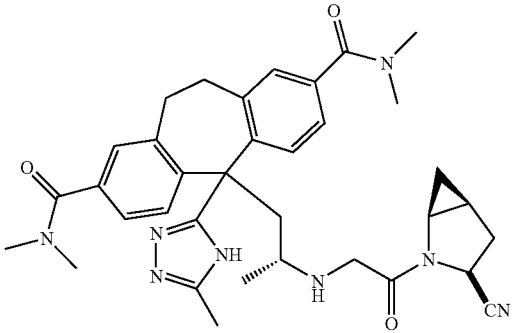 |
| 785 | 770 | 89 | 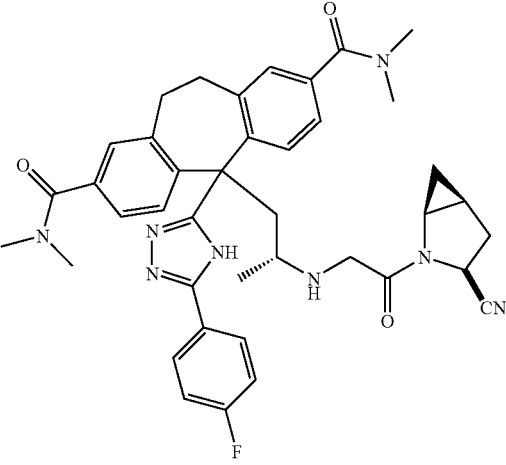 |

-continued

| Example | Preparative Example | Preparative Example | Product |
|---|---|---|---|
| 786 | 771 | 89 | |
| 787 | 789 | 89 | |
| 788 | 790 | 89 | |
| 789 | 791 | 89 | |

-continued
| Example | Preparative Example | Preparative Example | Product |
|---------|---------------------|---------------------|---------|
| 790 | 792 | 89 | 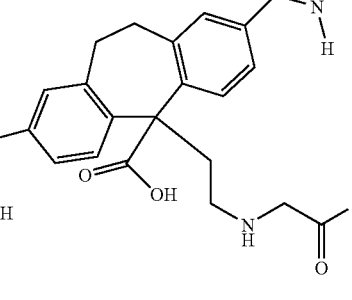 |
| 791 | 793 | 89 | 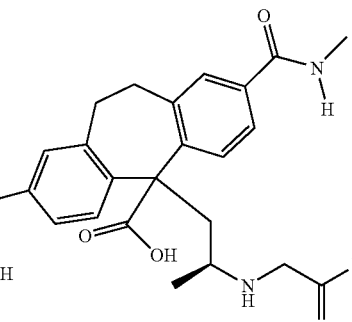 |
| 792 | 794 | 89 | 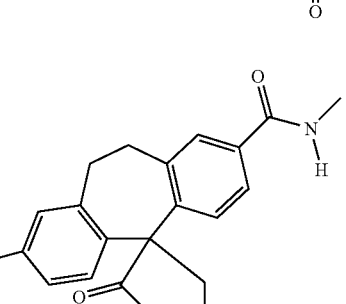 |
| 793 | 795 | 89 | 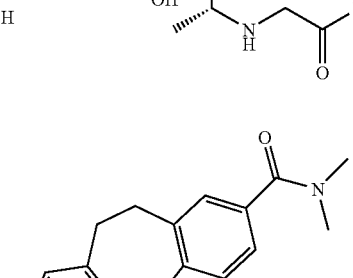 |

-continued

| Example | Preparative Example | Preparative Example | Product |
|---------|---------------------|---------------------|---------|
| 794 | 796 | 89 | (structure) |
| 795 | 797 | 89 | (structure) |

Examples 796-799 have been intentionally excluded.

Example 800-833

If one were to follow a similar procedure as that described in Examples 27 or 28, and treat the title compounds from the Preparative Examples in the table below as described in Preparative Example 69 and 71, except using the amines as indicated in the Table below, one Would obtain the desired product.

| Example | Preparative Example | Preparative Example | Amine | Product |
|---------|---------------------|---------------------|-------|---------|
| 800 | 61 Step B | 2 | NH$_3$ | (structure) |

| Example | Preparative Example | Preparative Example | Amine | Product |
|---|---|---|---|---|
| 801 | 62 | 2 | NH$_3$ | |
| 802 | 65 | 2 | NH$_3$ | |
| 803 | 61 Step B | 2 | NH$_3$ | |
| 804 | 62 | 2 | NH$_3$ | |

-continued
| Example | Preparative Example | Preparative Example | Amine | Product |
|---|---|---|---|---|
| 805 | 65 | 2 | NH₃ | 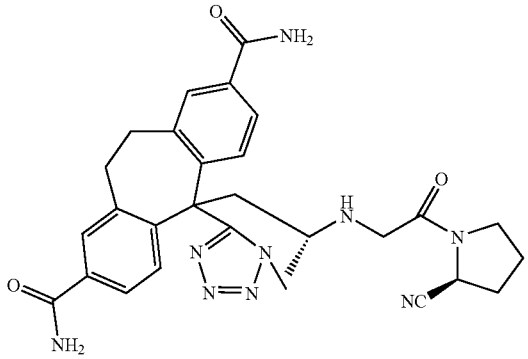 |
| 806 | 61 Step B | 2 | CH₃NH₂ | 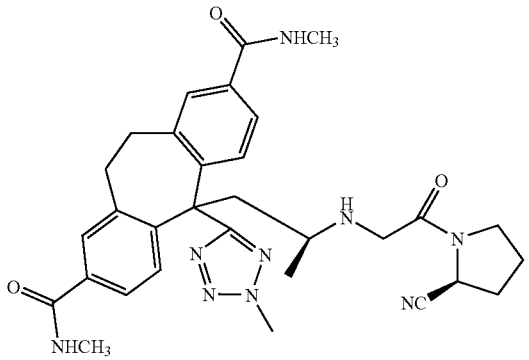 |
| 807 | 62 | 2 | CH₃NH₂ | 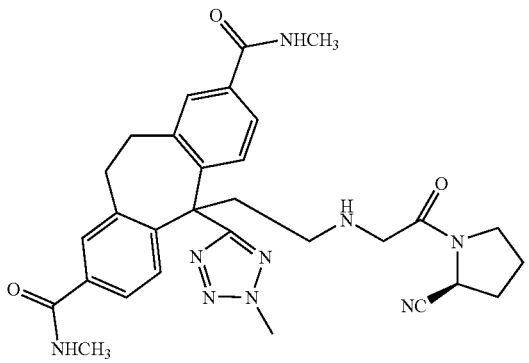 |
| 808 | 65 | 2 | CH₃NH₂ | 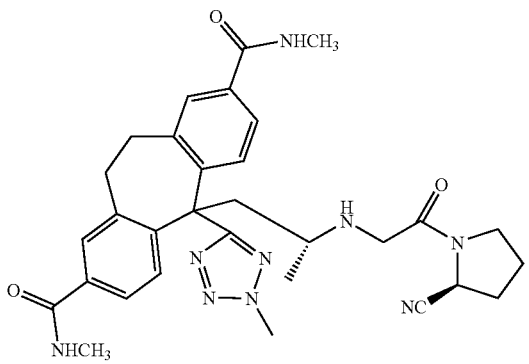 |

-continued
| Example | Preparative Example | Preparative Example | Amine | Product |
|---|---|---|---|---|
| 809 | 61 Step B | 2 | CH$_3$NH$_2$ | 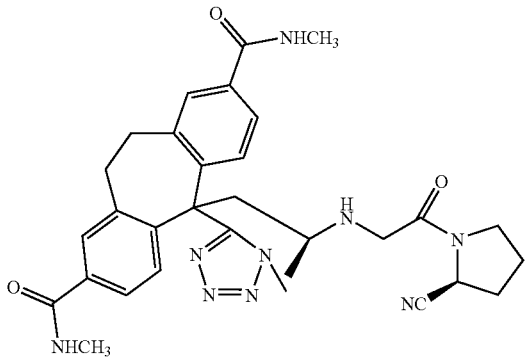 |
| 810 | 62 | 2 | CH$_3$NH$_2$ | 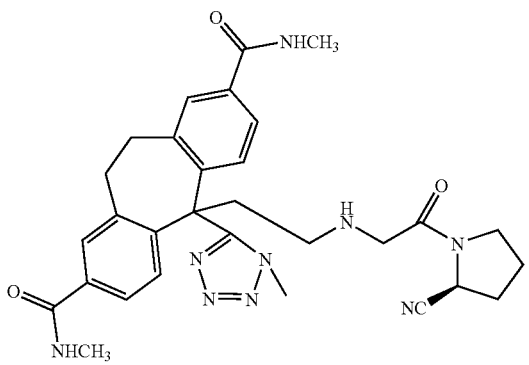 |
| 811 | 65 | 2 | CH$_3$NH$_2$ | 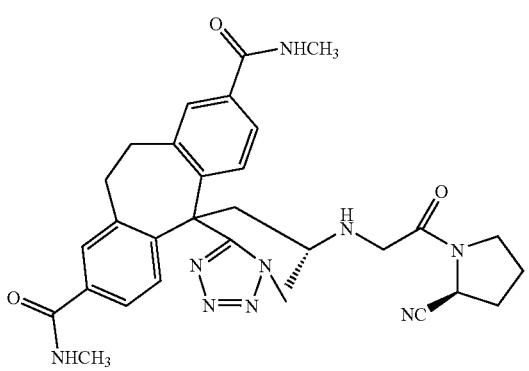 |
| 812 | 61 Step B | 2 | (CH$_3$)$_2$NH | 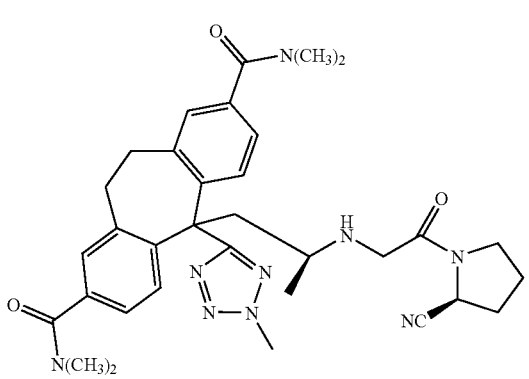 |

-continued

| Example | Preparative Example | Preparative Example | Amine | Product |
|---|---|---|---|---|
| 813 | 65 | 2 | $(CH_3)_2NH$ | |
| 814 | 61 Step B | 2 | $(CH_3)_2NH$ | |
| 815 | 65 | 2 | $(CH_3)_2NH$ | |
| 816 | 61 Step B | 89 | $NH_3$ | |

-continued
| Example | Preparative Example | Preparative Example | Amine | Product |
|---|---|---|---|---|
| 817 | 62 | 89 | NH₃ | 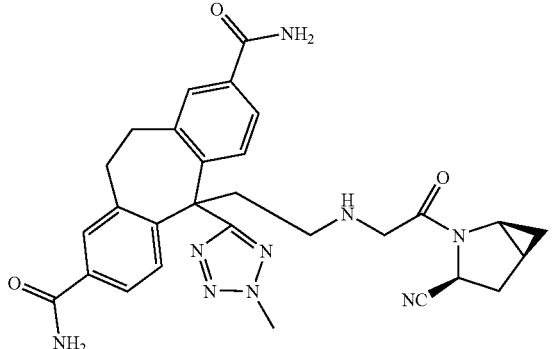 |
| 818 | 65 | 89 | NH₃ | 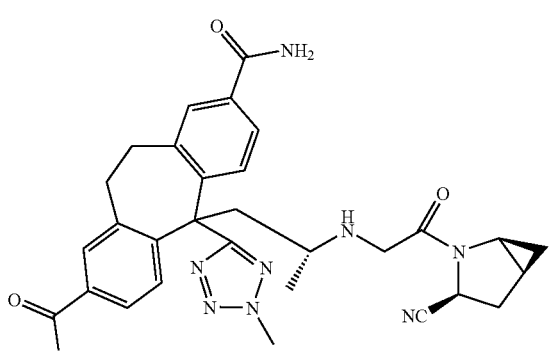 |
| 819 | 61 Step B | 89 | NH₃ | 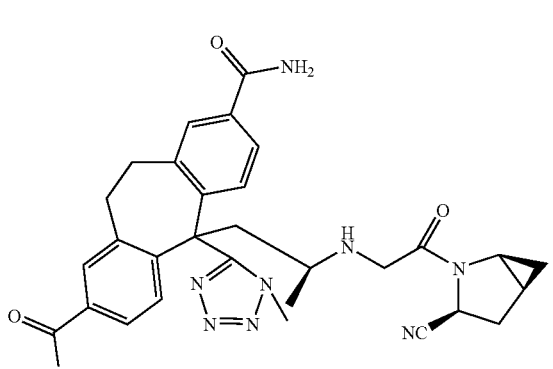 |
| 820 | 62 | 89 | NH₃ | 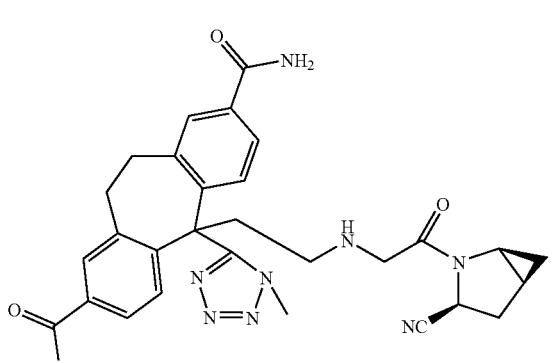 |

-continued

| Example | Preparative Example | Preparative Example | Amine | Product |
|---|---|---|---|---|
| 821 | 65 | 89 | NH₃ | *(structure)* |
| 822 | 61 Step B | 89 | CH₃NH₂ | *(structure)* |
| 823 | 62 | 89 | CH₃NH₂ | *(structure)* |
| 824 | 65 | 89 | CH₃NH₂ | *(structure)* |

-continued
| Example | Preparative Example | Preparative Example | Amine | Product |
|---|---|---|---|---|
| 825 | 61 Step B | 89 | CH₃NH₂ | 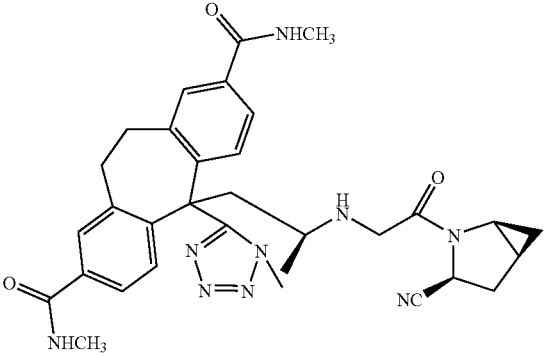 |
| 826 | 62 | 89 | CH₃NH₂ | 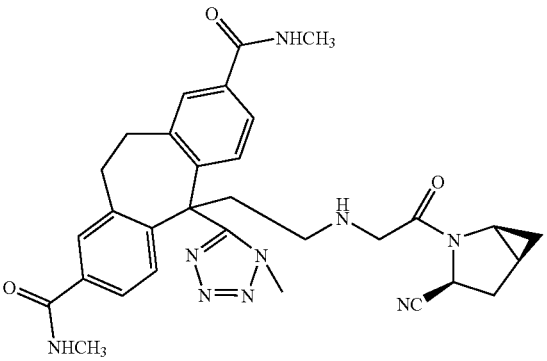 |
| 827 | 65 | 89 | CH₃NH₂ | 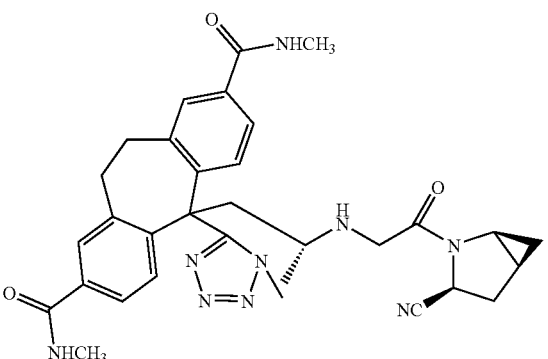 |
| 828 | 61 Step B | 89 | (CH₃)₂NH | 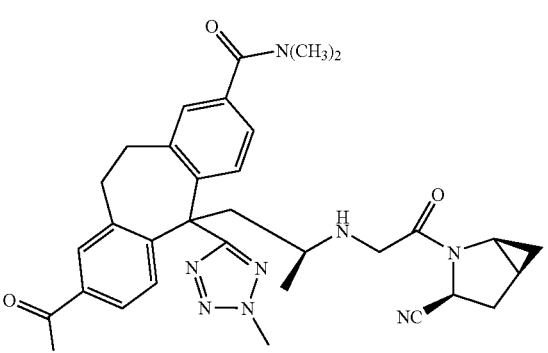 |

-continued

| Example | Preparative Example | Preparative Example | Amine | Product |
|---------|---------------------|---------------------|-------|---------|
| 829 | 62 | 89 | (CH₃)₂NH | |
| 830 | 65 | 89 | (CH₃)₂NH | |
| 831 | 61 Step B | 89 | (CH₃)₂NH | |
| 832 | 62 | 89 | (CH₃)₂NH | |

-continued

| Example | Preparative Example | Preparative Example | Amine | Product |
|---|---|---|---|---|
| 833 | 65 | 89 | (CH₃)₂NH | *(structure shown)* |

Examples 834-999 have been intentionally excluded.

Example 1000-1168

If one were to follow the procedures outlined in Examples 28 or 29 except using the compounds from the Preparative Examples as indicated in the Table below, one would obtain the indicated Product.

| Example | Preparative Example | Preparative Example | Product |
|---|---|---|---|
| 1000 | 801 | 2 | *(structure shown)* |
| 1001 | 804 | 2 | *(structure shown)* |
| 1002 | 805 | 2 | *(structure shown)* |

-continued

| Example | Preparative Example | Preparative Example | Product |
|---|---|---|---|
| 1003 | 800 | 2 | |
| 1004 | 802 | 2 | |
| 1005 | 803 | 2 | |
| 1006 | 801 | 89 | |
| 1007 | 804 | 89 | |

-continued
| Example | Preparative Example | Preparative Example | Product |
|---------|---------------------|---------------------|---------|
| 1008 | 805 | 89 | 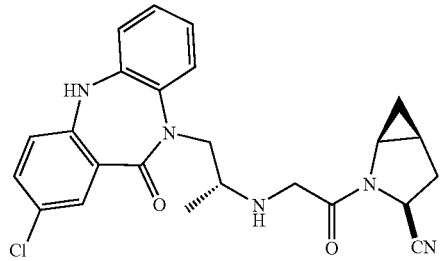 |
| 1009 | 800 | 89 | 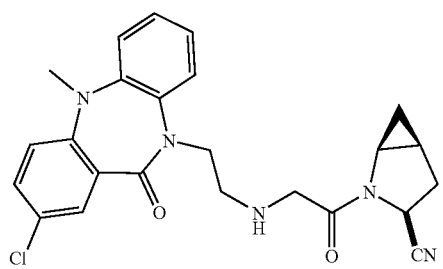 |
| 1010 | 802 | 89 | 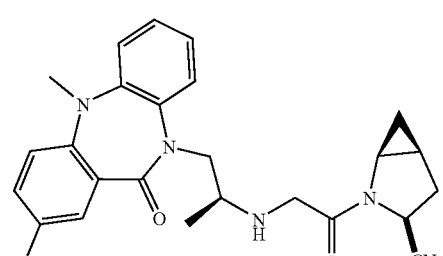 |
| 1011 | 803 | 89 | 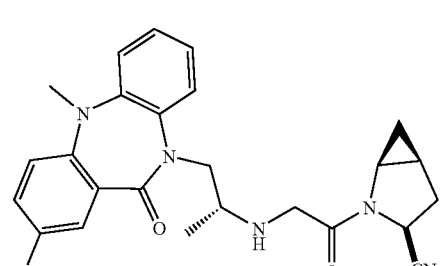 |
| 1012 | 810 | 2 | 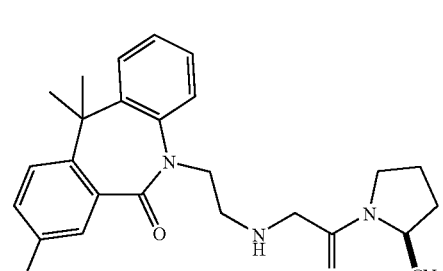 |

-continued
| Example | Preparative Example | Preparative Example | Product |
|---|---|---|---|
| 1013 | 812 | 2 | 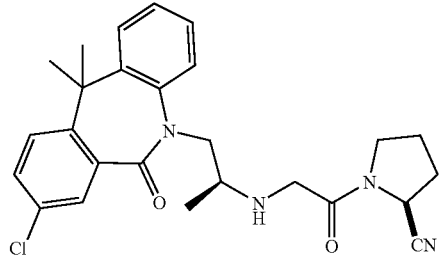 |
| 1014 | 811 | 2 | 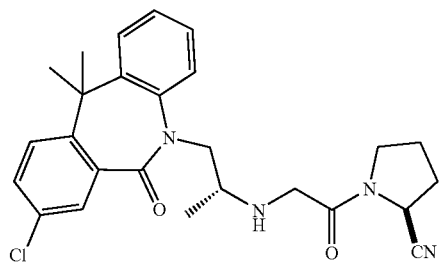 |
| 1015 | 810 | 89 | 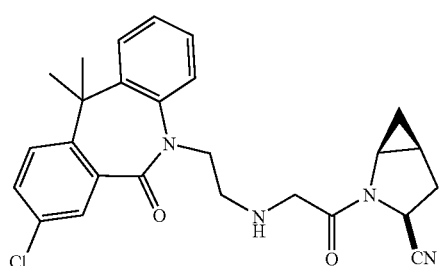 |
| 1016 | 812 | 89 | 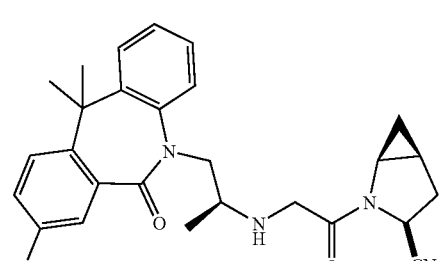 |
| 1017 | 811 | 89 | 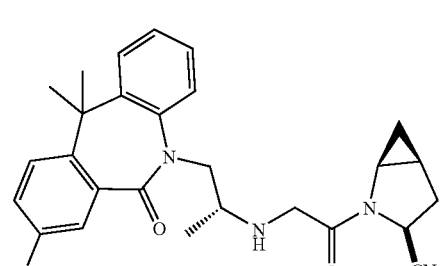 |

-continued
| Example | Preparative Example | Preparative Example | Product |
|---------|---------------------|---------------------|---------|
| 1018 | 831 | 2 | 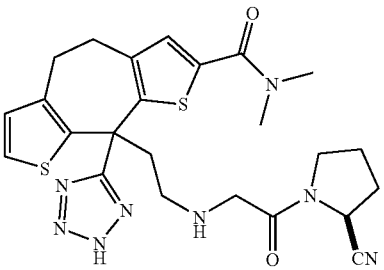 |
| 1019 | 832 | 2 | 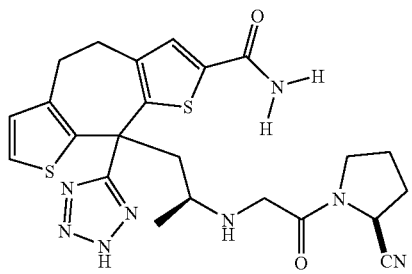 |
| 1020 | 833 | 2 | 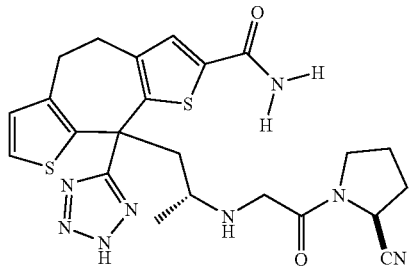 |
| 1021 | 834 | 2 | 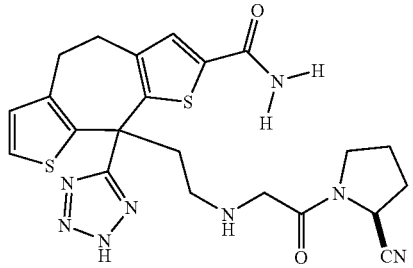 |
| 1022 | 835 | 2 | 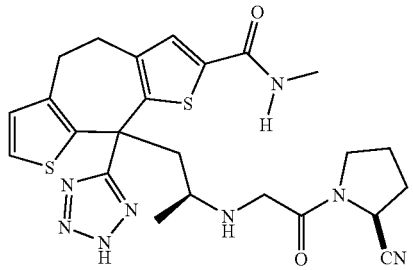 |

-continued

| Example | Preparative Example | Preparative Example | Product |
|---------|---------------------|---------------------|---------|
| 1023 | 836 | 2 | |
| 1024 | 837 | 2 | |
| 1025 | 838 | 2 | |
| 1026 | 839 | 2 | |
| 1027 | 851 | 2 | |

-continued
| Example | Preparative Example | Preparative Example | Product |
|---|---|---|---|
| 1028 | 852 | 2 | 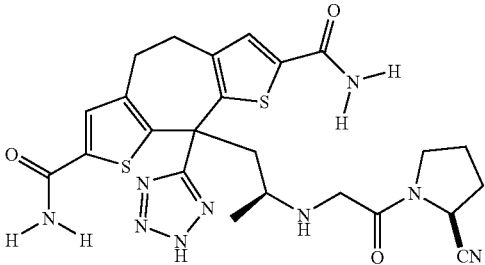 |
| 1029 | 853 | 2 | 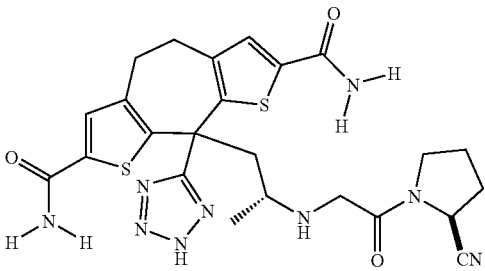 |
| 1030 | 854 | 2 | 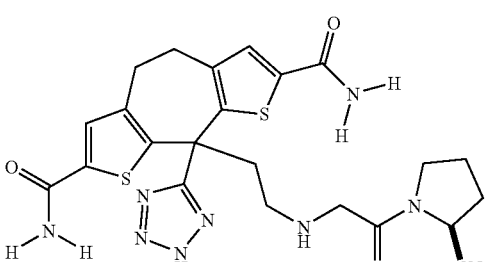 |
| 1031 | 855 | 2 | 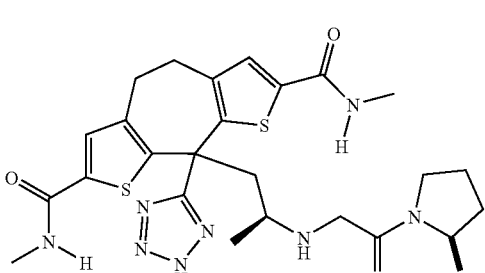 |
| 1032 | 856 | 2 | 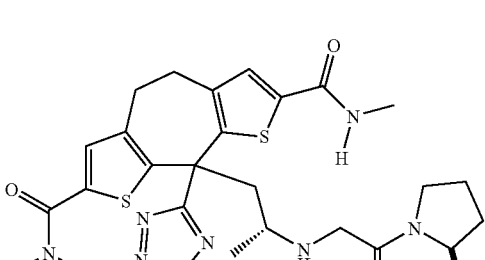 |

-continued
| Example | Preparative Example | Preparative Example | Product |
|---|---|---|---|
| 1033 | 857 | 2 | 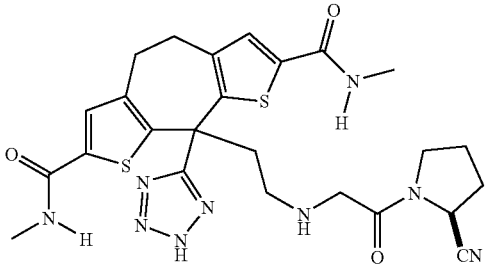 |
| 1034 | 858 | 2 | 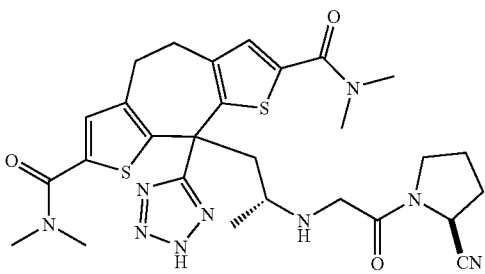 |
| 1035 | 859 | 2 | 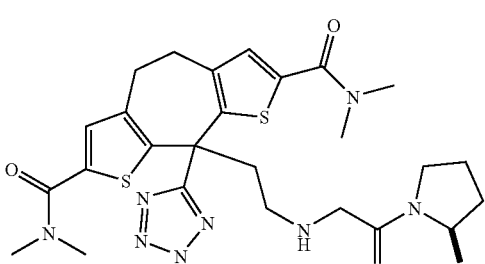 |
| 1036 | 901 | 2 | 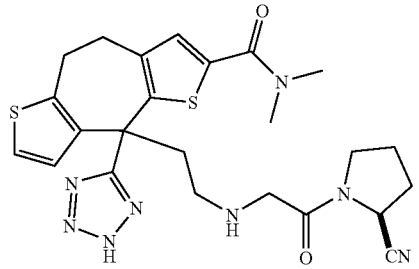 |
| 1037 | 902 | 2 | 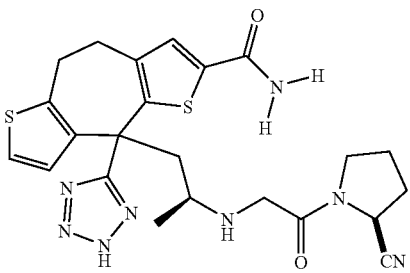 |

-continued
| Example | Preparative Example | Preparative Example | Product |
|---------|---------------------|---------------------|---------|
| 1038 | 903 | 2 | 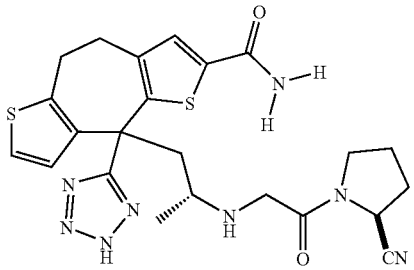 |
| 1039 | 904 | 2 | 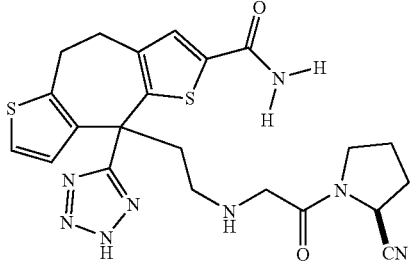 |
| 1040 | 905 | 2 | 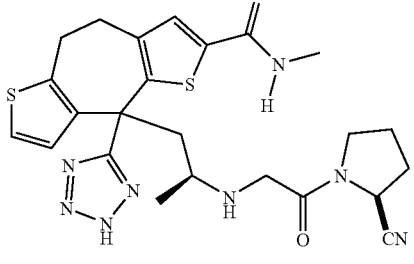 |
| 1041 | 906 | 2 | 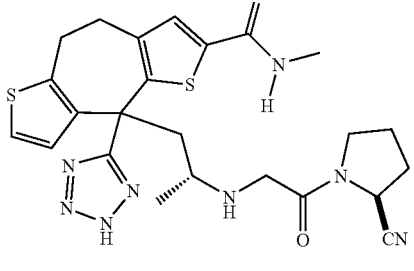 |
| 1042 | 907 | 2 | 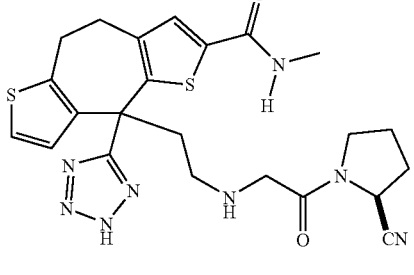 |

-continued
| Example | Preparative Example | Preparative Example | Product |
|---------|---------------------|---------------------|---------|
| 1043 | 908 | 2 | 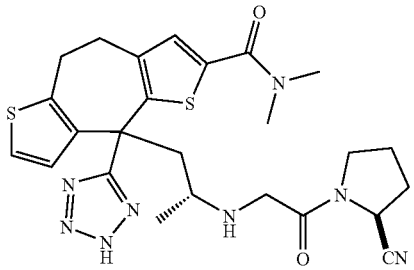 |
| 1044 | 909 | 2 | 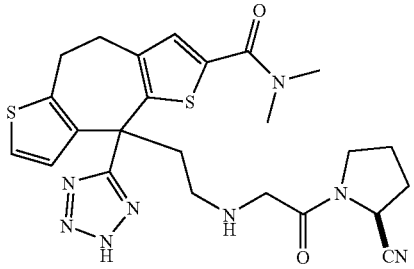 |
| 1045 | 921 | 2 | 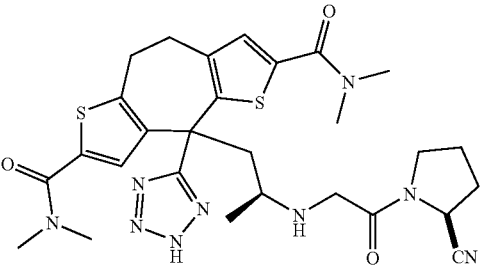 |
| 1046 | 922 | 2 | 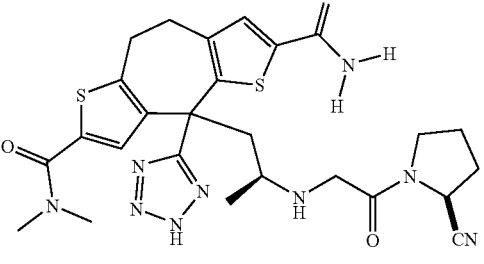 |
| 1047 | 923 | 2 | 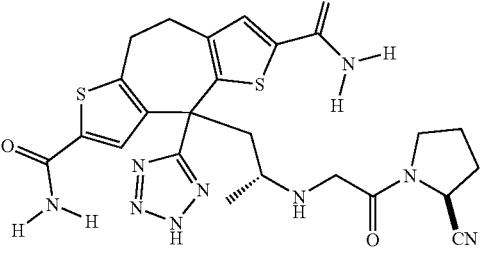 |

-continued
| Example | Preparative Example | Preparative Example | Product |
|---|---|---|---|
| 1048 | 924 | 2 | 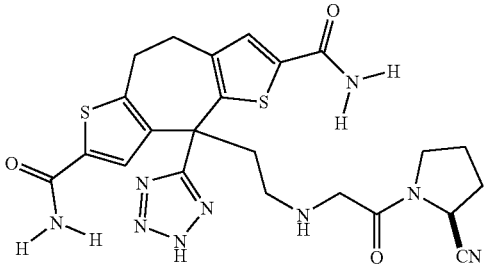 |
| 1049 | 925 | 2 | 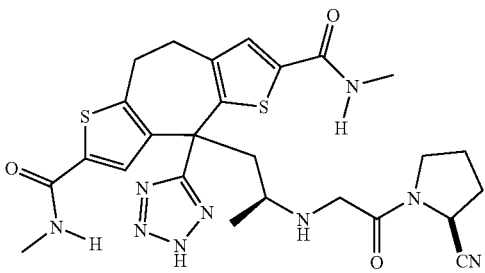 |
| 1050 | 926 | 2 | 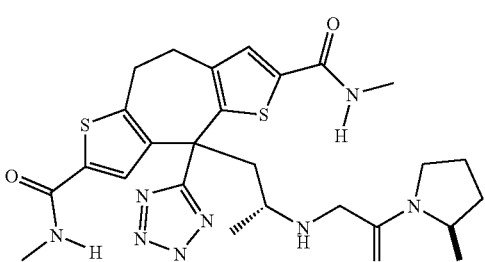 |
| 1051 | 927 | 2 | 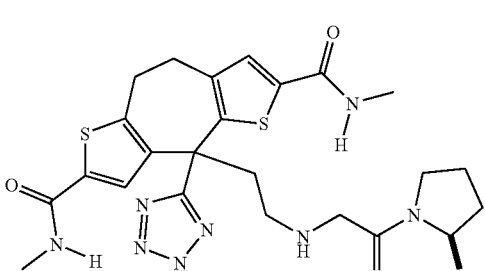 |
| 1052 | 928 | 2 | 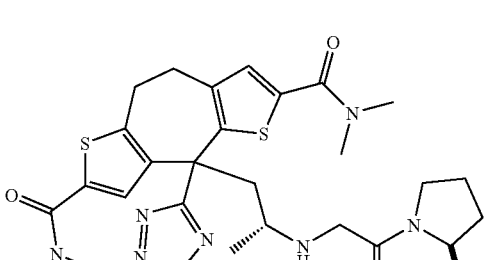 |

-continued
| Example | Preparative Example | Preparative Example | Product |
|---------|---------------------|---------------------|---------|
| 1053 | 929 | 2 | 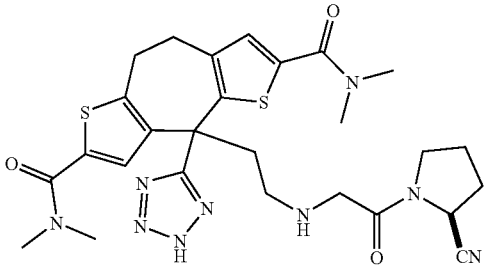 |
| 1054 | 831 | 89 | 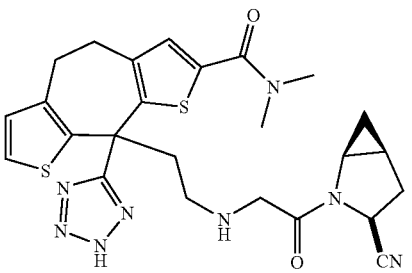 |
| 1055 | 832 | 89 | 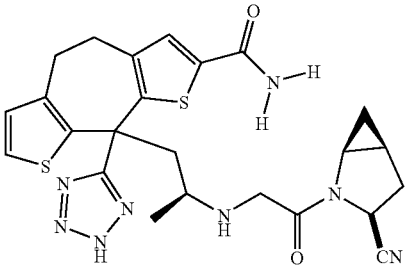 |
| 1056 | 833 | 89 | 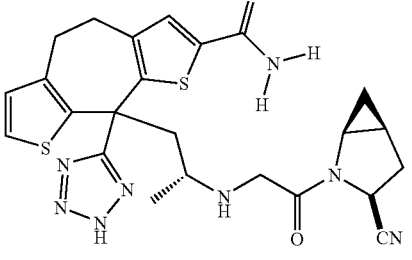 |
| 1057 | 834 | 89 | 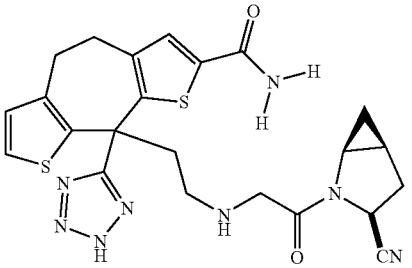 |

-continued

| Example | Preparative Example | Preparative Example | Product |
|---|---|---|---|
| 1058 | 835 | 89 | |
| 1059 | 836 | 89 | |
| 1060 | 837 | 89 | |
| 1061 | 838 | 89 | |
| 1062 | 839 | 89 | |

-continued
| Example | Preparative Example | Preparative Example | Product |
|---------|---------------------|---------------------|---------|
| 1063 | 851 | 89 | 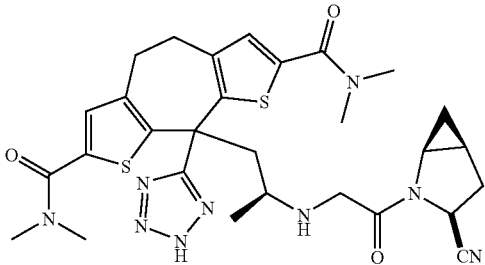 |
| 1064 | 852 | 89 | 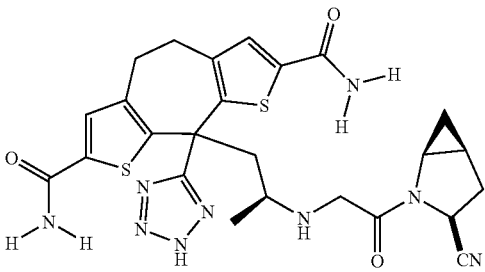 |
| 1065 | 853 | 89 | 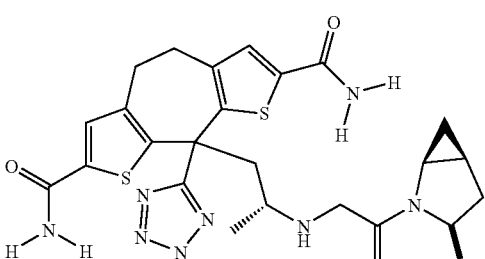 |
| 1066 | 854 | 89 | 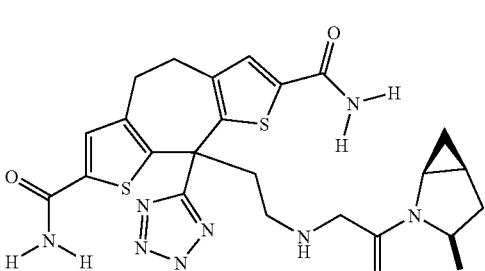 |
| 1067 | 855 | 89 | 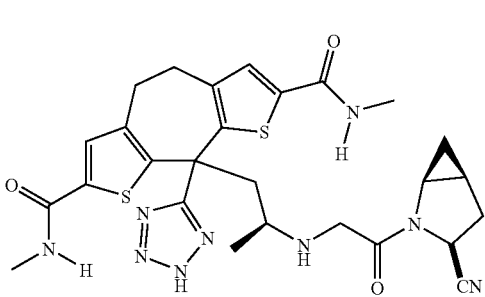 |

-continued

| Example | Preparative Example | Preparative Example | Product |
|---------|---------------------|---------------------|---------|
| 1068 | 856 | 89 | |
| 1069 | 857 | 89 | |
| 1070 | 858 | 89 | |
| 1071 | 859 | 89 | |
| 1072 | 901 | 89 | |

-continued

| Example | Preparative Example | Preparative Example | Product |
|---------|---------------------|---------------------|---------|
| 1073 | 902 | 89 | |
| 1074 | 903 | 89 | |
| 1075 | 904 | 89 | |
| 1076 | 905 | 89 | |
| 1077 | 906 | 89 | |

-continued

| Example | Preparative Example | Preparative Example | Product |
|---|---|---|---|
| 1078 | 907 | 89 | |
| 1079 | 908 | 89 | |
| 1080 | 909 | 89 | |
| 1081 | 921 | 89 | |
| 1082 | 922 | 89 | |

-continued

| Example | Preparative Example | Preparative Example | Product |
|---------|---------------------|---------------------|---------|
| 1083 | 923 | 89 | |
| 1084 | 924 | 89 | |
| 1085 | 925 | 89 | |
| 1086 | 926 | 89 | |
| 1087 | 927 | 89 | |

-continued
| Example | Preparative Example | Preparative Example | Product |
|---|---|---|---|
| 1088 | 928 | 89 | 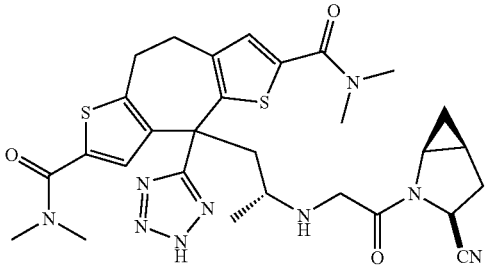 |
| 1089 | 929 | 89 | 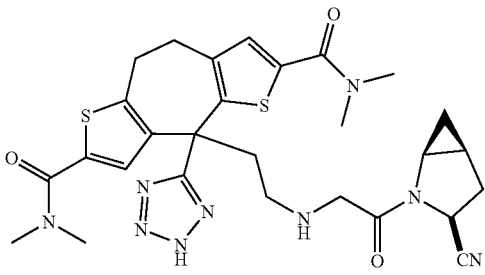 |
| 1090 | 1301 | 2 | 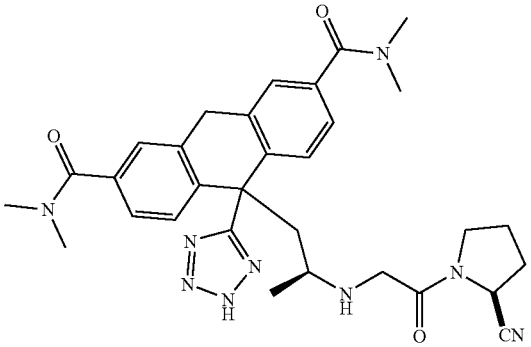 |
| 1091 | 1302 | 2 | 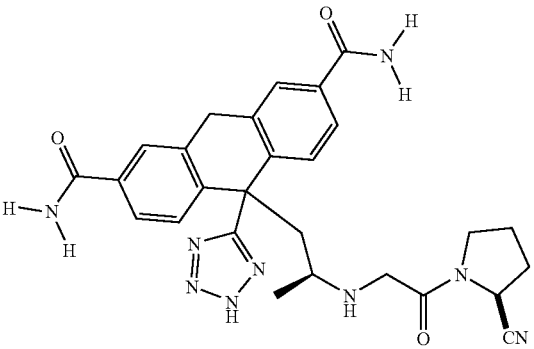 |

-continued

| Example | Preparative Example | Preparative Example | Product |
|---------|---------------------|---------------------|---------|
| 1092 | 1303 | 2 | |
| 1093 | 1304 | 2 | |
| 1094 | 1305 | 2 | |
| 1095 | 1306 | 2 | |

| Example | Preparative Example | Preparative Example | Product |
|---------|---------------------|---------------------|---------|
| 1096 | 1307 | 2 | |
| 1097 | 1308 | 2 | |
| 1098 | 1309 | 2 | |
| 1099 | 1351 | 2 | |

-continued
| Example | Preparative Example | Preparative Example | Product |
|---|---|---|---|
| 1100 | 1352 | 2 | 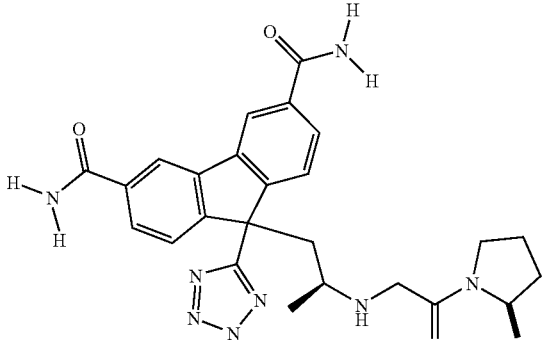 |
| 1101 | 1353 | 2 | 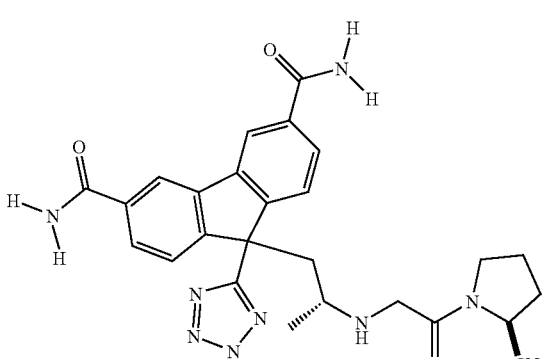 |
| 1102 | 1354 | 2 | 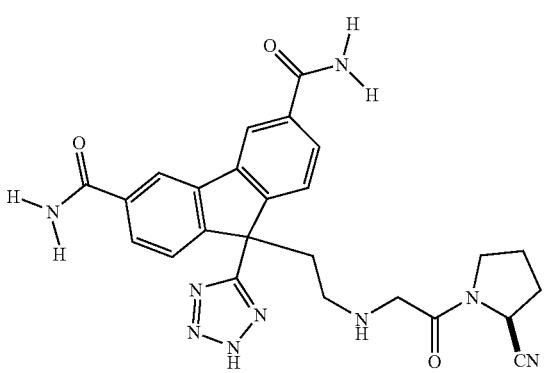 |
| 1103 | 1355 | 2 | 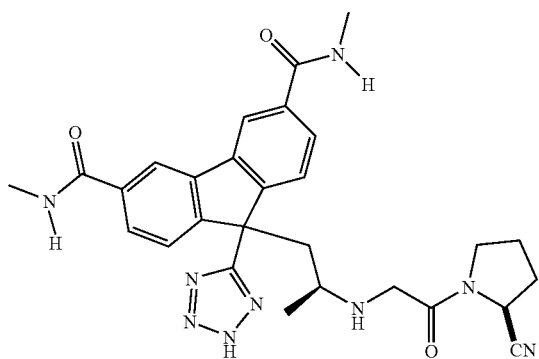 |

-continued

| Example | Preparative Example | Preparative Example | Product |
|---------|--------------------|--------------------|---------|
| 1104 | 1356 | 2 | |
| 1105 | 1357 | 2 | |
| 1106 | 1358 | 2 | |
| 1107 | 1359 | 2 | |

| Example | Preparative Example | Preparative Example | Product |
|---|---|---|---|
| 1108 | 1401 | 2 | 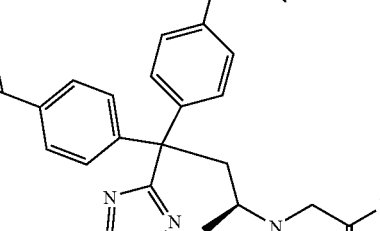 |
| 1109 | 1402 | 2 | 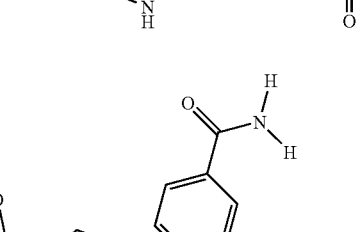 |
| 1110 | 1403 | 2 | 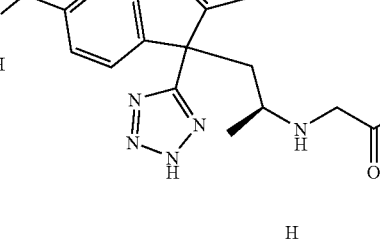 |
| 1111 | 1404 | 2 | 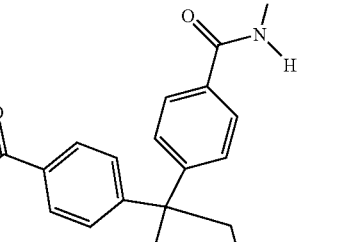 |

| Example | Preparative Example | Preparative Example | Product |
|---------|---------------------|---------------------|---------|
| 1112 | 1405 | 2 | |
| 1113 | 1406 | 2 | |
| 1114 | 1407 | 2 | |
| 1115 | 1408 | 2 | |

-continued

| Example | Preparative Example | Preparative Example | Product |
|---------|---------------------|---------------------|---------|
| 1116 | 1409 | 2 | |
| 1117 | 1301 | 89 | |
| 1118 | 1302 | 89 | |
| 1119 | 1303 | 89 | |

-continued
| Example | Preparative Example | Preparative Example | Product |
|---------|---------------------|---------------------|---------|
| 1120 | 1304 | 89 | 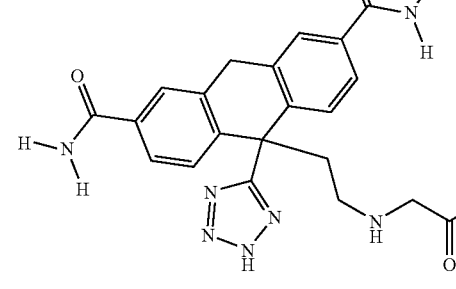 |
| 1121 | 1305 | 89 | 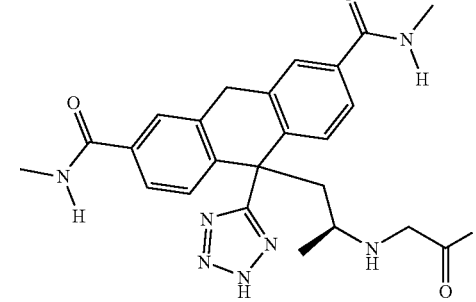 |
| 1122 | 1306 | 89 | 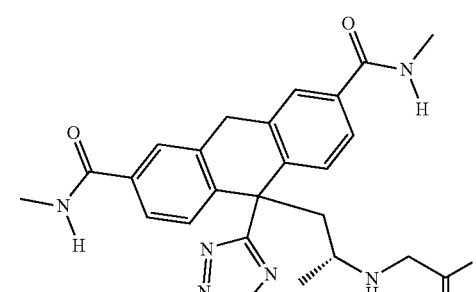 |
| 1123 | 1307 | 89 | 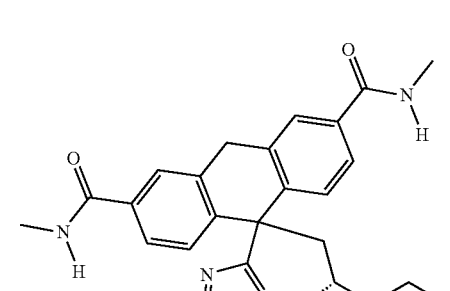 |

-continued
| Example | Preparative Example | Preparative Example | Product |
|---------|---------------------|---------------------|---------|
| 1124 | 1308 | 89 | 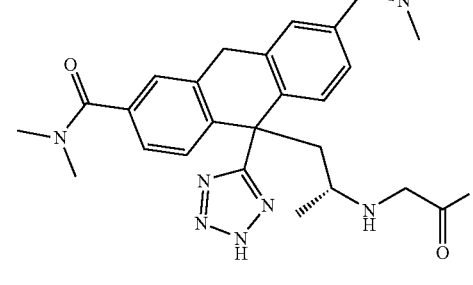 |
| 1125 | 1309 | 89 | 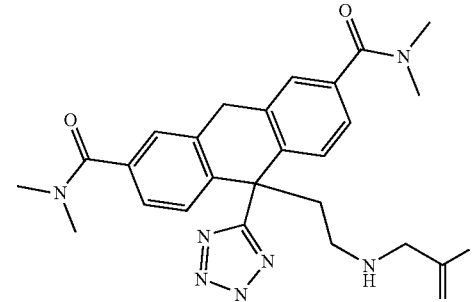 |
| 1126 | 1351 | 89 | 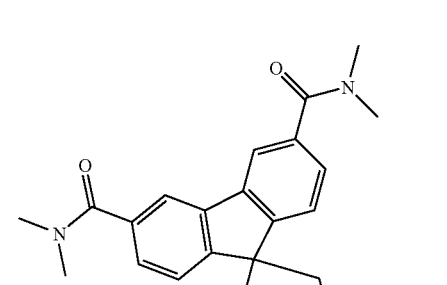 |
| 1127 | 1352 | 89 | 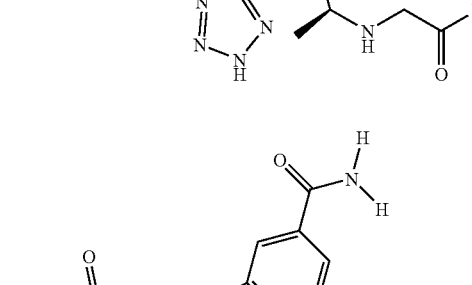 |

| Example | Preparative Example | Preparative Example | Product |
|---|---|---|---|
| 1128 | 1353 | 89 | |
| 1129 | 1354 | 89 | |
| 1130 | 1355 | 89 | |
| 1131 | 1356 | 89 | |

| Example | Preparative Example | Preparative Example | Product |
|---|---|---|---|
| 1132 | 1357 | 89 | 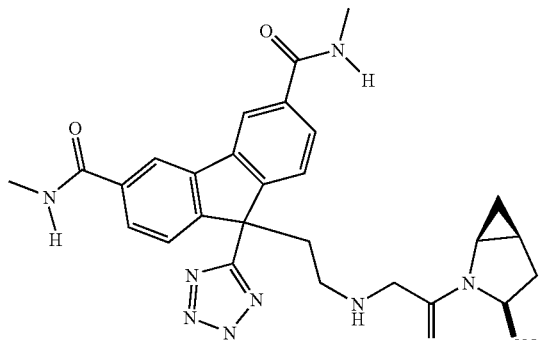 |
| 1133 | 1358 | 89 | 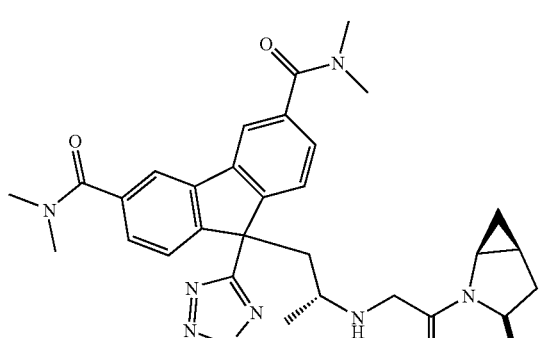 |
| 1134 | 1359 | 89 | 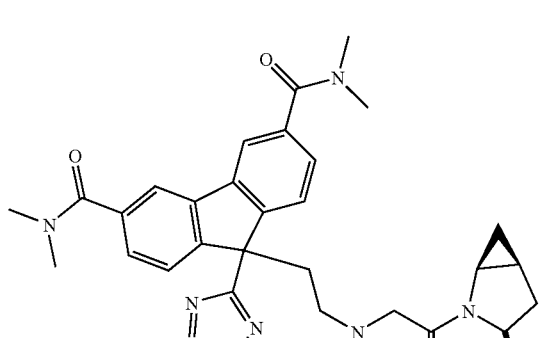 |
| 1135 | 1401 | 89 | 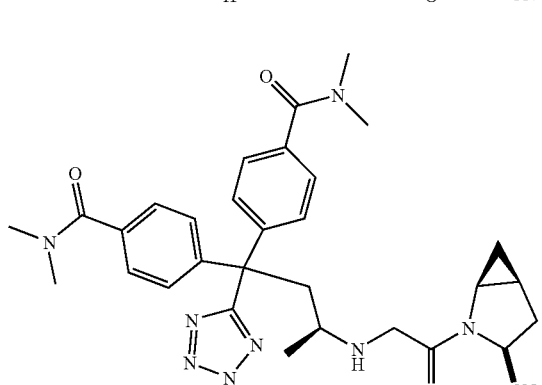 |

-continued

| Example | Preparative Example | Preparative Example | Product |
|---------|--------------------|--------------------|---------|
| 1136 | 1402 | 89 | |
| 1137 | 1403 | 89 | |
| 1138 | 1404 | 89 | |
| 1139 | 1405 | 89 | |

-continued
| Example | Preparative Example | Preparative Example | Product |
|---|---|---|---|
| 1140 | 1406 | 89 | 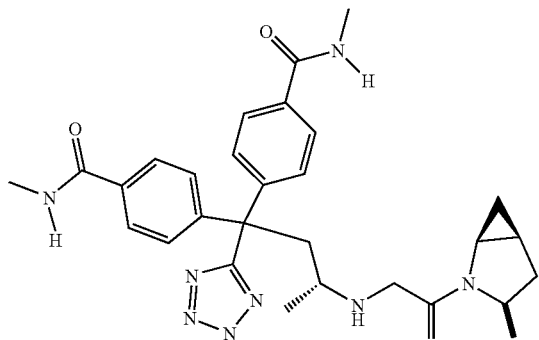 |
| 1141 | 1407 | 89 | 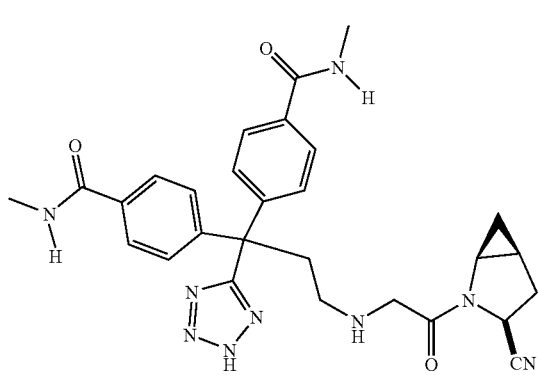 |
| 1142 | 1408 | 89 | 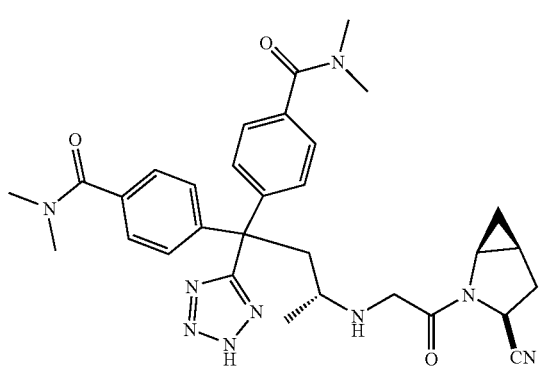 |
| 1143 | 1409 | 89 | 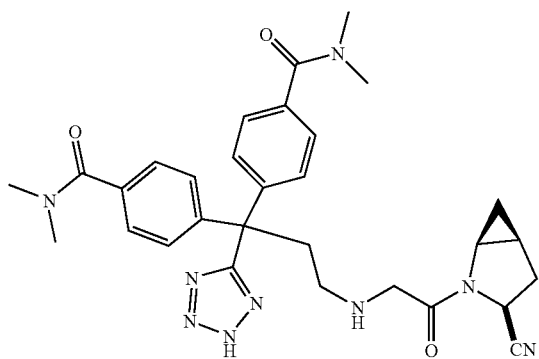 |

|Example|Preparative Example|Preparative Example|Product|
|---|---|---|---|
|1144|1450StepK|2|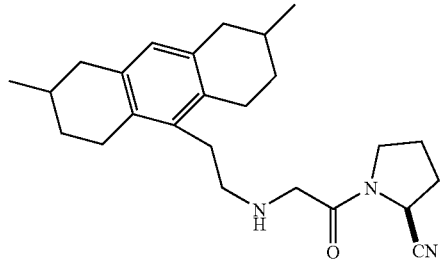|
|1145|1450StepO|2|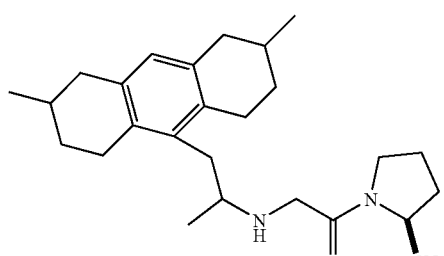|
|1146|1451Step F|2|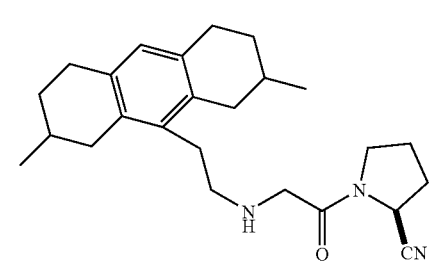|
|1147|1451Step J|2|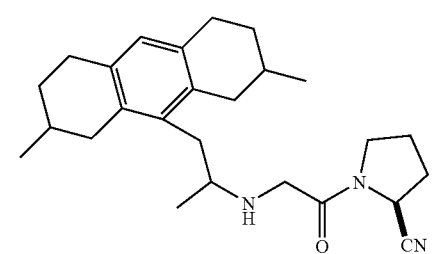|
|1148|1452Step F|2|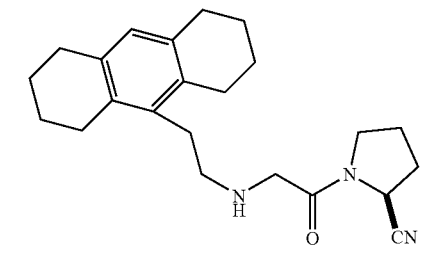|
|1149|1452Step J|2|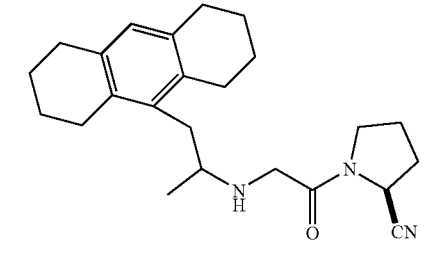|

| Example | Preparative Example | Preparative Example | Product |
|---|---|---|---|
| 1150 | 1453Step J | 2 | 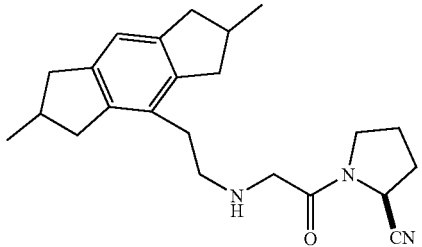 |
| 1151 | 1453StepM | 2 | 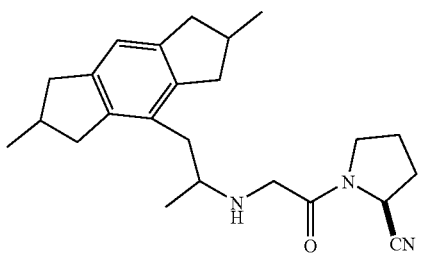 |
| 1152 | 1454Step I | 2 | 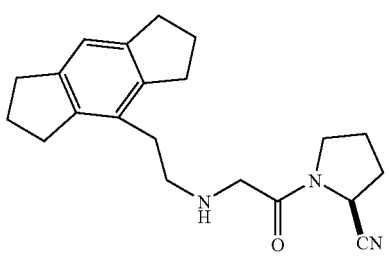 |
| 1153 | 1454Step L | 2 | 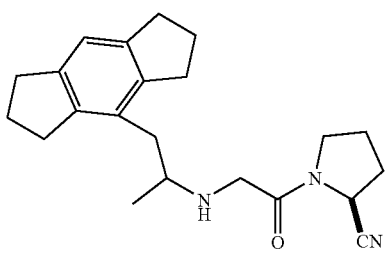 |
| 1154 | 1500 | 2 | 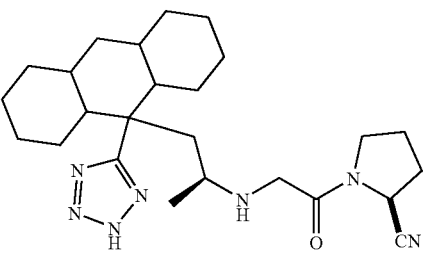 |
| 1155 | 1501 | 2 | 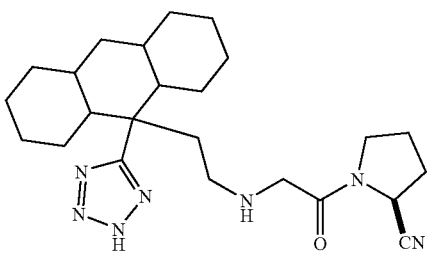 |

-continued

| Example | Preparative Example | Preparative Example | Product |
|---|---|---|---|
| 1156 | 1502 | 2 | |
| 1157 | 1450StepK | 89 | |
| 1158 | 1450StepO | 89 | |
| 1159 | 1451Step F | 89 | |
| 1160 | 1451Step J | 89 | |

-continued
| Example | Preparative Example | Preparative Example | Product |
|---|---|---|---|
| 1161 | 1452Step F | 89 | 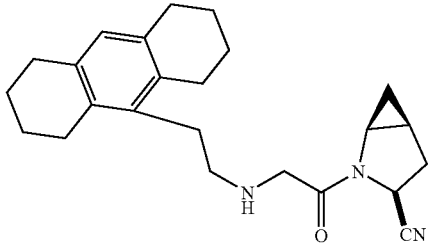 |
| 1162 | 1452Step J | 89 | 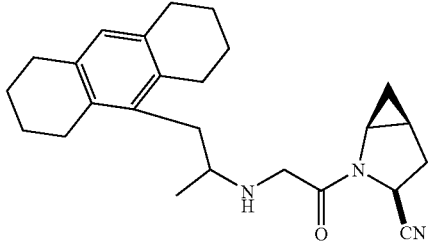 |
| 1163 | 1453Step J | 89 | 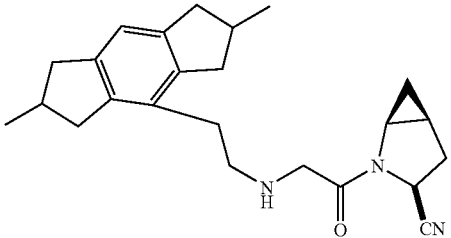 |
| 1164 | 1453StepM | 89 | 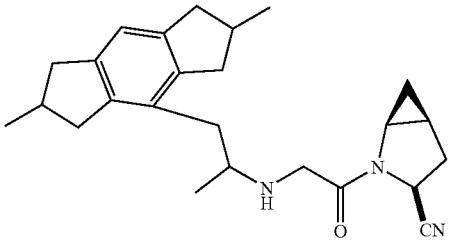 |
| 1165 | 1454Step I | 89 | 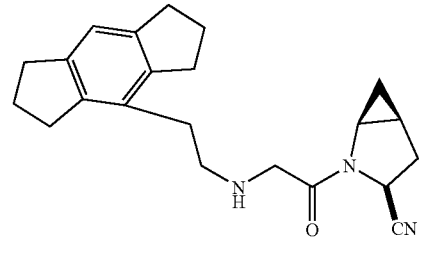 |
| 1166 | 1454Step L | 89 | 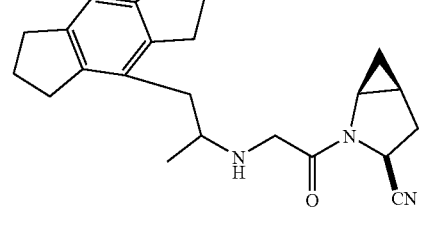 |

| Example | Preparative Example | Preparative Example | Product |
|---|---|---|---|
| 1167 | 1500 | 89 | 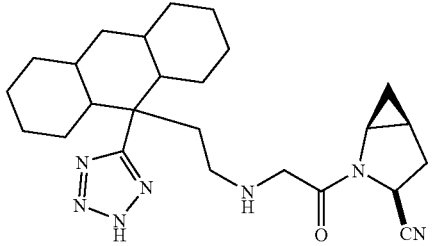 |
| 1168 | 1501 | 89 | 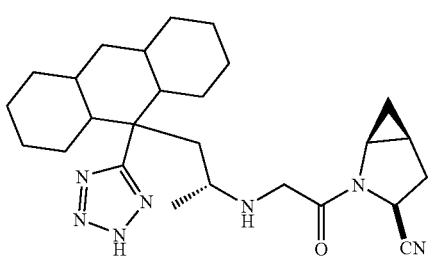 |

Examples 1169-1499 have been intentionally excluded.

Example 1500-1709

If one were to follow a similar procedure as that described in Preparative Example 48, except using the compounds from the Preparative Examples as indicated in the Table below, one would obtain the desired amine product.

| Example | Compound Preparative Example | Product |
|---|---|---|
| 1500 | 1000 | 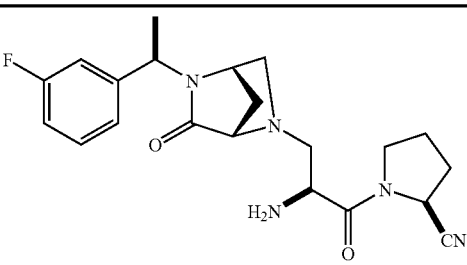 |
| 1501 | 1001 | 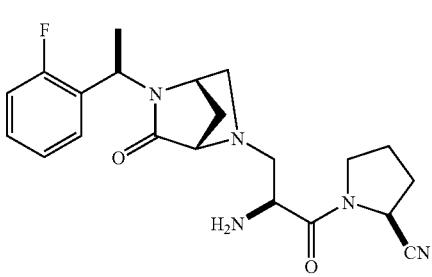 |

-continued
| Example | Compound Preparative Example | Product |
|---|---|---|
| 1502 | 1002 | 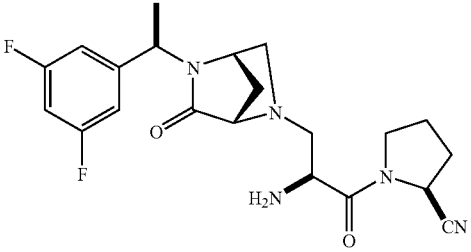 |
| 1503 | 1003 | 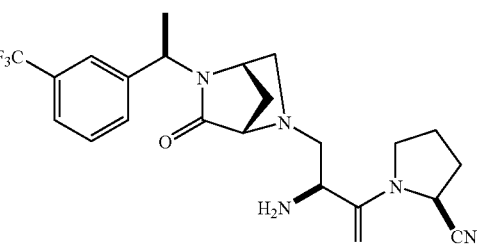 |
| 1504 | 1004 | 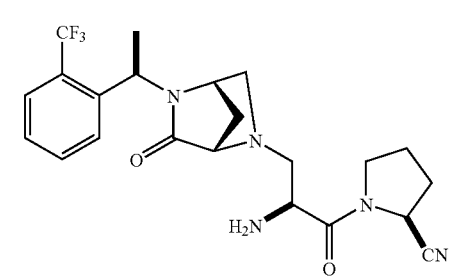 |
| 1505 | 1005 | 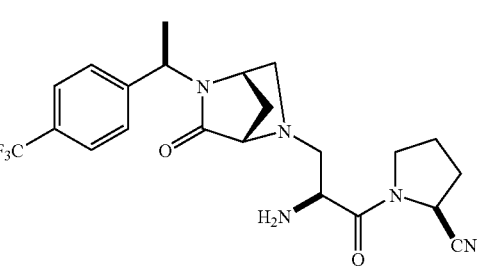 |
| 1506 | 1006 | 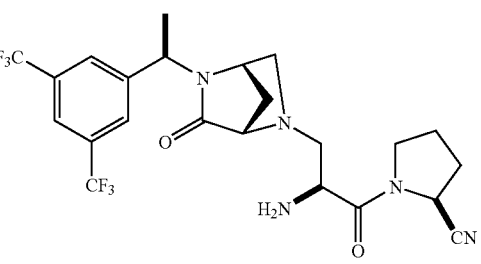 |
| 1507 | 1007 | 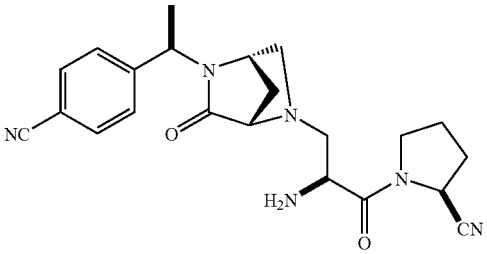 |

-continued
| Example | Compound Preparative Example | Product |
|---|---|---|
| 1508 | 1008 | 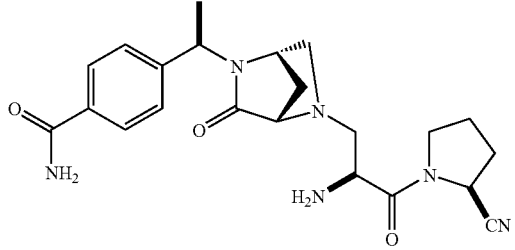 |
| 1509 | 1009 | 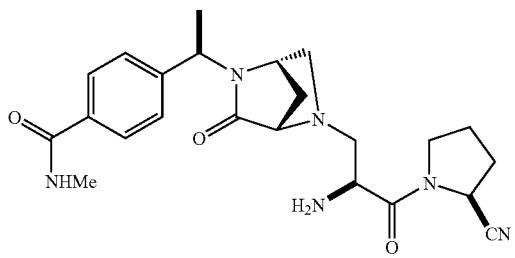 |
| 1510 | 1010 | 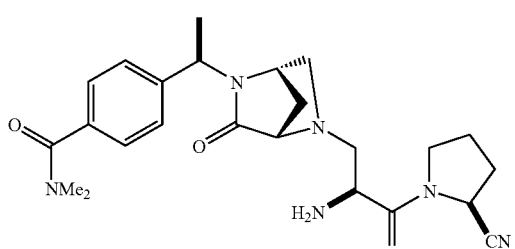 |
| 1511 | 1011 | 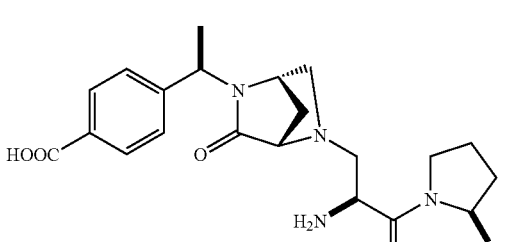 |
| 1512 | 1012 | 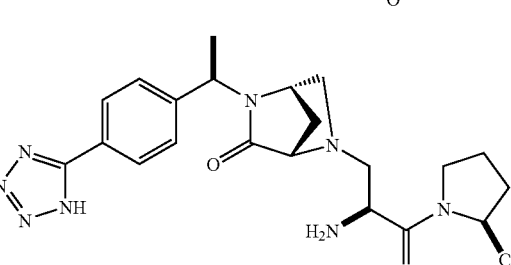 |
| 1513 | 1013 | 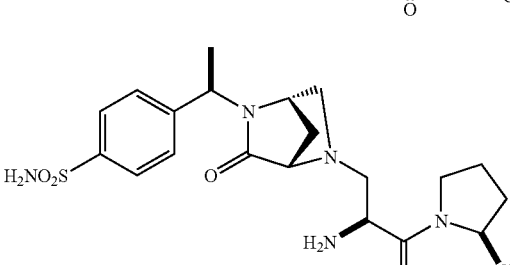 |

-continued
| Example | Compound Preparative Example | Product |
|---|---|---|
| 1514 | 1014 | 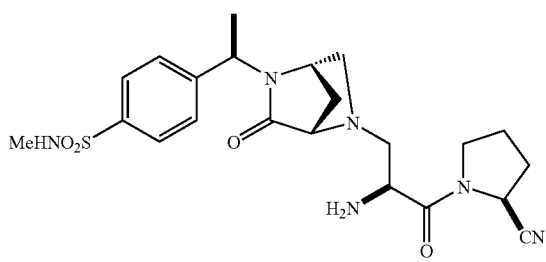 |
| 1515 | 1015 | 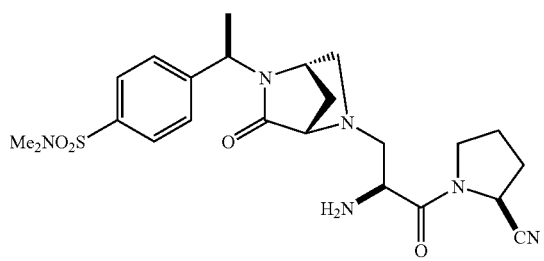 |
| 1516 | 1016 | 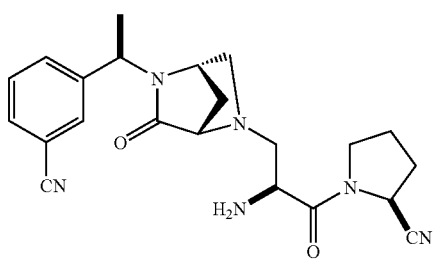 |
| 1517 | 1017 | 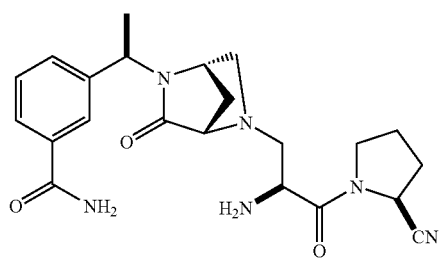 |
| 1518 | 1018 | 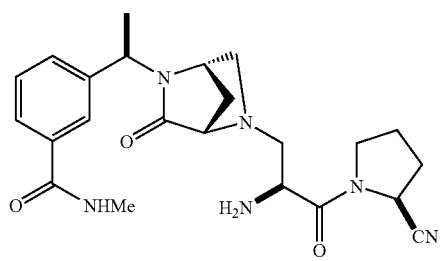 |

| Example | Compound Preparative Example | Product |
|---|---|---|
| 1519 | 1019 | |
| 1520 | 1020 | |
| 1521 | 1021 | |
| 1522 | 1022 | |
| 1523 | 1023 | |
| 1524 | 1024 | |

-continued
| Example | Compound Preparative Example | Product |
|---|---|---|
| 1525 | 1025 | 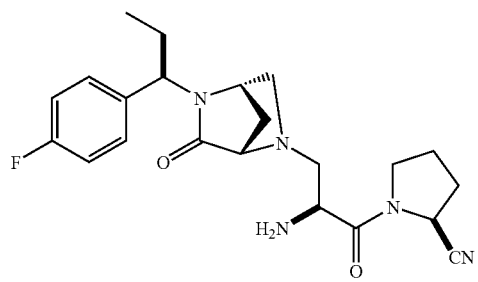 |
| 1526 | 1026 | 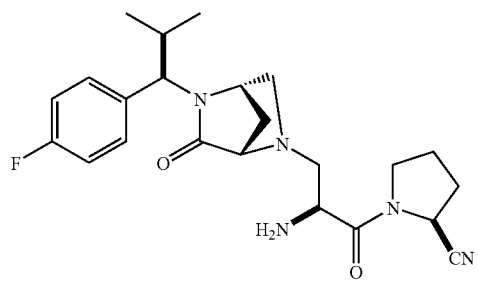 |
| 1527 | 1027 | 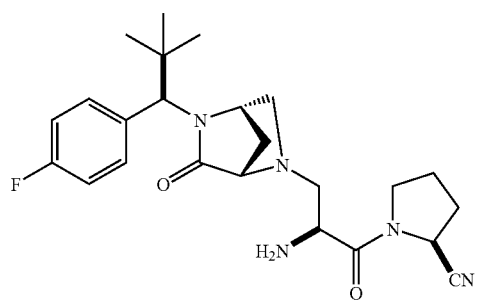 |
| 1528 | 1028 | 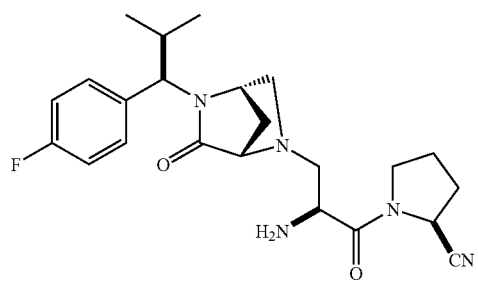 |
| 1529 | 1029 | 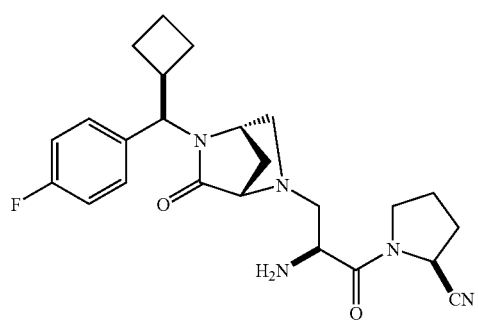 |

-continued
| Example | Compound Preparative Example | Product |
|---|---|---|
| 1530 | 1030 | 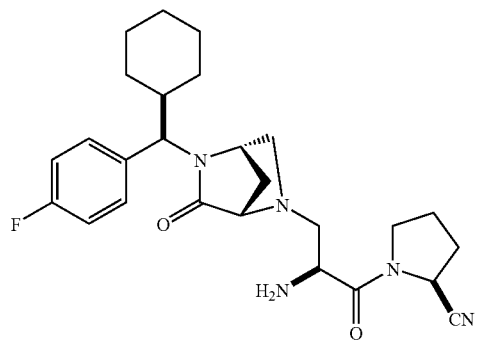 |
| 1531 | 1031 | 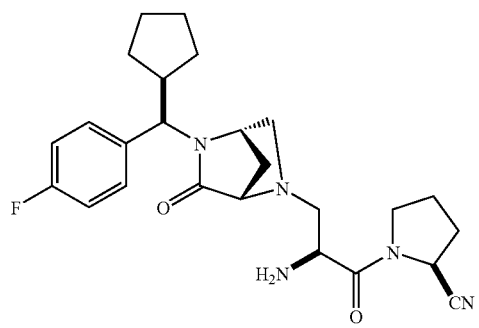 |
| 1532 | 1032 | 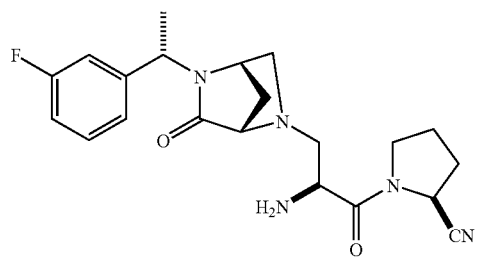 |
| 1533 | 1033 | 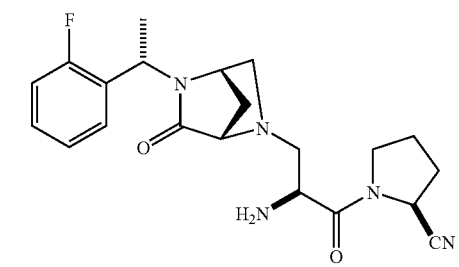 |
| 1534 | 1034 | 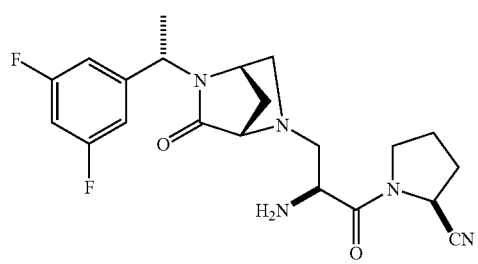 |

-continued

| Example | Compound Preparative Example | Product |
|---|---|---|
| 1535 | 1035 | 3-(trifluoromethyl)phenyl derivative |
| 1536 | 1036 | 2-(trifluoromethyl)phenyl derivative |
| 1537 | 1037 | 4-(trifluoromethyl)phenyl derivative |
| 1538 | 1038 | 3,5-bis(trifluoromethyl)phenyl derivative |
| 1539 | 1039 | 4-cyanophenyl derivative |
| 1540 | 1040 | 4-carbamoylphenyl derivative |

-continued

| Example | Compound Preparative Example | Product |
|---|---|---|
| 1541 | 1041 | |
| 1542 | 1042 | |
| 1543 | 1043 | |
| 1544 | 1044 | |
| 1545 | 1045 | |
| 1546 | 1046 | |

-continued

| Example | Compound Preparative Example | Product |
|---|---|---|
| 1547 | 1047 | |
| 1548 | 1048 | |
| 1549 | 1049 | |
| 1550 | 1050 | |
| 1551 | 1051 | |
| 1552 | 1052 | |

-continued
| Example | Compound Preparative Example | Product |
| --- | --- | --- |
| 1553 | 1053 | 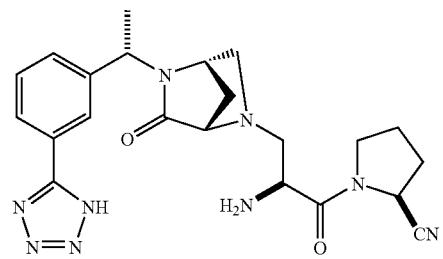 |
| 1554 | 1054 | 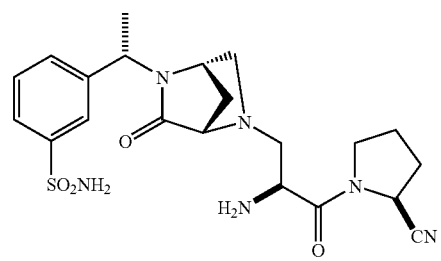 |
| 1555 | 1055 | 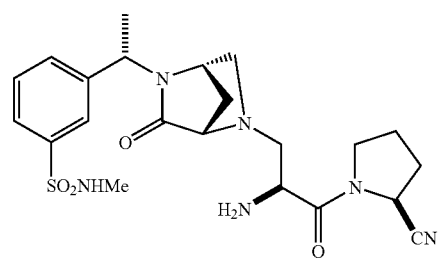 |
| 1556 | 1056 | 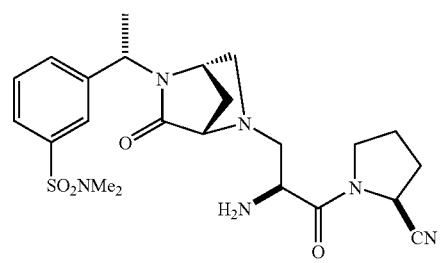 |
| 1557 | 1057 | 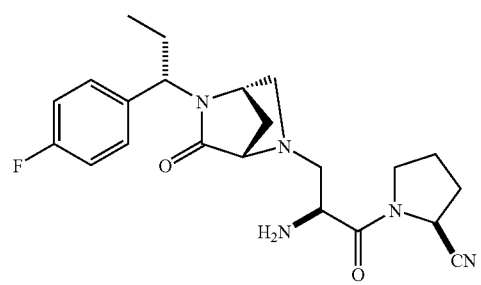 |

-continued

| Example | Compound Preparative Example | Product |
|---|---|---|
| 1558 | 1058 | |
| 1559 | 1059 | |
| 1560 | 1060 | |
| 1561 | 1061 | |
| 1562 | 1062 | |

-continued
| Example | Compound Preparative Example | Product |
|---------|------------------------------|---------|
| 1563 | 1063 | 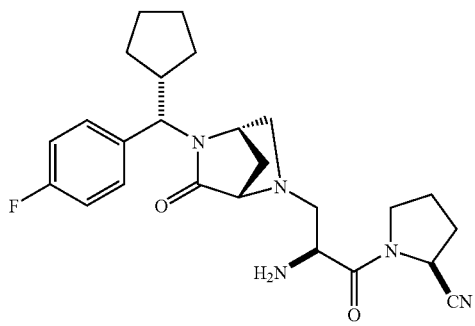 |
| 1564 | 1064 | 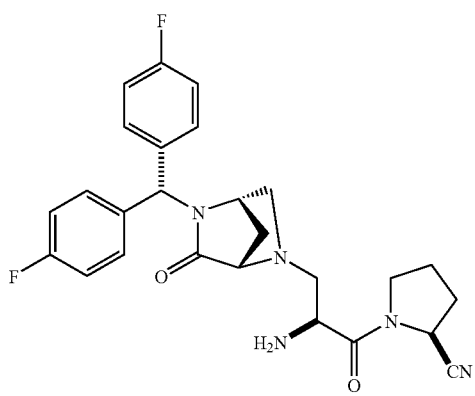 |
| 1565 | 1065 | 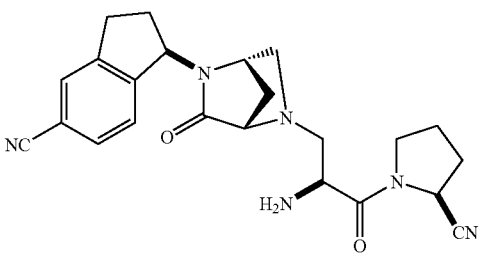 |
| 1566 | 1066 | 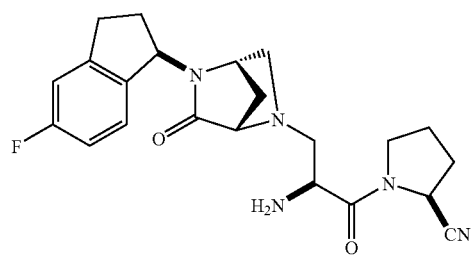 |
| 1567 | 1067 | 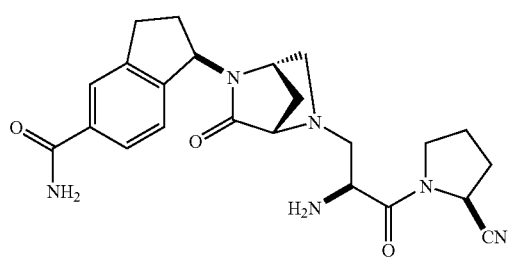 |

-continued

| Example | Compound Preparative Example | Product |
|---|---|---|
| 1568 | 1068 | |
| 1569 | 1069 | |
| 1570 | 1070 | |
| 1571 | 1071 | |
| 1572 | 1072 | |
| 1573 | 1073 | |

-continued
| Example | Compound Preparative Example | Product |
|---|---|---|
| 1574 | 1074 | 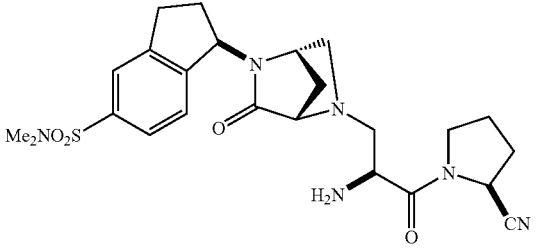 |
| 1575 | 1075 | 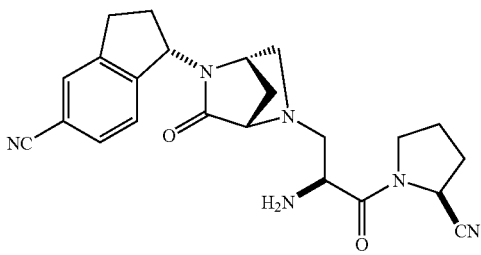 |
| 1576 | 1076 | 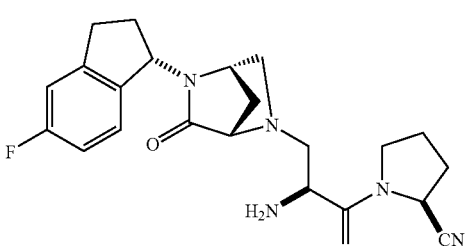 |
| 1577 | 1077 | 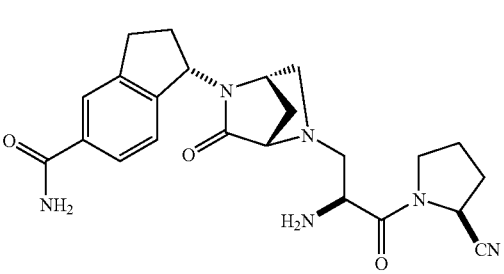 |
| 1578 | 1078 | 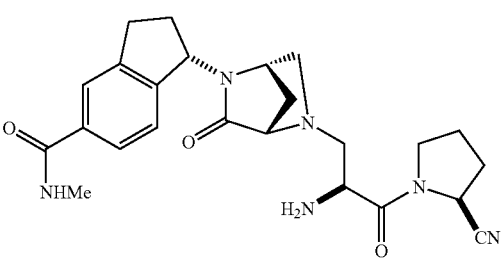 |
| 1579 | 1079 | 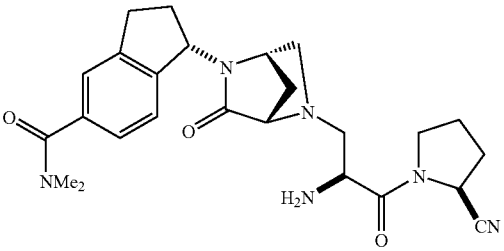 |

-continued

| Example | Compound Preparative Example | Product |
|---|---|---|
| 1580 | 1080 | |
| 1581 | 1081 | |
| 1582 | 1082 | |
| 1583 | 1083 | |
| 1584 | 1084 | |
| 1585 | 1085 | |

-continued

| Example | Compound Preparative Example | Product |
|---|---|---|
| 1586 | 1086 | |
| 1587 | 1087 | |
| 1588 | 1088 | |
| 1589 | 1089 | |
| 1590 | 1090 | |
| 1591 | 1091 | |

-continued

| Example | Compound Preparative Example | Product |
|---|---|---|
| 1592 | 1092 | |
| 1593 | 1093 | |
| 1594 | 1094 | |
| 1595 | 1095 | |
| 1596 | 1096 | |
| 1597 | 1097 | |

-continued

| Example | Compound Preparative Example | Product |
|---|---|---|
| 1598 | 1098 | |
| 1599 | 1099 | |
| 1600 | 1100 | |
| 1601 | 1101 | |
| 1602 | 1102 | |
| 1603 | 1103 | |

-continued

| Example | Compound Preparative Example | Product |
|---|---|---|
| 1604 | 1104 | |
| 1605 | 1105 | |
| 1606 | 1106 | |
| 1607 | 1107 | |
| 1608 | 1108 | |
| 1609 | 1109 | |

-continued
| Example | Compound Preparative Example | Product |
|---|---|---|
| 1610 | 1110 | 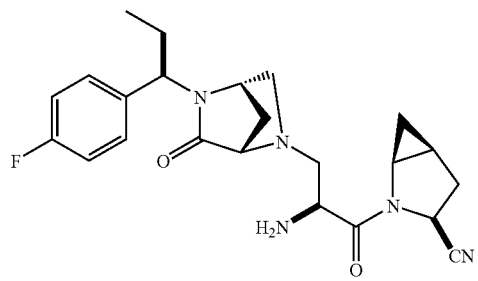 |
| 1611 | 1111 | 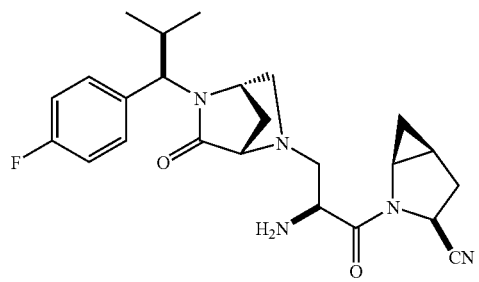 |
| 1612 | 1112 | 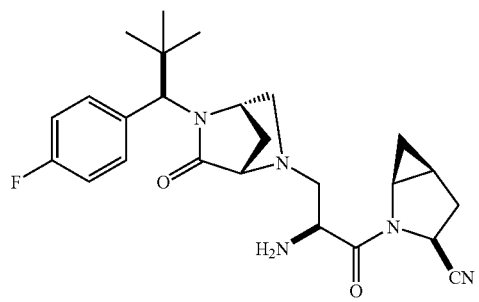 |
| 1613 | 1113 | 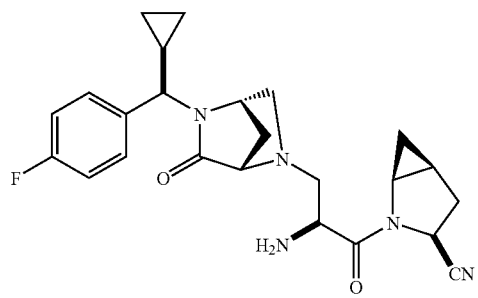 |
| 1614 | 1114 | 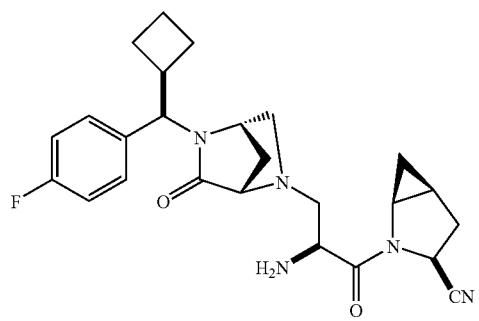 |

| Example | Compound Preparative Example | Product |
|---|---|---|
| 1615 | 1115 | 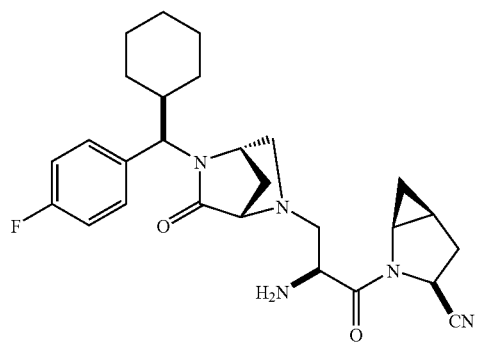 |
| 1616 | 1116 | 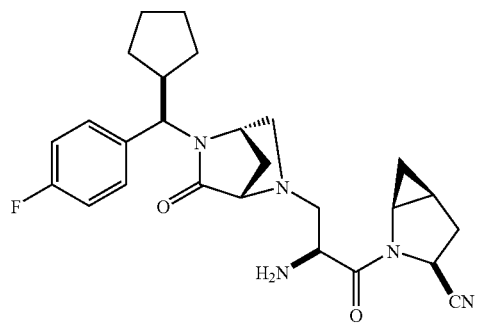 |
| 1617 | 1117 | 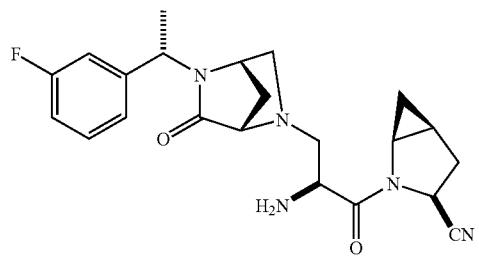 |
| 1618 | 1118 | 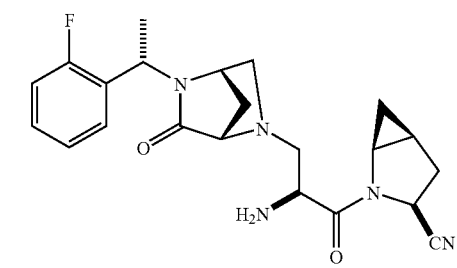 |
| 1619 | 1119 | 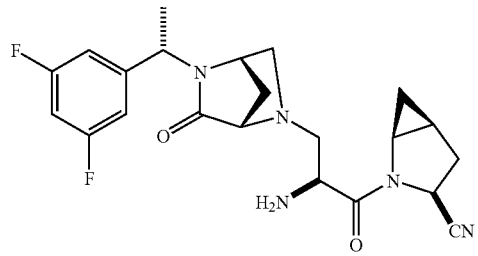 |

-continued

| Example | Compound Preparative Example | Product |
|---|---|---|
| 1620 | 1120 | |
| 1621 | 1121 | |
| 1622 | 1122 | |
| 1623 | 1123 | |
| 1624 | 1124 | |
| 1625 | 1125 | |

-continued

| Example | Compound Preparative Example | Product |
|---------|------------------------------|---------|
| 1626 | 1126 | |
| 1627 | 1127 | |
| 1628 | 1128 | |
| 1629 | 1129 | |
| 1630 | 1130 | |
| 1631 | 1131 | |

-continued
| Example | Compound Preparative Example | Product |
|---|---|---|
| 1632 | 1132 | 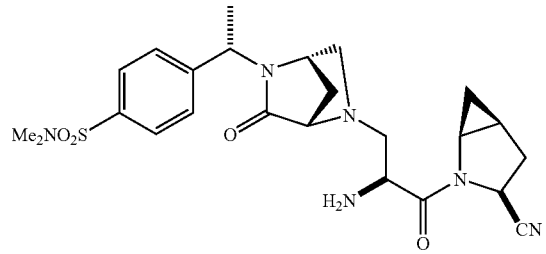 |
| 1633 | 1133 | 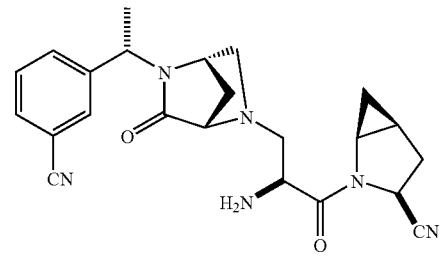 |
| 1634 | 1134 | 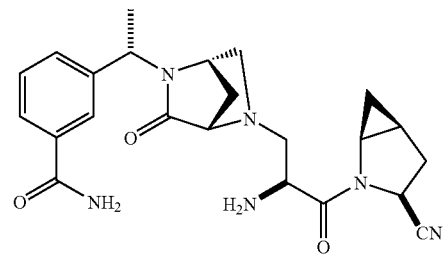 |
| 1635 | 1135 | 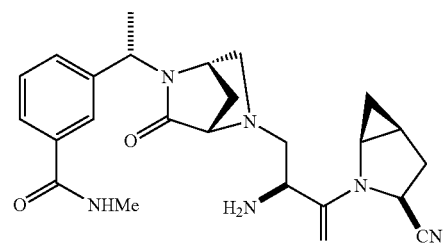 |
| 1636 | 1136 | 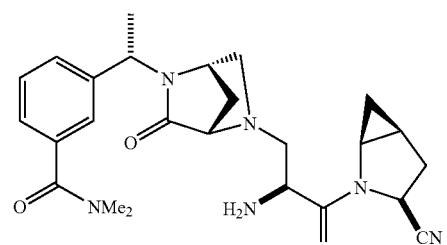 |
| 1637 | 1137 | 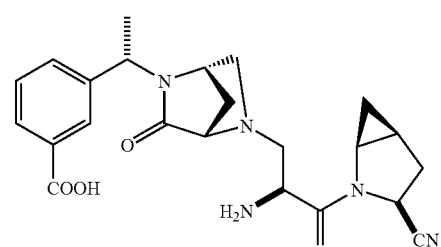 |

-continued
| Example | Compound Preparative Example | Product |
|---|---|---|
| 1638 | 1138 | 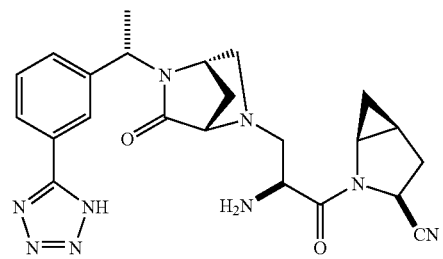 |
| 1639 | 1139 | 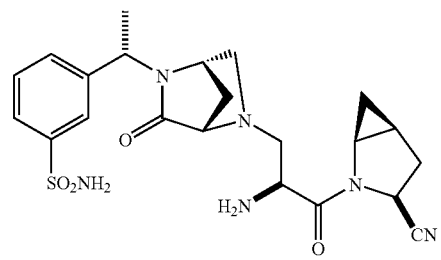 |
| 1640 | 1140 | 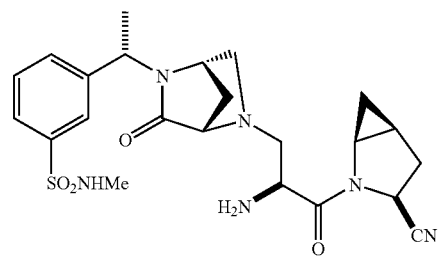 |
| 1641 | 1141 | 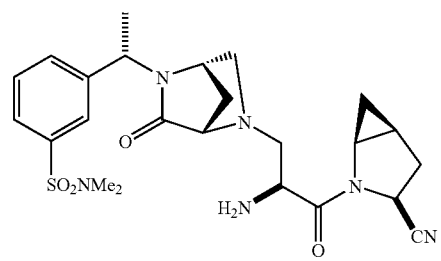 |
| 1642 | 1142 | 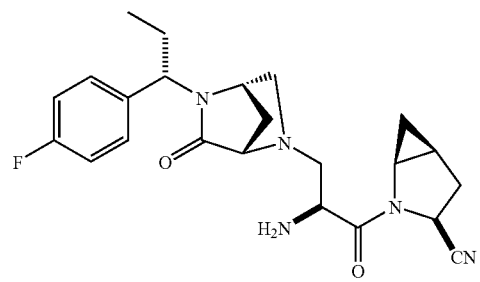 |

-continued
| Example | Compound Preparative Example | Product |
|---|---|---|
| 1643 | 1143 | 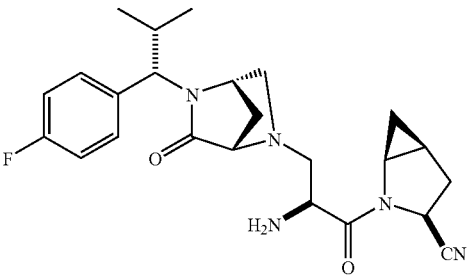 |
| 1644 | 1144 | 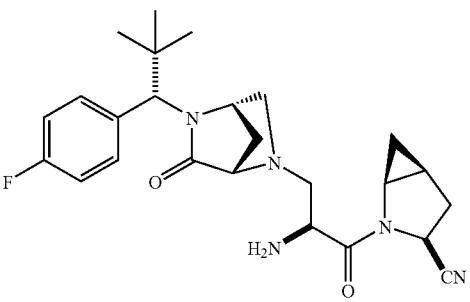 |
| 1645 | 1145 | 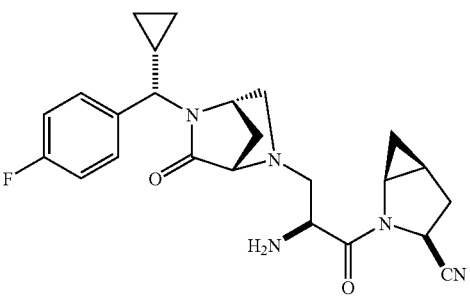 |
| 1646 | 1146 | 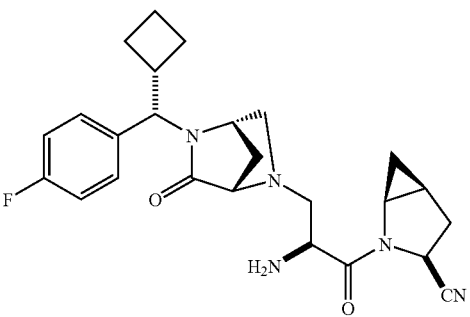 |
| 1647 | 1147 | 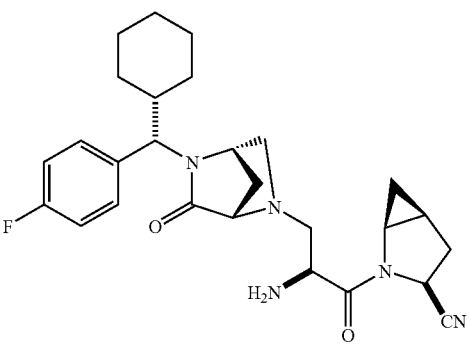 |

-continued
| Example | Compound Preparative Example | Product |
|---|---|---|
| 1648 | 1148 | 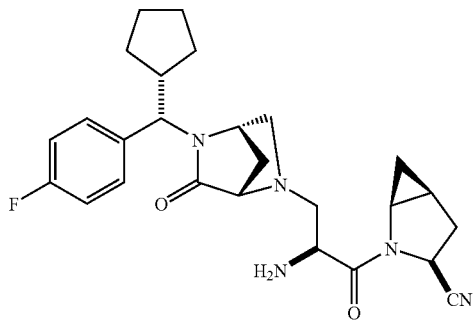 |
| 1649 | 1149 | 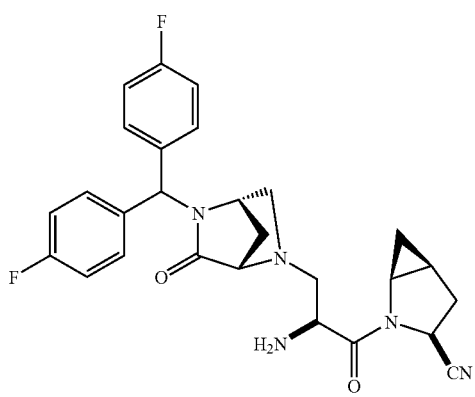 |
| 1650 | 1150 | 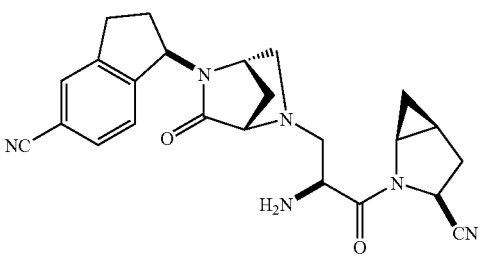 |
| 1651 | 1151 | 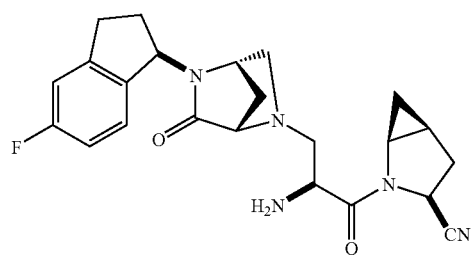 |
| 1652 | 1152 | 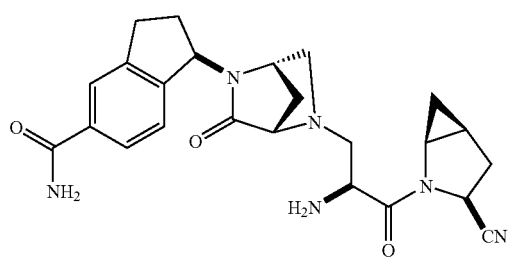 |

-continued

| Example | Compound Preparative Example | Product |
|---|---|---|
| 1653 | 1153 | |
| 1654 | 1154 | |
| 1655 | 1155 | |
| 1656 | 1156 | |
| 1657 | 1157 | |
| 1658 | 1158 | |

-continued

| Example | Compound Preparative Example | Product |
|---|---|---|
| 1659 | 1159 | |
| 1660 | 1160 | |
| 1661 | 1161 | |
| 1662 | 1162 | |
| 1663 | 1163 | |
| 1664 | 1164 | |

-continued

| Example | Compound Preparative Example | Product |
|---|---|---|
| 1665 | 1165 | |
| 1666 | 1166 | |
| 1667 | 1167 | |
| 1668 | 1168 | |
| 1669 | 1169 | |
| 1670 | 1170 | |

-continued
| Example | Compound Preparative Example | Product |
|---|---|---|
| 1671 | 1171 | 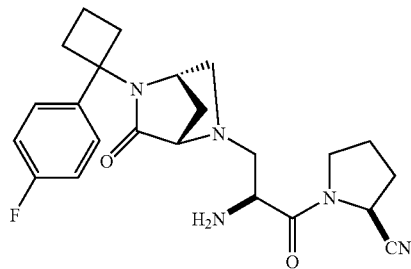 |
| 1672 | 1172 | 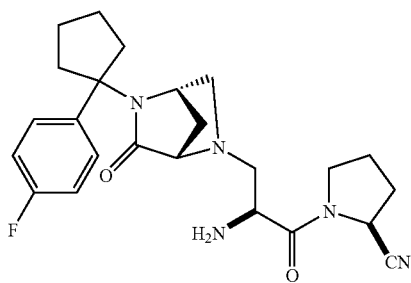 |
| 1673 | 1173 | 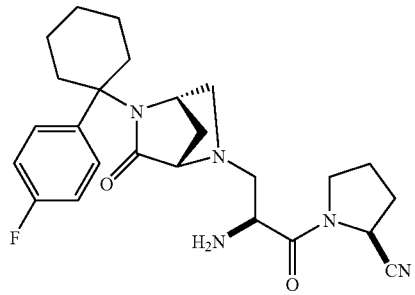 |
| 1674 | 1174 | 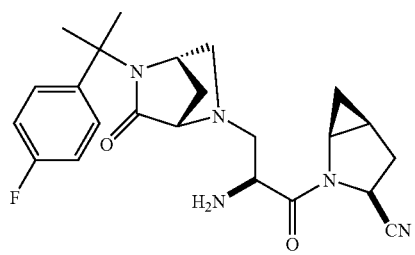 |
| 1675 | 1175 | 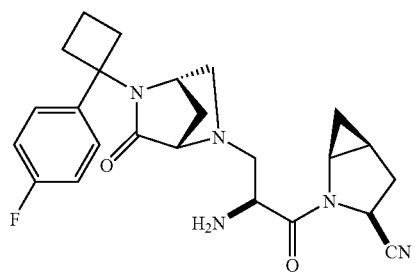 |

-continued
| Example | Compound Preparative Example | Product |
|---|---|---|
| 1676 | 1176 | 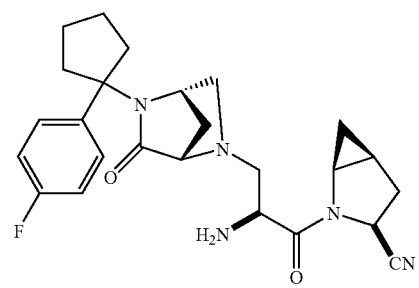 |
| 1677 | 1177 | 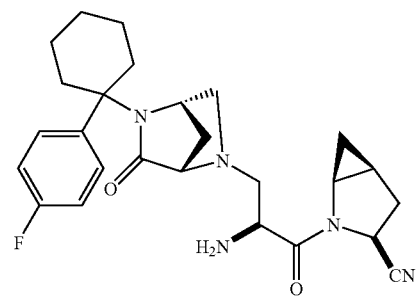 |
| 1678 | 1178 | 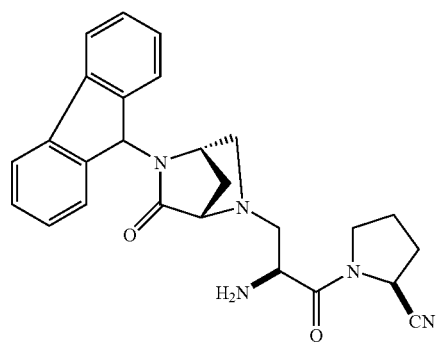 |
| 1679 | 1179 | 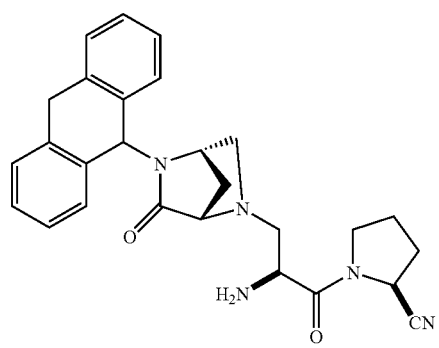 |

-continued

| Example | Compound Preparative Example | Product |
|---|---|---|
| 1680 | 1180 | |
| 1681 | 1181 | |
| 1682 | 1182 | |
| 1683 | 1183 | |
| 1684 | 1184 | |

-continued

| Example | Compound Preparative Example | Product |
|---|---|---|
| 1685 | 1185 | |
| 1686 | 1186 | |
| 1687 | 1187 | |
| 1688 | 1188 | |

-continued

| Example | Compound Preparative Example | Product |
|---|---|---|
| 1689 | 1189 | |
| 1690 | 1190 | |
| 1691 | 1191 | |
| 1692 | 1192 | |

-continued

| Example | Compound Preparative Example | Product |
|---|---|---|
| 1693 | 1193 | |
| 1694 | 1194 | |
| 1695 | 1195 | |
| 1696 | 1196 | |

-continued
| Example | Compound Preparative Example | Product |
|---------|------------------------------|---------|
| 1697 | 1197 | 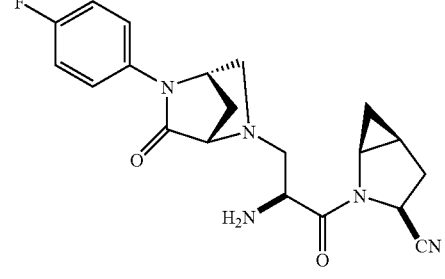 |
| 1698 | 1198 | 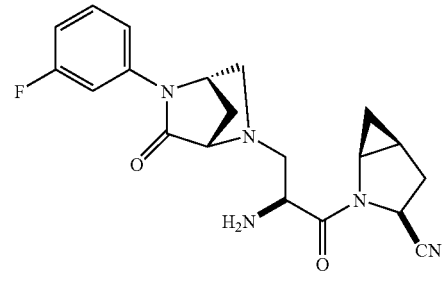 |
| 1699 | 1199 | 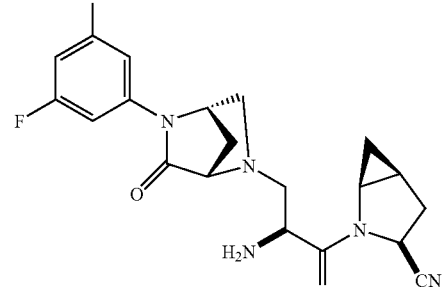 |
| 1700 | 1200 | 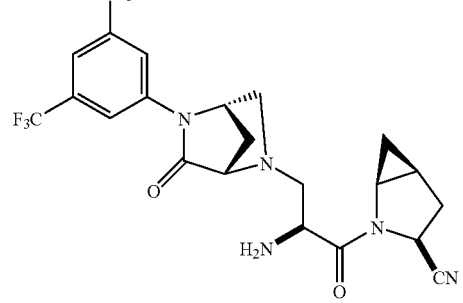 |
| 1701 | 1201 | 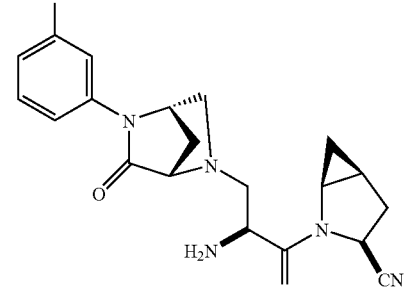 |

-continued

| Example | Compound Preparative Example | Product |
|---|---|---|
| 1702 | 1202 | |
| 1703 | 1203 | |
| 1704 | 1204 | |
| 1705 | 1205 | |

-continued
| Example | Compound Preparative Example | Product |
|---|---|---|
| 1706 | 1206 | 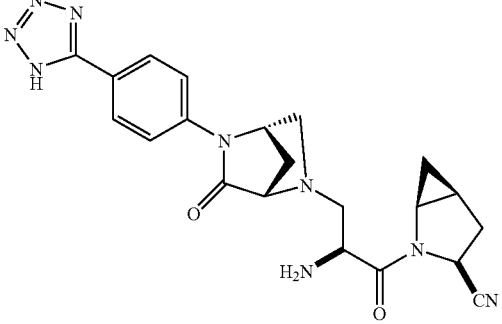 |
| 1707 | 1207 | 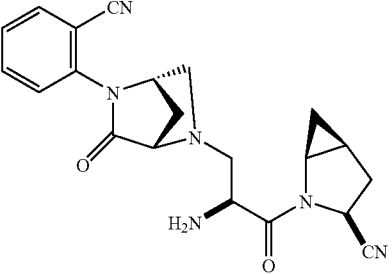 |
| 1708 | 1208 | 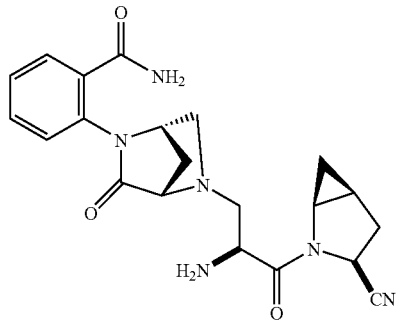 |
| 1709 | 1209 | 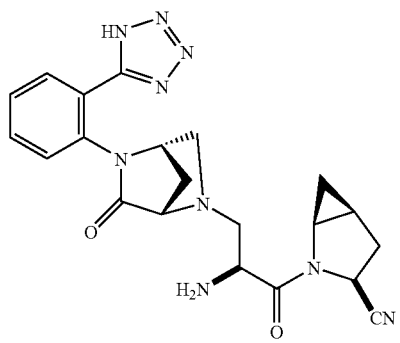 |
Examples 1710-1799 have been intentionally excluded.

Example 1800

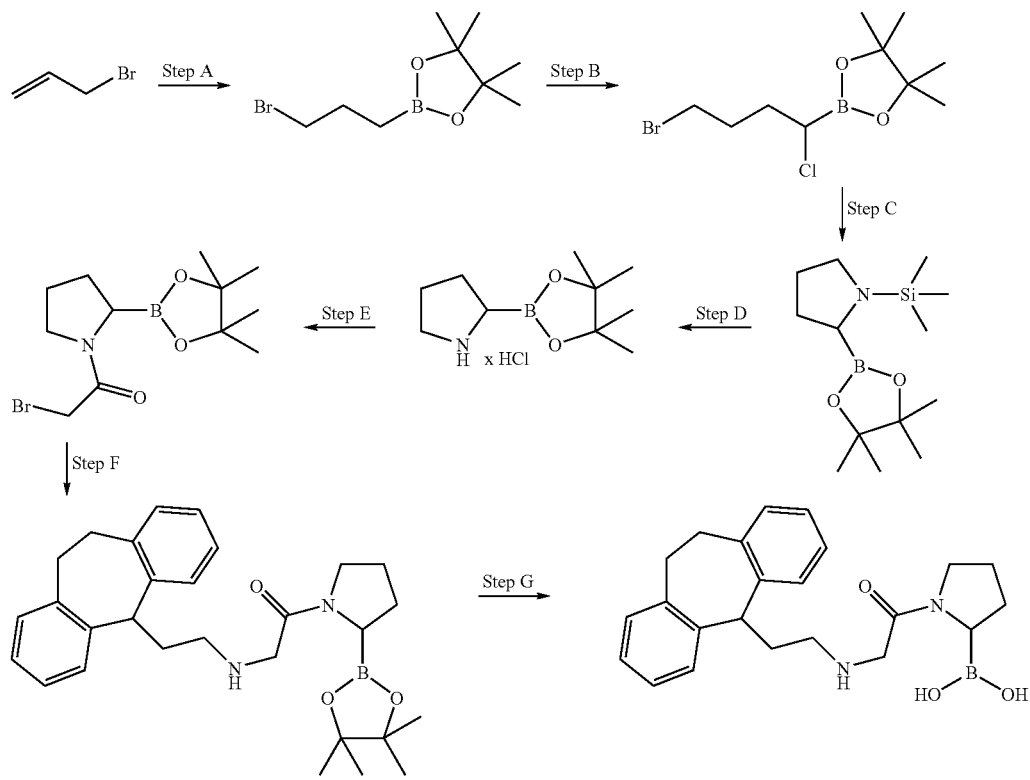

Step A

If one were to treat allyl bromide with 1.0 eq. catechol borane, heat the mixture at 100° C., distillate at reduced pressure, treat the intermediate with 2.0 eq. pinacol in THF at 0° C. and room temperature, evaporate, dissolve in hexane and remove pinacol by filtration, distillate at reduced pressure, one would obtain the title compound.

Step B

If one were to dissolve methylene chloride (1.0 eq.) in THF and then slowly add 1.54 N "BuLi in hexane (1.1 eq.) at −100° C., and would then add the title compound from Step A above (1.0 equ.), dissolved in THF, cooled to the freezing point of the solution, to the reaction mixture, followed by adding a suspension of zinc chloride (0.55 eq.) in THF, cooled to 0° C., in several portions to the reaction mixture, subsequently allowing the mixture to slowly warm to room temperature and to stir overnight, then, after evaporation of the solvent and redissolving the residue in hexane and washing with water, discarding insoluble material, drying (MgSO$_4$) and evaporation of the solvent, followed by distillation, one would obtain the title compound.

Step C

If one were to treat a fresh prepared LiHMDS solution in THF with 1 eq. of the title compound from Step B at −78° C., one would obtain after stirring overnight at rt, filtering of the precipitant and distillation of the filtrate the title compound as an oil.

Step D

If one were to treat the title compound from Step C above with 3 eq. of a 4 M HCl solution in dioxane at −78° C., one would obtain after stirring for 1 hour at rt and evaporation of the solvent the title compound as a HCl salt.

Step E

If one were to treat the title compound from Step D above with bromo acetyl bromide as described in Example 1, one would obtain the title compound.

Step F

If one were to treat the title compound from Step E above with the title compound from Preparative Example 15 as described in Example 1, one would obtain the title compound.

Step G

If one were to treat the title compound from Step F above with 6.0 eq. diethanolamine in THF at room temperature, add Et$_2$O to the mixture, separate the precipitate by filtration, dissolve the solid in an appropriate solvent and add Dowex AG 50-X8, filtrate and evaporate the filtrate, one would obtain the title compound.

Examples 1801-1849 have been intentionally excluded.

Example 1850

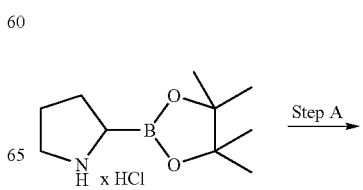

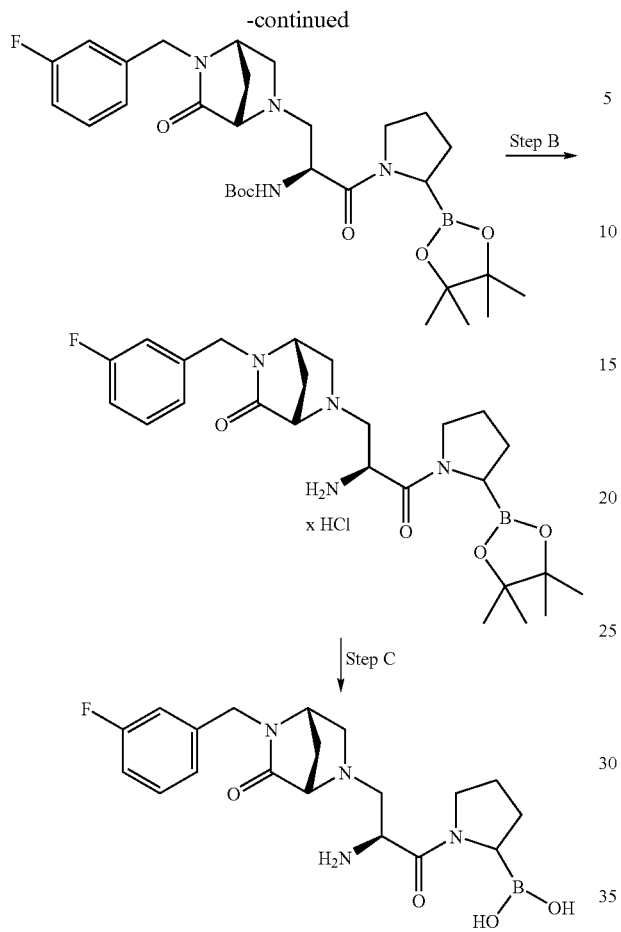

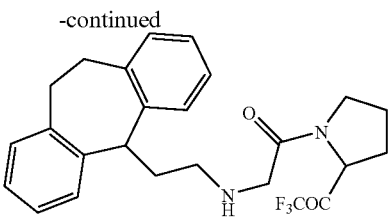

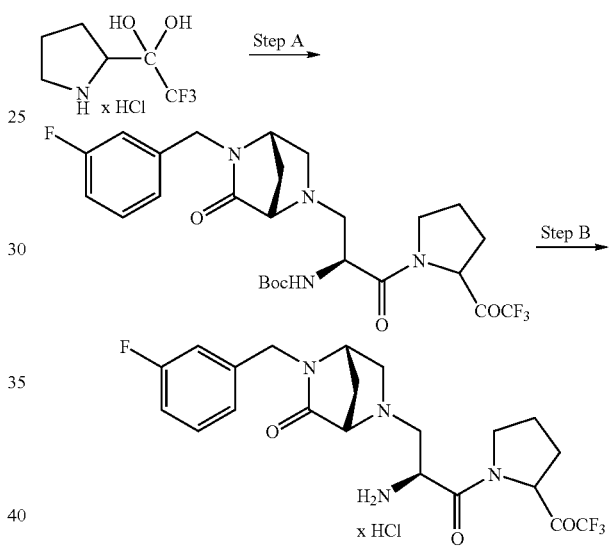

Step A
If one were to treat the title compound from Preparative Example 92 with the title compound from Example 1800, Step D, as described in Preparative Example 93, one would obtain the title compound.

Step B
If one were to treat the title compound from Step A above as described in Example 48, one would obtain the title compound. If one were to use a reverse phase HPLC separation (5-pm Nucleosil C18 HPLC column, acetonitrile:H$_2$O: 0.1% TFA), one could obtain the individual diastereomers.

Step C
If one were to treat the title compound from Step B above with 6.0 eq. diethanolamine in THF at room temperature, add Et$_2$O to the mixture, separate the precipitate by filtration, dissolve the solid in an appropriate solvent and add Dowex AG 50-X8, filtrate and evaporate the filtrate, one would obtain the title compound.

Examples 1851-1899 have been intentionally excluded.

Example 1900

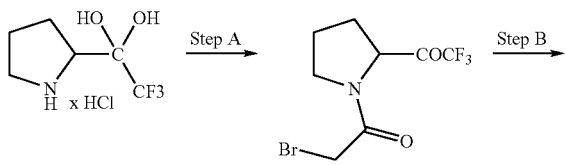

Step A
If one were to treat the title compound from Preparative Example 130 with bromoacetyl bromide as described in Preparative Example 1, one would obtain the title compound.

Step B
If one were to treat the title compound from Step A above with the title compound from Preparative Example 15 as described in Example 1, one would obtain the title compound.

Examples 1901-1949 have been intentionally excluded.

Example 1950

Step A
If one were to treat title compound from Preparative Example 130 with the title compound from Preparative Example 92 as described in Preparative Example 93, one would obtain the title compound.

Step B
If one were to treat the title compound from Step A above as described in Example 48, one would obtain the title compound.

Assay for Determining DP-IV Inhibition

The inhibitory activity of compounds against DPP-IV can be determined by in vitro assay systems, which are themselves well established in the art. The assay results given in Table 5 were obtained according to the following method, employing a modified version of the assay described by Leiting et al., in an article entitled "Catalytic properties and inhibition of proline-specific dipeptidyl peptidases II, IV and VII" in *Biochem. J.* Vol. 371, pages 525-532 (2003):

DPP-IV activity was determined fluorometrically with Gly-Pro-AMC (where AMC stands for 7-amido-4-methylcoumarin, Bachem AG, Switzerland) as substrate. The reaction mixture contained 10 µl of 1 ng/µl DPP-IV (R&D Systems GmbH, Germany) and 80 µl of 25 mM Tris/HCl buffer, pH 8.0. Compounds were supplied as DMSO stock solutions and diluted in assay buffer to a maximal DMSO concentration of 1% in the assay. Prior to start of the reaction, the mixture was incubated for 30 min at room temperature. The reaction was started by addition of 10 µl of 100 µM substrate solution.

The fluorescence intensity was measured at excitation and emission wavelengths of 355 and 460 nm, respectively, in a FluoStar Galaxy Multiwell Plate (BMG Labtech, Germany). Fluorescence was determined 3 and 4 minutes after start of reaction and increase in fluorescence was used for determination of enzymatic activity. IC(50) values of tested compounds were determined via plotting enzymatic activity versus concentration of test compound and determining the concentration of test compound which yields a 50% inhibition of enzymatic activity.

K(i) values were calculated using the Michaelis-Menten equation for competitive inhibition:

$$IC(50)=K(i)(1+[S]/Km)$$

As set forth in Table A, K(i) for each compound corresponds to A is K(i)<6 nM, B is K(i) 6-50 nM, C is K(i) from 51-500 nM and D is K(i) from 0.5-30 µM.

TABLE A

Activity Data for Inhibition of DPP-IV

| Example | Activity (K(i)) |
|---|---|
| 1 | C |
| 2 | D |
| 3 | D |
| 4 | D |
| 5 | D |
| 6 | C |
| 7 | C |
| 8 | C |
| 9 | C |
| 10 | C |
| 11 | C |
| 12 | C |
| 13 | C |
| 14 | D |
| 15 | D |
| 16 | C |
| 17 | B |
| 18 | A |
| 19 | B |
| 20 | C |
| 21 | C |
| 22 | A |
| 23 | B |
| 24 | A |
| 25 | B |
| 26 | C |
| 27 | A |
| 28 | A |
| 29 | A |
| 30 | A |
| 31 | B |
| 32 | A |
| 33 | A |
| 34 | A |
| 35 | A |
| 36 | B |
| 37 | B |
| 38 | B |
| 39 | B |
| 40 | D |
| 41 | B |
| 42 | C |
| 43 | A |
| 44 | A |
| 45 | B |
| 46 | D |
| 47 | A |
| 48 | A |
| 49 | A |
| 50 | B |
| 51 | A |
| 52 | A |

TABLE A-continued

Activity Data for Inhibition of DPP-IV

| Example | Activity (K(i)) |
|---|---|
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | B |
| 66 | B |
| 67 | A |
| 68 | B |
| 69 | B |
| 70 | B |
| 71 | B |
| 72 | A |
| 73 | B |
| 74 | C |
| 75 | C |
| 76 | B |
| 77 | A |
| 78 | B |

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What claimed is:

1. A compound according to the following formula:

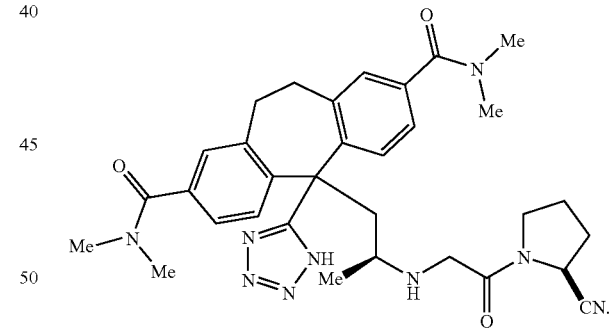

2. A compound according to the following formula:

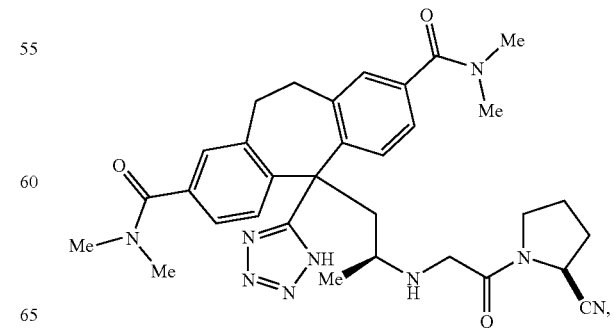

or a pharmaceutically acceptable salt thereof.

3. A pharmaceutical composition comprising a compound of the following formula:

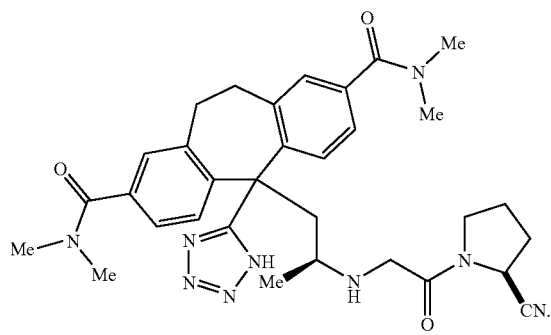

4. A pharmaceutical composition comprising a compound of the following formula:

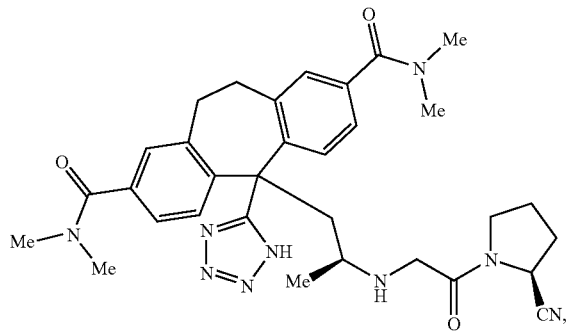

or a pharmaceutically acceptable salt thereof.

5. A method of treating type-2 diabetes comprising administering to a patient in need thereof an effective amount of a compound according to the following formula:

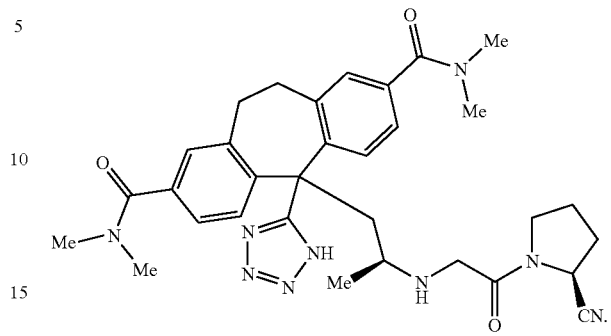

6. A method of treating type-2 diabetes comprising administering to a patient in need thereof an effective amount of a compound according to the following formula:

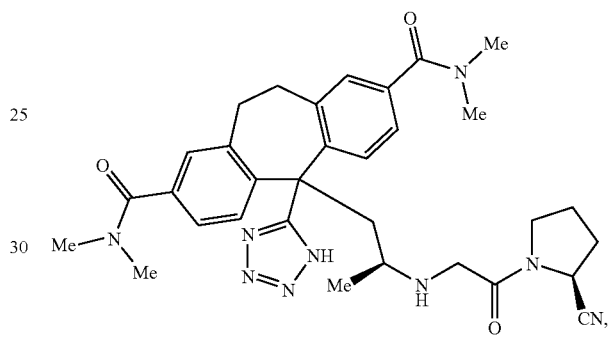

or a pharmaceutically acceptable salt.

* * * * *

UNITED STATES PATENT AND TRADEMARK OFFICE
CERTIFICATE OF CORRECTION

| | | |
|---|---|---|
| PATENT NO. | : 7,553,861 B2 | Page 1 of 1 |
| APPLICATION NO. | : 11/409481 | |
| DATED | : June 30, 2009 | |
| INVENTOR(S) | : Kroth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this
Twenty-third Day of August, 2011

David J. Kappos
*Director of the United States Patent and Trademark Office*